US007927606B2

(12) United States Patent
Dubensky, Jr. et al.

(10) Patent No.: US 7,927,606 B2
(45) Date of Patent: *Apr. 19, 2011

(54) MODIFIED FREE-LIVING MICROBES, VACCINE COMPOSITIONS AND METHODS OF USE THEREOF

(75) Inventors: Thomas W. Dubensky, Jr., Piedmont, CA (US); Dirk G. Brockstedt, Oakland, CA (US); Keith S. Bahjat, Concord, CA (US); John E. Hearst, Berkeley, CA (US); David N. Cook, Lafayette, CA (US); William S. Luckett, Jr., Richmond, CA (US)

(73) Assignee: Aduro Biotech, Berkeley, CA (US)

( * ) Notice: Subject to any disclaimer, the term of this patent is extended or adjusted under 35 U.S.C. 154(b) by 652 days.

This patent is subject to a terminal disclaimer.

(21) Appl. No.: 11/502,836

(22) Filed: Aug. 11, 2006

(65) Prior Publication Data

US 2008/0248066 A1    Oct. 9, 2008

Related U.S. Application Data

(63) Continuation of application No. 10/883,599, filed on Jun. 30, 2004, now Pat. No. 7,695,725, which is a continuation-in-part of application No. 10/773,618, filed on Feb. 6, 2004, now Pat. No. 7,883,775, which is a continuation-in-part of application No. 10/773,792, filed on Feb. 6, 2004, now Pat. No. 7,691,393.

(60) Provisional application No. 60/446,051, filed on Feb. 6, 2003, provisional application No. 60/449,153, filed on Feb. 21, 2003, provisional application No. 60/490,089, filed on Jul. 24, 2003, provisional application No. 60/511,869, filed on Oct. 15, 2003, provisional application No. 60/541,515, filed on Feb. 2, 2004, provisional application No. 60/511,719, filed on Oct. 15, 2003, provisional application No. 60/511,919, filed on Oct. 15, 2003, provisional application No. 60/532,598, filed on Dec. 24, 2003, provisional application No. 60/556,744, filed on Mar. 26, 2004.

(51) Int. Cl.
*A61K 39/02* (2006.01)
*A61K 45/00* (2006.01)
*C12N 15/01* (2006.01)

(52) U.S. Cl. .... 424/234.1; 424/9.1; 424/9.2; 424/184.1; 424/235.1; 424/278.1; 435/440; 435/441; 435/443

(58) Field of Classification Search .................... 424/9.1, 424/9.2, 184.1, 234.1, 235.1, 278.1; 435/440, 435/441, 443
See application file for complete search history.

(56) References Cited

U.S. PATENT DOCUMENTS

| | | |
|---|---|---|
| 4,545,987 A | 10/1985 | Giles et al. |
| 4,556,556 A | 12/1985 | Wiesehahn et al. |
| 4,791,062 A | 12/1988 | Wiesehahn et al. |
| 5,106,619 A | 4/1992 | Wiesehahn et al. |
| 5,171,568 A | 12/1992 | Burke et al. |
| 5,180,819 A | 1/1993 | Cayre |
| 5,399,719 A | 3/1995 | Wollowitz et al. |
| 5,593,823 A | 1/1997 | Wollowitz et al. |
| 5,691,132 A | 11/1997 | Wollowitz et al. |
| 5,830,702 A | 11/1998 | Portnoy et al. |
| 5,843,459 A | 12/1998 | Wang et al. |
| 5,877,159 A | 3/1999 | Powell et al. |
| 6,004,815 A | 12/1999 | Portnoy et al. |
| 6,051,237 A | 4/2000 | Paterson |
| 6,093,725 A | 7/2000 | Cook et al. |
| 6,099,848 A | 8/2000 | Frankel et al. |
| 6,133,460 A | 10/2000 | Wollowitz et al. |
| 6,143,490 A | 11/2000 | Cook et al. |
| 6,143,551 A | 11/2000 | Goebel |
| 6,150,170 A | 11/2000 | Powell et al. |
| 6,150,424 A | 11/2000 | Breitenbach et al. |
| 6,153,430 A | 11/2000 | Pastan et al. |
| 6,171,777 B1 | 1/2001 | Cook et al. |
| 6,177,441 B1 | 1/2001 | Cook et al. |
| 6,264,952 B1 * | 7/2001 | Enright et al. ............. 424/184.1 |
| 6,270,952 B1 | 8/2001 | Cook et al. |
| 6,287,556 B1 | 9/2001 | Portnoy et al. |
| 6,303,130 B1 * | 10/2001 | Purdy et al. ................ 424/255.1 |

(Continued)

FOREIGN PATENT DOCUMENTS

FR    2 686 896 A1    8/1993

(Continued)

OTHER PUBLICATIONS

Advisory Committee on Immunization Practices. (2001), "Case Report: Use of Anthrax Vaccine in the United States: Recommendations of Advisory Committee on Immunization Practices," *Clinical Toxicology* 39(1)85-100.

Aggarwal, A. et al. (Oct. 1990). "Oral Salmonella: Malaria Circumsporozoite Recombinants Induce Specific CD8+ Cytotoxic T Cells," *J. Exp. Med.* 172:1083-1090.

Alonso, J.C. et al. (1991). "Characterization of recF Suppressors in *Bacillus subtilis*," *Biochimie* 73:277-280.

Angelakopolous, H. et al. (Jul. 2002). "Safety and Shedding of an Attenuated Strain of *Listeria monocytogenes* with a Deletion of actA/plcB in Adult Volunteers: A Dose Escalation Study of Oral Inoculation," *Infection and Immunity* 70(7)3592-3601.

(Continued)

*Primary Examiner* — Rodney P. Swartz
(74) *Attorney, Agent, or Firm* — Michael A. Whittaker; BioTechnology Law Group

(57) ABSTRACT

Free-living microbes are provided in which the nucleic acid has been modified so that the microbe is attenuated for proliferation and/or which comprise genetic mutations that attenuate the ability of the microbe to repair its nucleic acid. Methods of using the modified microbes for the loading, activation, and/or maturation of antigen-presenting cells are also provided. Vaccine compositions comprising the modified microbes and/or the antigen-presenting cells and methods of using the vaccines are also provided. The microbes may be further modified to include heterologous antigens, such as tumor antigens or infectious disease antigens, for use as a vaccine against cancer or infectious diseases.

19 Claims, 61 Drawing Sheets

U.S. PATENT DOCUMENTS

| | | |
|---|---|---|
| 6,403,080 B1 | 6/2002 | Segal |
| 6,410,219 B1 | 6/2002 | Cook et al. |
| 6,440,735 B1 | 8/2002 | Gaeta |
| 6,455,286 B1 | 9/2002 | Wollowitz et al. |
| 6,497,876 B1 | 12/2002 | Maraskovsky et al. |
| 6,514,987 B1 | 2/2003 | Cook et al. |
| 6,565,852 B1 | 5/2003 | Paterson |
| 6,605,286 B2 | 8/2003 | Steidler et al. |
| 6,682,729 B1 | 1/2004 | Powell et al. |
| 6,709,810 B2 | 3/2004 | Cook et al. |
| 2001/0023072 A1 | 9/2001 | Crawford et al. |
| 2002/0025323 A1 | 2/2002 | Paterson et al. |
| 2002/0028206 A1 | 3/2002 | Paterson |
| 2002/0028432 A1 | 3/2002 | Cook et al. |
| 2002/0039588 A1 | 4/2002 | Collier et al. |
| 2002/0045587 A1 | 4/2002 | Goebel |
| 2002/0136738 A1 | 9/2002 | Agrewala et al. |
| 2002/0141977 A1 | 10/2002 | Collins et al. |
| 2002/0150588 A1 | 10/2002 | Allison et al. |
| 2002/0155108 A1 | 10/2002 | Barbera-Guillem |
| 2002/0182581 A1 | 12/2002 | Cook et al. |
| 2002/0192193 A1 | 12/2002 | Chokri et al. |
| 2003/0077263 A1 | 4/2003 | Maraskovsky et al. |
| 2003/0082510 A1 | 5/2003 | Wollowitz et al. |
| 2003/0092177 A1 | 5/2003 | Belardelli et al. |
| 2003/0113704 A1 | 6/2003 | Stassinopoulos et al. |
| 2003/0119187 A1 | 6/2003 | De Santis |
| 2003/0190682 A1 | 10/2003 | Law et al. |
| 2003/0202985 A1 | 10/2003 | Paterson |
| 2003/0203472 A1 | 10/2003 | Portnoy et al. |
| 2004/0009194 A1 | 1/2004 | Andrieu et al. |
| 2004/0013690 A1 | 1/2004 | Portnoy et al. |
| 2004/0022761 A1 | 2/2004 | Banchereau et al. |
| 2004/0029897 A1 | 2/2004 | Cook et al. |
| 2004/0037807 A1 | 2/2004 | Goldman |
| 2004/0038398 A1 | 2/2004 | Crawford et al. |
| 2004/0180321 A1 | 9/2004 | Cook et al. |
| 2004/0197343 A1 | 10/2004 | Dubensky, Jr. et al. |
| 2004/0228877 A1 | 11/2004 | Dubensky, Jr. et al. |
| 2005/0175630 A1 | 8/2005 | Raz et al. |
| 2005/0249748 A1 | 11/2005 | Dubensky et al. |
| 2005/0281783 A1 | 12/2005 | Kinch et al. |
| 2007/0031457 A1 | 2/2007 | Dubensky, Jr. et al. |

FOREIGN PATENT DOCUMENTS

| | | |
|---|---|---|
| FR | 2 686 896 B1 | 8/1993 |
| WO | WO-89/04669 A1 | 6/1989 |
| WO | WO-89/09616 A1 | 10/1989 |
| WO | WO-90/11089 A1 | 10/1990 |
| WO | WO-90/14436 A1 | 11/1990 |
| WO | WO-93/15212 A1 | 8/1993 |
| WO | WO-96/14087 A1 | 5/1996 |
| WO | WO-96/34631 A1 | 11/1996 |
| WO | WO-96/39818 A1 | 12/1996 |
| WO | WO-97/22349 A1 | 6/1997 |
| WO | WO-98/02523 A1 | 1/1998 |
| WO | WO-98/09616 A1 | 3/1998 |
| WO | WO-98/30545 A1 | 7/1998 |
| WO | WO-98/31786 A2 | 7/1998 |
| WO | WO-98/31786 A3 | 7/1998 |
| WO | WO-98/33386 A1 | 8/1998 |
| WO | WO-99/03976 A3 | 1/1999 |
| WO | WO-99/03979 A2 | 1/1999 |
| WO | WO-99/25376 A1 | 5/1999 |
| WO | WO-99/26476 A1 | 6/1999 |
| WO | WO-99/29884 A2 | 6/1999 |
| WO | WO-99/34007 A1 | 7/1999 |
| WO | WO-99/34839 A1 | 7/1999 |
| WO | WO-99/47646 A1 | 9/1999 |
| WO | WO-00/09156 A1 | 2/2000 |
| WO | WO-01/08701 A2 | 2/2001 |
| WO | WO-01/08701 A3 | 2/2001 |
| WO | WO-01/24637 A1 | 4/2001 |
| WO | WO-01/27295 A1 | 4/2001 |
| WO | WO-01/72329 A1 | 10/2001 |
| WO | WO-01/77358 A2 | 10/2001 |
| WO | WO-01/77358 A3 | 10/2001 |
| WO | WO-02/33109 A2 | 4/2002 |
| WO | WO-02/33109 A3 | 4/2002 |
| WO | WO-02/40046 A1 | 5/2002 |
| WO | WO-02/50262 A2 | 6/2002 |
| WO | WO-02/50262 A3 | 6/2002 |
| WO | WO-02/062298 A2 | 8/2002 |
| WO | WO-02/062298 A3 | 8/2002 |
| WO | WO-02/020982 A2 | 10/2002 |
| WO | WO-02/020982 A3 | 10/2002 |
| WO | WO-02/077249 A2 | 10/2002 |
| WO | WO-02/077249 A3 | 10/2002 |
| WO | WO-02/083879 A2 | 10/2002 |
| WO | WO-02/083879 A3 | 10/2002 |
| WO | WO-02/097044 A2 | 12/2002 |
| WO | WO-02/097044 A3 | 12/2002 |
| WO | WO-03/061379 A2 | 7/2003 |
| WO | WO-03-061379 A3 | 7/2003 |
| WO | WO-03/083056 A2 | 10/2003 |
| WO | WO-03/083056 A3 | 10/2003 |
| WO | WO-03/092600 A2 | 11/2003 |
| WO | WO-03/092600 A3 | 11/2003 |
| WO | WO-03/102168 A1 | 12/2003 |
| WO | WO-2004/006837 A2 | 1/2004 |
| WO | WO-2004/011492 A1 | 2/2004 |
| WO | WO-2004/084936 A2 | 10/2004 |
| WO | WO-2004/110481 A2 | 12/2004 |
| WO | WO-2005/009463 A2 | 2/2005 |
| WO | WO-2005/009463 A3 | 2/2005 |
| WO | WO-2005/037233 A2 | 4/2005 |
| WO | WO-2005/037233 A3 | 4/2005 |
| WO | WO-2005/067460 A2 | 7/2005 |
| WO | WO-2005/067460 A3 | 7/2005 |
| WO | WO-2005/071008 A2 | 8/2005 |
| WO | WO-2005/071088 A3 | 8/2005 |
| WO | WO-2005/092372 A2 | 10/2005 |

OTHER PUBLICATIONS

Anonymous (Feb. 4, 2003.) "Cerus Corporation Starts Vaccine Trial for Epstein-Barr Virus," *Press Release Cerus Corporation*, located at <http://www.cerus.com/pages/PR/2003/PRO20403.html> last visited on Nov. 8, 2004, two pages.

Anthony, D.A, et al. (2001), "DNA: Still A Target Worth Aiming At?" *Am. J. Pharmacogenomics* I(1):67-81.

Appelberg, R. et al. (Feb. 2000). "Mutants of *Listeria monocytogenes* Defective in In Vitro Invasion and Cell-to-Cell Spreading Still Invade and Proliferate in Hepatocytes of Neutropenic Mice," *Infection and Immunity* 68(2):912-914.

Aravind, L. et al. (1999). "Conserved Domains in DNA Repair Proteins and Evolution of Repair Systems," *Nucleic Acids Research* 27(5)1223-1242.

Argani, P, et al. (Dec. 2001), "Mesothelin Is Overexpressed in the Vast Majority of Ductal Adenocarcinomas of the Pancreas: Indentification of a New Pancreatic Cancer Market by Serial Analysis of Gene Exression (SAGE)," *Clin. Cancer Res.* 7:3862-38683.

Arikan, E. et al, (1986). "Sequences of the *E. coli uvrB* Gene and Protein," *Nucleic Acids Research* 14(6):2637-2650.

Armstrong, A.C., et al, (2002). "Cellular Vaccine Therapy for Cancer," *Expert Rev. Vaccines* 1(3):303-316.

Asano, K. et al, (May 8, 1998). "Structural Basis for Binding of the Plasmid CollB-P9 Antisense Inc RNA to Its Target RNA with the 5'-rUUGGCG-3' Motif in the Loop Sequence," *J. Biol. Chem.* 273(19):11826-11838.

Atalla, A. et al. (Aug. 2003). "The *pst* Operon of *Bacillus Subtilis* Is Specifically Induced by Alkali Stress," *J. Bacteriol.* 185(16):5019-5022.

Auerbach, V. et al, (Sep. 2001). "Development of a Competitive Index Assay to Evaluate the Virulence of *Listeria monocytogenes actA* Mutants During Primary and Secondary Infection of Mice," *Infection and Immunity* 69(9):5953-5957.

Aulinger, B.A. et al. (Jun. 2005). "Combining Anthrax Vaccine and Therapy: A Dominant-Negative Inhibitor of Anthrax Toxin Is Also a Potent and Safe Immunogen for Vaccines," *Infection and Immunity* 73(6):3408-3414.

Baer, R. et al. (Jul. 1984), "DNA Sequence and Expression of the B95 Epstein-Barr Virus Genome," *Nature* 310:207-211.

Bahjat, K.S. et al. (Nov. 2006). "Cytosolic Entry Controls CD8+-T-Cell Potency During Bacterial Infection," *Infection and Immunity* 74(11):6387-6397.

Baillie, L.W.J. et al. (Jun. 1, 1998). "A Heat-Inducible *Bacillus subtilis* Bacteriophage Φ 105 Expression System for the Production of the Protective Antigen of *Bacillus anthracis*," *FEMS Microbiol, Lett.* 163(1):43-47.

Bakardjiev, A. et al. (Jan. 2004), "Listeriosis in the Pregnant Guinea Pig: A Model of Vertical Transmission," *Infection and Immunity* 72(1):489-497.

Ballard, J.D. et al. (1996), "Antrax Toxin-Mediated Delivery of a Cytotoxic T-Cell Epitope in vivo," *Proc. Natl. Acad. Sci. USA* 93:12531-13534.

Banchereau, J. et al. (Mar. 19, 1998), "Dendntic Cells and the Control of Immunity," *Nature* 392(6673):245-252.

Banehereau, J. et al. (Sep. 1, 2001). "Immune and Clinical Responses in Patients with Metastatic Melanoma to CD34+ Progenitor-Derived Dendritic Cell Vaccine," *Cancer Res.* 61:6451-6458.

Barnard, J.P. et al. (Feb. 1999). "Vaccination Against Anthrax with Attenuated Recombinant Strains of *Bacillus anthracis* That Produce Protective Antigen," *Infection and Immunity* 67(2):562-567.

Barry, R.A. et al. (Apr. 1992), "Pathogenicity and Immunogenicity of *Listeria monocytogenes* Small-Plaque Mutants Defective for Intracellular Growth and Cell-to-Cell Spread," *Infection and Immunity* 60(4):1625-1632.

Bast, R.C. et al. (Mar. 1975), "Antitumor Activity of Bacterial Infection. I. Effect of *Listeria monocytogenes* on Growth of a Murine Fibrosarcoma," *Journal of the National Cancer Institue* 54(3):749-756.

Bast, R.C. et al. (Mar. 1975), "Antitumor Activity of Bacterial Infection. II. Effect of *Listeria monocytogenes* on Growth of a Guniea Pig Hepatoma," *Journal of the National Cancer Institute* 54(3):757-761.

Belitsky, B.R. et al. (Jul. 2002). "GabR, A Member of a Novel Protein Family, Regulates the Utilization of γ-Aminobutyrate in *Bacillus subtitis*," *Mol. Microbiol.* 45(2):569-583.

Bergmann, B. et al. (Feb. 2002). "In1A- but not In 1B-mediated Internalization of *Listeria monocytogenes* by Non-Phagocytic Mammalian Cells Needs the Support of Other Irsternalins," *Molecular Microbiology* 43(3):557-570.

Beverly, M.B. et al. (1996). "A Rapid Approach for the Detection of Dipicolinic Acid in Bacterial Spores Using Pyrolysis/Mass Spectrometry," *Rapid Commun. Mass Spectrom*, 10:455-458.

Bielecki, J. et al. (May 10, 1990). "*Bacillus subtilis*Expressing a Haemolysin Gene from *Listeria monocytogenes* Can Grow in Mammalian Cells," *Nature* 345(6271):175-176.

Bierne, H. et al. (Nov. 1997), "*uvrD* Mutations Enhance Tandem Repeat Deletion in the *Escherichia coli* Chromosome via *SOS* Induction of the ReeF Recombination Pathway," *Mol. Microbiol.* 26(3):557-567.

Bierne, H. et al. (Sep. 2002). "In IB, A Surface Protein of *Listeria monocytogenes* that Behaves as an Invasion and a Growth Factor," *Journal of Cell Science* 115:3357-3367.

Bishop, D.K. et al. (Sep. 15, 1987). "Adoptive Transfer of Immunity to *Listeria monocytogenes* The Influence of In Vitro Stimulation on Lymphocyte Subset Requirements," *J. Immunol.* 139(6):2005-2009.

Biswas, I. et al. (Jun. 1993). "High-Efficiency Gene Inactivation and Replacement System for Gram-Positive Bacteria," *J. Bacteriol.* 175(11):3628-3635.

Black, C.G. et al. (Feb. 16, 1998). "Absence of an SOS-like System in *Neisseria gonorrhoeae*," *Gene* 208:61-66.

Boon, T. et al. (1994). "Tumor Antigens Recognized by T Lymphocytes," *Annu. Rev, Immunol.* 12:337-365.

Bouwer, H,G.A. et al. (Apr. 14, 2003). "Recombinant *L. monocytogenes* as a Vaccine for Stimulation of Anti-Tumor Responses," (Abstract for the 90th Anniversary Meeting of the American Association of Immunologists, Denver, CO, May 6-10, 2003,) *FASEB Journal*, 17(7):C330-331, Abstract 162.17.

Bouwer, H.G.A. et al. (May 6, 2003), "Recombinant *L. monocytogenes* as a Vaccine For Stimulation of Anti-Tumor Responses," *Poster, presented at The American Association of Immunologits 90th Anniversay Meeting*, Denver, CO (May 6-10, 2003), one page.

Bowie, J.U. et al. (Mar. 16, 1990), "Deciphering the Message in Protein Sequences: Tolerance to Amino Acid Substitutions," *Science*, 247(4948): 1306-1310.

Boyaka, P.N. et al. (1999) "IL-12 Is an Effective Adjuvant for Induction of Mucosal Immunity," *The Journal of Immunology* 162:122-128.

Boyaka, P.N. et al. (Jun. 2003). "Effective Mucosal Immunity to Anthrax: Neutralizing Antibodies and Th Cell Responses Following Nasal Immunization with Protective Antigen," *The Journal of Immunology* 170:5636-5643.

Braun, L. et al. (Oct. 1999). "The 213-amino-acid Leucine-rich Repeat Region of the *Listeria monocytogenes* In1B Protein is Sufficient for Entry into Mammalian Cells, Stimulation of PI 3-Kinase and Membrane Ruffing," *Molecular Microbiology* 34(1):10-23.

Bridges, B.A. et al. (Aug. 1979). "Inactivation of *Escherichia coli* by Near-Ultraviolet Light and 8-Methoxypsoralen: Different Responses of Strains B/r and K-12," *Journal of Bacteriology* 139(2):454-459.

Brinkmann, U. et al. (Apr. 1, 1999). "Novel Genes in the PAGE and GAGE Family of Tumor Antigens Found by Homoly Walking in the dhEST Database," *Cancer Research* 59:1445-1448.

Brockstedt, D. et al. (Feb. 19, 2003). "Recombinant Attenuated *Listeria monocytogenes* Elicits Striking Antigen-Specific CD8+ T-Cell Responses that Correlate with Prolonged Survival in A Murine Transplant Model of Melanoma," *presented at Keystone Symposia Meeting*, Keystone, CO (Feb. 17-23, 2003), one page.

Brockstedt, D. et al. (Mar. 2003), "Recombinant Attenuated *Listeria monocytogenes* Elicits Robust Cellular Immune Response to Tumor-Associated Antigen in *Listeria* Immune Mice," *Proceedings of the American Association for Cancer Research, 94th Annual Meeting*, Apr. 5-9, 2003, Toronto, Ontario, Canada, 44:194, Abstract No. 851, one page.

Brockstedt, D. et al. (Jul. 2003). "Recombinant Attentuated *Lysteria monocytogenes* Elicits Robust Cellular Immune Reponse to Tumor-Associated Antigen in *Listera* Immune Mice," (Abstract for the 94th Annual Meeting of the American Association for Cancer Research, Washington, DC, USA, Jul 11-14, 2003) *Proceedings of the American Association For Cancer Research Annual Meeting* 44(2):168, Abstract No. 851.

Brockstedt, D. et al. (Oct. 3, 2003), "Novel Strategies to Develop *Listeria monocytogenes* Vaccine Strains for Cancer Immunotherapy Applications," *presented at Cancer Vaccines* 2003 (Oct. 1-3, 2003), one page.

Brockstedt, D. et al. (Mar. 2004). "The Living Dead: Psoralen-killed Metabolically Active *Listeria* DNA Repair Mutant-based Vaccines Induce Therapeutic Anti-tumor Efficacy Targeted Against an Endogenous Antigen," abstract *presented at the American Association for Cancer Research (AACR)*, Mar. 27-31, 2004, as posted on <http://www.cerus.com/pages/solution/abs156.html>, last visited on Aug. 26, 2004, two pages.

Brockstedt, D. et al. (Jul. 2004). "The Living Dead: Psoralen-killed Metabolically Active *Listeria* DNA Repair Mutant-based Vaccines Induce Therapeutic Anti-tumor Efficacy Targeted Against an Endogenous Antigen," abstract *presented at the Gordon Research Conference on Microbial Toxins and Pathogenicity*, Jul. 18-23, 2004, Andover, NH, as posted on <http://www.cerus.com/pages/solution/04_GordonResearchConf_Brockstedt.html>, last visited on Aug. 26, 2004, two pages.

Brockstedt, D.G. (Date Unknown). "*Listeria*-CEA Vaccine-Infected DC for Cancer Therapy," Abstract for Grant No. 1R43CAI08026-01 located at <http://crisp.cit.nih.gov/crisp/CRISP_LIB.getdoc?testkey=6787426&p_grant_num=IR43C...> last visited Jun. 27, 2004, two pages.

Brocksted, D.G. et al. (Aug. 2005) "Killed by Metabolically Active Microbes: A New Vaccine Paradigm for Eliciting Effector T-Cell Responses and Protective Immunity," *Nature Medicine* 11(8):853-860.

Brockstedt, D.G. et al. (Sep. 21, 2004). "*Listeria*-based Cancer Vaccines That Segregate Immunogenicity From Toxicity," *Proc. Natl. Acad. Sci. USA* 101(38):13832-13837.

Brocksted, D.G, et al. (Sep. 21, 2004). "*Listeria*-based Cancer Vaccines That Segregate Immunogenicity From Toxicity," Supporting Information, Table and Figures cited in *Proc. Natl. Acad. Sci. USA*

*Data Supplement* located at <http://www.pnas.org/cgi/content/full/0406035101/DC1>, last visited on Jul. 22, 2007, 9 pages.

Brook, I, et al. (2001). "Susceptibility of Irradiated Mice to *Bacillus anthracis* Sterne by the Intratacheal Route of Infection," *J. Med. Microbiol*. 50:702-711.

Brooks, P.C. et al, (Aug. 2001), "Identification of Some DNA Damage-Inducible Genes of *Mycobacterium tuberculosis*: Apparent Lack of Correlation with LexA Binding," *Journal of Bacteriology* 183(15):4459-4467.

Brossier, F. et al. (Aug. 1999). "Antigen Delivery by Attenuated *Bacillus anthracis*: New Prospects in Veterinary Vaccines," *Journal of Applied Microbiology* 87(2):298-302.

Brassier, F. et al. (Apr. 2000). "Protective Antigen-Mediated Antibody Respone Against a Heterologous Protein In Vivo by *Bacillus anthracis*," *Infection and Immunity* 68(10):5731-5734.

Brossier, F, et al. (Oct. 2000), "Role of Toxin Functional Domains in Anthrax Pathogenesis," *Infection and Immunity* 68(4):1781-1786.

Brown, D.P. et al. (May 1988). "Site-Specific Integration in *Saccharopolyspora erythraea* and Multisite Integration in *Streptomyces lividans* of Actinomycete Plasmid pSE101," *J. Bacteriology* 170(5):2287-2295.

Brown, D.P. et al. (Nov. 1994). "Characterization of *spo0A* Homologues in Diverse *Bacillus* and *Clostridium* Species Identifies a Probable DNA-Binding Domain," *Mol. Microbiol*. 14(3):411-426.

Brown, E.R. et al. (1955). "Specific Identification of *Bacillus anthracis* by Means of a Variant Bacteriophage," *J. Infect. Dis*. 96:34-39.

Bruno, J.G. et al. (1999). "In Vitro Selection of DNA Aptamers to Anthrax Spores with Electrochemiluminescence Detection," *Biosens. Bioelectron*. 14:457-464.

Camilli, A. et al. (1993). "Dual Roles of *plcA* in *Lysteria monocytogene* Pathogenesis," *Molecular Microbiology* 8(1):143-157.

Campbell, P.A. (1994). "Macrophage-*Listeria* Interactions," *Immunol. Ser*. 60:313-328.

Campoy, S. et al. (Nov. 2002), "A New Regulatoly DNA Motif of the Gamma Subclass *Proteobacteria*. Identification of the LexA Protein Binding Site of the Plant Pathogen *Xylella fastidiosa*," *Microbiology* 148:3583-3597.

Carl, M. et al. (Jun. 1992), "Detection of Spores of *Bacillus anthracis* Using the Polymerase Chain Reaction," *J. Infect. Dis*. 165(6):1145-1148.

Carles-Kinch, K. et al. (May 15, 2002). "Antibody Targeting of the EphA2 Tyrosine Kinase Inhibits Malignant Cell Behavior," *Cancer Research* 62:2840-2847.

Carrasco, B. et al, (2002), "Effect of the *recU* Suppressors *sms* and *subA* on DNA Repair and Homologous Recombination in *Bacillus subtilis*," *Mol. Genet. Genomics* 266:899-906.

Chan, A.Y, et al. (Oct. 10, 2003), "Interaction of a Putative Transcriptional Regulatory Protein and the Thermo-Inducible *cts*-52 Mutant Repressor in the *Bacillus subtilis* Phage φ 105 Genome,", *J. Mol. Biol*. 333(1):21-31.

Chang, D.H. et al. (Jun. 2003). "Dendritic Cells and Immunotherapy for Cancer," *Int. J. Hematol*. 77(5):439-443.

Chee, M.S. et al. (1990). "Analysis of the Protein-Coding Content of the Sequence of Human Cytomegalovirus Strain AD169" In *Cytomegaloviruses*, McDougall, J.K. ed., Springer Verlag, pp. 125-169.

Cheo, D.L. et al. (Sep. 1993), "Elucidation of Regulatory Elements That Control Damage Induction and Competence Induction of the *Bacillus subtilis* SOS System," *J. Bacteriol*. 175(18):5907-5915.

Clark, A.J. (1991), "*rec* Genes and Homologous Recombination Proteins in *Escherichio coli*," *Biochemie* 73:523-532.

Cohen, S. et al. (Aug. 2000). "Attenuated Nontoxinogenic and Nonencapsulated Recornbinant *Bacillus anthracis* Spore Vaccines Protect Againta Anthrax," *Infection and Immunity* 68(8):4549-4558.

Cole, R.S, (Sep. 1971). "Inactivation *Escherichia coli*, F Episomes at Transfer, and Bacteriophage lambda by Psoralen Plus 360-nm Light: Significance of Deoxyribonucleic Acid Cross-Links," *Journal of Bacteriology* 107(3):846-852.

Cole, R.S. et al. (1975). "Repair of Cross-Linked DNA in *Escherichia coli*" Chapter 66 In *Basic Life Sciences: Molecular Mechanisms for Repair of DNA Part B*, Hollaender, A. ed., Plenum Press, pp. 487-495.

Conradt , P. at al. (1999), "Cytolytic T-Cell Responses to Human Dendritic Cells and Macrophages Infected with *Mycobacterium bovis* BCG and Recombinant BCG Secreting Listeriolysin," *Microbes Infect*. 1:753-764.

Coote, J.G. et al. (Jan. 1996). "A Rapid, Colourimetric Assay for Cylotoxin Activity in *Campylobacter jejuni*," *FEMS Immunol. Med. Microbiol*. 13(1):65-70.

Cossart, P. et al. (1998). "Interactions of *Listeria monocytogenes* With Mammalian Cells During Entry and Actin-Based Movement: Bacterial Factors, Cellular Ligands and Signaling," *The EMBO Journal* 17(14):3797-3806.

Cossart, P. et al. (2001), "The Use of Host Cell Machinery in the Pathogenesis of *Listeria monobytogenes*," *Current Opinion in Immunology* 13:96-103.

Cossart, P. et al, (Jan. 2003). "Invasion of Mammalian Cells by *Listeria monoctyogenes*: Functional Mimicry to Subvert Cellular Functions," *TRENDS in Cell Biology* 13(1):23-31.

Courcelle, J. et al, (Jul. 17, 2001). "Participation of Recombination Proteins in Rescue of Arrested Replication Forks in UV-Irradiated *Escherichia coli* Need Not Involve Recombination," *Proc. Natl. Acad. Sci. USA* 98(15):8196-8202.

Crowley, D.J. et al. (May 10, 2001). "The SOS-Dependent of *uvrD* is not Required for Efficient Nucleotide Excision Repair of Ultraviolet Light Induced DNA Photoproducts in *Escherichia coli*," *Mutat. Res*. 485(4):319-329.

Da Ros, et al. (2001), "DNA-Photocleavage Agents," *Current Pharmaceutical Design* 7:1781-1821.

Davis, E.O. et al. (Jun. 2002), "Definition of the Mycobacterial SOS Box and Use to Identify LexA-Regulated Genes in *Mycobacterium tuberculosis*," *J. Bacteriol*. 184(12):3287-3295.

Davison, A.J. et al. (1986). "The Complete DNA Sequence of Varicella-Zoster Virus," *J. Gen. Virol*. 67:1759-1816.

Decatur, A.L. et al. (Nov. 3, 2000). "A PEST-Like Sequence in Listeriolysin O Essential for *Listeria monocytogenes* Pathogenicity," *Science* 290:992-995.

Deuerling, E. et al. (Jul. 1995) "The *fisH* Gene of *Bacillus subtilis* Is Transiently Induced after Osmotic and Temperature Upshift," *J. Bacteriol*. 177(14):4105-4112.

Dhodapkar, M.V. et al. (May 2000), "Active Immunization of Humans with Dendritic Cells," *J. Clin. Immunol*. 20(3):167-174.

Domann, E. et al. (Jan. 1997). "Identification and Characterization of a Novel PrfA-Regulated Gene in *Listeria manacytogenes* Whose Product, IrpA, Is Highly Homologous to Internalin Proteins, Which Contain Lencine-Rich Repeats" *Infection and Immunity* 65(1):101-109.

Drago, L. et al. (Nov. 2002). "Real-Time PCR Assay for Rapid Detection of *Baciltra anthracis* Spores in Clinical Samples," *J. Clin. Microbiol*. 40(11):4399.

Dramsi, S. et al. (1995). "Entry of *Listeria monocytogenes* Into Hepatocytes Requires Expression of InlB, a Surface Protein of the Internalin Multigene Family," *Molecular Microbiology* 16(2):251-261.

Dramsi, S. et al. (May 1997) "Identification of Four New Members of the Internalin Multigene Family of *Listeria monobytogenes* EGD," *Infection and Immunity* 65(5):1615-1625.

Drevets, D.A. (Jan. 1998). "*Lysteria monocytogenes* Virulence Factors That Stimulate Endothelial Cells," *Infection and Immunity* 66(1):232-238.

Drevets, D.A. (Jul. 1999). "Dissemination *Listeria monocytogenes* by Infected Phagocytes," *Infection and Immunity* 67(7):3512-3517.

Drevets, D.A. et al. (Nov. 1995). "*Listeria monocytogenes* Infects Human Endothelial Cells by Two Distinct Mechanisms," *Infection and Immunity* 63(11):4268-4276.

Dubensky, T. (Feb. 22, 2003). "Cancer Vaccines Derived from Selected Attenuated Strains of *Listeria monocytogenes*," *Presented at Keystone Symposia Meeting*, Keystone, CO (Feb. 17-23. 2003) 22 pages.

Dubensky, T. (Mar. 14, 2003). "Cancer Vaccines Derived From Selected Attenuated Strains of *Listeria monocytogenes*," *presented at Days of Molecular Medince—Immunotherapy*, 24 pages.

Dubensky, T. (Dec. 4, 2003), "Listeria-Based Therapeutic Vaccines for Infectious Disease and Cancer: Vaccines Disguised is an Invading Pathogen," *presented at Johns Hopkins University*, 57 pages.

Dubensky, T.W. (Date Unknown). "Listeria Immunotherapy for Pancreatic and Ovarian Cancer," Abstract for Grant No. 2R44CA101421-02 located at <http://crisp.cit.nih.gov/ensp/CRISP_LIB.getdoc?textkey=699210&p_grant_num=2R44C...> last visited Dec. 7, 2005, two pages.

Dubensky, T.W. (Date Unknown), "Listeria-Based Vaccines for Ovanian Cancer Therapy," Abstract for Grant No. 1R43CA101421-01 located at <http://crisp.cit.nih.gov/crisp/CRISP_LIB.getdoc?textkey=6645288&p_grant_num=1R43CA...> last visited Nov. 3, 2004, two pages.

Dubensky, T.W. (Date Unknown), "Psoralen-Killed, Metabolically-Active Anthrax Vaccine," Abstract for Grant No. 1U01A1061199-01 located at <http://crisp.cit.nih.gov/crisp/CRISP_LIB.getdoc?textkey=6818020&p_grant_num=1U01A1...> last visited Nov. 3, 2004, two pages.

Dubensky, T.W. (Date Unknown), "Psoralen-Killed, Metabolically-Active Anthrax Vaccine," Abstract for Grant No. 5U01A1061190-01 located at <http://crisp.cit.nih.gov/crisp/CRISP_LIB.getdoc?textkey=6916362%p_grant_num=5U01A...>last visited Dec. 7, 2005, two pages.

Dullaghan, E.M. et al. (Nov. 2002), "The Role of Multiple SOS Boxes Upstream of the *Mycobacterium turberculosia lexA* Gene—Identification of a Novel DNA-Damage-Inducible Gene," *Microbiology* 148(11):3609-3615.

Dustoor, M.M. et al. (Jan. 1979), "Antitumor Activity of *Listeria monocytogenes* on a Guinea Pig Fibrosarcoma," *Infection and Immunity* 23(1):54-60.

Engelgrecht, F. et al. (1996), "A New PrfA-Regulated Gene of *Listeria monocytogenes* Encoding a Small, Secreted Protein Which Belongs to the Family of Internalins ," *Molecular Microbiology* 21(4):823-837.

Esche, C. et al. (Feb. 1999). "The Use of Dendritic Cells for Cancer Vaccination," *Curr. Opin. Mol. Ther.* 1(1):72-81.

Esin, S. et al. (1996). "Proliferation of Distinct Human T Cell Subsets in Response to Live, Killed or Soluble Extracts of *Mycobacterium tuberculosis* and *Myco. avium*," *Clin. Exp. Immunol.* 104:419-425.

Ferguson, L.R. et al. (19871, "Frameshift Mutagenesis by Nitracrine Analogues in Wild-Type uvrB polA and recA Strains of *Salmonella typhimurium* With and Without Plasmid pKM101," *Mutation Research* 184:13-22.

Fisher, S.H. (Apr. 1999), "Regulation of Nitrogen Metabolism in *Bacillus subtilis*: Vive' La Difference!" *Mol. Microbiol.* 32;4223-232.

Fong, L. et al. (Mar. 15, 2001). "Dendritic Cells Injected Via Different Routes Induce Immunity in Cancer Patients," *Journal of Immunology* 166:4254-4259.

Fong, L. et al. (Jul. 17, 2000), "Altered Peptide Ligand Vaccination with Flt3 Ligand:Expanded Dendritic Cells for Tumor Immunotherapy," *Proc. Natl. Acad. Sci. USA* 98(15):8809-8814.

Fong, L. et al. (Nov. 2002). "Productive Infection of Plasmacytoid Dendritic Cells with Human Immunodeficiency Virus Type 1 Is Triggered by CD40 Ligation," *Journal of Virology* 76(21):11033-11041.

Foon, K.A, et al. (Nov. 1995) "Immune Responses in Patients with T-Cell Lymphoma Treated with an Anti-Idotype Antibody Mimicking a Highly Restricted T-Cell Antigen," *Clin. Cancer Res.* 1(11):1285-1294.

Fouet, A. et al. (2002). "*Bacillus arahracis* Cell Envelope Components" Chapter 5 *In Current Topics In Microbiology And Immunology*, Compans, R.W. et al. eds., Springer-Verlag: Germany, 271:87-113.

Frankel, F.R. et al. (Oct. 1994), "Delivery HIV Antigens Using *Listeria monocytogenes* as a Live Vaccine Vector," *Abstracts of Papers Presented at the 1994 Meeting on Molecular Approaches to the Control of Infectious Diseases*, Oct. 5-9, 1994, Cold Spring Harbor Laboratory Press: Cold Spring Harbor, NY, p. 56.

Frankel, F.R. et al. (1995). "Induction of Cell-Mediated Immune Responses to Human Immunodeficiency Virus Type 1 Gag Protein by Using *Listeria monocytogenes* as a Live Vaccine Vector," *The Journal of Immunology* 155:4775-4782.

Franklin. W.A. et a.l (Jun. 1984). "Removal of UV Light-Induced Pyrimidine-Pyrimidone(6-4) Products from *Escherichia coli* DNA Requires the *uvr A, uvrB*, and *urvC* Gene Products," *Proc. Natl. Acad. Sci. USA* 81(12):3821-3824.

Freitag, N.E. et al. (Apr. 1999), "Examination of *Listeria monocytogenes* Intracellular Gene Expression by Using the Green Fluorescent Protein of *Aequorea victoria*," *Infection and Immunity* 67(4):1844-1852.

Friedman, R.S. et al. (Nov. 2000). "Induction of Human Immunodeficiency Virus (HIV)-Specific CD8 T-Cells Responses by *Listeria monocytogenes* and a Hyperattenuated *Listeria* Strain Engineered to Express HIV Antigens," *Journal of Virology* 74(21):9987-9993.

Fuangthong, M. et al. (Jun. 2002), "Regulation of the *Bacillus subtilis fur* and *perR* Genes by PerR: Not All Members of the PerR Regulon Are Peroxide Inducible," *J. Bacteriol.* 184(12):3276-3286.

Gaillard, J.-L. et al. (Jun. 28, 1991). "Entry of *L. monocytogenes* into Cells Is Mediated by Intemalin, a Repeat Protein Reminiscent of Surface Antigens From Gram-Positive Cocci," *Cell* 65:1127-1141.

Gaillard, J,-L. et al (Feb. 1996). "The *inlAB* Locus Mediates the Entry of *Listeria monoctyogenes* into Hepatocytes In Vivo," *Journal of Experimental Medicine* 183(2):359-369.

Gedde, M.M. et al. (Feb. 2000). "Role of Listeriolysin O in Cell-To-Cell Spread of *Listeria monocytogenes*," *Infection and Immunity* 68(2):999-1003.

GenBank Accession No. AE17040 created on May 1, 2003, located at <http://www.ncbi.nlm.nih.gov>, last visited on Nov. 15, 2004, 159 pages.

GenBank Accession No. AF268967, created Jul. 31, 2000, located at <http://www.ncbi.nlm.nih.gov/entrez/viewer.fcgi?dc=nucleotide&val=9280532>, last visited by May 16, 2007, three pages.

GenBank Accession No, AF306778, Oct. 1, 2003, located at <http://www.ncbi.nlm.nih.gov/entrez/viewer.fcgi?db=nucleotide&val=10880942>, last visited on May 16, 2007, two pages.

GenBank Accession No. AJ271621, created Nov. 14, 2006, located at <http://www.ncbi.nlm.nih.gov/entrez/viewer.fcgi?db=nuccore&id=27527038>, last visited on Jun. 30, 2007, four pages.

GenBank Accession No. AJ409321, created Apr. 15, 2005, located at <http://www.ncbi.nlm.nih.gov/entrez/viewer.fcgi?40643279:EMBL:10447457>, last visited on Jul. 22, 2007, two pages.

GenBank Accession No. AL591824 created on Jul. 18, 2002, located at <http://www.ncbi.nlm.nih.gov>, last visited on Nov. 15, 2004, two pages.

GenBank Accession No. AL591974 created on Jun. 6, 2002, located at <http://www.ncbi.nlm.nih.gov>, last visited on Nov. 15, 2004, 87 pages.

GenBank Accession No. AL591975 created on Jun. 6, 2002, located as <http://www.ncbi.nlm.nih.gov>last visited on Nov. 15, 2004, 157 pages.

GenBank Accession No. AY700758, created Nov. 21, 2005, located at <http://www.ncbi.nlm.nih.gov/entrez/viewer.fcgi?db=nucleotide&val=51235129>, last visited on May 16, 2007, two pages.

Genbank Accession No. AY997299, created Apr. 26, 2005, located at <http://www.ncbi.nlm.nih.gov/entrez/viewer.fcgi?db=nucleotide&val=62823103>, last visited on May 16, 2007, two pages.

GenBank Accession No. M24199 created on Oct. 22, 1993, located at <http://www.ncbi.nlm.nih.gov>, last visited on Nov. 15, 2004, three pages.

GenBank Accession No. M67471 created on Apr. 26, 1993, located at <http://www/ncbi.nlm.nih.gov>, last visited on Nov. 15, 2004, four pages.

GenBank Accession No. NC_007530, created Apr. 3, 2006, located at <http://www.ncbi.nlm.nih.gov/entrez/viewer.fcgi?db=nucleotide&val=50196905>, last visited on May 16, 2007, 163 pages.

GenBank Accession No. V00328, created Apr. 18, 2005, located at <http://www.ncbi.nlm.nih.gov/entrez/viewer.fcgi=nucleotide&val=42672>, last visited on May 16, 2007, three pages.

GenBank Accession No. X81135, created Nov. 30, 2006, located at <http://www.ncbi.nlm.gov/entrez/viewer.fcgi?563492:EMBL:10735862>, last visited on Jul. 22, 2007, three pages.

Gentschev, I. et al. (Sep. 29, 2000). "Delivery of Protein Antigens and DNA by Virulence-Attenuated Strains of *Salmonella typhimurium* and *Listeria moncytogenes*," *Journal of Biotechnology* 83:19-26.

Gentschev, I. et al. (Feb. 2002), "Delivery of Protein Antigens and DNA by Attenuated Intracellular Bacteria," *Int. J. Med. Microbiol.* 291:577-582.

Giedlin, M. et al. (Date Unknow). "The Living Dead: Vaccines Against Microbial Pathogens Based on Psoralen-Killed Metabolically Active DNA Repair Mutants," Abstract 189 (H) located at <http://www.asmbiodefense.org/2004tueabs.asp>, last visited Nov. 5, 2004, one page.

Giedlin, M. et al. (Mar. 2004), "The Living Dead: Vaccines Against Microbial Pathogens Based on Psoralen-Killed Metabolically Active DNA Repair Mutants," abstract *presented at the American Society for Microbiology (ASM) Biodefense Research Meeting*, Mar. 7-10, 2004, as posted on <http://www.cerus.com/pages/solution/abs158.html>, last visited Jul. 18, 2004, two pages.

Giedlin, M. et al. (Mar. 9, 2004). "The Living Dead: Vaccines Against Microbial Pathogens Based on Psoralen-Killed Metabolically Active DNA Repair Mutants," Poster, *presented at American Society for Microbiology Biodefense Research Meeting* (Mar. 7-10, 2004) Baltimore, MD, one page.

Giedlin, M.A. (Date Unknown). "Listeria-Based Ovarian Cancer Polyepitope Vaccines," Abstract for Grant No. IR43CA109868-01A1 located at <http://crisp.cit.nih.gov/crisp/CRISP_LIB.getdoc?testkey=6932934&p_grant_num=IR43C...>, last visited Dec. 7, 2005, two pages.

Giedlin, M A. (Date Unknown). "Use of Listeria as Colon Cancer Vaccine Adjuvants," Abstract for Grant No. 1443CA101378-01 located at <http://crisp.cit.nih.gov/crisp/CRISP_LIB.getdoc?testkey=6645212&p_grant_num=1r43CA...>, last visited Nov. 3, 2004, two pages.

Giedlin, M.A. et al. (Mar. 2003). "Therapeutic Immunization with Attenuated Recombinant *Listeria monocytogenes* Prolongs Survival in a Murine Transplant Model of Melanoma," *Proceedings of the American Association for Cancer Research, 94th Annual Meeting*, Apr. 5-9, 2003, Toronto, Ontario, Canada, 44:194, Abstract No. 850, one page.

Giedlin, M.A. et al. (Jul. 2003), "Therapeutic Immunization with Attenuated Recombinant *Listeria monocytogenes* Prolongs Survival in a Murine Transplant Model of Melanoma," (Abstract for the 94th Annual Meeting of the American Association for Cancer Research, Washington, DC, USA, Jul. 11-14, 2003) *Proceedings of the American Association For Cancer Research Annual Meeting*, 44(2):167-168, Abstract No. 850.

Glaser, P. et al. (Oct. 26, 2001). "Comparative Genomics of *Listeria* Species," *Science* 294:849-852.

Glomski, I.J. et al. (Mar. 18, 2002), "The *Listeria monocytogenes* Hemolysin Has an Acidic pH Optimum to Compartmentalized Activity and Prevent Damage to Infected Host Cells," *Journal of Cell Biology* 156(6):1209-1038.

Glomski, I.J. et al. (Dec. 2003), "*Listeria monocytogenes* Mutants That Fail to Compartmentalized Listerolysin O Activity Are Cytotoxic, Avirulent, and Unable To Evade Host Extracellular Defenses," *Infect. Immun.* 71(12):6754-6765.

Gouin, E. et al. (Aug. 1994). "The Virulence Gene Cluster of *Listeria monocytogenes* Is Also Present in *Listeria ivanovii*, an Animal Pathogen, and *Listeria seeligeri*, a Nonpathogenic Species," *Infection and Immunity* 62(8):3550-3553.

Green, B.D. et al. (Aug. 1985). "Demonstration of a Capsule Plasmid in *Bacillus anthracis*," *Infection and Immunity* 49(2):291-297.

Gregory, S.H. et al. (Oct. 1996). "Expression of the *inlAB* Operon by *Listeria monocytogenes* Is Not Required for Entry into Hepatic Cells In Vivo," *Infection and Immunity* 64(10):3983-3986.

Gregory, S.H. et al. (Dec. 1997). "Intermalin B Promotes the Replication of *Listeria monoctyogenes* in Mouse Hepatocytes," *Infection and Immunity* 65(12):5137-5141.

Greiffenberg, L. et al. (Dec. 1, 1997). "*Lysteria monocytogenes*-infected Human Umbilical Vein Endothelial Cells: Internalin-Independent Invasion, Intracellular Growth, Movement, and Host Cell Reponses," *FEMS Microbiology Letters* 157:163-170.

Greiffenberg, L. et al. (Nov. 1998). "Interaction of *Listeria monocytogenes* with Human Brain Microvascular Endothelial Cells: In 1 B-Dependent Invasion, Long-Term Intacellular Growth, and Spread fromo Macrophages to Endothelial Cells," *Infection and Immunity* 66(11):5260-5267.

Griffiths, A.J.F. et al. (1999). *Modern Genetic Analysis Integrating Genes and Genomes*, Second Edition, W.H. Freeman and Company, New York, NY, p. 315.

Guerry, P. et al. (Feb. 1994). "Development and Characterization of *recA* Mutants of *Campylobacter jejuni* for Inclusion in Attenuated Vaccines," *Infection and Immunity* 62(2):426-432.

Guidi-Rontani, C. et al. (Jul. 1999). "Identification and Characterization of a Germination Operon on the Virulence Plasmid pXOI of *Bacillus anthracis*," *Mol. Microbiol.* 33(2):407-414.

Gunn, G.R. et al. (2001). "The *Listeria monocytogenes* Vaccine Vectors That Express Different Molecular Forms of Human Papilloma Virus-16 (HPV-16) E7 Induce Qualitatively Different T Cell Immunity That Correlates with Their Ability to Induce Regression of Established Tumors Immortalized by HPV-16," *The Journal of Immunology* 167:6471-6479.

Gunn, G.R. et al. (2002). "Recombinant Intra-Cellular Bacteria as Carriers for Tumor Antigens" Chapter 14 In *Vaccine Delivery Strategies*, Dietrich, G. et al. eds., Horizon Scientific Press: UK, pp. 315-348.

Guzman, C.A. et al. (Jun. 1998). "Attenuated *Listeria monocytogenes* Carrier Strains Can Deliver an HIV-1 gp120 T Helper Epitope to MHC Class II-Restricted Human CD4+ T Cells," *European Journal of Immunology* 28(6):1807-1814.

Haddad, E.E. et al. (Oct.-Dec. 1994). "Adaptation of the MTT (3-(4,5-Dirnethylthiazol-2-yl)-2,5-Diphenyl Tetrazolium Bromide) Assay for the Determination of Virus-Neutralizing Antibodies Using the Virus-Neutralization Assay," *Avain Dis.* 38(4):755-761.

Hall, J.D. et al. (Mar. 1975). "Temperature-Sensitive *recA* Mutant of *Escherichia coil* K-12: Deoxyribonucleic Acid Metabolism After Ultraviolet Irradiation," *J. Bacteriol.* 121(3):892-900.

Hammarstrom, S. (1999). "The Carcinoembroyonic Antigen (CEA) Family: Structures, Suggested Functions and Expression in Normal and Malignant Tissues," *Seminars in Cancer Biology* 9:67-81.

Hanna, M.N. et al. (Oct. 2001). "*uvrA* Is an Acid-Inducible Gene Involved in the Adaptive Response to Low pH in *Streptococcus mutans*," *J. Bacteriol.* 183(20):5964-5973.

Hansen, M.T. (1982). "Sensitivity of *Escherichia coli acrA* Mutants to Psoralen Plus Near-Ultraviolet Radiation," *Mutation Research* 106:209-216.

Harm, W. (1979). "Relative Effectiveness of the 300-320 NM Specrtal Region of Sunlight For The Production of Primary Lethal Damage in *E. coli* Cells," *Mutation Research* 60:263-270.

Hartley, H.A. et al. (Jun. 2003), "Biosensor for the Specific Detection of a Single Viable *B. anthracis* Spore," *Analy. Bioanal. Chem.* 376(3):319-327.

Hartman, P.E. et al. (1996). "Breakthrough of Ultraviolet Light From Various Brands of Fluorescent Lamps; Lethal Effects on DNA Repair-Defective Bacteria," *Environmental and Molecular Mutagenesis* 27:306-313.

Hecker, M. et al, (Feb. 1996). "Heat-Shock and General Stress Response; in *Bacillus subtilis*," *Mol. Microbiol.* 19(3):417-428.

Hei, D.J. et al. (Mar. 1999). "Elimination of Cytokine Production in Stored Platelet Concentrate Aliquots by Photochemical Treatment with Psoralen Plus Ultraviolet A Light," *Transfusion* 39:239-248.

Henderson, R.A. et al. (Jul. 15, 1997). "Activation of Human Dendritic Cells Following Infection with *Mycobactertium tuberculosis*," *The Journal of Immunology* 159(2):635-643.

Hering, D. et al. (Mar. 2004). "Validation of the Anthrax Lethal Toxin Neutralization Assay," *Biologicals* 32(1):17-27.

Hess, J. et al. (May 1995). "*Listeria monocytogenes* p60 Supports Host Cell Invasion by and In Vivo Survival of Attenuated *Salmonella ryphimurium*," *Infection and Immunity* 63(5):2047-2053.

Higgins, D.E. et al. (1999). "Delivery of Protein to the Cytosol of Macrophages using *Escherichia coli* K-12," *Molecular Microbiology* 31(6):1631-1641.

Hilbert, D.W. et al. (Mar. 2003). "Novel *spoIIE* Mutation That Causes Uncompartimentalized $\sigma^F$ Activiation in *Bacillus subtilis*," *J. Bacteriol.* 185(5):1590-1598.

Horton, R,M. et al. (1990). "Gene Splicing by Overlap Extension: Tailer-Made Genes Using the Polymerase Chain Reaction," *Biotechniques* 8(5):528-535.

Houghton, M. et al. (1991). "Molecular Biology of the Hepatitis C Viruses: Implications For Diagnosis, Development and Control of Viral Disease," *Hepathology* 14(2):381-388.

Huang, A.T.C. et al. (May 13, 1994). "Role of Bone Marrow-Derived Cells in Presenting MHC Class I-Restricted Tumor Antigens," *Science* 264:961-965.

Huang, E.H. et al. (Jun. 2002). "CEA-Based Vaccines," *Exper. Rev. Vaccines* 1(1):49-63.

Humrich, J. et al. (2003). "Viral Vectors for Dendritic Cell-Based Immunotherapy," Chapter 11 *In Dendritic Cells and Virus Infection*, Steinkasserer, A. ed., Springer-Verlag: Berlin, Germany, 276:241-259.

Husain, I. et al. (Apr. 15, 1986). "Sequences of *Escherichia coli uvrA* Gene and Protein Reveal Two Potential ATP Binding Sites," *The Journal of Biological Chemistry* 261(11):4895-4901.

Ikonomidis, G. et al. (1994), "Delivery of a Viral Antigen to the Class I Pathway by *Listeria monoctyogenes*: A Potential Vaccine Vector," *Abstracts of the 94th General Meeting of the American Society for Microbiology*, May 23-27, 1994, Las Vegas Convention Center, Las Vegas, NV, p. 159, Abstract No. E-90.

Ikonomidis, G. et al. (Dec. 1994), "Delivery of a Viral Antigen to the Class I Processing and Presentation Pathway by *Listeria monocytogenes*," *J. Exp. Med.* 180:2209-2218.

International Search Report issued for PCT Application No. PCT/US2004/003429 filed Feb. 6, 2004, mailed Dec. 7, 2004, 11 pages.

International Search Report issued for PCT Application No. PCT/US2004/003671 filed Feb. 6, 2004, mailed Apr. 13, 2005, 12 pages.

International Search Report issued for PCT Application No. PCT/US2004/023881 filed on Jul. 23, 2004, mailed Apr. 7, 2005, 11 pages.

International Search Report issued for PCT Application No. PCT/US2005/002987 filed Feb. 2, 2005, mailed Jan. 19, 2006, 11 pages.

Invitation To Pay Additional Fees mailed Jan. 5, 2005, for PCT Application No. PCT/US2004/023881 filed Jul. 23, 2004, seven pages.

Invitation To Pay Additional Fees mailed Jan. 18, 2005, for PCT Application No. PCT/US2004/003671 filed Feb. 6, 2004, seven pages.

Ireton, K. et al. (Jun. 11, 1999), "The *Listeria monoctyogenes* Protein In1B Is an Agonist of Mammalian Phosphoinositide 3-Kinase," *The Journal of Biological Chemistry* 2472(24):17025-17032.

Ivánovics, G. (1962). "The Pathogenicity of *Bacillus anthracis* Lysogenic with Mutants of Phage W," *J. Gen. Microbiol.* 28:87-101.

Johansson, J. et al. (Jun. 2003). "RNA-Mediated Control of Virulence Gene Expression in Bacterial Pathogens," *Trends Microbiol.* 11(6):280-285.

Jonston, J.L. et al. (Mar. 1997). "The *RecA* Gene from *Clostridium perfringens* is Induced by Methyl Methanesulphonate and Cortains an Upstream Cheo Box," *Microbiology* 143(3):885-890.

Jones, S. et al. (Dec. 1994). "Characterization of *Listeria monocytogenes* Pathogeneisis in a Strain Expressing Perfrigolysin O in Place of Listeriolysin O," *Infection and Immunity* 62(12):5608-5613.

Jung, S. et al. (Aug. 2002), "In Vivo Depletion of CD11c+ Dendritic Cells Abrogates Priming of CD8+ T Cells by Exogenous Cell-Associated Antigens," *Immunity* 17:211-220.

Kaan, T. et al. (Nov. 2002). "Genome-Wide Transcriptional Profiling of the *Bacillus subtilis* Cold-Shock Response," *Microbiol.* 148(11):3441-3455.

Karginov, V.A. et al. (Jan. 15, 2004). "Treatment of Anthrax Infection with Combination of Ciprofloxacin and Antibodies to Protective Antigen of *Bacillus anthracis*," *FEMS Immunol. Med. Microbiol.* 40(1):71-74.

Kawai, Y. et al. (Feb. 2003), "Identification of a Protein, YneA, Responsible for Cell Division Suppression During the SOS Response in *Bacillus subtilis*," *Mol. Microbiol.* 47(4):1113-1122.

Kawakami, Y. et al. (Jul. 1994). "Identification of a Human Melanoma Antigen Recognized by Tumor-Infiltrating Lymphocytes Associated with in vivo Tumor Rejection," *Proc. Natl. Acad. Sci. USA* 91:6458-6462.

Kawashima, H. et al. (1984). "Functional Domains of *Escherichia coli* recA Protein Deduced From the Mutational Sites in the Gene," *Mol. Gen. Genet.* 193:288-292.

Keogh, E. et al. (2001). "Identification of New Epitopes From Four Different Tumor-Associated Antigenes: Recognition of Naturally Processed Epitopes Correlates with HLA-A*0201-Binding Affinity," *The Journal of Immunology* 167:787-796.

Kiessling, A. et al. (Dec. 1, 2002). "Prostate Stem Cell Antigen: Identification of Immunogenic Peptides and Assessment of Reactive CD8+T Cells in Prostate Cancer Patients," *Int. J. Cancer* 102(4):390-397.

Kim, J.J. et al. (Apr. 2001). "Construction and Analysis of Photolyase Mutants of *Pseudomonas aeruginosa* and *Pseudomonas syringae*: Contribution of Photoreactivation, Nucleotide Excision Repair, and Mutagenic DNA Repair to Cell Survival and Mutability Following Exposure to UV-B Radiation," *Applied and Environmental Microbiology* 67(4):1405-1411.

King, D. et al. (Jul. 2003), "Performance Assessment of Three Commercial Assays for Direct Detection of *Bacillus anthracis* Spores," *J. Clin. Microbiol.* 41(7):3454-3455.

Ko, M. et al. (Jul. 2002), "Group I Self-Splicing Intron in the *recA* Gene of *Bacillus anthracis*," *Journal of Bacteriology* 184(14):3917-3922.

Kocks, C. et al. (Feb. 7, 1992). "*L. monocytogenes*-Induced Actin Assembly Requires the *ActA* Gene Product, a Surface Protein," *Cell* 68:521-531.

Kolb-Maurer, A. et al. (Jun. 2000). "*Listeria monocytogene*-Infected Human Dendritic Cells: Uptake and Host Cell Response," *Infection and Immunity* 68(6):3680-3688.

Kuzminov, A. (Dec. 1999), "Recombinational Repair of DNA Damage in *Escherichia coil* and Bacteriophage λ," *Microbiol. Mol. Rev.* 63(4):751-813.

Lage, C. et al. (Nov. 2003), "New Insights on How Nucleotide Excision Repair Could Remove DNA Adducts Induced by chemotherapeutic Agents and Psoralens Plus UV-A (PUVA) in *Escherichia coli* Cells," *Mutation Research* 544:143-157.

Lampson, L.A. et al. (Jan. 1, 1993). "Exploiting the *lacZ* Reporter Gene far Quantitative Analysis of Disseminated Tumor Growth within the Brain: Use of the *lacZ* Gene Product as a Tumor Antigen, for Evaluation of Antigenic Modulation, and to Facilitate Image Analysis of Tumor Growth in Situ," *Cancer Research* 53(1):176-182.

Lauer, P. et al. (Aug. 2002), "Construction, Characterization, and Use of Two *Listeria monoctyogenes* Site-Specific Phage Integration Vectors," *Journal of Bacteriology* 184(15):4177-4186.

Lauvau, G. et al. (Nov. 2001). "Priming of Memory But Not Effector CD8 T Cells by a Killed Bacterial Vaccine," *Science* 294:1735-1739.

Lebrun, M. et al. (Aug. 1996). "Internalin Must be on the Bacterial Surface to Mediate Entry of *Listeria monocytogenes* into Epithelial Cells," *Molecular Microbiology* 21(3):579-592.

Lecuit, M. (Dec. 1997). "Internalin of *Listeria monocytogene* with an Intact Leucine-Rich Repeat Region Is Sufficient To Promote Internalization," *Infection and Immunity* 65(12):5309-5319.

Lecuit, M. et al. (Jun. 1, 2001). "A Transgenic Model for Listeriosis: Role in Internalin in Crossing the Intestinal Barrier," *Science* 292:1722-1725.

Lenz, L.L, et al. (Oct. 14, 2003). "SecA2-Dependent Secretion of Autolytic Enzymes Promotes *Listeria monocytogenes* Pathogenesis," *Proc. Natl. Acad. Sci. USA* 100(21):12432-12437.

Leong, M. et al. (Feb. 3, 2004). "Recombinant Attenuated *Listeria monocytogenes* Elicit Functional Immune Response Specific to a Heterologous Antigen in the Presence of Listena-Specific Cellular and Humoral Immunity," *Gordon Research Conference on Immunochemistry & Immunobiology Conference* (Feb. 1-6, 2004), Buellton, CA 20 pages.

Liau, L.M. et al. (Apr. 15, 2002). "Tumor Immunity Within the Central Nervous System Stimulated by Recombinant *Listeria monocytogenes* Vaccination," *Cancer Research* 62:2287-2293.

Lillard, J.W. et al. (2001), "RANTES Potentiates Antigen-Specific Mucosal Immune Response," *The Journal of Immunology* 166:162-169.

Lim, S.H. et al. (Mar. 1, 2001). "Sperm Protein 17 is a Novel Cancer-Testis Antigen in Multiple Myeloma," *Blood* 97(5):1508-1510.

Lin, J-J. et al. (Dec. 5, 1990), "Reconstitution of Nucleotide Excision Nuclease with UvrA and Uvrb Proteins from *Escherichia coli* and UvrC Protein from *Bacillus subtilis*," *J. Biol. Chem.* 265(34):21337-21341.

Lin, L. et al. (May 1, 1994), "Photochemical Inactivation of Pathogenic Bacteria in Human Platelet Concentrates," *Blood* 83(9):2698-2706.

Lin, L. (Jan./Feb. 1998). "Psoralen Photochemical Treatment of Platelets," *Science and Medicine* pp. 54-63.

Lin, L., et al. (Apr. 1997), "Photochemical Inactivation of Viruses and Bacteria in Platelet Concentrates by Use of a Novel Psoralen and Long-Wavelength Ultraviolet Light," *Transfusion* 37(4):423-435.

Lingnau, A. et al. (Oct. 1995). "Expression of the *Listeria monocytogenes* EGD *inlA* and *inlB* Genes, Whose Products Mediate Bacterial Entry into Tissue culture Cell Lines, by PrfA-Dependent and -Independent Mechanisms," *Infection and Immunity* 63(10):3896-3903.

Lipman, D.J. (Sep. 15, 1997), "Making (Anti)Sense of Non-Coding Sequence Conservation," *Nueleic Acids Res.* 25(18):3580-3583.

Little, S.F. et al. (Dec. 1997). "Passive Protection by Polyclonal Antibodies Against *Bacillus anthracis* Infection in Guinea Pigs," *Infection and Immunity* 65(12):5171-5175.

Little, S.F. et al. (2004). "Defining a Serological Correlate of Protection in Rabbits for a Recombinant Anthrax Vaccine," *Vaccine* 22:422-430.

Liu, J. et al. (Dec. 1, 2003), "Computational Identification of the Spo0A-Phosphate Reguion That is Essential for the Cellular Differentiation and Development in Gram-Positive Spore-Forming Bacteria " *Nucleic Acids Res.* 31(23):6891-6903.

Lovett, C.M. Jr. et al. (Nov. 1993). "Purification of an SOS Repressor from *Bacillus subtilis*," *J. Bacteriol.* 175(21):6842-6849.

Lovett, C.M. Jr. et al. (Aug. 1994). "Analysis of the SOS Inducing Signal in *Bacillus subtilis* using *Escherichia coli* LexA as a Probe," *J. Bacteriol.* 176(16):4914-4923.

Lu, W. et al. (Jan. 2003). "Therapeutic Dendritic-Cell Vaccine for Simian AIDS," *Nature Medicine* 9(1):27-32.

Lutz, M.B. et al. (1999). "An Advanced Culture Method for Generating Large Quantities of Highly Pure Dendritic Cells From Mouse Bone Marrow," *J. Immunol. Methods* 223(1):77-92.

Mandl, S. et al. (Jul. 1998). "Poliovirus Vaccine Vectors Elicit Antigen-Specific Cytotoxic T Cells and Protect Mice Against Lethal Challenge with Malignant Melanoma Cells Expressing a Model Antigen," *Proc. Natl. Acad Sci. USA* 95:8216-8221.

Mansell, A. et al. (Nov. 23, 2001), "Internalin B Activates Nuclear Factor-κB Ras, Phosphoinositide 3-Kinase, and Akt," *The Journal of Biological Chemistry* 276(47):43597-43603.

Mao, J-R. et al. (Aug. 25, 1995), "Gene Regulation by Antisense DNA Produced in Vivo," *J. Biol. Chem.* 270(34):19684-19687.

Marquis, H. et al. (Jun. 16, 1997). "Protcolytic Pathways of Activation and Degradation of a Bacterial Phospholipase C During Intracellular Infection by *Lisieria monocytogenes*," *J. Cell Biol.* 137(6):1381-1392.

Maru, G.B. et al. (1937). "Formation and Persistence of Isoniazid-DNA Adducts in Mouse Tissues," *BIOSIS Database, Biosciences Information Service Database Accession No. PREV198783117667*, Abstract, one page.

Maru, G.B. et al. (1987). "Formation and Persistence of Isoniazid-DNA Adducts in Mouse Tissues," *Human Toxicology* 6(2):153-158.

Mata, M. et al. (Jan. 8, 2001). "Evaluation of a Recombinant *Listeria monocytogenes* Expressing an HIV Protein that Protects Mice Against Viral Challenge," *Vaccine* 19(11-12):1435-1445.

Mayordomo, J.I. et al. (Dec. 1995), "Bone Marrow-Derived Dendritic Cells Pulsed With Synthetic Tumour Peptides Elicit Protective and Therapeutic Antitumor Immunity," *Nat. Med.* 1(12):1297-1302.

McCloy, E.W. (1951). "Studies on a Lysogenic *Bacillus* Strain. I. A Bacteriophage Specific for *Bacillus anthracis*," *J. Hyg.* 49:114-125.

McGeoch, DJ. et al. (1988), "The Complete DNA Sequence of the Long Unique Region in the Genome of Herpes Simplex Virus Type I," *J. Gen. Virol.* 69:1531-1574.

McGuire, A.M. et al. (May 2000), "Conservation of DNA Regulatory Motifs and Discovery of New Motifs in Microbial Genomes," *Genome Res.* 10(5):744-757.

Meletiadis, J. et al. (Aug. 2000). "Comparison of NCCLS and 3-(4,5-Dimethyl-2-Thiazyl)-2,5-Diphenyl-2H-Tetrazolium Bromide (MTT) Methods of In Vitro Susceptibility Testing of Filamentous Fungi and Development of a New Simiplified Method," *J. Clin. Microbiol.* 38(8):2949-2954.

Mengaud, J. et al. (Mar. 22, 1996). "E-Cadherin Is the Retvplor for Internalin, a Surface Protein Required for Entry, of *L. monocytogenes* into Epithelial Cells," *Cell* 84:923-932.

Merino, LD et al. (2002), "A Hypermutator Phenotype Attenuates the Virulence of *Listeria monocytogenes* in a Mouse Model," *Molecular Microbiology* 44(3):877-887.

Mesnage, S. et al. (Jan. 1998), "The Capsule and S-Layer: Two Independent and Yet Compatible Macromolecular Structures in *Bacillus anthracis*," *J. Bacteriol.* 180(1):52-58.

Mikesell, P. et al. (Jan. 1983). "Evidence for Plasmid-Mediated Toxin Production in *Bacillus anthracis*," *Infection and Immunity* 39(1):371-376.

Miller, M.C. et al. (Dec. 27, 1996). "The *Bacillus subtilis dinR* Gene Codes for the Analogue of *Escherichia coli* LexA," *J. Biol. Chem.* 271(52):33502-33508.

Mitsuyama, P. et al. (May 1990). "Difference in the Induction of Macrophage Interleukin-I Production Between Viable and Killed Cells of *Listeria monobytogenes*," *Infection and Immunity* 58(5):1254-12610.

Mock, M. et al. (2001). "Anthrax," *Ann. Rev. Microbiol.* 55:647-671.

Molldrem, J. et al. (Oct. 1, 1996). "Targeted T-cell Therapy for Human Leukemia: Cytotoxic T Lymphocytes Specific for a Peptide Derived from Proteinase 3 Preferentially Lyse Human Myeloid Leukemia Cells," *Blood* 88(7):2450-2457.

Molldrem, J.J. et al. (Oct. 1, 1997), "Cytotoxic T Lymphocytes Specific for a Nonpolymorphic Proteinase 3 Peptide Preferentially Inhibit Chronic Myeloid Leukemia Colony-Forming Units," *Blood* 90(7):2529-2534.

Molldrem, J.J. et al. (Jun. 1, 1999). "A PR1-Human Leukocyte Antigen-A2 Tetramer Can Be Used to Isolate Low-Frequency Cytotoxic T Lymphocytes From Healthy Donors That Selectively Lyse Chronic Myelogenous Leukemia," *Cancer Research* 59;2675-2681.

Molldrem, J.J. et al. (Sep. 2000). "Evidence That Specific T Lymphocytes May Participate in the Elimination of Chronic Myelogenous Leukemia," *Nature Medicine* 6(8):1018-1023.

Molldrem, et al. (Dec. 2002), "The Basis of T-Cell-Mediated Immunity to Chronic Myelogenous Leukemia," *Oncogene* 21:8668-8673.

Mollet, B. et al. (Jul. 1993). "Directed Genomic Integration, Gene Replacement, and Integrative Gene Expression in *Streptococcus thermophilus*," *J. Bacteriology* 175(14):4315-4324.

Mongkolsuk, S. et al. (Jul. 2002). "Regulation of Inducible Peroxide Stress Responses," *Mol. Microbiol.* 45(I):9-15.

Moody, G. et al. (Mar. 2004). "Recombinant *Listeria monocytogenes*-Based Immunotherapy Targeting the Receptor Tyrosine Kinase EphA2," abstract *presented at the American Association far Cancer Research (AACR)*, Mar. 27-31, 2004, as posted on <http://www.cerus.com/pages/solution/abs155.html>, last visited on Aug. 26, 2004, two pages.

Moors, M.A. et al. (Jan. 1999). "Expression of Listeriolysin O and ActA by Intracellular and Extracellular *Listeria monocytogenes*," *Infection and Immunity* 67(1):131-139.

Morgan, D.J. et al. (1998). "Activation of Low Avidity CTL Specific for a Self Epitope Results in Tumor Rejection But Not Autoimmunity," *J. Immunol.* 160:643-651.

Morse, M.A. et al. (Jun. 1999). "A Phase I Study of Active Immunotherapy with Carcinoembryonic Antigen Peptide (CAP-1)-pulsed, Autologous Human Cultured Dendritic Cells in Patients with Metastatic Malignancies Expressing Carcinoembryonic Antigen," *Clin. Cancer Res.* 5:1331-1338.

Mota, L.J. et al. (Jul. 2001). "Control of the Arabinose Regulon in *Bacillus subtilis* by AraR In Vivo: Crucial Role of Operators, Cooperativity, and DNA Looping," *J. Bacteriol.* 183(14):4190-4201.

Mourez, M. et al. (Oct. 2001). "Designing a Polyvalent Inhibitors of Anthrax Toxin," *Nature Biotech.* 19(10):958-961.

Movabedzadeh, F. et al. (Mar. 1997). "Characterization of *Mycobacterium tuberculosis* LexA: Recognition of a Cheo (*Bacillas*-type SOS) Box," *Microbiology* 143(3):929-936.

Mu, D. et al. (1997). "DNA Excision Repair Assays" *In Progress in Nucleic Acid Research and Molecular Biology*, Cohn, W.E. et al. eds., Academic Press, Inc.: San Diego, CA, 56:63-81.

Muller-Berat, N. et al. (Jan. 1994). "The Phylogeny of Proteinase 3/Mycloblastin, The Autoantigen in Wegener's Granulomatosis, and Myeloperoxidase as Shown by Immunohistochemical Studies on Human Leukemic Cell Lines," *Clin. Immunol. Immunopath.* 70(1):51-59.

Munakata, N. et al. (Nov. 1991), "Inactivation Action Spectra of *Bacillus subtilis* Spores in Extended Ultraviolet Wavelengths (50-300 nm) Obtained with Synchrotron Radiation," *Photochem. Photobiol.* 54(5):761-768.

Nickel, M. et al. (Aug. 2004). "Cold Induction of the *Bacillus subtilis bkd* Operon is Mediated by Increased mRNA Stability," *Mol. Genet Genomics* 272(1):98-107.

Nicolaou, K.C, et al. (Jul. 1993), "Chemistry and Biology of Natural and Designed Enediynes," *Proc. Natl Acad. Sci USA* 90:5881-5888.

Nishiyama, T. et al. (Jan. 2001). "Immunotherapy of Bladder Cancer Using Autologous Dendritic Cells Pulsed with Human Lymphocyte Antigen-A24-Specific MAGE-3 Peptide," *Clinical Cancer Research* 7:23-31.

Noone, D. et al. (Mar. 2000). "Expression of *ykdA*, Encoding a *Bacillus subtilis* Homologue of HtrA, Is Heat Shock Inducible and Negatively Autoregulated," *J. Bacteriol.* 182(6):1592-1599.

Office Action mailed Aug. 29, 2006, for U.S. Appl. No. 10/883,539, filed Jun. 30, 2004, 7 pages.

Office Action mailed Jan. 26, 2007, for U.S. Appl. No. 10/773,618, filed Feb. 6, 2004, 22 pages.

Office Action mailed Jan. 31, 2007, for U.S. Appl. No. 10/773,792, filed Feb. 6, 2004, 20 pages.

Office Action mailed Mar. 8, 2007, for U.S. Appl. No. 10/883,559, filed Jun. 30, 2004, 6 pages.

O'Riordan, m. et al. (Oct. 17, 2003). "*Listeria* Intrucellular Growth and Virulence Require Host-Derived Lipoic Acid," *Science* 302:462-464.

Pace, J.L. et al. (1998), "Inactivated Whole-Cell Bacterial Vaccines: Current Status and Novel Strategoes." *Vaccine* 16(16):1563-1574.

Paglia, P. et al. (Jun. 1997). "The Defined Attenuated *Listeria monocytogenes* Δmpl2 Mutant is an Effective Oral Vaccine Carrier to Trigger a Long-Lasting Immune Response Against a Mouse Fibrosarcoma," *Eur. J. Immunol.* 27(6):1570-1575.

Palucka, A.K. et al. (Sep./Oct. 2003). "Single Injection of CD34+ Progenitor-Derived Dendritic Cell Vaccine Can Lead to Induction of T-Cell Immunity in Patients With Stage IV Melanoma," *J. Immunother.* 26(5):432-439.

Palucka, K. et al. (Aug. 1999), "Linking Innate and Adaptive Immunity," *Nature Medicine* 5(8):868-870.

Pan, Z-K. et al. (May 1995). "A Recombinant *Listeria monocytogenes* Vaccine Expressing a Model Tumour Antigen Protects Mice Against Lethal Tumour Cell Challenge and Causes Regression of Established Tumours," *Nature Medicine* 1(5):471-477.

Pan, Z-K. et al. (Nov. 1, 1995). "Regression of Established Tumors in Mice Mediated by the Oral Administration of a Recombinant *Listeria monocytogenes* Vaccine," *Cancer Research* 55:4776-4779.

Pan, Z-K. et al. (Oct. 15, 1999). "Regression of Established BI6F10 Melanoma with a Recombinant *Listeria monocytogenes* Vaccine," *Cancer Research* 59:5264-5269.

Panda, S.K. et al. (Apr. 1998). "Internalin B is Essential for Adhesion and Mediates the Invasion of *Listeria monocytogenes* into Human Endothelial Cells," *Molecular Microbiology* 28(1):81-93.

Peters, C. et al. (Jan. 2003). "Tailoring Host Immune Responses to *Listeria* by Manipulation of Virulence Genes—The Interface Between Innate and Acquired Immunity," *FEMS immunology and Medical Microbiology* 35:243-253.

Pombo, M. et al. (Sep. 2004), "Validation of an Anti-PA-ELISA for the Potency Testing of Anthrax Vaccine in Mice," *Biologicals* 32(3):157-163.

Portnoy, D.A. et al. (Aug. 5, 2002), "The Cell Biology of *Listeria monocytogenes* Infection: The Intersection of Bacterial Pathogenesis and Cell-Mediated Immunity," *The Journal of Cell Biology* 158(3):409-414.

Price, B.M. et al. (Jul. 2001). "Protection Against Anthrax Lethal Toxin Challenge by Genetic Immunization with a Plasmid Encoding the Lethal Factor Protein," *Infection and Immunity* 69(7):4509-4515.

Raffelsbauer, D. et al. (1988), "The Gene Cluster *inlC2DE* of *Listeria monocytogenes* Contains Additional new Internalin Genes and Is Important for Virulence in Mice," *Mol. Gen. Genet.* 260:144-158.

Ramaswamy, M. et al. (Jan. 7, 1994). "Sequence-Specific Interactions of UvrABC Endonuelease with Psoralen Interstrand Cross-Links," *J. Biol. Chem.* 269(1):485-492.

Read, T.D. et al. (Jun. 14, 2002). "Comparative Genome Sequencing For Discovery of Novel Polymorphisms in *Bacillus anthracis*," *Science* 296:2028-2033.

Reiter, R.E. et al. (Feb. 1998). "Prostate Stem Cell Antigen: A Cell Surface Marker Overexpressed in Prostate Cancer," *Proc. Natl. Acad. Sci. USA* 95:1735-1740.

Renkvist, N. et al. (2001), "A Listing of Human Tumor Antigens Recognised by T Cells," *Cancer Immunol. Immunother.* 50:3-15.

Repoila, F, et al. (Nov. 2003), "Temperature Sensing by the *dsrA* Promoter," *J. Bacteriol.* 185(22):6609-6614.

Rescigno, M. et al. (Mar. 2001). "Dendritic Cells, Loaded with Recombinant Bacteria Expressing Tumor Antigens, Induce a Protective Tumor-Specific Response," *Medline Database, U.S. National Library of Medicine (NLM) Database Accession No. NLM11300484*, Abstract, one page.

Rescigno, M. et al. (Mar. 2001). "Dendritic Cells, Loaded vith Recombinant Bacteria Expressing Tumor Antigens, Induce a Protective Tumor-Specific Response," *Clinical Cancer Research* 7(Suppl. ):865s-870s.

Rhie, G-E. et al. (Sep. 16, 2003). "A Dually Active Anthrax Vaccine That Confers Protection Against Both Bacilli and Toxins," *Proc. Natl. Acad. Sci. USA* 100(19);10925-10930.

Rolph, M.S. et al. (2001), "CD40 Signaling Converts a Minimally Immunogenic Antigen Into a Potent Vaccine Against the Intracellular Pathogen *Listeria monocytogenes*," *The Journal of Immunology* 166:5115-5121.

Sakamoto, T. et al. (Feb. 2002). "Regulation of the Desaturation of Fatty Acids and its Role in Tolerance to Cold and Salt Stress," *Curr. Opin. Microbiol.* 5(1):206-210.

Salazar, E. et al. (2000). "Agonist Peptide From a Cytotoxic T-Lymphocyte Epitope of Human Carcinoembryonic Antigen Stimulates Production of TC1-Type Cytokines and Increases Tyrosine Phosphorylation More Efficiently Than Cognate Peptide," *Int. J. Cancer* 85:829-838.

Sancar, A. (1996). "DNA Excision Repair," *Annu. Rev. Biochem.* 65:43-81.

Sancar, A. et al. (1988), "DNA Repair Enzymes," *Ann. Rev. Biochem.* 57:29-67.

Sander, P. et al. (Jun. 2001). "*Mycobacterium bovis* BCG *recA* Deletion Mutant Shows Increased Susceptibility to DNA-Damaging Agents but Wild-Type Survival in a Mouse Infection Model," *Infection and Immunity* 69(6):3562-3568.

Sanderson, S. et al. (1994). "LacZ Inducible, Antigen/MHC-Specific T Cell Hybrids," *International Immunology* 6(3):369-376.

Santini, S.M. et al. (2003). "Advances in the Use of Dendritic Cells and New Adjuvants for the Development of Therapeutic Vaccines," *Stem Cells* 21(4):495-505.

Sashinami, H. et al. (Jan. 2003), "Effective Induction of Acquired Resistance to *Listeria monocytogenes* by Immunizing Mice With In Vivo-Infected Dendritic Cells," *Infection and Immunity* 71(1):117-125.

Sawyer, R.T. et al. (Nov. 1996), "Intemalin A Can Mediate Phagocytosis of *Listeria monocytogenes* by Mouse Macrophage Cell Lines," *Journal of Leukocyte Biology* 60:603-610.

Schafer, R. et al. (Jul. 1, 1992). "Induction of a Cellular Immune Response to a Foreign Antigen by a Recombinant *Listeria monocytogenes* Vaccine," *The Journal of Immunology* 149:53-59.

Scheirlinck, T. et al. (Sep. 1989). "Integration and Expression of α-Amylase and Endoglucanase Genes in the *Lactobacillu splantarum* Chromosome," *Applied and Environmental Microbiology* 55(9):2130-2137.

Schofield, D.A. et al. (Jun. 2903). "Development of a Thermally Regulated Broad-Spectrum Promoter System for Use in Pathogenic Gram-Positive Species," *Appl. Environ Microbiol.* 69(6):3385-3392.

Schönert, S. et al. (Apr. 1999). "Properties of Maliose-Inducible α-Glucosidase MaiL (Sucrase-Isomaltase-Maltase) in *Bacillus subtilis*: Evidence for its Contribution to Maltodextrin Utilization," *Res. Microbiol.* 150(3):167-177.

Schuler, G. et al. (Apr. 2003). "The Use of Dendritic Cells in Cancer Immunotherapy," *Curr. Opin. Immunol.* 15(2):138-147.

Sellman, B.R. et al. (Mar. 16, 2001). "Point Mutations in Anthrax Protective Antigen That Block Translocation," *J. Biol. Chem.* 276(11):8371-8376.

Sellman, B.R. et al, (Apr. 27, 2001). "Dominant-Negative Mutants of a Toxin Subunit: An Approach to Therapy of Anthrax," *Science* 292(5517):695-697.

Sharma, N. et al. (Jul. 1, 2004). "Potent Role of Vaccines Prepared from Macrophages Infected with Live Bacteria in Protection against *Mycobacterium tuberculosis* and *Salmonella typhimurium* Infections," *Journal of Infectious Diseases* 190(1):107-114.

Sheehan, B. et al. (Nov. 1995). "Differential Activation of Virulence Gene Expression by PrfA, the *Listeria monocytogenes* Virulence Regulator," *Journal of Bacteriology* 177(22):6469-6476.

Shen, H. et al. (Apr. 1995), "Recombinant *Listeria monocytogenes* as a Live Vaccine Vehicle for the Induction of Protective Anti-Viral Cell-Mediated Immunity," *Proc. Natl. Acad. Sci. USA* 92:3987-3991.

Shen, H. et al. (Feb. 20, 1998). "Compartmentalization of Bacterial Antigens: Differential Effects on Priming of CD8 T Cells and Protective Immunity," *Cell* 92:535-545.

Shen, Z. et al. (1997), "Cloned Dendritic Cells Can Present Exogenous Antigens on Both MHC Class I and Class II Molecules," *The Journal of Immunology* 158:2723-2730.

Shimizu, K. et al. (Mar. 15, 2001). "Enhancement of Tumor-Lysate— and Peptide-pulsed Dendritic Cell-based Vaccines by the Addition of Foreign Helper Protein," *Cancer Research* 61:2618-2624.

Simon, R. et al. (Nov. 1983). "A Broad Host Range Mobilization System for In Vivo Genetic Engineering: Transposon Mutagenesis in Gram Negative Bacteria," *Bio/Technology* pp. 784-791.

Sinden, R.R. et al. (Nov. 1978). "Repair of Cross-Linked DNA and Survival of *Escherichia coli* Treated with Psoralen and Light: Effects of Mutations Influencing Genetic Recombination and DNA Metabolism," *Journal of Bacteriology* 136(2):538-547.

Skoble, J. et al. (Aug. 7, 2000). "Three Regions Within ActA Promote Arp2/3 Complex-Mediated Actin Nucleation and *Listeria monocytogenes* Motility," *The Journal of Cell Biology* 150(3):527-538.

Slansky, J.E. et al. (Oct. 2000). "Enhanced Antigen-Specific Antitumor Immunity with Altered Peptide Ligands that Stabilize the MHC-Peptide-TCR Complex," *Immunity* 13:529-538.

Smith, B.T. et al. (Jan. 2002), "Localization of UvrA and Effect of DNA Damage on the Chromosome of *Bacillus subtilis*," *Journal of Bacteriology* 184(2):488-493.

Smith, G.A. et al. (Sep. 1995). "Asymmetric Distribution of the *Listeria monocytogenes* ActA Protein is Required and Sufficient to Direct Actin-Based Motility," *Molecular Microbiology* 17(5):945-951.

Smith, K. et al. (1992), "Use of a New Integrational Vector to Investigate Compartment-Specific Expression of the *Bacillus subtilis spoIfM* Gene," *Biochimie* 74:705-711.

Snyder. J.T. et al. (Jul. 2004). "Protection Against Lethal Vaccinia Virus Challenge in HLA-A2 Transgenic Mice by Immunization with a Single CD8+ T-Cell Peptide Epitope of Vaccinia and Variola Viruses," *The Journal of Virology* 78(13):7052-7060.

Song, F. et al. (1996). "Differential Effects of Viable and Killed Bacteria on IL-12 Expression of Macrophages," *The Journal of Immunology* 156:2979-2984.

Stahl, M.L. et al. (May 1984), "Replacement of the *Bacillus subtilis* Subtilisin Structural Gene with an In Vitro-Derived Deletion Mutation," *J. Bacteriology* 158(2):411-418.

Starks, H. et al, (Jul. 1, 2004), "*Listeria monocytogenes* as a Vaccine Vector: Virulence Attenuation or Existing Antivector Immunity Does Not Diminish Therapeutic Efficacy," *The Journal of Immunology* 173:420-427.

Starnbach, M.N. et al. (Aug. 2003). "Anthrax Delivers a Lethal Blow to Host Immunity," *Nature Medicine* 9(8):996-997.

Strugnell, R.A. et al. (1990). "Stable Expression of Foreign Antigens from the Chromosome of *Salmonella typhimurium* Vaccine Strains," *Gene* 88(1):57-63.

Stülke, J. et al. (Jul. 1997), "Induction of the *Bacillus subtilis ptsGH1* Operon by Glucose is Controlled by a Novel Antiterminator, GlcT," *Mol. Microbiol.* 25(1):65-78.

Suárez, M. et al. (Dec. 2001). "A Role for ActA in Epithelial Cell Invasion by *LIsteria monocytogenes*," *Cellular Microbiology* 3(12):853-864.

Subklewe, M. et al. (Aug. 15, 1999). "Induction of Epstein-Barr Virus-Specific Cytotoxic T-Lymphocyte Responses Using Dendritic Cells Pulsed With EBNA-3A Peptides or UV-Inactivated, Recombinant EBNA-3A Vaccinia Virus," *Blood* 94(4):1372-1381.

Sun, A. et al. (Nov. 1990). "Isolation of *Listeria monocyagenes* Small-Plaque Mutants Defective for Intracellular Growth and Cell-To-Cell Spread," *Infect. Immun.* 58(11):3770-3778.

Svensson, M. (Jun. 1996). "Dendritic Cells Can Process Viable Bacteria and Present Bacterial Antigens on MHC-1 Molecules," *Scandinavian Journal of Immunology* 43(6);723, Abstract No. 121.

Svensson, M. et al. (May 1, 1997), "Bone Marrow-Derived Dendritic Cells Can Process Bacteria for MHC-I and MHC-II Presentation to T Cells," *The Journal of Immunology* 158(9):4229-4236.

Tatsumi, T. et al. (Aug. 1, 2003). "Disease Stage Variation in CD4+ and CD8+ T-Cell Reactivity to the Receptor Tyrosine Kinase EphA2 in Patients with Renal Cell Carcinoma," *Cancer Res.* 63(15):4481-4489.

Tessman, J.W. et al. (1985). "Photochemistry of the Furan-Side 8-Methoxypsorafen-Thymidine Monoadduct Inside the DNA Helix. Conversion to Diadduct and to Pyrone-Side Monoadduct," *Biochemistry* 24:1669-1676.

Thorne, C.B. (Jul. 1968), "Transducing Bacteriophage for *Bacillus cereus*," *J. Virology* 2(7):657-662.

Thorne, C.B. et al. (1957). "An Agar-Diffusion Method for Titrating *Bacillus anthracis* Immunizing Antigen and its Application to a Study of Antigen Production," *J. Gen. Microbiol.* 17:505-516.

Tilney, L.G. et al. (Oct. 1989). "Actin Filaments and the Growth, Movement, and Spread of the Intracellular Bacterial Parasite, *Listeria monocytogenes*," *The Journal of Cell Biology* 109:1597-1608.

Tsang, K.Y. et al. (1995). "Generation of Human Cytotoxic T Cells Specific for Human Carcinoembryonic Antigen Epitopes From Patients Immunized With Recombinant Vaccinia-CEA Vaccine," *J. Natl. Cancer Inst.* 87(13):982-990.

Tsung, K. et al. (Jan. 1996), "Gene Expression and Cytopathic Effect of Vaccinia Virus Inactivated by Psoralen and Long-Wave UV LIght," *Journal of Virology* 70(1):165-171.

Uchida, I. et al. (1997). "Cross-Talk to the Genes for *Bacillus anthracis* Capsule Synthesis by *aixA*, The Gene Encoding the Trans-Activator of Anthrax Toxin Synthesis," *Mol. Microbiol.* 23:1229-1240.

Uchijima, M. et al. (1998). "Optimization of Codon Usage of Plasmid DNA Vaccine Is Required for the Effective MHC Class I-Restricted T Cell Responses Against an Intracellular Bacterium," *The Journal of Immunology* 161:5594-5599.

Van Pinxtaaren, L.A.H. et al. (2000). "Control of Latent *Mycobacterium tuberculosis* Infection is Dependent on CD8 T cells," *Eur. J. Imminol.* 30:3689-3698.

Vazquez-Boland, J.A. et al. (Jul. 2001). "*Listeria* Pathogenesis and Molecular Virulence Determinants," *Chemical Microbiology Reviews* 14(3):584-640.

Vazquez-Boland, J-A. et al. (Jan. 1992). "Nucleotide Sequence of the Lecithinase Operon of *Listeria monocytogenes* and Possible Role of Lecithinase in Cell-to-Cell Spread," *Infection and Immunity* 60(1):219-230.

Wagner, E.G.H. et al. (1994). "Antisense RNA Control in Bacteria, Phages, and Plasmids," *Ann. Rev. Microbiol.* 48:713-742.

Walsh, S.R. et al. (Apr. 2003). "Dendritic Cells and the Promise of Therapeutic Vaccines for Human Immunodeficiency Virus (HIV)-1," *Curr. HIV Res.* 1:205-216.

Wang, B. et al. (Mar. 28, 2003). "Assessment of the Utilization of the Antisense RNA Strategy to Identify Essential Genes in Heterologous Bacteria," *FEMS Microbiol. Lett*, 220(2):171-176.

Weiskirch, L.M. et al., (1997). "*Listeria monocytogenes*: A Potent Vaccine Vector for Neoplastic and Infectious Disease," *Immunological Reviews* 158:159-169.

Welch, M.D. et al. (Jul. 3, 1998). "Interaction of Human Arp2/3 Complex and the *Listeria monocytogenes* ActA Protein in Actin Filament Nucleation," *Science* 281:105-108.

Wemmer, D. (Mar. 1998). "Reading DNA," *Nature Structural Biology* 5(3):169-171.

Winterling, K.W. et al. (Mar. 1997). "Characterization of DinR, the *Bacillus subtilis* SOS Repressor," *J. Bacteriol.* 179(5):1698-1703.

Winterling, K.W. et al. (Apr. 1998), "The *Bacillus subtilis* DinR Binding Site: Redefinition of the Consenses Sequence," *J. Bacteriol.* 180(8):2201-2211.

Wirth, R. et al. (Mar. 1986), "Highly Efficient Protoplast Transformation System for *Streptococcus faecalis* and a New *Escherichia coli-S.faecalis* Shuttle Vector," *Journal of Bacteriology* 165(3):831-836.

Wolfgang, C.D. et al, (Aug. 15, 2000). "TARP: A Nuclear Protein Expressed in Prostate and Breast Cancer Cells Derived from an Alternate Reading Frame of the T Cell Receptor ☐ Chain Locus," *Proc. Natl. Acad. Sci. USA* 97(17):9437-9442.

Wong, K.K.Y. et al. (2004). "Evidence Implicating the 5' Untranslated Region of *Listeria monocytogenes actA* in the Regulation of Bacterial Actin-Based Motility," *Cellular Microbiology* 6(2):155-166.

Worgall, S. et al. (Jul. 2001). "Protection Against Pulmonary Infection with *Pseudomonas aeruginosa* Following Immunization with *P. aeruginosa*-Pulsed Dendritic Cells," *Infection and Immunity* 69(7):4521-4527.

World Health Organization. (1970). *Health Aspects of Chemical and Biological Weapons: A Report of a WHO Group of Consultants* World Health Organization: Geneva, Switzerland, pp. 5-7 (Table of Contents Only.).

Worsham, P.L. et al. (Jan. 1999). "Isolation of an Asporogenic (*spoOA*) Protective Antigen-Producing Strain of *Bacillus anthracis*," *Can. J. Microbiol.* 45(1):1-8.

Written Opinion issued for PCT Application No. PCT/US2004/003429 filed Feb. 6, 2004, mailed Dec. 7, 2004, 9 pages.

Written Opinion issued for PCT Application No. PCT/US2004/003671 filed Feb. 6, 2004, mailed Apr. 13, 2005, 15 pages.

Written Opinion issued for PCT Application No. PCT/US2004/023881 filed Jul. 23, 2004, mailed Apr. 7, 2005, 11 pages.

Written Opinion issued for PCT Application No. PCT/US2005/002987 filed Feb. 2, 2005, mailed Jan. 19, 2006, 9 pages.

Wurtz, N.R. et al. (Feb. 14, 2000), "Sequence Specific Alkylation of DNA by Hairpin Pyrrole-Imidazole Polyamide Conjugates," *Chemistry & Biology* 7:153-161.

Xiong, H. et al. (1998). "Administration of Killed Bacteria Together with Listerioysin O Induces Protective Immunity Against *Listeria momocytogenes* in Mice," *Immunology* 94:14-21.

Yan, M. et al. (Jan./Feb. 2003),"Characterization of Dominant-Negative Forms of Anthrax Protective Antigen," *Molecular Medicine*, pp. 46-51.

Yansura, D.G. et al. (Jan. 1984). "Use of the *Escherichia coli lac* Repressor and Operator to Control Gene Expression in *Bacillus subtilis*," *Proc. Natl. Acad. Sci USA* 81(2):439-443.

Yasbin, R.E. et al. (May 1992), "Inducible DNA Repair and Differentiation in *Baccillus subtilis*: Interactions Between Global Regulation, " *Mol. Microbiol.* 6(10):1263-1270.

Zantek, N.D. et al. (Sep. 1999). "E-Cadherin Regulates the Function of the EphA2 Receptor Tyrosine Kinase," *Cell Growth Differ.* 10:629-638.

Zaremba, S. et al. (Oct. 15, 1997). "Identification of an Enhancer Agonist Cytotoxic T Lymphocyte Peptide From Human Carcinoembryonic Antigen," *Cancer Res*, 57:4570-4577.

Zhang, X. et al. (Nov. 6, 2002), "Advances in Dendritic Cell-Based Vaccine of Cancer," *Cancer Biother. Radiopharm.* 17(6):601-619.

Zhou, B. et al. (Apr. 16, 2002). "Human Antibodies Against Spores of the Genus *Bacillus*: A Model Study for Detection of and Protection Against Anthrax and the Bioterrorist Threat," *Proc. Natl. Acad. Sci. USA* 99(8):5241-5246.

Zhou, Y. et al. (Jul. 2002). "Current Methods for Loading Dendritic Cells With Tumor Antigen for the Induction of Antitumor Immunity," *The Journal of Immunology* 25(4):289-303.

Zhukov-Verezhnikov, N.N. et al. (1981). "Antigens Common to Human Milignant Tumors and Certain Species of Microorganisms," *Bulletin of Exp. Biol. Med.* 92:1234-1237.

Bruhn, K.W. et al. (2007). "*Listeria* as a Vaccine Vector," *Microbes and Infection* 9(10):1226-1235.

Darji, A. et al. (Jun. 1, 2003), "Induction of Immune Responses by Attenuated Isogenic Mutant Strains of *Listeria monocytogenes,*" *Vaccine* 21 :S2/102-S2/109.

Frankel, F.R. (Aug. 2005), "Vaccine Wakes from the Dead," *Nature Medicine* 11(8):833-834.

Jensen, E.R. et al. (1997). "Recombinant *Listeria monocytogenes* as a Live Vaccine Vehicle and a Probe for Studying Cell-Medated Immunity," *Immunological Reviews* 158:147-157.

Jiang, A. et al. (Oct. 2007). "Disruption of E-Cadherin-Mediated Adhesion Induces a Functionally Distinct Pathway of Dendritic Cell Maturation," *Immunity* 27:610-624.

Lankowski, A.J. (Apr. 15, 2007, e-pub. Mar. 5, 2007). "Killed but Metabolically Active *Salmonell typhimurium*: Application of a New Technology to an Old Vector," *The Journal of Infectious Diseases* 195:1203-1211.

Liu, D. (Nov. 2006), "*Listeria*-Based Anti-Infective Vaccine Strategies," *Recent Patents on Anti-Infective Drug Discovery* 1(3):281-290.

Riedl, E. et al. (Dec. 15, 2000). "Ligation of E-Cadherin on In Vitro-Generated Immature Langerhans-Type Dendritic Cells Inhibits their Maturation," *Blood* 96(13):4276-4284.

Shen, A. et al. (2005). "The 5' Untranslated Region-Mediated Enhancement of Intracellular Listeriolysin O Production is Required for *Listeria monocytogenes* Pathogenicity," *Molecular Microbiology* 57(5):1460-1473.

Shen, Y. (Oct. 27, 2000). "InlB-Dependent Internalization of *Listeria* Is Mediated by the Met Receptor Tyrosine Kinase," *Cell* 103:501-510.

Smith, G.A. et al, (Nov. 1995). "The Two Distinct Phospholipases C of *Listeria monocytogenes* Have Overlapping Roles in Escape from a Vacuole and Cell-to-Cell Spread," *Infection and Immunity* 63(11):4231-4237.

Truitt, R.L. et al. (1999). "Photochemical Treatment with S-59 Psoralen and Ultraviolet A Light to Control the Fate of Naive or Primed T Lymphocytes In Vivo After Allogeneic Bone Marrow Transplantation," *The Journal of Immunology* 163:5145-5156.

Van Den Broek, M. (Oct. 2007). "Dendritic Cells Break Bones to Tolerize," *Immunity* 27:544-546.

Zenewicz, L.A. et al. (2002). "Nonsecreted Bacterial Proteins Induce Recall CD8 T Cell Responses But Do Not Serve as Protective Antigens," *The Journal of Immunology* 169:5805-5812.

Prosecution History for U.S. Appl. No. 10/773,618: All office actions and responses.

Prosecution History for U.S. Appl. No. 10/773,792: All office actions and responses.

Prosecution History for U.S. Appl. No. 10/883,599: All office actions and responses.

\* cited by examiner

Strain

ΔuvrAB wild type 0   2   4   8   18

Hours post S-59 UVA inactivation

Figure 22

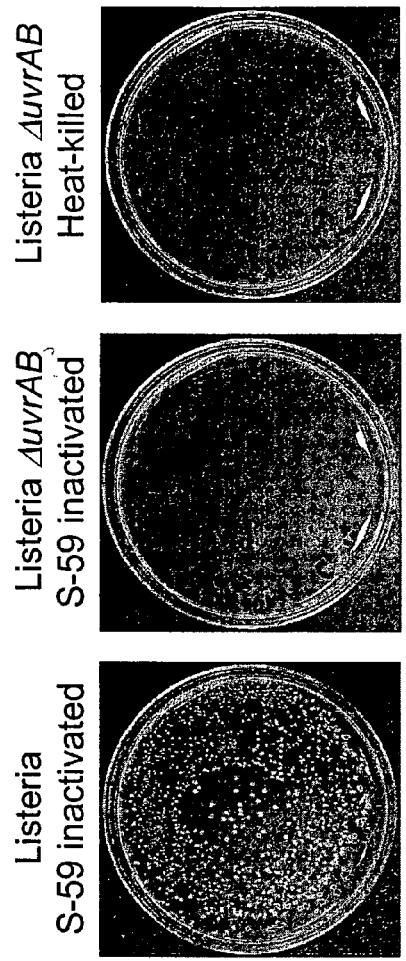
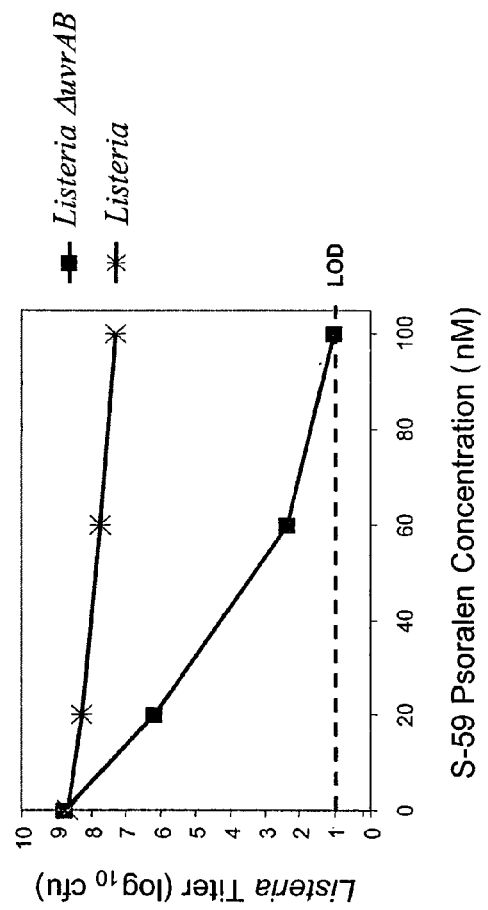
Figure 25

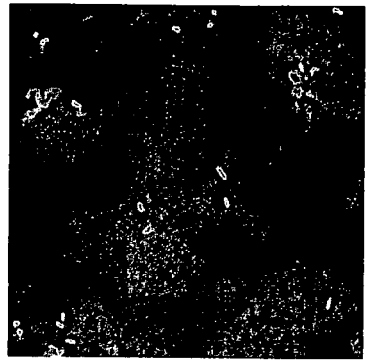
C. Listeria Δhly (LLO-)
B. Wild type
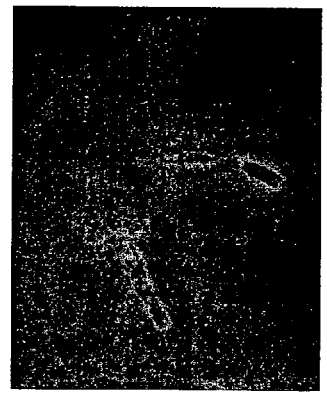
E. Listeria ΔuvrAB
S-59 UVA inactivated
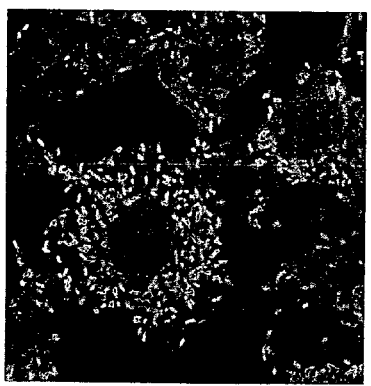
A. Wild type
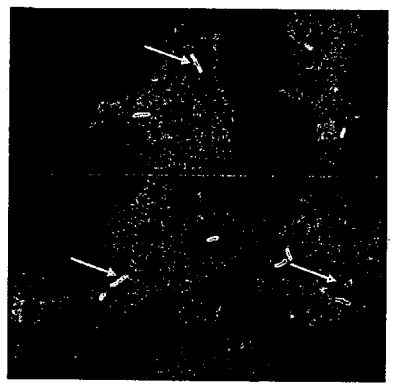
D. Listeria ΔuvrAB
S-59 UVA inactivated
Figure 27

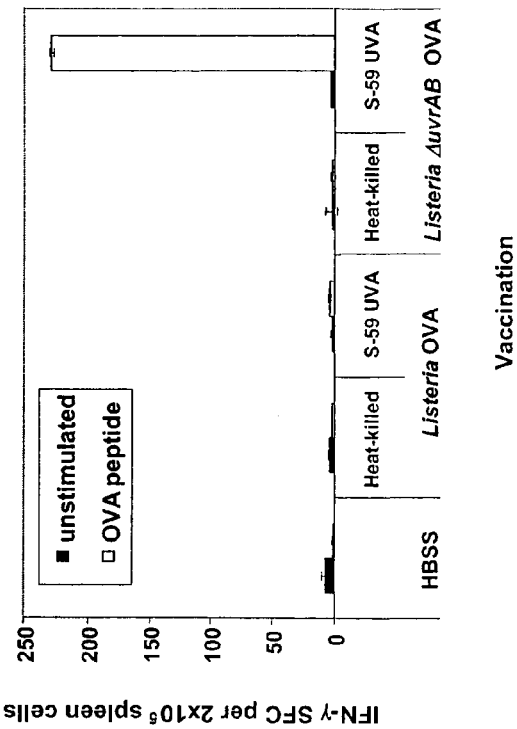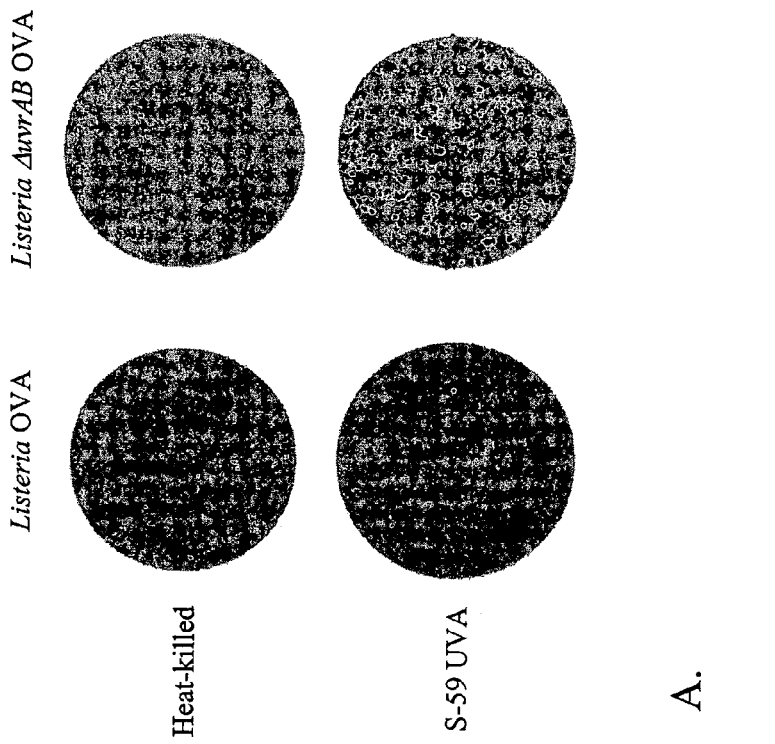
Figure 30

LLO(ss-PEST)-OVA/PR3 class I
Primary Amino Acid Sequence

MKKIMLVFITLILVSLPIAQQTEAKDASAFNKENSISSMAPPASPPAS
PKTPIEKKHADEIDSPSYYHQFAADQARELINSWVESQTNGIRNVL
QPSSVDSQTAMVLVNAIVFKGLWEKTFKDEDTQAMPFRVTEQESKP
VQMMYQIGLFRVASMASEKMKILELPFASGTMSMLVLLPDEVSGLEQ
LESIINFEKLTEWTVLQELNVTRTSSNVMEERKIKVYLPRMKMEEK
YNLTSVLMAMGITDVFSSSANLSGISSAESLKISQAVHAAHAEINEA
GREVVGSAEAGVDAASVSEEFRADHPFLFCIKHIATNAVLFFGRCVS
P

S I I N F E K L: OVA H-2 K^b epitope

V L Q E L N V T V: PR3 HLA A-2 restricted class I epitope (a.k.a. PR1)

Listeria secA1 signal peptide and PEST sequence is underlined

Listeria hly DP-L4056 and EGD Alignment

```
Query:    Listeria EGD
Subject:  DP-L4056 (wild-type, Portnoy strain)

prfA Box
Query:   1   ggtacctccttgattagtatattcctatcttaaagtgactttatgttgaggcattaac  60
             ||||||||||||||||||||||||||||||||||||||||||||||||||||||||||||
Sbjct:   1   ggtacctccttgattagtatattcctatcttaaagtttatgtggaggcattaac  60

Query:  61   atttgttaacgacgataaagggacagcaggactagaataaagctataaagcaagcatata  120
             ||||||||  ||||  | ||   |||  || ||||||||||||||||||||||||||||
Sbjct:  61   atttgttaatgacgtcaaaaggatagcaagactagaataaagctataaagcaagcatata  120

Query: 121   atattgcgtttcatctttagaagcgaatttcgccaatattattatcaaaagagagagg  180
             ||||||||||||||||||||||||||||||||||||||||||||||||||||||||||
Sbjct: 121   atattgcgtttcatctttagaagcgaatttcgccaatattattatcaaaagagagaggg  180

Shine-Dalgarno           LLO start
Query: 181   gtggcaaacggtatttggcattattaggttaaaaaatgtagaaggagagtgaaacccatg  240   (SEQ ID NO:61)
             ||||||||||||||||||||||||||||||||||||||||||||||||||||||||||||
Sbjct: 181   gtggcaaacggtatttggcattattaggttaaaaaatgtagaaggagagtgaaacccatg  240   (SEQ ID NO:62)
```

FIGURE 34

Codon Optimized LLOss-PEST-FLAG-NYESO1-myc-CodonOp
(Codon Optimized L. monocytogenes LLO signal peptide + PEST-Codon optimized -FLAG-NYESO1-Myc)
Nucleotide Sequence (including *hly* promoter)

GGTACCTCCTTTGATTAGTATATTCCTATCTTAAAGTTACTTTTATGTGGAGGCATTA
ACATTTGTTAATGACGTCAAAAGGATAGCAAGACTAGAATAAAGCTATAAAGCAAG
CATATAATATTGCGTTTCATCTTTAGAAGCGAATTTCGCCAATATTATAATTATCAAA
AGAGAGGGGTGGCAAACGGTATTTGGCATTATTAGGTTAAAAAATGTAGAAGGAGA
GTGAAACCCATGAAAAAAATTATGTTAGTTTTTATTACATTAATTTTAGTTAGTTTAC
CAATTGCACAACAAACAGAAGCAAAAGATGCAAGTGCATTTAATAAAGAAAATAGT
ATTAGTAGTATGGCACCACCAGCAAGTCCACCAGCAAGTCCAAAAACACCAATTGA
AAAAAAACATGCAGATGGATCCCAAGCAGAAGGTCGCGGAACAGGAGGAAGTACA
GGAGATGCAGACGGACCAGGAGGACCAGGAATACCAGACGGACCAGGAGGAAATG
CAGGAGGCCCAGGCGAAGCAGGCGCAACAGGAGGAAGAGGACCAAGAGGAGCAG
GAGCAGCACGAGCATCAGGACCAGGAGGCGGAGCACCAAGAGGACCACATGGCGG
AGCGGCAAGCGGATTAAATGGATGTTGTAGATGTGGAGCACGCGGACCAGAATCAA
GACTTTTAGAATTTTATTTAGCCATGCCATTTGCAACCCCAATGGAAGCAGAATTAG
CACGAAGATCATTAGCACAAGATGCCCCACCATTACCAGTACCAGGAGTTTTATTAA
AAGAGTTTACAGTATCAGGCAATATTTTAACAATACGTTTAACAGCAGCAGACCATC
GTCAATTACAACTATCTATCAGTTCATGTTTACAACAATTATCCTTATTAATGTGGAT
TACACAATGTTTTTTACCAGTTTTTTTAGCACAACCACCATCAGGACAAAGAAGATA
AGAGCTC   (SEQ ID NO:63)

FIGURE 35

Codon Optimized LLOss-PEST-FLAG-NYESO1-myc-CodonOp
(Codon Optimized L. monocytogenes LLO signal peptide + PEST-Codon optimized -FLAG-NYESO1-Myc)
Primary amino acid sequence M K K I M L V F I T L I L V S L P I A Q Q T E A K D A S A F N K E N
S I S S M A P P A S P P A S P K T P I E K K H A D G S Q A E G R G T
G G S T G D A D G P G G P G I P D G P G G N A G G P G E A G A T G
G R G P R G A G A A R A S G P G G G A P R G P H G G A A S G L N G
C C R C G A R G P E S R L L E F Y L A M P F A T P M E A E L A R R S
L A Q D A P P L P V P G V L L K E F T V S G N I L T I R L T A A D H
R Q L Q L S I S S C L Q Q L S L L M W I T Q C F L P V F L A Q P P S
G Q R R (SEQ ID NO:64)

FIGURE 36

Human Mesothelin Gene
Codon-Optimized for Expression in Listeria

ATGGCATTGCCAACTGCACGTCCATTACTAGGTAGTTGCGGTACACCAGCACTAGGT
TCTTTATTATTTTTGTTATTTTCTCTAGGTTGGGTTCAACCAAGTCGTACATTAGCAG
GTGAAACAGGTCAAGAAGCAGCACCACTTGACGGTGTATTAACGAATCCACCAAAT
ATATCAAGTTTAAGTCCACGTCAATTATTAGGTTTTCCATGTGCAGAAGTTTCAGGTT
TAAGTACAGAACGTGTCCGTGAGTTAGCAGTTGCATTAGCACAAAAAAACGTTAAA
TTATCTACAGAACAGTTACGTTGTTTAGCCCATAGATTAAGCGAACCACCAGAAGAC
TTAGATGCACTTCCTTTAGACCTTCTTTTATTCTTAAATCCAGATGCATTTTCAGGAC
CACAAGCATGTACACGTTTTTTAGTCGAATTACAAAAGCCAATGTTGATTTATTAC
CTCGTGGGGCTCCTGAAAGACAACGTTTATTACCTGCTGCATTAGCATGCTGGGGTG
TTCGCGGTAGCTTATTAAGTGAAGCCGATGTTCGTGCTTTAGGGGGTTTAGCATGTG
ATTTACCTGGTCGTTTCGTTGCAGAATCAGCAGAAGTGTTATTACCGAGATTAGTTTC
ATGCCCAGGACCTTTAGATCAAGATCAACAAGAGGCAGCTAGAGCAGCTCTTCAAG
GAGGAGGCCCACCATATGGCCCACCAAGTACATGGAGTGTTTCTACAATGGATGCG
TTAAGAGGTTTATTACCGGTTTTAGGACAACCAATTATTCGTAGTATTCCACAAGGC
ATTGTAGCAGCATGGCGTCAACGTAGTTCTCGTGATCCGTCTTGGCGACAACCAGAA
CGTACAATTCTACGTCCAAGATTTCGTAGAGAAGTAGAAAAAACGGCGTGTCCTAGT
GGCAAAAAAGCACGTGAAATTGATGAAAGTTTAATTTTTATAAAAAATGGGAATT
AGAAGCATGTGTCGATGCAGCATTACTAGCTACACAAATGGATCGTGTTAATGCTAT
TCCATTCACATATGAACAATTAGATGTTTTAAAGCATAAATTAGACGAATTATATCC
ACAAGGTTATCCAGAATCAGTTATTCAACATTTAGGTTACTTATTTTTAAAAATGAG
TCCAGAAGACATACGCAAATGGAATGTTACAAGTTTAGAAACATTAAAAGCGCTTTT
AGAAGTTAACAAAGGTCATGAAATGAGTCCACAAGTTGCTACGTTAATTGATAGATT
CGTTAAAGGCCGTGGTCAATTAGATAAAGATACTTTAGATACATTAACAGCATTTTA
TCCTGGCTACTTATGCAGTTTATCACCAGAAGAATTAAGTTCCGTTCCACCGAGTAG
TATCTGGGCAGTTCGTCCGCAAGATTTAGATACATGCGACCCACGTCAATTAGATGT
TTTATATCCAAAAGCAAGATTAGCTTTCCAAAATATGAACGGTAGTGAATATTTCGT
AAAAATTCAATCCTTTTTAGGTGGTGCACCAACTGAAGATCTAAAAGCATTAAGCCA
ACAAAATGTAAGTATGGATTTAGCTACGTTTATGAAATTACGTACAGATGCAGTTCT
ACCATTAACAGTTGCAGAAGTTCAAAAATTATTAGGTCCACACGTAGAAGGATTAA
AAGCAGAAGAACGTCACCGTCCAGTTCGCGATTGGATTTTACGTCAACGTCAAGATG
ATTTAGATACATTAGGTTTAGGTTTACAAGGCGGTATTCCGAATGGATATTTAGTGT
TAGATTTATCTGTTCAAGAAGCATTAAGTGGTACACCGTGTTTATTAGGTCCAGGTC
CAGTTTTAACAGTGTTAGCATTATTATTAGCCAGTACATTAGCTTAA (SEQ ID NO:65)

FIGURE 37

```
M A L P T A R P L L G S C G T P A L G S L L F L L F S L G W V Q P S
R T L A G E T G Q E A A P L D G V L T N P P N I S S L S P R Q L L G
F P C A E V S G L S T E R V R E L A V A L A Q K N V K L S T E Q L R
C L A H R L S E P P E D L D A L P L D L L F L N P D A F S G P Q A
C T R F F S R I T K A N V D L L P R G A P E R Q R L L P A A L A C W
G V R G S L L S E A D V R A L G G L A C D L P G R F V A E S A E V
L L P R L V S C P G P L D Q D Q Q E A A R A A L Q G G G P P Y G P P
S T W S V S T M D A L R G L L P V L G Q P I I R S I P Q G I V A A W
R Q R S S R D P S W R Q P E R T I L R P R F R R E V E K T A C P S G
K K A R E I D E S L I F Y K K W E L E A C V D A A L L A T Q M D R
V N A I P F T Y E Q L D V L K H K L D E L Y P Q G Y P E S V I Q H L
G Y L F L K M S P E D I R K W N V T S L E T L K A L L E V N K G H E
M S P Q V A T L I D R F V K G R G Q L D K D T L D T L T A F Y P G
Y L C S L S P E E L S S V P P S S I W A V R P Q D L D T C D P R Q L
D V L Y P K A R L A F Q N M N G S E Y F V K I Q S F L G G A P T E D
L K A L S Q Q N V S M D L A T F M K L R T D A V L P L T V A E V Q
K L L G P H V E G L K A E E R H R P V R D W I L R Q R Q D D L D T
L G L G L Q G G I P N G Y L V L D L S V Q E A L S G T P C L L G P G
P V L T V L A L L L A S T L A (SEQ ID NO:66)
```

FIGURE 38

Murine Mesothelin Gene
Codon-Optimized for Expression in Listeria

ATGGCATTACCAACGGCTCGCCCATTATTAGGTTCTTGTGGTTCACCAATTTGTAGTC
GCAGTTTTTTATTATTATTACTATCTTTAGGTTGGATTCCGCGTTTACAAACACAAAC
CACTAAAACAAGTCAAGAAGCTACATTATTGCATGCAGTCAATGGCGCAGCAGATT
TTGCAAGTTTACCAACAGGCTTATTTCTTGGTCTTACATGTGAAGAAGTTAGTGATTT
AAGTATGGAACAAGCAAAAGGTTTAGCGATGGCGGTTCGCCAAAAAAATATTACAT
TACGTGGTCATCAATTACGTTGTTAGCACGTCGTTTACCACGACATTTAACAGATG
AAGAATTAAATGCTCTACCATTAGACTTATTATTATTTTTAAATCCAGCAATGTTTCC
AGGTCAACAAGCATGTGCCCATTTTTTCAGTTTAATTTCGAAAGCAAATGTAGATGT
TTTACCGAGACGTAGCTTAGAACGTCAACGTCTTTTAATGGAAGCATTAAAATGTCA
AGGTGTTTATGGTTTCCAAGTTAGTGAAGCAGATGTTCGTGCACTTGGTGGTTTAGC
TTGTGATTTACCAGGGAAATTTGTAGCACGTTCTAGTGAAGTATTATTACCATGGTT
AGCAGGTTGTCAAGGTCCATTAGATCAAAGTCAAGAAAAGCAGTTCGTGAAGTCT
TACGTAGTGGTCGTACTCAATATGGCCCACCTAGCAAATGGAGTGTTAGTACGTTAG
ATGCATTACAAAGTTTAGTAGCTGTTTTAGATGAAAGTATTGTTCAGAGTATTCCAA
AAGATGTGAAAGCAGAGTGGTTACAACATATTTCCCGTGACCCATCTCGTTTAGGTA
GTAAATTAACAGTTATTCATCCACGTTTTCGCCGCGACGCAGAACAAAAAGCATGTC
CACCAGGTAAAGAACCATATAAAGTAGATGAAGATTTAATTTTTTATCAGAATTGGG
AATTAGAAGCCTGTGTTGATGGTACAATGTTAGCACGTCAAATGGATTTAGTTAATG
AAATTCCATTTACATATGAACAATTAAGTATCTTTAAACATAAATTAGATAAAACAT
ATCCACAAGGTTATCCAGAATCGTTAATTCAACAATTAGGTCATTTTTTCGTTATGT
TAGTCCAGAAGACATTCATCAATGGAATGTTACAAGTCCAGATACAGTTAAAACTTT
ATTAAAAGTTAGTAAAGGTCAAAAAATGAATGCTCAAGCAATTGCATTAGTCGCAT
GTTATTTACGTGGAGGTGGTCAATTAGATGAAGATATGGTTAAAGCATTAGGGGATA
TTCCATTATCATATTTATGTGATTTCTCCCCACAAGACTTACATTCAGTTCCAAGTAG
TGTTATGTGGTTAGTTGGTCCACAAGGTTTAGATAAATGTAGTCAACGTCATTTAGG
TTTACTTTATCAAAAAGCATGTAGTGCGTTTCAAAATGTTAGTGGTTTAGAATATTTT
GAAAAAATCAAAACATTTTTAGGAGGTGCATCTGTAAAAGATTTACGCGCATTAAGT
CAACATAATGTAAGTATGGATATCGCAACATTTAAACGTTTACAAGTCGATAGTCTA
GTTGGTCTTAGTGTAGCAGAAGTTCAAAAATTATTAGGGCCGAATATTGTAGATTTA
AAAACAGAAGAAGATAAAAGTCCAGTTCGTGACTGGTTATTTCGACAACATCAGAA
AGACTTAGATCGTCTTGGATTAGGTTTACAAGGTGGTATTCCAAATGGTTATTTAGTT
TTAGATTTTAATGTACGTGAAGCATTTAGTTCAAGAGCGAGTTTATTAGGTCCAGGT
TTTGTGTTAATTTGGATTCCAGCATTACTACCAGCACTTCGTTTATCATAA
(SEQ ID NO:67)

FIGURE 39

Murine Mesothelin Primary Amino Acid Sequence

M A L P T A R P L L G S C G S P I C S R S F L L L L L S L G W I P R L
Q T Q T T K T S Q E A T L L H A V N G A A D F A S L P T G L F L G L
T C E E V S D L S M E Q A K G L A M A V R Q K N I T L R G H Q L R
C L A R R L P R H L T D E E L N A L P L D L L F L N P A M F P G Q
Q A C A H F F S L I S K A N V D V L P R R S L E R Q R L L M E A L K
C Q G V Y G F Q V S E A D V R A L G G L A C D L P G K F V A R S S
E V L L P W L A G C Q G P L D Q S Q E K A V R E V L R S G R T Q Y
G P P S K W S V S T L D A L Q S L V A V L D E' S I V Q S I P K D V K
A E W L Q H I S R D P S R L G S K L T V I H P R F R R D A E Q K A C
P P G K E P Y K V D E D L I F Y Q N W E L E A C V D G T M L A R Q
M D L V N E I P F T Y E Q L S I F K H K L D K T Y P Q G Y P E S L I
Q Q L G H F F R Y V S P E D I H Q W N V T S P D T V K T L L K V S K
G Q K M N A Q A I A L V A C Y L R G G G Q L D E D M V K A L G D I
P L S Y L C D F S P Q D L H S V P S S V M W L V G P Q G L D K C S Q
R H L G L L Y Q K A C S A F Q N V S G L E Y F E K I K T F L G G A S
V K D L R A L S Q H N V S M D I A T F K R L Q V D S L V G L S V A
E V Q K L L G P N I V D L K T E E D K S P V R D W L F R Q H Q K D
L D R L G L G L Q G G I P N G Y L V L D F N V R E A F S S R A S L L
G P G F V L I W I P A L L P A L R L S (SEQ ID NO:68)

MODIFIED FREE-LIVING MICROBES, VACCINE COMPOSITIONS AND METHODS OF USE THEREOF

CROSS-REFERENCE TO RELATED APPLICATIONS

This application is a continuation of U.S. patent application Ser. No. 10/883,599, filed Jun. 30, 2004 now U.S. Pat. No. 7,695,725, which claims the priority benefit of U.S. Provisional Application No. 60/490,089, filed Jul. 24, 2003, U.S. Provisional Application No. 60/511,869, filed Oct. 15, 2003, U.S. Provisional Application No. 60/511,719, filed Oct. 15, 2003, U.S. Provisional Application No. 60/511,919, filed Oct. 15, 2003, U.S. Provisional Application No. 60/532,598, filed Dec. 24, 2003, U.S. Provisional Application No. 60/541,515, filed Feb. 2, 2004, and U.S. Provisional Application No. 60/556,744, filed Mar. 26, 2004; which U.S. patent application Ser. No. 10/883,599 is also a continuation-in-part of U.S. application Ser. No. 10/773,618, filed Feb. 6, 2004 now U.S. Pat. No. 7,833,775, which claims the priority benefit of U.S. Provisional Application No. 60/446,051, filed Feb. 6, 2003, U.S. Provisional Application No. 60/449,153, filed Feb. 21, 2003, U.S. Provisional Application No. 60/490,089, filed Jul. 24, 2003, U.S. Provisional Application No. 60/511,869, filed Oct. 15, 2003, and U.S. Provisional Application No. 60/541,515, filed Feb. 2, 2004; and which U.S. patent application Ser. No. 10/883,599 is also a continuation-in-part of U.S. application Ser. No. 10/773,792, filed Feb. 6, 2004 now U.S. Pat. No. 7,691,393, which claims the benefit of U.S. Provisional Application No. 60/446,051, filed Feb. 6, 2003, U.S. Provisional Application No. 60/449,153, filed Feb. 21, 2003, U.S. Provisional Application No. 60/490,089, filed Jul. 24, 2003, U.S. Provisional Application No. 60/511,719, filed Oct. 15, 2003, U.S. Provisional Application No. 60/511,919, filed Oct. 15, 2003, U.S. Provisional Application No. 60/511,869, filed Oct. 15, 2003, and U.S. Provisional Application No. 60/541,515, filed Feb. 2, 2004, the disclosures of each of which are herein incorporated by reference in their entirety.

FIELD OF THE INVENTION

The present invention relates generally to vaccine compositions and immunotherapy. In particular, the present invention relates to vaccine compositions comprising a population of a modified free-living microbe that can be used to deliver a particular antigen to an individual. In such compositions, the vaccine is directed against the microbe itself or against a heterologous antigen that has been incorporated into the microbe. The present invention also relates to the use of the modified microbes to load and to induce the activation and maturation of antigen-presenting cells, such as dendritic cells, and the use of those cells as vaccines.

BACKGROUND OF THE INVENTION

A variety of vaccines have been developed for clinical use, mostly targeting the prevention of infectious diseases caused by viruses, bacteria and parasites. Vaccines can be prepared from live attenuated microbes, inactivated (killed) microbes, or components of the microbes themselves. Live attenuated microbes contain genetic alterations, such as deletion or modification of virulence factors, resulting in a less virulent microbe. For inactivated vaccines, a microbe may be chemically or physically inactivated. Ideally, such vaccines cannot cause an infection but are still able to stimulate a desired immune response. Examples of inactivated vaccines include polio and influenza viruses, and bacterial vaccines against cholera and pertussis, although live attenuated vaccines are an option for polio, influenza, and cholera as well. In order to elicit the desired immune response, it is important that the inactivated microbe comprises the appropriate antigens prior to inactivation. It has been observed in some cases that inactivating the microbe results in a significantly reduced immune response because de novo gene expression by an infecting microbe is required to stimulate an optimal immune response. This is particularly important for intracellular bacteria. Methods that have been used to inactivate bacteria include the use of acetone, alcohol, formalin, glutaraldehyde, paraformaldehyde, or phenol, heating, or ultraviolet irradiation [Pace et al., Vaccine 16(16):1563 (1998)].

In addition to using microbial vaccines to prevent infectious diseases caused by the microbe itself, the microbes can be modified to contain heterologous nucleic acid sequences that encode a certain protein or antigen. Such recombinant microbes are used as delivery vehicles and may be used as vaccines to stimulate an immune response to the heterologous antigens. These recombinant vaccines have been shown to be effective in animal models. An oral vaccine of live attenuated *Salmonella* modified to express *Plasmodium berghei* circumsporozite antigen has been shown to protect mice against malaria [Aggarwal et al., J Exp Med 172(4):1083 (1990)]. Similarly, U.S. Pat. No. 6,051,237 describes a live recombinant form of *Listeria monocytogenes* that grows and spreads and expresses a tumor-specific antigen for use as a cancer vaccine. While such recombinant vaccines may be effective, each microbe strain must be genetically modified to provide the vaccine. It would therefore be desirable to develop a method of producing a safe and effective microbial vaccine that can be applied to any microbe, whether or not the microbe comprises recombinant antigens.

Dendritic cell (DC)-based immunotherapy has been widely investigated and demonstrated to provide a clinical benefit for the treatment of a wide range of tumor types. A variety of strategies are presently being developed to isolate and generate autologous dendritic cells (DC), and subsequently load them with antigen or peptides ex vivo prior to patient vaccination. Recent advances in the understanding of immune mechanisms have, in addition to efficient antigen loading, highlighted the importance of the activation and maturation state of DC used for vaccination on the efficacy of cancer immunotherapy. Whereas immature DC are more effective in the uptake and processing of antigen, activated/mature DC lose this capacity, yet are more potent at presenting antigen to naïve T lymphocytes in the context of MHC molecules. In fact, mature DCs have been found to be potent antigen presenting cells (APC) to induce primary T lymphocyte responses, overcoming peripheral T cell tolerance and enhance anti-tumor immunity. Despite the development of a variety of methods to load and to stimulate the activation and maturation of DC that has led to encouraging clinical data, there still are not standard efficient and cost effective methods for combining antigen loading with DC activation and maturation.

SUMMARY OF THE INVENTION

The invention involves free-living microbes useful in vaccine compositions. For instance, the invention provides free-living microbes, including, but not limited to bacteria, in which the proliferation of the microbe is attenuated while maintaining sufficient microbial gene expression, and wherein the attenuation can be controlled in a dose-dependent manner. The invention provides methods for the attenuation of the free-living microbes. The invention also includes vaccine compositions comprising these attenuated microbes. In addition, the invention provides free-living microbes, such as bacteria, which are attenuated for nucleic acid repair and which are particularly useful in conjunction with the modifications that attenuate proliferation. Vaccine compositions comprising these attenuated microbes and methods of using the vaccines are also provided. The present invention also provides novel uses of modified microbes such as bacteria, and attenuated *Listeria*, in particular, to load and to induce the activation and maturation of antigen-presenting cells, such as dendritic cells, in vitro or ex vivo. The resulting antigen-presenting cells are useful in vaccines and immunotherapy. In particular embodiments, the provided vaccines and immunotherapy are directed against cancer.

In one aspect, the invention provides a vaccine comprising a free-living microbe (e.g., a bacterium), wherein the nucleic acid of the microbe (e.g., genomic nucleic acid) is modified so that the microbe is attenuated for proliferation. In some embodiments, the attenuation of the proliferation of the microbe is controllable in a dose-dependent manner. In some embodiments, microbial gene expression in the microbe is substantially unaffected by attenuation of the proliferation of the microbe. In some embodiments, the microbe in the vaccine expresses an antigen at a sufficient level to induce an immune response to the antigen in an individual upon administration of the vaccine to the individual. In some embodiments, the nucleic acid has been modified by reaction with a nucleic acid targeted compound (alternatively termed a nucleic acid "targeting" compound) which reacts directly with the nucleic acid. In one embodiment, the nucleic acid target compound is an alkylator such as β-alanine, N-(acridin-9-yl), 2-[bis(2-chloroethyl)amino]ethyl ester. In other embodiments, the nucleic acid targeted compound is a psoralen compound (e.g., 4'-(4-amino-2-oxa)butyl-4,5',8-trimethylpsoralen, also referred to herein as "S-59") activated by UVA irradiation. In some embodiments, the microbe in the vaccine comprises a genetic mutation that attenuates the ability of the microbe to repair its nucleic acid that has been modified. In some embodiments, the microbe is a bacterium, such as *Bacillus anthracis* or *Listeria monocytogenes*. In some embodiments, the microbe comprises a heterologous nucleic acid sequence encoding an antigen. In some embodiments, the vaccine further comprises a pharmaceutically acceptable carrier and/or an adjuvant. The invention further provides a method of preventing or treating a disease in a host, comprising administering to the host an effective amount of the vaccine. The invention also provides a method of inducing an immune response in a host to an antigen comprising administering to the host an effective amount of the vaccine, wherein the microbe expresses the antigen.

In another aspect, the invention provides a vaccine comprising a free-living microbe (e.g., a bacterium) which is defective with respect to at least one DNA repair enzyme. In some embodiments, the free-living microbe comprises a genetic mutation in one or more gene selected from the group consisting of phrB, uvrA, uvrB, uvrC, uvrD and recA, or in a functional equivalent of one or more gene selected from the group consisting of phrB, uvrA, uvrB, uvrC, uvrD and recA. In some embodiments, the microbe comprises genetic mutations in both uvrA and uvrB (or in functional equivalents of both uvrA and uvrB, depending upon the genus and species of the microbe). In some embodiments, the microbe is defective with respect to RecA (or the functional equivalent of RecA, depending upon the genus and species of the microbe). In some embodiments, the microbe is defective with respect to UvrC (or the functional equivalent of UvrC, depending upon the genus and species of the microbe). In some embodiments, the microbe comprises a heterologous nucleic acid sequence encoding an antigen (for instance, a cancer antigen, or an infectious disease antigen foreign to the microbe). In some embodiments, the vaccine further comprises a pharmaceutically acceptable carrier or an adjuvant. The invention further provides method of preventing or treating a disease in a host, comprising administering to the host an effective amount of the vaccine. The invention also provides a method of inducing an immune response in a host to an antigen comprising administering to the host an effective amount of the vaccine wherein the microbe expresses the antigen.

In some embodiments, the invention includes a vaccine comprising bacteria that has been reacted with a psoralen compound and UVA light, wherein the proliferation of the bacteria are attenuated. In some embodiments, the bacterial expression is sufficiently active after the psoralen modification such that the psoralen attenuated bacteria can continue to express a protein antigen, wherein when the bacteria are administered to an individual, an immune response to the antigen is elicited. In one embodiment, the desired immune response is to the bacteria itself. In one embodiment, the bacteria are a recombinant strain that expresses a heterologous protein antigen, wherein when the bacteria are administered to an individual, an immune response to the heterologous antigen is elicited. Such a vaccine comprising a heterologous antigen may be designed to treat or prevent a variety of diseases including infectious diseases, autoimmune diseases, allergies, cancers, and other hyperproliferative diseases.

For the treatment or prevention of infectious diseases, the disease causing agent may be prepared according to the methods of the invention to be used as the vaccine. In one embodiment, a vaccine can be prepared from a microbe of the invention comprising a heterologous antigen from the disease-causing agent, such as a virus, bacterium or parasite. Such a vaccine may provide a level of benefit when the health risk of receiving the bacterial vector is significantly less than the risks associated with possible infection by the infectious agent. A heterologous vaccine for the treatment or prevention of infectious disease that is attenuated by the methods of the present invention may have other benefits as well. First, it may not be possible to prepare an attenuated live vaccine or a killed vaccine directly from the infectious agent itself. Second, if a live vaccine is required, it may not be possible to otherwise attenuate the infectious agent and still maintain an appropriate immune response.

Another possibility is that the antigen inserted into the bacterial vector does not stimulate an immune response in an individual in the absence of the innate immune response induced by the bacterial vector. For example, diseases in which autologous cells proliferate improperly may contain antigens that do not typically stimulate an immune response. It may be useful to fight such diseases by finding a way to stimulate such an immune response against an autologous antigen. In one embodiment the proliferating cells express or over express an antigen at higher levels than on a normal cell so that the immune response is largely specific to the proliferating cells. Diseases that may be treated with such a vaccine include, but are not limited to, autoimmune diseases, allergies, cancers and other hyperproliferative cellular diseases. In another embodiment, the vaccine may target a product of the disease or a disease related target rather than the diseased cells themselves. For example, tumors may be treated with a vaccine targeting vascular endothelial growth factor (VEGF), which is essential for generation of new blood vessels required to feed tumor cells. The VEGF is peripheral to the tumor cells themselves but is prevalent in areas of tumor growth and is a viable vaccine target that could potentially limit the growth of the tumor cells. Another example is a vaccine that comprises an antigen that will elicit a response to a disease related protein, such as the proteins that cause the amyloid plaques characteristic of Alzheimer's disease or Creutzfeldt-Jakob disease. Similarly, the vaccine may target proteins involved in autoimmune or allergic responses. The vaccine may comprise an idiotype antigen that can elicit a response to the specific antibodies or cells, such as B-cells or T cells, causing an autoimmune or allergic response.

In one embodiment, the invention includes a vaccine composition comprising a free-living microbial population (e.g., a bacterial population) in which the microbial nucleic acid is modified so that the proliferation of the microbial population is attenuated, wherein the microbial gene expression is substantially unaffected. In one embodiment, the microbial gene expression is substantially unaffected so that an antigen is expressed at a level sufficient to stimulate an immune response upon administration of the microbial population to an individual. In one embodiment, the proliferation of the microbial population is attenuated by at least about 0.3 log, also at least about 1 log, about 2 log, about 3 log, about 4 log, about 6 log, or at least about 8 log. In another embodiment, the proliferation of the microbial population is attenuated by about 0.3 to >10 log, about 2 to >10 log, about 4 to >10 log, about 6 to >10 log, about 0.3-8 log, about 0.3-6 log, about 0.3-5 log, about 1-5 log, or about 2-5 log. In one embodiment, the expression of an antigen by the microbial population is at least about 10%, about 25%, about 50%, about 75%, or at least about 90% of the expression of the antigen by a microbial population in which the microbial nucleic acid is not modified. In one embodiment, the antigen expressed is an antigen from the microbe itself. In one embodiment, the microbe comprises a heterologous nucleic acid sequence encoding an antigen. In one embodiment, the antigen is a disease associated antigen. In one embodiment, the antigen is associated with a disease selected from the group consisting of infectious diseases, autoimmune diseases, allergies, cancers, and other hyperproliferative diseases. In one embodiment, the antigen is a tumor associated antigen. In one embodiment, the tumor antigen is selected from the group consisting of differentiation antigens, tissue-specific antigens, developmental antigens, tumor-associated viral antigens, cancer-testis antigens, embryonic antigens, oncoprotein antigens, over-expressed protein antigens and mutated protein antigens. In one embodiment, the tumor antigen is selected from the group consisting of mesothelin, Sp17, gp100, EphA2, PR3, PAGE-4, TARP, and SPAS-1. In one embodiment, the microbial nucleic acid is modified by a method selected from the group consisting of exposing the microbe to radiation and reacting the microbe with a nucleic acid targeted compound that causes the modification of the microbial nucleic acid. In a preferred embodiment, the microbial nucleic acid is modified by reacting the microbial population with a nucleic acid targeted compound that reacts directly with the nucleic acid. In one embodiment, the nucleic acid targeted compound is targeted to the nucleic acid by a mode selected from the group consisting of intercalation, minor groove binding, major groove binding, electrostatic binding, and sequence-specific binding. In one embodiment, the nucleic acid targeted compound comprises a nucleic acid alkylator. In a preferred embodiment, the nucleic acid targeted compound is β-alanine, N-(acridin-9-yl), 2-[bis(2-chloroethyl)amino]ethyl ester. In one embodiment, the nucleic acid targeted compound that reacts directly with the nucleic acid reacts upon activation of the compound by irradiation, preferably by UVA irradiation. In one embodiment, the nucleic acid targeted compound activated by UVA irradiation is a psoralen. In a preferred embodiment, the psoralen is 4'-(4-amino-2-oxa)butyl-4,5',8-trimethylpsoralen. In one embodiment, the nucleic acid targeted compound indirectly causes the modification of the nucleic acid. In one embodiment, the nucleic acid targeted compound indirectly causes modification upon activation by irradiation, preferably by UVA irradiation. In one embodiment, the microbe comprises a genetic mutation. In one embodiment, the genetic mutation results in the attenuation of the ability of the microbe to repair microbial nucleic acid that has been modified. In one embodiment, the genetic mutation is in the gene selected from the group consisting of phrB, uvrA, uvrB, uvrC, uvrD and recA, or their functionally equivalent genes, depending on the genus and species of the microbe. In one embodiment, the genetic mutation is in more than one of the genes selected from the group consisting of phrB, uvrA, uvrB, uvrC, uvrD and recA, or their functionally equivalent genes, depending on the genus and species of the microbe. In an embodiment where the mutation is in the recA gene, whether alone or in combination with one or more other mutations, the recA mutation is a conditional mutation. In one embodiment, the genetic mutation results in the attenuation in the activity of at least one of a DNA repair enzyme selected from the group consisting of PhrB, UvrA, UvrB, UvrC, UvrD and RecA. In one embodiment, attenuation in the activity of RecA is conditional. In a further embodiment, the microbes containing these mutations are modified by reaction with a psoralen activated by UVA irradiation. In a preferred embodiment, the psoralen is 4'-(4-amino-2-oxa)butyl-4,5',8-trimethylpsoralen. In one embodiment, the microbe is selected from the group consisting of bacteria, protozoa and fungi. In one embodiment, the microbe is a bacteria. In one embodiment, the bacteria are a mycobacteria. In one embodiment, the mycobacteria is *Mycobacterium tuberculosis*. In one embodiment, the bacteria are intracellular bacteria. In one embodiment, the intracellular bacteria are *Bacillus anthracis*. In one embodiment, the intracellular bacteria are *Yersinia pestis*. In a preferred embodiment, the bacteria are *Listeria*, preferably *Listeria monocytogenes*. In one embodiment, the *Listeria* comprises a mutation that results in the attenuation of the ability of the *Listeria* to invade non-phagocytic cells without significantly affecting the uptake of the *Listeria* by phagocytic cells. In one embodiment, the *Listeria* mutation is in an internalin gene(s). In one embodiment, the *Listeria* mutation is in the gene selected from the group consisting of inlA, inlB, and any gene encoding an internalin. In one embodiment, the *Listeria monocytogenes* comprises a genetic mutation in both the inlA and inlB genes. In one embodiment, the *Listeria* comprises a mutation that results in the attenuation of the ability of the *Listeria* to escape the phagolysosome of an infected cell. In one embodiment, the *Listeria* mutation is in the hly gene. In one embodiment, the *Listeria* comprises a mutation that results in the attenuation of the polymerization of actin by the *Listeria*. In one embodiment, the *Listeria* mutation is in the actA gene. In one embodiment, the *Listeria monocytogenes* comprises more than one mutation. In a preferred embodiment, the *Listeria* mutations are in both the actA and inlB genes, preferably deletion mutations in both the actA and inlB genes.

In one embodiment, the invention includes a vaccine comprising a microbial population (e.g., a bacterial population) in which the microbial nucleic acid is modified by reaction with a nucleic acid targeted compound that reacts directly with the nucleic acid so that the proliferation of the microbial population is attenuated, wherein the microbial gene expression is substantially unaffected, and wherein the microbe of the population comprises a heterologous nucleic acid sequence encoding a tumor antigen. In one embodiment, the microbial gene expression is substantially unaffected so that the tumor antigen is expressed at a level sufficient to stimulate an immune response upon administration of the microbe to an individual. In one embodiment, the proliferation of the microbial population is attenuated by at least about 0.3 log, also at least about 1 log, about 2 log, about 3 log, about 4 log, about 6 log, or at least about 8 log. In another embodiment, the proliferation of the microbial population is attenuated by about 0.3 to >10 log, about 2 to >10 log, about 4 to >10 log, about 6 to >10 log, about 0.3-8 log, about 0.3-6 log, about 0.3-5 log, about 1-5 log, or about 2-5 log. In one embodiment, the expression of the tumor antigen by the microbial population is at least about 10%, about 25%, about 50%, about 75%, or at least about 90% of the expression of the tumor antigen by a microbial population in which the microbial nucleic acid is not modified. In one embodiment, the tumor antigen is selected from the group consisting of differentiation antigens, tissue-specific antigens, developmental antigens, tumor-associated viral antigens, cancer-testis antigens, embryonic antigens, oncoprotein antigens, over-expressed protein antigens and mutated protein antigens. In one embodiment, the tumor antigen is selected from the group consisting of mesothelin, Sp17, gp100, EphA2, PR3, PAGE-4, TARP, and SPAS-1. In one embodiment, the nucleic acid targeted compound comprises an alkylator. In one embodiment, the alkylator is selected from the group consisting of mustards, mustard intermediates and mustard equivalents. In one embodiment, the nucleic acid targeted compound comprises a nucleic acid targeting group selected from the group consisting of intercalators, minor groove binders, major groove binders, electrostatic binders, and sequence-specific binders. In one embodiment, the nucleic acid targeted compound is β-alanine, N-(acridin-9-yl), 2-[bis(2-chloroethyl)amino] ethyl ester. In one embodiment, the nucleic acid targeted compound reacts directly with the nucleic acid upon activation of the compound. In one embodiment, the activation of the compound is by irradiation. In one embodiment, the irradiation is UVA irradiation. In a preferred embodiment, the nucleic acid targeted compound is a psoralen compound activated by UVA irradiation. In a preferred embodiment, the psoralen is 4'-(4-amino-2-oxa)butyl-4,5',8-trimethylpsoralen. In one embodiment, the microbe of the population comprises a genetic mutation. In one embodiment, the genetic mutation results in the attenuation of the ability of the microbe to repair microbial nucleic acid that has been modified. In one embodiment, the genetic mutation is in the gene selected from the group consisting of phrB, uvrA, uvrB, uvrC, uvrD and recA, or their functionally equivalent genes, depending on the genus and species of the microbe. In one embodiment, the genetic mutation is in more than one of the genes selected from the group consisting of phrB, uvrA, uvrB, uvrC, uvrD and recA, or their functionally equivalent genes, depending on the genus and species of the microbe. In an embodiment where the mutation is in the recA gene, whether alone or in combination with one or more other mutations, the recA mutation is a conditional mutation. In one embodiment, the genetic mutation results in the attenuation in the activity of at least one of a DNA repair enzyme selected from the group consisting of PhrB, UvrA, UvrB, UvrC, UvrD and RecA. In one embodiment, attenuation in the activity of RecA is conditional. In a further embodiment, the microbes containing these mutations are modified by reaction with a psoralen activated by UVA irradiation. In a preferred embodiment, the psoralen is 4'-(4-amino-2-oxa)butyl-4,5',8-trimethylpsoralen. In one embodiment, the microbe is selected from the group consisting of bacteria, protozoa and fungi. In one embodiment, the microbe is a bacteria. In one embodiment, the bacteria are intracellular bacteria. In a preferred embodiment, the bacteria are *Listeria*, preferably *Listeria monocytogenes*. In one embodiment, the *Listeria* comprises a mutation that results in the attenuation of the ability of the *Listeria* to invade non-phagocytic cells without significantly affecting the uptake of the *Listeria* by phagocytic cells. In one embodiment, the *Listeria* mutation is in an internalin gene(s). In one embodiment, the *Listeria* mutation is in the gene selected from the group consisting of inlA, inlB, and any gene encoding an internalin. In one embodiment, the *Listeria monocytogenes* comprises a genetic mutation in both the inlA and inlB genes. In one embodiment, the *Listeria* comprises a mutation that results in the attenuation of the ability of the *Listeria* to escape the phagolysosome of an infected cell. In one embodiment, the *Listeria* mutation is in the hly gene. In one embodiment, the *Listeria* comprises a mutation that results in the attenuation of the polymerization of actin by the *Listeria*. In one embodiment, the *Listeria* mutation is in the actA gene. In one embodiment, the *Listeria monocytogenes* comprises more than one mutation. In a preferred embodiment, the *Listeria* mutations are in both the actA and inlB genes, preferably deletion mutations in both the actA and inlB genes. In a preferred embodiment, the *Listeria monocytogenes* actA/inlB deletion mutant further comprises a deletion mutation in the uvrAB gene.

In one embodiment, the invention includes a vaccine comprising a *Listeria monocytogenes* population in which the listerial nucleic acid is modified by reaction with a psoralen activated by UVA irradiation so that the proliferation of the listerial population is attenuated, wherein the listerial gene expression is substantially unaffected, and wherein the *Listeria monocytogenes* comprises a heterologous nucleic acid sequence encoding a tumor antigen. In a preferred embodiment, the psoralen is 4'-(4-amino-2-oxa)butyl-4,5',8-trimethylpsoralen. In one embodiment, the listerial gene expression is substantially unaffected so that the tumor antigen is expressed at a level sufficient to stimulate an immune response upon administration of the *Listeria* to an individual. In one embodiment, the proliferation of the listerial population is attenuated by at least about 0.3 log, also at least about 1 log, about 2 log, about 3 log, about 4 log about 6 log, or at least about 8 log. In another embodiment, the proliferation of the listerial population is attenuated by about 0.3 to >10 log, about 2 to >10 log, about 4 to >10 log, about 6 to >10 log, about 0.3-8 log, about 0.3-6 log, about 0.3-5 log, about 1-5 log, or about 2-5 log. In one embodiment, the expression of the tumor antigen by the listerial population is at least about 10%, at least about 25%, at least about 50%, at least about 75%, or at least about 90% of the expression of the tumor antigen by a listerial population in which the listerial nucleic acid is not modified. In one embodiment, the tumor antigen is selected from the group consisting of differentiation antigens, tissue-specific antigens, developmental antigens, tumor-associated viral antigens, cancer-testis antigens, embryonic antigens, oncoprotein antigens, over-expressed protein antigens and mutated protein antigens. In one embodiment, the tumor antigen is selected from the group consisting of mesothelin, Sp17, gp100, EphA2, PR3, PAGE-4, TARP, and SPAS-1. In one embodiment, the *Listeria monocytogenes* comprises a genetic mutation. In one embodiment, the genetic mutation results in the attenuation of the ability of the *Listeria monocytogenes* to repair nucleic acid that has been modified. In one embodiment, the genetic mutation is in the gene selected from the group consisting of phrB, uvrA, uvrB, uvrC, uvrD and recA. In one embodiment, the genetic mutation is in more than one of the genes selected from the group consisting of phrB, uvrA, uvrB, uvrC, uvrD and recA. In an embodiment where the mutation is in the recA gene, whether alone or in combination with one or more other mutations, the recA mutation is a conditional mutation. In one embodiment, the genetic mutation results in the attenuation in the activity of at least one of a DNA repair enzyme selected from the group consisting of PhrB, UvrA, UvrB, UvrC, UvrD and RecA. In one embodiment, attenuation in the activity of RecA is conditional. In one embodiment, the genetic mutation results in the attenuation of the ability of the *Listeria monocytogenes* to invade non-phagocytic cells without significantly affecting the uptake of the *Listeria monocytogenes* by phagocytic cells. In one embodiment, the genetic mutation is in an internalin gene(s). In one embodiment, the *Listeria* mutation is in the gene selected from the group consisting of inlA, inlB, and any gene encoding an internalin. In one embodiment, the *Listeria monocytogenes* comprises a genetic mutation in both the inlA and inlB genes. In one embodiment, the *Listeria* comprises a mutation that results in the attenuation of the ability of the *Listeria* to escape the phagolysosome of an infected cell. In one embodiment, the *Listeria* mutation is in the hly gene. In one embodiment, the genetic mutation results in the attenuation of the polymerization of actin by the *Listeria*. In one embodiment, the *Listeria* mutation is in the actA gene. In one embodiment, the *Listeria monocytogenes* comprises more than one mutation. In a preferred embodiment, the *Listeria* mutations are in both the actA and inlB genes, preferably deletion mutations in both the actA and inlB genes. In a preferred embodiment, the *Listeria monocytogenes* actA/inlB deletion mutant further comprises a deletion mutation in the uvrAB gene.

In another aspect, the invention provides an isolated mutant *Listeria* strain, such as a mutant *Listeria monocytogenes* strain, comprising a genetic mutation that attenuates its ability to repair its nucleic acid. In some embodiments, the mutant *Listeria* strain is defective with respect to at least one DNA repair enzyme (such as UvrA and/or UvrB). In some embodiments, the mutant *Listeria* strain comprises a genetic mutation in the uvrA gene and/or the uvrB gene. In some embodiments, the mutant strain is defective with respect to UvrC. In some embodiments, the mutant strain is defective with respect to RecA. In some embodiments, the mutant strain is the *Listeria monocytogenes* actA$^-$/uvrAB$^-$ strain deposited with the American Type Culture Collection (ATCC) and identified by accession number PTA-5563. In other embodiments, the strain is a mutant of the *Listeria monocytogenes* actA$^-$/uvrAB$^-$ strain deposited with the American Type Culture Collection (ATCC) and identified by accession number PTA-5563, wherein the mutant of the deposited strain is defective with respect to UvrA, UvrB, and ActA. The invention further provides vaccines and professional antigen-presenting cells comprising the mutant *Listeria* strain. Methods of using the modified *Listeria* strain to induce immune responses and to prevent or treat disease are also provided.

In another aspect, the invention provides an isolated mutant *Bacillus anthracis* strain, comprising a genetic mutation that attenuates its ability to repair its nucleic acid. In some embodiments, the mutant strain is defective with respect to at least one DNA repair enzyme (such as UvrA and/or UvrB). In some embodiments, the mutant strain comprises a genetic mutation in the uvrA gene and/or the uvrB gene. In some embodiments, the mutant strain is defective with respect to RecA. In some embodiments, the mutant strain is defective with respect to UvrC. In some embodiments, the mutant strain comprises a genetic mutation in the recA gene. In some embodiments, the mutant strain comprises one or more mutations in the lef gene, cya gene, or both genes, that decreases the toxicity of the strain. The invention further provides vaccines and professional antigen-presenting cells comprising the mutant strain. Methods of using the modified *Bacillus anthracis* strain to induce immune responses and to prevent or treat disease are also provided.

In another aspect, the invention provides a professional antigen-presenting cell (e.g., a dendritic cell) comprising a free-living microbe (e.g., a bacterium), wherein the nucleic acid of the microbe is modified so that the microbe is attenuated for proliferation. In some embodiments, the attenuation of the proliferation of the microbe is controllable in a dose-dependent manner. In some embodiments, microbial gene expression in the microbe is substantially unaffected by attenuation of the proliferation of the microbe. In some embodiments, the microbe in the vaccine expresses an antigen at a sufficient level to induce an immune response to the antigen in an individual upon administration of the vaccine to the individual. In some embodiments, the nucleic acid has been modified by reaction with a nucleic acid targeted compound which reacts directly with the nucleic acid. In one embodiment, the nucleic acid target compound is an alkylator such as β-alanine, N-(acridin-9-yl), 2-[bis(2-chloroethyl)amino]ethyl ester. In other embodiments, the nucleic acid targeted compound is a psoralen compound (e.g., 4'-(4-amino-2-oxa)butyl-4,5',8-trimethylpsoralen, also referred to herein as "S-59") activated by UVA irradiation. In some embodiments, the microbe in the vaccine comprises a genetic mutation that attenuates the ability of the microbe to repair its nucleic acid that has been modified. In some embodiments, the microbe is a bacterium. In some embodiments, the microbe comprises a heterologous nucleic acid sequence encoding an antigen. The invention also provides a vaccine comprising the antigen-presenting cell. The invention further provides a method of preventing or treating a disease in a host, comprising administering to the host an effective amount of the antigen-presenting cell. The invention also provides a method of inducing an immune response in a host to an antigen comprising administering to the host an effective amount of the antigen-presenting cell, wherein the microbe expresses the antigen. The invention further provides a method of activating naïve T cells ex vivo and/or in vitro (not mutually exclusive), comprising contacting the naïve T cells with the professional antigen-presenting cell under suitable conditions and for a sufficient time to activate the naïve T-cells.

In another aspect, the invention provides an isolated professional antigen-presenting cell (e.g., a dendritic cell) comprising a free-living microbe (e.g., a bacterium) which is defective with respect to at least one DNA repair enzyme. In some embodiments, the microbe comprises a genetic mutation is in one or more gene selected from the group consisting of phrB, uvrA, uvrB, uvrC, uvrD and recA, or in a functional equivalent of one or more gene selected from the group consisting of phrB, uvrA, uvrB, uvrC, uvrD and recA. For instance, the microbe may comprise genetic mutations in both uvrA and uvrB, or in functional equivalents of both uvrA and uvrB (depending on the genus and species of the microbe). In some embodiments, the microbe in the antigen presenting cell is defective with respect to RecA, or the functional equivalent of RecA. In some embodiments, the microbe is defective with respect to UvrC (or the functional equivalent of UvrC, depending upon the genus and species of the microbe). In some embodiments, the microbe comprises a heterologous nucleic acid sequence encoding an antigen. Methods of preventing or treating a disease in a host, comprising administering to the host an effective amount of the antigen-presenting cell are also provided, as are methods of inducing an immune response in a host to an antigen comprising administering to the host an effective amount of the antigen-presenting cell, wherein the microbe expresses the antigen.

In another aspect, the invention provides a method of loading professional antigen-presenting cells with an antigen comprising contacting the professional antigen-presenting cells (in vitro or in vivo) with a free-living microbe that comprises a nucleic acid sequence encoding the antigen, under suitable conditions and for a sufficient time to load the professional antigen-presenting cells, wherein the nucleic acid of the microbe is modified (e.g., has been modified by reaction with a nucleic acid targeted compound that reacts directly with the nucleic acid) so that the microbe is attenuated for proliferation.

In still another aspect, the invention provides a method of activating and/or maturing professional antigen-presenting cells comprising contacting the professional antigen-presenting cells (in vitro or in vivo) with a free-living microbe that comprises a nucleic acid sequence encoding an antigen, under suitable conditions and for a sufficient time to load the professional antigen-presenting cells, wherein the nucleic acid of the microbe is modified (e.g., has been modified by reaction with a nucleic acid targeted compound that reacts directly with the nucleic acid) so that the microbe is attenuated for proliferation.

In yet another aspect, the invention provides a method of preventing or treating a disease in a host, comprising the following steps. (a) loading professional antigen-presenting cells with an antigen by contacting the cells with a free-living microbe that comprises a nucleic acid sequence encoding an antigen, wherein the nucleic acid of the microbe is modified so that the microbe is attenuated for proliferation; and (b) administering an effective amount of a composition comprising the loaded professional antigen-presenting cells to the host. In some embodiments, the microbe has been modified by reaction with a nucleic acid targeted compound that reacts directly with the nucleic acid.

In still another aspect, the invention provides a method of loading professional antigen-presenting cells, such as dendritic cells, with an antigen(s), comprising contacting the cells in vitro or ex vivo with a modified microbe expressing the antigen, under suitable conditions and for a time sufficient to load the antigen-presenting cells. In some embodiments, proliferation of the microbe is attenuated. In some embodiments, the microbe maintains sufficient gene expression to effect antigen presentation by the cell, even though proliferation of the microbe is attenuated. The antigen presentation can be MHC class I presentation or MHC class II presentation.

In another aspect, the invention provides a method of activating and/or maturing antigen-presenting cells (for instance, dendritic cells) comprising contacting the antigen-presenting cells in vitro or ex vivo with a modified microbe under suitable conditions and for a time sufficient to activate the dendritic cells and/or to allow the antigen-presenting cells to mature. In one embodiment, proliferation of the microbe is attenuated. In another embodiment, the microbe maintains sufficient gene expression to effect activation and/or maturation of the cell, even though proliferation of the microbe is attenuated.

In still another aspect, the invention provides a method of inducing an immune response to an antigen, comprising administering to the host an effective amount of an immunogenic composition comprising an antigen presenting cell (such as a dendritic cell) presenting the antigen, wherein the antigen-presenting cell comprises a modified microbe. In one embodiment, proliferation of the microbe has been attenuated. In another embodiment, the microbe maintains sufficient gene expression to effect antigen presentation by the cell, even though proliferation of the microbe is attenuated. In one embodiment, the immune response is a $CD8^+$ T-cell response. In another embodiment, the immune response is a $CD4^+$ T-cell response.

In yet another aspect, the invention provides a method of inducing an immune response to an antigen, comprising the following steps: (a) contacting antigen-presenting cells (such as dendritic cells) in vitro or ex vivo with Listeria expressing the antigen under suitable conditions and for a time sufficient to load the antigen-presenting cells with the antigen and to effect activation and/or maturation of the antigen-presenting cells; and (b) administering an effective amount of the antigen-presenting cells to the host. In one embodiment, proliferation of the microbe is attenuated. In another embodiment, the microbe which is contacted with the antigen-presenting cells maintains sufficient gene expression to effect both presentation of the antigen on the antigen-presenting cell and activation and/or maturation of the antigen-presenting cell, even though proliferation of the microbe is attenuated. In one embodiment, the immune response is a $CD8^+$ T-cell response. In another embodiment, the immune response is a $CD4^+$ T-cell response.

In another aspect, the invention provides an ex vivo or in vitro professional antigen-presenting cell comprising a modified microbe, wherein proliferation of the microbe is attenuated. In another embodiment, the modified microbe maintains sufficient gene expression to effect antigen presentation by the dendritic cell, even though proliferation of the microbe is attenuated. In one embodiment, the antigen-presenting cell is a dendritic cell.

In yet another aspect, the invention provides a vaccine comprising an antigen-presenting cell (such as a dendritic cell), wherein the antigen-presenting cell comprises a modified microbe. In some embodiments, the microbe is a bacterium. In some embodiments, the microbe is Listeria. In one embodiment, proliferation of the Listeria has been attenuated. In another embodiment, the Listeria maintains sufficient gene expression to effect antigen presentation on the cell, even though proliferation of the Listeria is attenuated.

In a still further aspect, the invention provides a pharmaceutical composition comprising an antigen-presenting cell (such as a dendritic cell) and a pharmaceutically acceptable carrier, wherein the antigen-presenting cell comprises modified Listeria. In one embodiment, proliferation of the Listeria has been attenuated. In another embodiment, the Listeria maintains sufficient gene expression to effect antigen presentation by the cell, even though proliferation of the Listeria is attenuated.

In some embodiments of each of the aforementioned aspects, the modified microbe is a modified bacterium. In some embodiments of each of the aforementioned aspect, the modified microbe is an intracellular bacterium.

In some embodiments of each of the aforementioned aspects, the modified microbe is a modified Listeria. In additional embodiments of each of the aforementioned aspects, the Listeria is Listeria monocytogenes. In still further embodiments, the Listeria comprises a mutation in one or more genes selected from the group consisting of phrB, uvrA, uvrB, uvrC, uvrD, and recA. For instance, in any of the aforementioned aspects, the Listeria optionally comprises a mutation in uvrAB. In alternative embodiments, the Listeria optionally comprises both a mutation in uvrAB and actA.

In other embodiments of each of the aforementioned aspects, the attenuation of the *Listeria* has been effected by exposure of the *Listeria* to a cross-linking agent. In some embodiments of each of the aforementioned aspects, the cross-linking agent is β-alanine, N-(acridin-9-yl), 2-[bis(2-chloroethyl)amino]ethyl ester. In other embodiments of each of the aforementioned aspects, the cross-linking agent is a psoralen derivative and the *Listeria* is exposed to UVA light. In some embodiments of each of the aforementioned aspects, the cross-linking agent is 4'-(4-amino-2-oxa)butyl-4,5',8-trimethylpsoralen (also referred to herein as "S-59").

In one aspect, the invention provides a vaccine comprising a *Listeria monocytogenes* bacterium that has been modified by reaction with a nucleic acid targeted compound that reacts directly with the nucleic acid so that the bacterium is attenuated for proliferation and that is defective with respect to at least one DNA repair enzyme. The invention further provides a method of inducing an immune response in a host to an antigen comprising administering to the host an effective amount of the vaccine, wherein the bacterium expresses the antigen.

The invention also provides a vaccine comprising a *Listeria monocytogenes* bacterium that has been modified by reaction with a nucleic acid targeted compound that reacts directly with the nucleic acid so that the bacterium is attenuated for proliferation and that is defective with respect to both UvrA and UvrB. In addition, the invention provides a method of inducing an immune response in a host to an antigen comprising administering to the host an effective amount of the vaccine, wherein the bacterium expresses the antigen.

The invention further provides a vaccine comprising a *Bacillus anthracis* bacterium that has been modified by reaction with a nucleic acid targeted compound that reacts directly with the nucleic acid so that the bacterium is attenuated for proliferation and that is defective with respect to both UvrA and UvrB. The invention also provides a method of inducing an immune response in a host to an antigen comprising administering to the host an effective amount of the vaccine, wherein the bacterium expresses the antigen.

Also provided is a vaccine comprising a bacterium, wherein the bacterium has been modified by reaction with a nucleic acid targeted compound that reacts directly with its nucleic acid so that the bacterium is attenuated for proliferation and wherein the bacterium is defective with respect to at least one DNA repair enzyme. In some embodiments, the bacterium is *Listeria monocytogenes*. In some embodiments, the bacterium is *Bacillus anthracis*. In some embodiments, the bacterium is defective with respect to both UvrA and UvrB (e.g., a uvrAB deletion mutant). In some embodiments, the bacterium is defective with respect to UvrC. In some embodiments, the bacterium is defective with respect to RecA. Methods of inducing an immune response in a host to an antigen comprising administering to the host an effective amount of the vaccine, wherein the bacterium expresses the antigen, are also provided.

In another aspect, the invention provides a vaccine comprising an antigen-presenting cell, wherein the antigen-presenting cell comprises a bacterium, wherein the bacterium has been modified by reaction with a nucleic acid targeted compound that reacts directly with its nucleic acid so that the bacterium is attenuated for proliferation and wherein the bacterium is defective with respect to at least one DNA repair enzyme. In some embodiments, the bacterium is *Listeria monocytogenes*. In some embodiments, the bacterium is defective with respect to both UvrA and UvrB (e.g., a uvrAB deletion mutant). In some embodiments, the bacterium is defective with respect to UvrC. In some embodiments, the bacterium is defective with respect to RecA. Methods of preventing or treating disease in a host, comprising administering an effective amount of the vaccine to the host, are also provided.

Methods of making vaccine compositions comprising the modified microbes described herein are also provided.

DRAWINGS

Figure 6A:
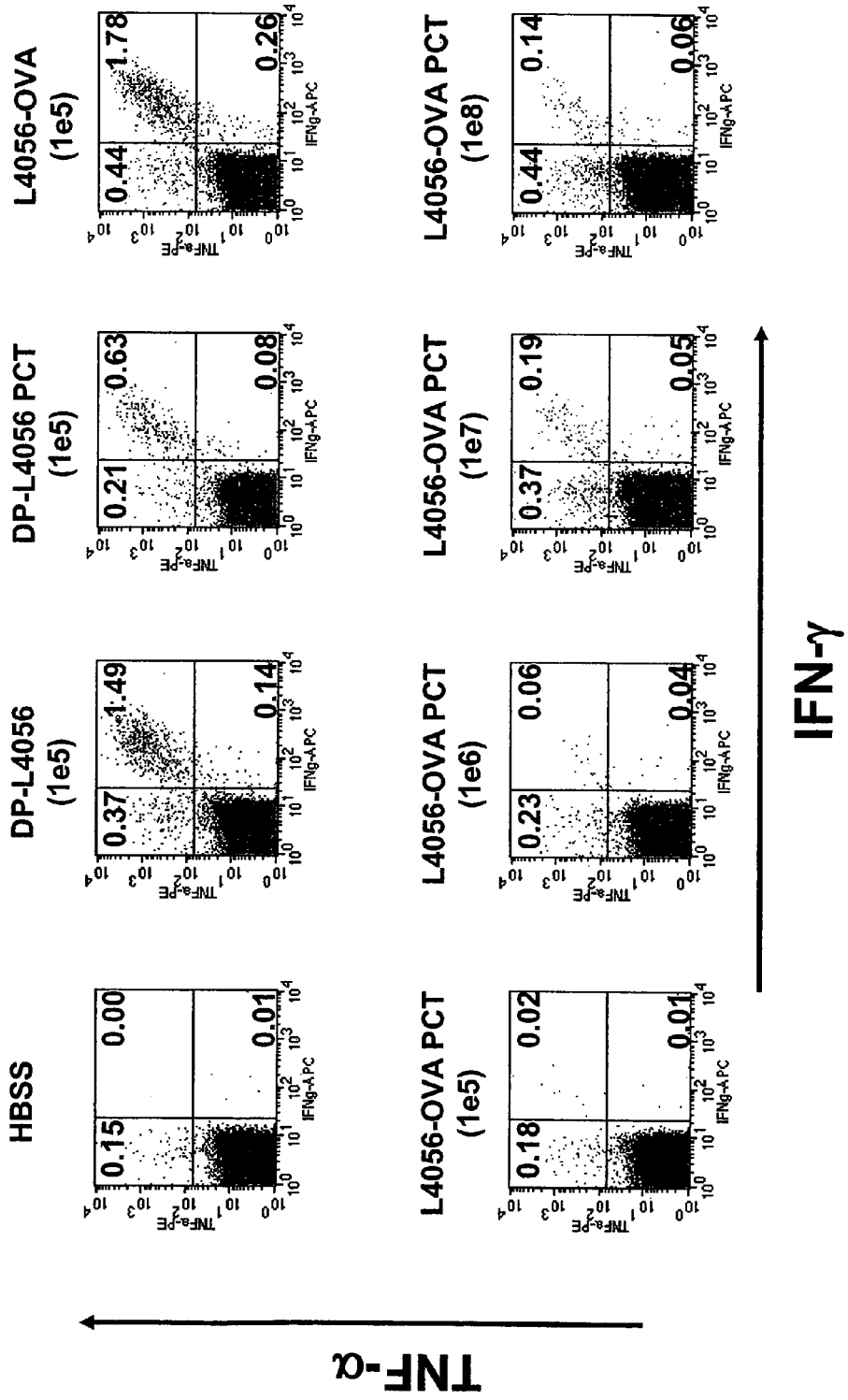
Figure 6B:
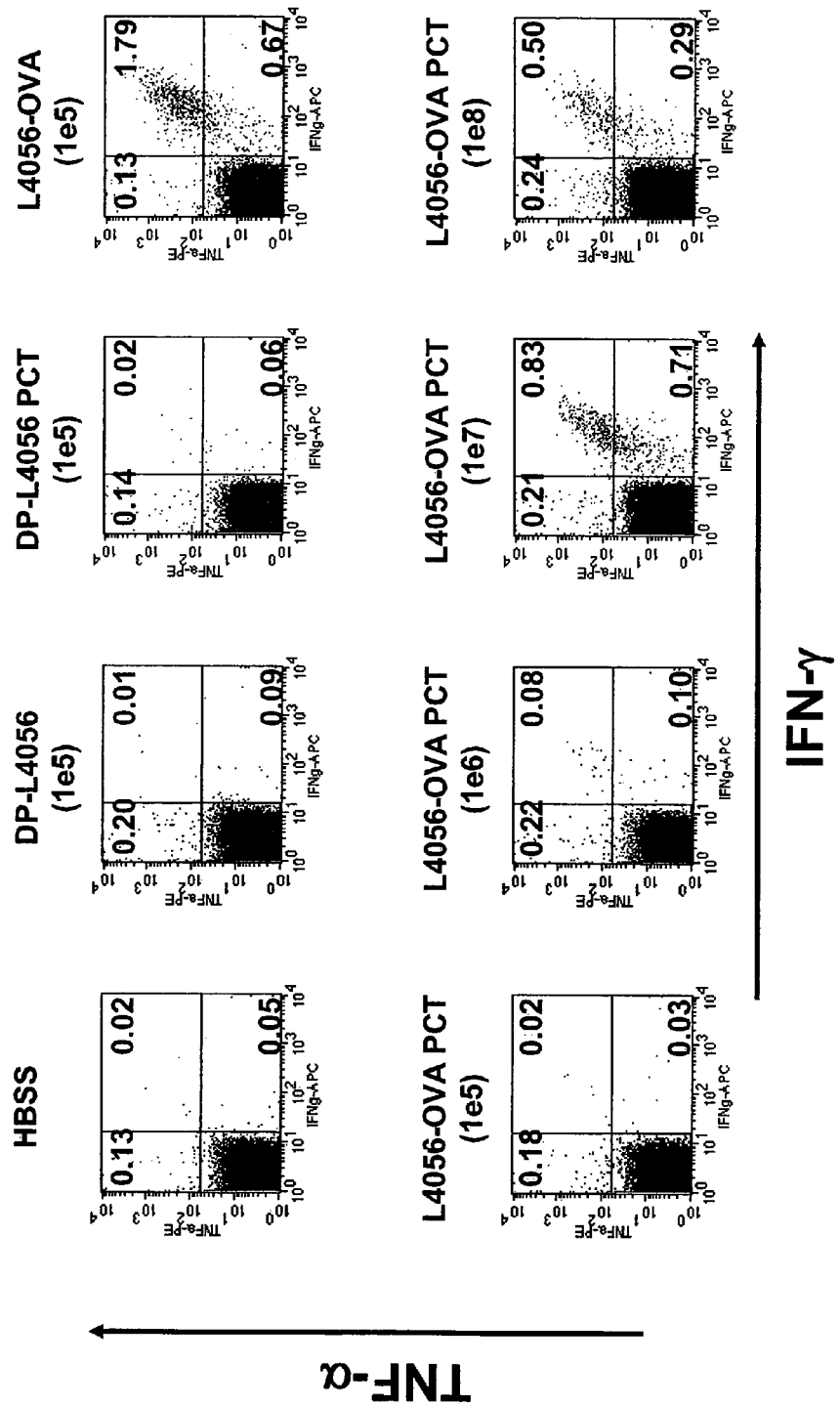

FIG. 6 shows flow cytometry results showing a population of spleen cells that are TNF-α and IFN-γ positive from mice vaccinated with wild type *Listeria* with and without OVA expression, with and without S-59 UVA treatment (PCT). FIG. 6A shows the population of cells specific for LLO$_{190-210}$. FIG. 6B shows the population of cells specific for OVA.

Figure 7:
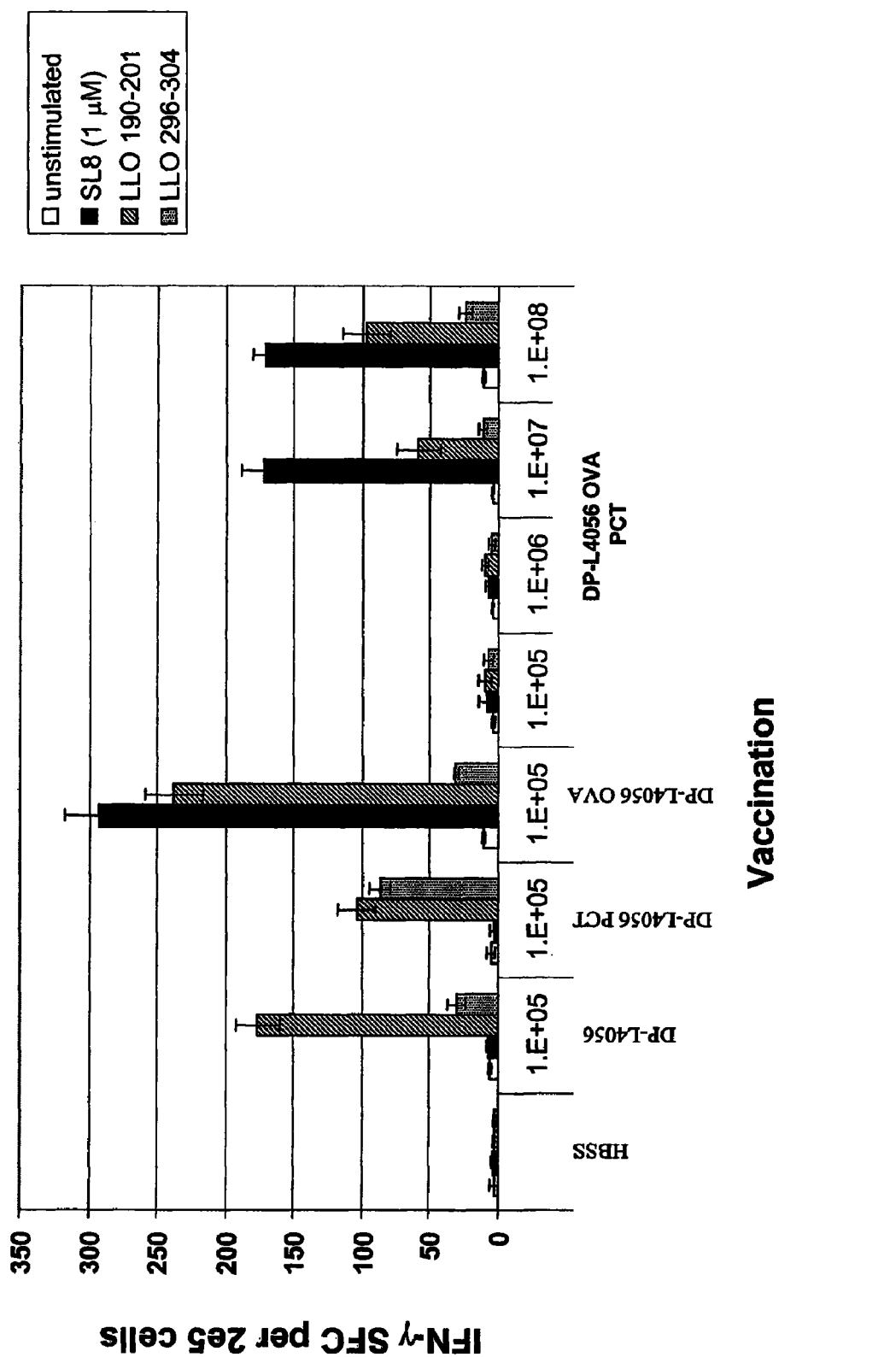

FIG. 7 shows ELISPOT results showing the number of IFN-γ spot forming cells per 2×10$^5$ spleen cells upon stimulation with either SL8, LLO$_{190-201}$, or LLO$_{296-304}$, from mice vaccinated with the indicated wild type *Listeria* strains with or without S-59 UVA treatment (PCT).

Figure 8A:
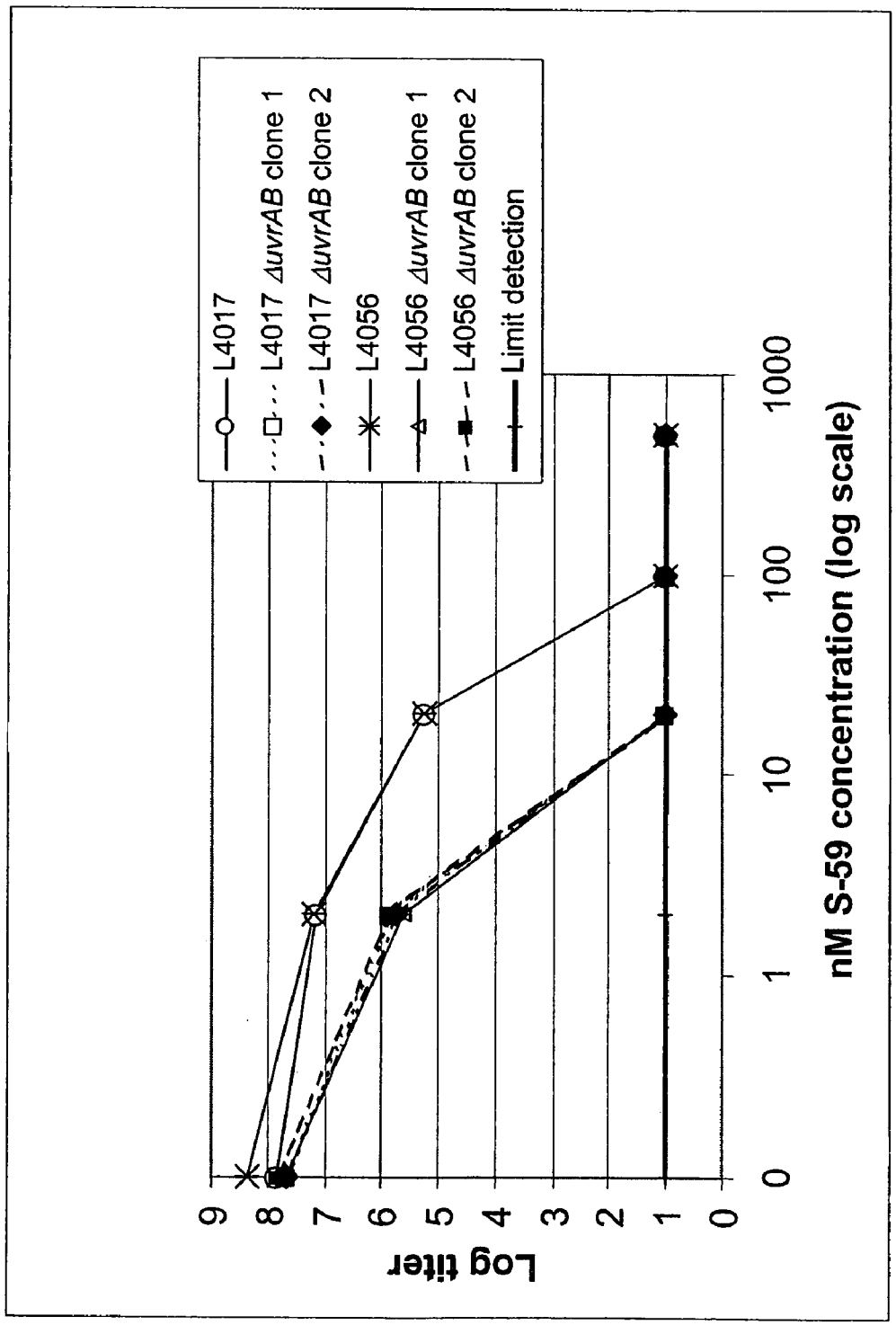
Figure 8B:
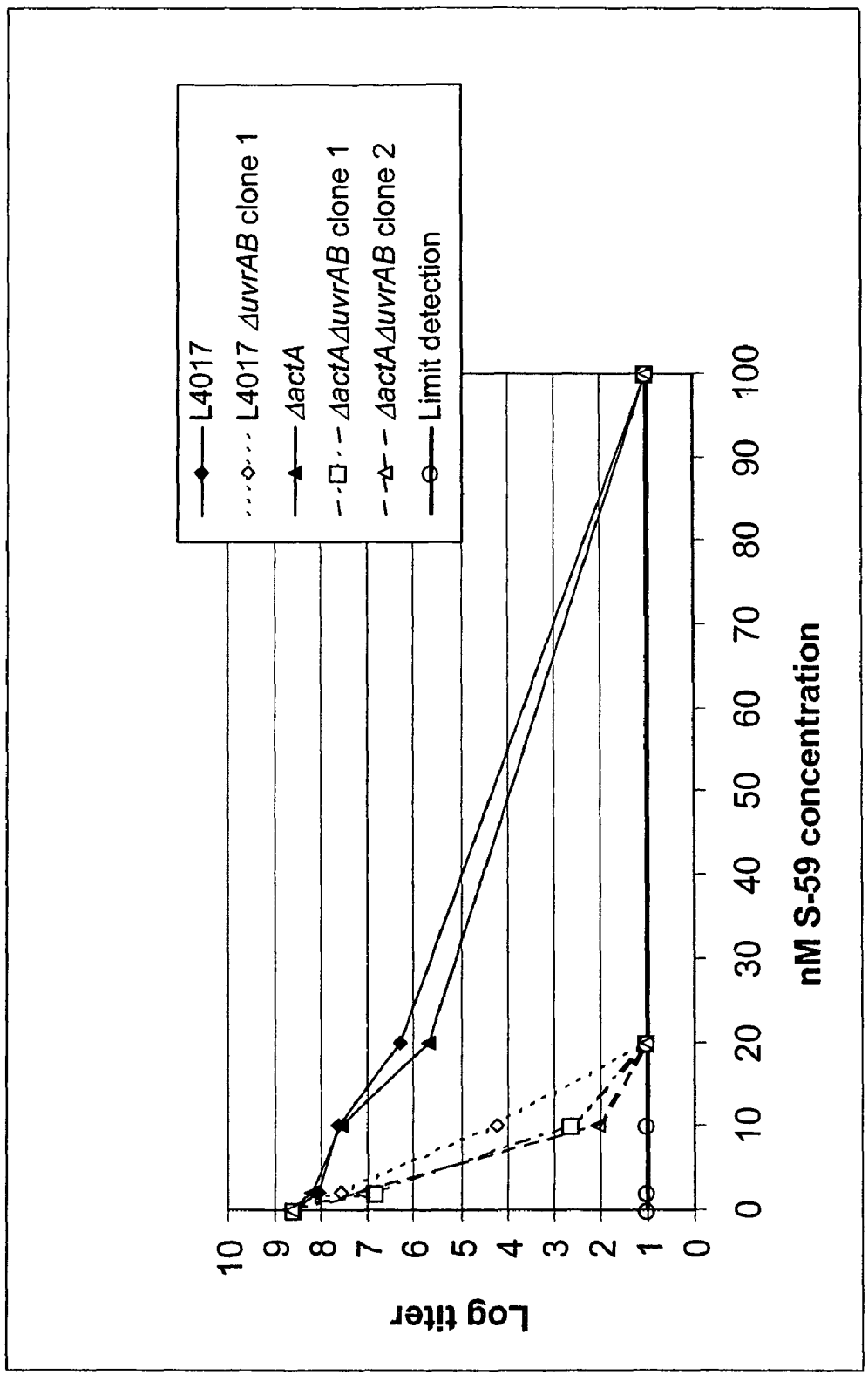
Figure 9A:
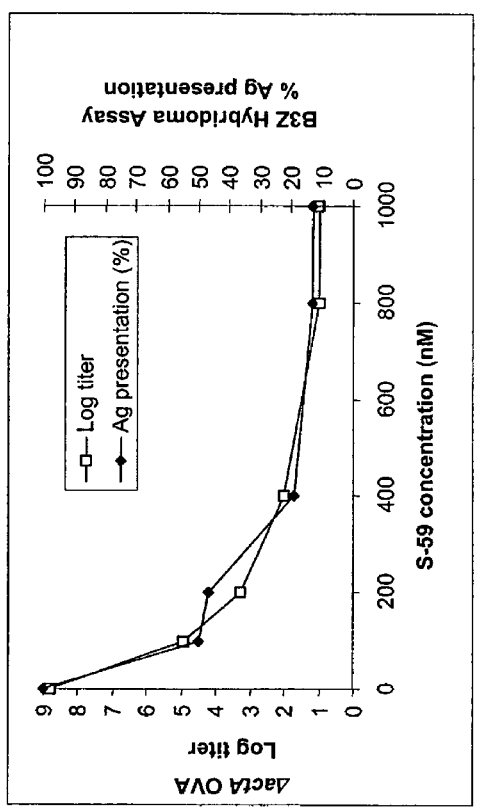
Figure 9B:
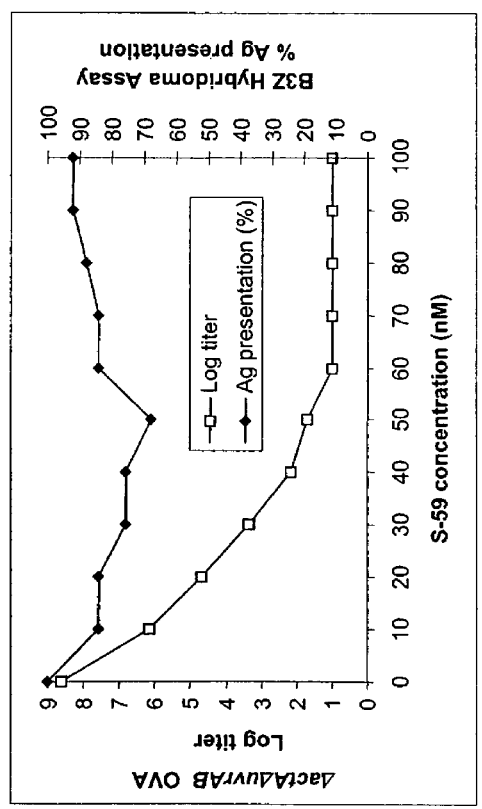
Figure 9C:
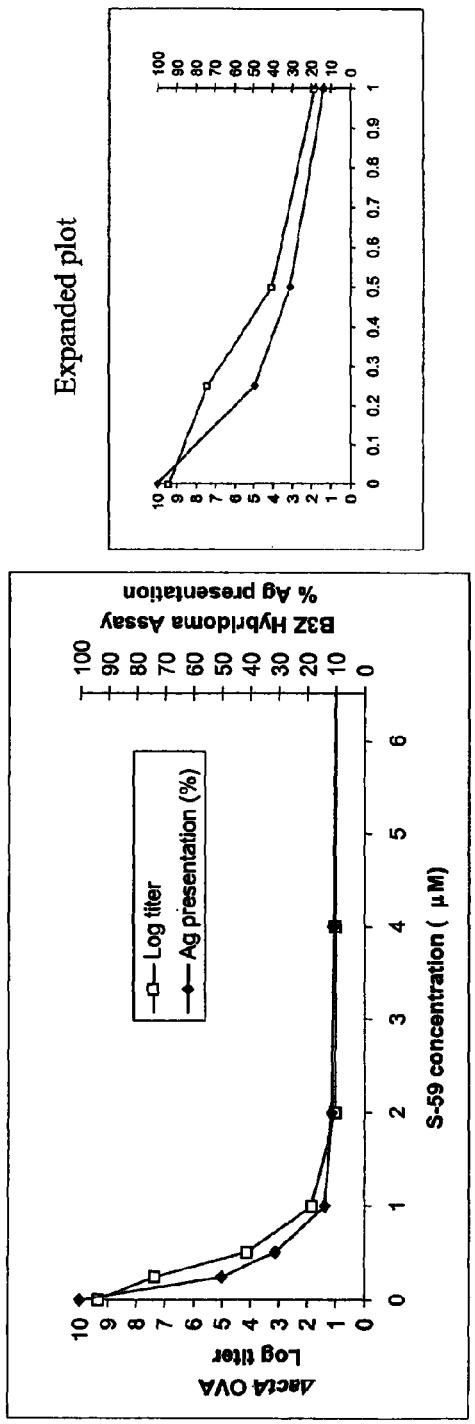
Figure 9D:
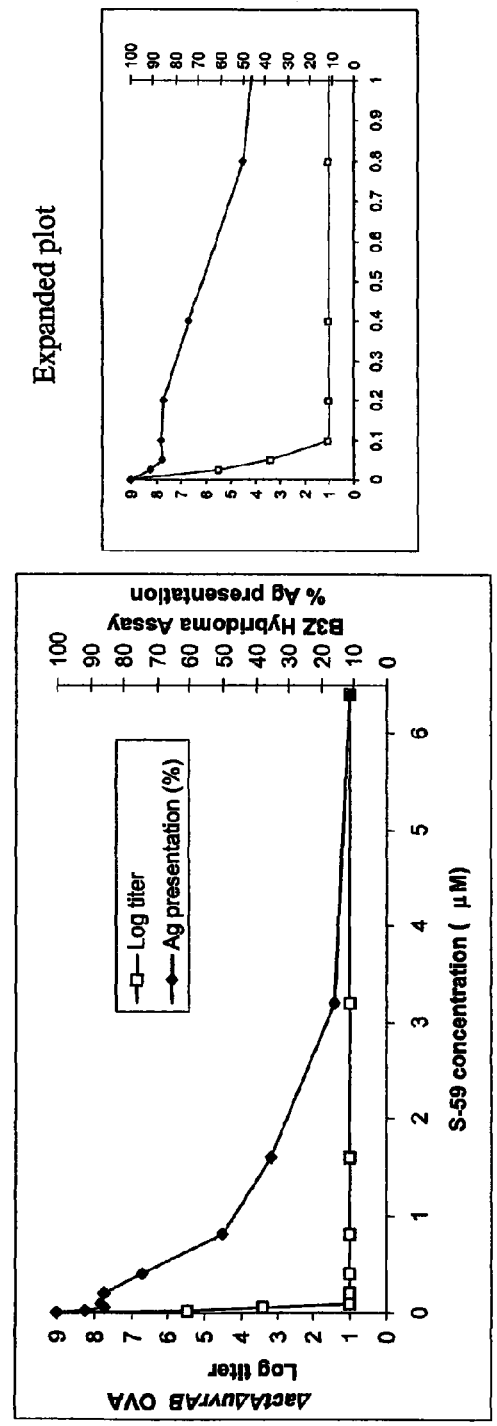

FIG. 8 shows the attenuation of *Listeria* strains with and without deletion of uvrAB. The log titer is plotted vs. nM concentration of psoralen S-59 used (6 J/cm$^2$). FIG. 8A, strains DP-L4017(L461T LLO mutant) and wild type (DP-L4056). FIG. 8B, strains DP-L4017 and DP-L4029 (ΔactA).

FIG. 9 shows the attenuation of DP-L4029 (ΔactA) *Listeria* strain containing OVA antigen as a function of psoralen S-59 concentration along with the measurement of OVA antigen presentation to a dendritic cell line. The parent strain (in this case, ΔactA; 9A, 9C) is compared to the strain with a uvrAB deletion (ΔuvrAB; 9B, 9D). The bacterial log titer and % of antigen presentation relative to untreated are plotted vs. mM S-59. FIGS. 9A, 9B, dosed with 0.5 J/cm$^2$ UVA, washed *Listeria* once, dosed again with 5.5 J/cm$^2$ UVA, antigen presentation measured at 1 *Listeria* per DC 2.4 cell. FIGS. 9C, 9D, *Listeria* was grown in the presence of S-59, then dosed with 6 J/cm$^2$ UVA, antigen presentation measured at 10 *Listeria* per DC 2.4 cell. (Expanded plots of the data are also provided in FIGS. 9C and 9D.)

Figure 10:
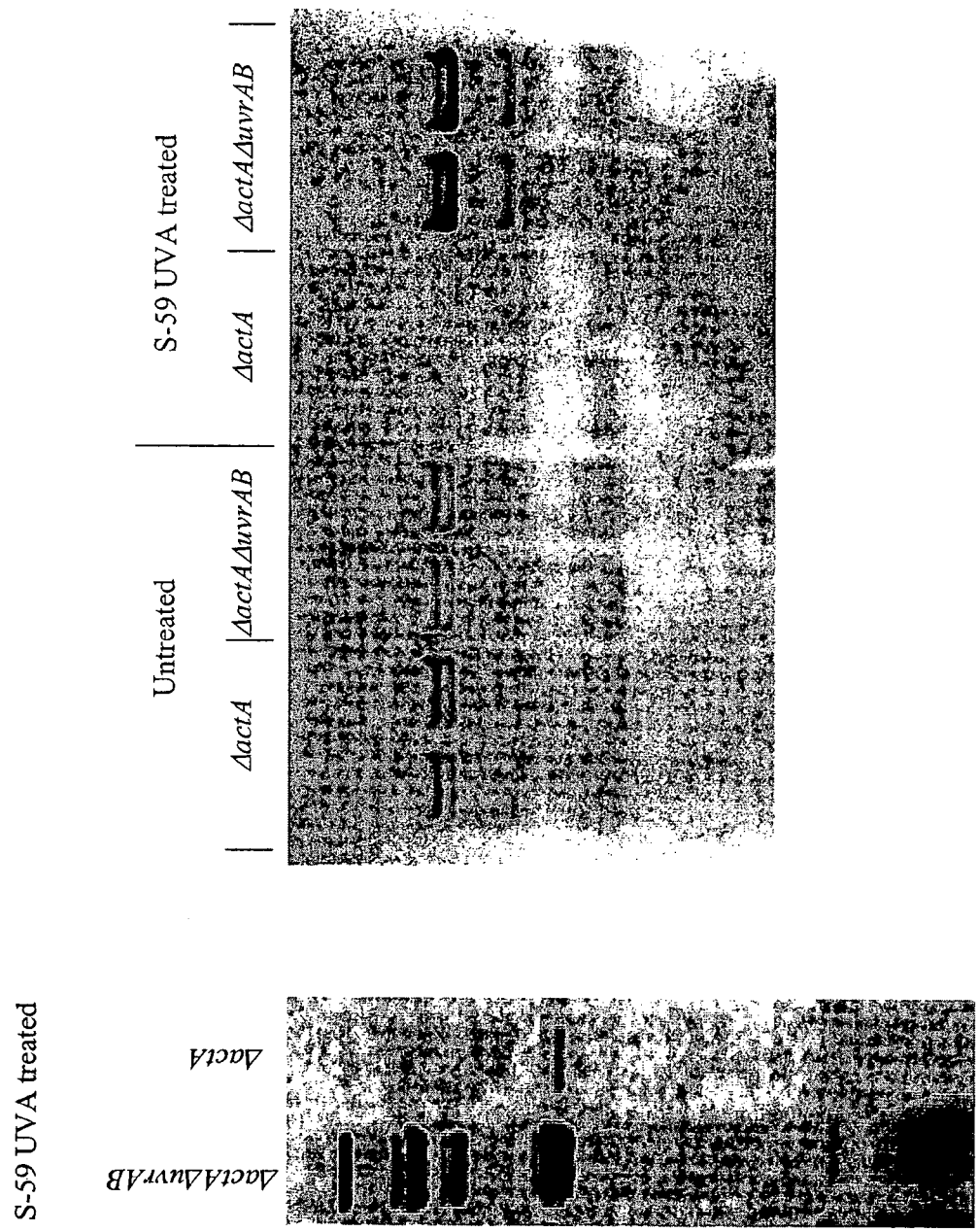

FIG. 10 shows polyacrylamide gels of $^{35}$S methionine/cysteine incorporated into protein synthesized by S-59/UVA treated *Listeria monocytogenes* strains DP-L4029 (ΔactA) and DP-L4029 uvrAB (ΔactAΔuvrAB).

Figure 11A:
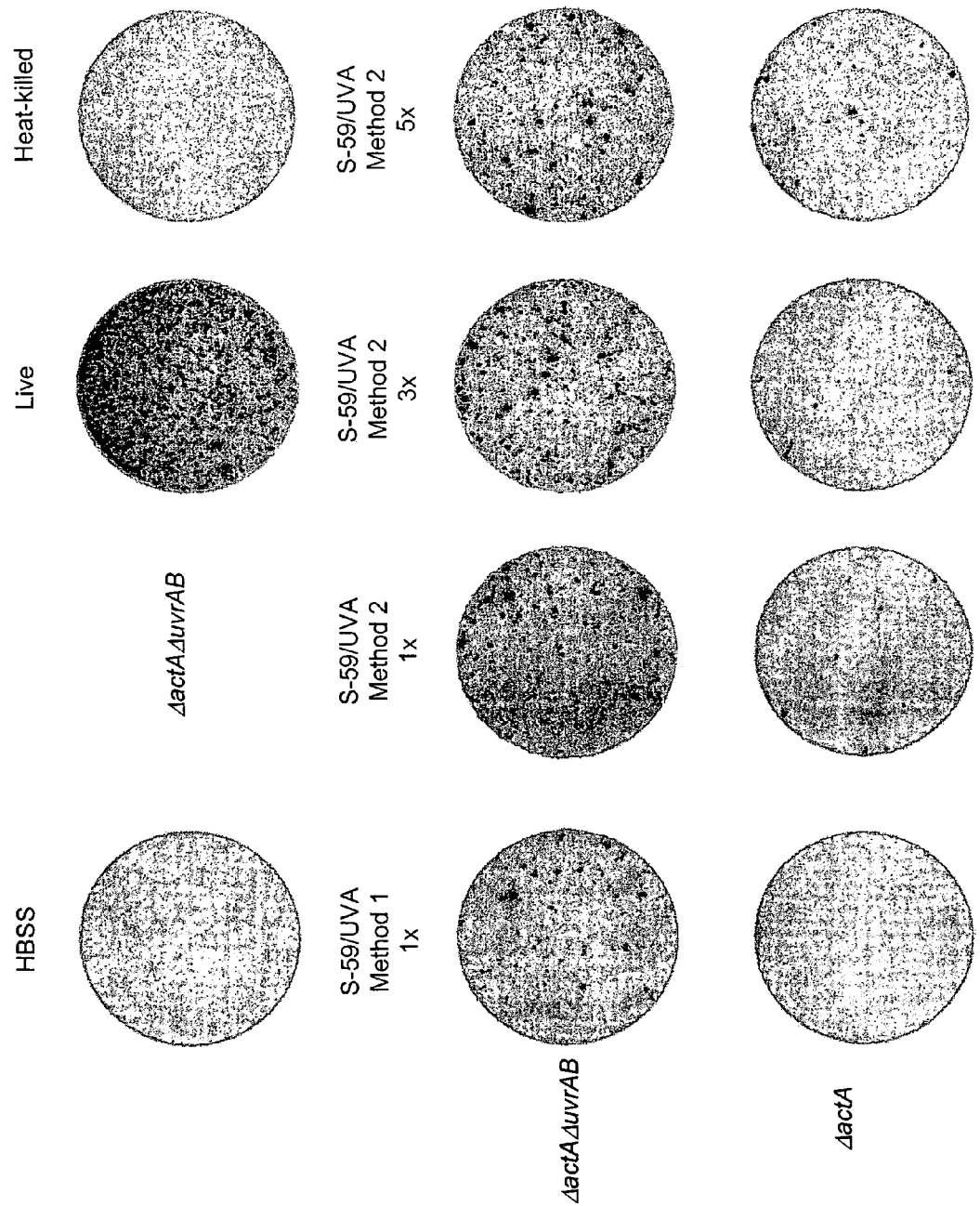
Figure 11B:
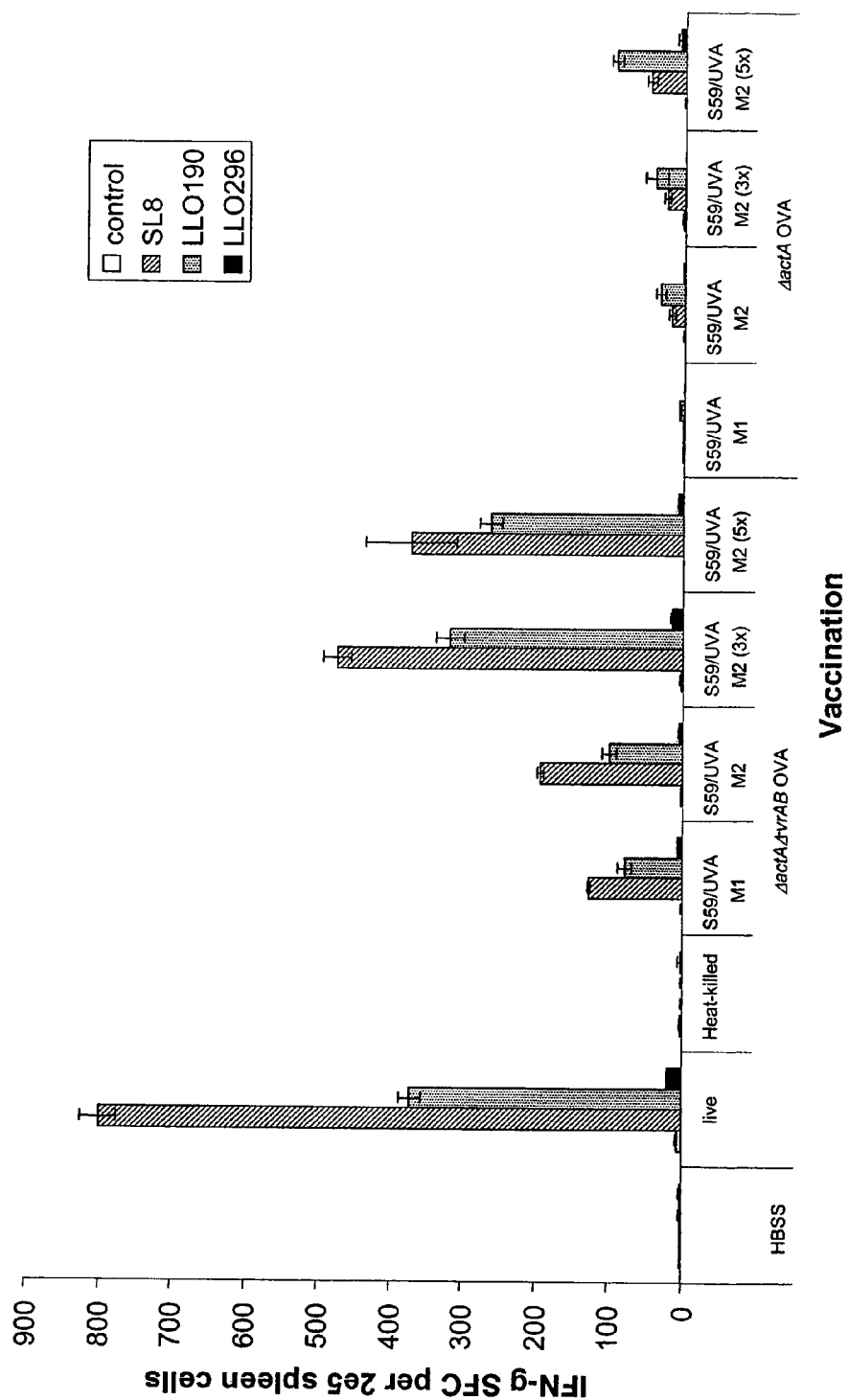

FIG. 11 shows the ELISPOT assay for spleen cells from mice vaccinated with 59/UVA treated (two methods) *Listeria monocytogenes* strains DP-L4029(ΔactA)-OVA or ΔactAΔuvrAB-OVA, stimulated with OVA specific antigen SL8, LLO specific antigens LLO 190 and LLO 296. FIG. 11A shows spot forming colonies on plates stimulated with OVA specific antigen, FIG. 11B plots the IFN-γ spot forming cells per $2 \times 10^5$ spleen cells for all three antigens.

FIG. 12 shows the Intracellular Cytokine Staining (ICS) assay for spleen cells from mice vaccinated with S-59/UVA treated (two methods) *Listeria monocytogenes* strains DP-L4029(ΔactA)-OVA or ΔactAΔuvrAB-OVA, stimulated with OVA derived T cell epitope SL8 (12A), LLO specific class II antigen $LLO_{190-201}$ (12B), or LLO specific class I antigen $LLO_{296-304}$ (12C). The S-59/UVA treated *Listeria* are marked "PCT" (stands for photochemical treatment) in the figure.

Figure 13A:
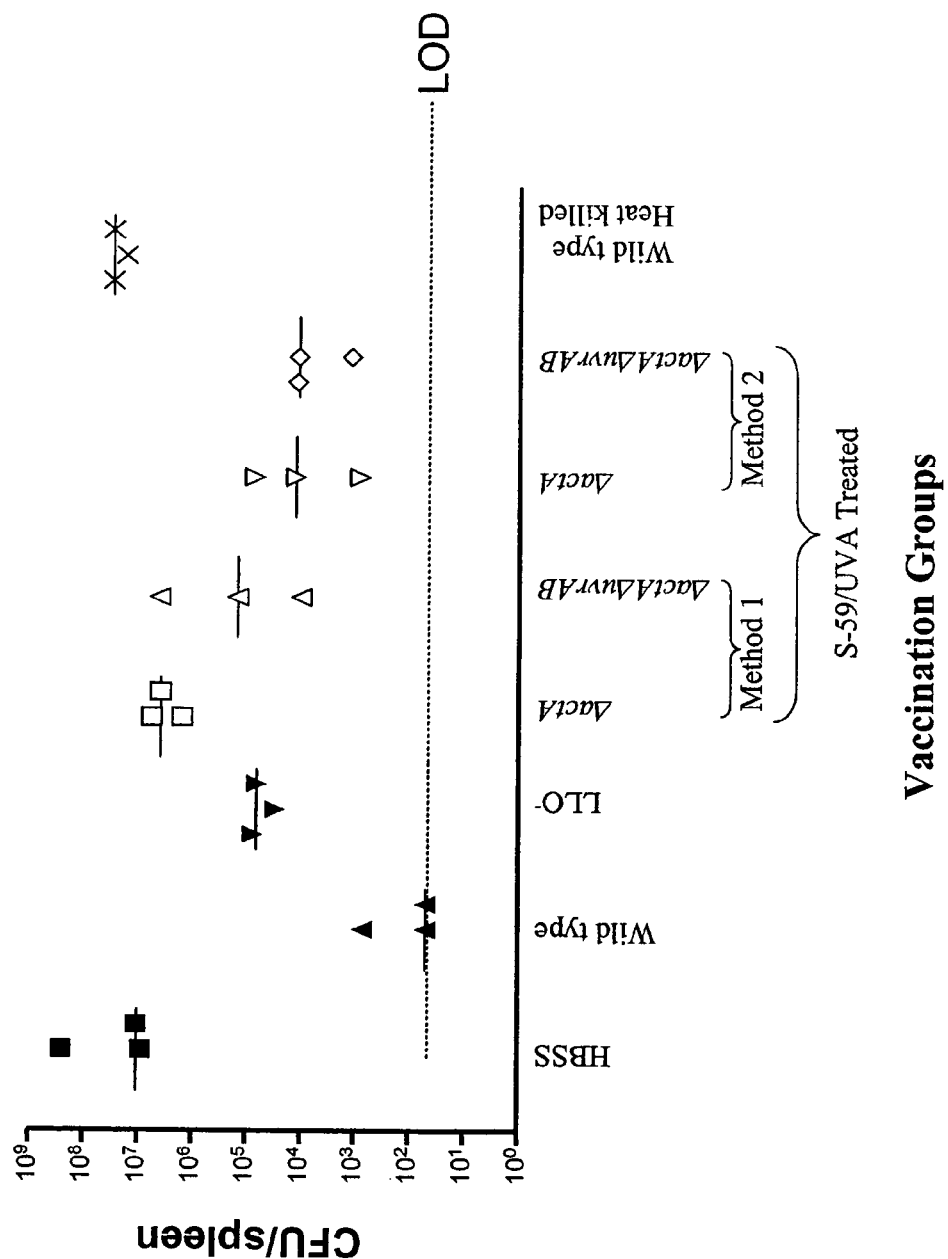
Figure 13B:
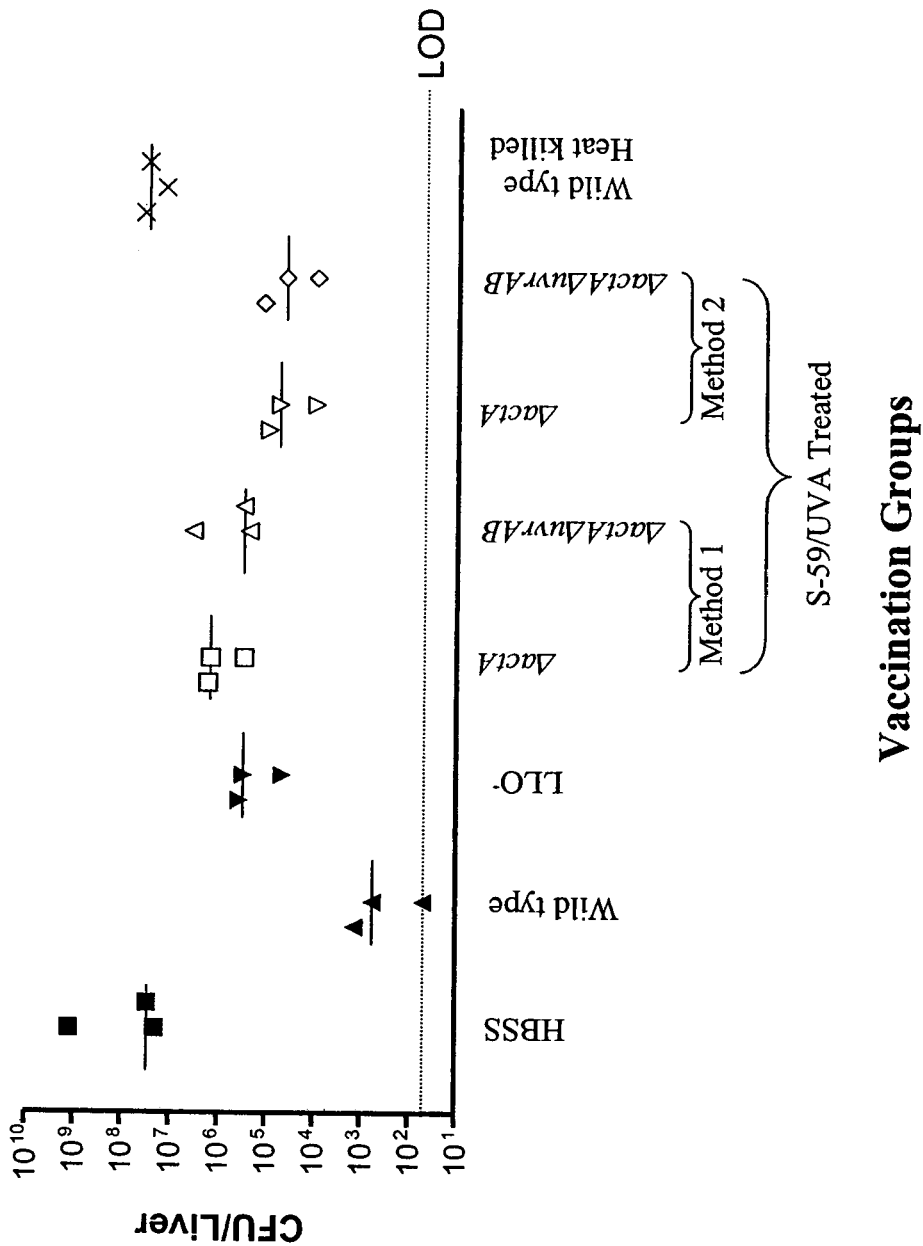

FIG. 13 shows the number of colony forming units isolated per spleen (13A) or liver (13B) from mice vaccinated with S-59/UVA treated (two methods) *Listeria monocytogenes* strains DP-L4029(ΔactA) or ΔactAΔuvrAB and challenged with wild type *Listeria monocytogenes* thirty days after vaccination.

Figure 14A:
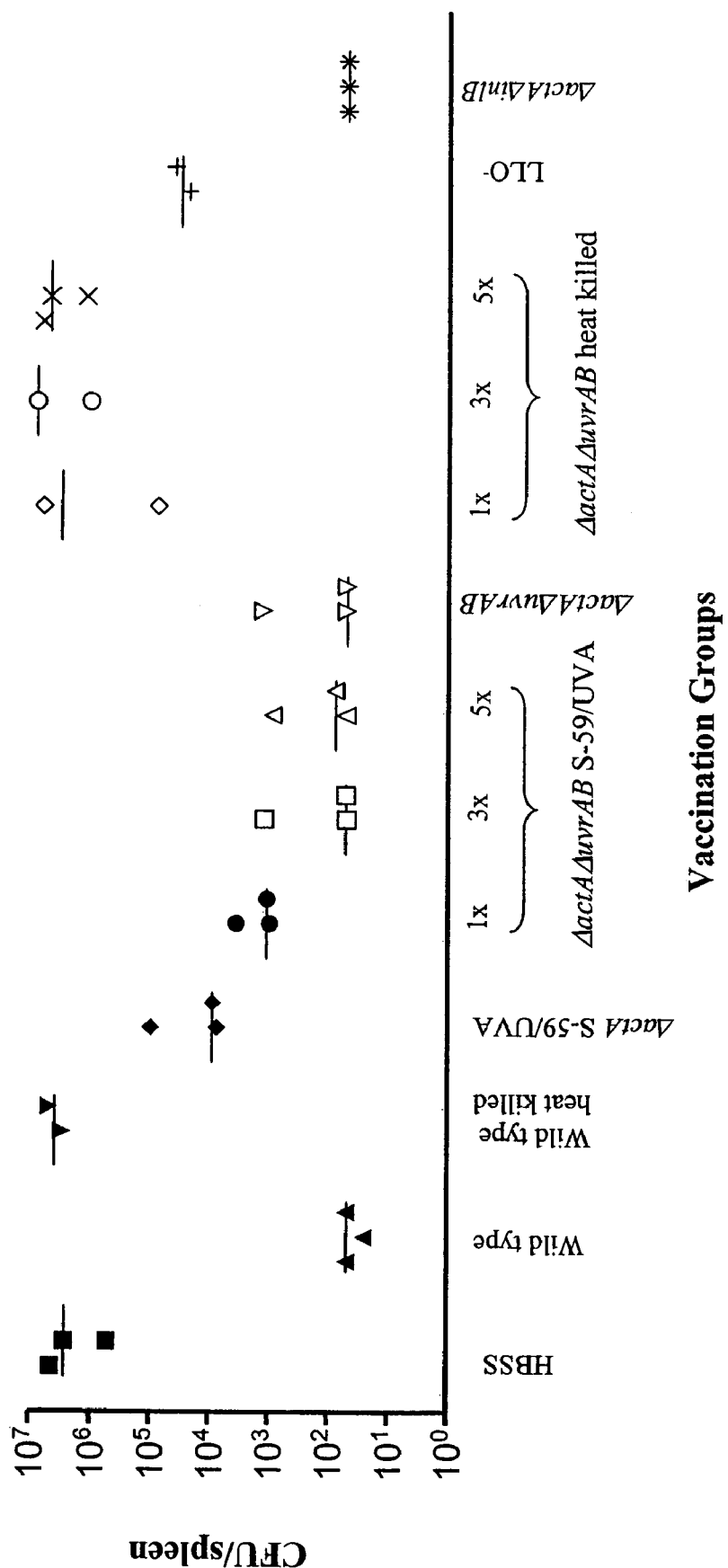
Figure 14B:
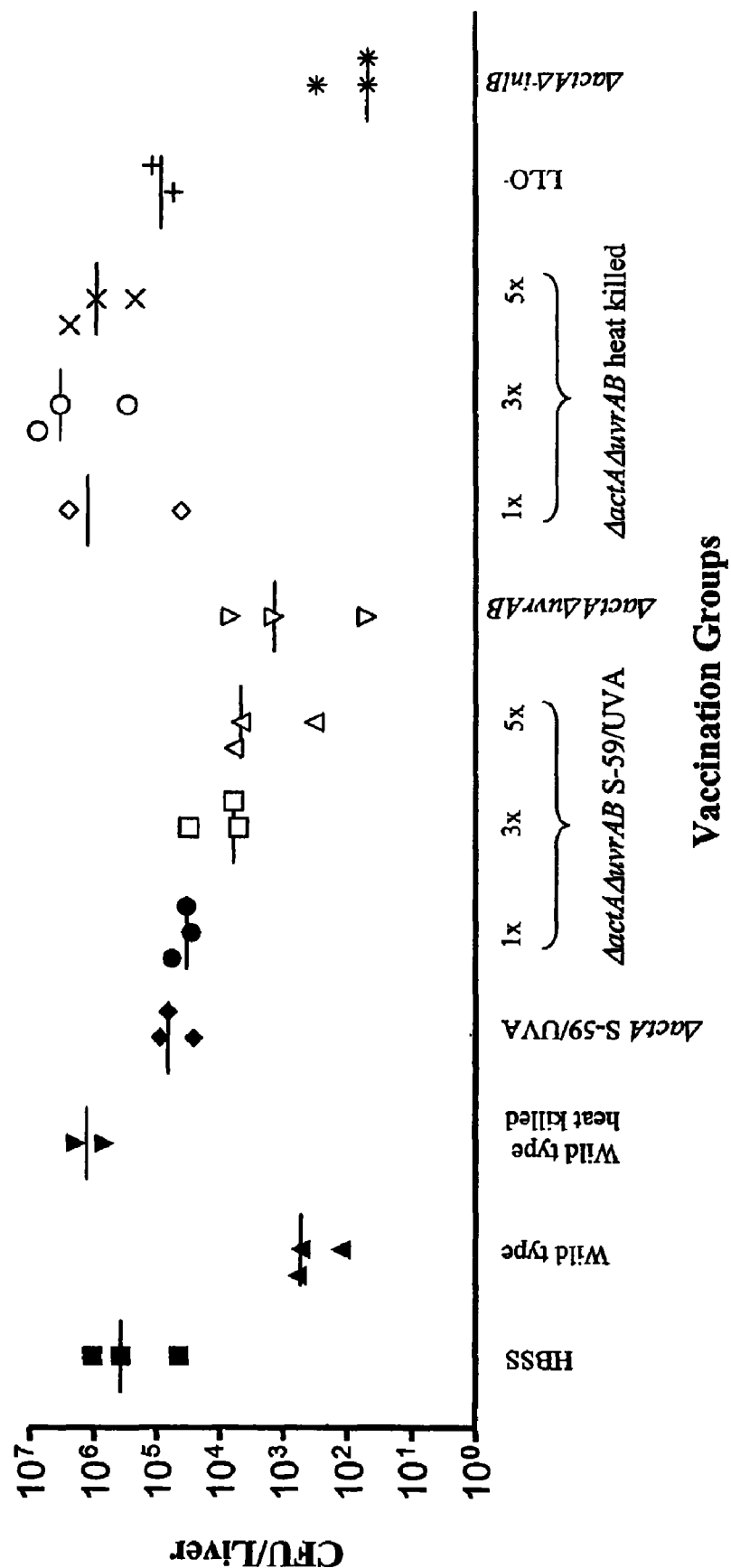

FIG. 14 shows the number of colony forming units isolated per spleen (14A) or liver (14B) from mice vaccinated with S-59/UVA treated (grown with psoralen, then UVA treated) *Listeria monocytogenes* strains DP-L4029(ΔactA) or DP-L4029 ΔactAΔuvrAB (1×, 3×, or 5× vaccination) and challenged with wild type *Listeria monocytogenes* thirty days after vaccination.

Figure 15:
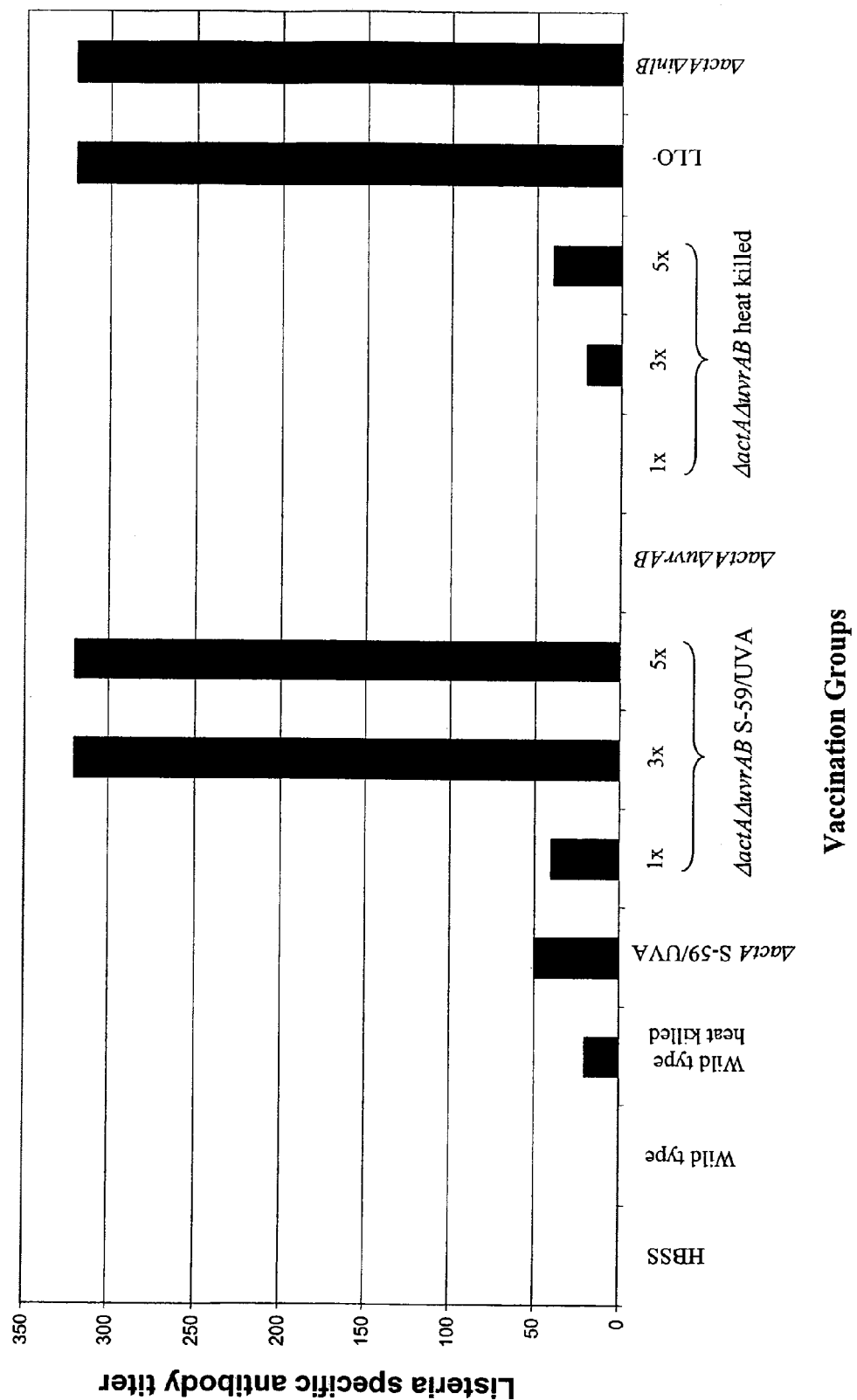

FIG. 15 shows the antibody titer of *Listeria* specific antibodies from serum of mice vaccinated with S-59/UVA treated (grown with psoralen, then UVA treated) *Listeria monocytogenes* strains DP-L4029(ΔactA) or ΔactAΔuvrAB (1×, 3×, or 5× vaccination).

Figure 16:
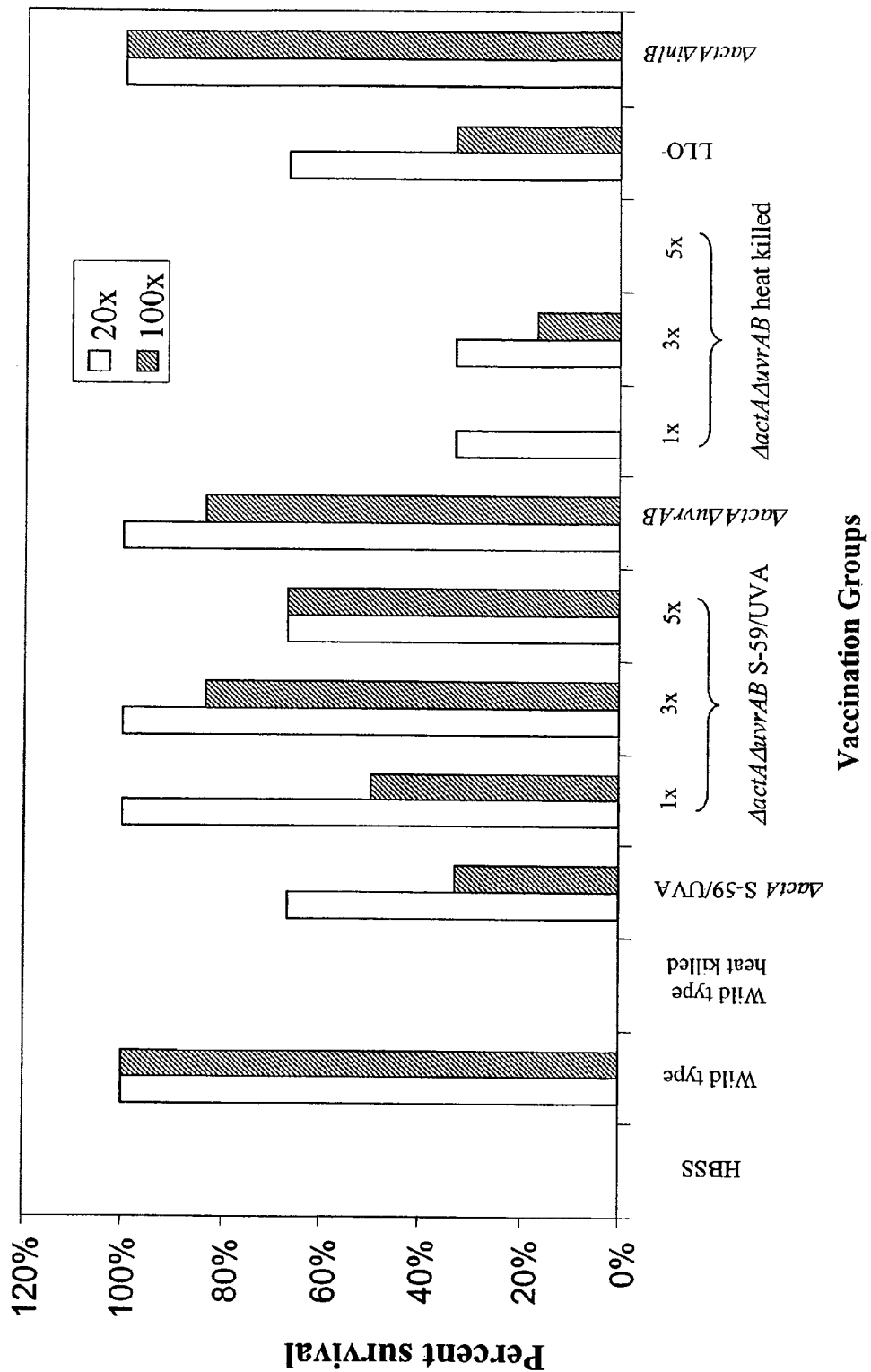

FIG. 16 shows the percent survival (10 days post challenge) of mice vaccinated with S-59/UVA treated (grown with psoralen, then UVA treated) *Listeria monocytogenes* strains DP-L4029(ΔactA) or ΔactAΔuvrAB (1×, 3×, or 5× vaccination) and challenged with $20 \times LD_{50}$ or $100 \times LD_{50}$ wild type *Listeria monocytogenes* thirty days after vaccination.

Figure 17:
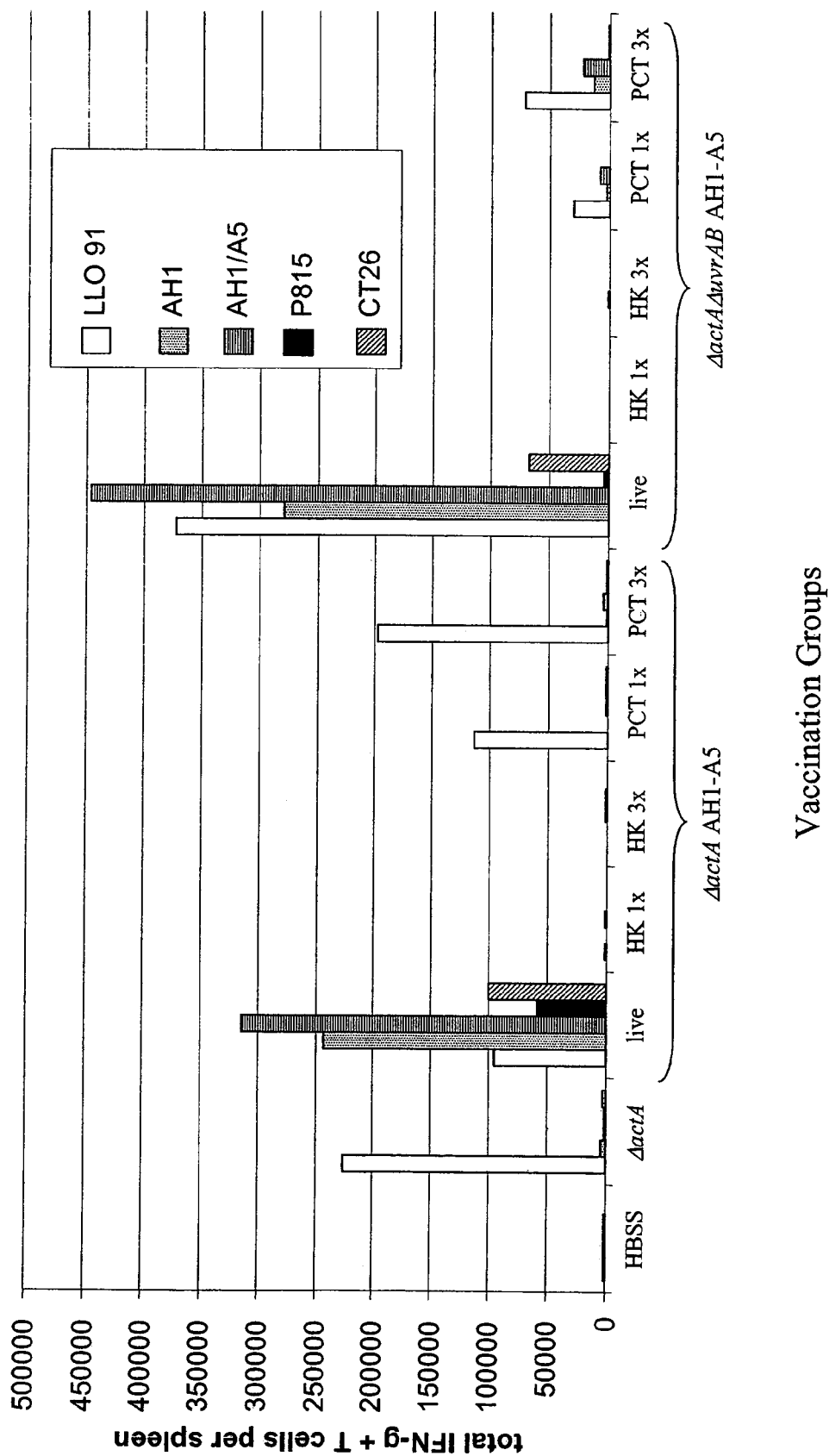

FIG. 17 shows the results of an ICS assay for spleen cells from mice vaccinated with S-59/UVA treated (grown with psoralen, then UVA treated) *Listeria monocytogenes* strains DP-L4029(ΔactA)-OVA AH1A5 or ΔactAΔuvrAB-OVA AH1A5, stimulated with antigens LLO91, AH1, AH1A5, or cells P815 or CT26 cells.

Figure 18A:
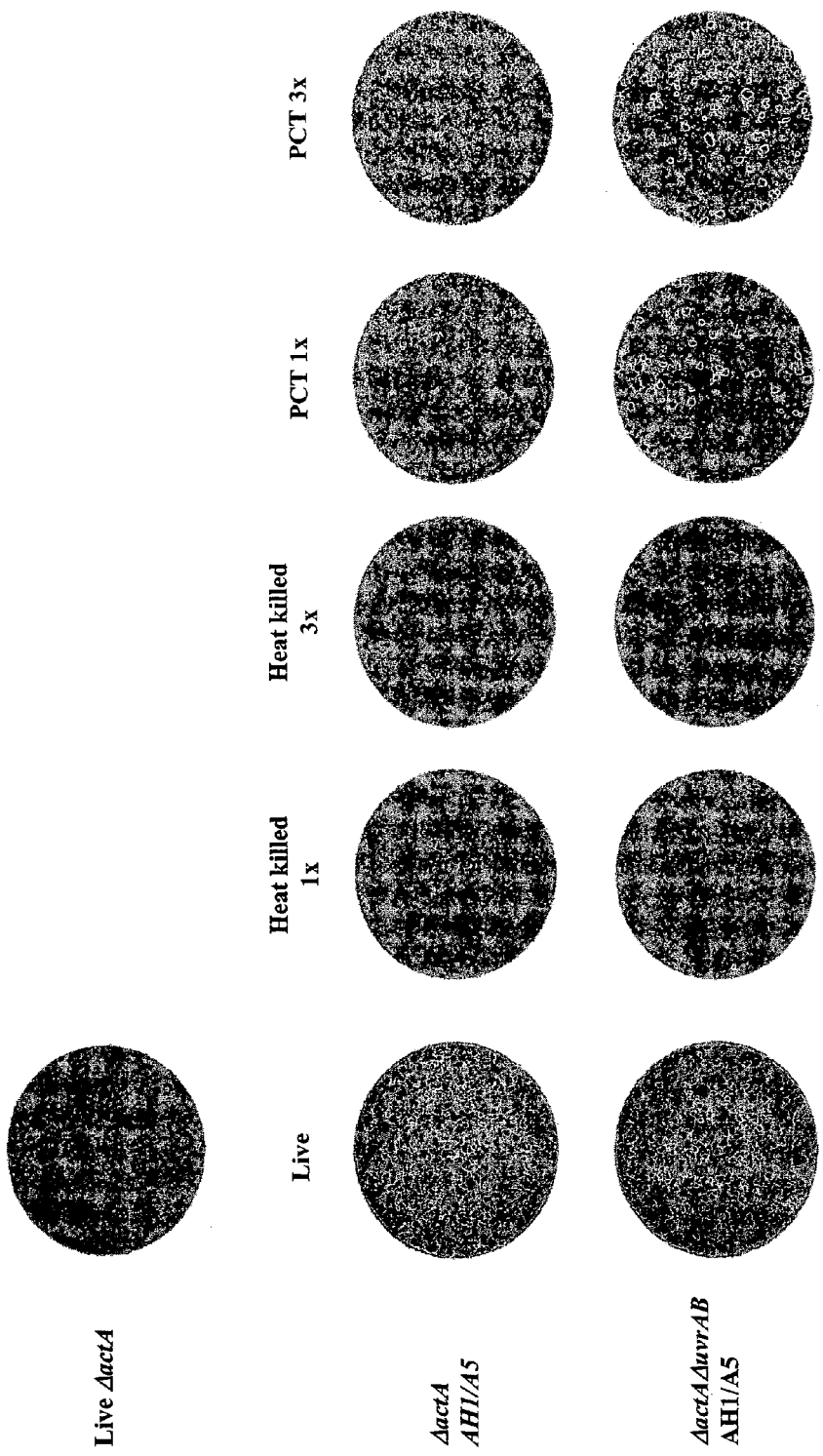
Figure 18B:
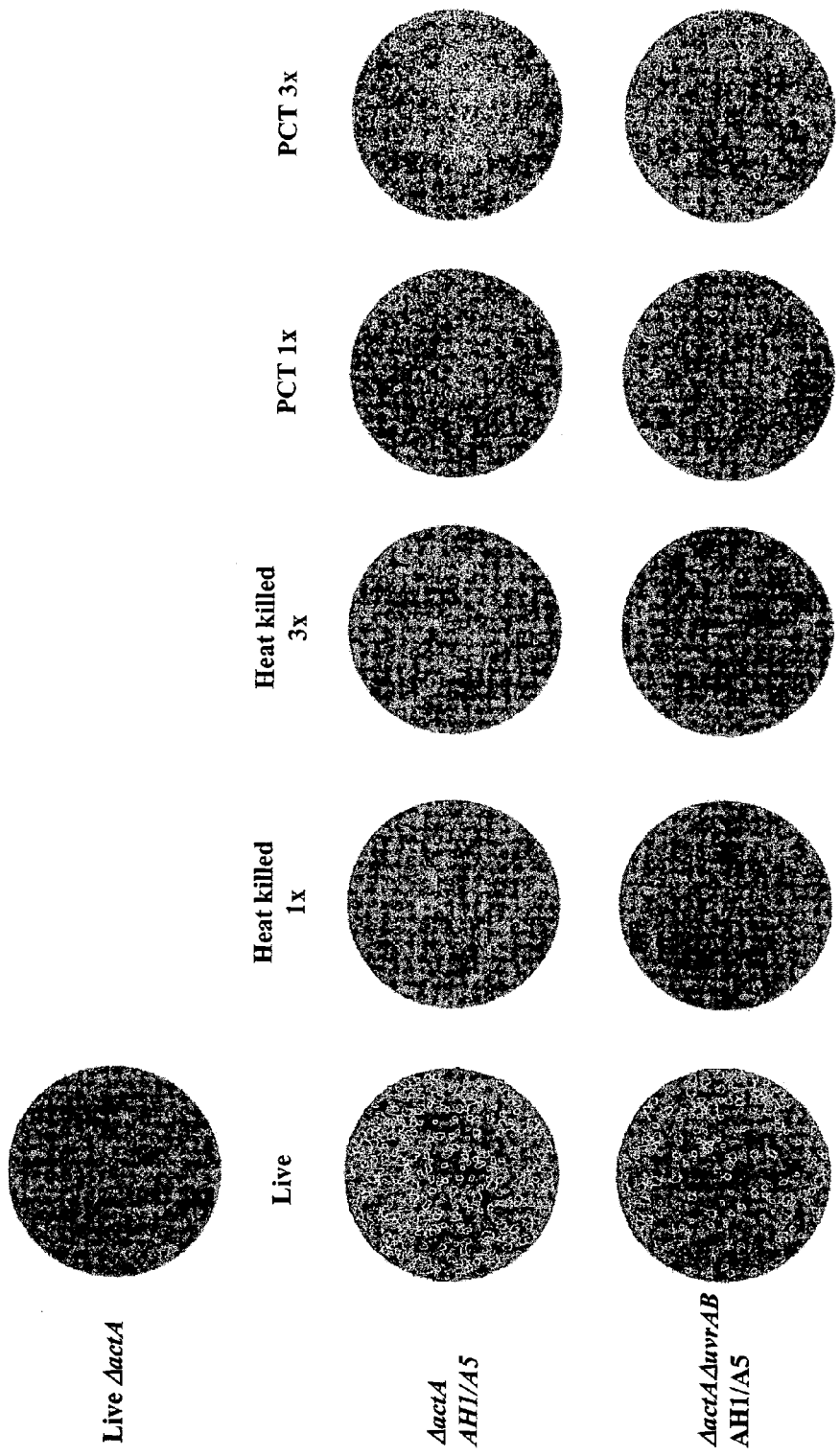

FIG. 18 shows the results of an ELISPOT assay showing plates with spot forming colonies for spleen cells from mice vaccinated with S-59/UVA treated (grown with psoralen, then UVA treated) *Listeria monocytogenes* strains DP-L4029 (ΔactA)-OVA AH1A5 or ΔactAΔuvrAB-OVA AH1A5, stimulated with AH1A5 (18A) or AH1 (18B) antigen.

Figure 19A:
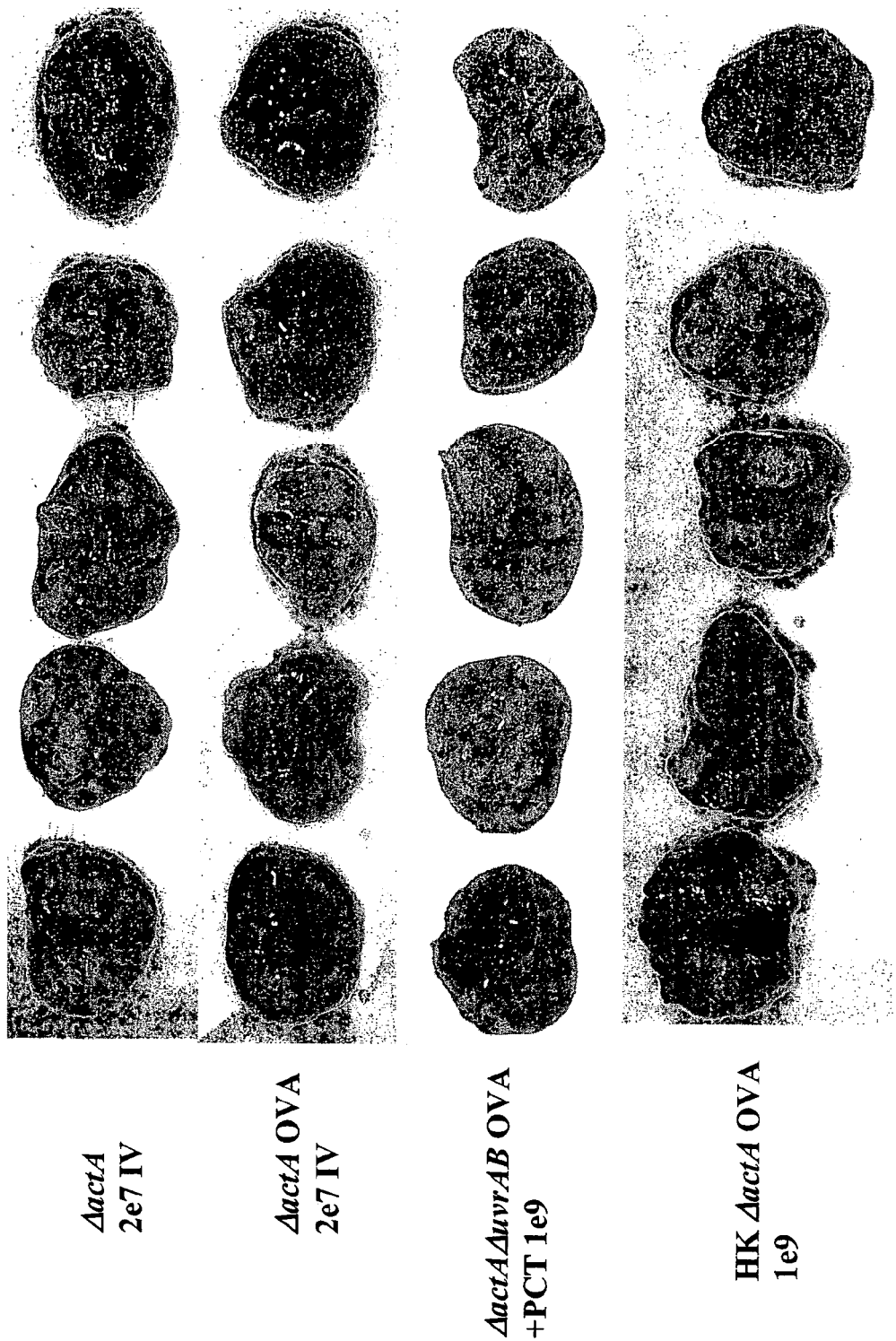
Figure 19B:
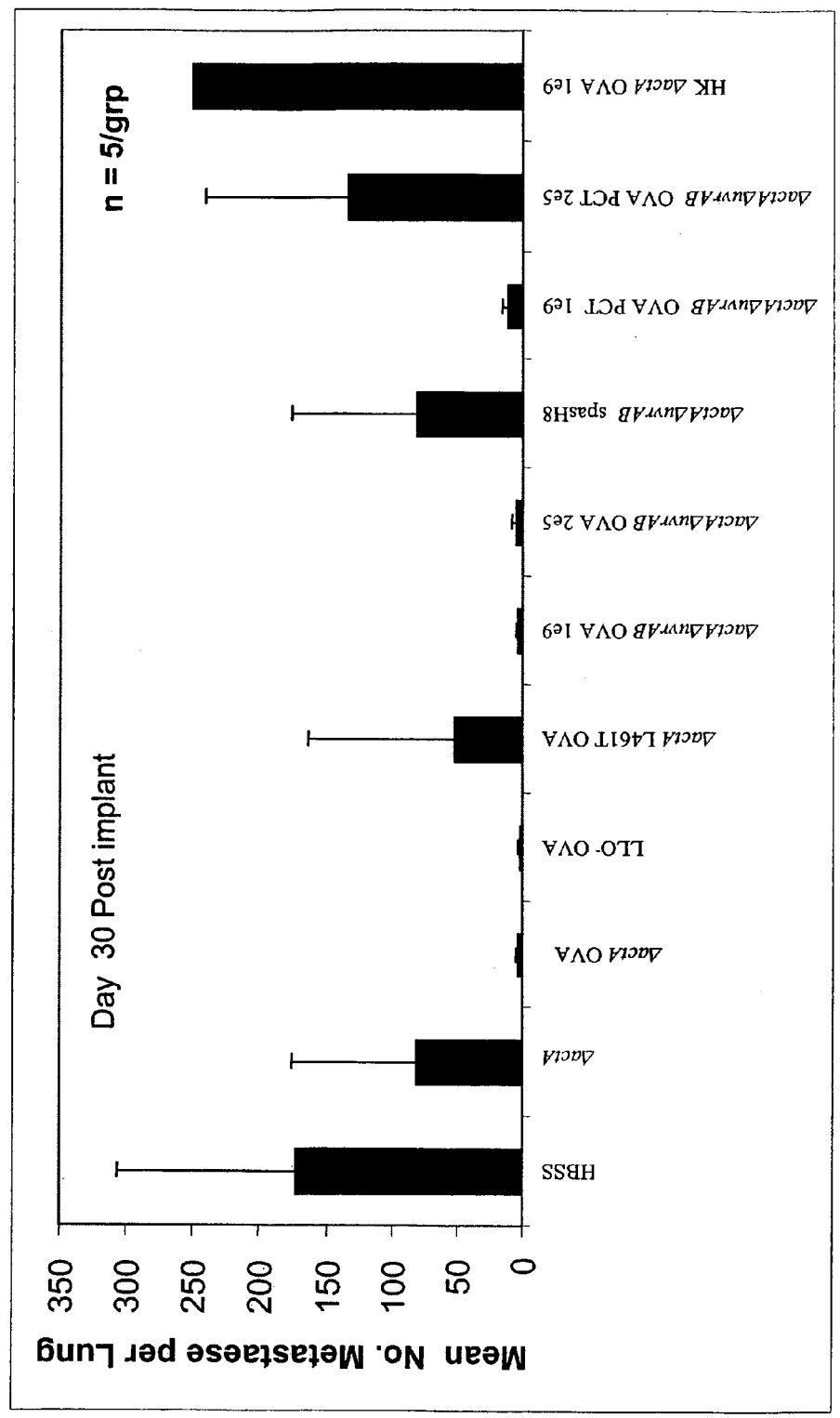
Figure 19C:
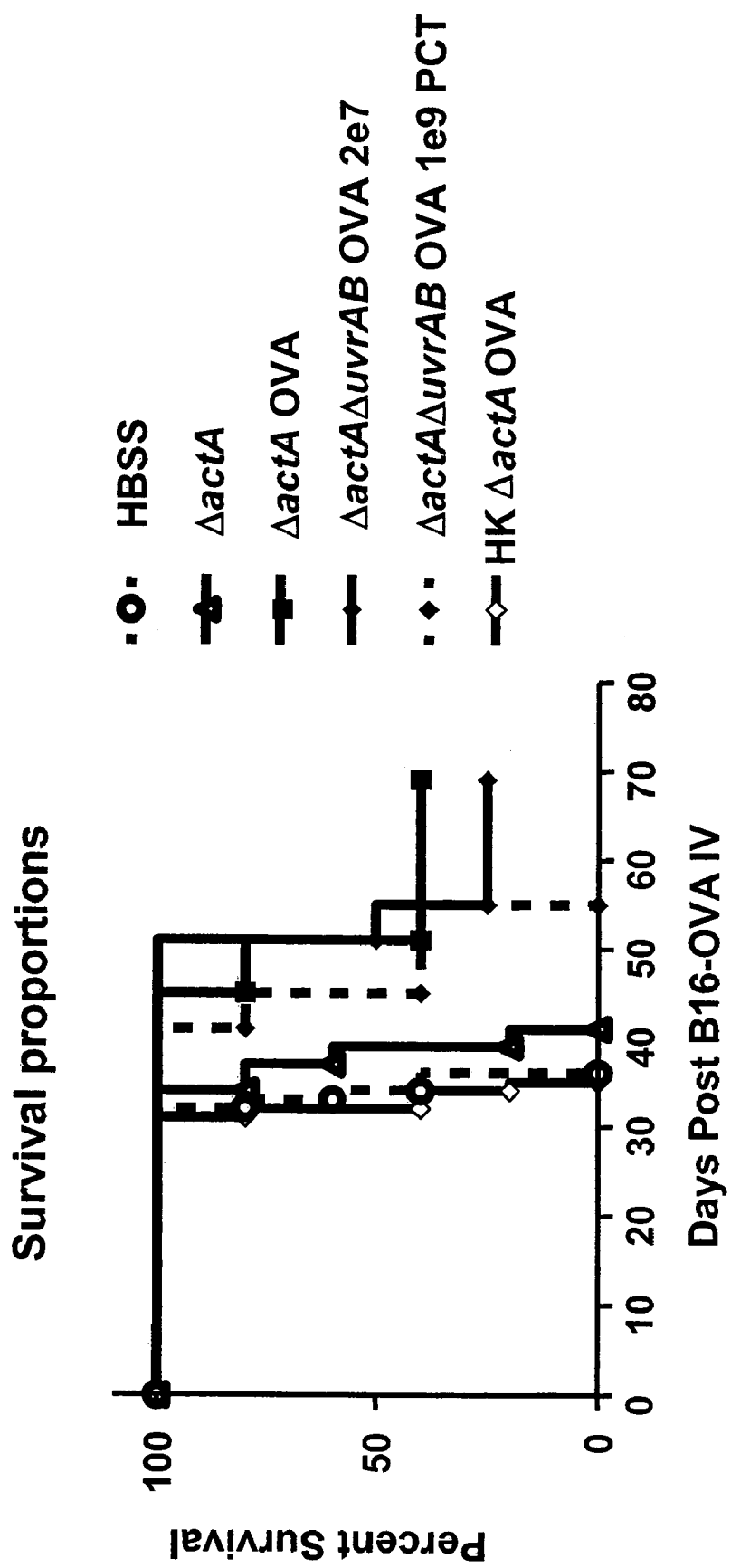

FIG. 19 shows lungs from mice with established CT26 lung tumors given a therapeutic vaccination with S-59/UVA treated DP-L4029, with or without a ΔuvrAB mutation (19A). The number of lung metastases are plotted for each vaccine strain (19B). The survival of the remaining mice is plotted in FIG. 19C.

FIG. 20 shows mice with established CT26 tumors were given therapeutic vaccination with *Listeria monocytogenes* ΔactA, ΔactA AH1-A5, ΔactAΔuvrAB AH1-A5 and actAΔ-inlB AH1-A5. The ΔuvrAB strain was either no treatment, heat-killed (HK) or S-59 UVA (PCT) treated. The lungs harvested from a subset of the mice are shown in FIG. 20A, with the number of lung metastases in each group plotted in FIG. 20B. Survival of the remaining mice is plotted in FIG. 20C (parent strain) and 20D (ΔuvrAB strain).

Figure 21A:
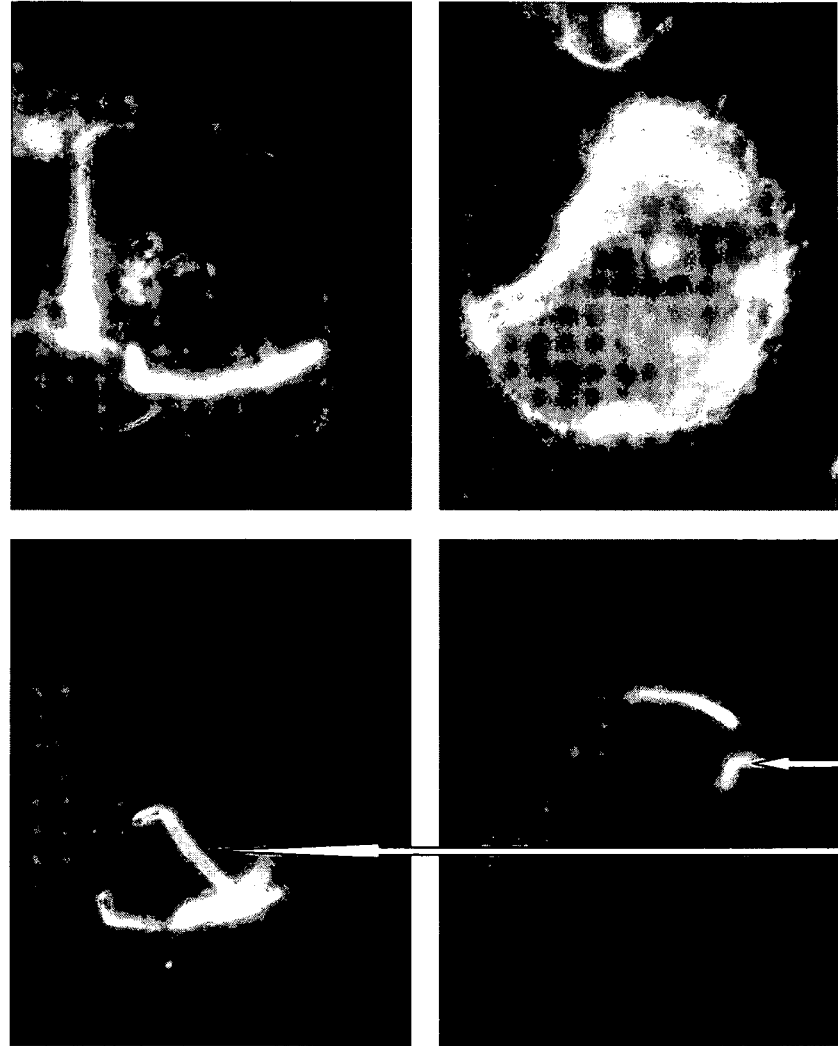
Figure 21B:
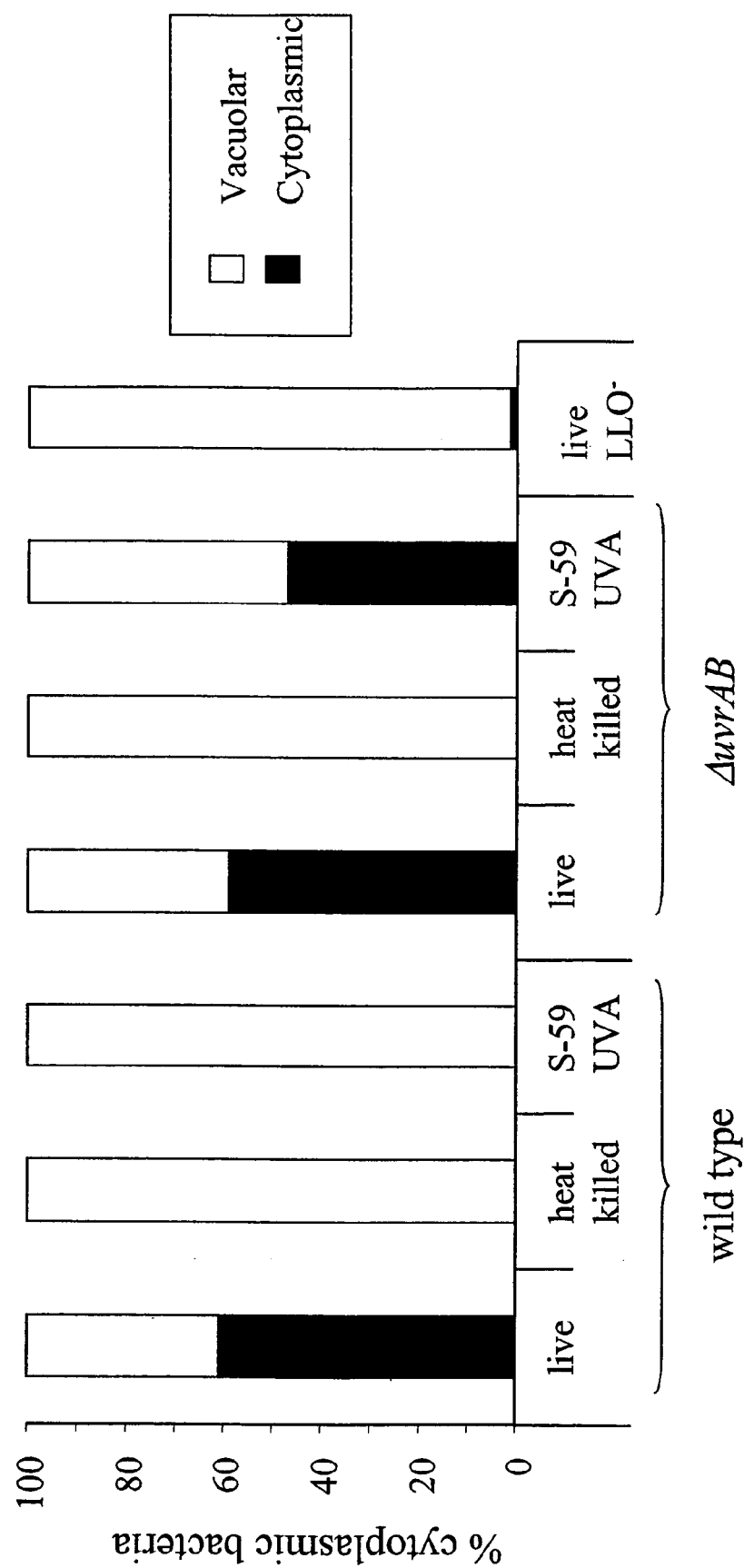

FIG. 21A shows fluorescent microscopy images of DC 2.4 cells infected by wild type *Listeria monocytogenes* uvrAB mutant that has been S-59/UVA treated, showing merged image (both *Listeria* and actin positive) and Rhodamine image (only actin positive). FIG. 21B is a plot of the percentage of the *Listeria monocytogenes* that is in the cytoplasm for wild type and ΔuvrAB strains (live, heat-killed or S-59 UVA treated) compared to LLO⁻.

FIG. 22 shows a negative image photomicrograph of Gram stained *Listeria monocytogenes* wild-type and ΔuvrAB strains that have been S-59/UVA treated.

Figure 23A:
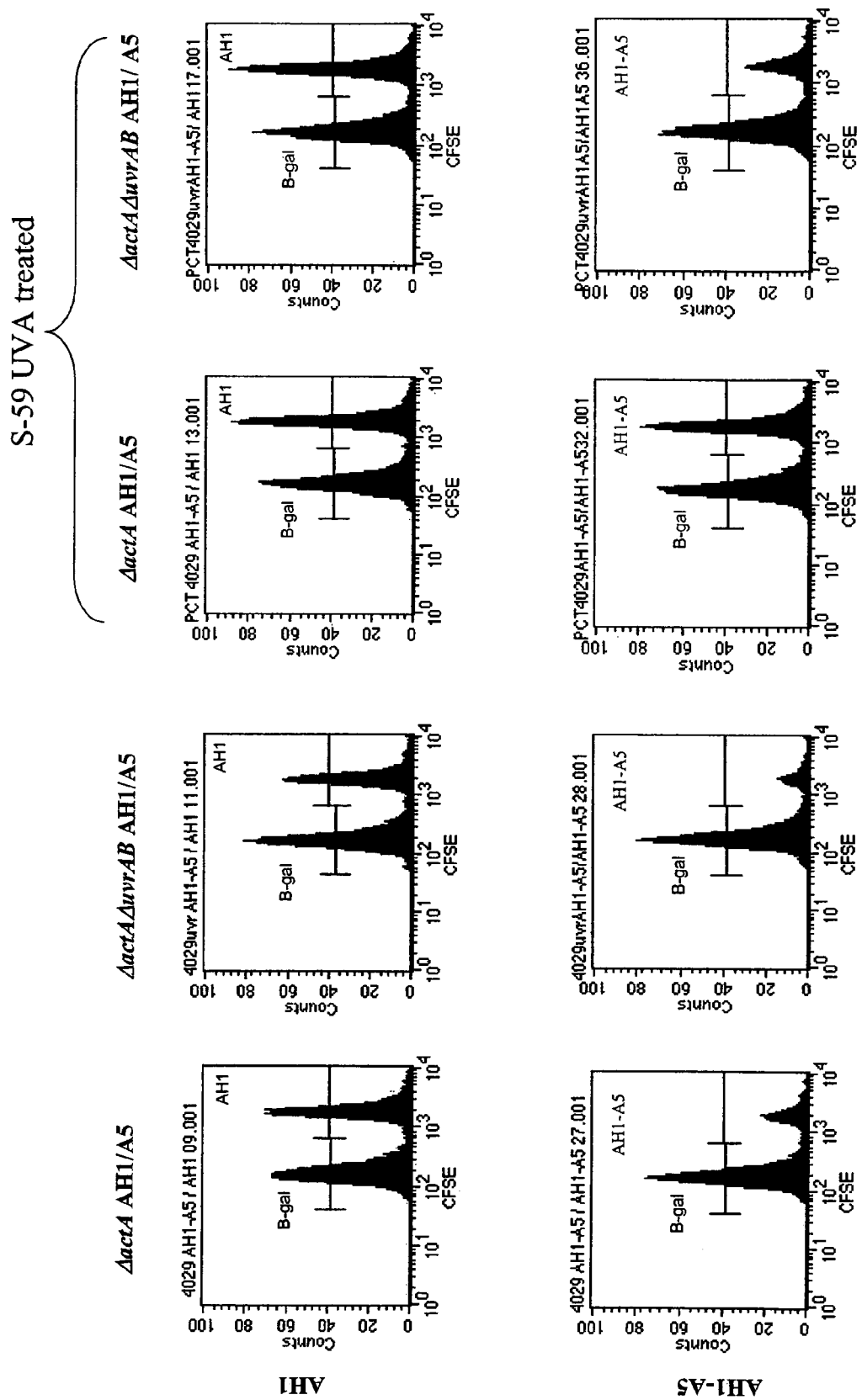
Figure 23B:
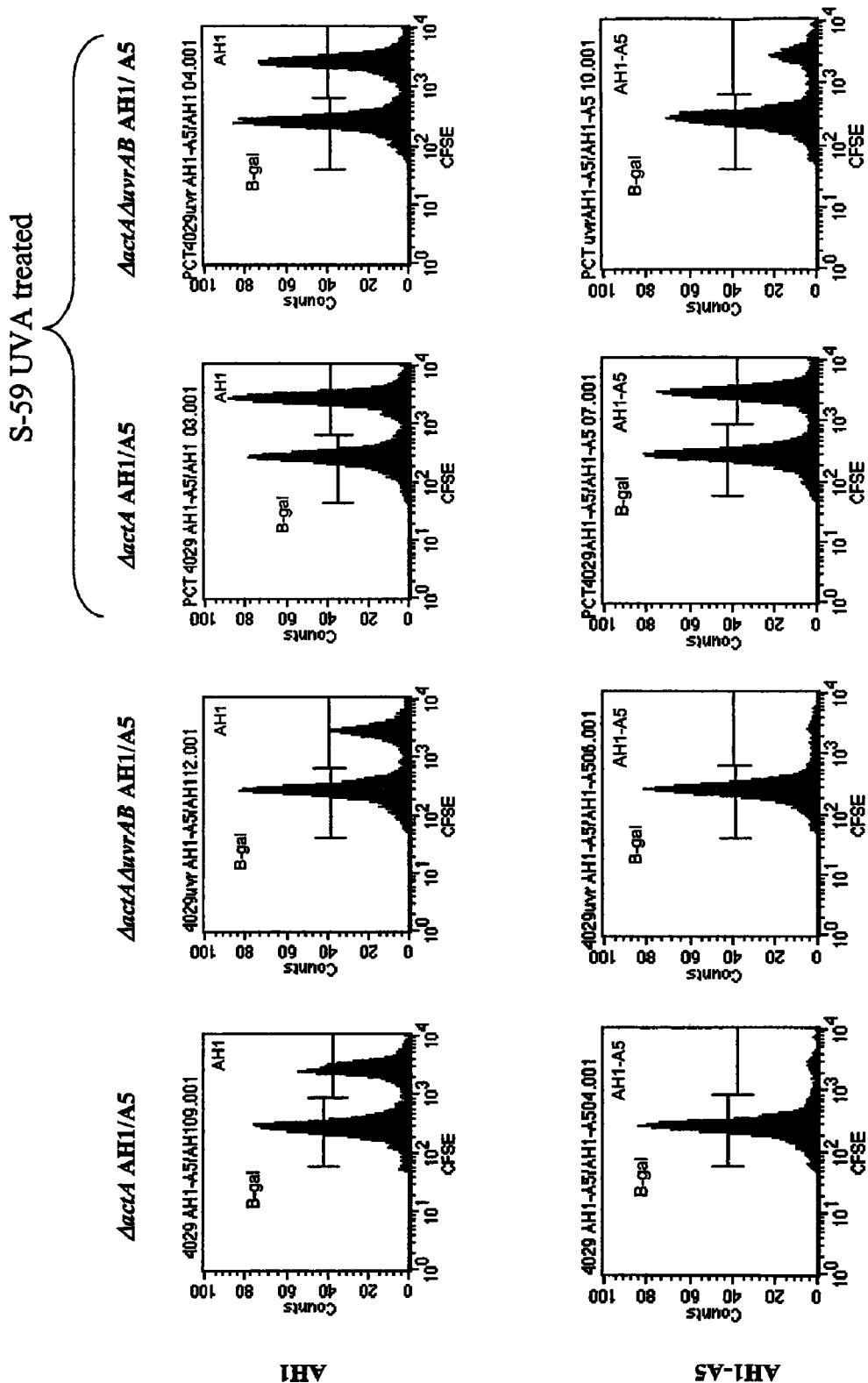
Figure 23C:
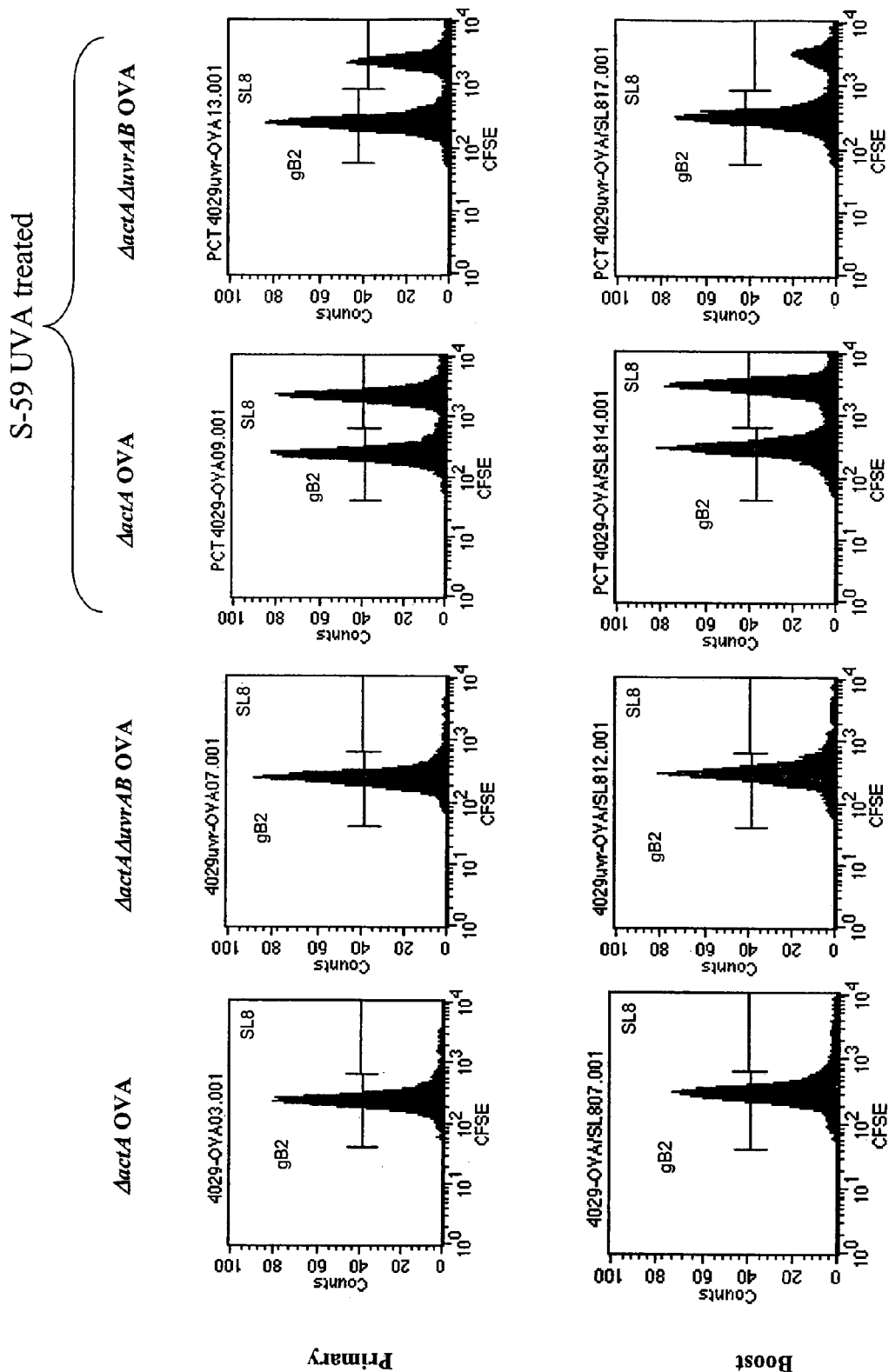

FIG. 23 shows the target cell populations following injection into mice vaccinated with the indicated *Listeria* strains or vehicle control. The reduced levels of antigen-specific target cells relative to non-specific target cells indicates in vivo cytotoxicity of T cells in response to the vaccination. FIG. 23A shows results for AH1-A5 expressing vaccines with vaccination at days 0 (also 1 and 2 for S-59 UVA treated strains). (The top row in 23A and 23B shows results for mice vaccinated with the indicated vaccines for AH1 target cells. The bottom row shows results for mice vaccinated with the indicated vaccines for AH1-A5 target cells.) FIG. 23B has a repeat vaccination at day 14 (15 and 16 for S-59 UVA treated) and FIG. 23C looks at an OVA specific response.

Figure 24:
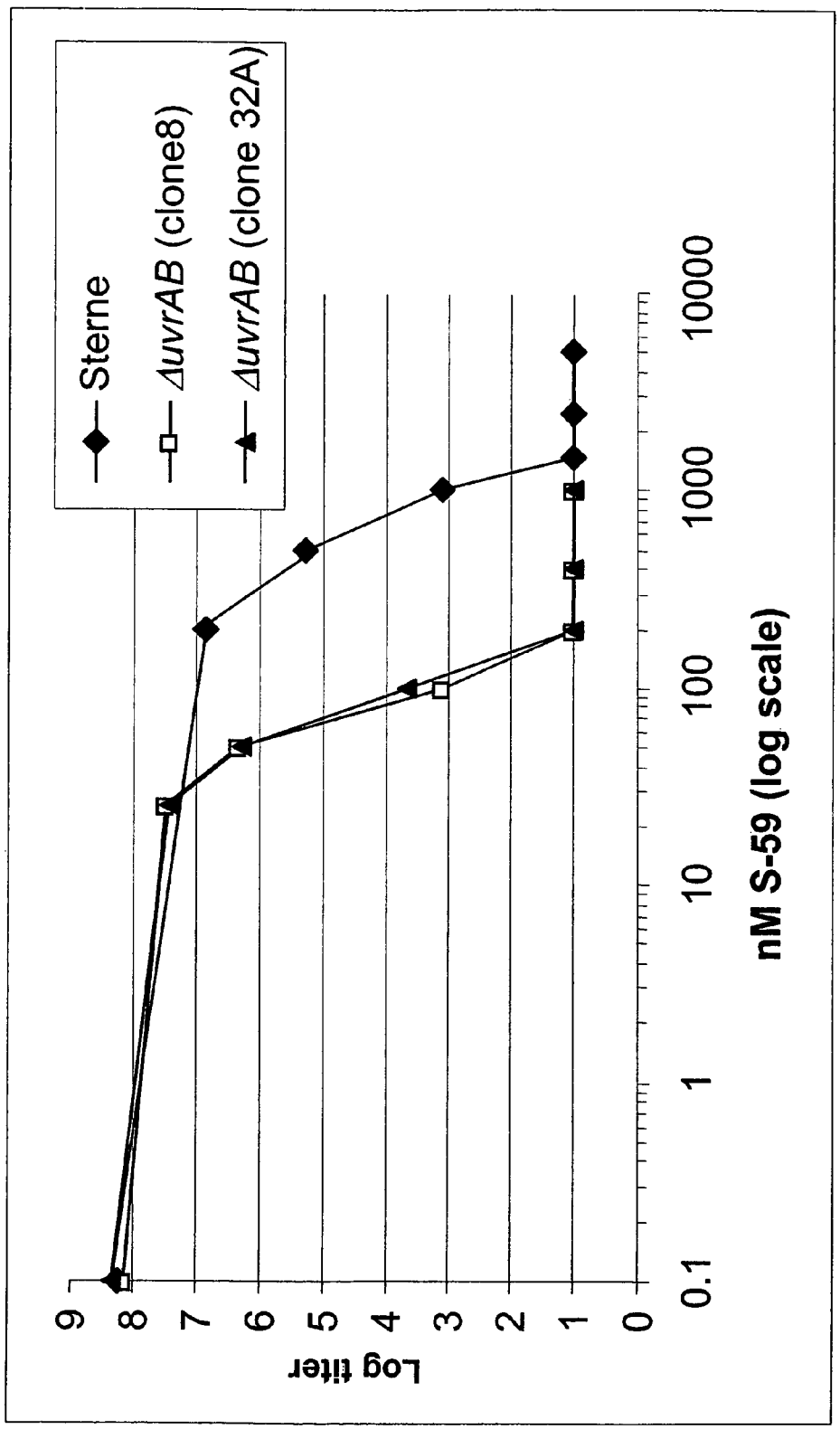

FIG. 24 shows the attenuation of *Bacillus anthracis* Sterne strain with and without deletion of uvrAB. The log titer is plotted vs. nM concentration of psoralen S-59 present during growth and UVA irradiation (6 J/cm²).

FIG. 25 shows *Listeria* uvrAB⁻ are more susceptible to S-59/UVA light inactivation. *Listeria* were grown to mid-log phase, washed in PBS, incubated for 5 min with varying concentrations of S-59 and illuminated at 2.1 J/cm2 of UVA light. The viability of *Listeria* was assessed by growth on BHI agar plates. (A) Representative BHI agar plates of *Listeria* treated at 100 nM S-59. Heat-killed *Listeria* served as control; (B) Viability of *Listeria* treated at varying concentrations of S-59 to form colonies on BHI agar plates.

Figure 26:
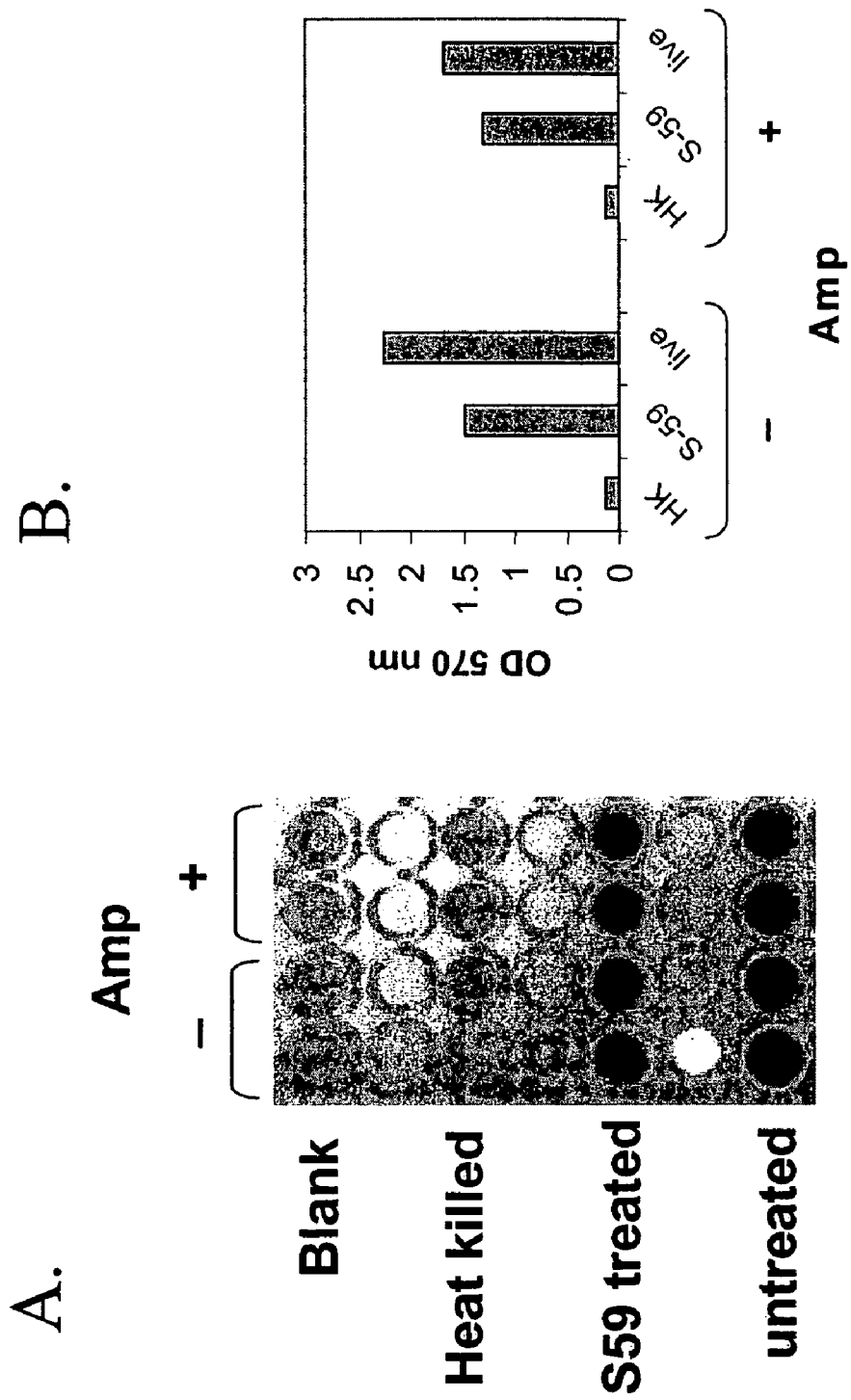

FIG. 26 shows that S-59/UVA treated, non-viable *Listeria* uvrAB retain their metabolic activity and the expression of their genomic repertoire. (A) Metabolic activity determined in a MTT assay of S-59/UVA inactivated *Listeria* urvAB. Live and heat-killed *Listeria* uvrAB served as control; (B) Quantification of the metabolic activity of inactivated *Listeria* uvrAB strain determined in a MTT assay.

FIG. 27 shows that fully inactivated *Listeria* uvrAB retain their capacity to infect DC and to escape from the phagolysosome. The murine DC line, DC2.4, grown on coverslips was infected at an MOI of 1 for 30 min at 37° C. Extracellular bacteria were carefully removed by several washes and infected cells were incubated for 5 hrs at 37° C. in the presence of gentamicin to prevent growth of extracellular bacteria. DC2.4 cells were fixed with 3.5% formaldehyde and then stained with rabbit anti-Listeria antibody, detected with a goat-anti-rabbit FITC secondary antibody. Actin was detected with Phalloidin-rhodamine and the nucleus was visualized using DAPI.

Figure 28:
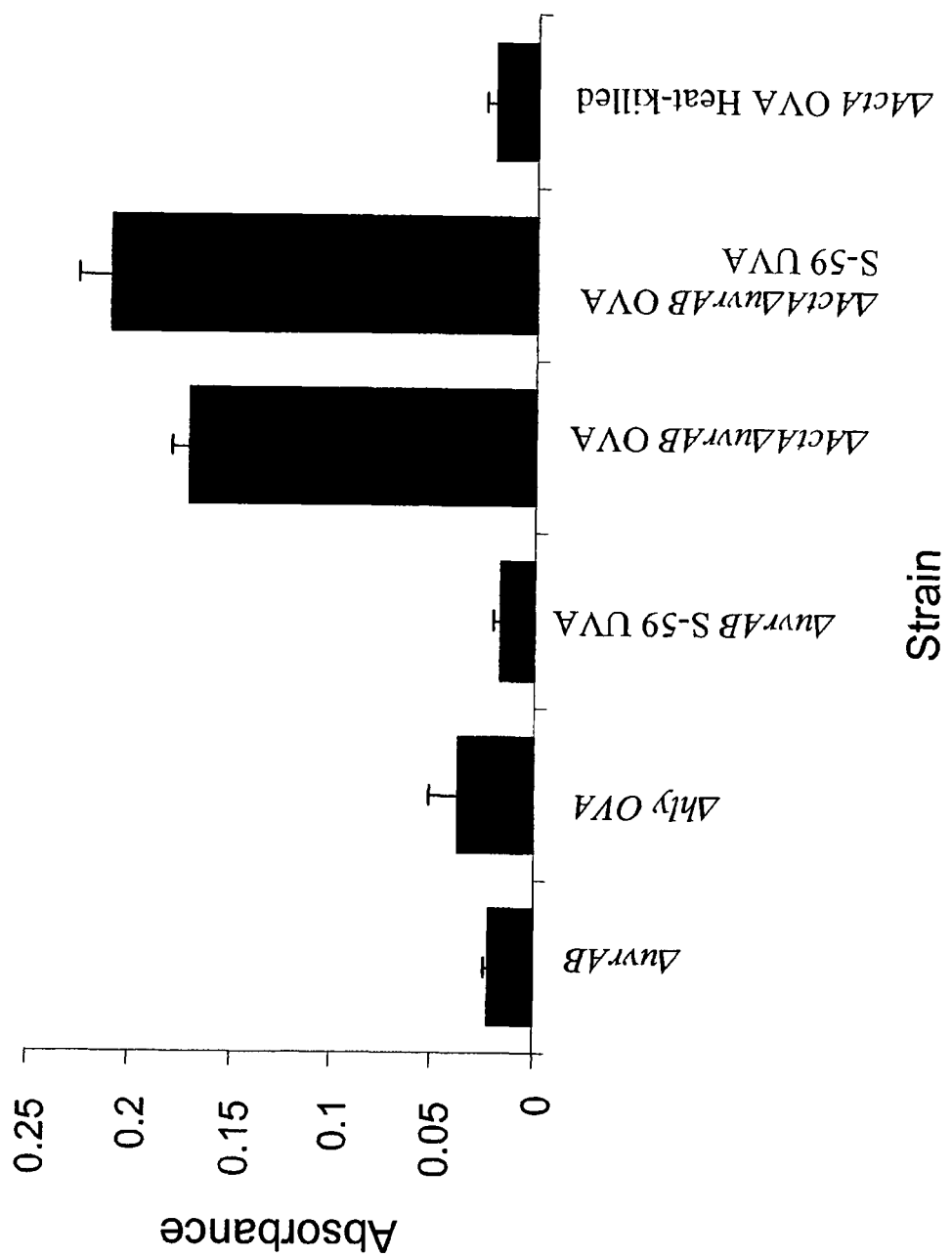

FIG. 28 shows that fully inactivated *Listeria* uvrAB efficiently load antigen into the MHC class I pathway of murine bone marrow-derived DC (BM-DC). Day 5 BM-DC were infected with a MOI of 100 for 30 min at 37° C. Extracellular bacteria were removed by several washes. Infected BM-DC were co-incubated with B3Z overnight and activation was determined by hydrolysis of the chromogenic substrate CPRG (absorbance).

Figure 29A:
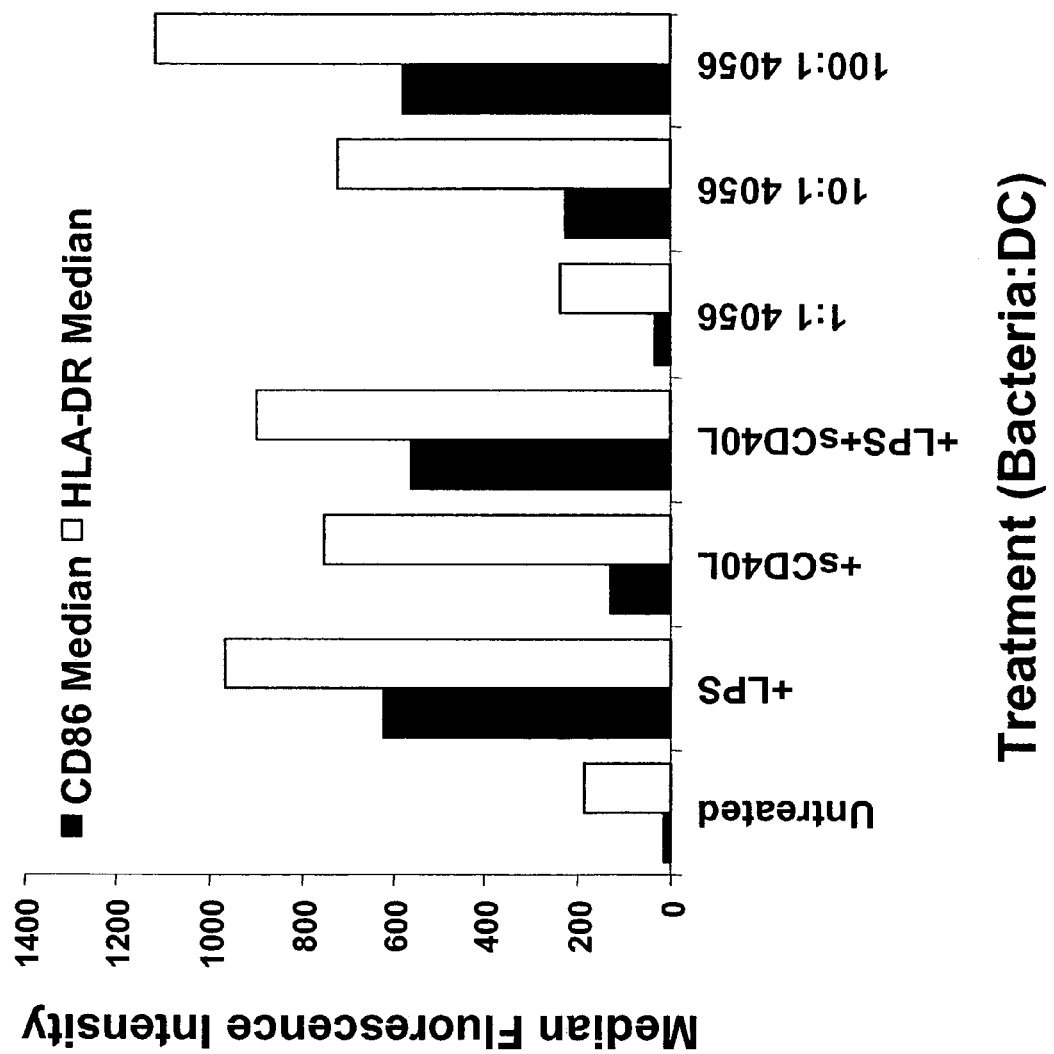
Figure 29B:
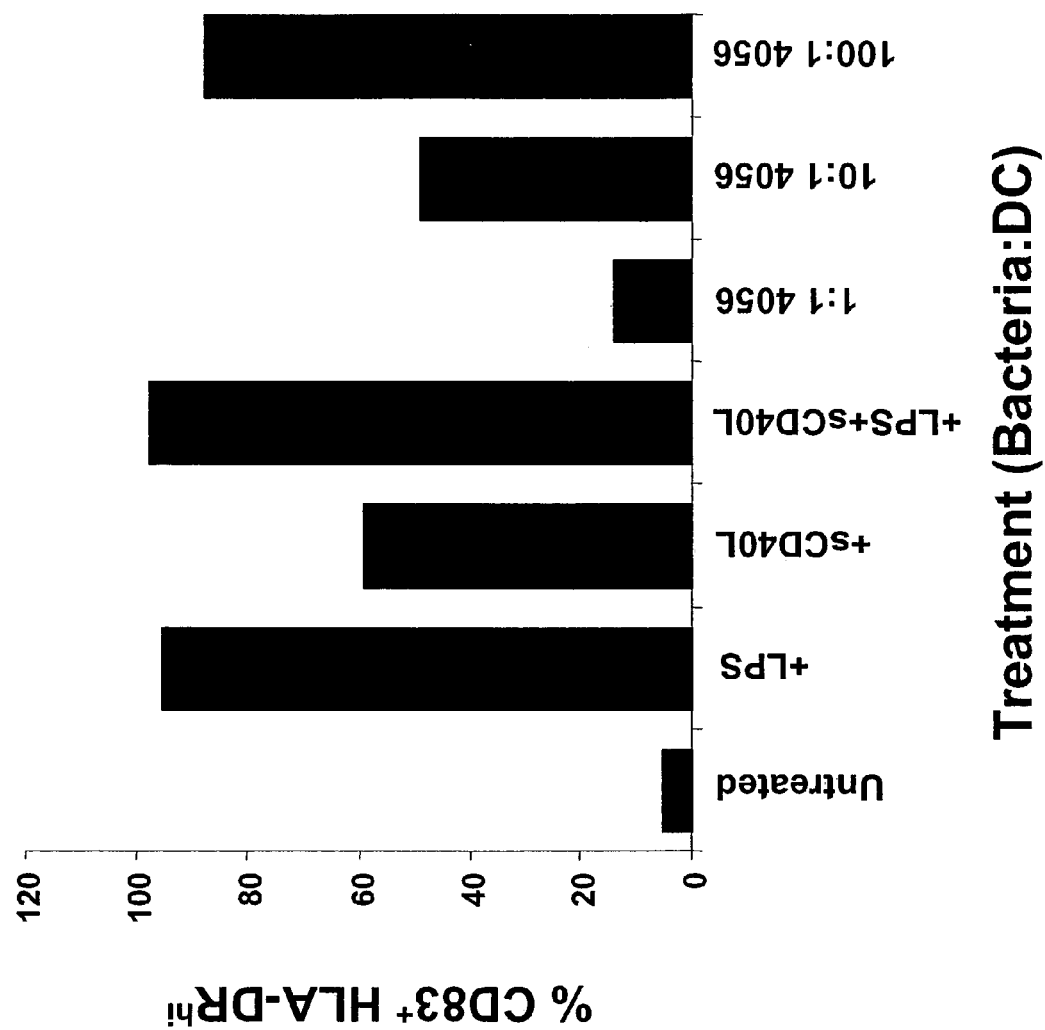
Figure 29C:
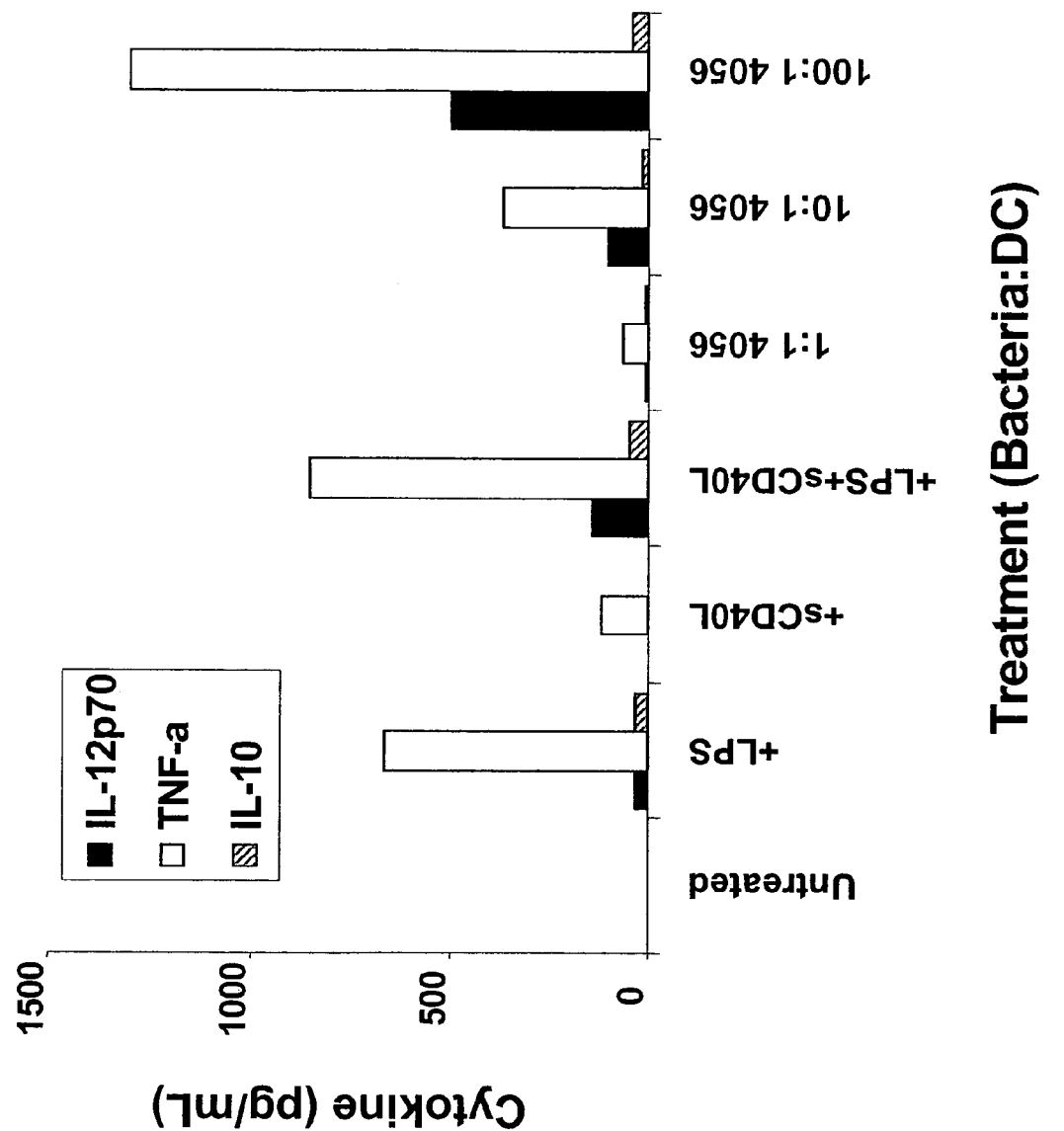

FIG. 29 shows that *Listeria* infected human immature monocyte-derived DC upregulate activation (29A) and maturation markers (29B) as well as secrete pro-inflammatory cytokines (29C). DCs were infected with *Listeria* at different MOI for 1 hour. Infected DCs were cultured for additional 24 hours in the presence of gentamicin to prevent the growth of extracellular bacteria. Phenotypic changes were determined by flow cytometry. Cytokine levels were determined from cell supernatants using the Cytometric bead array kit (Pharmingen).

FIG. 30 shows that S-59/UVA inactivated *Listeria* uvrAB OVA induce OVA-specific immunity in vivo. Female C57BL/6 mice were administered intravenously with $1 \times 10^8$ CFU of S-59/UVA inactivated *Listeria* uvrAB OVA. The S-59/UVA inactivated parent *Listeria* strain and heat-killed *Listeria* served as control. Seven days later, spleens were harvested and OVA-specific CD8+ T cell responses were assessed by IFN-γ ELISPOT. (A) Representative ELISPOT wells are shown; (B) OVA-specific immunity assessed by ELISPOT. Spleen cells of vaccinated mice were cultured with or without OVA257-264 peptide.

FIG. 31 shows the primary amino acid sequence of the heterologous antigen LLO-OVA/PR3 (SEQ ID NO:48). The figure also shows the OVA H-2 $K^b$ epitope (SEQ ID NO:49) and the PR3HLA A-2 restricted class I epitope (a.k.a. PR1) (SEQ ID NO:50).

Figure 32:
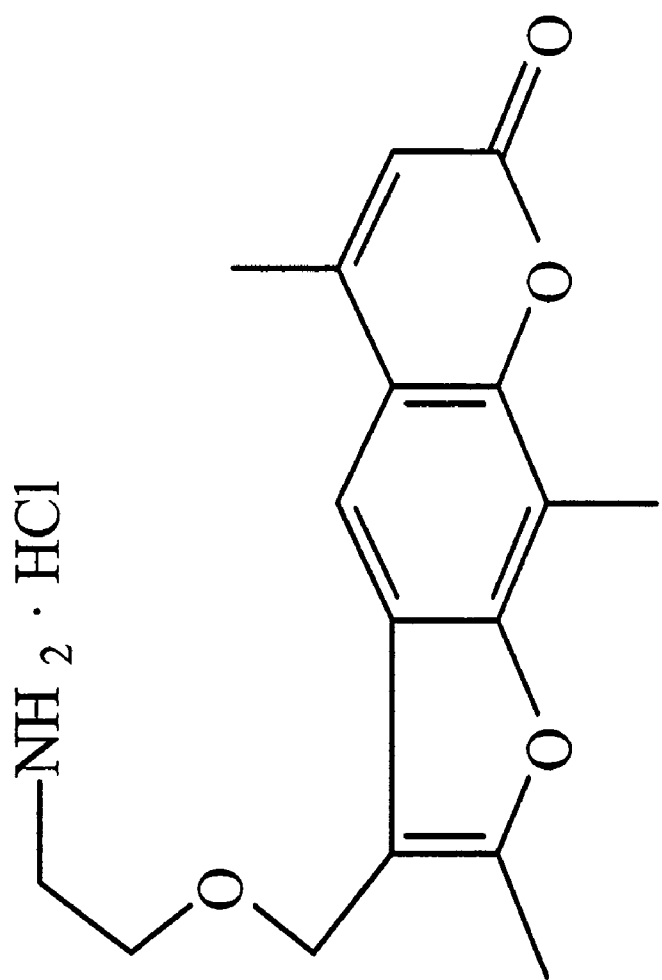

FIG. 32 shows the compound 4'-(4-amino-2-oxa)butyl-4, 5',8-trimethylpsoralen (S-59).

FIG. 33 shows the hly promoter alignment for the *Listeria monocytogenes* DP-L4056 and EGD strains.

FIG. 34 shows a codon-optimized expression cassette comprising the hly promoter and encoding a fusion protein comprising an LLO signal peptide and the NY-ESO-1 antigen. Both the sequences encoding the signal peptide and the antigen are codon-optimized for expression in *Listeria monocytogenes*.

FIG. 35 shows the amino acid sequence encoded by the expression cassette of FIG. 34.

FIG. 36 shows the coding sequence for human mesothelin which has been codon-optimized for expression in *Listeria monocytogenes*.

FIG. 37 shows the amino acid sequence of human mesothelin.

FIG. 38 shows the coding sequence for murine mesothelin which has been codon-optimized for expression in *Listeria monocytogenes*.

FIG. 39 shows the amino acid sequence of murine mesothelin.

Figure 40:
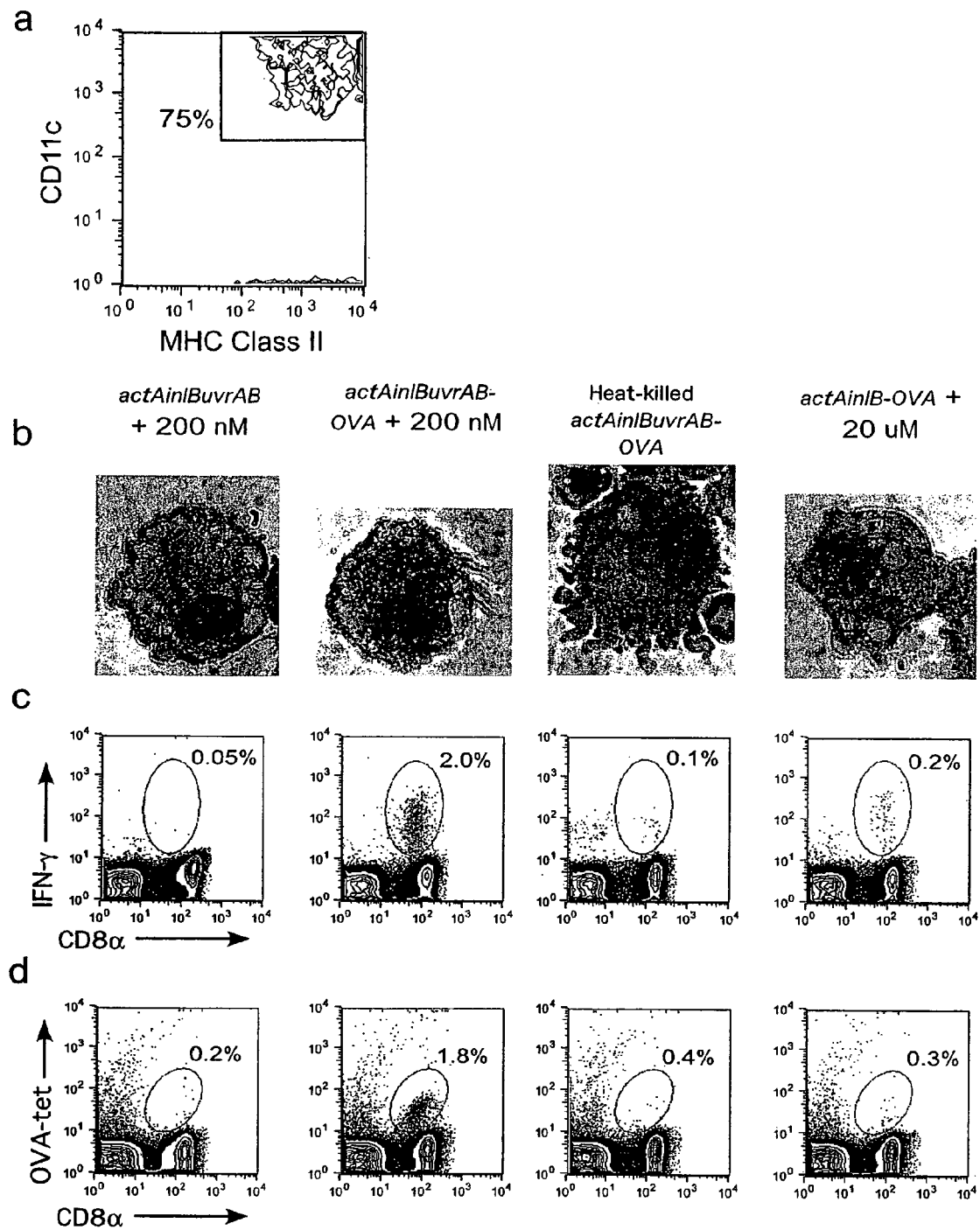

FIG. 40 shows that the induction of potent OVA-specific CD8+ T cell responses in C57BL/6 mice immunized intravenously with autologous bone marrow-derived DC infected with S-59 psoralen/UVA inactivated *Listeria*-OVA is dependent on deletion of the bacterial uvrAB genes. (a) Phenotypic verification of dendritic cells prior to infection, as shown by double staining of CD11$c^{hi}$/MHC class II$^{hi}$; (b) photomicrographs of DC at one hour post infection with indicated *Listeria* vaccine and treatment; (c) ICS analysis of splenocytes from immunized mice; and, (d) $K^b$-SINFEKL (SEQ ID NO:49) tetramer analysis of splenocytes from immunized mice.

Figure 41:
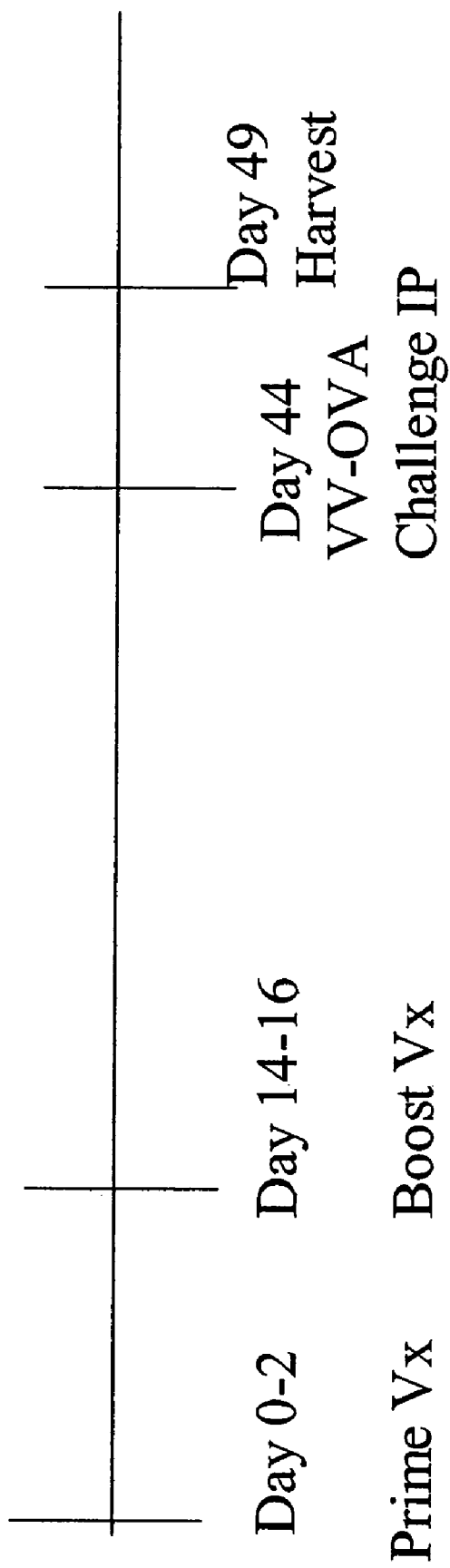

FIG. 41 shows the protocol for the vaccine challenge experiments.

Figure 42:
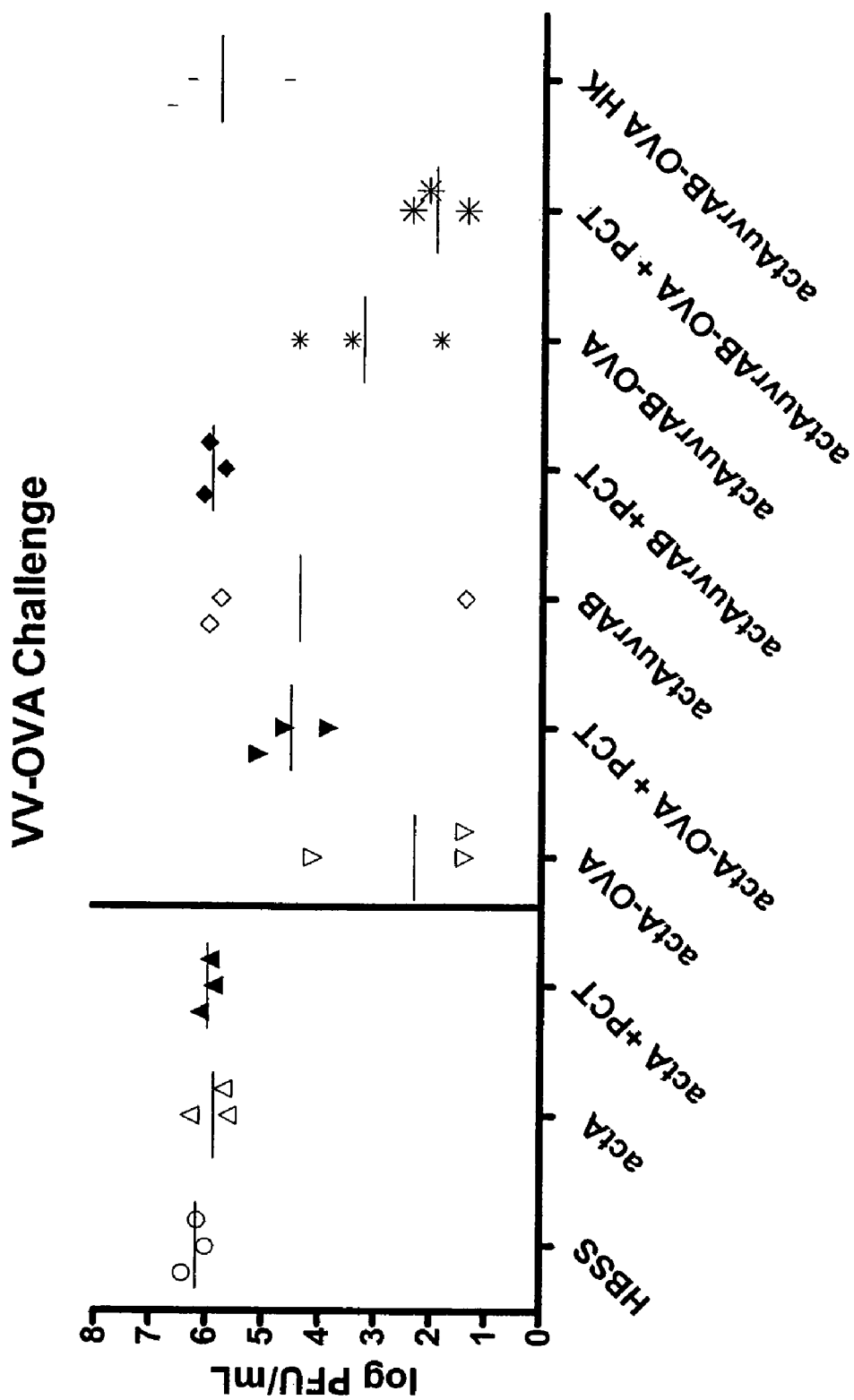

FIG. 42 shows that the vaccination of mice with S-59/UVA inactivated *Listeria* ΔactAΔuvrAB-OVA, but not S-59/UVA inactivated *Listeria* ΔactA—OVA are protected against challenge with VV-OVA.

DETAILED DESCRIPTION OF THE INVENTION

The present invention involves modified free-living microbes (e.g., modified bacteria) and the use of modified free-living microbes in vaccine compositions, wherein the nucleic acid of the microbe is modified so that proliferation of the microbe is attenuated. In some embodiments, the microbial gene expression of the modified microbe is substantially unaffected by the modification. The invention also provides free-living microbes, such as bacteria, which are mutants attenuated for nucleic acid repair and which are particularly useful in conjunction with the modifications that attenuate proliferation. Vaccines comprising the modified microbes are also provided. The present invention also involves the use of the modified microbes for antigen loading and induction of the activation/maturation of antigen presenting cells (APCs), in vitro or ex vivo. The antigen may be either an antigen produced naturally by the modified microbe, or may be a heterologous antigen expressed by a recombinant microbe. The resulting antigen presenting cells are suitable for use in vaccine compositions and for immunotherapy. The immune response stimulated by administration of the resulting vaccine compositions may be a $CD4^+$ or a $CD8^+$ immune response.

One such modified microbe is *Listeria monocytogenes*. The inventors have engineered *Listeria* to be particularly sensitive to inactivation by psoralens, a group of compounds that form irreversible cross-links in the genomes of bacteria after illumination with ultraviolet A (UVA) light, so that they are non-viable. (See Example 3, below.) The attenuation of proliferation of wild-type and modified *Listeria* while maintaining expression of model antigens has now been shown (see Example 1-2 and 11, below). The modified *Listeria* is also shown to provide an anti-tumor response (Examples 4 and 14-16, below) and induce antigen-specific T-cell responses (Example 5) and in vivo cytotoxic responses (Example 20). *Listeria* is rapidly phagocytosed by DC and transported into the phagolysosomal compartment. This encounter results in the phenotypic maturation of the DC and subsequent secretion of a broad profile of immunostimulatory cytokines, including IFN-γ, IL-12, and TNF-α. The inventors have now demonstrated that infection of immature DC with recombinant *Listeria* results in rapid DC activation/maturation, together with MHC class I-restricted presentation of an encoded heterologous antigen. Additionally, degradation of *Listeria* vaccines within the phagolysosome results in presentation of encoded antigen via the MHC class II pathway. (See Examples, Below)

Another such modified microbe is *Bacillus anthracis*. The inventors have also engineered an attenuated strain of *Bacillus anthracis* which is particularly sensitive to inactivation by psoralens (see Example 21, below).

Accordingly, the invention provides a vaccine comprising a free-living microbe (e.g., a bacterium), wherein the nucleic acid of the microbe is modified so that the microbe is attenuated for proliferation. In some embodiments, the attenuation of the proliferation of the microbe is controllable in a dose-dependent manner. In some embodiments, microbial gene expression in the microbe is substantially unaffected by attenuation of the proliferation of the microbe. In some embodiments, the microbe in the vaccine expresses an antigen at a sufficient level to induce an immune response to the antigen in an individual upon administration of the vaccine to the individual. In some embodiments, the nucleic acid has been modified by reaction with a nucleic acid targeted compound which reacts directly with the nucleic acid. In one embodiment, the nucleic acid targeted compound is an alkylator such as β-alanine, N-(acridin-9-yl), 2-[bis(2-chloroethyl)amino]ethyl ester. In other embodiments, the nucleic acid targeted compound is a psoralen compound (e.g., 4'-(4-amino-2-oxa)butyl-4,5',8-trimethylpsoralen, also referred to herein as "S-59") activated by UVA irradiation. In some embodiments, the microbe in the vaccine comprises a genetic mutation that attenuates the ability of the microbe to repair its nucleic acid that has been modified. In some embodiments, the microbe is a bacterium, such as Bacillus anthracis or Listeria monocytogenes. In some embodiments, the microbe comprises a heterologous nucleic acid sequence encoding an antigen. In some embodiments, the vaccine further comprises a pharmaceutically acceptable carrier and/or an adjuvant. The invention further provides a method of preventing or treating a disease in a host, comprising administering to the host an effective amount of the vaccine. The invention also provides a method of inducing an immune response in a host to an antigen comprising administering to the host an effective amount of the vaccine, wherein the microbe expresses the antigen.

The invention also provides an isolated mutant Listeria strain, such as a mutant Listeria monocytogenes strain, comprising a genetic mutation that attenuates its ability to repair its nucleic acid. In some embodiments, the mutant Listeria strain is defective with respect to at least one DNA repair enzyme (such as UvrA and/or UvrB). In some embodiments, the mutant Listeria strain comprises a genetic mutation in the uvrA gene and/or the uvrB gene. In some embodiments, the mutant strain is the Listeria monocytogenes ΔactA/ΔuvrAB strain deposited with the American Type Culture Collection (ATCC) and identified by accession number PTA-5563. In other embodiments, the strain is a mutant of the Listeria monocytogenes ΔactA/ΔuvrAB strain deposited with the American Type Culture Collection (ATCC) and identified by accession number PTA-5563, wherein the mutant of the deposited strain is defective with respect to UvrA, UvrB, and ActA. The invention further provides vaccines and professional antigen-presenting cells comprising the mutant Listeria strain. Methods of using the modified Listeria strain to induce immune responses and to prevent or treat disease are also provided.

The invention provides an isolated mutant Bacillus anthracis strain, comprising a genetic mutation that attenuates its ability to repair its nucleic acid. In some embodiments, the mutant strain is defective with respect to at least one DNA repair enzyme (such as UvrA and/or UvrB). In some embodiments, the mutant strain comprises a genetic mutation in the uvrA gene and/or the uvrB gene. In some embodiments, the mutant strain is defective with respect to UvrC. In some embodiments, the mutant strain is attenuated with respect to RecA. In some embodiments, the mutant strain comprises a genetic mutation in the recA gene. In some embodiments, the mutant strain comprises one or more mutations in the lef gene, cya gene, or both genes, that decreases the toxicity of the strain. The invention further provides vaccines and professional antigen-presenting cells comprising the mutant strain. Methods of using the modified Bacillus anthracis strain to induce immune responses and to prevent or treat disease are also provided.

In addition, the invention provides a professional antigen-presenting cell (e.g., a dendritic cell) comprising a free-living microbe (e.g., a bacterium), wherein the nucleic acid of the microbe is modified so that the microbe is attenuated for proliferation. In some embodiments, the attenuation of the proliferation of the microbe is controllable in a dose-dependent manner. In some embodiments, microbial gene expression in the microbe is substantially unaffected by attenuation of the proliferation of the microbe. In some embodiments, the microbe in the vaccine expresses an antigen at a sufficient level to induce an immune response to the antigen in an individual upon administration of the vaccine to the individual. In some embodiments, the nucleic acid has been modified by reaction with a nucleic acid targeted compound which reacts directly with the nucleic acid. In one embodiment, the nucleic acid target compound is an alkylator such as β-alanine, N-(acridin-9-yl), 2-[bis(2-chloroethyl)amino] ethyl ester. In other embodiments, the nucleic acid targeted compound is a psoralen compound activated by UVA irradiation. In some embodiments, the microbe in the vaccine comprises a genetic mutation that attenuates the ability of the microbe to repair its nucleic acid that has been modified. In some embodiments, the microbe is a bacterium. In some embodiments, the microbe comprises a heterologous nucleic acid sequence encoding an antigen. The invention also provides a vaccine comprising the antigen-presenting cell. The invention further provides a method of preventing or treating a disease in a host, comprising administering to the host an effective amount of the antigen-presenting cell. The invention also provides a method of inducing an immune response in a host to an antigen comprising administering to the host an effective amount of the antigen-presenting cell, wherein the microbe expresses the antigen. The invention further provides a method of activating naïve T cells ex vivo or in vitro, comprising contacting the naïve T cells with the professional antigen-presenting cell under suitable conditions and for a sufficient time to activate the naïve T-cells.

The invention provides a method of loading professional antigen-presenting cells with an antigen comprising contacting the professional antigen-presenting cells with a free-living microbe that comprises a nucleic acid sequence encoding the antigen, under suitable conditions and for a sufficient time to load the professional antigen-presenting cells, wherein the nucleic acid of the microbe is modified so that the microbe is attenuated for proliferation.

The invention also provides a method of activating and/or maturing professional antigen-presenting cells comprising contacting the professional antigen-presenting cells with a free-living microbe that comprises a nucleic acid sequence encoding an antigen, under suitable conditions and for a sufficient time to load the professional antigen-presenting cells, wherein the nucleic acid of the microbe is modified so that the microbe is attenuated for proliferation.

The invention further provides a method of preventing or treating a disease in a host, comprising the following steps. (a) loading professional antigen-presenting cells with an antigen by contacting the cells with a free-living microbe that comprises a nucleic acid sequence encoding an antigen, wherein the nucleic acid of the microbe is modified so that the microbe is attenuated for proliferation; and (b) administering an effective amount of a composition comprising the loaded professional antigen-presenting cells to the host.

The invention also provides a method of loading antigen-presenting cells, such as dendritic cells, with an antigen, comprising contacting the cells in vitro or ex vivo with a modified microbe expressing the antigen, under suitable conditions and for a time sufficient to load the antigen-presenting cells.

The invention provides a method of activating and/or maturing antigen-presenting cells comprising contacting the antigen-presenting cells in vitro or ex vivo with a modified microbe under suitable conditions and for a time sufficient to effect activation and/or maturation of the dendritic cells and/or to allow the antigen-presenting cells to mature.

The invention provides a method of inducing an immune response to an antigen, comprising administering to the host an effective amount of an immunogenic composition comprising an antigen presenting cell presenting the antigen, wherein the antigen-presenting cell comprises a modified microbe.

In addition, the invention provides a method of inducing an immune response to an antigen, comprising the following steps: (a) contacting antigen-presenting cells in vitro or ex vivo with *Listeria* expressing the antigen under suitable conditions and for a time sufficient to load the antigen-presenting cells with the antigen and to effect activation and/or maturation of the antigen-presenting cells; and (b) administering an effective amount of the antigen-presenting cells to the host. In one embodiment, proliferation of the microbe is attenuated.

The invention also provides an ex vivo or in vitro professional antigen-presenting cell comprising a modified microbe, wherein proliferation of the microbe is attenuated.

Additionally, the invention provides a vaccine comprising an antigen-presenting cell, wherein the antigen-presenting cell comprises a modified microbe and a pharmaceutical composition comprising a antigen-presenting cell and a pharmaceutically acceptable carrier, wherein the antigen-presenting cell comprises *Listeria*.

In one aspect, the invention provides a vaccine comprising a *Listeria monocytogenes* bacterium that has been modified by reaction with a nucleic acid targeted compound that reacts directly with the nucleic acid so that the bacterium is attenuated for proliferation and that is defective with respect to at least one DNA repair enzyme. The invention further provides a method of inducing an immune response in a host to an antigen comprising administering to the host an effective amount of the vaccine, wherein the bacterium expresses the antigen.

The invention also provides a vaccine comprising a *Listeria monocytogenes* bacterium that has been modified by reaction with a nucleic acid targeted compound that reacts directly with the nucleic acid so that the bacterium is attenuated for proliferation and that is defective with respect to both UvrA and UvrB. In addition, the invention provides a method of inducing an immune response in a host to an antigen comprising administering to the host an effective amount of the vaccine, wherein the bacterium expresses the antigen.

The invention further provides a vaccine comprising a *Bacillus anthracis* bacterium that has been modified by reaction with a nucleic acid targeted compound that reacts directly with the nucleic acid so that the bacterium is attenuated for proliferation and that is defective with respect to both UvrA and UvrB. The invention also provides a method of inducing an immune response in a host to an antigen comprising administering to the host an effective amount of the vaccine, wherein the bacterium expresses the antigen.

Also provided is a vaccine comprising a bacterium, wherein the bacterium has been modified by reaction with a nucleic acid targeted compound that reacts directly with its nucleic acid so that the bacterium is attenuated for proliferation and wherein the bacterium is defective with respect to at least one DNA repair enzyme. In some embodiments, the bacterium is *Listeria monocytogenes*. In some embodiments, the bacterium is *Bacillus anthracis*. In some embodiments, the bacterium is defective with respect to both UvrA and UvrB (e.g., a uvrAB deletion mutant). In some embodiments, the bacterium is defective with respect to UvrC. In some embodiments, the bacterium is defective with respect to RecA. Methods of inducing an immune response in a host to an antigen comprising administering to the host an effective amount of the vaccine, wherein the bacterium expresses the antigen, are also provided.

In another aspect, the invention provides a vaccine comprising an antigen-presenting cell, wherein the antigen-presenting cell comprises a bacterium, wherein the bacterium has been modified by reaction with a nucleic acid targeted compound that reacts directly with its nucleic acid so that the bacterium is attenuated for proliferation and wherein the bacterium is defective with respect to at least one DNA repair enzyme. In some embodiments, the bacterium is *Listeria monocytogenes*. In some embodiments, the bacterium is defective with respect to both UvrA and UvrB (e.g., a uvrAB deletion mutant). In some embodiments, the bacterium is defective with respect to UvrC. In some embodiments, the bacterium is defective with respect to RecA. Methods of preventing or treating disease in a host, comprising administering an effective amount of the vaccine to the host, are also provided.

I. Vaccines

In some embodiments, the vaccines of the invention are modified microbe-based vaccines. In some embodiments, the vaccines comprise antigen-presenting cells prepared using modified microbes. The modified microbes used either directly in or for preparation of the aforementioned vaccines are as described herein.

A. Modified Microbe-Based Vaccines

The present invention involves modified free-living microbes and the use of modified free-living microbes in a vaccine composition, wherein the nucleic acid of the microbe is modified so that proliferation of the microbe is attenuated. In some embodiments, the microbial gene expression is substantially unaffected by the modification.

It has been observed that killed microbial vaccines are often inferior to live attenuated microbial vaccines [Lauvau et al., Science 294:1735-1739 (2001)]. In completely killed microbes, the de novo microbial gene expression is essentially eliminated. Therefore, the modification of the microbial nucleic acid to an appropriate level such that proliferation is attenuated while maintaining a sufficient level of microbial gene expression may be more effective than a killed microbial vaccine and provides an approach to vaccine preparation that can be applied to any microbial vector, whether the vaccine targets the prevention of infectious disease caused by the microbial vector, or the vector is used to deliver a heterologous antigen. It is to be understood that the use of the term microbes as it relates to all embodiments of the present invention is intended to mean free-living microbes and is not intended to include viruses. Such a microbe-based vaccine may be used to deliver a specific antigen to an individual. In one embodiment, the vaccine delivers more than one antigen. Such vaccines are designed to stimulate an immune response to one or more antigens, resulting in an individual who is immunized against the antigen or antigens. The immune response that is generated can be either an antibody mediated response, a cell mediated response, or both. The term vaccine is intended to encompass a preventative vaccine, i.e. one that is given to stimulate an immune response so that if the individual subsequently is exposed to the antigen in nature, the pre-formed immune response will increase the individual's ability to fight off the agent or cells carrying the antigen. The term vaccine is also intended to encompass a therapeutic vaccine, i.e. one that is given to an individual who already has a disease associated with the vaccine antigen, wherein the vaccine can elicit an immune response or boost the individual's existing immune response to the antigen to provide an increased ability to fight the agent or cells carrying the antigen. This includes an immune response to a diseased cell, such as a cancer cell, as well as an immune response to a disease associated protein such as a prion. In one embodiment, the free-living microbe is selected from the group consisting of bacteria, protozoa, and fungi. In one embodiment, the free-living microbe is a bacteria selected from the group consisting of Gram positive bacteria, Gram negative bacteria, intracellular bacteria and mycobacteria.

The present invention includes various levels of modification of the nucleic acid of microbes. It is understood that the metabolism of the microbial nucleic acid occurs in several ways. Replication of the microbe involves the copying of the DNA of the entire microbial genome in order to replicate the microbe and the subsequent partitioning of the DNA molecules into separate cells, i.e. the cell divides with the resulting cells both having a complete copy of the DNA of the microbial genome. Microbial nucleic acid metabolism also involves the combination of transcription of DNA into RNA and translation of RNA to produce proteins. The transcription of the microbial genome involves the copying of portions of the DNA of the microbial genome into RNA, either messenger or transfer RNA. The translation of the messenger RNA involves the reading of this RNA in order to produce a specific protein or portion of a protein. In the present invention the nucleic acid of a population of microbes is modified to a desired extent based upon the nature of the microbe and its intended use. In some embodiments, the desired extent of modification is such that replication of the microbe's genome is significantly attenuated while the production of proteins remains sufficiently active (i.e. the microbe is metabolically active). It is to be understood that whatever the nature of the modification, the level of modification can be represented in terms of the number of modifications on average per base pair of the microbial genome. For example, if the modification is due to covalent binding of a compound to the nucleic acid (adducts), the modification can be represented in terms of the average number of base pairs between adducts. In some embodiments, the microbes of the invention can be modified to levels of about 1 modification per $10^3$-$10^8$ base pairs, about 1 modification per $10^4$-$10^8$ base pairs, about 1 modification per $10^4$-$10^7$, about 1 modification per $10^5$-$10^7$, or about 1 modification per $10^5$-$10^6$ base pairs. In one embodiment, the level of modification is adjusted to the minimum amount required to block DNA replication in the microbial population, such that the population shows no observable proliferation, while maintaining sufficient activity of transcription and translation of individual genes (i.e. maintains some metabolic activity) to achieve a safe and effective vaccine.

In one aspect, the invention provides a vaccine comprising a free-living microbe, wherein the nucleic acid of the microbe is modified so that the microbe is attenuated for proliferation. In some embodiments, the attenuation of the proliferation of the microbe is controllable in a dose-dependent manner. In some embodiments, microbial gene expression in the microbe is substantially unaffected by attenuation of the proliferation of the microbe. In some embodiments, the microbe in the vaccine expresses an antigen at a sufficient level to induce an immune response to the antigen in an individual upon administration of the vaccine to the individual. In some embodiments, the nucleic acid has been modified by reaction with a nucleic acid targeted compound which reacts directly with the nucleic acid. In one embodiment, the nucleic acid target compound is an alkylator such as β-alanine, N-(acridin-9-yl), 2-[bis(2-chloroethyl)amino]ethyl ester. In other embodiments, the nucleic acid targeted compound is a psoralen compound (e.g., 4'-(4-amino-2-oxa)butyl-4,5',8-trimethylpsoralen, also referred to herein as "S-59") activated by UVA irradiation. In some embodiments, the microbe in the vaccine comprises a genetic mutation that attenuates the ability of the microbe to repair its nucleic acid that has been modified. In some embodiments, the microbe is a bacterium, such as *Bacillus anthracis* or *Listeria monocytogenes*. In some embodiments, the microbe comprises a heterologous nucleic acid sequence encoding an antigen. In some embodiments, the vaccine further comprises a pharmaceutically acceptable carrier and/or an adjuvant. The invention further provides a method of preventing or treating a disease in a host, comprising administering to the host an effective amount of the vaccine. The invention also provides a method of inducing an immune response in a host to an antigen comprising administering to the host an effective amount of the vaccine, wherein the microbe expresses the antigen.

The invention further provides vaccines comprising a mutant *Listeria monocytogenes* strain or a mutant *Bacillus anthracis* strain, wherein the mutant *Listeria monocytogenes* strain or *Bacillus anthracis* strain comprises a genetic mutation that attenuates its ability to repair its nucleic acid.

In one embodiment, the invention includes a vaccine composition comprising a free-living microbe in which the microbial nucleic acid is modified so that the proliferation of the microbe is attenuated, wherein the microbial gene expression is substantially unaffected. In one embodiment, the microbial gene expression is substantially unaffected so that an antigen is expressed at a level sufficient to stimulate an immune response upon administration of the microbe to an individual. In one embodiment, the proliferation of the microbe is attenuated by at least about 0.3 log, also at least about 1 log, about 2 log, about 3 log, about 4 log, about 6 log, or at least about 8 log. In another embodiment, the proliferation of the microbe is attenuated by about 0.3 to >10 log, about 2 to >10 log, about 4 to >10 log, about 6 to >10 log, about 0.3-8 log, about 0.3-6 log, about 0.3-5 log, about 1-5 log, or about 2-5 log. In one embodiment, the expression of an antigen by the microbe is at least about 10%, about 25%, about 50%, about 75%, or at least about 90% of the expression of the antigen by a microbe in which the microbial nucleic acid is not modified. In one embodiment, the antigen expressed is an antigen from the microbe itself. In one embodiment, the microbe comprises a heterologous nucleic acid sequence encoding an antigen. In one embodiment, the antigen is a disease associated antigen. In one embodiment, the antigen is associated with a disease selected from the group consisting of infectious diseases, autoimmune diseases, allergies, cancers, and other hyperproliferative diseases. In one embodiment, the antigen is a tumor associated antigen. In one embodiment, the tumor antigen is selected from the group consisting of differentiation antigens, tissue-specific antigens, developmental antigens, tumor-associated viral antigens, cancer-testis antigens, embryonic antigens, oncoprotein antigens, over-expressed protein antigens and mutated protein antigens. In one embodiment, the tumor antigen is selected from the group consisting of mesothelin, Sp17, gp100, PR3, PAGE-4, TARP, WT-1, NY-ESO-1 and SPAS-1. In one embodiment, the microbial nucleic acid is modified by a method selected from the group consisting of exposing the microbe to radiation and reacting the microbe with a nucleic acid targeted compound that causes the modification of the microbial nucleic acid. In a preferred embodiment, the microbial nucleic acid is modified by reacting the microbe with a nucleic acid targeted compound that reacts directly with the nucleic acid. In one embodiment, the nucleic acid targeted compound is targeted to the nucleic acid by a mode selected from the group consisting of intercalation, minor groove binding, major groove binding, electrostatic binding, and sequence-specific binding.

In one embodiment, the nucleic acid targeted compound comprises a nucleic acid alkylator. In a preferred embodiment, the nucleic acid targeted compound is β-alanine, N-(acridin-9-yl), 2-[bis(2-chloroethyl)amino]ethyl ester. In one embodiment, the nucleic acid targeted compound that reacts directly with the nucleic acid reacts upon activation of the compound by irradiation, preferably by UVA irradiation. In one embodiment, the nucleic acid targeted compound activated by UVA irradiation is a psoralen. In a preferred embodiment, the psoralen is 4'-(4-amino-2-oxa)butyl-4,5',8-trimethylpsoralen. In one embodiment, the nucleic acid targeted compound indirectly causes the modification of the nucleic acid. In one embodiment, the nucleic acid targeted compound indirectly causes modification upon activation by irradiation, preferably by UVA irradiation. In one embodiment, the microbe comprises a genetic mutation. In one embodiment, the genetic mutation results in the attenuation of the ability of the microbe to repair microbial nucleic acid that has been modified. In one embodiment, the genetic mutation is in the gene selected from the group consisting of phrB, uvrA, uvrB, uvrC, uvrD and recA, or their functionally equivalent genes, depending on the genus and species of the microbe. In one embodiment, the mutation is in one or more of the genes selected from the group consisting of phrB, uvrA, uvrB, uvrC, uvrD and recA, or their functionally equivalent genes. In one embodiment, the genetic mutation results in the attenuation in the activity of a DNA repair enzyme selected from the group consisting of PhrB, UvrA, UvrB, UvrC, UvrD and RecA. In a further embodiment, the microbes containing these mutations are modified by reaction with a psoralen activated by UVA irradiation. In a preferred embodiment, the psoralen is 4'-(4-amino-2-oxa)butyl-4,5',8-trimethylpsoralen. In one embodiment, the microbe is selected from the group consisting of bacteria, protozoa and fungi. In one embodiment, the microbe is a bacteria. In one embodiment, the bacteria are intracellular bacteria. In a preferred embodiment, the bacteria are *Listeria*, preferably *Listeria monocytogenes*. In one embodiment, the *Listeria* comprises a mutation that results in the attenuation of the ability of the *Listeria* to invade non-phagocytic cells without significantly affecting the uptake of the *Listeria* by phagocytic cells. In one embodiment, the *Listeria* mutation is in an internalin gene(s). In one embodiment, the *Listeria* mutation is in the gene selected from the group consisting of inlA, inlB, and any gene encoding an internalin. In one embodiment, the *Listeria monocytogenes* comprises a genetic mutation in both the inlA and inlB genes. In one embodiment, the *Listeria* comprises a mutation that results in the attenuation of the ability of the *Listeria* to escape the phagolysosome of an infected cell. In one embodiment, the *Listeria* mutation is in the hly gene. In one embodiment, the *Listeria* comprises a mutation that results in the attenuation of the polymerization of actin by the *Listeria*. In a preferred embodiment, the *Listeria* mutation is in the actA gene. In one embodiment, the *Listeria* comprises mutations in the actA gene and one or more internalin genes. In a preferred embodiment, the *Listeria* comprises a mutation in the actA gene and the inlB gene, preferably the *Listeria* comprises an actA/inlB deletion mutant. In a preferred embodiment, the *Listeria monocytogenes* actA/inlB deletion mutant further comprises a deletion mutation in the uvrAB gene.

In one embodiment, the invention includes a vaccine composition comprising a bacterium in which the bacterial nucleic acid is modified so that the proliferation of the bacterium is attenuated, wherein the bacterial gene expression is substantially unaffected. In one embodiment, the bacterial gene expression is substantially unaffected so that an antigen is expressed at a level sufficient to stimulate an immune response to the bacteria upon administration of the bacteria to an individual. In one embodiment, the proliferation of the bacteria are attenuated by at least about 0.3 log, also at least about 1 log, about 2 log, about 3 log, about 4 log, about 6 log, or at least about 8 log. In another embodiment, the proliferation of the microbe is attenuated by about 0.3 to >10 log, about 2 to >10 log, about 4 to >10 log, about 6 to >10 log, about 0.3-8 log, about 0.3-6 log, about 0.3-5 log, about 1-5 log, or about 2-5 log. In one embodiment, the expression of an antigen by the bacteria are at least about 10%, about 25%, about 50%, about 75%, or at least about 90% of the expression of the antigen by a bacteria in which the bacterial nucleic acid is not modified. In one embodiment, the bacterial nucleic acid is modified by a method selected from the group consisting of exposing the bacteria to radiation and reacting the bacteria with a nucleic acid targeted compound that causes the modification of the bacterial nucleic acid. In a preferred embodiment, the bacterial nucleic acid is modified by reacting the bacteria with a nucleic acid targeted compound that reacts directly with the nucleic acid. In one embodiment, the nucleic acid targeted compound is targeted to the nucleic acid by a mode selected from the group consisting of intercalation, minor groove binding, major groove binding, electrostatic binding, and sequence-specific binding. In one embodiment, the nucleic acid targeted compound comprises a nucleic acid alkylator. In a preferred embodiment, the nucleic acid targeted compound is β-alanine, N-(acridin-9-yl), 2-[bis(2-chloroethyl)amino]ethyl ester. In one embodiment, the nucleic acid targeted compound that reacts directly with the nucleic acid reacts upon activation of the compound by irradiation, preferably by UVA irradiation. In one embodiment, the nucleic acid targeted compound activated by UVA irradiation is a psoralen. In a preferred embodiment, the psoralen is 4'-(4-amino-2-oxa)butyl-4,5',8-trimethylpsoralen. In one embodiment, the nucleic acid targeted compound indirectly causes the modification of the nucleic acid. In one embodiment, the nucleic acid targeted compound indirectly causes modification upon activation by irradiation, preferably by UVA irradiation. In one embodiment, the bacteria comprises a genetic mutation. In one embodiment, the genetic mutation results in the attenuation of the ability of the bacteria to repair bacterial nucleic acid that has been modified. In one embodiment, the genetic mutation is in the gene selected from the group consisting of phrB, uvrA, uvrB, uvrC, uvrD and recA, or their functionally equivalent genes, depending on the genus and species of the bacteria. In one embodiment, the mutation is in one or more of the genes selected from the group consisting of phrB, uvrA, uvrB, uvrC, uvrD and recA, or their functionally equivalent genes. In one embodiment, the genetic mutation results in the attenuation in the activity of a DNA repair enzyme selected from the group consisting of PhrB, UvrA, UvrB, UvrC, UvrD and RecA. In a preferred embodiment, the bacteria containing these mutations are modified by reaction with a psoralen activated by UVA irradiation. In a preferred embodiment, the psoralen is 4'-(4-amino-2-oxa)butyl-4,5',8-trimethylpsoralen. In one embodiment, the bacteria are selected from the group consisting of Gram positive bacteria, Gram negative bacteria, intracellular bacteria and mycobacteria. In one embodiment, the bacteria are selected from the group consisting of *Bacillus anthracis, Cholera, Bordetella pertussis, Corynebacterium diphtheriae, E. coli, Borrelia burgdorferi* (Lyme), *Streptococcus pneumoniae, Salmonella, Staphylococcus* sp., *Mycobacterium tuberculosis, Brucella abortus, Brucella melitensis, Haemophilus influenzae, Neisseria meningitides, Yersinia pestis, Shigella* sp., *Francisella tulraensis*, and *Streptococcus pyogenes*. In one embodiment, the bacteria are mycobacteria. In one embodiment, the mycobacteria are *Mycobacterium tuberculosis*. In one embodiment, the *Mycobacterium tuberculosis* comprises a uvrAB deletion mutation. In one embodiment, the *Mycobacterium tuberculosis* comprises a conditional recA mutation. In one embodiment, the bacteria are intracellular bacteria. In one embodiment, the intracellular bacteria belong to the species *Bacillus anthracis*. In one embodiment, the *Bacillus anthracis* comprises a uvrAB deletion mutation. In one embodiment, the *Bacillus anthracis* comprises a conditional recA mutation. In one embodiment, the intracellular bacteria are *Yersinia pestis*. In one embodiment, the *Yersinia pestis* comprises a uvrAB deletion mutation. In one embodiment, the *Yersinia pestis* comprises a conditional recA mutation.

In one aspect, the invention provides a vaccine comprising a *Listeria monocytogenes* bacterium that has been modified by reaction with a nucleic acid targeted compound that reacts directly with the nucleic acid so that the bacterium is attenuated for proliferation and that is defective with respect to at least one DNA repair enzyme.

The invention also provides a vaccine comprising a *Listeria monocytogenes* bacterium that has been modified by reaction with a nucleic acid targeted compound that reacts directly with the nucleic acid so that the bacterium is attenuated for proliferation and that is defective with respect to both UvrA and UvrB.

The invention further provides a vaccine comprising a *Bacillus anthracis* bacterium that has been modified by reaction with a nucleic acid targeted compound that reacts directly with the nucleic acid so that the bacterium is attenuated for proliferation and that is defective with respect to both UvrA and UvrB.

Also provided is a vaccine comprising a bacterium, wherein the bacterium has been modified by reaction with a nucleic acid targeted compound that reacts directly with its nucleic acid so that the bacterium is attenuated for proliferation and wherein the bacterium is defective with respect to at least one DNA repair enzyme. In some embodiments, the bacterium is *Listeria monocytogenes*. In some embodiments, the bacterium is *Bacillus anthracis*. In some embodiments, the bacterium is defective with respect to both UvrA and UvrB (e.g., a uvrAB deletion mutant). In some embodiments, the bacterium is defective with respect to UvrC. In some embodiments, the bacterium is defective with respect to RecA.

B. Antigen-Presenting Cell Vaccines.

The present invention involves modified free-living microbes and the use of modified free-living microbes in the preparation of vaccine compositions based on antigen-presenting cells (e.g, dendritic cells), wherein the nucleic acid of the microbe is modified so that proliferation of the microbe is attenuated. In some embodiments, the microbial gene expression of the modified microbe is substantially unaffected. Any of the modified microbes described herein, including those described with respect to microbe-based vaccines, can be used in the production of antigen-presenting cell vaccines.

In one embodiment of the invention, the antigen-presenting cells used in the vaccines are professional antigen presenting cells. Professional antigen-presenting cells include macrophages, dendritic cells and B cells. Other professional antigen-presenting cells include monocytes, marginal zone Kupffer cells, microglia, Langerhans' cells, interdigitating dendritic cells, follicular dendritic cells, and T cells. In one embodiment, the professional antigen-presenting cells are dendritic cells. In another embodiment, the professional antigen-presenting cells are macrophages or dendritic cells (DCs). In one embodiment the antigen-presenting cells are human cells.

In one embodiment, immature antigen-presenting cells, such as DCs, are isolated from a patient and infected with a modified microbe expressing an antigen. The resulting, loaded, antigen-presenting cells are then transferred back into the patient as an autologous APC vaccine, thereby inducing either a CD4+ or a CD8+ immune response.

Accordingly, one example of a method of preparing and using an antigen-presenting cell vaccine of the invention is as follows: Immature DCs are isolated from colon cancer patients and infected with S-59/UVA-inactivated, non-viable, metabolically active recombinant *Listeria*-CEA vaccines. DC Infection with *Listeria* results in efficient loading of CEA tumor antigen into the MHC class I and II pathways. *Listeria* infection stimulates DC to undergo rapid activation and maturation, critical for DC to become potent APCs capable of inducing primary T cell responses in vivo. Mature DC upregulate the expression of CD83, co-stimulatory molecules such as CD80, CD86, as well as MHC molecules. *Listeria* vaccine-loaded DCs are washed and infused back into the patient as an autologous DC vaccine to stimulate a CEA-specific T cell response. An exemplary demonstration of the ability of DC-based vaccines infected with modified microbes such as those described herein, to stimulate an in vivo immune response is provided in Example 50, below.

Particular embodiments are exemplified in the specific Examples listed below. It is understood, however, that the general methods and techniques described herein may be more broadly applied to a wide variety of modified microbes, antigens, and diseases. One of ordinary skill in the art will be able to readily adapt the teachings described herein.

In an alternative embodiment, immature antigen-presenting cells, such as DCs, are infected in vitro with a modified microbe expressing an antigen. The resulting, loaded, antigen-presenting cells are then used to prime a T-cell population which is then transferred into the patient, thereby inducing either a CD4+ or a CD8+ immune response to the antigen.

In another aspect, the invention provides a professional antigen-presenting cell (e.g., a dendritic cell) comprising a free-living microbe (e.g., a bacterium), wherein the nucleic acid of the microbe is modified so that the microbe is attenuated for proliferation. In some embodiments, the attenuation of the proliferation of the microbe is controllable in a dose-dependent manner. In some embodiments, microbial gene expression in the microbe is substantially unaffected by attenuation of the proliferation of the microbe. In some embodiments, the microbe in the vaccine expresses an antigen at a sufficient level to induce an immune response to the antigen in an individual upon administration of the vaccine to the individual. In some embodiments, the nucleic acid has been modified by reaction with a nucleic acid targeted compound which reacts directly with the nucleic acid. In one embodiment, the nucleic acid target compound is an alkylator such as β-alanine, N-(acridin-9-yl), 2-[bis(2-chloroethyl) amino]ethyl ester. In other embodiments, the nucleic acid targeted compound is a psoralen compound activated by UVA irradiation. In some embodiments, the microbe in the vaccine comprises a genetic mutation that attenuates the ability of the microbe to repair its nucleic acid that has been modified. In some embodiments, the microbe is a bacterium. In some embodiments, the microbe comprises a heterologous nucleic acid sequence encoding an antigen. The invention also provides a vaccine comprising the antigen-presenting cell. The invention further provides a method of preventing or treating a disease in a host, comprising administering to the host an effective amount of the antigen-presenting cell. The invention also provides a method of inducing an immune response in a host to an antigen comprising administering to the host an effective amount of the antigen-presenting cell, wherein the microbe expresses the antigen. The invention further provides a method of activating naïve T cells ex vivo or in vitro, comprising contacting the naïve T cells with the professional antigen-presenting cell under suitable conditions and for a sufficient time to activate the naïve T-cells.

In one embodiment, the invention includes a vaccine composition comprising an antigen-presenting cell that has been antigen-loaded and/or activated or matured through infection with a free-living microbe in which the microbial nucleic acid is modified so that the proliferation of the microbe is attenuated, wherein the microbial gene expression is substantially unaffected. In one embodiment, the microbial gene expression is substantially unaffected so that an antigen is expressed at a level sufficient to stimulate an immune response upon administration of the microbe to an individual. In one embodiment, the proliferation of the microbe is attenuated by at least about 0.3 log, also at least about 1 log, about 2 log, about 3 log, about 4 log, about 6 log, or at least about 8 log. In another embodiment, the proliferation of the microbe is attenuated by about 0.3 to >10 log, about 2 to >10 log, about 4 to >10 log, about 6 to >10 log, about 0.3-8 log, about 0.3-6 log, about 0.3-5 log, about 1-5 log, or about 2-5 log. In one embodiment, the expression of an antigen by the microbe is at least about 10%, about 25%, about 50%, about 75%, or at least about 90% of the expression of the antigen by a microbe in which the microbial nucleic acid is not modified. In one embodiment, the antigen expressed is an antigen from the microbe itself. In one embodiment, the microbe comprises a heterologous nucleic acid sequence encoding an antigen. In one embodiment, the antigen is a disease associated antigen. In one embodiment, the antigen is associated with a disease selected from the group consisting of infectious diseases, autoimmune diseases, allergies, cancers, and other hyperproliferative diseases. In one embodiment, the antigen is a tumor associated antigen. In one embodiment, the tumor antigen is selected from the group consisting of differentiation antigens, tissue-specific antigens, developmental antigens, tumor-associated viral antigens, cancer-testis antigens, embryonic antigens, oncoprotein antigens, over-expressed protein antigens and mutated protein antigens. In one embodiment, the tumor antigen is selected from the group consisting of mesothelin, Sp17, gp100, PR3, PAGE-4, TARP, WT-1, NY-ESO-1 and SPAS-1. In one embodiment, the microbial nucleic acid is modified by a method selected from the group consisting of exposing the microbe to radiation and reacting the microbe with a nucleic acid targeted compound that causes the modification of the microbial nucleic acid. In a preferred embodiment, the microbial nucleic acid is modified by reacting the microbe with a nucleic acid targeted compound that reacts directly with the nucleic acid. In one embodiment, the nucleic acid targeted compound is targeted to the nucleic acid by a mode selected from the group consisting of intercalation, minor groove binding, major groove binding, electrostatic binding, and sequence-specific binding. In one embodiment, the nucleic acid targeted compound comprises a nucleic acid alkylator. In a preferred embodiment, the nucleic acid targeted compound is β-alanine, N-(acridin-9-yl), 2-[bis(2-chloroethyl)amino]ethyl ester. In one embodiment, the nucleic acid targeted compound that reacts directly with the nucleic acid reacts upon activation of the compound by irradiation, preferably by UVA irradiation. In one embodiment, the nucleic acid targeted compound activated by UVA irradiation is a psoralen. In a preferred embodiment, the psoralen is 4'-(4-amino-2-oxa)butyl-4,5',8-trimethylpsoralen. In one embodiment, the nucleic acid targeted compound indirectly causes the modification of the nucleic acid. In one embodiment, the nucleic acid targeted compound indirectly causes modification upon activation by irradiation, preferably by UVA irradiation. In one embodiment, the microbe comprises a genetic mutation. In one embodiment, the genetic mutation results in the attenuation of the ability of the microbe to repair microbial nucleic acid that has been modified. In one embodiment, the genetic mutation is in the gene selected from the group consisting of phrB, uvrA, uvrB, uvrC, uvrD and recA, or their functionally equivalent genes, depending on the genus and species of the microbe. In one embodiment, the mutation is in one or more of the genes selected from the group consisting of phrB, uvrA, uvrB, uvrC, uvrD and recA, or their functionally equivalent genes. In one embodiment, the genetic mutation results in the attenuation in the activity of a DNA repair enzyme selected from the group consisting of PhrB, UvrA, UvrB, UvrC, UvrD and RecA. In a further embodiment, the microbes containing these mutations are modified by reaction with a psoralen activated by UVA irradiation. In a preferred embodiment, the psoralen is 4'-(4-amino-2-oxa)butyl-4,5',8-trimethylpsoralen. In one embodiment, the microbe is selected from the group consisting of bacteria, protozoa and fungi. In one embodiment, the microbe is a bacteria. In one embodiment, the bacteria are intracellular bacteria. In a preferred embodiment, the bacteria are *Listeria*, preferably *Listeria monocytogenes*. In one embodiment, the *Listeria* comprises a mutation that results in the attenuation of the ability of the *Listeria* to invade non-phagocytic cells without significantly affecting the uptake of the *Listeria* by phagocytic cells. In one embodiment, the *Listeria* mutation is in an internalin gene(s). In one embodiment, the *Listeria* mutation is in the gene selected from the group consisting of inlA, inlB, and any gene encoding an internalin. In one embodiment, the *Listeria monocytogenes* comprises a genetic mutation in both the inlA and inlB genes. In one embodiment, the *Listeria* comprises a mutation that results in the attenuation of the ability of the *Listeria* to escape the phagolysosome of an infected cell. In one embodiment, the *Listeria* mutation is in the hly gene. In one embodiment, the *Listeria* comprises a mutation that results in the attenuation of the polymerization of actin by the *Listeria*. In a preferred embodiment, the *Listeria* mutation is in the actA gene. In one embodiment, the *Listeria* comprises mutations in the actA gene and one or more internalin genes. In a preferred embodiment, the *Listeria* comprises a mutation in the actA gene and the inlB gene, preferably the *Listeria* comprises an actA/inlB deletion mutant. In a preferred embodiment, the *Listeria monocytogenes* actA/inlB deletion mutant further comprises a deletion mutation in the uvrAB gene.

In another aspect, the invention provides a vaccine comprising an antigen-presenting cell, wherein the antigen-presenting cell comprises a bacterium, wherein the bacterium has been modified by reaction with a nucleic acid targeted compound that reacts directly with its nucleic acid so that the bacterium is attenuated for proliferation and wherein the bacterium is defective with respect to at least one DNA repair enzyme. In some embodiments, the bacterium is *Listeria monocytogenes*. In some embodiments, the bacterium is defective with respect to both UvrA and UvrB (e.g., a uvrAB deletion mutant). In some embodiments, the bacterium is defective with respect to UvrC (e.g., a uvrC deletion). In some embodiments, the bacterium is defective with respect to RecA.

The invention also provides a vaccine comprising an antigen-presenting cell comprising a free-living microbe (e.g., a bacterium) which is defective with respect to at least one DNA repair enzyme.

C. Modified Microbes

A variety of modified microbes are provided by the present invention. It is understood that each of the modified microbes described herein can be used in the microbe-based vaccines and antigen-presenting cell based vaccines described herein.

In some embodiments, the modified microbe is selected from the group consisting of bacteria, protozoa and fungi. In some embodiments, the modified microbe is a bacterium. In one embodiment, the bacterium is a mycobacterium. In one embodiment, the mycobacterium is *Mycobacterium tuberculosis*. In one embodiment, the bacterium is an intracellular bacterium. In one embodiment, the intracellular bacterium belongs to the species *Bacillus anthracis*. (For additional information regarding the use of *B. anthracis* as a modified microbe see also U.S. Provisional Application 60/584,886, Dubensky et al., "Modified *Bacillus Anthracis*, Vaccine Compositions and Methods of Use Thereof", filed Jun. 30, 2004, incorporated by reference herein in its entirety.) In one embodiment, the intracellular bacterium belongs to the species *Yersinia pestis*. In a preferred embodiment, the bacterium belongs to the genus *Listeria*, and preferably the species *Listeria monocytogenes*.

In some embodiments, the modified microbe that is used in the vaccine or to make the vaccine is a wild-type microbe. In some embodiments, the modified microbe is a mutant microbe. In some embodiments, the modified microbe has been recombinantly engineered. In some embodiments, the modified microbe in the microbe-based vaccine or used to make the APC-based vaccine is a clinical isolate (i.e., has been obtained from a patient infected with the microbe). In other embodiments, the modified microbe used in the vaccine or to make the vaccine is derived from a clinical isolate.

1. Attenuation of Microbial Replication.

The present invention involves the modification of microbial nucleic acid in order to attenuate replication of the microbe. This attenuation in replication can be used to increase the level of safety upon administration of the microbes to individuals. The ability of a microbe to proliferate can be measured by culturing a population of microbes under conditions that provide normal growth. The normal growth of a population of microbes is considered to be the growth of microbes having no modifications to the nucleic acid of the microbe. The modification of the microbial genome will result in some attenuation so that the microbe will not undergo normal growth. Some microbes will form colonies that can be counted on solidified growth medium. Attenuation of the replication of the microbe can thus be measured as a reduction in the number of colony forming units (CFU). A stock solution of the microbe colony will be serially diluted until the number of colony forming units can be easily measured (e.g. 50-500 CFU). Typically, dilutions are 10-fold and the number of colonies counted for one or more of the diluted samples is used to estimate the log titer of the sample. For example, an aliquot of diluted microbe stock is plated on growth media and the resulting colonies are counted. The colony forming units per mL (CFU/mL) of the dilution is calculated, and the colony forming units per mL of the original stock (known as the titer) is calculated from the dilution. The log number is known as the log titer. As an example, 24 colony forming units on plating a 0.2 mL aliquot of a $1\times10^5$ dilution gives a $1.2\times10^7$ titer, or 7.08 log titer stock. The attenuation can be measured as the comparison of microbial titer prior to modification of the microbial nucleic acid to that after modification of the microbial nucleic acid. The log of the ratio of the titer of unmodified microbe to the titer of microbe after modification represents the log attenuation (or simply the difference in log titer of the two). For example, if an unmodified microbe titer measures $1.2\times10^7$ and a modified microbe titer measures $4.3\times10^2$, the resulting level of attenuation is 4.45 log. This method can be used to assess the attenuation of any microbe, whether pathogenic or non-pathogenic. For some microbes, rather than measuring the growth of the microbe directly, a plaque assay that measures the microbe by its ability to kill infected cells can be used. For example, certain intracellular bacteria can be grown on a lawn of mammalian cells that it can infect. After appropriate incubation conditions, the lawn can be observed for plaques (clear areas in the cell layer that represent killed cells). The above calculations are similar, where the number of plaque forming units is substituted for colony forming units to assess attenuation of the number of plaque forming units by modification of the nucleic acid of the microbe. For embodiments of the invention, the desired amount of attenuation can range from a two-fold reduction to much greater levels of attenuation, including a level where essentially no proliferation is observed, depending on the desired level of safety and the intended application of the microbe. A two-fold attenuation in replication would be observed if for a given dilution, there are half as many colonies (or plaques) in the population of a microbe where the nucleic acid is modified as there are in an unmodified population of the microbe (about 0.3 log attenuation). In some embodiments, the attenuation is at least about 0.3 log, about 1 log, about 2 log, about 3 log, about 4 log about 5 log, about 6 log, or at least about 8 log. In some embodiments, the attenuation is in the range of about 0.3 to >10 log, about 2 to >10 log, about 4 to >10 log, about 6 to >10 log, about 0.3-8 log, also about 0.3-7 log, also about 0.3-6 log, also about 0.3-5 log, also about 0.3-4 log, also about 0.3-3 log, also about 0.3-2 log, also about 0.3-1 log. In some embodiments, the attenuation is in the range of about 1 to >10 log, 1-8 log, 1-6 log, also about 2-6 log, also about 2-5 log, also about 3-5 log. In one embodiment of the invention, the attenuation results in essentially complete inactivation (e.g. where no colonies or plaques are observed to the limit of detection), wherein the microbial gene expression is sufficiently active. Such a population of microbes can be achieved by titrating the concentration of the agent used to modify the microbial nucleic acid to find the lowest concentration at which no colonies or plaques are observed at the limit of detection.

In the case of pathogenic microbes, it is also possible to assess the attenuation in terms of biological effects of the microbe. For example, the pathogenicity of a microbe can be assessed by measurement of the median lethality ($LD_{50}$) in mice or other vertebrates. The $LD_{50}$ is the amount (e.g. CFU) of microbe injected into the vertebrate that would result in the death of half of the population of the vertebrate. The $LD_{50}$ values can be compared for modified and unmodified microbes as a measure of the amount of attenuation. For example, if an unmodified population of microbes has an $LD_{50}$ of $10^3$ microbes and the population of microbes in which the nucleic acid has been modified has an $LD_{50}$ of $10^5$ microbes, the microbe has been attenuated so that its $LD_{50}$ is increased 100-fold, or by 2 log. In some embodiments, the $LD_{50}$ is 2-fold to 1000-fold higher. In some embodiments, an attenuated strain is used that already has a relatively high $LD_{50}$. In such cases, the modified microbes increase in $LD_{50}$ will be limited by how much material can be infused without causing harm. For example, the $LD_{50}$ of a heat killed organism would not be much higher than about $1\text{-}5\times10^9$ simply because of the loading of biological material into the mice and/or the inflammatory reaction to the bacterial wall components. The degree of attenuation may also be measured qualitatively by other biological effects, such as the extent of tissue pathology or serum liver enzyme levels. Typically, alanine aminotransferase (ALT), aspartate aminotransferase (AST), albumin, and billirubin levels in the serum are determined at a clinical laboratory for mice injected with microbes of the present invention. Comparisons of these effects in mice or other vertebrates would be made for unmodified and modified microbe as a way to assess the attenuation of the microbe. In addition to measuring the effects of the microbes on the tissues, the amount of viable microbe that can be recovered from infected tissues such as liver or spleen as a function of time could also be used as a measure of attenuation by comparing these values in mice injected with unmodified vs. modified microbes.

2. Expression of Proteins by Microbes of the Invention.

In some embodiments, the modification of the nucleic acid of the microbe, in addition to attenuating proliferation of the microbe, is controlled so that microbial gene expression is substantially unaffected. To be substantially unaffected, the microbial gene expression need not be completely active upon modification of the nucleic acid. It is only necessary that in a population of a microbe in which the nucleic acid is modified to attenuate replication, microbial gene expression is sufficiently active to provide an adequate level of expression of the desired protein by the microbe. An adequate level of expression depends to some extent on the intended use of the microbe. For example, if the microbe contains a particular antigen that is to be used as a vaccine, adequate expression would be determined as the minimum level of expression that provides an effective protective or therapeutic immune response to the vaccine. The microbial gene expression can also be assessed by both in vitro and in vivo methods in order to assess whether such a vaccine might provide an effective immune response. In general, a population of a microbe in which the nucleic acid has been modified can be compared to an unmodified population of the microbe with respect to a particular antigen.

One possibility is to measure the presentation of the antigen of interest by an antigen presenting cell that has been mixed with a population of the microbe. The microbes may be mixed with a suitable antigen presenting cell or cell line, for example a dendritic cell, and the antigen presentation by the dendritic cell to a T cell that recognizes the antigen can be measured. If the microbes are expressing the antigen at a sufficient level, it will be processed into peptide fragments by the dendritic cells and presented in the context of MHC class I or class II to CD8+ or CD4+ T cells, respectively. For the purpose of detecting the presented antigen, a T cell clone or T cell line responsive to the particular antigen may be used. The T cell may also be a T cell hybridoma, where the T cell is immortalized by fusion with a cancer cell line. Such T cell hybridomas, T cell clones, or T cell lines can comprise either CD8+ or CD4+ T cells. The antigen presenting cell can present to either CD8+ or CD4+ T cells, depending on the pathway by which the antigens are processed. CD8+ T cells recognize antigens in the context of MHC class I while CD4+ T cells recognize antigens in the context of MHC class II. The T cell will be stimulated by the presented antigen through specific recognition by its T cell receptor, resulting in the production of certain proteins, such as IL-2 or interferon-γ (IFN-γ), that can be quantitatively measured (for example using an ELISA assay). Alternatively, a hybridoma can be designed to include a reporter gene, such as β-galactosidase, that is activated upon stimulation of the T cell hybridoma by the presented antigens. The increase in the production of β-galactosidase can be readily measured by its activity on a substrate, such as chlorophenolred-β-D-galactopyranoside, which results in a color change. The color change can be directly measured as an indicator of specific antigen presentation (Examples 1, 2 and 11). Additional in vitro and in vivo methods for assessing the antigen expression of microbial vaccines of the present invention can be found in Example 5. It is also possible to directly measure the expression of a particular protein by microbes of the present invention. For example, a radioactively labeled amino acid can be added to a cell population and the amount of radioactivity incorporated into a particular protein can be determined. The proteins synthesized by the cell population can be isolated, for example by gel electrophoresis or capillary electrophoresis, identified as the protein of interest, e.g. by binding with an antibody-specific for the protein, and the amount of radioactivity can be quantitatively measured to assess the expression level of the particular protein. Alternatively, the proteins can be expressed without radioactivity and detected by various methods, such as an ELISA assay or by gel electrophoresis and Western blot with detection using an enzyme linked antibody or fluorescently labeled antibody.

While it is possible that the modification of the microbial nucleic acid reduces the level of protein expression as compared to an unmodified microbe, it is to be understood that this may still provide an effective vaccine. It is the combination of attenuation of proliferation with adequate protein expression that is important in some embodiments of the invention. The efficacy of a vaccine is generally related to the dose of antigen that can be delivered by the microbe, and in some instances, some level of active gene expression by the microbe is necessary. The attenuation of replication of the microbe may be several log while the microbial gene expression is still sufficiently maintained. If the same dose of an attenuated microbe is compared to that of an unmodified microbe, the resulting antigen expression (as assessed by the methods discussed above) in the attenuated microbe population is at least about 1%, about 5%, about 10%, about 25%, about 50%, about 75% or at least about 90% of the antigen expression in the unmodified microbe population. Since there may be several log attenuation in replication, the dose of the modified microbe may be safely increased by up to several log, resulting in an equivalent or greater amount of the antigen presented by the attenuated microbes relative to unmodified microbes upon vaccination.

3. Microbial Nucleic Acid Modification.

The nucleic acid of a population of a microbe can be modified by a variety of methods. The nucleic acid of the microbe can be modified by physical means, e.g. irradiation with ultraviolet light or ionizing radiation. Ionizing radiation, such as x-rays or γ-rays, may be used to cause single-strand or double-strand breaks in the nucleic acid. Ultraviolet radiation may be used to cause pyrimidine dimers in the nucleic acid. The appropriate dose of radiation is determined by assessing the effects of the radiation on replication and protein expression as detailed above.

The nucleic acid of the microbe can also be modified by chemical means, e.g. by reaction with a nucleic acid targeted compound (also referred to herein as a nucleic acid targeting compound). In some embodiments, the microbe is treated with a nucleic acid targeted compound that can modify the nucleic acid such that proliferation of the microbe is attenuated. In some embodiments, the microbe is treated with a nucleic acid targeted compound that can modify the nucleic acid such that the proliferation of the microbe is attenuated, wherein the microbial population is still able to express a desired protein antigen to a degree sufficient to elicit an immune response. The nucleic acid targeted compound is not limited to a particular mechanism of modifying the nucleic acid. Such compounds modify the nucleic acid either by reacting directly with the nucleic acid (i.e. all or some portion of the compound covalently binds to the nucleic acid), or by indirectly causing the modification of the nucleic acid (e.g. by causing oxygen damage via generation of singlet oxygen or oxygen radicals, by generating radicals of the compound that cause damage, or by other mechanisms of reduction or oxidation of the nucleic acid). Enediynes are an example of a class of compounds that form radical species that result in the cleavage of DNA double strands [Nicolaou et al., Proc. Natl. Acad. Sci. USA, 90:5881-5888 (1993)]. Compounds that react directly with the nucleic acid may react upon activation of the compound, for example upon radiation of the compound. Compounds that react indirectly to cause modification of the nucleic acid may require similar activation to generate either an activated species of the compound or to generate some other active species. While not being limited to the means for activation of nucleic acid targeted compounds, one embodiment of the invention includes the use of photoactivated compounds that either react directly with the nucleic acid or that generate a reactive species such as a reactive oxygen species (e.g. singlet oxygen) which then reacts with the nucleic acid.

The nucleic acid targeted compounds preferentially modify nucleic acids without significantly modifying other components of a biological sample. Such compounds provide adequate modification of the nucleic acid without significantly altering or damaging cell membranes, proteins, and lipids. Such compounds may modify these other cell components to some degree that is not significant. These cell components such as cell membranes, proteins and lipids are not significantly altered if their biological function is sufficiently maintained. In the case of treating a microbe with a nucleic acid targeted compound, the nucleic acid modification is such that the replication of the microbe is attenuated while the cell membranes, proteins and lipids of the microbe are essentially unaffected such that microbial gene expression is active (e.g. the enzymes required for this are not significantly affected), and the surface of the microbe maintains essentially the same antigenicity as a microbe that has not been treated with the compound. As a result, such compounds are useful in preparing an inactivated microbe for use as a vaccine since the proliferation of the microbe is sufficiently attenuated while maintaining sufficient antigenicity or immunogenicity to be useful as a vaccine. Because the compounds specifically modify nucleic acids, the modification can be controlled to a desired level so that replication is attenuated while maintaining a sufficient level of protein expression. The modification can be controlled by varying the parameters of the reaction, such as compound concentration, reaction media, controlling compound activation factors such as light dose or pH, or controlling compounds that cause oxygen damage by controlling the oxygen concentration (either physically, e.g. by degassing, or chemically, by use of oxygen scavengers). A nucleic acid targeted compound is any compound that has a tendency to preferentially bind nucleic acid, i.e. has a measurable affinity for nucleic acid. Such compounds have a stronger affinity for nucleic acids than for most other components of a biological sample, especially components such as proteins, enzymes, lipids and membranes. The nucleic acid targeting provides specificity for the modification of nucleic acids without significantly affecting other components of the biological sample, such as the machinery for gene transcription and protein translation.

Compounds can be targeted to nucleic acids in a number of modes. Compounds which bind by any of the following modes or combinations of them are considered nucleic acid targeted compounds. Intercalation, minor groove binding, major groove binding, electrostatic binding (e.g. phosphate backbone binding), and sequence-specific binding (via sequence recognition in the major or minor groove) are all non-covalent modes of binding to nucleic acids. Compounds that include one or more of these modes of binding will have a high affinity for nucleic acids. While the invention is not limited to the following compounds, some examples of compounds having these modes of binding to nucleic acid are as follows: intercalators are exemplified by acridines, acridones, proflavin, acriflavine, actinomycins, anthracyclinones, beta-rhodomycin A, daunamycin, thiaxanthenones, miracil D, anthramycin, mitomycin, echinomycin, quinomycin, triostin, diacridines, ellipticene (including dimers, trimers and analogs), norphilin A, fluorenes and flourenones, fluorenodiamines, quinacrine, benzacridines, phenazines, phenanthradines, phenothiazines, chlorpromazine, phenoxazines, benzothiazoles, xanthenes and thio-xanthenes, anthraquinones, anthrapyrazoles, benzothiopyranoindoles, 3,4-benzpyrene, benzopyrene diol epoxidie, 1-pyrenyloxirane, benzanthracene-5,6-oxide, benzodipyrones, benzothiazoles, quinolones, chloroquine, quinine, phenylquinoline carboxamides, furocoumarins (e.g. psoralens, isopsoralens, and sulfur analogs thereof), ethidium salts, propidium, coralyne, ellipticine cation and derivatives, polycyclic hydrocarbons and their oxirane derivatives, and echinimycin; minor groove binders are exemplified by distamycin, mitomycin, netropsin, other lexitropsins, Hoechst 33258 and other Hoechst dyes, DAPI (4',6'-diamidine-2-phenylindole), berenil, and triarylmethane dyes; major groove binders are exemplified by aflatoxins; electrostatic binders are exemplified by spermine, spermidine, and other polyamines; and sequence-specific binders are exemplified by nucleic acids or analogues which bind by such sequence-specific interactions as triple helix formation, D-loop formation, and direct base pairing to single stranded targets. Other sequence-specific binding compounds include poly pyrrole compounds, poly pyrrole imidazole compounds, cyclopropylpyrroloindole compounds and related minor groove binding compounds [Wemmer, Nature Structural Biology, 5(3):169-171 (1998), Wurtz et al., Chemistry & Biology 7(3):153-161 (2000), Anthoney et al., Am. J. Pharmacogenomics 1(1):67-81 (2001)].

In addition to targeting nucleic acids, the compounds are also able to react with the nucleic acid, resulting in covalent binding to the nucleic acid. Nucleic acid alkylators are a class of compounds that can react covalently with nucleic acid and include, but are not limited to, mustards (e.g. mono or bis haloethylamine groups, and mono haloethylsulfide groups), mustard equivalents (e.g. epoxides, alpha-halo ketones) and mustard intermediates (e.g. aziridines, aziridiniums and their sulfur analogs), methanesulphonate esters, and nitroso ureas. The nucleic acid alkylators typically react with a nucleophilic group on the nucleic acid. It is the combination of the nucleic acid alkylating activity and the nucleic acid targeting ability of these compounds that gives them the ability to covalently react specifically with nucleic acids, providing the desired modification of the nucleic acid of microbes for use in the present invention. The specificity of these compounds may be further enhanced by the use of a quencher that will not enter the microbe. Such a quencher will quench reactions with the surface of the microbe while still allowing the nucleic acid targeted compounds to react with the microbial nucleic acid. A discussion of such quenching can be found in U.S. Pat. No. 6,270,952, the disclosure of which is hereby incorporated by reference herein. The modification of the microbial nucleic acid can be controlled by adjusting the compound concentration and reaction conditions. The appropriate concentration and reaction conditions are determined by assessing their effects on replication and protein expression as detailed above. The compounds used in the present invention are effective at concentrations of about 10 pM to 10 mM, also about 100 pM to 1 mM, also about 1 nM to 10 µM, also about 1-500 nM, also about 1-200 nM or about 1-100 nM. A discussion of nucleic acid targeted, nucleic acid reactive compounds for specific reaction with nucleic acids, in particular microbial nucleic acids, can be found in U.S. Pat. Nos. 6,143, 490 and 6,093,725, the disclosures of which are hereby incorporated by reference.

The nucleic acid can be modified by using a nucleic acid targeted compound that requires activation with radiation in order to cause the nucleic acid modification. Such compounds are targeted to nucleic acids as discussed above. These compounds include, but are not limited to, acridines, acridones, anthyrl derivatives, alloxazines (e.g. riboflavin), benzotriazole derivatives, planar aromatic diazo derivatives, planar aromatic cyano derivatives, toluidines, flavines, phenothiazines (e.g. methylene blue), furocoumarins, angelicins, psoralens, sulfur analogs of psoralens, quinolones, quinolines, quinoxalines, napthyridines, fluoroquinolones, anthraquinones, and anthracenes. Many of these compounds are used as DNA photocleavage agents [Da Ros et al., Current Pharmaceutical Design 7:1781 (2001)]. While the invention is not limited to the method of activation of the nucleic acid targeted compounds, typically, the compounds can be activated with light of particular wavelengths. The effective wavelength of light depends on the nature of the compound and can range anywhere from approximately 200 to 1200 nm. For some of these compounds, activation causes modification of the nucleic acid without direct binding of the compound to the nucleic acid, for example by generating reactive oxygen species in the vicinity of the nucleic acid. For some of these compounds, activation results in binding of the compound directly to the nucleic acid (i.e. the compound binds covalently). Some of these compounds can react with the nucleic acid to form an interstrand crosslink. Psoralens are an example of a class of compounds that crosslink nucleic acids. These compounds are typically activated with UVA light (320-400 nm). Psoralen compounds for use in the present invention are exemplified in U.S. Pat. Nos. 6,133,460 and 5,593,823, the disclosures of which are hereby incorporated by reference. Again, it is the combination of nucleic acid targeting and the ability to modify the nucleic acid upon activation that provide specific reactivity with nucleic acids. The modification of the microbial nucleic acid can be controlled by adjusting the compound concentration, reaction conditions and light dose. The appropriate concentration and light dose are determined by assessing their effects on replication and protein expression as detailed above. In addition to compound concentration and level of light exposure, the reaction is affected by the conditions under which the sample is dosed with UVA light. For example, the required overall concentration for irradiating a population of microbes in a buffered media is going to vary from a population that is cultured in a growth media (e.g. BHI, Triptase Soy Broth). The photoreaction may be affected by the contents of the growth media, which may interact with the psoralen, thereby requiring a higher overall concentration of the psoralen. In addition, the effective dosing of the microbes may depend on the growth phase of the organism and the presence or absence of compound during the growth phase. In one embodiment, the population of microbes comprises growth media during the psoralen UVA treatment. In one embodiment, the psoralen is added to the population of microbes, the population is cultured to grow the microbes in the presence of psoralen and growth media, and the UVA treatment is performed at some point in the growth phase of the microbes. In one embodiment, the population is grown to an OD of 0.5-1 ($1\times10^7$ to $1\times10^9$ CFU/mL) in the presence of the psoralen prior to irradiation with an appropriate dose of UVA light. Psoralen compounds are effective at concentrations of about 10 pM to 10 mM, also about 100 pM to 1 mM, also about 1 nM to 10 µM, also about 1-500 nM, also about 1-200 nM or about 1-100 nM, with the UVA light dose ranging from about 0.1-100 $J/cm^2$, also about 0.1-20 $J/cm^2$, or about 0.5-10 $J/cm^2$, 0.5-6 $J/cm^2$ or about 2-6 $J/cm^2$. In one embodiment, the microbe is treated in the presence of growth media at psoralen concentrations of about 10 pM to 10 mM, also about 1-5000 nM, also about 1-500 nM, also about 5-500 nM, or about 10-400 nM. In one embodiment, the microbe treated in the presence of growth media is grown to an OD of 0.5-1 in the presence of psoralen at concentrations of about 10 pM to 10 mM, also about 1-5000 nM, also about 1-500 nM, also about 5-500 nM, or about 10-400 nM. Following the growth to an OD of 0.5-1, the microbe population is irradiated with UVA light at a dose ranging from about 0.1-100 $J/cm^2$, also about 0.1-20 $J/cm^2$, or about 0.5-10 $J/cm^2$, 0.5-6 $J/cm^2$ or about 2-6 $J/cm^2$.

In some embodiments, the nucleic acid targeting compound used to modify the nucleic acid of the microbe is an alkylator such as β-alanine, N-(acridin-9-yl), 2-[bis(2-chloroethyl)amino]ethyl ester. In other embodiments, the nucleic acid targeting compound used to modify the nucleic acid of the microbe is a psoralen compound (e.g., 4'-(4-amino-2-oxa) butyl-4,5',8-trimethylpsoralen, also referred to herein as "S-59") activated by UVA irradiation.

In one embodiment, the invention includes a method of making a vaccine composition comprising treating a microbial population so that the microbial nucleic acid is modified so that the proliferation of the microbial population is attenuated, wherein the microbial gene expression is substantially unaffected. In another embodiment, the invention includes a method of making a vaccine composition comprising treating a microbial population so that the microbial nucleic acid is modified so that the proliferation of the microbial population is attenuated, wherein the microbial gene expression is substantially unaffected, and then using that microbial population to load an antigen-presenting cell with antigen and induce activation/maturation of the antigen-presenting cell. In one embodiment, the microbial population is treated by irradiation. In one embodiment, the microbial population is treated by reacting with a nucleic acid targeted compound that indirectly causes the modification of the nucleic acid. In a further embodiment, the nucleic acid targeted compound is activated by irradiation, wherein activation of the compound causes the indirect modification of the nucleic acid. In a further embodiment, activation of the nucleic acid targeted compound results in a reactive oxygen species that modifies the nucleic acid. In one embodiment, the microbial population is treated by reacting with a nucleic acid targeted compound that reacts directly with the nucleic acid. In one embodiment, the nucleic acid targeted compound is reacted at a concentration of about 10 pM to 10 mM, also about 100 pM to 1 mM, also about 1-500 nM, also about 1-200 nM or about 1-100 nM. In one embodiment, the nucleic acid targeted compound comprises an alkylator. In one embodiment, the alkylator is selected from the group consisting of mustards, mustard intermediates and mustard equivalents. In one embodiment, the nucleic acid targeted compound comprises a nucleic acid targeting group selected from the group consisting of intercalators, minor groove binders, major groove binders, electrostatic binders, and sequence-specific binders. In one embodiment, the nucleic acid targeted compound reacts directly with the nucleic acid upon activation of the compound. In one embodiment, the activation of the compound is by irradiation. In one embodiment, the irradiation is UVA irradiation. In a preferred embodiment, the nucleic acid targeted compound is a psoralen compound activated by UVA irradiation. In one embodiment, the psoralen compound is at a concentration of about 10 pM to 10 mM, also about 100 pM to 1 mM, also about 1-500 nM, also about 1-200 nM or about 1-100 nM, and the UVA irradiation is at a dose of about 0.1-100 $J/cm^2$, also about 0.1-20 $J/cm^2$, or about 0.5-5 $J/cm^2$ or about 2-4 $J/cm^2$. In one embodiment, the proliferation of the microbial population is attenuated by at least about 0.3 log, also at least about 1 log, about 2 log, about 3 log, about 4 log, about 6 log, or at least about 8 log. In another embodiment, the proliferation of the microbial population is attenuated by about 0.3 to >10 log, about 2 to >10 log, about 4 to >10 log, about 6 to >10 log, about 0.3-8 log, about 0.3-6 log, about 0.3-5 log, about 1-5 log, or about 2-5 log. In one embodiment, the expression of an antigen by the microbial population is at least about 10%, about 25%, about 50%, about 75%, or at least about 90% of the expression of the antigen by a microbial population that has not been treated to modify the nucleic acid. In one embodiment, the antigen expressed is an antigen from the microbe itself. In one embodiment, the microbe is *Mycobacterium tuberculosis* and the antigen is from *Mycobacterium tuberculosis*. In one embodiment, the microbe is *Bacillus anthracis* and the antigen is from *Bacillus anthracis*. In one embodiment, the microbe comprises a heterologous nucleic acid sequence encoding an antigen. In one embodiment, the antigen is a disease associated antigen. In one embodiment, the antigen is associated with a disease selected from the group consisting of infectious diseases, autoimmune diseases, allergies, cancers, and other hyperproliferative diseases. In one embodiment, the antigen is a tumor associated antigen. In one embodiment, the tumor antigen is selected from the group consisting of differentiation antigens, tissue specific antigens, developmental antigens, tumor-associated viral antigens, cancer-testis antigens, embryonic antigens, oncoprotein antigens, over-expressed protein antigens and mutated protein antigens. In one embodiment, the tumor antigen is selected from the group consisting of mesothelin, Sp17, gp100, PR3, PAGE-4, TARP, WT-1, NY-ESO-1 and SPAS-1. In one embodiment, the microbe comprises a genetic mutation. In one embodiment, the genetic mutation results in the attenuation of the ability of the microbe to repair microbial nucleic acid that has been modified. In one embodiment, the genetic mutation is in the gene selected from the group consisting of phrB, uvrA, uvrB, uvrC, uvrD and recA, or their functionally equivalent genes, depending on the genus and species of the microbe. In one embodiment, the genetic mutation is in one or more of the genes selected from the group consisting of phrB, uvrA, uvrB, uvrC, uvrD and recA, or their functionally equivalent genes. In one embodiment, the genetic mutation results in the attenuation in the activity of a DNA repair enzyme selected from the group consisting of PhrB, UvrA, UvrB, UvrC, UvrD and RecA. In a further embodiment, microbes having these mutations are treated with a psoralen activated by UVA irradiation. In one embodiment, the microbe is selected from the group consisting of bacteria, protozoa and fungi. In one embodiment, the bacteria is a bacteria. In one embodiment, the bacteria are intracellular bacteria. In a preferred embodiment, the bacteria are *Listeria*, preferably *Listeria monocytogenes*. In one embodiment, the *Listeria* comprises a mutation that results in the attenuation of the ability of the *Listeria* to invade non-phagocytic cells without significantly affecting the uptake of the *Listeria* by phagocytic cells. In one embodiment, the *Listeria* mutation is in an internalin gene(s). In one embodiment, the *Listeria* mutation is in the gene selected from the group consisting of inlA, inlB, and any gene encoding an internalin. In one embodiment, the *Listeria monocytogenes* comprises a genetic mutation in both the inlA and inlB genes. In one embodiment, the *Listeria* comprises a mutation that results in the attenuation of the ability of the *Listeria* to escape the phagolysosome of an infected cell. In one embodiment, the *Listeria* mutation is in the hly gene. In one embodiment, the *Listeria* comprises a mutation that results in the attenuation of the polymerization of actin by the *Listeria*. In a preferred embodiment, the *Listeria* mutation is in the actA gene. In one embodiment, the *Listeria* comprises mutations in the actA gene and one or more internalin genes. In a preferred embodiment, the *Listeria* comprises a mutation in the actA gene and the inlB gene, preferably the *Listeria* comprises an actA/inlB deletion mutant. In a preferred embodiment, the *Listeria monocytogenes* actA/inlB deletion mutant further comprises a deletion mutation in the uvrAB gene.

4. Microbes Comprising Heterologous Nucleic Acid Molecules

Optionally, the vaccines comprise microbes and/or are made using microbes which comprise at least one heterologous nucleic acid molecules. In some embodiments, the microbes comprise more than one heterologous nucleic acid molecule. The heterologous nucleic acid molecules are, in some embodiments, expression cassettes or expression vectors. Typically, although not necessarily, these expression cassettes or expression vectors encode heterologous antigens (i.e., antigens foreign to the microbes in which they are expressed). In some embodiments, at least one sequence in the expression cassette and/or vector contained within a microbe is codon-optimized for expression in the microbe. Optionally, the antigen-encoding sequence and/or the signal sequence of the expression vector is codon-optimized for expression in the microbe.

a. Expression Cassettes and Expression Vectors

Expression cassettes suitable for use in the microbes described herein are known to those of ordinary skill in the art. For instance, it is known that an expression cassette suitable for use in the microbes typically comprises a polynucleotide encoding a polypeptide (e.g., a heterologous protein) and a promoter operably linked to the protein-encoding polynucleotide. The expression cassette optionally further comprises a polynucleotide encoding a signal peptide sequence, so that the expression cassette comprises a promoter, polynucleotide encoding a signal peptide sequence, and a coding sequence, all operably linked, so that the expression cassette encodes a fusion protein comprising both the signal peptide sequence and the desired polypeptide sequence. For prokaryotes, an expression cassette optionally comprises the following elements: (1) prokaryotic promoter; (2) Shine-Dalgarno sequence; (3) a polynucleotide encoding a signal peptide; and, (4) a polynucleotide encoding a polypeptide (such as a heterologous protein).

In some embodiments, the expression cassette may also contain a transcription termination sequence inserted downstream from the C-terminus of the translational stop codon related to the heterologous polypeptide. For instance, a transcription termination sequence may be used in constructs designed for stable integration within the bacterial chromosome. While not required, inclusion of a transcription termination sequence as the final ordered element in a heterologous gene expression cassette may prevent polar effects on the regulation of expression of adjacent genes, due to read-through transcription. Appropriate sequence elements known to those who are skilled in the art that promote either rho-dependent or rho-independent transcription termination can be placed in the heterologous protein expression cassette.

For microbes which are members of the genus *Listeria*, suitable promoters include an hly promoter, prfA-dependent promoters (e.g., an actA promoter) and constitutive promoters (e.g., a p60 promoter). One of ordinary skill in the art will be readily able to identify additional prokaryotic and/or Listerial promoters suitable for use in the expression cassettes in view of the intended use of the expression cassette and host bacteria into which the expression cassette will be placed.

In some embodiments, the promoter used in an expression cassette described herein is a constitutive promoter. In other embodiments, the promoter used in an expression cassette described herein is an inducible promoter. The inducible promoter can be induced by a molecule (e.g., a protein) endogenous to the bacteria in which the expression cassette is to be used. Alternatively, the inducible promoter can be induced by a molecule (e.g. a small molecule or protein) heterologous to the bacteria in which the expression cassette is to be used. A variety of inducible promoters are well-known to those of ordinary skill in the art.

Optionally, at the 3'-end of the promoter is a poly-purine Shine-Dalgarno sequence, the element required for engagement of the 30S ribosomal subunit (via 16S rRNA) to the heterologous gene RNA transcript and initiation of translation. The Shine-Dalgarno sequence has typically the following consensus sequence: 5'-NAGGAGGU-$N_{5-10}$-AUG (start codon)-3' (SEQ ID NO:59). There are variations of the poly-purine Shine-Dalgarno sequence. Notably, the *Listeria* hly gene that encodes listerolysin O (LLO) has the following Shine-Dalgarno sequence: AAGGAGAGTGAAACCCATG (SEQ ID NO:60; Shine-Dalgarno sequence is underlined, and the translation start codon is bolded).

Suitable signal sequences are also known to those of ordinary skill in art. For instance, where the microbe is a bacterium (e.g., *Listeria*), a sequence encoding a secA1 signal peptide can be used in the expression cassette and/or expression vector. An example of a secA1 signal peptide suitable for use in *Listeria* is the Listeriolysin O (LLO) signal peptide from *Listeria monocytogenes*. Another example of a secA1 signal peptide suitable for use in a microbe such as *Bacillus anthracis* comes from the Pag (Protective Antigen) gene from *Bacillus anthracis*. Information on these exemplary secA1 signal peptides is provided in Table 1, below.

The expression cassette is optionally contained within an expression vector, such as, but not limited to, a plasmid. In some embodiments, the vector is an integration vector. In some embodiments, the modified microbe comprises an expression cassette integrated within its genome.

For instance, expression vectors suitable for use in bacteria such as *Listeria* are known to those of ordinary skill in the art. There are a variety of vectors suitable for use as a plasmid construct backbone for assembly of the expression cassettes. A particular plasmid construct backbone is selected based on whether expression of the heterologous gene from the bacterial chromosome or from an extra-chromosomal episome is desired.

Incorporation of the heterologous gene expression cassette into the bacterial chromosome of *Listeria monocytogenes* (*Listeria*) can be accomplished with an integration vector that contains an expression cassette for a listeriophage integrase that catalyzes sequence-specific integration of the vector into the *Listeria* chromosome. For example, the integration vectors known as pPL1 and pPL2 program stable single-copy integration of a heterologous protein expression cassette within an innocuous region of the bacterial genome, and have been described in the literature (Lauer et. al. 2002 J. Bacteriol. 184:4177-4178; U.S. Patent Publication No. 20030203472). The integration vectors are stable as plasmids in *E. coli* and are introduced via conjugation into the desired *Listeria* background. Each vector lacks a *Listeria*-specific origin of replication and encodes a phage integrase, such that the vectors are stable only upon integration into a chromosomal phage attachment site. Starting with a desired plasmid construct, the process of generating a recombinant *Listeria* strain expressing a desired protein(s) takes approximately one week. The pPL1 and pPL2 integration vectors are based, respectively, on the U153 and PSA listeriophages. The pPL1 vector integrates within the open reading frame of the comK gene, while pPL2 integrates within the tRNAArg gene in such a manner that the native sequence of the gene is restored upon successful integration, thus keeping its native expressed function intact. The pPL1 and pPL2 integration vectors contain a multiple cloning site sequence in order to facilitate construction of plasmids containing the heterologous protein expression cassette. Some specific examples of the use of the pPL2 integration vector are described in, for instance, Example 19 and Example 46, below.

Alternatively, incorporation of an antigen expression cassette into the *Listeria* chromosome can be accomplished through allelic exchange methods, known to those skilled in

TABLE 1

Some exemplary secA1 signal peptides

| Signal Peptide Amino Acid Sequence ($NH_2$—$CO_2$) | Signal peptidase Site (cleavage site represented by ') | Gene | Genus/species |
|---|---|---|---|
| MKKIMLVFITLILVSLPIAQQ TEAKDASAFNKENSISSMAP PASPPASPKTPIEKKHAD (SEQ ID NO:53) | TEA'KD (SEQ ID NO:69) | hly (LLO) | *Listeria monocytogenes* |
| MKKRKVLIPLMALSTILVSS TGNLEVIQAEV (SEQ ID NO:54) | IQA'EV (SEQ ID NO:70) | pag (Protective Antigen) | *Bacillus anthracis* |

Additional signal sequences useful in expression cassettes in the modified microbes described herein are described in U.S. Ser. Nos. 60/532,598 and 60/556,744, each of which is incorporated by reference herein in its entirety.

the art. In particular, compositions in which it is desired to not incorporate a gene encoding an antibiotic resistance protein as part of the construct containing the heterologous gene expression cassette, methods of allelic exchange are desirable. For example, the pKSV7 vector (Camilli et. al. *Mol. Microbiol.* 1993 8, 143-157), contains a temperature-sensitive *Listeria* Gram-positive replication origin which is exploited to select for recombinant clones at the non-permissive temperature that represent the pKSV7 plasmid recombined into the *Listeria* chromosome. The pKSV7 allelic exchange plasmid vector contains a multiple cloning site sequence in order to facilitate construction of plasmids containing the heterologous protein expression cassette, and also a chloramphenicol resistance gene. For insertion into the *Listeria* chromosome, the heterologous antigen expression cassette construct may be flanked by approximately 1 kb of chromosomal DNA sequence that corresponds to the precise location of desired integration. The pKSV7-heterologous protein expression cassette plasmid may be introduced into a desired bacterial strain by electroporation, according to standard methods for electroporation of Gram positive bacteria. A non-limiting example of a method of effecting allelic exchange in *Listeria* using the pKSV7 vector is provided in Example 47 below.

In other embodiments, it may be desired to express a heterologous protein in a microbe, such as *Listeria*, from a stable plasmid episome. Maintenance of the plasmid episome through passaging for multiple generations requires the co-expression of a protein that confers a selective advantage for the plasmid-containing bacterium. As non-limiting examples, the protein co-expressed from the plasmid in combination with a heterologous protein may be an antibiotic resistance protein, for example chloramphenicol, or may be a bacterial protein (that is expressed from the chromosome in wild-type bacteria), that can also confer a selective advantage. Non-limiting examples of bacterial proteins include enzyme required for purine or amino acid biosynthesis (selection under defined media lacking relevant amino acids or other necessary precursor macromolecules), or a transcription factor required for the expression of genes that confer a selective advantage in vitro or in vivo (Gunn et. al. 2001 J. Immuol. 167:6471-6479). As a non-limiting example, pAM401 is a suitable plasmid for episomal expression of a selected heterologous protein in diverse Gram-positive bacterial genera (Wirth et. al. 1986 J. Bacteriol 165:831-836). For further description of exemplary uses of pAM401, see Examples 46, below.

Incorporation of the heterologous gene expression cassette into the bacterial chromosome of *B. anthracis* can be accomplished with an integration vector that contains an expression cassette for a listeriophage integrase that catalyzes sequence-specific integration of the vector into the *B. anthracis* chromosome. For example, as indicated above, the integration vector pPL2 programs stable single-copy integration of a heterologous protein expression cassette within an innocuous region of the bacterial genome, and has been described in the literature (Lauer et. al. 2002 J. Bacteriol. 184:4177-4178; U.S. Patent Publication No. 20030203472). The integration pPL2vector is stable as a plasmid in *E. coli* and is introduced via conjugation into the desired *B. anthracis* background. The vector lacks a *B. anthracis*-specific origin of replication and encodes a phage integrase, such that the vectors are stable only upon integration into a chromosomal phage attachment site. The pPL2 integration vector is based on the PSA listeriophage. The pPL2 vector integrates within the tRNA$^{Arg}$ gene in such a manner that the native sequence of the gene is restored upon successful integration, thus keeping its native expressed function intact. The tRNA$^{Arg}$ gene is conserved between *Listeria* and *Bacillus* species. The pPL2 integration vector contains a multiple cloning site sequence in order to facilitate construction of plasmids containing the heterologous protein expression cassette. Alternatively, *B. anthracis*-specific integration vectors are derived using the integrase and attachment site derived from a *B. anthracis*-specific bacteriophage.

Alternatively the integrase and attachment site of a *B. anthracis* phage is used to derive an integration vector, to incorporate desired antigen expression cassettes into the vaccine composition. As a non-limiting example, the integrase and attachment site from the *B. anthracis* temperate phage w-alpha (Ref belos) is used to derive a *B. anthracis* specific integration vector (McCloy, E. W. 1951. Studies on a lysogenic *Bacillus* stain. I. A bacteriophage specific for *Bacillus anthracis*. J. Hyg. 49:114-125).

Alternatively, incorporation of an antigen expression cassette into the *B. anthracis* chromosome can be accomplished through allelic exchange methods, known to those skilled in the art. In particular, compositions in which it is desired to not incorporate a gene encoding an antibiotic resistance protein as part of the construct containing the heterologous gene expression cassette, methods of allelic exchange are desirable. For example, the pKSV7 vector (Camilli et. al. *Mol. Microbiol.* 1993 8, 143-157), contains a temperature-sensitive *Listeria*-derived Gram positive replication origin which is exploited to select for recombinant clones at the non-permissive temperature that represent the pKSV7 plasmid recombined into the *Listeria* chromosome. The pKSV7 allelic exchange plasmid vector contains a multiple cloning site sequence in order to facilitate construction of plasmids containing the heterologous protein expression cassette, and also a chloramphenicol resistance gene. For insertion into the *Bacillus anthracis* chromosome, the heterologous antigen expression cassette construct may be flanked by approximately 1 kb of chromosomal DNA sequence that corresponds to the precise location of desired integration. The pKSV7-heterologous protein expression cassette plasmid may be introduced into a desired bacterial strain by electroporation, according to standard methods for electroporation of Gram positive bacteria. A non-limiting example of a method of effecting allelic exchange in *B. anthracis* using the pKSV7 vector is provided in the Examples, below. This result demonstrates that the pKSV7 vector-based technique of allelic exchange can be used to effect genetic modification in *Bacillus* species, which, like *Listeria*, are low G+C content organisms. In particular, allelic exchange using the pKSV7 vector can be used in strains of *B. anthracis* to delete or modify DNA repair genes, such as uvrAB, or to add a desired antigen expression cassette at any desired location within the bacterial chromosome.

Addition information regarding some recombinant *Bacillus anthracis* strains useful as modified microbes in the vaccine compositions of the present invention are described in the U.S. Provisional Application 60/584,886, Dubensky et al., "Modified *Bacillus Anthracis*, Vaccine Compositions and Methods of Use Thereof", filed Jun. 30, 2004, incorporated by reference herein in its entirety.

b. Antigens Encoded by the Expression Cassettes

The microbes used in and/or to make the vaccines described herein optionally express antigens endogenous to the microbes. Optionally, the microbes express antigens which are heterologous antigens (i.e., foreign to the microbe in which the antigen is expressed). In other cases, the microbes express both endogenous and heterologous antigens. A microbe which expresses a heterologous antigen comprises a heterologous nucleic acid (expression cassette and/or expression vector) that encodes the heterologous antigen. Alternatively, heterologous nucleic acids can be used to overexpress endogenous antigens within the microbes.

Thus, in some embodiments, the microbes in the vaccines and/or used to make the vaccines are altered to include a heterologous nucleic acid sequence that can be expressed by the microbe. The heterologous sequence can encode at least one specific protein antigen. The microbes may be altered by methods known to one skilled in the art [Sambrook and Russell, Molecular Cloning: A Laboratory Manual, Third Edition, Cold Spring Harbor Laboratory Press, (2000)]. The microbes can be altered to contain one or more sequences that encode one or more antigens. The heterologous nucleic acid sequence encoding a specific antigen is not limited to an exact nucleic acid sequence but is of a sequence that is sufficient to provide the expression of an antigen that will elicit the desired immune response when administered to an individual. The heterologous sequence can be expressed as an antigen related to a particular disease. The microbe expressing such antigens can be used as a vaccine, wherein the vaccine may be used as a preventative treatment or a therapeutic treatment. Diseases that can be treated by such vaccines include infectious diseases, autoimmune diseases, allergies, cancers and other hyperproliferative diseases, as described below.

The microbes of the invention may be altered to contain a heterologous nucleic acid sequence encoding a specific tumor antigen. A large number of tumor specific antigens that are recognized by T cells have been identified [Renkvist et al., Cancer Immunol Innumother 50:3-15 (2001)]. These tumor antigens may be differentiation antigens (e.g., PSMA, Tyrosinase, gp100), tissue-specific antigens (e.g. PAP, PSA), developmental antigens, tumor-associated viral antigens (e.g. HPV 16 E7), cancer-testis antigens (e.g. MAGE, BAGE, NY-ESO-1), embryonic antigens (e.g. CEA, alpha-fetoprotein), oncoprotein antigens (e.g. Ras, p53), over-expressed protein antigens (e.g. ErbB2 (Her2/Neu), MUC1), or mutated protein antigens. The tumor antigens that may be encoded by the heterologous nucleic acid sequence include, but are not limited to, 707-AP, Annexin II, AFP, ART-4, BAGE, β-catenin/m, BCL-2, bcr-abl, bcr-abl p190, bcr-abl p210, BRCA-1, BRCA-2, CAMEL, CAP-1, CASP-8, CDC27/m, CDK-4/m, CEA, CT9, CT10, Cyp-B, Dek-cain, DAM-6 (MAGE-B2), DAM-10 (MAGE-B1), ELF2M, EphA2, ETV6-AML1, G250, GAGE-1, GAGE-2, GAGE-3, GAGE-4, GAGE-5, GAGE-6, GAGE-7B, GAGE-8, GnT-V, gp100, HAGE, HER2/neu, HLA-A*0201-R1701, HPV-E7, HSP70-2M, HST-2, hTERT, hTRT, iCE, inhibitors of apoptosis (e.g. survivin), KIAA0205, LAGE, LAGE-1, LDLR/FUT, MAGE-1, MAGE-2, MAGE-3, MAGE-6, MAGE-A1, MAGE-A2, MAGE-A3, MAGE-A4, MAGE-A6, MAGE-A10, MAGE-A12, MAGE-B5, MAGE-B6, MAGE-C2, MAGE-C3, MAGE-D, MART-1, MART-1/Melan-A, MC1R, MDM-2, mesothelin, Myosin/m, MUC1, MUC2, MUM-1, MUM-2, MUM-3, neo-polyA polymerase, NA88-A, NY-ESO-1, NY-ESO-1a (CAG-3), PAGE-4, PAP, Proteinase 3 (PR3), P15, p190, Pm1/RARα, PRAME, PSA, PSCA, PSM, PSMA, RAGE, RAS, RCAS1, RU1, RU2, SAGE, SART-1, SART-2, SART-3, SP17, SPAS-1, TEL/AML1, TPI/m, Tyrosinase, TARP, TRP-1 (gp75), TRP-2, TRP-2/INT2, WT-1, and alternatively translated NY-ESO-ORF2 and CAMEL proteins, derived from the NY-ESO-1 and LAGE-1 genes. The microbes of the present invention encompass any tumor antigen that can elicit a tumor-specific immune response, including antigens yet to be identified. The microbes may be altered to contain more than one heterologous sequence encoding more than one tumor antigen. Preferred antigens include mesothelin [Argani et al., Clin Cancer Res. 7 (12):3862-8 (2000], Sp17 [Lim et al., Blood. 97(5):1508-10 (2000], gp100 [Kawakami et al., Proc. Natl. Acad. Sci. USA 91:6458 (1994)], PAGE-4 [Brinkmann et al., Cancer Res. 59(7):1445-8 (1999)], TARP [Wolfgang et al., Proc. Natl. Acad. Sci. USA 97(17):9437-42 (2000)], EphA2 [Tatsumi et al., Cancer Res. 63(15):4481-9 (2003)], PR3 [Muller-Berat et al., Clin. Immunol. Immunopath. 70(1):51-9 (1994)], prostate stem cell antigen (PSCA) [Reiter et al., Proc. Natl. Acad. Sci., 95:1735-40 (1998); Kiessling et al., Int. J. Cancer, 102: 390-7 (2002)] and SPAS-1 [U.S. Patent Application Publication Number 20020150588].

In one embodiment of the invention, the heterologous antigen expressed by the modified microbe is CEA. CEA is a 180-kDA membrane intercellular adhesion glycoprotein that is over-expressed in a significant proportion of human tumors, including 90% of colorectal, gastric, and pancreatic, 70% of non-small cell lung cancer, and 50% of breast cancer (Hammarstrom, *Semin. Cancer Biol.*, 9:67-81). A variety of immunotherapeutics such as anti-idiotype monoclonal antibody mimicking CEA (Foon et al., *Clin. Cancer Res.*, 87:982-90 (1995), or vaccination using a recombinant vaccinia virus expressing CEA (Tsang et al., *J. Natl. Cancer Inst.*, 87:982-90 (1995)) have been investigated, unfortunately, however, with limited success. Nonetheless, investigators have identified a HLA*0201-restricted epitope, CAP-1(CEA605-613), that is recognized by human T cell lines that were generated from vaccinated patients. Vaccination of patients with DC pulsed with this epitope failed to induce clinical responses (Morse et al., *Clin. Cancer Res.*, 5:1331-8 (1999)). Recently, a CEA605-613 peptide agonist was identified with a heteroclitic aspartate to asparagine substitution at position 610 (CAP1-6D). Although this amino acid substitution did not alter MHC binding affinity of this peptide, the use of the altered peptide ligand (APL) resulted in improved generation of CEA-specific cytotoxic T lymphocytes (CTL) in vitro. CAP1-6D-specific CTL maintained their ability to recognize and lyse tumor cells expressing native CEA (Zaremba et al., *Cancer Res.*, 57: 4570-7 (1997); Salazar et al., *Int. J. Cancer*, 85:829-38 (2000)). Fong et al. demonstrated induction of CEA-specific immunity in patients with colon cancer vaccinated with Flt3-ligand expanded DC incubated with this APL. Encouragingly, 2 of 12 patients after vaccination experienced dramatic tumor regressions that correlated with the induction of peptide-MHC tetramer$^+$ T cells (Fong et al., *Proc. Natl. Acad. Sci. U.S.A.*, 98:8809-14 (2001)). Taken together, this work provides significant validation for CEA-targeted immunotherapy for colorectal cancer.

In another embodiment, the heterologous antigen expressed by the modified microbe is proteinase-3 or is derived from proteinase-3. For instance, in one embodiment, the antigen comprises the HLA-A2.1-restricted peptide PR1 (aa 169-177; VLQELNVTV (SEQ ID NO:50)). Information on proteinase-3 and/or the PR1 epitope is publicly available in the following references: U.S. Pat. No. 5,180,819, Molldrem, et al., *Blood*, 90:2529-2534 (1997); Molldrem et al., *Cancer Research*, 59:2675-2681 (1999); Molldrem, et al., *Nature Medicine*, 6:1018-1023 (2000); and Molldrem et al., *Oncogene*, 21: 8668-8673 (2002).

Accordingly, in some embodiments, the modified microbe (e.g., modified bacteria) comprises a nucleic acid molecule encoding an antigen such as mesothelin, SPAS-1, proteinase-3, EphA2, SP-17, gp100, PAGE-4, TARP, Her-2/neu, WT-1, NY-ESO-1, PSMA, K-ras, or CEA, or an antigen derived from one of those proteins. In some embodiments, the modified microbe comprises a nucleic acid molecule encoding an antigen such as mesothelin, SPAS-1, proteinase-3, SP-17, gp100, PAGE-4, TARP, WT-1, NY-ESO-1 or CEA, or an antigen derived from one of those proteins. In some embodiments, the modified microbe comprises a nucleic acid molecule encoding human mesothelin, or an antigen derived from human mesothelin. In other embodiments, the modified microbe comprises a nucleic acid molecule encoding human EphA2, or derived from human EphA2.

In some embodiments, the modified microbe comprises an expression cassette encoding an antigen such as mesothelin, PSCA, NY-ESO-1, WT-1, survivin, gp100, PAP, or proteinase 3. In some embodiments, the antigen expressed by the modified microbe used in either a microbe-based vaccine or an antigen-presenting cell vaccine is mesothelin. In some embodiments, the antigen expressed by the modified microbe used in either a microbe-based vaccine or an antigen-presenting cell vaccine is PSCA. In some embodiments, the antigen expressed by the modified microbe used in either a microbe-based vaccine or an antigen-presenting cell vaccine is NY-ESO-1. In some embodiments, the antigen expressed by the modified microbe used in either a microbe-based vaccine or an antigen-presenting cell vaccine is WT-1. In some embodiments, the antigen expressed by the modified microbe used in either a microbe-based vaccine or an antigen-presenting cell vaccine is survivin. In some embodiments, the antigen expressed by the modified microbe used in either a microbe-based vaccine or an antigen-presenting cell vaccine is gp100. In some embodiments, the antigen expressed by the modified microbe used in either a microbe-based vaccine or an antigen-presenting cell vaccine is PAP. In some embodiments, the antigen expressed by the modified microbe used in either a microbe-based vaccine or an antigen-presenting cell vaccine is proteinase 3.

In some embodiments, the antigen expressed by the expression cassette in the modified microbe is not identical to a tumor-associated antigen, but rather is derived from a tumor-associated antigen. For instance, the antigen may comprise a fragment of a tumor-associated antigen, a variant of a tumor-associated antigen, or a fragment of a variant of a tumor-associated antigen. In some cases, an antigen, such as a tumor antigen, is capable of inducing a more significant immune response in a vaccine when the sequence differs from that endogenous to a host. In some embodiments, the variant of a tumor-associated antigen, or a fragment of a variant of a tumor-associated antigen, differs from that of the tumor-associated antigen, or its corresponding fragment, by one or more amino acids. The antigen derived from a tumor-associated antigen will comprise at least one epitope sequence capable of inducing the desired immune response upon expression of the polynucleotide encoding the antigen within a host.

In some embodiments, the modified microbe comprises an expression cassette encoding an antigen derived from mesothelin, PSCA, NY-ESO-1, WT-1, survivin, gp100, PAP, or proteinase 3. In some embodiments, the antigen expressed by the modified microbe used in either a microbe-based vaccine or an antigen-presenting cell vaccine is derived from mesothelin. In some embodiments, the antigen expressed by the modified microbe used in either a microbe-based vaccine or an antigen-presenting cell vaccine is derived from PSCA. In some embodiments, the antigen expressed by the modified microbe used in either a microbe-based vaccine or an antigen-presenting cell vaccine is derived from NY-ESO-1. In some embodiments, the antigen expressed by the modified microbe used in either a microbe-based vaccine or an antigen-presenting cell vaccine is derived from WT-1. In some embodiments, the antigen expressed by the modified microbe used in either a microbe-based vaccine or an antigen-presenting cell vaccine is derived from survivin. In some embodiments, the antigen expressed by the modified microbe used in either a microbe-based vaccine or an antigen-presenting cell vaccine is derived from gp100. In some embodiments, the antigen expressed by the modified microbe used in either a microbe-based vaccine or an antigen-presenting cell vaccine is derived from PAP. In some embodiments, the antigen expressed by the modified microbe used in either a microbe-based vaccine or an antigen-presenting cell vaccine is derived from proteinase 3.

Alternatively, the microbes of the invention may be altered to contain a heterologous nucleic acid sequence encoding a specific infectious disease antigen. In one embodiment, the antigen is derived from a human or animal pathogen. The pathogen is optionally a virus, bacterium, fungus, or a protozoan. For instance, the antigen may be a viral or fungal or bacterial antigen.

For instance, the antigen may be derived from Human Immunodeficiency virus (such as gp120, gp 160, gp41, gag antigens such as p24gag and p55gag, as well as proteins derived from the pol, env, tat, vif, rev, nef, vpr, vpu and LTR regions of HIV), Feline Immunodeficiency virus, or human or animal herpes viruses. In one embodiment, the antigen is derived from herpes simplex virus (HSV) types 1 and 2 (such as gD, gB, gH, Immediate Early protein such as ICP27), from cytomegalovirus (such as gB and gH), from Human Metapneumovirus, from Epstein-Barr virus or from Varicella Zoster Virus (such as gpI, II or III). (See, e.g. Chee et al. (1990) Cytomegaloviruses (J. K. McDougall, ed., Springer Verlag, pp. 125-169; McGeoch et al. (1988) J. Gen. Virol. 69: 1531-1574; U.S. Pat. No. 5,171,568; Baer et al. (1984) Nature 310: 207-211; and Davison et al. (1986) J. Gen. Virol. 67: 1759-1816.)

In another embodiment, the antigen is derived from a hepatitis virus such as hepatitis B virus (for example, Hepatitis B Surface antigen), hepatitis A virus, hepatitis C virus, delta hepatitis virus, hepatitis E virus, or hepatitis G virus. See, e.g., WO 89/04669; WO 90/11089; and WO 90/14436. The HCV genome encodes several viral proteins, including E1 and E2. See, e.g., Houghton et al., *Hepatology* 14: 381-388 (1991).

An antigen that is a viral antigen is optionally derived from a virus from any one of the families Picornaviridae (e.g., polioviruses, rhinoviruses, etc.); Caliciviridae; Togaviridae (e.g., rubella virus, dengue virus, etc.); Flaviviridae; Coronaviridae; Reoviridae (e.g., rotavirus, etc.); Birnaviridae; Rhabodoviridae (e.g., rabies virus, etc.); Orthomyxoviridae (e.g., influenza virus types A, B and C, etc.); Filoviridae; Paramyxoviridae (e.g., mumps virus, measles virus, respiratory syncytial virus, parainfluenza virus, etc.); Bunyaviridae; Arenaviridae; Retroviradae (e.g., HTLV-I; HTLV-11; HIV-1 (also known as HTLV-111, LAV, ARV, hTLR, etc.)), including but not limited to antigens from the isolates HIVI11b, HIVSF2, HTVLAV, HIVLAI, HIVMN); HIV-1CM235, HIV-1; HIV-2, among others; simian immunodeficiency virus (SIV); Papillomavirus, the tick-borne encephalitis viruses; and the like. See, e.g. Virology, 3rd Edition (W. K. Joklik ed. 1988); Fundamental Virology, 2.sup.nd Edition (B. N. Fields and D. M. Knipe, eds. 1991), for a description of these and other viruses.

In some alternative embodiments, the antigen is derived from bacterial pathogens such as *Mycobacterium, Bacillus, Yersinia, Salmonella, Neisseria, Borrelia* (for example, OspA or OspB or derivatives thereof), *Chlamydia*, or *Bordetella* (for example, P.69, PT and FHA), or derived from parasites such as *plasmodium* or *Toxoplasma*. In one embodiment, the antigen is derived from *Mycobacterium tuberculosis* (e.g. ESAT-6, 85A, 85B, 72F), *Bacillus anthracis* (e.g. PA), or *Yersinia pestis* (e.g. F1, V). In addition, antigens suitable for use in the present invention can be obtained or derived from known causative agents responsible for diseases including, but not limited to, Diptheria, Pertussis, Tetanus, Tuberculosis, Bacterial or Fungal Pneumonia, Otitis Media, Gonorrhea, Cholera, Typhoid, Meningitis, Mononucleosis, Plague, Shigellosis or Salmonellosis, Legionaire's Disease, Lyme Disease, Leprosy, Malaria, Hookworm, Onchocerciasis, Schistosomiasis, Trypanosomiasis, Leishmaniasis, *Giardia, Amoebiasis, Filariasis, Borelia*, and Trichinosis.

The microbes of the invention may be altered to contain a heterologous nucleic acid sequence encoding an autoimmune disease-specific antigen. In a T cell mediated autoimmune disease, a T cell response to self antigens results in the autoimmune disease. The type of antigen for use in treating an autoimmune disease with the vaccines of the present invention might target the specific T cells responsible for the autoimmune response. For example, the antigen may be part of a T cell receptor, the idiotype, specific to those T cells causing an autoimmune response, wherein the antigen incorporated into a vaccine of the invention would elicit an immune response specific to those T cells causing the autoimmune response. Eliminating those T cells would be the therapeutic mechanism to alleviating the autoimmune disease. Another possibility would be to incorporate an antigen that will result in an immune response targeting the antibodies that are generated to self antigens in an autoimmune disease or targeting the specific B cell clones that secrete the antibodies. For example, an idiotype antigen may be incorporated into the microbe that will result in an anti-idiotype immune response to such B cells and/or the antibodies reacting with self antigens in an autoimmune disease. Autoimmune diseases that may be treatable with vaccine microbes of the present invention include, but are not limited to, rheumatoid arthritis, multiple sclerosis, Crohn's disease, lupus, myasthenia gravis, vitiligo, scleroderma, psoriasis, pemphigus vulgaris, fibromyalgia, colitis and diabetes. A similar approach may be taken for treating allergic responses, where the antigens incorporated into the vaccine microbe target either T cells, B cells or antibodies that are effective in modulating the allergic reaction. In some autoimmune diseases, such as psoriasis, the disease results in hyperproliferative cell growth with expression of antigens that may be targeted as well. Such an antigen that will result in an immune response to the hyperproliferative cells is considered.

Optionally, the microbes of the present invention comprise antigens that target unique disease associated protein structures. One example of this is the targeting of antibodies, B cells or T cells using idiotype antigens as discussed above. Another possibility is to target unique protein structures resulting from a particular disease. An example of this would be to incorporate an antigen that will generate an immune response to proteins that cause the amyloid plaques observed in diseases such as Alzheimer's disease, Creutzfeldt-Jakob disease (CJD) and Bovine Spongiform Encephalopathy (BSE). While this approach may only provide for a reduction in plaque formation, it may be possible to provide a curative vaccine in the case of diseases like CJD. This disease is caused by an infectious form of a prion protein. The vaccine incorporates an antigen to the infectious form of the prion protein such that the immune response generated by the vaccine may eliminate, reduce, or control the infectious proteins that cause CJD.

The polynucleotide encoding a specific antigen is not limited to an exact nucleic acid sequence but is of a sequence that is sufficient to provide the expression of an antigen that will elicit the desired immune response when administered to an individual. The term "antigen," as used herein, is also understood to include fragments of proteins that are antigenic. Similarly for polynucleotides encoding other proteins, the sequences of the polynucleotides encoding a given protein may vary so long as the desired protein is expressed in order to provide the desired effect (e.g. a palliative effect) when administered to an individual.

In still other embodiments, the antigen is obtained or derived from a biological agent involved in the onset or progression of neurodegenerative diseases (such as Alzheimer's disease), metabolic diseases (such as Type I diabetes), and drug addictions (such as nicotine addiction). Alternatively, the antigen encoded by the recombinant nucleic acid molecule is used for pain management and the antigen is a pain receptor or other agent involved in the transmission of pain signals.

In some embodiments, the antigen is a human protein or is derived from a human protein. In other embodiments, the antigen is a non-human protein or is derived from a non-human protein (a fragment and/or variant thereof). In some embodiments, the antigen portion of the fusion protein encoded by the expression cassette is a protein from a non-human animal or is a protein derived from a non-human animal. For instance, even if the antigen is to be expressed in a *Listeria*-based vaccine that is to be used in humans, the antigen can be murine mesothelin or derived from murine mesothelin.

Another option for heterologous protein expression is to utilize a protein "scaffold" into which a heterologous protein is functionally inserted "in-frame." In this composition, whole genes or components of the gene corresponding to, for example, MHC class I or MHC class II epitopes are inserted within and through a scaffold protein. The scaffold protein can be a highly expressed *Listeria* protein, for example LLO or p60, but in another embodiment can be a heterologous protein that is selected for its high expression, stability, secretion, and or (lack) of immunogenicity. Representative examples of scaffold proteins are chicken ovalbumin, or other human proteins, such as β-globin or albumin.

c. Other Proteins Encoded by the Expression Cassettes

In some embodiments, the microbes used for the vaccine compositions of the invention comprise heterologous expression cassettes which encode proteins such as cytolysins. Preferably, expression of the proteins enhances the potency of the immune response to the vaccine containing the microbe upon administration to an animal. For instance, the modified microbes of the invention optionally comprise heterologous nucleic acids such as expression cassettes or expression vectors which encode cytolysin. The modified microbes of the invention optionally comprise heterologous nucleic acids, such as expression cassettes or expression vectors, which encode cytolysins. In some embodiments, the vaccines of the present invention comprise microbes which express cytolysins heterologous to the microbes. The heterologous cytolysin expressed by the microbe in the vaccine is optionally Listeriolysin O (LLO), Streptolysin, or Perfringolysin, or a mutant version of Listeriolysin O (LLO), Streptolysin, or Perfringolysin. Accordingly, in some embodiments, the vaccine comprises and/or has been prepared using a modified non-Listerial microbe, such as *Bacillus anthracis* or *Mycobacterium tuberculosis*, which expresses LLO.

For instance, the vaccine compositions of the present invention are optionally enhanced by the expression and secretion of Listeriolysin O (LLO), the cholesterol-dependent, pore-forming cytolysin from *Listeria monocytogenes*. LLO is a critical virulence factor from *Listeria* because its expression in the phagolysosome allows *Listeria* to escape into the host cell cytosol. Importantly, it has been shown that expression of LLO by other microorganisms, such as *Bacillus subtilis* (Bielecki et al, Nature. 1990 345:175-6), *E. coli* (Higgins et al, Mol. Microbiol. 1999 31:1631-41), or *Mycobacte-*

*rium bovis* BCG (Conradt et al, Microbes Infect. 1999 1:753-64), allows these organisms or their protein antigens to enter the cytosol. This leads to improved antigen presentation via the MHC class I pathway and subsequent generation of CD8+ T cell responses.

In some embodiments, the LLO protein expressed by the microbe is an LLO fusion protein that comprises a signal sequence, allowing it to be secreted from the intact microbe. In this mode, the whole microbe can gain access to the host cell cytosol. In some alternative embodiments, LLO protein that is expressed by the microbe does not comprise a signal sequence, and the LLO protein is expressed and accumulated inside the microbe without secretion. In this case, degradation and rupture of the vaccine microbe within the phagolysosome ultimately leads to the release of antigens into the cytosol.

In some embodiments, the heterologous cytolysin that is expressed is a naturally occurring cytolysin. In other embodiments, the cytolysin that is expressed is a mutant form of the naturally occurring cytolysin. In some cases, the mutant cytolysin is more active than the naturally occurring cytolysin.

For instance, mutant forms of LLO that are more active than the native protein at neutral pH have been isolated from *Listeria* and characterized (Glomski et al., Infect Immun. 2003 71: 6754-65). These mutant LLO proteins retain activity in the host cell cytosol and are thus cytotoxic to the host cell. The primary stimulus by which wild-type LLO activity is regulated is pH, which differs between the phagolysosome and the cytosol. Normally, LLO is active in the acidic environment of the phagolysosome, but is significantly less active in the cytosol. This enables *Listeria* to replicate and survive in the infected host cell long enough to infect adjacent cells by direct cell-to-cell spread. The increased activity of mutant LLO proteins in the neutral pH environment of the cytosol leads to premature host cell death and an enhanced immune response, including an anti-listerial response. In the context of the vaccine compositions described here, mutant cytolysins, such as the alternative LLO proteins described here, can be useful in non-Listerial species as a way of augmenting CD8+ T cell activation by promoting MHC class I antigen processing.

Mutant LLO proteins have other advantages as well. For instance, *Mycobacterium tuberculosum*, the causative agent of TB, is known to block maturation and acidification of the phagosome in macrophages. This mechanism allows *Mycobacterium* to survive in the phagosome. BCG vaccination leads primarily to the production of antigen-specific CD4+ T cells due to the fact that BCG remains localized in the immature phagosome. The expression and secretion of a mutant LLO protein by a mycobacterial vaccine would enhance the ability of the vaccine strain to escape from the immature phagosome because the mutant LLO protein would be sufficiently active in the neutral pH of the immature phagosome. This would also enhance CD8+ T cell response, which is highly desirable for a TB vaccine since CD8+ T cells are thought to be essential for preventing reactivation of latent infections (van Pinxteren et al, Eur J Immunol. 2000 30: 3689-98).

Thus, in some embodiments, the modified microbes used in or to make the vaccine compositions comprise a heterologous expression cassette which encodes a mutant LLO protein.

Other cytolysins, such as Streptolysin and Perfringolysin O, can also be used to enhance the potency of responses to the vaccine.

d. Codon-Optimization of the Expression Cassettes

The expression cassettes in those modified microbes which contain heterologous nucleic acids optionally comprise codon-optimized sequences. For instance, the heterologous expression cassettes in those modified microbes optionally comprise polynucleotide sequences encoding proteins (such as antigens or cytolysins), wherein the coding sequences have been codon-optimized for expression in the microbe. Optionally, the expression cassettes also comprise polynucleotide sequences encoding signal peptides, wherein the signal peptide-encoding polynucleotide sequences have also been codon-optimized for expression in the microbe. In some alternative embodiments, the polynucleotide sequences encoding the signal peptide have been codon optimized for expression in the microbe, but the coding sequence of the protein to be secreted has not.

In some embodiments, the modified microbe (e.g., bacterium) used in the vaccines described herein (either microbe-based or APC-based) comprises a heterologous expression cassette comprising a polynucleotide sequence encoding an antigen wherein the sequence encoding the antigen is codon-optimized for expression in the microbe.

In some embodiments, the modified microbe (e.g., bacterium) used in the vaccines described herein comprises a heterologous expression cassette comprising a polynucleotide sequence encoding an antigen fused to a signal peptide wherein the sequence encoding the antigen fused to the signal peptide is codon-optimized for expression in the microbe (i.e., the coding sequence of both the antigen and the signal peptide are codon-optimized for expression in the microbe).

In some embodiments, a heterologous nucleic acid sequence encoding a protein may be codon-optimized to match the codon preference of the microbial host (e.g., bacterial host) expressing the protein. In addition, the sequence encoding a signal peptide fused to the expressed protein may also be codon-optimized to match the codon preference of the microbial host (e.g., bacterial host). In preferred embodiments, the bacterial host is *Listeria* and either or both of the heterologous protein encoding sequence and the sequence encoding a signal peptide may be codon-optimized. For further information on codon optimization of antigens and signal sequences in bacteria such as *Listeria*, see U.S. Ser. Nos. 60/532,598 and 60/556,744, each incorporated by reference herein.

In some embodiments, a modified microbe comprises a heterologous expression cassette comprising the following: (a) a polynucleotide encoding a polypeptide foreign to the microbe, wherein the polynucleotide is codon-optimized for expression in the microbe; and (b) a promoter, operably linked to the polynucleotide encoding the foreign polypeptide. In some embodiments, the polypeptide that is encoded by the expression cassette is an antigen or is derived from an antigen described above. In some embodiments, the expression cassette further comprises a polynucleotide encoding a signal peptide. The polynucleotide encoding the signal peptide is also operably linked with the promoter so that the expression cassette expresses a fusion protein comprising both the foreign polypeptide and the signal peptide. The polynucleotide encoding the signal peptide is optionally also codon-optimized for expression in the microbe.

Accordingly, a microbe used in this invention optionally comprises a heterologous expression cassette comprising the following: (a) a first polynucleotide encoding a signal peptide, wherein the first polynucleotide is codon-optimized for expression in the microbe; (b) a second polynucleotide encoding a polypeptide, wherein the second polynucleotide is in the same translational reading frame as the first polynucleotide; and (c) a promoter operably linked to the first and second polynucleotides, so that the expression cassette encodes a fusion protein comprising the signal peptide and the polypeptide.

A polynucleotide comprising a coding sequence is codon-optimized if at least one codon of the coding sequence of the polynucleotide has been replaced with a codon that is more frequently used by the organism in which the coding sequence is to be expressed (the "target organism") than the original codon. For instance, a polynucleotide encoding a non-bacterial antigen that is to be expressed in a particular species of bacteria is codon-optimized if at least one of the codons is replaced with a codon that is preferentially expressed in that particular species of bacteria. As another example, a polynucleotide encoding a human cancer antigen that is to be part of an expression cassette in recombinant Listeria monocytogenes is codon-optimized if at least one codon in the polynucleotide sequence is replaced with a codon that is more frequently used by Listeria monocytogenes for that amino acid than the codon in the original human sequence would be. Likewise, a polynucleotide encoding a Listerial signal peptide (such as the LLO signal peptide) that is to be part of an expression cassette to encode a fusion protein comprising a human cancer antigen in recombinant Listeria monocytogenes is codon-optimized if at least one codon in the polynucleotide sequence is replaced with a codon that is more frequently used by Listeria monocytogenes for that amino acid than the codon in the original Listerial sequence would be. In some embodiments, the at least one codon that is replaced in the codon-optimized sequence is replaced with the codon most frequently used by the target organism to code for the same amino acid.

In some embodiments, at least about 10% of the codons in the codon-optimized polynucleotide have been replaced with codons more frequently (or most frequently) used by the target organism. In other embodiments, at least about 25% of the codons in the codon-optimized polynucleotide have been replaced with codons more frequently used (or most frequently) used by the target organism. In other embodiments, at least about 50% of the codons in the codon-optimized polynucleotide have been replaced with codons more frequently used (or most frequently) used by the target organism. In still other embodiments, at least about 75% of the codons in the codon-optimized polynucleotide have been replaced with codons more frequently used (or most frequently used) by the target organism.

Codon usage tables are publicly available for a wide variety of microbes. An exemplary codon usage table for Listeria monocytogenes is reproduced for convenience below in Table 2A. Exemplary codon usage tables for Bacillus anthracis and Mycobacterium tuberculosis are also provided in Tables 2B and 2C, respectively, below.

TABLE 2A

Codon Usage Table for Listeria monocytogenes
Listeria monocytogenes: 3262 CDS's (1029006 codons)
fields: [triplet] [frequency: per thousand] ([number])

| | | | |
|---|---|---|---|
| UUU 29.4 (30274) | UCU 13.2 (13586) | UAU 22.9 (23604) | UGU 3.8 (3960) |
| UUC 14.1 (14486) | UCC 6.5 (6714) | UAC 10.7 (11055) | UGC 1.9 (1972) |
| UUA 36.8 (37821) | UCA 10.4 (10751) | UAA 2.2 (2307) | UGA 0.6 (583) |
| UUG 12.3 (12704) | UCG 6.1 (6278) | UAG 0.4 (372) | UGG 9.3 (9580) |
| CUU 21.0 (21567) | CCU 8.4 (8622) | CAU 12.0 (12332) | CGU 12.6 (12930) |
| CUC 5.4 (5598) | CCC 1.7 (1780) | CAC 5.2 (5336) | CGC 7.0 (7215) |
| CUA 12.9 (13279) | CCA 18.5 (18996) | CAA 29.9 (30719) | CGA 5.6 (5732) |
| CUG 5.0 (5120) | CCG 7.0 (7219) | CAG 5.1 (5234) | CGG 2.8 (2884) |
| AUU 49.3 (50692) | ACU 17.1 (17614) | AAU 33.0 (33908) | AGU 14.1 (14534) |
| AUC 18.4 (18894) | ACC 6.9 (7089) | AAC 15.3 (15790) | AGC 8.8 (9031) |
| AUA 9.4 (9642) | ACA 26.5 (27318) | AAA 61.6 (63379) | AGA 6.9 ( 7111) |
| AUG 25.9 (26651) | ACG 12.9 (13285) | AAC 10.4 (10734) | AGG 1.2 (1254) |
| GUU 26.4 (27202) | GCU 24.3 (24978) | GAU 39.8 (40953) | GGU 24.2 (24871) |
| GUC 8.7 (8990) | GCC 8.4 (8612) | GAC 14.3 (14751) | GGC 14.2 (14581) |
| GUA 21.6 (22247) | GCA 28.6 (29401) | GAA 60.4 (62167) | GGA 19.1 (19612) |
| GUG 13.1 (13518) | GCG 16.6 (17077) | GAG 13.1 (13507) | GGG 8.7 (9003) |

TABLE 2B

Codon Usage Table for *Bacillus anthracis*
*Bacillus anthracis* [gbbct]: 312 CDS's (90023 codons)
fields: [triplet] [frequency: per thousand] ([number])

| | | | |
|---|---|---|---|
| UUU 32.4 (2916) | UCU 17.2 (1547) | UAU 31.9 (2876) | UGU 5.1 (455) |
| UUC 10.4 (934) | UCC 5.0 (453) | UAC 9.5 (853) | UGC 1.8 (164) |
| UUA 43.7 (3931) | UCA 14.8 (1330) | UAA 2.2 (199) | UGA 0.5 (47) |
| UUG 11.4 (1024) | UCG 4.2 (375) | UAG 0.7 (66) | UGG 9.3 (835) |
| CUU 14.4 (1300) | CCU 10.7 (967) | CAU 15.5 (1392) | CGU 9.8 (883) |
| CUC 3.7 (335) | CCC 2.7 (242) | CAC 4.2 (379) | CGC 2.5 (223) |
| CUA 12.4 (1117) | CCA 17.8 (1599) | CAA 32.3 (2912) | CGA 6.3 (569) |
| CUG 4.4 (392) | CCG 5.9 (534) | CAG 9.5 (859) | CGG 2.0 (179) |
| AUU 44.5 (4009) | ACU 21.0 (1890) | AAU 44.0 (3959) | AGU 17.4 (1565) |
| AUC 11.9 (1072) | ACC 5.0 (453) | AAC 14.1 (1268) | AGC 5.2 (467) |
| AUA 22.7 (2042) | ACA 26.8 (2414) | AAA 64.3 (5786) | AGA 13.7 (1236) |
| AUG 23.3 (2098) | ACG 9.4 (844) | AAG 22.7 (2047) | AGG 4.1 (368) |
| GUU 20.3 (1824) | GCU 17.8 (1598) | GAU 39.3 (3536) | GGU 17.9 (1611) |
| GUC 4.6 (414) | GCC 4.1 (372) | GAC 9.0 (811) | GGC 5.8 (524) |
| GUA 26.4 (2374) | GCA 23.5 (2117) | GAA 53.9 (4855) | GGA 24.5 (2203) |
| GUG 10.8 (973) | GCG 7.9 (709) | GAG 17.9 (1614) | GGG 12.0 (1083) |

Coding GC 34.55% 1st letter GC 44.99% 2nd letter GC 33.16% 3rd letter GC 25.51%

TABLE 2C

Codon Usage Table for *Mycobacterium tuberculosis*
*Mycobacterium tuberculosis* [gbbct]:
363 CDS's (131426 codons)
fields: [triplet] [frequency: per thousand] ([number])

| | | | |
|---|---|---|---|
| UUU 5.4 (709) | UCU 2.0 (265) | UAU 6.0 (788) | UGU 2.5 (326) |
| UUC 25.6 (3359) | UCC 11.4 (1499) | UAC 17.6 (2307) | UGC 5.6 (738) |
| UUA 1.8 (231) | UCA 4.3 (571) | UAA 0.4 (52) | UGA 1.5 (201) |
| UUG 14.8 (1945) | UCG 19.2 (2522) | UAG 0.8 (103) | UGG 17.9 (2352) |
| CUU 5.9 (778) | CCU 3.9 (511) | CAU 5.4 (711) | CGU 8.0 (1048) |
| CUC 17.7 (2329) | CCC 18.3 (2411) | CAC 14.7 (1928) | CGC 26.7 (3508) |
| CUA 4.0 (521) | CCA 6.4 (843) | CAA 7.8 (1030) | CGA 5.8 (764) |
| CUG 45.9 (6032) | CCG 33.2 (4359) | CAG 24.2 (3176) | CGG 21.1 (2772) |
| AUU 7.6 (993) | ACU 4.1 (545) | AAU 4.8 (637) | AGU 4.0 (531) |
| AUC 32.7 (4300) | ACC 36.0 (4735) | AAC 26.3 (3451) | AGC 15.0 (1976) |
| AUA 2.1 (282) | ACA 4.7 (616) | AAA 5.8 (761) | AGA 1.5 (192) |
| AUG 19.7 (2591) | ACG 16.4 (2158) | AAG 26.5 (3485) | AGG 3.3 (429) |
| GUU 8.3 (1095) | GCU 11.2 (1473) | GAU 15.6 (2046) | GGU 18.7 (2455) |
| GUC 32.3 (4249) | GCC 51.5 (6769) | GAC 44.6 (5858) | GGC 48.6 (6383) |
| GUA 4.7 (622) | GCA 12.4 (1625) | GAA 16.8 (2211) | GGA 9.0 (1183) |
| GUG 35.7 (4687) | GCG 41.7 (5482) | GAG 35.8 (4702) | GGG 16.9 (2215) |

Coding GC 64.43% 1st letter GC 65.27% 2nd letter GC 48.28% 3rd letter GC 79.75%

In some embodiments of the invention, at least about 10%, at least about, 25%, at least about 50%, or at least about 75% of the codons in a codon-optimized coding sequence are the most preferred codon for that amino acid used in the target organism. In other embodiments, 100% of the codons in the codon-optimized coding sequence are the most preferred codon for that amino acid in the target organism. For instance, in Example 48 shown below, all of the codons of the sequences characterized as codon-optimized were the optimal (most frequently used) codons for the target organism. Table 3, below shows the optimal codon usage in *Listeria monocytogenes* for each amino acid.

TABLE 3

Optimal codon Usage Table for *Listeria Monocytogenes*.

| Amino Acid | One Letter Code | Optimal Listeria Codon |
|---|---|---|
| Alanine | A | GCA |
| Arginine | R | CGU |
| Asparagine | N | AAU |
| Aspartate | D | GAU |
| Cysteine | C | UGU |
| Glutamine | Q | CAA |
| Glutamate | E | GAA |
| Glycine | G | GGU |
| Histidine | H | CAU |
| Isoleucine | I | AUU |
| Leucine | L | UUA |
| Lysine | K | AAA |
| Methionine | M | AUG |
| Phenylalanine | F | UUU |
| Proline | P | CCA |
| Serine | S | AGU |
| Threonine | T | ACA |
| Tryptophan | W | UGG |
| Tyrosine | Y | UAU |
| Valine | V | GUU |

Non-limiting examples of antigen-encoding sequences codon optimized for expression in *Listeria monocytogenes* are shown in Example 48, below.

E. Microbes Containing Mutations

In some embodiments, the modified microbes of the invention comprise one or more mutations. A "mutation" or "genetic mutation" may be a mutation of any type. For instance, the mutation may constitute a point mutation, a frame-shift mutation, an insertion, or a deletion of part or all of a gene. In addition, in some embodiments of the modified microbes, a portion of the microbial genome has been replaced with a heterologous polynucleotide. In some embodiments, the mutations are naturally-occurring. In other embodiments, the mutations are the results of artificial mutation pressure. In still other embodiments, the mutations in the microbial genome are the result of genetic engineering. A mutant in which a gene "xyz" has been deleted is alternatively referred to herein as Δxyz or xyz⁻ or an xyz deletion mutant. For instance, a bacterial strain in which the uvrA gene has been deleted is alternatively referred to herein as uvrA mutant, ΔuvrA, or uvrA⁻. In addition, it will be understood by one of ordinary skill in the art that a reference to a particular mutant or strain as an "xyz" mutant or "xyz" strain will sometimes refer to a mutant or strain in which the xyz gene has been deleted.

In some embodiments, the invention includes a vaccine comprising a microbe wherein the nucleic acid of the microbe is modified so that the proliferation of the microbe is attenuated, wherein the microbial population is still able to express a desired antigen to an extent that is sufficient to elicit an immune response, and wherein the microbe is further attenuated by at least one genetic mutation. The mutation in the microbe may affect a variety of features of the microbe. In some cases, the mutation affects the ability of the microbe to invade certain cells. For example, certain intracellular bacteria can invade a variety of cell types depending on receptors present on the bacteria. The mutation may alter the expression of certain receptors so that the bacteria are taken up by some cell types but not others. As an example of this, *Listeria* is typically taken up by phagocytic cells and also actively invades non-phagocytic cells (e.g. hepatic cells). A mutation of *Listeria* may be used in which the invasion of non-phagocytic cells is significantly reduced or eliminated while the uptake by phagocytic cells is sufficiently active. Such a mutation may provide for a better immune response as the vaccine would be preferentially taken up by phagocytic cells, which are important in presenting the bacterial antigens to the immune system. It is understood that the mutation can be to any gene that results in an attenuation of the ability of the microbe to invade certain cell types, and that this is exemplified by mutations to internalin genes in *Listeria* (e.g. inlA, inlB). Similar genes may exist (e.g. invasin genes in *Salmonella, Bacillus anthracis,* and *Yersinia*) in other bacteria, and mutations in these genes are encompassed by the present invention. The mutation might impact other features of the microbe, such as a virulence factor or a gene that allows for growth and spreading, thereby reducing the virulence of the microbe. For example, a mutation in the actA gene of *Listeria* causes a deficiency in the polymerization of host cell actin, which inhibits the ability of the *Listeria* to spread to other cells. A mutation in the hly gene of *Listeria* (listeriolysin (LLO) protein) impacts the ability of the *Listeria* to escape the phagolysosome of an infected cell. A mutation in either the plcA or plcB genes of *Listeria* impacts the ability of the *Listeria* to spread from cell to cell. A mutation in the yop gene of *Yersinia* affects the ability of the *Yersinia* to prevent phagocytosis by macrophages. In another embodiment the genetic mutation attenuates the expression of certain antigens, for example, antigens that would normally result in an immune response to the microbe itself. Such a mutation may be useful if the microbe is used as a vaccine comprising a heterologous antigen in order to stimulate a strong immune response to the heterologous antigen but with a reduced immune response to the delivery microbe compared to the non-mutated microbe. In one embodiment, the microbe is attenuated by a mutation in more than one gene. In one embodiment, one of the mutations is in an internalin gene of *Listeria* or a similar gene in other bacteria. In one embodiment, the mutation is in one or more of an internalin gene of *Listeria* or similar gene in other bacteria. In one embodiment, one of the mutations is in the actA gene. In one embodiment, the microbe comprises *Listeria monocytogenes* with mutations in the actA gene and one or more internalin genes. In a preferred embodiment, the *Listeria monocytogenes* comprises a mutation in the actA gene and the inlB gene, preferably the *Listeria monocytogenes* comprises an actA/inlB deletion mutant (which is alternatively referred to herein as either ΔactAΔinlB or actA⁻inlB⁻). The sequences of a variety of *Listeria* genes including those described herein are found in Genbank accession no. NC_003210.

The microbe might contain a mutation that significantly reduces the ability of the microbe to repair modifications to their nucleic acid. Such a mutation could be in any of a variety of genes that are involved in the DNA repair mechanisms of microbes [Aravind et al., Nucleic Acids Research 27(5): 1223-1242 (1999)]. Microbes that are deficient in their ability to repair damage to their nucleic acid provide an added level of safety and efficacy to the use of the microbes of the present invention. Using the appropriate repair deficient mutants, the microbes are exquisitely sensitive to nucleic acid modification. The nucleic acid of the microbes may be modified to a lesser degree yet still ensure the desired amount of attenuation of proliferation. This provides a larger window of efficacy in which to operate so that the expression of the microbial nucleic acid is sufficient to generate the desired proteins. In the case where de novo antigen expression is required, this provides a vaccine that will elicit an effective immune response. It also provides an added level of safety as the level of attenuation of proliferation achieved can not be compromised by repair of the modified nucleic acid. In another embodiment, the genetic mutation alters the susceptibility of the microbe to treatment with a nucleic acid targeted compound, for example by altering the permeability of the microbe to the compound or by altering the ability of the compound to access and bind the microbial nucleic acid. Such mutations may also impact the efficacy of the process of attenuating proliferation while leaving microbial gene expression substantially unaffected.

To illustrate the advantages of using a repair deficient mutant, one can consider the mechanism of the attenuation of microbial proliferation. The microbial nucleic acid is modified either by strand breakage or pyrimidine dimers, or by chemical modifications such as monoadducts or crosslinks. If the mechanisms for repair of these modifications are intact, a certain number of modifications will be required in order to achieve sufficient attenuation of proliferation. The greater the modification of nucleic acid, the greater the reduction in protein expression. Even though the levels of modification required to attenuate proliferation are much lower than the levels required to stop protein expression, protein expression will still be reduced to some extent, possibly to an unacceptable level. The use of repair deficient mutants significantly reduces the levels needed to attenuate proliferation such that a lower modification level will result in adequate attenuation of proliferation. Since the nucleic acid modification is much lower, the expression of proteins will be less affected, providing for a higher level of expression of the protein of interest. Such repair deficient mutants may be particularly useful in the preparation of vaccines, such as vaccines to the microbe itself, where the safety of the vaccine can be increased by a slight modification of the nucleic acid, leaving a sufficiently high level of protein expression, in particular the antigen to which the immune response is targeted.

In one embodiment the repair deficient mutant lacks the ability to make PhrB (a photolyase), which repairs pyrimidine dimers. For example, the mutation may be in the phrB gene, or a functionally equivalent gene, depending on the genus and species of the microbe. Such a mutant could be used in conjunction with ultraviolet irradiation (e.g. UVB, UVC) of the microbe to produce pyrimidine dimers in the microbial nucleic acid.

In one embodiment the repair deficient mutant is unable to repair interstrand crosslinks. Such mutants include, but are not limited to, mutations in uvr genes, i.e. uvrA, uvrB, uvrC, and uvrD genes as well as recA genes, or functionally equivalent genes, depending on the genus and species of the microbe. The mutations may be in one or more of these genes. These mutations result in attenuation in the activity of the corresponding enzymes UvrA (an ATPase), UvrB (a helicase), UvrC (a nuclease), UvrD (a helicase II) and RecA (a recombinase). These mutants would be used in conjunction with a crosslinking compound, such as a psoralen. Since the microbial nucleic acid is crosslinked in some locations, and these crosslinks can not be repaired, the microbe is unable to replicate as the original strands of nucleic acid can not be separated. Since they can not be repaired, very few crosslinks are needed, the microbial nucleic acid is for the most part accessible for transcription, and protein expression is not altered significantly. In a preferred embodiment, a population of repair deficient microbial mutants that are unable to repair interstrand crosslinks are suitably crosslinked such that essentially every microbe in the population contains at least one crosslink, such that attenuation of replication is essentially complete, wherein the microbial gene expression of the population is sufficiently active.

In some embodiments, the microbe used in (and/or to make) the vaccine compositions of the invention are defective with respect to one or more DNA repair enzymes (i.e., nucleic acid repair enzymes). In some embodiments, the microbes are entirely defective with respect to a DNA repair enzyme (e.g., a DNA repair enzyme deletion mutant and some mutants containing point mutations). In some embodiments, the microbes are partially defective (e.g., some mutants containing point mutations). In some embodiments, the microbe that is defective with respect to a DNA repair enzyme is a conditional mutant or a repressible mutant.

In some embodiments, the modified microbes (e.g., modified bacteria) used in the microbe-based vaccines or the antigen-presenting cell vaccines are microbes containing mutations that attenuate the microbes for nucleic acid repair. In some embodiments, the modified microbes used as vaccines or in antigen-presenting cell vaccines are defective with respect to a DNA repair enzyme. In some embodiments, the modified microbes are defective with respect to UvrA and UvrB. In some embodiments, the uvrA and uvrB genes are deleted. In some embodiments the modified microbes are defective with respect to UvrC. In some embodiments, the modified microbes are defective with respect to RecA. In some embodiments, the modified microbes are modified bacteria defective with respect to UvrA and UvrB (e.g., a uvrAB deletion mutant). In some embodiments the modified microbes are modified bacteria defective with respect to UvrC. In some embodiments, the modified microbes are modified bacteria defective with respect to RecA.

In some embodiments, the microbe used in or for the vaccines of the invention is defective with respect to RecA. In some embodiments the microbe defective with respect to RecA comprises a mutation in the RecA gene. In some embodiments, the microbe that is defective with respect to RecA is a conditional recA mutant. In some embodiments, the microbe that is defective with respect to RecA comprises a repressible recA gene.

In one embodiment, a mutation in the recA gene is a conditional mutation. In such a mutation, the mutation in the recA gene results in the attenuation in the activity of recA only under certain conditions (i.e. non-permissive conditions), such as a suitable pH or temperature of the microbial population. A microbe comprising a conditional recA mutation can be cultured under permissive conditions in order to grow sufficient levels of the microbe and then placed under non-permissive conditions for treatment to modify the nucleic acid, then stored under non-permissive conditions such that the nucleic acid damage is not adequately repaired. As an example of this, a recA temperature sensitive mutant is grown at 30° C., where it grows well, and is treated to modify the nucleic acid at 42° C., which is non-permissive for recA such that it is very sensitive to treatment, such as psoralen crosslinking.

While the treated microbe may be stored under non-permissive conditions, it is possible that upon vaccination, the conditions may permit expression of recA, resulting in some repair and presenting a safety issue. It is possible to construct the microbe such that the recA is under the control of the lac repressor, such that growth of the strain can be induced by isopropyl-β-D-thiogalactopyranoside (IPTG) when growth is desirable, but not during photochemical inactivation or post-immunization. The possibility of recA expression can then be eliminated for the inactivation and/or immunization steps by withholding further IPTG from the strain and/or eliminating IPTG from the strain's environment.

For instance, to generate a *Listeria* bacterium which is a lac repressible recA mutant for use in the vaccines of the invention, two expression cassettes are introduced into the genome of the *Listeria* (e.g., *Listeria* ΔuvrAB). The first expression cassette enodes the lac $I^q$ protein under the control of the highly-active constitutive *Listeria* p60 promoter. The second cassette expresses RecA anti-sense RNA, also under the control of the p60 promoter, but, importantly, the lacOip operator will be placed at its 3' end. Thus, expression of the RecA anti-sense RNA is prevented in the presence of the lac $I^q$ protein. In this configuration, functional RecA protein is produced under normal growth conditions, due to constitutive expression of the lac $I^q$ protein. Addition of IPTG to the culture will result in binding of this inducer molecule to the lac $I^q$ repressor, and its inactivation. This results in the high-level synthesis of RecA anti-sense RNA and, in turn, inhibition of translation of RecA protein, mediated through complementary binding of RecA message. The expression cassettes can be assembled onto the pKSV7 integration vector and introduced into *Listeria* ΔuvrAB at the comK-attBB' junction or downstream of orfXYZ of the 3' end of the prfA regulon. Each of these *Listeria* loci has been shown to be permissive for integration of heterologous expression cassettes without impacting the phenotype of the parental strain. In this setting, the expression of recA is shut-off by addition of IPTG to the fermentation culture prior to illumination with UVA light.

In one embodiment, the microbe comprises at least one mutation that reduces (preferably, significantly reduces) the ability of the microbe to repair modifications to their nucleic acid in combination with at least one mutation not related to repair mechanisms. The mutation that is not related to repair mechanisms may affect a variety of features of the microbe, such as the ability of the microbe to invade certain cells, a mutation in a virulence factor or a gene that allows for growth and spreading, or a mutation that attenuates the expression of certain antigens. Such mutations are discussed above and include, but are not limited to, mutations in internalin genes (e.g. inlB), actA gene, hly gene, plcA gene, or plcB gene of *Listeria*, invasion genes (e.g. *Salmonella, Bacillus anthracis*, and *Yersinia*) or the yop gene of *Yersinia*. In one embodiment, the microbe comprises *Listeria monocytogenes* having a mutation in the actA gene. In one embodiment, the *Listeria monocytogenes* comprises a mutation in the actA gene and in an internalin gene. In one embodiment, the *Listeria monocytogenes* comprises an actA mutation and a uvrAB mutation, preferably actA/uvrAB deletion mutations (which may be referred to as either ΔactAΔuvrAB or $actA^-uvrAB^-$). In one embodiment, the *Listeria monocytogenes* comprises an actA mutation, an inlB mutation, and a uvrAB mutation, preferably actA/inlB/uvrAB deletion mutations. In some other embodiments, the microbe comprises *Bacillus anthracis* having a uvrAB mutation, such as a deletion.

In addition, the microbe used in the vaccine may comprise at least one mutation in a gene encoding a cytolysin. In some embodiments, the mutation renders the cytolysin more active relative to the non-mutated cytolysin. In some embodiments, the mutation in the cytolysin enhances entry of the microbe into the cytosol of a host cell. In some embodiments, mutation in the cytolysin enhances the potency of the immune response to a vaccine comprising the mutant microbe. An example of such a mutant cytolysin is the mutant LLO that is more active than the native protein at neutral pH that is described above and in Glomski et al., Infect Immun. 2003 71:6754-65 (2003).

In another embodiment, the invention provides an isolated mutant *Listeria* strain, such as a mutant *Listeria monocytogenes* strain, comprising a genetic mutation that attenuates its ability to repair its nucleic acid. In some embodiments, the mutant *Listeria* strain is defective with respect to at least one DNA repair enzyme (such as UvrA and/or UvrB). In some embodiments, the mutant *Listeria* strain comprises a genetic mutation in the uvrA gene and/or the uvrB gene. In some embodiments, the mutant strain is the *Listeria monocytogenes* ΔactAΔuvrAB strain deposited with the American Type Culture Collection (ATCC) and identified by accession number PTA-5563. In other embodiments, strain is a mutant of the *Listeria monocytogenes* ΔactAΔuvrAB strain deposited with the American Type Culture Collection (ATCC) and identified by accession number PTA-5563, wherein the mutant of the deposited strain is defective with respect to UvrA, UvrB, and ActA.

In some embodiments, the invention provides a free-living microbe which is defective with respect to at least one DNA repair enzyme (relative to wild type). In some embodiments, the microbe that is defective with respect to at least one DNA repair enzyme is attenuated for DNA repair relative to wild type. In some embodiments, the capacity of the microbe for DNA repair by at least one pathway is reduced by at least about 10%, at least about 25%, at least about 50%, at least about 75%, or at least about 90% relative to wild type. Methods for assessing the ability of a microbe to effect DNA repair are well known to those of ordinary skill in the art. In some embodiments, the microbe is defective with respect to one or more of the following enzymes: PhrB, UvrA, UvrB, UvrC, UvrD, and RecA. In some embodiments, the microbe is defective with respect to UvrA, UvrB, or both enzymes. In some embodiments, the microbe is defective with respect to RecA, or a functional equivalent of Rec A. In some embodiments, the microbe comprise a genetic mutation in one or more gene selected from the group consisting of phrB, uvrA, uvrB, uvrC, uvrD and recA, or in a functional equivalent of one or more gene selected from the group consisting of phrB, uvrA, uvrB, uvrC, uvrD and recA. In some embodiments, the microbe comprises genetic mutations in both uvrA and uvrB, or in functional equivalents of both uvrA and uvrB. In some embodiments, the microbe comprises a genetic mutation in recA. In some embodiments, the microbe is a bacterium. For instance, in some embodiments, the microbe is *Mycobacterium tuberculosis, Listeria monocytogenes*, or *Bacillus anthracis*.

The invention also provides an isolated mutant *Listeria monocytogenes* strain, comprising a genetic mutation that attenuates its ability to repair its nucleic acid. In some embodiments, the mutant strain is defective with respect to at least one DNA repair enzyme (such as UvrA and/or UvrB). In some embodiments, the mutant strain comprises a genetic mutation in the uvrA gene and/or the uvrB gene. In some embodiments, the uvrA gene, the uvrB gene, or both genes are deleted. In some embodiments, the mutant strain is attenuated with respect to RecA. In some embodiments, the mutant strain comprises a genetic mutation in the recA gene. In some embodiments, the mutant microbe is the *Listeria monocytogenes* $actA^-/uvrAB^-$ strain deposited with the American Type Culture Collection (ATCC) and identified by accession number PTA-5563, or a mutant of the deposited strain which is defective with respect to UvrA, UvrB, and ActA. In some embodiments, the mutant microbe is the *Listeria monocytogenes* actA⁻/uvrAB⁻ strain deposited with the American Type Culture Collection (ATCC) and identified by accession number PTA-5563.

The invention also provides an isolated mutant *Bacillus anthracis* strain, comprising a genetic mutation that attenuates its ability to repair its nucleic acid. In some embodiments, the mutant strain is defective with respect to at least one DNA repair enzyme (such as UvrA and/or UvrB). In some embodiments, the mutant strain comprises a genetic mutation in the uvrA gene and/or the uvrB gene. In some embodiments, the uvrA gene (SEQ ID NO:18), the uvrB gene (SEQ ID NO:19), or both genes are deleted. In some embodiments, the mutant microbe is the *Bacillus anthracis* Sterne ΔuvrAB strain deposited with the American Type Culture Collection (ATCC) and identified by accession number PTA-5825, or a mutant of the deposited strain which is defective with respect to UvrA and UvrB. In some embodiments, the mutant microbe is the *Bacillus anthracis* Sterne ΔuvrAB strain deposited with the American Type Culture Collection (ATCC) and identified by accession number PTA-5825. In some embodiments, the mutant strain is attenuated with respect to RecA. In some embodiments, the mutant strain comprises a genetic mutation in the recA gene. In some embodiments, the mutant strain comprises a mutation in the recA gene that makes expression of the recA protein temperature sensitive. In some alternative embodiments, a mutant strain of *B. anthracis* is constructed which is under control of the lac repressor (inducible by IPTG), permitting expression of recA during growth, but not during inactivation (such as with S-59/UVA) and/or post-immunization. In some embodiments, the mutant strain comprises one or more mutations in the lef gene, cya gene, or both genes, that decreases the toxicity of the strain.

As with any microbe of the invention, the modification of the DNA of the repair deficient (e.g. uvr deficient) bacteria with psoralen can be controlled by adjusting the compound concentration, reaction conditions and light dose. The appropriate concentration, reaction conditions and light dose are determined by assessing their effects on replication and protein expression as detailed above. The use of repair deficient mutants provides an additional level of control of proliferation while maintaining adequate protein expression such that the parameters of concentration, reaction conditions and light dose can be adjusted over a wider range of conditions to provide a suitable population of microbes. For example, there will be a broader range of nucleic acid modification density over which proliferation can be completely inhibited without significantly affecting protein expression. The minimum level of modification required to completely inhibit repair deficient strains is much less than for non-repair deficient strains (see Examples 3, 7, 11, and 21). As a result, the modification level can be higher than the minimum level required to stop proliferation (ensuring complete inactivation) yet still be below a level that is detrimental to protein expression. Thus, while the invention is effective for non-repair deficient strains, uvr deficient strains provide greater flexibility in preparing a desirable population of microbes that would be effective as a vaccine. Psoralen compounds are effective at concentrations of about 10 pM to 10 mM, also about 100 pM to 1 mM, also about 1 nM to 10 μM, also about 1-500 nM, also about 1-200 nM or about 1-100 nM, with the UVA light dose ranging from about 0.1-100 J/cm², also about 0.1-20 J/cm², also about 0.5-10 J/cm², or about 0.5-6 J/cm² or about 2-6 J/cm². In one embodiment, the microbe is treated in the presence of growth media at psoralen concentrations of about 10 pM to 10 mM, also about 1-5000 nM, also about 1-500 nM, also about 5-500 nM, or about 10-400 nM. In one embodiment, the microbe treated in the presence of growth media is grown to an OD of 0.5-1 in the presence of psoralen at concentrations of about 10 pM to 10 mM, also about 1-5000 nM, also about 1-500 nM, also about 5-500 nM, or about 10-400 nM. Following the growth to an OD of 0.5-1, the microbe population is irradiated with UVA light at a dose ranging from about 0.1-100 J/cm², also about 0.1-20 J/cm², or about 0.5-10 J/cm², 0.5-6 J/cm² or about 2-6 J/cm².

In order to generate primarily psoralen crosslinks in any microbe, particularly uvr deficient mutant bacteria, it is possible to dose the psoralen and UVA light initially to form adducts and follow this with a second dose of UVA light alone to convert some or most of the monoadducts to crosslinks. The psoralen photochemistry is such that absorption of a photon of appropriate energy will first form a monoadduct. Absorption of an additional photon will convert this monoadduct to a crosslink when a furan side monoadduct is appropriately situated in the DNA double helix [Tessman et al., Biochemistry 24:1669-1676 (1985)]. The sample can be dosed with a lower UVA dose at a desired concentration of psoralen and the unreacted psoralen can be removed, e.g. by washing, dialysis or ultrafiltration of the bacteria. The bacteria containing psoralen adducts (monoadducts and crosslinks) can be further dosed with UVA light to convert some or most of the monoadducts to crosslinks without resulting in significant additional adducts to the bacteria. This allows for the controlled addition of a low number of psoralen adducts with the initial light dose, then converting a substantial number of any monoadducts to crosslink with the second dose. This provides for modification of the microbial genome at sufficiently low levels wherein a majority of the adducts formed will be crosslinks. This is particularly effective for blocking replication with uvr deficient mutants. In such embodiments, psoralen compounds are effective at concentrations of about 10 pM to 10 mM, also about 100 pM to 1 mM, also about 1-500 nM, also about 1-200 nM or about 1-100 nM, with the UVA light dose ranging from about 0.1-10 J/cm², also about 0.1-2 J/cm², or about 0.5-2 J/cm². Following removal of most of the unreacted psoralen by washing, dialysis or ultrafiltration of the bacteria, the bacteria may be dosed with UVA light ranging from 0.1-100 J/cm², also about 0.1-20 J/cm², or about 0.5-10 J/cm² or about 2-6 J/cm².

D. Formulations and In Vivo Efficacy

Vaccine compositions of the invention comprise a microbe in which the microbial nucleic acid is modified and/or comprise an antigen-presenting cell which has been antigen-loaded and/or activated/matured by infection with a microbe in which the microbial nucleic acid is modified so that the proliferation of the microbe is attenuated, wherein the microbial gene expression is substantially unaffected, as discussed above. The vaccine compositions of the present invention can be used to stimulate an immune response in an individual. The formulations can be administered to an individual by a variety of administration routes. Methods of administration of such a vaccine composition are known in the art, and include oral, nasal, intravenous, intradermal, intraperitoneal, intramuscular, intralymphatic and subcutaneous routes of administration. The vaccine compositions may further comprise additional components known in the art to improve the immune response to a vaccine, such as adjuvants, T cell co-stimulatory molecules, or antibodies, such as anti-CTLA4. The invention also includes medicaments comprising the pharmaceutical compositions of the invention. An individual to be treated with such vaccines, is any vertebrate, preferably a mammal, including domestic animals, sport animals, and primates, including humans. The vaccine may be administered as a prophylactic, where the individual is vaccinated in order to immunize the individual against a particular disease. While the vaccine can be given to any individual, in some instances, such as with cancer vaccines, the individual treated might be limited to those individuals at higher risk of developing a cancer. The vaccine may also be administered as a therapeutic, where the individual having a particular disease is vaccinated in order to improve the immune response to the disease or a disease related protein. In this embodiment, the vaccine may result in a lessening of the physical symptoms associated with the disease. For example, with cancer vaccines, the vaccination may result in stopping the growth of a tumor, preferably a lessening of the mean tumor volume, more preferably elimination of any tumors. In one embodiment, the mean tumor volume decreases by at least about 5%, also about 10%, also about 25%, also about 50%, also about 75%, also about 90% or about 100%. Similarly, the vaccination may result in stopping the metastases of a tumor, preferably resulting in a reduction in the number of tumor metastases. An additional effect of a cancer vaccine would be an extension of the median survival of the individual. In humans, the median survival may be extended by at least about 3 months, also at least about 6 months, or at least about 12 months.

Vaccine formulations are known in the art. Known vaccine formulations can include one or more possible additives, such as carriers, preservatives, stabilizers, adjuvants, antibiotics, and other substances. Preservatives, such as thimerosal or 2-phenoxy ethanol, can be added to slow or stop the growth of bacteria or fungi resulting from inadvertent contamination, especially as might occur with vaccine vials intended for multiple uses or doses. Stabilizers, such as lactose or monosodium glutamate (MSG), can be added to stabilize the vaccine formulation against a variety of conditions, such as temperature variations or a freeze-drying process. Adjuvants, such as aluminum hydroxide or aluminum phosphate, are optionally added to increase the ability of the vaccine to trigger, enhance, or prolong an immune response. Additional materials, such as cytokines, chemokines, and bacterial nucleic acid sequences, like CpG, are also potential vaccine adjuvants. Antibiotics, such as neomycin and streptomycin, are added to prevent the potentially harmful growth of germs. Vaccines may also include a suspending fluid such as sterile water or saline. Vaccines may also contain small amounts of residual materials from the manufacturing process, such as cell or bacterial proteins, egg proteins (from vaccines that are produced in eggs), DNA or RNA, or formaldehyde from a toxoiding process.

The modified microbe-based vaccine or APC-based vaccine is optionally administered to a host in a physiologically acceptable carrier. Optionally, the vaccine formulation further comprises an adjuvant. Useful carriers known to those of ordinary skill in the art include, e.g., citrate-bicarbonate buffer, buffered water, 0.4% saline, and the like.

Vaccine compositions comprising the modified microbe are optionally lyophilized (i.e., freeze-dried). The lyophilized preparation can be combined with a sterile solution (e.g., citrate-bicarbonate buffer, buffered water, 0.4% saline, or the like) prior to administration.

The efficacy of the vaccines can be evaluated in an individual, for example in mice. A mouse model is recognized as a model for efficacy in humans and is useful in assessing and defining the vaccines of the present invention. The mouse model is used to demonstrate the potential for the effectiveness of the vaccines in any individual. Vaccines can be evaluated for their ability to provide either a prophylactic or therapeutic effect against a particular disease. For example, in the case of infectious diseases, a population of mice can be vaccinated with a desired amount of the appropriate vaccine of the invention, where the microbe expresses an infectious disease associated antigen. This antigen can be from the delivery microbe itself or can be a heterologous antigen. The mice can be subsequently infected with the infectious agent related to the vaccine antigen and assessed for protection against infection. The progression of the infectious disease can be observed relative to a control population (either non vaccinated or vaccinated with vehicle only or a microbe that does not contain the appropriate antigen).

In the case of cancer vaccines, tumor cell models are available, where a tumor cell line expressing a desired tumor antigen can be injected into a population of mice either before (therapeutic model) or after (prophylactic model) vaccination with a microbe of the invention containing the desired tumor antigen. Vaccination with a microbe containing the tumor antigen can be compared to control populations that are either not vaccinated, vaccinated with vehicle, or with a microbe that expresses an irrelevant antigen. In addition, the relative efficacy of the vaccines of the invention can be compared to a population of microbe in which the microbial nucleic acid has not been modified. The effectiveness of the vaccine in such models can be evaluated in terms of tumor volume as a function of time after tumor injection or in terms of survival populations as a function of time after tumor injection (e.g. Example 4). In one embodiment, the tumor volume in mice vaccinated with nucleic acid modified microbe is about 5%, about 10%, about 25%, about 50%, about 75%, about 90% or about 100% less than the tumor volume in mice that are either not vaccinated or are vaccinated with vehicle or a microbe that expresses an irrelevant antigen. In another embodiment, this differential in tumor volume is observed at least about 10, about 17, or about 24 days following the implant of the tumors into the mice. In one embodiment, the median survival time in the mice vaccinated with nucleic acid modified microbe is at least about 2, about 5, about 7 or at least about 10 days longer than in mice that are either not vaccinated or are vaccinated with vehicle or a microbe that expresses an irrelevant antigen. In addition to an effective immune response to the vaccines of the present invention, the modified microbes provide an added level of safety such that a higher dose of the microbe may be administered relative to the corresponding unmodified microbe. In one embodiment of the invention, the vaccination with the nucleic acid modified microbe is done at a dose of microbes that is the same as the dose of the corresponding unmodified microbe. In another embodiment, the vaccination of nucleic acid modified microbe is safely dosed at a level that is at least about 2, about 5, about 10, about $10^2$ about $10^3$, or at least about $10^4$ fold higher than the vaccination dose of the corresponding unmodified microbe, wherein the resulting tumor volume and median survival times discussed above are observed for the nucleic acid modified microbe.

II. Methods of Use

A variety of methods of using the modified microbes, mutant strains, antigen-presenting cells, vaccines, and pharmaceutical compositions described herein are provided by the present invention. For instance, methods of using the modified microbes, antigen-presenting cells, vaccines, and pharmaceutical compositions described herein to induce immune responses and/or to treat or prevent disease are provided. Methods of using the modified microbes and/or mutant strain to prepare vaccines and other compositions are also provided.

For instance, in one aspect, the invention provides a method of inducing an immune response in a host to an antigen, comprising administering to the host an effective amount of a composition comprising a free-living microbe that expresses the antigen, wherein the nucleic acid of the microbe is modified so that the microbe is attenuated for proliferation. In some embodiments, the composition comprising the microbe is a vaccine. In some embodiments, the composition comprising the microbe is a professional antigen-presenting cell. The antigen may be heterologous or autologous to the microbe as described above. In some embodiments, the nucleic acid of the microbe has been modified by reaction with a nucleic acid targeted compound that reacts directly with the nucleic acid.

The invention also provides a method of inducing an immune response in a host to an antigen, comprising administering to the host an effective amount of a composition comprising a mutant strain of Listeria monocytogenes that expresses the antigen, wherein the mutant strain comprises a genetic mutation that attenuates its ability to repair its nucleic acid. The antigen may be a Listerial or non-Listerial antigen. In some embodiments, the nucleic acid of the Listeria has been modified so that the microbe is attenuated for proliferation (e.g., by S-59/UVA treatment).

The invention also provides a method of inducing an immune response in a host to an antigen, comprising administering to the host an effective amount of a composition comprising a mutant strain of Bacillus anthracis that expresses the antigen, wherein the mutant strain comprises a genetic mutation that attenuates its ability to repair its nucleic acid. In some embodiments, the nucleic acid of the Bacillus has been modified so that the microbe is attenuated for proliferation (e.g., by S-59/UVA treatment).

The invention also provides a method of preventing or treating a disease in a host, comprising administering to the host an effective amount of a composition comprising a free-living microbe, wherein the nucleic acid of the microbe is modified so that the microbe is attenuated for proliferation. In some embodiments, the composition comprising the microbe is a vaccine. In some embodiments, the composition comprising the microbe is a professional antigen-presenting cell.

The invention also provides a method of preventing or treating a disease in a host, comprising administering to the host an effective amount of a composition comprising a mutant strain of Listeria monocytogenes, wherein the mutant strain comprises a genetic mutation that attenuates its ability to repair its nucleic acid. In some embodiments, the nucleic acid of the Listeria has been modified so that the microbe is attenuated for proliferation (e.g., by S-59/UVA treatment). In some embodiments, the disease is an infectious disease. In other embodiments, the disease is cancer.

The invention also provides a method of preventing or treating disease in a host, comprising administering to the host an effective amount of a composition comprising a mutant strain of Bacillus anthracis, wherein the mutant strain comprises a genetic mutation that attenuates its ability to repair its nucleic acid. In some embodiments, the nucleic acid of the Bacillus has been modified so that the microbe is attenuated for proliferation (e.g., by S-59/UVA treatment).

The invention also provides a free-living microbe for medical use, wherein the nucleic acid of the microbe is modified so that the microbe is attenuated for proliferation and/or the microbe is defective with respect to a DNA repair enzyme. It is understood that medical use encompasses both therapeutic and preventative medical applications (e.g., for use as a vaccine). In some embodiments, the microbe has been modified by reaction with a nucleic acid targeted compound that reacts directly with the nucleic acid so that the microbe is attenuated for proliferation. In some embodiments, the microbe is Listeria monocytogenes or Bacillus anthracis.

In other aspects, the invention provides a professional antigen-presenting cell for medical use, wherein the antigen-presenting cell comprises a free-living microbe, wherein the nucleic acid of the microbe is modified so that the microbe is attenuated for proliferation and/or the microbe is defective with respect to a DNA repair enzyme. In some embodiments, the microbe has been modified by reaction with a nucleic acid targeted compound that reacts directly with the nucleic acid so that the microbe is attenuated for proliferation. In some embodiments, the microbe is Listeria monocytogenes or Bacillus anthracis.

The invention also provides a mutant Listeria monocytogenes strain for medical use, wherein the mutant Listeria monocytogenes strain comprises a genetic mutation that attenuates its ability to repair its nucleic acid.

In addition, the invention provides a mutant Bacillus anthracis strain for medical use, wherein the mutant Bacillus anthracis strain comprises a genetic mutation that attenuates its ability to repair its nucleic acid.

The invention further provides the use of a free-living microbe, wherein the nucleic acid has been modified so that the microbe is attenuated for proliferation, for the manufacture of a medicament for a disease unrelated and/or not caused by the free-living microbe. In some embodiments, the disease is cancer. In some embodiments, the disease is an infectious disease unrelated to the free-living microbe.

The invention further provides the use of a free-living microbe for the manufacture of a medicament for a disease unrelated and/or not caused the microbe, wherein the microbe is defective with respect to at least one DNA repair enzyme. In some embodiments, the disease is cancer. In some embodiments, the disease is an infectious disease unrelated to the microbe.

The invention also provides a method of inducing an immune response in a host to an antigen comprising administering to the host an effective amount of a vaccine comprising a bacterium, wherein the bacterium has been modified by reaction with a nucleic acid target compound that reacts directly with its nucleic acid so that the bacterium is attenuated for proliferation, wherein the bacterium is defective with respect to at least one DNA repair enzyme, and wherein the bacterium expresses the antigen. (The antigen expressed can be either heterologous to the bacterium or endogenous to the bacterium.)

The invention also provides a method of preventing or treating disease in a host, comprising administering an effective amount of a vaccine comprising a bacterium, wherein the bacterium has been modified by reaction with a nucleic acid target compound that reacts directly with its nucleic acid so that the bacterium is attenuated for proliferation, wherein the bacterium is defective with respect to at least one DNA repair enzyme, and wherein the bacterium expresses the antigen.

The invention also provides a method of preventing or treating disease in a host, comprising administering an effective amount of a vaccine comprising an antigen-presenting cell, wherein the antigen-presenting cell comprises a bacterium, wherein the bacterium has been modified by reaction with a nucleic acid target compound that reacts directly with its nucleic acid so that the bacterium is attenuated for proliferation, and wherein the bacterium is defective with respect to at least one DNA repair enzyme.

Additionally, the invention provides the use of a professional antigen-presenting cell, wherein the antigen-presenting cell comprises a free-living microbe, wherein the nucleic acid of the microbe is modified so that the microbe is attenuated for proliferation and/or wherein the microbe is defective with respect to at least one DNA repair enzyme, for the manufacture of a medicament for a disease unrelated and/or not caused by the free-living microbe. In some embodiments, the disease is cancer. In some embodiments, the disease is an infectious disease unrelated to the free-living microbe.

The invention further provides the use of a mutant strain of *Listeria monocytogenes*, wherein the mutant *Listeria monocytogenes* strain comprises a genetic mutation that attenuates its ability to repair its nucleic acid, for the manufacture of a medicament for a disease unrelated and/or not caused by *Listeria monocytogenes*. In some embodiments, the disease is cancer. In some embodiments, the disease is an infectious disease unrelated to the *Listeria monocytogenes*.

In another aspect, the invention provides a method of activating naïve T cells, comprising contacting the naïve T cells with a professional antigen-presenting cell under suitable conditions and for a sufficient time to activate the naïve T cells, wherein the antigen-presenting cell comprises a free-living microbe, wherein the nucleic acid of the microbe is modified so that the microbe is attenuated for proliferation. The contacting step of this method may be performed either in vitro or in vivo. Suitable conditions and a sufficient time for activating the naïve T-cells would be known to one of ordinary skill of the art. In addition, examples of such conditions are provided in the specific Examples, below.

A method of loading professional antigen-presenting cells with an antigen is also provided. The method comprises contacting the professional antigen-presenting cells with a free-living microbe that comprises a nucleic acid sequence encoding the antigen, under suitable conditions and for a sufficient time to load the professional antigen-presenting cells (e.g., dendritic cells), wherein the nucleic acid of the microbe is modified so that the microbe is attenuated for proliferation and/or the microbe is defective with respect to at least one DNA repair enzyme. The contacting step of the method may be performed in vitro, ex vivo, or in vivo. The antigen may be heterologous or autologous to the microbe. Suitable conditions and a sufficient time for loading antigen-presenting cells would generally be known to one of ordinary skill of the art. In addition, examples of such conditions are provided in the specific Examples, below.

In another aspect, the invention provides a method of activating and/or maturing professional antigen-presenting cells comprising contacting the professional antigen-presenting cells (in vitro, ex vivo, and/or in vivo) with a free-living microbe that comprises a nucleic acid sequence encoding an antigen, under suitable conditions and for a sufficient time to activate and/or bring to maturation the professional antigen-presenting cells, wherein the nucleic acid of the microbe is modified so that the microbe is attenuated for proliferation. The contacting step of the method may be performed either in vitro or in vivo. The antigen may be heterologous or autologous to the microbe. Suitable conditions and a sufficient time for activating antigen-presenting cells and/or bringing antigen-presenting cells to maturation would generally be known to one of ordinary skill of the art. In addition, examples of such conditions are provided in the specific Examples, below.

In another aspect, the invention provides a method of preventing or treating a disease in a host, comprising the following steps. (a) loading professional antigen-presenting cells with an antigen by contacting the cells with a free-living microbe that comprises a nucleic acid sequence encoding an antigen, wherein the nucleic acid of the microbe is modified so that the microbe is attenuated for proliferation; and (b) administering an effective amount of a composition comprising the loaded professional antigen-presenting cells to the host.

In still another aspect, the invention provides a method of inducing an immune response to an antigen in a host, comprising the following steps. (a) loading professional antigen-presenting cells with the antigen by contacting the cells with a free-living microbe that comprises a nucleic acid sequence encoding the antigen, wherein the nucleic acid of the microbe is modified so that the microbe is attenuated for proliferation; and (b) administering an effective amount of a composition comprising the loaded professional antigen-presenting cells to the host.

The invention includes medicaments comprising the above compositions and methods of use of the above compositions, such as vaccination of an individual. In one embodiment, the invention includes a method of using a vaccine of the present invention comprising administering the vaccine to an individual. In one embodiment, the vaccination is performed by administration of the vaccine by a route selected from the group consisting of oral, nasal, intravenous, intradermal, intraperitoneal, intramuscular, intralymphatic, and subcutaneous. In one embodiment, the vaccine is administered using a prophylactic regimen to an individual having no signs of the disease against which the vaccine is targeted. In one embodiment, the vaccine is administered using a therapeutic regimen to an individual having symptoms of the disease against which the vaccine is targeted. In one embodiment, the vaccine comprises a tumor antigen targeting a cancer and the therapeutic vaccination results in a lessening of the symptoms of the cancer. In one embodiment, the mean tumor volume in a vaccinated individual decreases by at least about 5%, also about 10%, also about 25%, also about 50%, also about 75%, also about 90% or about 100%. In one embodiment, the vaccine is administered to a mouse using either a prophylactic or therapeutic regimen, wherein the mouse is a model system that can be implanted with tumor cells in order to establish tumors in the mice, wherein the vaccine contains at least one antigen of the implanted tumor. The tumors are implanted in the mice either after (prophylactic regimen) or before (therapeutic regimen) the vaccine is administered to the mice. In one embodiment, the mean tumor volumes in mice vaccinated using either a prophylactic or a therapeutic regimen are less than the tumor volumes in similar mice that are either not vaccinated, or are vaccinated with a similar vaccine vehicle that expresses an irrelevant antigen (control mice). In one embodiment, the mean tumor volumes in the vaccinated mice is at least about 5%, about 10%, about 25%, about 50%, about 75%, about 90% or about 100% less than the mean tumor volumes in the control mice. In one embodiment, the median survival time of the mice vaccinated using either a prophylactic or a therapeutic regimen is at least about 2, about 5, about 7 or at least about 10 days longer than in the control mice.

III. Kits

The invention further provides kits (or articles of manufacture) comprising each of the modified microbes and mutant strains described herein. In addition, the invention provides kits (or articles of manufacture) comprising the vaccines described herein.

For instance, in one aspect, the invention provides a kit comprising both (a) a composition comprising a mutant *Listeria monocytogenes* strain comprising a genetic mutation that attenuates its ability to repair its nucleic acid, a mutant *Bacillus anthracis* strain comprising a genetic mutation that attenuates its ability to repair its nucleic acid, or a free-living microbe, wherein the nucleic acid of the microbe is modified so that the microbe is attenuated for proliferation; and (b) instructions for the use of the composition in the prevention or treatment of a disease in a host. In some embodiments, the instructions are on a label. In other embodiments, the instructions are on an insert contained within the kit.

In another aspect, the invention provides a kit comprising both (a) a composition comprising a mutant *Listeria monocytogenes* strain comprising a genetic mutation that attenuates its ability to repair its nucleic acid, a mutant *Bacillus anthracis* strain comprising a genetic mutation that attenuates its ability to repair its nucleic acid, or a free-living microbe, wherein the nucleic acid of the microbe is modified so that the microbe is attenuated for proliferation; and (b) instructions for the administration of the composition to a host. In some embodiments, the instructions are on a label. In other embodiments, the instructions are on an insert contained within the kit.

In another aspect, the invention provides a kit comprising both (a) a composition comprising a mutant *Listeria monocytogenes* strain comprising a genetic mutation that attenuates its ability to repair its nucleic acid, a mutant *Bacillus anthracis* strain comprising a genetic mutation that attenuates its ability to repair its nucleic acid, or a free-living microbe, wherein the nucleic acid of the microbe is modified so that the microbe is attenuated for proliferation; and (b) instructions for selecting a host to which the composition is to be administered. In some embodiments, the instructions are on a label. In other embodiments, the instructions are on an insert contained within the kit.

In some embodiments of each of the aforementioned aspects, the composition is a vaccine. In some embodiments of each of the aforementioned aspects, the composition is a professional-antigen-presenting cell. In some embodiments of each of the aforementioned aspects, the nucleic acid of the free-living microbe has been modified by reaction with a nucleic acid targeted compound that reacts directly with the nucleic acid. In some embodiments, the microbe has been s-59/UVA treated. In some embodiments, the microbe is defective with respect to a DNA repair enzyme.

EXAMPLES

Example 1

Psoralen Treatment of *Listeria* Strains Providing Attenuation of Proliferation while Maintaining Expression of OVA Antigen Several strains of *Listeria monocytogenes* that have been modified to express ovalbumin, a heterologous chicken OVA antigen, were reacted with 4'-(4-amino-2-oxa)butyl-4,5',8-trimethylpsoralen (S-59 prepared from solid (Ash-Stevens, Riverview, Mich.) as 3 mM solution by Ben Venue, Cleveland, Ohio (see U.S. Pat. No. 5,399,719)) and UVA light (320-400 nm). The resulting *Listeria* were assayed to assess the reduction in the log titer of viable *Listeria* as well as for the expression of the OVA antigen by the *Listeria*. The *Listeria* strains were provided by Dr. Dan Portnoy at the University of California, Berkeley and modified to contain the OVA antigen as discussed in Example 8. These were DP-L4056 (wild-type), DP-L4029 (10403S ΔactA, phage cured deletion mutation in the Act A gene, see Skoble et al., Journal of Cell Biology, 150:527-537 (2000) and Lauer et al., Journal of Bacteriology 184(15):4177-4186 (2002)), DP-L4364 (10403S ΔlplA, deletion mutation in phospholipase A gene) and DP-L4017 (10403S hly$_{L461T}$, point mutation in the hemolysin gene, see Glomski et al., Journal of Cell Biology 156(6): 1029-1038, (2002)). The strains were grown in BHI medium (Brain Heart Infusion, Fisher Scientific) at 37° C. at 300 rpm to a concentration of approximately $1 \times 10^9$ CFU/mL (to an absorbance at 600 nm of 0.5). A 1.0 mL aliquot of each strain was transferred to duplicate 15 mL tubes. Each tube was centrifuged at 4° C. for 20 minutes at 2300×g, the supernatant removed and 5 mL of PBS (phosphate buffered saline, Hyclone) with 1% BSA with and without the S-59 was added to the duplicate tubes ($1 \times 10^8$ CFU/mL). The S-59 was added at a concentration of 100 nM. Samples were placed in 6 well culture plates and UVA irradiated at a dose of approximately 2 J/cm$^2$ (FX1019 irradiation device, Baxter Fenwal, Round Lake, Ill.). Each sample was then transferred to a 15 mL tube, centrifuged as above, and the supernatant removed. These were washed with 5 mL of PBS, centrifuged and the supernatant removed and the final bacterial pellet was suspended in 0.5 mL of PBS. A 100 μL sample of each was used to determine the bacterial titer by serial dilution. Each dilution was plated onto an LB (Luria-Bertani, Q-Biogene, Carlsbad, Calif.) plate and incubated overnight at 37° C. and the colonies were counted to measure the bacterial titer.

The antigen presentation of the bacterial samples was assessed using a murine DC 2.4 cell line (dendritic cell line from the Dana Farber Cancer Institute, see Shen et al., J Immunol 158(6):2723-30 (1997)) and a B3Z T cell hybridoma (obtained from Dr. Shastri, University of California, Berkeley). The B3Z is a lacZ inducible CD8+ T cell hybridoma that expresses a β-galactosidase gene upon recognition of OVA antigen in context of MHC class I molecules. The metabolism of CPRG (chlorophenolred-β-D-galactopyranoside, Calbiochem, La Jolla, Calif.), a substrate for the β-galactosidase, was used to assess the level of β-galactosidase produced, which is directly correlated to the amount of OVA antigen presented by the DC 2.4 cells. The DC 2.4 cells and the B3Z T cell hybrid were maintained in RPMI 1640 culture medium (RPMI, Invitrogen) with 10% FBS (fetal bovine serum, HyClone). The DC 2.4 cells were transferred in 200 μL aliquots to the wells of a 96 well culture plate ($1 \times 10^5$ DC 2.4 per well). The bacterial samples were serially diluted 50 μL stock to 450 μL PBS down to $1 \times 10^5$ CFU/mL (S-59 treated samples are CFU equivalents, i.e. it is the number of colony forming units prior to S-59 treatment). A 20 μL aliquot of each dilution is transferred to a well containing the DC 2.4 cells to give approximately $1 \times 10^4$, $1 \times 10^5$, $1 \times 10^6$, $1 \times 10^7$, or $1 \times 10^8$ CFU/mL. In addition, a 20 μL aliquot of PBS only was added as a negative control. The samples were incubated for 1 hour at 37° C. in 5% CO$_2$. The plate was washed three times with PBS to remove extracellular bacteria. A 200 μL aliquot of B3Z T cells ($1 \times 10^5$ cell) and 100 μg/mL Gentamycin (Sigma) was added to each well. As a positive control, 100 nM SL8 OVA$_{257-264}$ peptide (SL8 OVA antigen, SIINFEKL, SEQ ID NO:1, Invitrogen, San Diego, Calif.) was added to a well containing $1 \times 10^5$ each of the DC 2.4 and B3Z cells. The samples were incubated overnight at 37° C. in 5% CO$_2$. The plate was centrifuged for 3 minutes at 400×g and each well washed with 250 μL of PBS. A 100 μL aliquot of PBS containing 100 μM 2-mercaptoethanol, 9 mM MgCl$_2$, 0.125% Igepal CA-630 ((Octaphenoxy)polyethoxyethanol, Sigma), and 0.15 mM CPRG was added to each well. The samples were incubated at 37° C. for at least 4 hours. The absorbance was measured at 595 nm with a reference measurement at 655 nm using a plate reader. The results for the bacterial titer and the antigen presentation of S-59 treated relative to the untreated (100 bacteria per DC 2.4) is given in Table 4. The results indicate that at a level of 100 bacterial cells added per DC 2.4, the antigen presentation is approximately 55-85% of the untreated sample. Since the bacterial titer was reduced by approximately 10$^4$, this indicates that sufficient antigen presentation is maintained with considerable attenuation of the proliferation of the *Listeria*.

TABLE 4

Log attenuation and antigen presentation of *Listeria* strains expressing OVA antigen treated with 100 nM psoralen S-59 and 2 J/cm² UVA light.

| *Listeria* strain | Log attenuation | % antigen presented* |
|---|---|---|
| DP-L4056 | 4.02 | 74.6 |
| DP-L4029 | 4.14 | 54.9 |
| DP-L4364 | 4.53 | 84.3 |
| DP-L4017 | 4.11 | 55.2 |

*As percent of untreated, measured at 100 *Listeria* per DC 2.4 cell.

Figure 1:
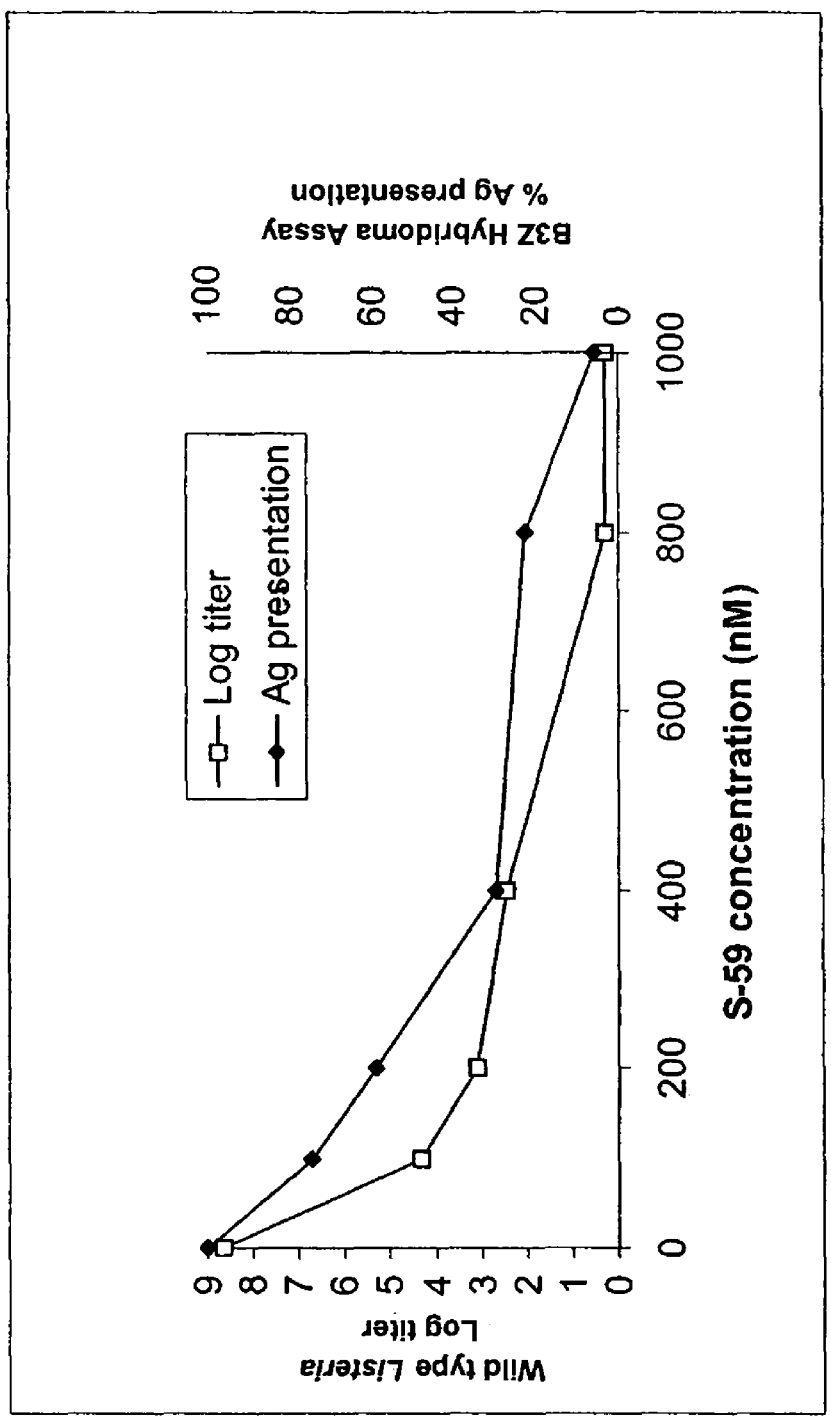
FIG. 1 shows the attenuation of wild-type *Listeria* DP-L4056 containing OVA antigen as a function of psoralen S-59 concentration (2 J/cm$^2$ UVA) along with the measurement of OVA antigen presentation to a dendritic cell line. The bacterial log titer and % of antigen presented relative to untreated (data is for 100 *Listeria* per DC 2.4 cell) are plotted vs. nM S-59.

A similar procedure was done using the DP-L4056 wild-type strain. The bacteria was treated with 100, 200, 400, 800 or 1000 nM S-59, the remaining titer determined and the antigen presentation measured as detailed above. The results for the bacterial titer and antigen presentation (100 *Listeria* per DC 2.4 cell) are shown in Table 5 and plotted in FIG. 1. This data indicates that the antigen presentation is significant over a broad range of attenuation in the *Listeria* growth, including presentation of antigen with complete inhibition of proliferation (i.e. to the limit of detection).

TABLE 5

Log attenuation and antigen presentation of *Listeria* strain DP-L4056 expressing OVA antigen treated with varying concentrations of psoralen S-59 and 2 J/cm² UVA light.

| S-59 concentration (nM) | Log titer | Log attenuation | % antigen presented* |
|---|---|---|---|
| 0 | 8.64 | 0 | — |
| 100 | 4.34 | 4.30 | 75.0 |
| 200 | 3.10 | 5.54 | 58.9 |
| 400 | 2.48 | 6.16 | 30.3 |
| 800 | <1 | >7.64 | 23.6 |
| 1000 | <1 | >7.64 | 5.6 |

*As percent of untreated, measured at 100 *Listeria* per DC 2.4 cell.

Example 2

**DNA Targeted Alkylator Treatment of *Listeria* Strains Providing Attenuation of Proliferation while Maintaining Expression of OVA Antigen**

Figure 2A:
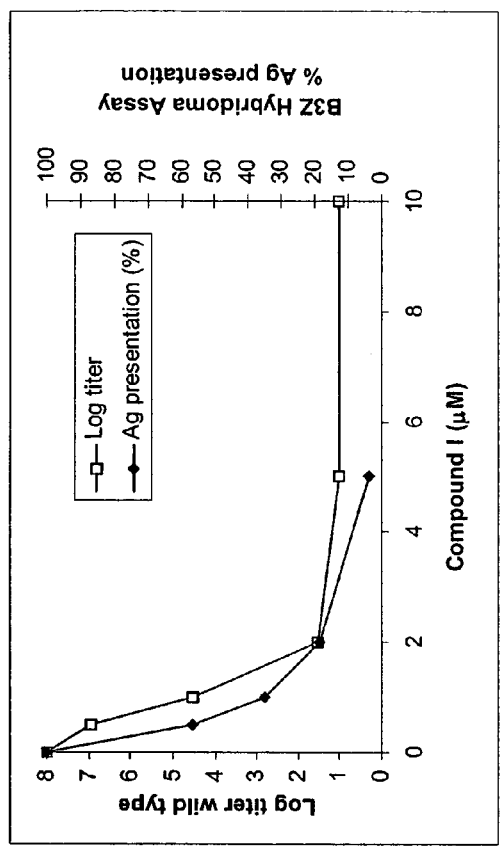
FIG. 2 shows the attenuation of wild-type *Listeria* DP-L4056 (2A) and LLO-mutant DP-L4027 (2B) containing OVA antigen as a function of alkylator compound I concentration along with the measurement of OVA antigen presentation to a dendritic cell line. The bacterial log titer and % of antigen presented relative to untreated (data is for 1 *Listeria* per DC 2.4 cell) are plotted vs. μM compound I.
Figure 2B:
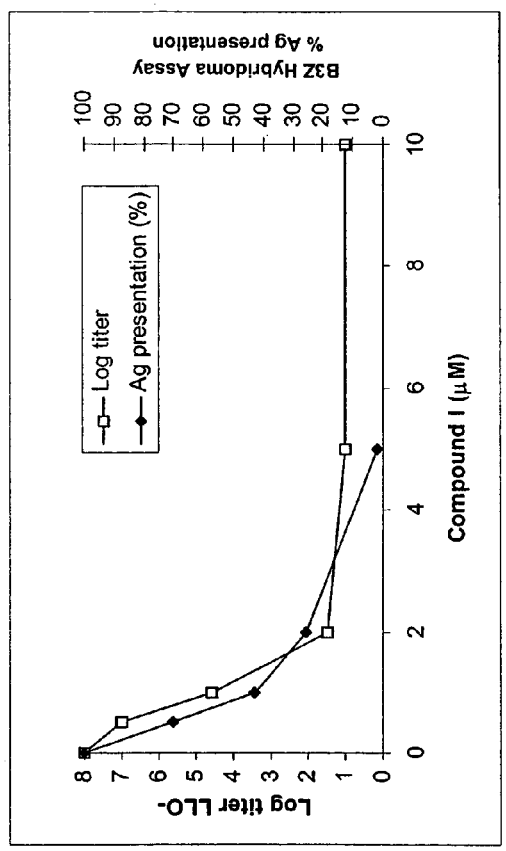

A procedure was done similarly to Example 1 only using the compound β-alanine, N-(acridin-9-yl), 2-[bis(2-chloroethyl)amino]ethyl ester (Compound 1, ChemSyn, Harrisonville, Mo., see U.S. Pat. No. 6,093,725). The *Listeria* strains used were DP-L4056 and DP-L4017. Compound 1 (1 mM in acidic BBS (blood bank saline), 135 μl of 1.48 M $H_3PO_4$ per 100 mL BBS) was added to 5 mL of bacteria at $1 \times 10^8$ CFU/mL to concentrations of 0, 0.5, 1, 2, 5, and 10 μM and the samples incubated for 2 hours at room temperature. After the incubation, the bacterial titer and antigen presentation was assessed as per Example 1. For the antigen presentation, the *Listeria* strains were diluted to $1 \times 10^2$, $1 \times 10^3$, $1 \times 10^4$, $1 \times 10^5$, $1 \times 10^6$ or $1 \times 10^7$ CFU/mL. The log titer, log attenuation and antigen presentation as a percent of untreated (1 *Listeria* per DC 2.4) as a function of compound 1 concentration is given in Table 6 and FIGS. 2A,B. The results indicate that compound 1 is also effective, e.g. at 1 μM, at providing sufficient antigen presentation with considerable attenuation of the proliferation of the *Listeria*.

TABLE 6

Log attenuation and antigen presentation of *Listeria* strains treated with varying concentrations of compound 1.

| [compound 1] | Log attenuation | | % antigen presented* | |
|---|---|---|---|---|
| μM | DP-L4056 | DP-L4017 | DP-L4056 | DP-L4017 |
| 0.5 | 1.04 | 1.02 | 56.6 | 70.0 |
| 1 | 3.47 | 3.43 | 35.0 | 43.0 |
| 2 | 6.47 | 6.52 | 18.5 | 25.4 |
| 5 | >7.0 | >7.0 | 3.7 | 2.0 |
| 10 | >7.0 | >7.0 | Not measured | Not measured |

*As percent of untreated, measured at 1 *Listeria* per DC 2.4 cell.

Example 3

**Comparison of Attenuation of Proliferation by Psoralen Treatment of uvrAB Mutant Vs. Wild-Type *Escherichia coli***

Figure 3:
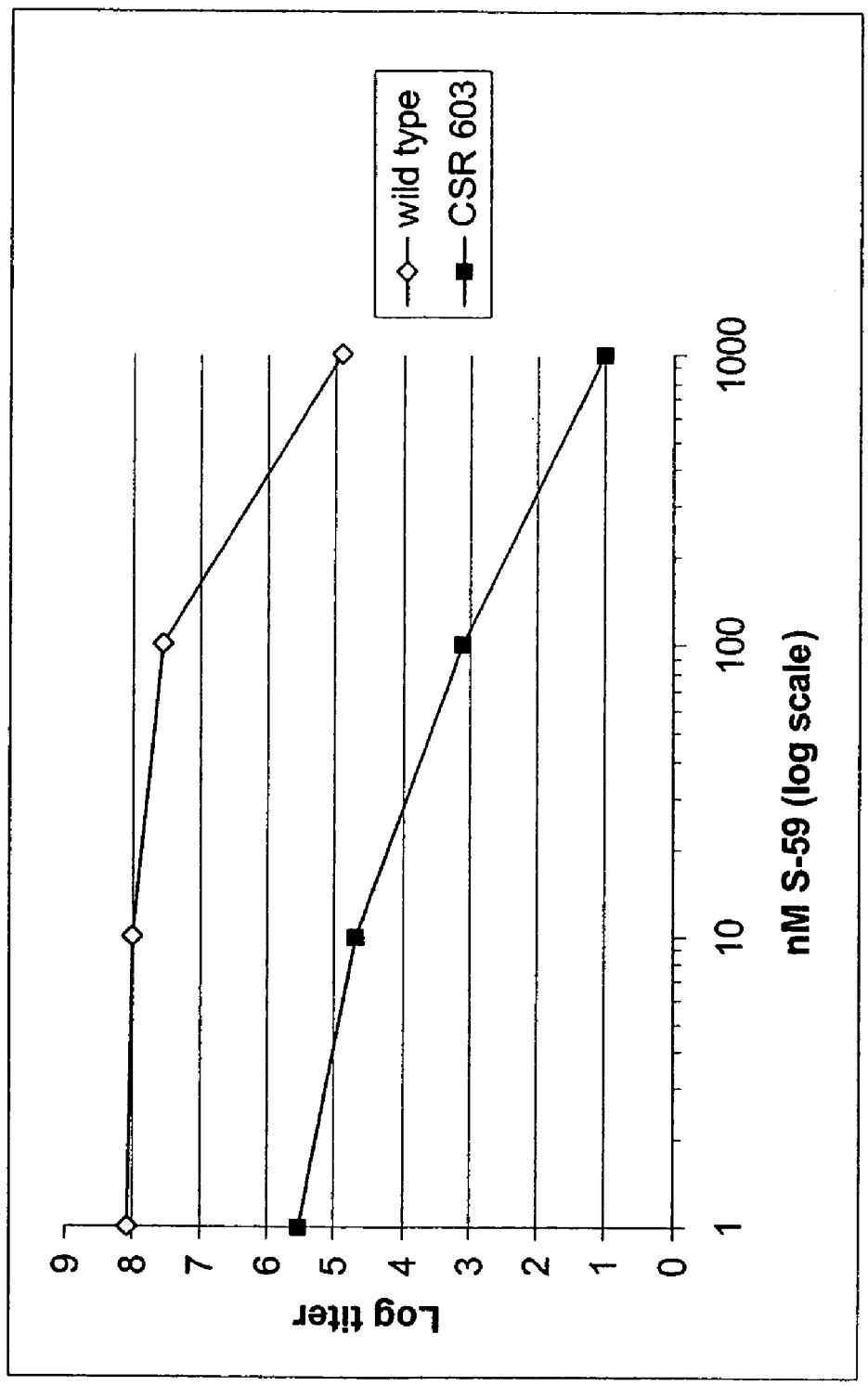
FIG. 3 shows a comparison of the inactivation of wild type *E. coli* to repair deficient mutant CSR 603 (uvrA recA phr mutant) as a function of S-59 concentration (2 J/cm$^2$ UVA). The bacterial log titer is plotted vs. nM S-59 (log scale).

The psoralen treatment of a mutant *Escherichia coli* (*E. coli*) strain that is deficient in the ability to repair nucleic acid damage was compared to a wild-type strain. *E. coli* strains AB1157 (wild-type) and CSR 603 (uvrA, recA, phr mutant obtained from Dr. Aziz Sancar, University of North Carolina, see Harm, Mutation Research 60:263-270 (1979)). This example compares the attenuation of AB 1157 vs mutant CSR603 grown in 3 mL of LB media with streptomycin overnight at 37° C. on an orbital shaker at 250 rpm. A 2 mL aliquot of this was added to 100 mL of LB media at 30° C. and placed on the shaker for approximately 5 hours, until the absorbance at 600 nm was 0.9 OD, approximately $1 \times 10^9$ CFU/mL. For each strain, approximately 0.5 mL of the bacterial stock was added to a 15 mL tube and centrifuged at 4° C. for 20 minutes at 2300×g. The supernatant was removed and each pellet was suspended in 5 mL of PBS containing 0, 1, 10, 100, and 1000 nM of psoralen S-59. Each sample was transferred to a 6 well culture plate and irradiated as per Example 1. The samples were serially diluted and the titer determined as per Example 1. The results are shown in Table 7 and FIG. 3. The results indicate that psoralen treatment of the uvrABC mutant results in greater attenuation in the proliferation of the bacteria (lower titer remaining) for a given psoralen concentration.

TABLE 7

Attenuation of *E coli* wild-type vs. uvrABC mutant with psoralen treatment.

| [S-59] | Bacterial log titer | | Log attenuation | |
|---|---|---|---|---|
| nM | Wild-type | uvrABC mutant | Wild-type | uvrABC mutant |
| 0 | 8.0 | 7.75 | — | — |
| 1 | 8.08 | 5.52 | 0 | 2.23 |
| 10 | 7.99 | 4.68 | 0.01 | 3.07 |
| 100 | 7.57 | 3.1 | 0.43 | 4.9 |
| 1000 | 4.91 | <1 | 3.09 | >6.65 |

Example 4

**Therapeutic Vaccination of Mice Using *Listeria* Strains with and without S-59 Treatment**

Figure 4:
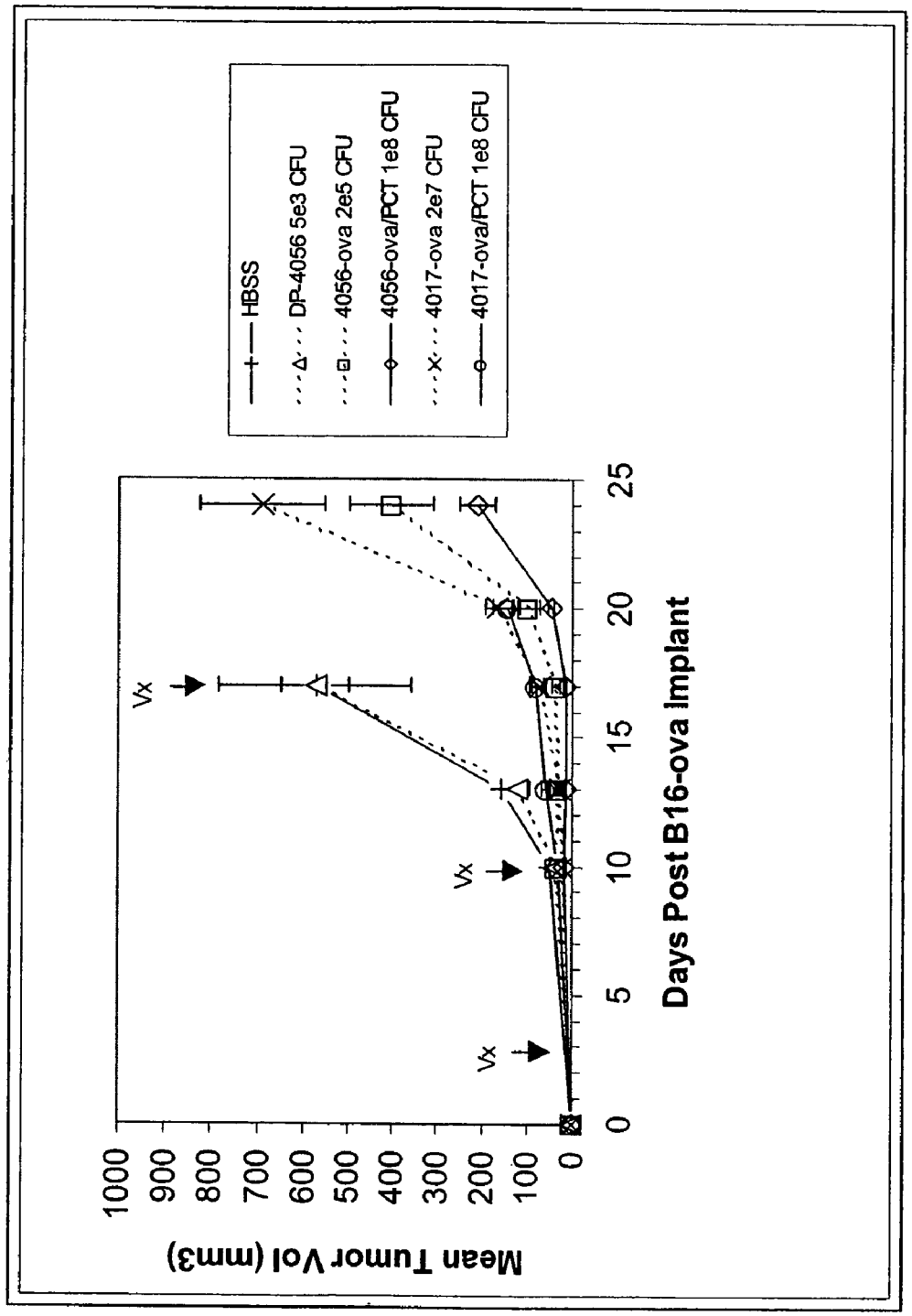
FIG. 4 shows the mean tumor volume as a function of days post implant of B16 OVA tumors into C57B1/6 mice that are vaccinated at days 3, 7, and 14. The vaccines tested are with and without S-59 treatment.
Figure 5:
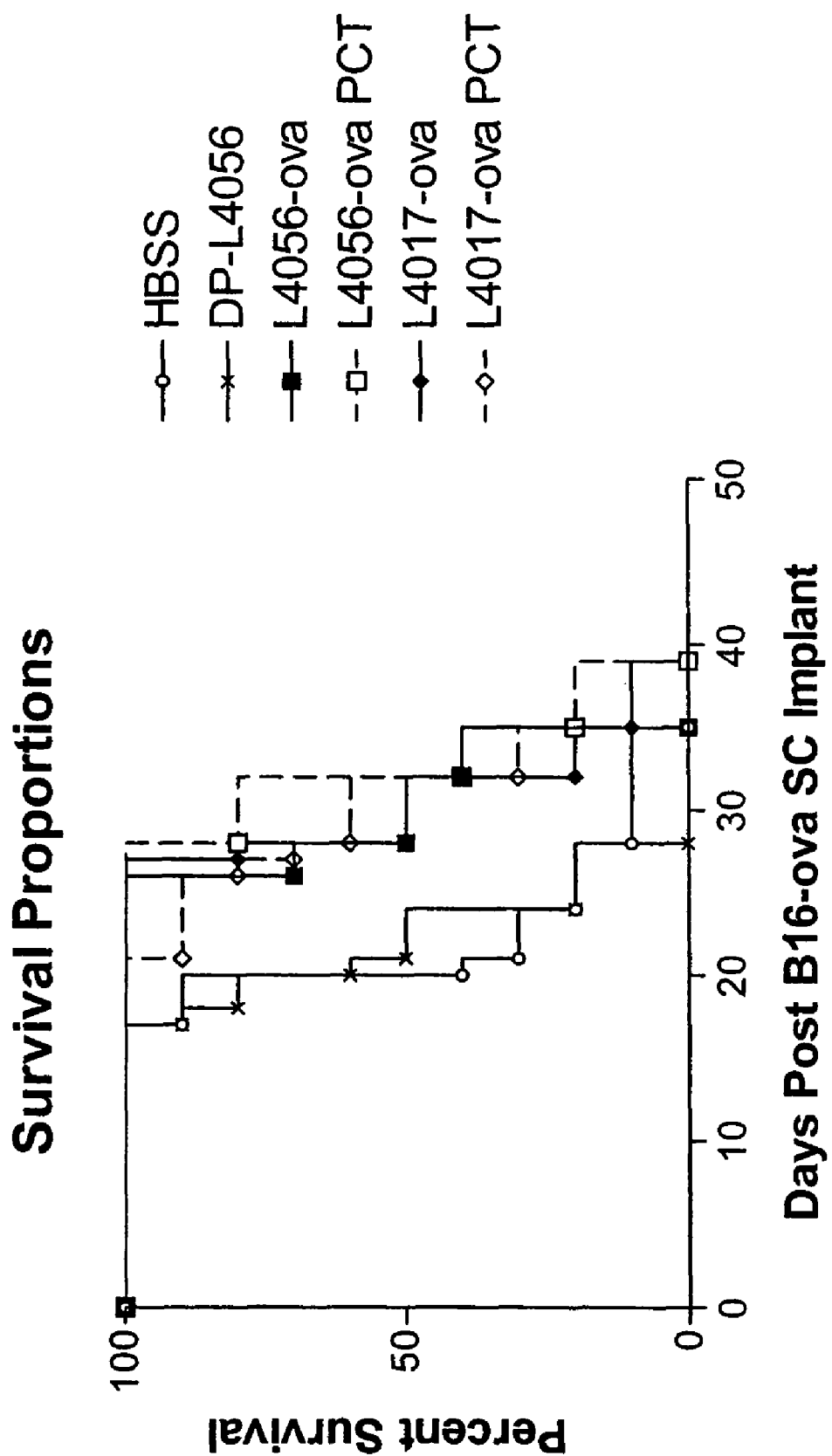
FIG. 5 shows the percent survival as a function of days post implant of B16 OVA tumors into C57B1/6 mice that are vaccinated at days 3, 7, and 14. The vaccines tested are with and without S-59 treatment.

In order to assess the utility of S-59 treated *Listeria* as a vaccine, a C57B1/6 mouse melanoma tumor model was used. C57B1/6 mice (Charles River, Hollister, Calif.) were shaved and implanted subcutaneously with $2 \times 10^5$ B16.F10.Mo520.10 cells (B16-OVA expressing melanoma cells obtained from Dr. Kenneth Rock, University of Massachusetts, see Mandl et al., Proc Natl Acad Sci USA 95:8216 (1998)) in 100 μL of HBSS. *Listeria monocytogenes* strains DP-L4056 and DP-L4017 containing the OVA antigen were prepared with or without S-59 treatment (20 nM S-59 UVA dosed as per Example 1). In addition, the wild-type strain DP-L4056 without the OVA antigen was used as a control. The log titer of the S-59 treated samples was determined to assess the log attenuation due to the psoralen treatment (Table 8). The *Listeria* were suspended in HBSS (Hanks Balanced Salt Medium, Gibco) and groups of 10-12 mice were vaccinated three times with a 100 μL intraperitoneal injection of each strain, as well as a group injected with HBSS vehicle. The vaccination dose (total CFU per vaccination) for the various strains is indicated in Table 8. The doses corresponded to 0.1 $LD_{50}$ for the non S-59 treated *Listeria* and the maximum possible dose for the S-59 treated *Listeria*. The vaccination was done at 3, 10 and 17 days after tumor implant. The mice were observed for palpable tumors. Once observed, the opposing diameters of the tumors were measured twice a week. If the tumor measured 20 mm in any direction, the mice were sacrificed. The mean tumor volume as a function of days post B16-OVA implant are shown in FIG. 4 and Table 8. The percent survival of mice per group is plotted in FIG. 5 and the median survival is given in Table 9. This example shows that high doses of S-59 treated *Listeria* strains can be safely given to mice, resulting in a good anti tumor response.

TABLE 8

Tumor volume at days post implant for mice implanted with B16-OVA and vaccinated with the identified *Listeria* strains.

| Vaccine sample | Mean tumor volume (mm²) | | | | |
|---|---|---|---|---|---|
| | Day 10 | Day 13 | Day 17 | Day 20 | Day 24 |
| HBSS | 48.2 | 158.8 | 515.1 | 1603 | 2444 |
| DP-L4056 | 35.3 | 123.6 | 571.8 | 1304 | 2123 |
| DP-L4056-OVA | 34.6 | 31.8 | 36.6 | 101.3 | 404.8 |
| DP-L4056-OVA + S-59 | 18.9 | 14.6 | 14.9 | 46.2 | 210.4 |
| DP-L4017-OVA | 22.7 | 26.8 | 73.8 | 164.6 | 689.5 |
| DP-L4017-OVA + S-59 | 33.5 | 56.7 | 79.3 | 146.3 | 464.0 |

TABLE 9

Vaccination dose and median survival for *Listeria* strains with and without 20 nM S-59 treatment (2 J/cm² UVA).

| Vaccination sample | Dose (CFU) | Median survival (days) | Log titer reduction |
|---|---|---|---|
| HBSS | — | 20 | — |
| DP-L4056 | $5 \times 10^3$ | 22.5 | — |
| DP-L4056-OVA | $2 \times 10^5$ | 30 | — |
| DP-L4056-OVA + S-59 | $1 \times 10^8$ | 30 | 3.76* |
| DP-L4017-OVA | $1 \times 10^7$ | 30 | — |
| DP-L4017-OVA + S-59 | $1 \times 10^8$ | 32 | 4.27* |

*Value is average of three preparations.

Example 5

Assessment of Antigen-Specific Immune Responses after Vaccination

The vaccines of the present invention can be assessed using a variety of in vitro and in vivo methods. These methods are exemplified using a *Listeria* based vaccine but can be used to evaluate the potential efficacy of any microbial based vaccine of the present invention.

Some assays involve the analysis of antigen-specific T cells from the spleens of mice that have been vaccinated. C57B1/6 mice are vaccinated, for example intraperitoneal injection of 0.1 $LD_{50}$, with a *Listeria*-OVA strain, where the *Listeria* may be treated to attenuate proliferation (e.g. S-59 treatment). Seven days after the vaccination, the spleen cells of the mice are harvested (typically 3 mice per group) by placing the spleens into ice cooled RPMI 1640 medium and preparing a single cell suspension from this. As an alternative, the lymph nodes of the mice could be similarly harvested, prepared as a single cell suspension and substituted for the spleen cells in the assays described below. Typically, spleen cells are assessed for intravenous or intraperitoneal administration of the vaccine while spleen cells and cells from lymph nodes are assessed for intramuscular, subcutaneous or intradermal administration of the vaccine.

Unless otherwise noted, all antibodies used in these examples can be obtained from Pharmingen, San Diego, Calif.

ELISPOT Assay:

A *Listeria* strain having an OVA antigen is assessed for the quantitative frequency of antigen-specific T cells generated upon immunization in a mouse model using an ELISPOT assay. The antigen-specific T cells evaluated are OVA specific CD8+ or LLO specific CD8+ or CD4+ T cells. This OVA antigen model assesses the immune response to a heterologous tumor antigen inserted into the vaccine and could be substituted with any antigen of interest. The LLO antigen is specific to *Listeria*, and could be substituted for an appropriate antigen for any microbial vector used as the vaccine vehicle. The specific T cells are assessed by detection of cytokine release (e.g. IFN-γ) upon recognition of the specific antigen. PVDF-based 96 well plates (BD Biosciences, San Jose, Calif.) are coated overnight at 4° C. with an anti-murine IFN-γ monoclonal antibody (mAb R4; 5 μg/mL). The plates are washed and blocked for 2 hours at room temperature with 200 μL of complete RPMI. Spleen cells from vaccinated mice (or non vaccinated control mice) are added at $2 \times 10^5$ cells per well and incubated for 20 to 22 hours at 37° C. in the presence of various concentrations of peptides ranging from about 0.01 to 10 μM. The peptides used are either SL8, an MHC class I epitope for OVA, $LLO_{190}$ (NEKYAQAYPNVS, SEQ ID NO:2, Invitrogen) an MHC class II epitope for listeriolysin O (*Listeria* antigen), or $LLO_{296}$ (VAYGRQVYL, SEQ ID NO:3), an MHC class I epitope for listeriolysin O. After washing, the plates are incubated with secondary biotinylated antibodies specific for IFN-γ (XMG1.2) diluted in PBS to 0.5 μg/mL. After incubation at room temperature for 2 hours, the plates are washed and incubated for 1 hour at 37° C. with a 1 nm gold goat anti-biotin conjugate (GAB-1; 1:200 dilution; Ted Pella, Redding, Calif.) diluted in PBS containing 1% BSA. After thorough washing, the plates are incubated at room temperature for 2 to 10 minutes with substrate (Silver Enhancing Kit; 30 μL/well; Ted Pella) for spot development. The plates are then rinsed with distilled water to stop the substrate reaction. After the plates have been air-dried, spots in each well are counted using an automated ELISPOT plate reader (CTL, Cleveland, Ohio). The cytokine response is expressed as the number of IFN-γ spot-forming cells (SFCS) per $10^6$ spleen cells for either the OVA specific T cells or the *Listeria* specific T cells.

Intracellular Cytokine Staining Assay (ICS):

In order to further assess the number of antigen-specific CD8+ or CD4+ T cells and correlate the results with those obtained from ELISPOT assays, ICS is performed and the cells evaluated by flow cytometry analysis. Spleen cells from vaccinated and control groups of mice are incubated with SL8 (stimulates OVA specific CD8+ cells) or $LLO_{190}$ (stimulates LLO specific CD4+ cells) for 5 hours in the presence of Brefeldin A (Pharmingen). The Brefeldin A inhibits secretion of the cytokines produced upon stimulation of the T cells. Spleen cells incubated with an irrelevant MHC class I peptide are used as controls. PMA (phorbol-12-myristate-13-acetate, Sigma) 20 ng/mL and ionomycin (Sigma) 2 μg/mL stimulated spleen cells are used as a positive control for IFN-γ and TNF-α intracellular cytokine staining. For detection of cytoplasmic cytokine expression, cells are stained with FITC-anti-CD4 mAb (RM 4-5) and PerCP-anti-CD8 mAb (53-6.7), fixed and permeabilized with Cytofix/CytoPerm solution (Pharmingen), and stained with PE-conjugated anti-TNF-α mAb (MP6-XT22) and APC-conjugated anti-IFN-γ mAb (XMG1.2) for 30 minutes on ice. The percentage of cells expressing intracellular IFN-γ and/or TNF-α was determined by flow cytometry (FACScalibur, Becton Dickinson, Mountain View, Calif.) and data analyzed using CELLQuest software (Becton Dickinson Immunocytometry System). As the fluorescent labels on the various antibodies can all be distinguished by the FACScalibur, the appropriate cells are identified by gating for those CD8+ and CD4+ that are stained with either or both of the anti-IFN-γ or anti-TNF-α. This method can also be used to determine the immunogenicity of microbial vaccines, wherein a dendritic cell population, or another antigen presenting cell such as a macrophage population, is incubated with the microbial vector. The resulting antigen presenting cells are injected into the feet of the mice and the cell population from the lymph nodes is assessed for T cells as above.

Cytokine Expression of Stimulated Spleen Cells:

The level of cytokine secretion by the spleen cells of mice can also be assessed for control and vaccinated C57B1/6 mice. Spleen cells are stimulated for 24 hours with SL8 or $LLO_{190}$. Stimulation with irrelevant peptide HSV-gB² (Invitrogen, SSIEFARL, SEQ ID NO:4) is used as a control. The supernatants of the stimulated cells are collected and the levels of T helper-1 and T helper 2 cytokines are determined using an ELISA assay (eBiosciences, CO) or a Cytometric Bead Array Kit (Pharmingen).

Assessment of Cytotoxic T Cell Activity:

The OVA specific CD8+ T cells can be further evaluated by assessing their cytotoxic activity, either in vitro or directly in C57B1/6 mouse in vivo. The CD8+ T cells recognize and lyse their respective target cells in an antigen-specific manner. In vitro cytotoxicity is determined using a chromium release assay. Spleen cells of naïve and Listeria-OVA (internal) vaccinated mice are stimulated at a 10:1 ratio with either irradiated EG7.OVA cells (EL-4 tumor cell line transfected to express OVA, ATCC, Manassas, Va.) or with 100 nM SL8, in order to expand the OVA specific T cells in the spleen cell population. After 7 days of culture, the cytotoxic activity of the effector cells is determined in a standard 4-hour $^{51}$Cr-release assay using EG7.OVA or SL8 pulsed EL-4 cells (ATCC, Manassas, Va.) as target cells and EL-4 cells alone as negative control. The YAC-1 cell line (ATCC, Manassas, Va.) is used as targets to determine NK cell activity, in order to distinguish the activity due to T cells from that due to NK cells. The percentage of specific cytotoxicity is calculated as 100×(experimental release−spontaneous release)/(maximal release−spontaneous release). Spontaneous release is determined by incubation of target cells without effector cells. Maximal release is determined by lysing cells with 0.1% Triton X-100. Experiments are considered valid for analysis if spontaneous release is <20% of maximal release.

For the assessment of cytotoxic activity of OVA-specific CD8+ T cells in vivo, spleen cells from naïve C57B1/6 mice are split into two equivalent aliquots. Each group is pulsed with a specific peptide, either target (SL8) or control (HSV-gB²), at 0.5 μg/mL for 90 minutes at 37° C. Cells are then washed 3 times in medium, and twice in PBS+0.1% BSA. Cells are resuspended at $1\times10^7$ per mL in warm PBS+0.1% BSA (10 mL or less) for labeling with carboxyfluorescein diacetate succinimidyl ester (CFSE, Molecular Probes, Eugene, Oreg.). To the target cell suspension, 1.25 μL of a 5 mM stock of CFSE is added and the sample mixed by vortexing. To the control cell suspension, a ten-fold dilution of the CFSE stock is added and the sample mixed by vortexing. The cells are incubated at 37° C. for 10 minutes. Staining is stopped by addition of a large volume (>40 mL) of ice-cold PBS. The cells are washed twice at room temperature with PBS, then resuspended and counted. Each cell suspension is diluted to $50\times10^6$ per mL, and 100 μL of each population is mixed and injected via the tail vein of either naïve or vaccinated mice. After 12-24 hours, the spleens are harvested and a total of $5\times10^6$ cells are analyzed by flow cytometry. The high (target) and low (control) fluorescent peaks are enumerated, and the ratio of the two is used to establish the percentage of target cell lysis. The in vivo cytotoxicity assay permits the assessment of lytic activity of antigen-specific T cells without the need of in vitro re-stimulation. Furthermore, this assays assesses the T cell function in their native environment.

Example 6

ELISPOT and ICS Analysis of Spleen Cells from Mice Vaccinated with Listeria DP-L4056 with and without S-59 Treatment Listeria strain DP-L4056 with or without the OVA antigen was prepared with or without S-59 treatment and used to vaccinate C57B1/6 mice as per Example 4 (HBSS control as well), with the exception that administration was intravenous. The vaccination was done on naïve mice at the doses indicated in Tables 8 and 9. The spleens were harvested at 12 days post vaccination. The spleens were assessed by ICS and ELISPOT assays as per Example 5. In addition, the $LD_{50}$ was assessed for these Listeria. The ICS assay results for both $LLO_{190}$ specific CD4⁺ T cells and OVA specific CD8⁺ T cells, in terms of percent of cells positive for both TNF-α and IFN-γ, are given in Table 10 and FIGS. 6A,B. The ELISPOT assays, in terms of IFN-γ SFC per $2\times10^5$ spleen cells is given in Table 11 and FIG. 7. These results indicate that the S-59 treated sample with OVA stimulates an OVA specific response when dosed at 100-fold excess of the non S-59 treated sample. While the positive OVA specific response is not observed at lower doses, this still provides an increased safety margin as the S-59 treated sample was attenuated by 4 log. In addition, the $LD_{50}$ was $10^3$-fold higher for the S-59 treated relative to the untreated sample, indicating that even dosing at 100-fold higher levels, there is a 10-fold level of safety relative to the untreated Listeria.

TABLE 10

Percent of spleen cells that are both TNF-α and IFN-γ positive for mice vaccinated with DP-L4056 with or without OVA, with or without S-59 treatment.

| Vaccine sample | S-59 treatment | Vaccination dose | % TNF-α/IFN-γ positive | |
|---|---|---|---|---|
| | | | LLO | OVA |
| HBSS | No | | 0.00 | 0.02 |
| DP-L4056 | No | $1 \times 10^5$ | 1.49 | 0.01 |
| DP-L4056 | Yes | $1 \times 10^5$ | 0.63 | 0.02 |
| DP-L4056-OVA | No | $1 \times 10^5$ | 1.78 | 1.79 |
| DP-L4056-OVA | Yes | $1 \times 10^5$ | 0.02 | 0.02 |
| DP-L4056-OVA | Yes | $1 \times 10^6$ | 0.06 | 0.08 |
| DP-L4056-OVA | Yes | $1 \times 10^7$ | 0.19 | 0.83 |
| DP-L4056-OVA | Yes | $1 \times 10^8$ | 0.14 | 0.50 |

TABLE 11

IFN-γ SFC per $10^6$ spleen cells for mice vaccinated with DP-L4056 with or without OVA, with or without S-59 treatment.

| Vaccine sample | Dose | SCF per $2 \times 10^5$ spleen cells for indicated peptide | | | |
|---|---|---|---|---|---|
| | | Control | SL8 | $LLO_{190}$ | $LLO_{296}$ |
| HBSS | | 3 | 4 | 3 | 3 |
| DP-L4056 | $1 \times 10^5$ | 6 | 7 | 176 | 31 |
| DP-L4056 + S-59 | $1 \times 10^5$ | 5 | 3 | 104 | 87 |
| DP-L4056-OVA | $1 \times 10^5$ | 11 | 292 | 238 | 31 |
| DP-L4056-OVA + S-59 | $1 \times 10^5$ | 3 | 8 | 9 | 7 |
| DP-L4056-OVA + S-59 | $1 \times 10^6$ | 4 | 7 | 10 | 4 |
| DP-L4056-OVA + S-59 | $1 \times 10^7$ | 4 | 172 | 59 | 11 |
| DP-L4056-OVA + S-59 | $1 \times 10^8$ | 10 | 171 | 97 | 24 |

Example 7

Construction of pKSV7-dlBsrFI uvrAB for Deletion of uvrAB from *Listeria* by Allelic Exchange A mutant strain of *Listeria* unable to repair damage to DNA induced by treatment with psoralen and UVA light was created by substantially deleting the ultraviolet light resistance (uvr) AB gene (uvrAB) in *Listeria*. These mutants are known as DNA repair mutants, or alternatively, nucleotide excision repair (NER) mutants. Deletion of uvrAB from *Listeria* was accomplished by allelic exchange [Camilli et al., Molecular Microbiology 8:143-147 (1993)]. As an example that uvrAB could be deleted from any *Listeria* strain, uvrAB was deleted from the *Listeria monocytogenes* strains shown in Table 12.

TABLE 12

Parent *Listeria monocytogenes* strains used for deletion of uvrAB by allelic exchange.

| *Listeria* strain | Genotype | Reference |
|---|---|---|
| DP-L4056 | 10403S wild-type, phage cured | Lauer et. al., J. Bacteriol. 184: 4177-4186 (2002). |
| DP-L4017 | 10403S, L461T LLO | Glomski et. al., J. Cell Biol. 156: 1029-1038 (2001). |
| DP-L4029 | 10403S ΔactA, phage cured | Lauer et. al., J. Bacteriol. 184: 4177-4186 (2002); Skoble et. al., J Cell Biol. 150: 527-38 (2000). |

The uvrA and uvrB genes encode 2 of the 3 proteins of the ABC excinuclease complex required for nucleotide-excision repair (NER) in *Listeria* and other bacterial strains of DNA damage inflicted by UV and other agents. The uvrA and uvrB genes comprise the same operon in the *Listeria* genome, and were thus deleted together in the *Listeria* strains shown in Table 12. The uvrA gene maps from *Listeria* nts. 2562547 to 2565461 (SEQ ID NO:5), and the uvrB gene maps from *Listeria* nts. 2565469 to 2567459 (SEQ ID NO:6)[Glaser et. al., Science 294:849-852 (2001)]. To delete uvrAB by allelic exchange, the uvrAB gene was first amplified by PCR, using forward and reverse primers that were approximately 900 base pairs (bps) upstream and downstream, respectively, of uvrAB. The *Listeria* uvrAB amplicon was generated using PCR primers Lm-2561677F (SEQ ID NO:7) and Lm-2568330R (SEQ ID NO:8) and DP-L4056 as template, and was 6654 base bps long, encompassing *Listeria* nts. 2561677-2568330 (SEQ ID NO:9). *Listeria* wild-type strain DP-L4056 was cultured overnight at 30° C. in Brain Heart Infusion broth (BHI, Difco), and 10 μL of a washed bacterial suspension (prepared by centrifugation of the 3 ml overnight culture, re-suspension of the bacterial pellet in 5 ml PBS, re-centrifugation, and followed by a final re-suspension of the *Listeria* pellet in 1 ml of PBS), was added to a PCR reaction having a final volume of 100 μL, that also contained 0.2 μM each of Lm-2561677F and Lm-2568330R primers, 2 μL pf Vent DNA polymerase (New England Biolabs), together with deoxynucleotide triphospates, buffer, and $MgSO_4$ according to the recommendations of the supplier. Successful PCR was confirmed by 0.8% agarose gel electrophoresis in TAE buffer, as demonstrated by the presence of a distinct 6654 bp band following staining with ethidium bromide and visualization by illumination with UV light. The amplicon product was purified from the PCR reaction using GeneClean (Qbiogene, Carlsbad, Calif.), in a final volume of 50 μL. Subsequently, the amplicon was inserted into the pCR2.1-TOPO vector (Invitrogen, Carlsbad, Calif.), using 5 μL of the purified uvrAB amplicon in the ligation mixture. Restriction enzymes were purchased from New England Biolabs (Beverly, Mass.). The correct construction of the pCR2.1-TOPO-uvrAB plasmid was verified by digestion with BsrFI (New England Biolabs), followed by 1% agarose/TAE electrophoresis, yielding fragments of 4612, 1388, 1094, 181, 886 and 2424 base pairs.

The pCR2.1-TOPO-uvrAB plasmid was used subsequently to generate a plasmid for allelic exchange, in which nts 2562709 to 2567320 of uvrAB (4612 bps) were deleted. All restriction enzymes and T4 DNA ligase for recombinant plasmid construction were obtained from New England Biolabs. To accomplish the deletion of uvrAB sequence, one aliquot of the pCR-TOPO/uvrAB plasmid (approximately 2 μg) was digested with HindIII, BsrFI, and BglII and the 1092 base pair fragment was purified by 1% agarose/TAE gel electrophoresis and GeneClean. In parallel, a second aliquot (approximately 2 μg) was digested with XhoI, BsrFI, and BglII enzymes, and the 1050 base pair fragment was purified by 1% agarose/TAE gel electrophoresis and GeneClean. The two 1092 bp and 1050 bp fragments containing compatible BsrFI ends were ligated together and the 2142 bp ligation product was purified using GeneClean. One portion of the 2142 bp ligation product was digested with PstI and the 1486 bp fragment was purified by 1% agarose/TAE gel electrophoresis and GeneClean. A second portion of the 2142 bp ligation product was digested with KpnI and PstI, and the 622 bp fragment was purified by 1% agarose/TAE gel electrophoresis and GeneClean. The parent plasmid vector for allelic exchange, pKSV7 [Camilli et al., Molecular Microbiology 8:143-147 (1993)], was digested with KpnI and PstI and treated with Calf Intestinal Alkaline Phosphatase (CIAP, New England Biolabs) and the 622 bp fragment having KpnI and PstI compatible ends was inserted into the pKSV7 plasmid vector to give pKSV7-K/P-338. Subsequently, the 1486 bp fragment having PstI compatible ends was inserted into the vector construct pKSV7-K/P-338 that was digested with PstI and treated with CIAP. Insertion of the 1486 bp construct in the correct orientation was determined by digestion with KpnI and HindIII to yield fragment sizes of 1253 bp, 865 bp, and 6.9 kb. This plasmid contruct is known as pKSV7-dlBsrFI uvrAB. The *Listeria* dlBsrFI uvrAB portion of the pKSV7 recombinant plasmid was sequenced to verify the fidelity of the *Listeria* sequence and the precise deletion in the uvrAB gene of nts. 2562709 to 2567320 (deletion from uvr coordinates nts. 2562547 to 2567459). The deleted region is SEQ ID NO:10, with the amplicon sequence remaining given in SEQ ID NO:11.

The uvrAB genes of *Listeria* strains DP-L4056, DP-L4017, and DP-L4029 (Table 12) were deleted by allelic exchange using plasmid pKSV7-dlBsrFI uvrAB, as described previously [Camilli et al., Molecular Microbiology 8:143-147 (1993)]. The plasmid pKSV7-dlBsrFI uvrAB was introduced into *Listeria* strains DP-L4056, DP-L4017, and DP-L4029 by electroporation. The *Listeria* strains were made competent for electroporation by first growing a 10 mL overnight culture from an isolated bacterial colony in BHI with shaking at 37° C. A log-phase culture of each strain was then derived by innoculating 2 mL of the overnight culture into 100 mL 0.5M sucrose/BHI (sterile filtered) in a 250 mL flask. The culture was grown to mid-log phase by shaking at 37° C. for 2-3 hours until a bacterial density of $OD_{600}$=0.2 was reached. Subsequently, the culture was treated to generate bacteria lacking the peptidoglycan cell wall, known as spheroplasts. 100 uL of a penicillin G stock solution (10 mg/mL, sterile filtered) was added to the mid-log phase culture, followed by shaking at 37° C. for 2 hours. The spheroplast culture was pelleted in a 100 mL centrifuge bottle, resuspended with 45 mL of an ice-cold HEPES/sucrose stock solution (1 mM HEPES, pH 7.0/0.5M sucrose, sterile filtered), and pelleted again by centrifugation. The bacterial pellet was resuspended with 20 mL of HEPES/sucrose, transferred to a 40 mL centrifuge tube, pelleted, and resuspended in 10 mL HEPES/sucrose. 100 μL of a 10 mg/mL lysozyme stock was then added to the bacterial solution, mixed thoroughly, and the culture was incubated 15 minutes at 37° C. without shaking, but was inverted gently twice at 5 minute intervals. The lysozyme-treated culture was then centrifuged at 5000 rpm (3000×g) for 10 min. at 4° C., and resuspended in 10 mL HEPES/sucrose; this process was repeated twice, with careful and thorough resuspension each time. The final step to yield electrocompetent *Listeria* was to resuspend the bacterial pellet in 500 μL HEPES/sucrose.

For electroporation, 2 μg of pKSV7-dlBsrFI uvrAB plasmid DNA was added to 10 μL of DP-L4056, DP-L4017, and DP-L4029 electrocompetent *Listeria*, and the solution was added to a 0.1 cm cuvette. The cuvettes were placed in the electroporation device that was set at 1 KV, 400 ohms, and 25 μFD, and then pulsed. This typically resulted in a time constant of about 5 milli-seconds. The cells were immediately added to 1 mL BHI/sucrose media that was pre-warmed to 30° C., and then incubated for 1 hour at 30° C., without shaking. Following the incubation period, the bacteria were pelleted, resuspended in 200 ml of BHI broth, and the suspension was plated on BHI-agar containing 10 μg/mL chloramphenicol (BHI/CM10). The plates were then incubated overnight at 30° C., after which colonies corresponding to pKSV7-dlBsrFI uvrAB plasmid transformants were visible. The plasmid pKSV7 contains a temperature-sensitive *Listeria* replicon, and thus the plate must be incubated at 30° C. in order to visualize chloramphenicol-resistant colonies.

Allelic exchange of the native uvrAB gene in *Listeria* strains DP-L4056, DP-L4017, and DP-L4029 transformed by electroporation with pKSV7-dlBsrFI uvrAB plasmid containing a 4612 bp deletion in uvrAB was accomplished in two steps comprised of plasmid integration, followed by plasmid excision (including native uvrAB) and curing, as described previously [Camilli et al., Molecular Microbiology 8:143-147 (1993)]. Two isolated chloramphenicol-resistant colonies resulting from each of the *Listeria* strains DP-L4056, DP-L4017, and DP-L4029 electroporated with pKSV7-dlBsrFI uvrAB plasmid DNA were selected and then each selected colony was streaked onto fresh BHI/CM10 plates, and incubated overnight at 30° C. The next day, a colony was selected from each plate and used to inoculate 10 mL of BHI/CM10 contained in a 250 mL flask, which was then incubated overnight at 30° C. with shaking. 10 μL of each of the overnight cultures were then used to inoculate 10 mL of fresh BHI/CM10 media (1:1000 dilution), which were then grown at 41° C. with shaking until the cultures reached stationary phase. Following sampling of 10 μL, a plasmid preparation was performed with the remaining overnight *Listeria* culture to insure the presence of the pKSV7-dlBsrFI uvrAB plasmid DNA. Once at stationary phase, 10 μL of the cultures were used to inoculate 10 mL of fresh BHI/CM10 media, which was pre-warmed to 41° C., and then incubated overnight at 41° C., with shaking. A sample was then taken from each 41° C. overnight culture, and used to streak for isolated colonies on BHI/CM10 plates, that were pre-warmed at 41° C. As the plasmid pKSV7 contains a temperature-sensitive *Listeria* replicon, incubation at 41° C. selects for colonies arising from integration through homologous recombination of the pKSV7-dlBsrFI uvrAB plasmid with the native uvrAB gene in the *Listeria* genome, and thus amplification and expression of the chloramphenicol drug-resistance marker through bacterial cell growth and division. At this point, the *Listeria* strains are merodiploid for the uvrAB gene, comprised of the native uvrAB gene and the 4612 bp deleted uvrAB gene, arising from integration by homologous recombination of the pKSV7-dlBsrFI uvrAB plasmid.

For excision and curing of the native uvrAB gene with the pKSV7 plasmid, a single colony was selected from each of the BHI/CM10 plates incubated at 41° C. from the step above, and used to inoculate 10 ml of BHI media without chloramphenicol, and then incubated at 30° C. overnight with shaking. The cultures were then diluted 1:1000 in 10 mL of fresh BHI media without chloramphenicol, and then incubated at 30° C. overnight with shaking for 6 hours. This step was repeated twice. Upon passage of the merodiploid intermediate strains for several generations without drug-selective pressure at a temperature permissive for the pKSV7 plasmid replicon, spontaneous excision of the integrated pKSV7 plasmid occurs, and eventual curing of the plasmid from the bacterium previously. [Camilli et al., Molecular Microbiology 8:143-147 (1993)]. Following the third 1:1000 dilution and 6-hour incubation period, a sample from each culture was taken, and used to streak for isolated colonies on BHI plates (without chloramphenicol), and incubated overnight at 37° C. One hundred isolated colonies were selected from each BHI plate with a toothpick, and a 5 mM-long streak was made with each colony first on a BHI/CM10 plate, followed by a BHI plate. Plates were marked using a grid so that each matched pair of BHI/CM10 and BHI plates were replicates. The BHI/CM10 and BHI replicate plates were incubated overnight at 37° C. Approximately 5% of the colonies replica-plated on BHI/CM10 and BHI plates originating from the two chloramphenicol-resistant colonies from electroporation with DP-L4056, DP-L4017, or DP-L4029 with pKSV7-dlBsrFI uvrAB plasmid DNA were drug sensitive (i.e., growth only on BHI plates). These drug-sensitive colonies represented candidates containing the 4612 bp deletion in uvrAB. Each of the drug-sensitive colonies were re-streaked for isolated colonies on both BHI/CM10 and BHI plates and incubated overnight at 37° C., to ensure that candidate clones were both pure and drug sensitive. The chloramphenicol-sensitive clones were subjected to PCR using primers Lm-2561677F and Lm-2568330R (ibid), in order to identify clones that also contained the uvrAB deletion. The amplicon size of clones with the native uvrAB gene was 6654 bps, and the amplicon size of the deleted uvrAB gene was 2042 bps; about 50% of the chloramphenicol-sensitive clones also contained the deleted uvrAB gene. Two clones of the uvrAB deleted strains derived from DP-L4056, DP-L4017, and DP-L4029 were selected for further characterization. Glycerol stocks (30° C. overnight culture diluted 1:1 with sterile LB/40% glycerol) were made for each uvrAB mutant strain and stored at −80° C. These strains are known as shown in Table 13. DP-L4029uvrAB (actA/uvrAB) was deposited with ATCC on Oct. 3, 2003, assigned PTA-5563.

TABLE 13 uvrAB mutant *Listeria* strains generated by allelic exchange

| uvrAB mutant *Listeria* strain | Parent *Listeria* Strain |
|---|---|
| L4056/uvrAB clone 1 | DP-L4056 |
| L4056/uvrAB clone 2 | DP-L4056 |
| L4017/uvrAB clone 1 | DP-L4017 |
| L4017/uvrAB clone 2 | DP-L4017 |
| L4029/uvrAB clone 1 | DP-L4029 |
| L4029/uvrAB clone 2 | DP-L4029 |

To demonstrate the increased sensitivity to attenuation with S-59 psoralen and UVA light, a preparation of $1\times10^9$ CFU of the uvrAB mutant *Listeria* strains shown in Table 13 were treated either with 2, 20, 100 and 500 nM S-59 (both clones of L4017/uvrAB and L4056/uvrAB) or 2, 10, 20, and 100 nM S-59 (clone 1 of L4017/uvrAB and both clones of L4029/uvrAB), UVA irradiated at a dose of 6 J/cm² (FX1019), and tested for viability by plating dilutions on BHI plates, exactly as described in Example 1. The results of this study are shown in Table 14A-B (log attenuation as a function of S-59 dose) and FIG. 8A-B (log titer remaining as a function of S-59 dose). The results demonstrate clearly that the DNA NER repair mutant strains shown in Table 13 were dramatically more susceptible to photochemical attenuation with psoralen and UVA irradiation, as compared to the parent strains. This data provides unequivocal evidence that significantly and substantially lower levels of S-59 psoralen can be used to inactivate uvrAB mutant bacteria to the same extent, as compared to their isogenic counterpart.

TABLE 14A

Log attenuation of *Listeria monocytogenes* strains after irradiation (6 J/cm2 UVA) at indicated S-59 concentration.

| | 0 nM S-59 | Log attenuation of *Listeria monocytogenes* S-59 concentration (nM) | | | |
|---|---|---|---|---|---|
| *Listeria* strain | Log titer | 2 | 20 | 100 | 500 |
| DP-L4017 | 7.81 | 0.66 | 2.58 | >6.81 | >6.81 |
| L4017/uvrAB clone 1 | 7.67 | 1.82 | >6.67 | >6.67 | >6.67 |

TABLE 14A-continued

Log attenuation of *Listeria monocytogenes* strains after irradiation (6 J/cm2 UVA) at indicated S-59 concentration.

| | 0 nM S-59 | Log attenuation of *Listeria monocytogenes* S-59 concentration (nM) | | | |
|---|---|---|---|---|---|
| *Listeria* strain | Log titer | 2 | 20 | 100 | 500 |
| L4017/uvrAB clone 2 | 7.68 | 1.96 | >6.68 | >6.68 | >6.68 |
| DP-L4056 | 8.36 | 1.18 | 3.10 | >6.36 | >6.36 |
| L4056/uvrAB clone 1 | 7.65 | 2.04 | >6.65 | >6.65 | >6.65 |
| L4056/uvrAB clone 2 | 7.84 | 1.96 | >6.84 | >6.84 | >6.84 |

TABLE 14B

Log attenuation of *Listeria monocytogenes* strains after irradiation (6 J/cm2 UVA) at indicated S-59 concentration.

| | 0 nM S-59 | Log attenuation of *Listeria monocytogenes* S-59 concentration (nM) | | | |
|---|---|---|---|---|---|
| *Listeria* strain | Log titer | 2 | 10 | 20 | 100 |
| DP-L4017 | 8.62 | 0.56 | 0.97 | 2.33 | >7.62 |
| L4017/uvrAB clone 1 | 8.67 | 1.09 | 4.44 | >7.67 | >7.67 |
| DP-L4029 | 8.68 | 0.48 | 1.10 | 2.98 | >7.68 |
| L4029/uvrAB clone 1 | 8.59 | 1.78 | 5.99 | >7.59 | >7.59 |
| L4029/uvrAB clone 2 | 8.63 | 1.50 | 6.60 | >7.63 | >7.63 |

The uvrAB mutant strains can be used directly as a parent strain in which to incorporate expression cassettes encoding heterologous antigens relevant to malignant or to infectious disease. In this configuration, following photochemical attenuation with S-59 and UVA light, the bacterium retains its ability to program MHC class I-restricted responses, because while the ability to replicate its DNA has been abrogated via cross-linking, the ability to express its genetic complement remains essentially intact. Furthermore, as a result of the requirement of significantly fewer DNA cross-links to inactivate uvrAB mutants, in the context of the population of bacterial genomes comprising a vaccine dose, the expression of any one gene will not be significantly affected, due to the low level of DNA crosslinking resulting in essentially no interruption of expression, at that given gene. Finally, the uvrAB mutation can be combined with any other attenuating mutation(s), in order to derive a safe and efficacious vaccine platform combining both photochemical and genetic attenuation. In the composition described herein, the uvrA, uvrB, or uvrC genes, or any *Listeria* gene involved in NER, alone, or in any combination, can be mutated such that a functional form of the protein is not expressed. These compositions can be used as an approach for deriving a safe and efficacious vaccine derived from a selected bacterial pathogen, in order to protect against challenge with the wild-type pathogen in vaccinated individuals. Alternatively, these compositions can be used as an approach for deriving a safe and efficacious recombinant vaccine platform for the expression of heterologous antigens relevant to any selected infectious or malignant disease.

Example 8

Insertion of Antigen Expression Cassettes into the Genomes of Selected *Listeria* Strains by Allelic Exchange or by a Site-Specific Integration Vector The strains described in Example 7, any selected *Listeria* strain, or any bacterial strain, can be modified further to express a heterologous protein or antigen relevant to malignant or infectious disease. Expression of the heterologous protein can be via a plasmid containing a replicon that is compatible with the selected host bacterium so that the plasmid is stably maintained. Alternatively, a prokaryotic expression cassette can be integrated stably into the genome of the host bacterium using a variety of methods, including allelic exchange as described in Example 7, or with vectors that integrate randomly or site-specifically, that are derived from selected transposons or bacteriophage.

As an example, the derivation of recombinant *Listeria monocytogenes* derived from the uvrAB nucleotide excision repair (NER) mutant strains described in Example 7, by utilizing a site-specific integration vector known as pPL2, which is derived from the listeriophage PSA (Phage from ScottA), is described here [Lauer et. al., J. Bacteriol. 184:4177-4186 (2002)]. Specifically, the pPL2 integration vector is engineered to express the chicken ovalbumin (OVA) model antigen as a fusion partner with the amino-terminal half of the Listeriolysin O (LLO) protein that includes the secretion signal and PEST sequence [Decatur and Portnoy, Science 290:992-995 (2000)], but lacking hemolysin activity, that is fused in-frame with OVA. Expression of the truncated LLO-OVA fusion protein is driven by the hly promoter, which is a prfA-dependent promoter that drives the expression of *Listeria* virulence genes, including LLO. This vector is known as pPL2/LLO$_{ss\text{-}PEST}$-OVA. The pPL2 vector integrates within the tRNA$^{Arg}$ gene of *Listeria* in such a manner that the native sequence of the tRNA gene is restored upon successful integration, thus keeping its native expressed function intact.

The first step in the construction of pPL2/LLO$_{ss\text{-}PEST}$-OVA is to amplify the hly promoter and LLO$_{ss\text{-}PEST}$ sequence together from DP-L4056 wild-type *Listeria* genomic DNA, by PCR using the primer pair of forward primer KpnI-LLO nts. 1257-1276 (SEQ ID NO:12) and reverse primer XhoI-LLO1665R (SEQ ID NO:13). The 426 bp amplicon is purified with GeneClean, digested with KpnI and XhoI, and ligated into pPL2 plasmid, which is prepared by digesting with KpnI and XhoI, treatment with calf intestinal alkaline phosphatase (CIAP), and purified with GeneClean. Correct plasmids containing the LLO$_{ss\text{-}PEST}$ sequence are verified by digesting with KpnI and XhoI and 1% agarose/TAE electrophoresis, yielding DNA fragments of 418 bps and 6112 bps. This intermediate plasmid DNA construct is known as pPL2/LLO$_{ss\text{-}PEST}$.

The OVA sequence can be amplified by PCR from any number of plasmids that are used by those in the art, including pDP3616 plasmid DNA from DP-E3616 *E. coli* [Higgins et. al., Mol. Molbiol. 31:1631-1641 (1999)], using the primer pair of forward primer XhoI-NcoI OVA cDNA nts. 174-186 (SEQ ID NO:14) and reverse primer XhoI-NotI-HindIII (SEQ ID NO: 15).

The 1013 bp amplicon is purified with GeneClean, digested with XhoI and NotI, and ligated into pPL2/LLO$_{ss\text{-}PEST}$ plasmid, prepared by digesting with XhoI and NotI, treatment with CIAP, and purified with GeneClean. The correct plasmid construct containing the LLO$_{ss\text{-}PEST}$ and OVA sequence is verified by digesting with KpnI, XhoI, and NotI and 1% agarose/TAE electrophoresis, yielding DNA fragments of 994 bps, 1560 bps, and 6039 bps. The precise expected sequence of the LLO and OVA regions of plasmid pPL2/LLO$_{ss\text{-}PEST}$-OVA is confirmed by sequencing.

The pPL2/LLO$_{ss\text{-}PEST}$-OVA plasmid is incorporated into the tRNA$^{Arg}$ gene in the genome of selected *Listeria* uvrAB mutant strains described in Example 7, exactly according to the methods as described previously [Lauer et. al., J. Bacteriol. 184, 4177-4186 (2002)]. Briefly, the plasmid pPL2/LLO$_{ss\text{-}PEST}$-OVA is first introduced into the *E. coli* host strain SM10 (Simon et. al., Bio/Technology 1:784-791 (1983)] by electroporation or by chemical means. Subsequently, the pPL2/LLO$_{ss\text{-}PEST}$-OVA plasmid is transferred from transformed SM10 to the selected *Listeria* strains by conjugation. Following incubation on drug-selective BHI agar plates containing 7.5 μg of chloramphenicol per ml and 200 μg of streptomycin per ml as described, selected colonies are purified by passaging 3 times on plates with the same composition. To verify integration of the pPL2 vector at the phage attachment site, individual colonies are picked and screened by PCR using the primer pair of forward primer NC16 (SEQ ID NO:16) and reverse primer PL95 (SEQ ID NO:17). Selected colonies having the pPL2/LLO$_{ss\text{-}PEST}$-OVA plasmid incorporated into the tRNA$^{Arg}$ gene in the genome of selected *Listeria* uvrAB mutant strains will yield a diagnostic DNA amplicon of 499 bps.

The ability of the recombinant *Listeria* uvrAB mutants harboring a stable integrant of pPL2/LLO$_{ss\text{-}PEST}$-OVA to be taken up by antigen presenting cells and subsequently program presentation of OVA via the MHC class I pathway is tested, using the cloned C57B1/6-derived dendritic cell line DC2.4, as described in Example 1. Presentation of OVA peptide by DC2.4 cells on class I molecules following phagocytosis of *Listeria* is measured after incubation with B3Z cells, also as described in Example 1. These procedures verify that the recombinant *Listeria* strains are functional, and can be used further as described in the Examples contained herein.

Thus, this example provides instructions for introducing a prokaryotic expression cassette encoding any desirable antigen(s) related to selected infectious and malignant diseases into DNA repair mutant *Listeria* strains containing a deletion within the uvrAB gene. The said recombinant *Listeria* strains can be inactivated by treatment with psoralens as described in Example 1 and can be used subsequently for a variety of applications, including, for example, prophylactic and therapeutic vaccines for infectious and malignant disease.

Example 9

Bacterial Vaccines Derived from Nucleotide-Excision Repair (NER) Mutants

The examples described herein illustrate the efficacy of vaccine compositions utilizing genomic inactivation through photochemical treatment of the recombinant delivery platform encoding antigens related to infectious and malignant disease. According to this composition, while the genomes are inactivated and cannot separate during replication, the transcriptional profile remains largely intact, thus resulting in antigen expression de novo in the vaccinated individual, and optimal induction of pathogen-specific immune responses, including CD8+ cytotoxic T cells (CTL). Furthermore, as described in Example 7, by utilizing a vaccine platform in this composition in which the DNA nucleotide excision repair (NER) machinery has been inactivated by any number of means, including by engineered genetic deletion, the sensitivity to photochemical inactivation in these mutants is dramatically increased.

As a result of the requirement of significantly fewer DNA cross-links to inactivate the DNA repair mutants, in the context of the population of bacterial genomes comprising a vaccine dose, the expression of any one gene will not be significantly affected, due to the low level of DNA crosslinking resulting in essentially no interruption of expression, at that given gene.

Thus, the overall utility of gene-based vaccines utilizing bacterial platforms derived from pathogens can be increased dramatically by combining photochemical inactivation with a vector defective in NER. While the inactivated vaccine cannot cause disease, it still retains its efficient ability to induce potent immunity, including T-cell mediated cellular immunity, specific for the vector-expressed heterologous antigens. Furthermore, the uvrAB mutation can be combined with any other attenuating mutation(s), in order to derive a safe and efficacious vaccine platform combining both photochemical and genetic attenuation.

Significantly, these compositions can be used as an approach for deriving a safe and efficacious vaccine derived from a selected bacterial pathogen, in order to protect against challenge with the wild-type pathogen in vaccinated individuals. According to this application, it is not feasible in many cases to derive a safe and efficacious vaccine that is derived from an attenuated viable form of the pathogen, as the possibility for reactivity and disease pathogenesis in particular individuals receiving the vaccine remain high. While subunit or inactivated vaccines related to a selected bacterial pathogen might be safe, on the other hand, these vaccines are often not efficacious because they do not efficiently elicit the breadth, depth, and durability of pathogen-specific immune responses that are required to protect the vaccinated individual against challenge with the wild-type form of the said pathogen. Thus, it is well known in the art that there is a clear need for vaccine compositions that combine safety with an efficient ability to elicit the type of immune responses in vaccinated individuals that are protective.

As such, mutants in the nucleotide-excision repair (NER) pathway of pathogenic microbes provide a composition that can be used for safe and efficacious vaccines that elicit protection against challenge in immunized individuals with amounts of the said microbe that are sufficient to cause disease in non-vaccinated individuals. NER is catalyzed by an ATP-dependent nuclease made of three subunits, known as the ABC excinuclease, and encoded by the genes uvrA, uvrB, and uvrC. Mutations in any one or more than one of the three uvr genes results in cells, including microbes of pathogenic organisms, extremely sensitive to photochemical inactivation utilizing psoralens and UVA light.

As an example, mutation of the uvr genes of *Bacillus anthracis* (*B. anthracis*), the etiological agent of Anthrax, is provided. The current a cellular anthrax vaccines that are licensed for human use are based on sterile culture supernatants of attenuated *B. anthracis* adsorbed on alum hydroxide (U.S. vaccine), or precipitated with alum phosphate (U.K. vaccine). It is well known that these vaccines are rather weak, requiring at least six immunizations for protection as well as annual boosters.

In the composition described herein, the uvrA, uvrB, or uvrC genes, or any *B. anthracis* gene involved in NER, alone, or in any combination, is mutated such that a functional form of the protein is not expressed.

As an example, mutation in the uvrA, uvrB, or uvrC genes, or any *B. anthracis* gene involved in NER, can be performed, for example, by allelic exchange, as described in Example 7. While the uvr genes of *B. anthracis* have not been identified through targeted deletion and characterization of the phenotypes of the resulting mutant strains, the uvr genes can be identified through a homology search with the genomes of related organisms in whose uvr genes are known. For example, the genome of *B. anthracis*, that is, the main chromosome and the two virulence plasmids can be compared with *Bacillus Subtilis* (*B. Subtilis*), a related bacterium from the same genera as *B. anthracis*. The genomic scaffold representing the main chromosome of the Florida *B. anthracis* isolate (Read et. al. 2002. *Science* 296, 2028-2033) has a GenBank accession number of AAAC010000001. *B. subtilis* has a GenBank accession number of NC_000964. The *B. subtilis* uvrA gene encompasses nts. 3609064 to 3611997, and the *B. subtilis* uvrB gene encompasses nts. 3612005-3613990. A BLAST search was performed using the *B. subtilis* uvrA and uvrB coding sequences against the *B. anthracis* sequence. This analysis identified a region of 72% sequence identity in the genome of *B. anthracis* that corresponds to the uvrA and uvrB genes of this organism. The *B. anthracis* uvrA gene maps from 226021-228783, and bears 72% sequence homology to the *B. subtilis* uvrA gene (2082/2867 identical sequence homology alignment). The *B. anthracis* uvrB gene maps from 228864-230771, and bears 72% sequence homology to the *B. subtilis* uvrB gene (1401/1925 identical sequence homology alignment). Thus, the *B. anthracis* uvrAB genes include nts. 226021 to 230771 of the main chromosome of *B. anthracis*.

Deletion of the *B. anthracis* uvrAB genes, including nts. 226021 to 230771 of the main bacterial chromosome can be accomplished according to the methods described in Example 7 for the deletion of uvrAB genes in *L. monocytogenes*. Briefly, this region and approximately 1000 bps both upstream and downstream of the *B. anthracis* genome are amplified by PCR, and subsequently cloned into the pKSV7 allelic exchange plasmid vector. As an alternative, a *Bacillus* genera-specific or *B. anthracis*-specific temperature-sensitive (ts) replicon may be substituted for the *Listeria* ts replicon present in the pKSV7 allelic exchange plasmid vector. Using convenient restriction endonuclease recognition sites mapping specifically within the uvrAB region, any part of the uvrA, uvrB, or all of the uvrAB genes sequence are deleted. Finally, the allelic exchange plasmid is introduced into *B. anthracis* and NER mutants are selected as described in Example 7. Any selected *B. anthracis* strain can be used as a parent strain for derivation of the NER-defective vaccine, including, for example, the following strains: Ames, Vollum, A1.a/10, A1.b/23, A2/29, A3.a/34, A3.b/57, A4/69, B/80, Δsterne, VN41Δ1, Dames, NNR1Δ1, and DNH1. Additionally, other attenuating mutations can be incorporated into the genome of the selected NER mutant *B. anthracis* strain, to enable vaccine compositions combining photochemical with genetic inactivation. Such *B. anthracis* vaccine compositions are able to induce immune responses against known correlates of anthrax immunity and protection, including lethal factor (LF), edema factor (EF), and protective antigen (PA). Additionally, as a result that the expression profile of the NER mutant vaccine composition remains intact, immune responses against other unknown correlates of anthrax immunity and protection, including those expressed from the two virulence plasmids pXO1 and pXO2 and the main chromosome are also induced.

The compositions described herein, using *B. anthracis* as an example utilizing NER mutants as a component of vaccine, can be used in either a prophylactic or a therapeutic immunization setting against all three types of anthrax according to the route of infection, including cutaneous, gastrointestinal and respiratory. Furthermore it can be appreciated that the approach for generating NER mutants of *B. anthracis* to derive a safe and efficacious vaccine can be adopted to derive safe and efficacious vaccines for any microbial pathogen that utilizes NER.

Example 10

Use of Microbe-Based Vaccines of the Invention for the In Vivo Treatment of Human Cancers As an example of the treatment or prevention of a human cancer, a vaccine comprising a microbial population in which the microbial nucleic acid is modified so that the proliferation of the microbial population is attenuated, wherein the microbial gene expression is substantially unaffected, is administered to an individual. The microbe can be prepared following the protocols of examples 7 and 8, wherein any desired prokaryotic expression cassettes encoding human tumor antigen(s) are incorporated into the microbe, by utilizing, for example the pPL2 integration vector described in Example 8, or any modifications thereof, or by any methods that are common to those in the art. The resulting population may be formulated in crude, or preferably purified form. They may be prepared as a liquid suspension or may be freeze-dried and resuspended in a suitable carrier for administration. In addition, they may be formulated with additives such as preservatives (e.g. thimerosal, 2-phenoxy ethanol), stabilizers (e.g. lactose, monosodium glutamate), adjuvants (e.g. aluminum hydroxide, aluminum phosphate, cytokines), antibiotics (e.g. neomycin, streptomycin) or other substances. Formulations may be resuspended or diluted in a suitable diluent such as sterile water, saline, isotonic buffered saline (e.g. phosphate buffered to physiological pH), or other suitable diluent.

The vaccine may be administered by a variety of routes, including oral, nasal, intravenous, intradermal, intraperitoneal, intramuscular, intralymphatic and subcutaneous routes, as well as by any route that is relevant for any given malignant or infectious disease. An effective amount of the vaccine will be administered to an individual for treatment. For a therapeutic treatment, an effective amount is a dose that will result in the desired immune response, wherein the immune response either slows the growth of the targeted tumors, reduces the size of the tumors, or preferably eliminates the tumors completely. The administration of the vaccine may be repeated at appropriate intervals, and may be administered simultaneously at multiple distinct sites in the vaccinated individual. For the prophylactic treatment, an effective amount is a dose that will result in a protective immune response such that the likelihood of an individual to develop the cancer is significantly reduced. The vaccination regimen may be comprised of a single dose, or may be repeated at suitable intervals until a protective immune response is established.

The therapeutic treatment of an individual may be started on an individual who has been diagnosed with a cancer as an initial treatment, or may be used in combination with other treatments. For example, individuals who have had tumors surgically removed or who have been treated with radiation therapy or by chemotherapy may be treated with the vaccine in order to reduce or eliminate any residual tumors in the individual, or to reduce the risk of a recurrence of the cancer. The prophylactic treatment of an individual would be started on an individual who has an increased risk of contracting certain cancers, either due to environmental conditions or genetic predisposition.

Example 11

**Antigen Presentation of *Listeria* Strain DP-L4029 with and without uvrAB Mutation Following S-59 Psoralen UVA Treatment**

The *Listeria* strain DP-L4029 uvrAB mutant clone 1 of Example 7 was modified to express the OVA antigen using the procedure of Example 8. This strain and DP-L4029 modified to express OVA were treated with the psoralen S-59 at various concentrations. The *Listeria* strains were grown overnight at 37° C. and a 2 mL aliquot was diluted into 100 mL of BHI and grown approximately 4 hours at 37° C. to an OD600 of 0.5 (approximately $1\times10^9$ CFU/mL). A 5 mL aliquot of each *Listeria* strain was added to a 15 mL tube and centrifuged for 20 minutes at 2300×g, the supernatant removed, and the bacteria resuspended in 5 mL of PBS resulting in approximately $1\times10^9$ CFU/mL. For the uvrAB mutant strain, 3 mM S-59 stock was diluted 33.3 µL to 10 mL PBS to give a 10 µM solution, and appropriate aliquots of this was added to the *Listeria* to final concentrations of 10, 20, 30, 40, 50, 60, 70, 80, 90, and 100 nM, while for the DP-L4029, S-59 was added to final concentrations of 100, 200, 400, 800, and 1000 nM in a final volume of 5 mL. These were transferred to a 6 well culture plate and irradiated for a dose of 0.5 J/cm$^2$ (FX1019 UVA device). The samples were transferred to 15 mL tubes, 5 mL PBS was added, and they were centrifuged for 20 minutes at 2300×g to wash out unreacted psoralen. The supernatant was removed and the bacteria resuspended in 5 mL PBS and transferred to new 6 well plates. These were irradiated at a UVA dose of 5.5 J/cm$^2$ in order to convert psoralen monoadducts to crosslinks. A sample of each *Listeria* strain was also heat killed by treating at 72° C. for 3 hours. The log titer and OVA antigen presentation were assessed as per Example 1. The results for the S-59 treated samples are found in Table 15A and FIGS. 9A and 9B (antigen presentation at 1 *Listeria* per DC 2.4 cell, calculated without subtracting background levels). The results for both heat killed strains showed a titer below the limit of detection (complete inactivation) and the heat killed bacteria did not present OVA antigen in the B3Z assay. The results indicate that the uvrAB mutant shows very strong antigen presentation even with attenuation of proliferation to the limit of detection where the non uvrAB mutant strain shows a greater reduction in the antigen presentation as a function of attenuation of proliferation (to approximately background levels with essentially complete inactivation). This demonstrates that the uvrAB mutant retains MHC class I presentation in the context of psoralen attenuated *Listeria* and should provide a vaccine with an effective immune response and significantly increased level of safety.

TABLE 15A

Log attenuation and OVA antigen presentation of *Listeria* strains UVA treated with varying concentrations of psoralen S-59.

| | Log attenuation | | % OVA antigen presented* | |
|---|---|---|---|---|
| [S-59] nM | DP-L4029-OVA | DP-L4029 uvrAB-OVA | DP-L4029-OVA | DP-L4029 uvrAB-OVA |
| 10 | | 2.47 | | 84 |
| 20 | | 3.93 | | 84 |
| 30 | | 5.28 | | 76 |
| 40 | | 6.44 | | 76 |
| 50 | | 6.92 | | 68 |
| 60 | | >7.62 | | 84 |
| 70 | | >7.62 | | 84 |
| 80 | | >7.62 | | 88 |
| 90 | | >7.62 | | 92 |
| 100 | 3.85 | >7.62 | 50 | 92 |
| 200 | 5.48 | | 47 | |
| 400 | 6.78 | | 19 | |
| 800 | >7.78 | | 13 | |
| 1000 | >7.78 | | 13 | |

*As percent of untreated, measured at 1 *Listeria* per DC 2.4 cell.

Another study was done using the same strains. In this study the *Listeria* were grown in BHI at 37° C. overnight. These were diluted 1:50 into BHI and grown at 37° C. at 300 rpm to an OD$_{600}$ of 0.5, at which point 50 mL of solution was transferred to a clean flask and S-59 was added to the levels indicated in Table 15B. These samples were incubated at 37° C. at 300 rpm for approximately 1 hour (OD$_{600}$ approximately 1.0, approximately $1\times10^9$/mL). A 1 mL aliquot was removed to assess the titer and the remaining was transferred to a 150 mm Petri dish and irradiated at a dose of 6 J/cm$^2$ (FX1019). The titer post irradiation was determined for each sample and the OVA antigen presentation was assessed as above. The results are found in Table 15B and FIGS. 9C and 9D (antigen presentation at 10 *Listeria* per DC 2.4 cell, calculated without subtracting background levels). The results indicate that for the parent strain, the antigen presentation is at background levels where there is essentially complete inactivation whereas for the uvrAB mutant, there is an approximately 10-fold range of S-59 concentration over which there is essentially complete inactivation along with adequate antigen presentation.

TABLE 15B

Log attenuation and OVA antigen presentation of *Listeria* strains UVA treated with varying concentrations of psoralen S-59 present during growth of the bacteria.

| [S-59] μM | Log attenuation | | % OVA antigen presented* | |
|---|---|---|---|---|
| | DP-L4029-OVA | DP-L4029 uvrAB-OVA | DP-L4029-OVA | DP-L4029 uvrAB-OVA |
| 0.025 | | 3.64 | | 91 |
| 0.05 | | 5.70 | | 86 |
| 0.1 | | >8.10 | | 87 |
| 0.2 | | >8.10 | | 86 |
| 0.25 | 2.00 | | 50 | |
| 0.4 | | >8.10 | | 74 |
| 0.5 | 5.28 | | 31 | |
| 0.8 | | >8.10 | | 50 |
| 1.0 | 7.57 | | 14 | |
| 1.6 | | >8.10 | | 35 |
| 2.0 | >8.38 | | 11 | |
| 3.2 | | >8.10 | | 16 |
| 4.0 | >8.38 | | 10 | |
| 6.4 | | >8.10 | | 11 |
| 8.0 | >8.38 | | 10 | |
| 16.0 | >8.38 | | 11 | |

*As percent of untreated, measured at 10 *Listeria* per DC 2.4 cell.

Example 12

Protein Synthesis in S-59/UVA Treated *Listeria monocytogenes* DP-L4029 Compared to DP-L4029 uvrAB

*Listeria monocytogenes* DP-L4029 and DP-L4029uvrAB were grown in BHI at 37° C. overnight. These were diluted 1:50 into BHI and grown at 37° C. at 300 rpm to an OD600 of 0.5, at which point 50 mL of solution was transferred to a clean flask and S-59 was added to a level of 2500 nM for the 4029 and 200 nM for the 4029 uvrAB mutant strain. These samples were incubated at 37° C. at 300 rpm for approximately 1 hour (OD600 approximately 1.0). A 1 mL aliquot was removed to assess the titer and the remaining was transferred to a 150 mm Petri dish and irradiated at a dose of 6 J/cm$^2$ (FX1019). The titer post irradiation was determined for each sample to assess the level of inactivation, resulting in essentially complete inactivation. It has been determined that this treatment is approximately the lowest S-59 dose that provides inactivation to the limit of detection for both strains. For each strain, $1\times10^{10}$ bacteria, based on the OD$_{600}$ vs. titer CFU/mL growth curve, was transferred to a 15 mL centrifuge tube. The sample was centrifuged at 4° C. for 20 minutes at 2300×g, the supernatant removed and the pellet washed with 50 mL of PBS. This was repeated for a total of three washes. The final pellet was suspended in 2 mL of DMEM without methionine or cysteine (Gibco) and incubated at 37° C. in 5% CO$_2$ incubator with shaking for 30 minutes. The samples were centrifuged in 2 mL centrifuge tubes at 1600 rpm for 2 minutes, the supernatant removed and 2 mL of DMEM without methionine or cysteine was added. An 80 μCi aliquot of $^{35}$S methionine-cysteine was added (Perkin Elmer Life Sciences) and the sample incubated at 37° C. in 5% CO$_2$ incubator with shaking for 30 minutes. The samples were centrifuged as above and the supernatant removed. A 50 μL aliquot of each supernatant were loaded in adjacent lanes onto an SDS-PAGE gel (Invitrogen, NuPage 4-12% Bis-Tris gel) and run at 100 volts for approximately 1.5 hours. The gel was fixed with 10% acetic acid and 30% ethanol, then soaked in enhancer (Enlightning, NEN Life Sciences) for 15 minutes. The gel was dried for 3 hours at 80° C. and the bands visualized by exposure to X-ray film. The results for two studies are shown in FIG. 10, indicating considerable protein synthesis in the uvrAB mutant strain while the parent strain shows limited protein synthesis.

Example 13

Comparison of S-59/UVA Inactivation with or without S-59 Present During Growth of *Listeria*

Two inactivation methods were compared with respect to inactivation of *Listeria monocytogenes* strains. In the first method, the *Listeria* was grown in BHI at 37° C. at 300 rpm overnight, then diluted 1:50 into BHI and grown at 37° C. at 300 rpm to an OD$_{600}$ of 0.7-1.00. These were centrifuged and suspended in PBS with 1% BSA to a level of $1\times10^9$/mL. S-59 was added to a level of 120 nM for the parent strain and 30 nM for the uvrAB mutant strain. The samples were incubated on ice for approximately 60 minutes, then transferred to a 150 mm Petri dish and irradiated at a dose of 6 J/cm$^2$ (FX1019). In the second method, the *Listeria* was similarly grown to an OD$_{600}$ of 0.5, at which point 50 mL of solution was transferred to a clean flask and S-59 was added to a level of 2500 nM for the parent strain and 200 nM for the uvrAB mutant strain. These samples were incubated at 37° C. at 300 rpm for approximately 1 hour (OD$_{600}$ approximately 1.0, approximately $1\times10^9$/mL). A 1 mL aliquot was removed to assess the titer and the remaining was transferred to a 150 mm Petri dish and irradiated as per the first method. The titer post irradiation was determined for each sample, resulting in essentially complete inhibition of proliferation for all samples (>8 log inactivated). In a study done with DP-L4029 vs. DP-L4029uvrAB, the entire sample containing approximately $1\times10^{11}$ bacteria treated by the second method, the entire sample was plated, indicating approximately 9 log kill for the parent strain and >10 log kill for the uvrAB mutant. The results on four different preparations of *Listeria* are given in Table 16.

TABLE 16

Inactivation of *Listeria monocytogenes* actA$^-$ and actA$^-$uvrAB$^-$ with S-59/UVA, measurement of entire sample to assess log titer inactivation.

| | Batch | Titer treated | Residual colonies | Log inactivation |
|---|---|---|---|---|
| actA$^-$ | 1 | $1.0 \times 10^{11}$ | 100 | 9 |
| 2.5 μM S-59 | 2 | $1.1 \times 10^{11}$ | 28 | 9.6 |
| 6 J/cm$^2$ | 3 | $1.1 \times 10^{11}$ | 200 | 8.7 |
| | 4 | $1.1 \times 10^{11}$ | 160 | 8.8 |
| actA-uvrAB$^-$ | 1 | $1.0 \times 10^{11}$ | 0 | 11 |
| 200 nM S-59 | 2 | $1.1 \times 10^{11}$ | 11 | 10 |

TABLE 16-continued

Inactivation of *Listeria monocytogenes* actA⁻ and actA⁻uvrAB⁻ with S-59/UVA, measurement of entire sample to assess log titer inactivation.

|  | Batch | Titer treated | Residual colonies | Log inactivation |
|---|---|---|---|---|
| 6 J/cm² | 3 | $1.1 \times 10^{11}$ | 0 | 11 |
|  | 4 | $1.1 \times 10^{11}$ | 1 | 11 |

Figure 12A:
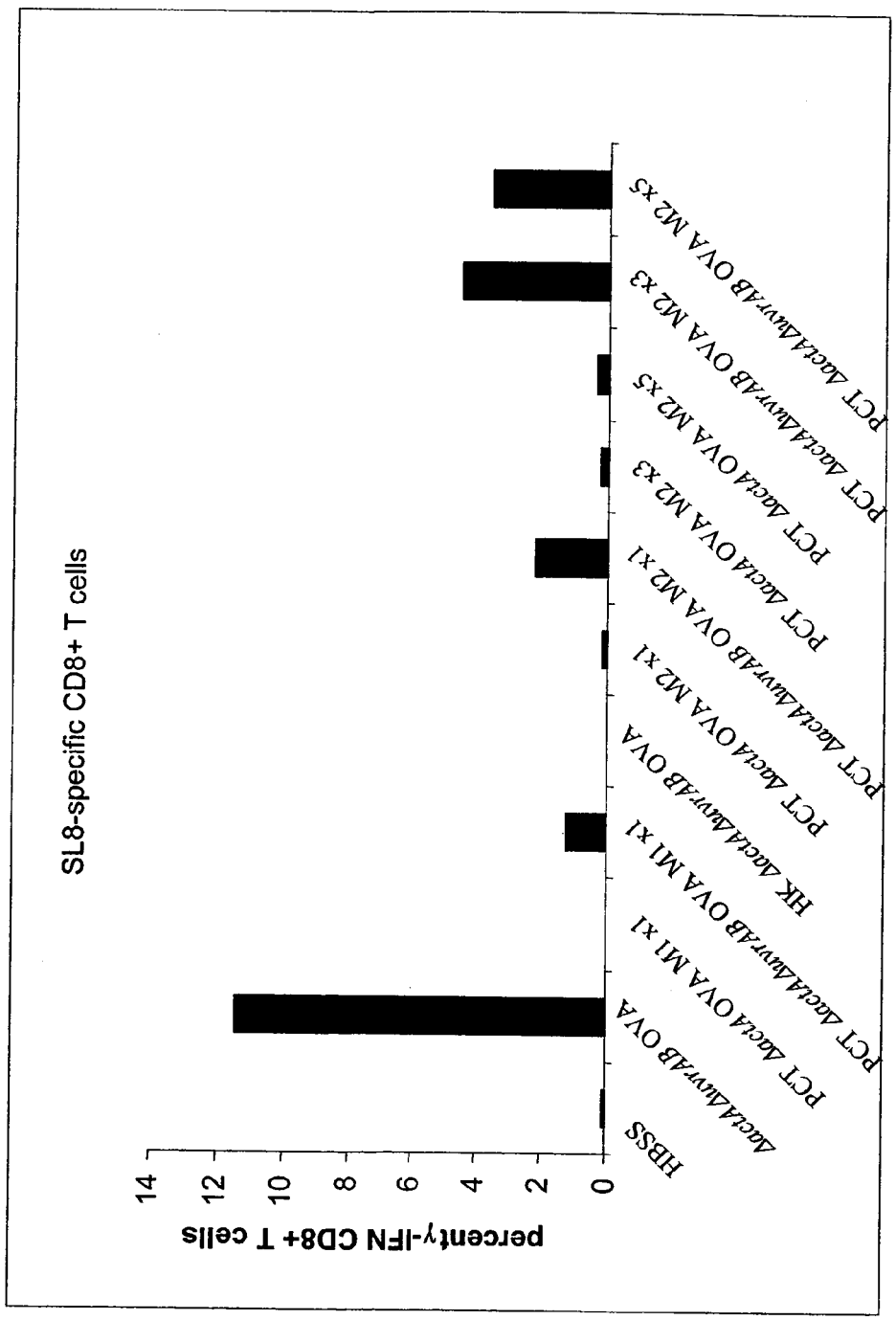
Figure 12B:
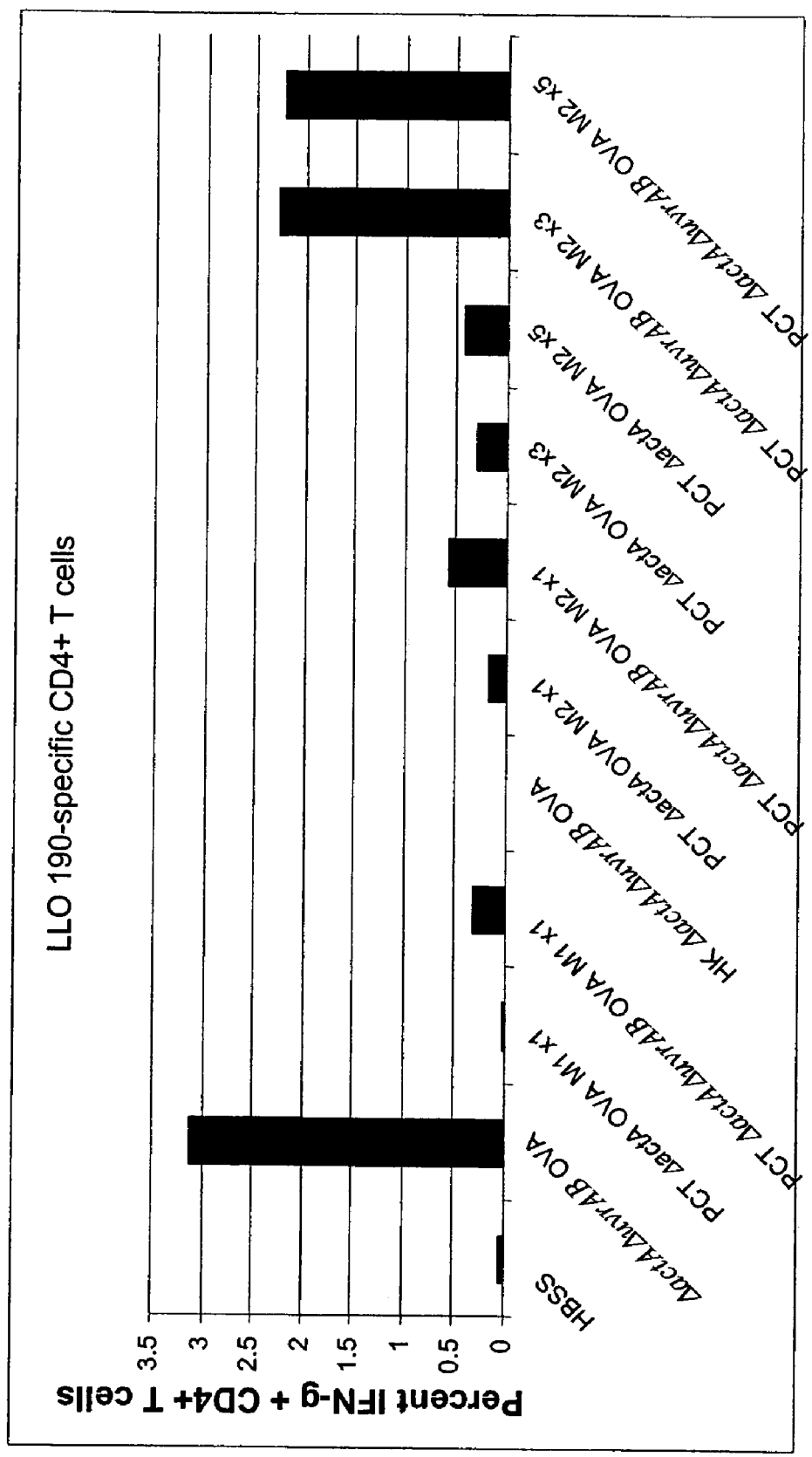
Figure 12C:
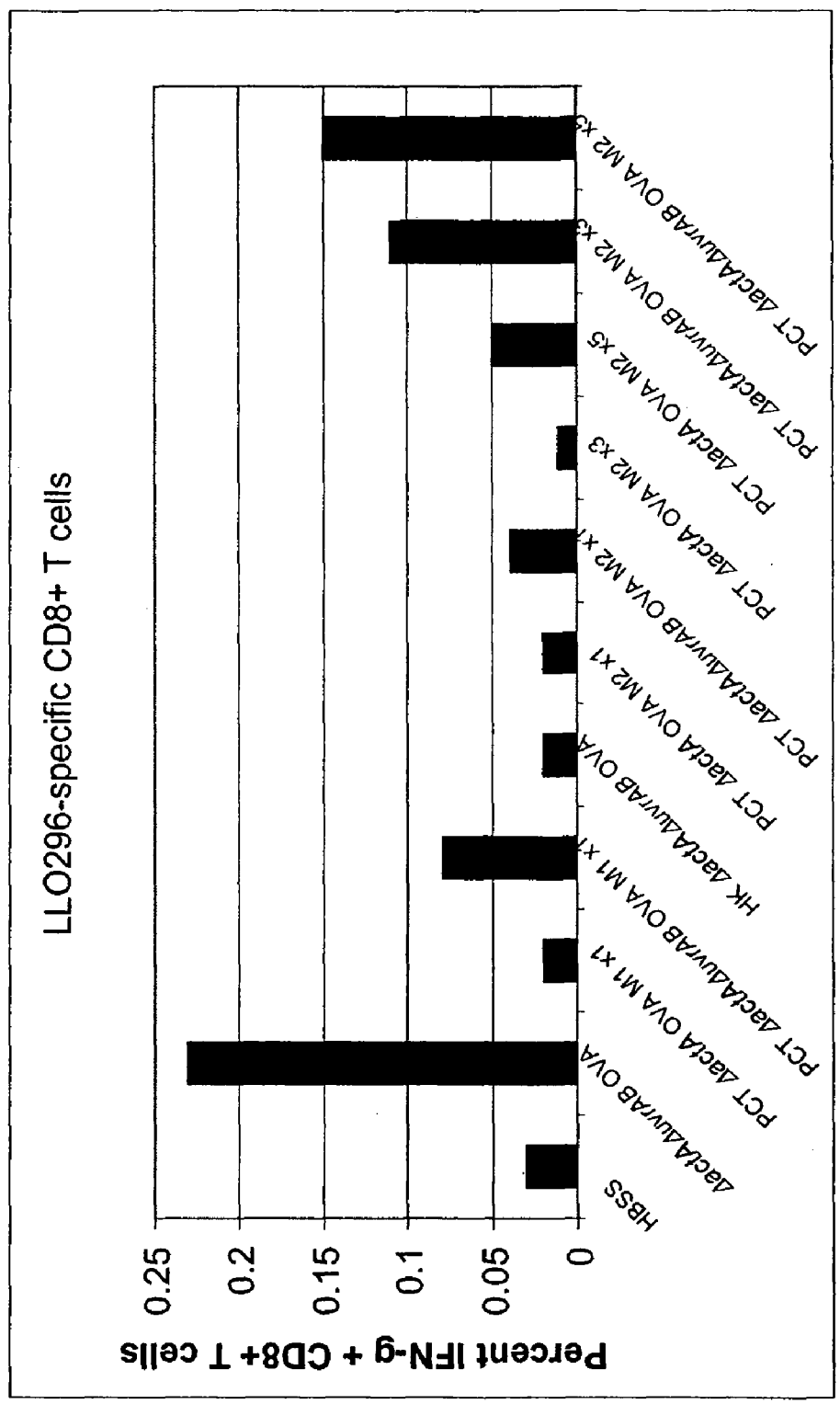

In one study, the two methods were compared using *Listeria monocytogenes* DP-L4029-OVA and DP-L4029 uvrAB-OVA. Samples were prepared as above and were centrifuged for 20 minutes at 2300×g, the supernatant removed and the bacteria washed once with PBS. After centrifuging and removing the PBS wash, the final pellet was resuspended in 8% DMSO in PBS, then quickly frozen in cryo-vials, either using liquid nitrogen or dry ice, and stored at −80° C. Sets of three mice (C57B1/6) were injected intravenously with $1\times10^8$ *Listeria* in 200 μL (frozen stock diluted approximately 1:40 into HBSS). In addition to the S-59/UVA treated strains, injections were made with live and heat killed DP-L4029 uvrAB-OVA, as well as HBSS control. For the comparison of the two S-59 methods, mice were injected at day 0. For the samples prepared by the second method, additional sets of mice were injected again either on days 2 and 3 or on days 2, 3, 4, and 5. All mice were sacrificed on day 7 post vaccination and the spleens removed for analysis. The spleen cells were assessed for an OVA specific immune response by ELISPOT assay as described in Example 5, stimulating the cell population with SL8 (OVA specific). The results are shown in FIG. 11A, indicating that the *Listeria* prepared by the second method, for both the parental strain and the uvrAB mutant, result in a more potent OVA specific immune response than for strains prepared by the first method. The ELISPOT assay was also done with stimulation using LLO class II antigen LLO190, or class I antigen LLO296. The ELISPOT results comparing all three antigens is shown in FIG. 11B, indicating that the LLO specific CD 4⁺ response is similar to the OVA specific response. The spleen cells were also assessed by ICS as described in Example 5, stimulating with either SL8, LLO190, or LLO296. The results are shown in FIGS. 12A-C, indicating a stronger immune response for both OVA and LLO in the second method. The data also demonstrates the improved response for the uvrAB strain over the parent strain. In both strains, additional vaccination on successive days results in improved response to both OVA and LLO antigens (1 vs. 3 days).

In another study, DP-L4029 and DP-L4029 uvrAB strains are assessed for their ability to provide protective immunity against a wild type challenge in mice. Balb/c mice were vaccinated in groups as described in Table 17 with HBSS, DP-L4056 wild type (+/−heat killed), DP-L4027 (LLO deletion), DP-L4029 S-59/UVA treated (first and second methods as above), DP-L4029uvrAB S-59/UVA treated (first and second methods as above). Twenty-seven days after the vaccination, three mice per group were challenged with $2\times LD_{50}$ and six mice per group with $100\times LD_{50}$ of wild type *Listeria monocytogenes*. Three days post challenge, the mice challenged with $2\times LD_{50}$ were sacrificed and the spleen and liver were isolated and cultured for growth of *Listeria*. The spleen or liver from each mouse was homogenized in sterile distilled water with 0.5% Triton X-100 (Sigma). Serial 10-fold dilutions were plated on BHI agar plates containing streptomycin (50 μg/mL) and incubated at 37° C. overnight. The number of colony forming units per spleen or liver was determined as an indication of immunity to the wild type challenge. FIGS. 13A,B show that S-59/UVA treated samples give approximately 3 log reduction in CFU per organ compared to HBSS (non-vaccinated) controls, with the samples prepared by the second method showing more reduction in CFU than those prepared with the first method. In addition, the treated uvrAB mutant strain shows slightly better CFU reduction than the treated parent strain. While the CFU reduction is not as good as vaccination with wild type, the S-59/UVA treated strains show some efficacy for reduction in CFU, which generally correlates with protective immunity. The six mice challenged with $100\times LD_{50}$ were monitored for survival for ten days, with only the mice vaccinated with wild type *Listeria* surviving.

TABLE 17

Dosing of Balb/c mice for assessment of protective immunity comparing two S-59/UVA methods.

| Vaccine composition | S-59/6 J/cm² UVA Method | Dose of vaccination (200 μL IV) |
|---|---|---|
| HBSS | — | — |
| DP-L4056 | — | $5 \times 10^3$ |
| DP-L4027 | — | $1 \times 10^8$ |
| DP-L4029 | Method 1 (120 nM S-59 in PBS) | $1 \times 10^8$ |
| DP-L4029 | Method 2 (2500 nM S-59 in BHI) | $1 \times 10^8$ |
| DP-L4029uvrAB | Method 1 (30 nM S-59 in PBS) | $1 \times 10^8$ |
| DP-L4029uvrAB | Method 2 (200 nM S-59 in BHI) | $1 \times 10^8$ |
| DP-L4056 heat killed | — | $1 \times 10^9$ |

An additional study was done in Balb/c mice using HBSS, DP-L4056 wild type (+/−heat killed), DP-L4027 (LLO deletion), DP-L4406actA (actA/inlB deletion double mutant, deposited on Oct. 3, 2003, ATCC number PTA-5562) DP-L4029+S-59/UVA (second method), DP-L4029uvrAB+/−S-59/UVA treated (second method only) or +heat killed, where vaccination was done daily for 1, 3, or 5 days for S-59 and heat killed strains. The dosing is summarized in Table 18. Twenty-nine days post the first vaccination, three mice from each group were challenged with $20\times LD_{50}$, and six from each group were challenged with $100\times LD_{50}$ of wild type *Listeria monocytogenes*. These mice were monitored for survival for ten days. Thirty-two days post first vaccination, three additional mice from each group were challenged with $2\times LD_{50}$ of wild type and three days later sacrificed and the spleen and liver were isolated and cultured for growth of *Listeria*. In addition, the anti-*Listeria* antibody titer of the mice sera was assessed by doing an ELISA assay. Frozen, ground *Listeria* in a sodium bicarbonate buffer was plated and incubated with serum from the vaccinated mice with serial dilutions, then bound antibody was detected with goat anti-mouse antibody conjugated to HRP. An HRP substrate was added and the level of antibody determined by quantitatively measuring the color change. These were compared to naïve mice to assess *Listeria* specific antibody, where a sample was considered positive for *Listeria* if greater than one standard deviation above the measurement of a naïve serum sample. The CFU per spleen or liver results are shown in FIGS. 14A,B, the anti-Listeria antibody titer is shown in FIG. 15, and the survival results are shown in FIG. 16. This study demonstrates good CFU reduction and protective immunity of the S-59 treated uvrAB strain with 3 or 5 vaccinations, approaching that of the untreated uvrAB strain, and is nearly as effective as the wild type strain.

TABLE 18

Dosing of Balb/c mice for assessment of protective immunity, multiple vaccinations with S-59/UVA treated strains.

| Vaccine composition | Treatment | Days vaccinated | Dose of vaccination (200 µL IV) |
|---|---|---|---|
| HBSS | — | 1 | — |
| DP-L4056 | — | 1 | $5 \times 10^3$ |
| DP-L4056 heat killed | — | 1 | $1 \times 10^9$ |
| DP-L4029 | S-59 Method 2 | 1 | $1 \times 10^8$ |
| DP-L4029uvrAB | S-59 Method 2 | 1 | $1 \times 10^8$ |
| DP-L4029uvrAB | S-59 Method 2 | 3 | $1 \times 10^8$ (day 0) $2 \times 10^7$ (day 2-3) |
| DP-L4029uvrAB | S-59 Method 2 | 5 | $1 \times 10^8$ (day 0) $4 \times 10^7$ (day 2-5) |
| DP-L4029uvrAB | — | 1 | $5 \times 10^6$ |
| DP-L4029uvrAB | Heat killed | 1 | $1 \times 10^9$ |
| DP-L4029uvrAB | Heat killed | 3 | $1 \times 10^9$ (day 0) $2 \times 10^8$ (day 2-3) |
| DP-L4029uvrAB | Heat killed | 5 | $1 \times 10^9$ (day 0) $4 \times 10^8$ (day 2-5) |
| DP-L4027 | — | 1 | $1 \times 10^8$ |
| DP-L4406actA | — | 1 | $5 \times 10^7$ |

Example 14

Demonstration of Breaking of Immune Tolerance Using S-59/UVA Treated Strains in a Mouse Model DP-L4029 and DP-L4029 uvrAB strains expressing Gp-70-AH1A5 and OVA were S-59/UVA treated according to the second method of Example 13. Gp-70 is an autologous mouse antigen that is expressed by CT-26 tumor cells. The AH1A5 is a single base mutation of the natural sequence which has been shown to induce an immune response when expressed in live strains (AH1 peptide is SPSYVYHQF (SEQ ID NO:20), AH1A5 peptide is SPSYAYHQF (SEQ ID NO:21)). In a prophylactic immunization study, Balb/c mice were vaccinated intravenously (100 µL) in groups of 8 mice according to Table 19 (day 7 post the first set of vaccinations, 3 mice per group were sacrificed and the spleens harvested). At day 21 post initial vaccination, the remaining 5 mice per group were injected intravenously with $1 \times 10^5$ CT-26 colon epithelial tumor cells (ATCC) and monitored for survival.

TABLE 19

Vaccine strains and treatment regimen.

| Group | Vaccine strain | Treatment | Dosing day | Dose per injection |
|---|---|---|---|---|
| 1 | HBSS control | — | 0, 14, 15 | — |
| 2 | DP-L4029 | — | 0, 14, 15 | $1 \times 10^7$ |
| 3 | DP-L4029 AH1A5/OVA | — | 0, 14, 15 | $1 \times 10^7$ |
| 4 | DP-L4029 AH1A5/OVA | Heat killed | 0, 14 | $3 \times 10^8$ |
| 5 | DP-L4029 AH1A5/OVA | Heat killed | 0, 1, 2, 14 | $1 \times 10^8$ |
| 6 | DP-L4029 AH1A5/OVA | S-59/UVA | 0, 14 | $3 \times 10^7$ |
| 7 | DP-L4029 AH1A5/OVA | S-59/UVA | 0, 1, 2, 14 | $1 \times 10^7$ |
| 8 | DP-L4029 uvrAB AH1A5/OVA | — | 0, 14, 15 | $1 \times 10^7$ |
| 9 | DP-L4029 uvrAB AH1A5/OVA | Heat killed | 0, 14 | $3 \times 10^8$ |
| 10 | DP-L4029 uvrAB AH1A5/OVA | Heat killed | 0, 1, 2, 14 | $1 \times 10^8$ |
| 11 | DP-L4029 uvrAB AH1A5/OVA | S-59/UVA | 0, 14 | $3 \times 10^7$ |
| 12 | DP-L4029 uvrAB AH1A5/OVA | S-59/UVA | 0, 1, 2, 14 | $1 \times 10^7$ |

The T cell population of the harvested spleen cells was assessed by ICS according to Example 5, using LLO91, AH1, AH1/A5 peptides or P815 and CT26 cells (completely inactivated with 150 mM S-59 and 3 J/cm² UVA) to stimulate the cells. The P815 cells serve as a negative control for CT26 whole cell stimulation, as the P815 does not express gp70 antigen. The results are shown in FIG. 17, indicating that the treated uvrAB mutants result in an AH1A5 or AH1 specific response that can be improved with additional vaccinations. The cells were also assessed by ELISPOT assay according to Example 5. The cells were stimulated with either AH1A5 or AH1 peptides. The results are shown in FIGS. 18A, B indicating an immune response to both the AH1A5 and the AH1 with the uvrAB mutant strains.

Example 15

Therapeutic Vaccination of Mice Using Psoralen Attenuated *Listeria* Strains with uvrAB Deletion Using C57Bl/6 mice, B16.F10.MO5.10.H3 (OVA⁺, this is a subclone of the cells used in Example 4 which have increased homogeneity for OVA expression) melanoma tumor cells were injected into the mice ($1 \times 10^6$ in 100 µL HBSS IV) to establish lung metastases. *Listeria monocytogenes* strains DP-L4029-OVA, DP-L4027-OVA, DP-L4038-OVA (actA/461T double mutant), and DP-L4029uvrAB-OVA were used for vaccinating groups of ten mice. The DP-L4029uvrAB-OVA strain was used with and without S-59 treatment (>8 log kill by first method of Example 13) and heat killed DP-L4029-OVA was used as a control along with HBSS only. The mice were vaccinated (100 µL IV in HBSS) on day 3 post tumor implant with the dose given in Table 20. Thirty days post tumor implant, five mice per group were sacrificed and the lungs harvested. The number of metastases per lung were counted. The remaining five mice per group were monitored for survival. The number of lung metastases and median survival days are indicated in Table 20. The lungs for the actA⁻, actA⁻ OVA, and actA⁻ uvrAB⁻ OVA S-59/UVA treated and heat killed are shown in FIG. 19A, number of lung metastases plotted in FIG. 19B, and the survival is plotted in FIG. 19C. This data shows that the S-59/UVA treated uvrAB mutant can be administered as a therapeutic vaccine, resulting in significantly reduced lung metastases and extended survival compared to non-vaccinated, heat killed control, or DP-L4029 without OVA.

TABLE 20

Therapeutic vaccination of mice in an OVA lung tumor model.

| Vaccine strain | Dose (CFU) | Mean # of lung mets per lung | Median survival days |
|---|---|---|---|
| HBSS | — | 173 | 34 |
| DP-L4029 | $2 \times 10^7$ | 81 | 39 |
| DP-L4029-OVA | $2 \times 10^7$ | 3 | 51 |
| DP-L4029-OVA heat killed | $1 \times 10^9$ | 250 | 32 |
| DP-L4029uvrAB-OVA | $2 \times 10^7$ | 3 | 53 |
| DP-L4029uvrAB-OVA | $2 \times 10^5$ | 4 | 45 |
| DP-L4029uvrAB-OVA (S-59) | $1 \times 10^9$ | 11 | 45 |
| DP-L4029uvrAB-OVA (S-59) | $2 \times 10^5$ | 134 | 36 |
| DP-L4027-OVA | $2 \times 10^7$ | 2 | 48 |
| DP-L4038-OVA | $2 \times 10^7$ | 52 | 51 |

Example 16

Figure 20A:
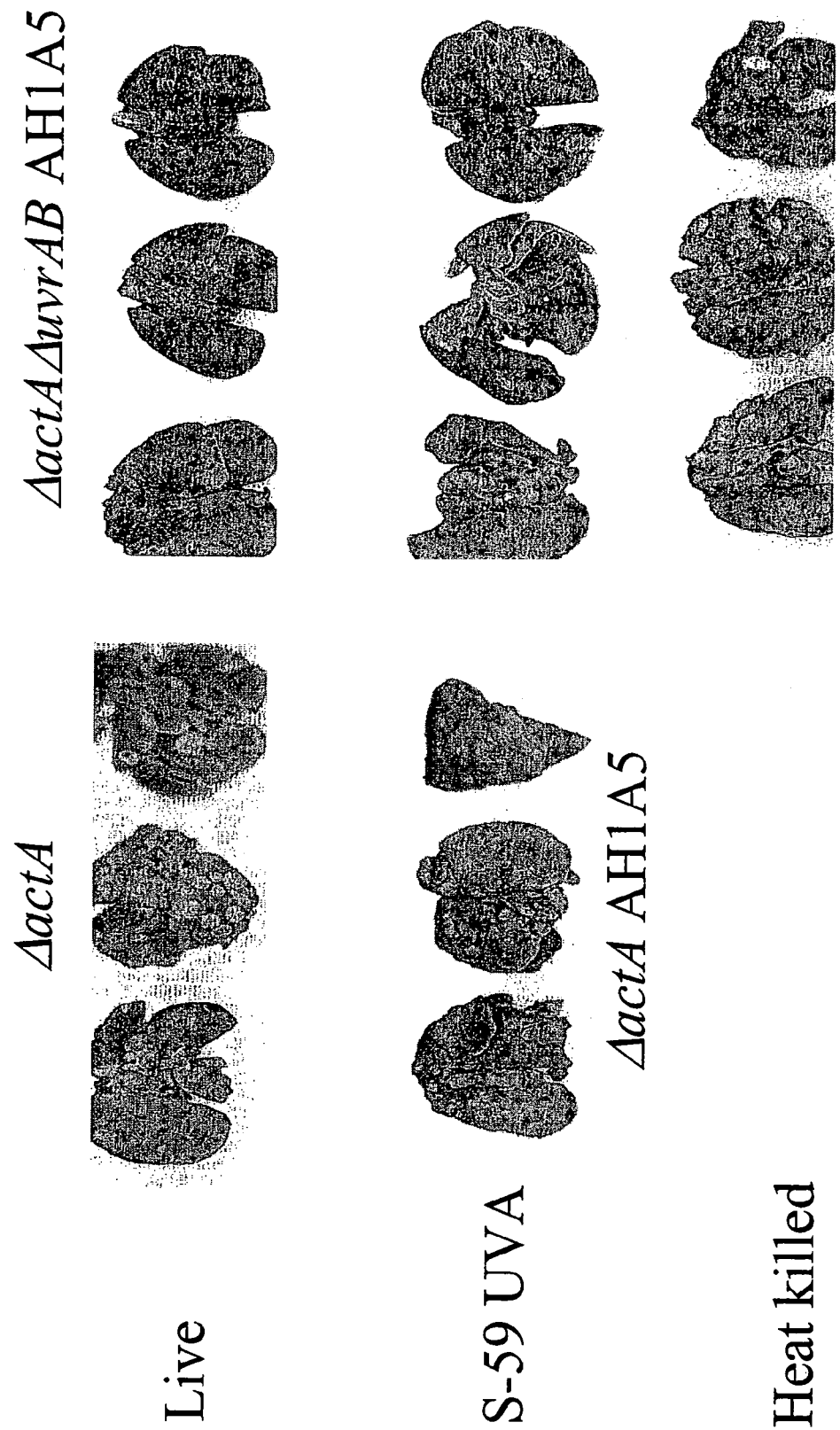
Figure 20B:
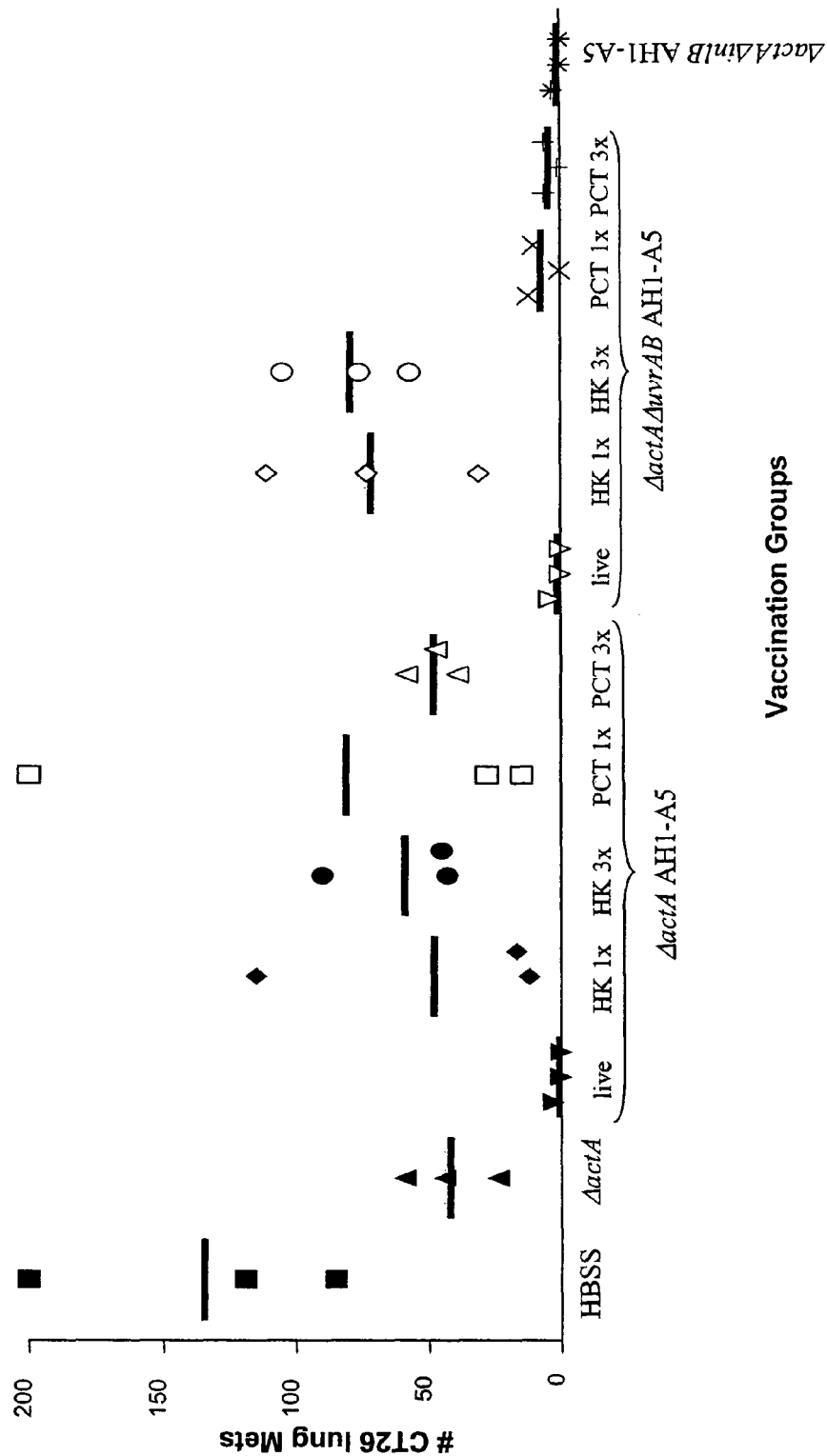
Figure 20C:
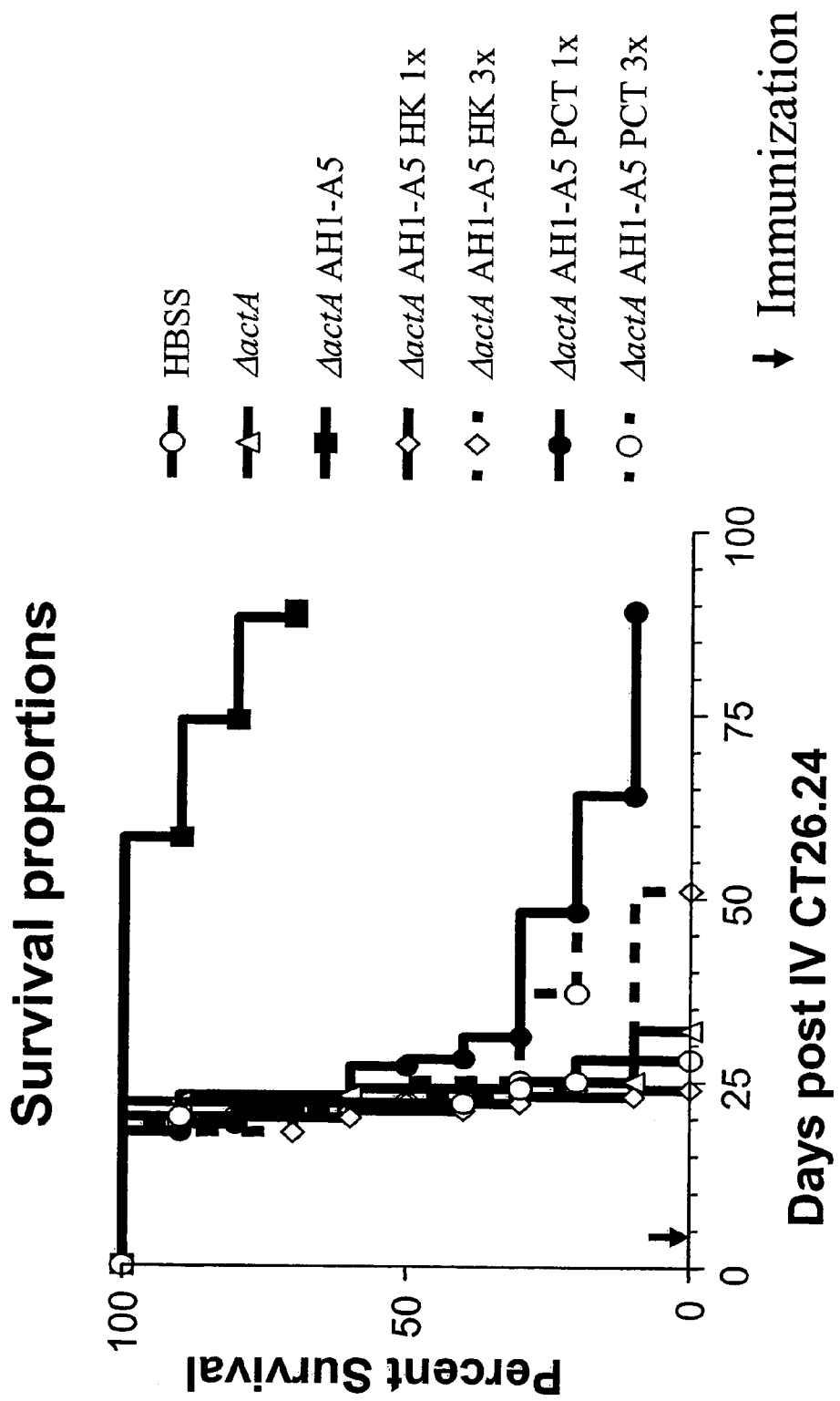
Figure 20D:
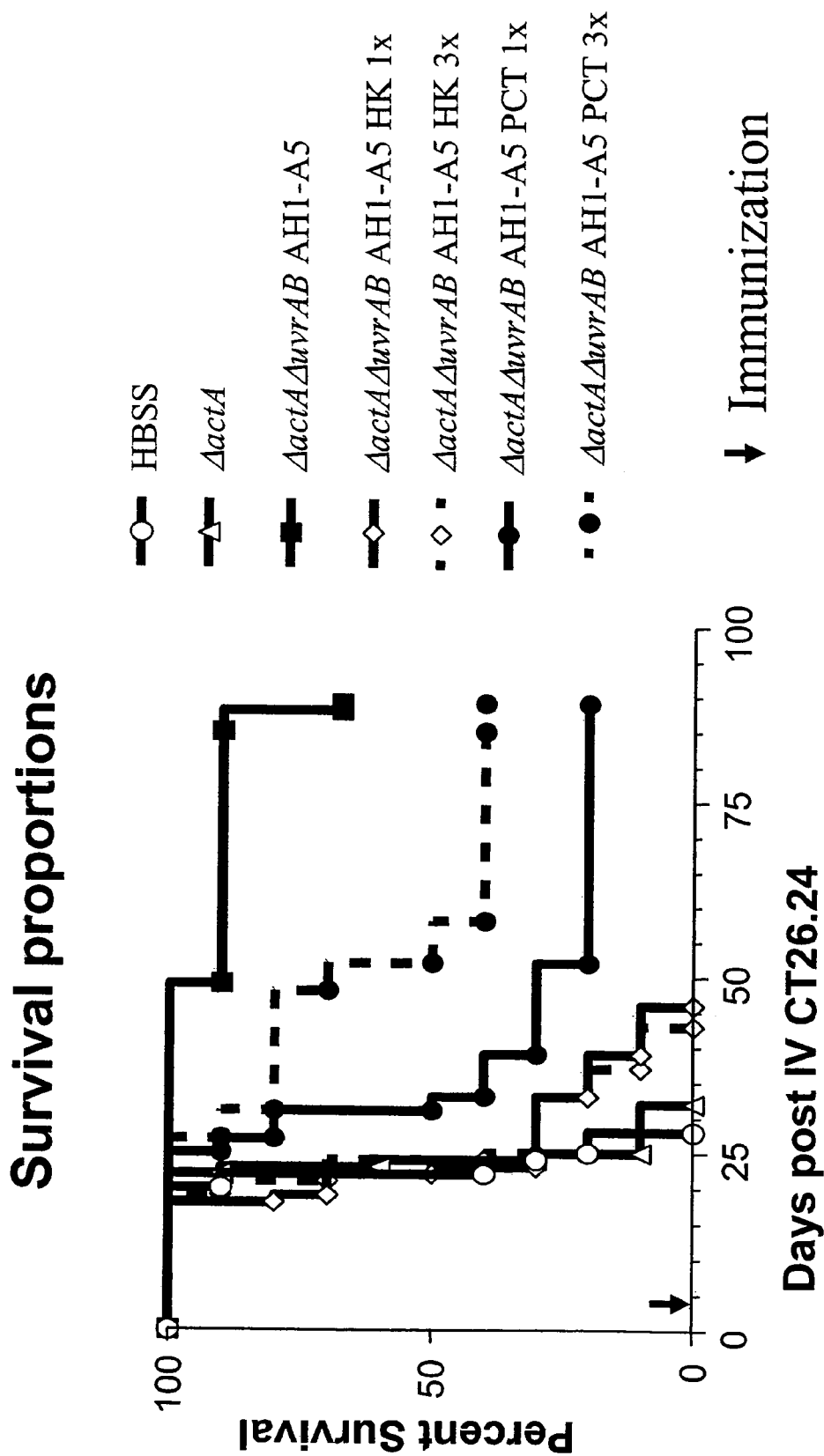

Therapeutic Vaccination with S-59 Inactivated *Listeria* Strains Expressing gp70 Mouse Antigen Using Balb/c mice, CT26 tumor cells (which express AH1) modified to express a human antigen (the human antigen being irrelevant for this experiment) were injected into the mice ($2 \times 10^5$ in 100 µL IV in HBSS) to establish lung metastases. *Listeria monocytogenes* strains DP-L4029, DP-L4029-AH1A5, DP-L4029uvrAB-AH1A5, and DP-L4406actA-AH1A5(actA/inlB double mutant) were used for vaccinating groups of thirteen mice. The AH1A5 strains also express the OVA antigen. The DP-L4029uvrAB-AH1A5 strain was used without treatment, heat killed, or S-59 treated (per second method of Example 13). The mice were vaccinated (100 µL HBSS IV) beginning 4 days after the tumor implant according to Table 21. Nineteen days post tumor implant, three mice per group were sacrificed and the lungs harvested. The number of metastases per lung were counted. The remaining ten mice per group were monitored for survival. The results for the lung metastases are shown in FIG. 20A (lung pictures) and 20B (number of lung metastases plotted) and survival is indicated in Table 21 and FIG. 20C (ΔactA samples) and 20D (ΔactAΔuvrAB samples). The AH1A5 antigen is endogenous to the mice, such that any immunization effect would be breaking immune tolerance in the mice. The results indicate that the S-59 treated uvrAB mutant strain is able to break tolerance in the mice, resulting in significantly reduced lung metastases and extended survival. The therapeutic effect is improved when the vaccine is dosed over three days compared to a single vaccination (total dose delivered over three days is equal to the single day).

TABLE 21

Therapeutic vaccination of mice using *Listeria* modified to express AH1A5.

| Vaccination strain | Vaccination days | Dose (CFU) | Med. Survival (days) | # survivors day 43 |
|---|---|---|---|---|
| HBSS | Day 4 | — | 22 | 0 |
| DP-L4029 | Day 4 | $1 \times 10^7$ | 24 | 0 |
| DP-L4029-AH1A5 | Day 4 | $1 \times 10^7$ | >43 | 10 |
| DP-L4029-AH1A5 heat killed | Day 4 | $3 \times 10^8$ | 21 | 0 |
| DP-L4029-AH1A5 heat killed | Day 4, 5, 6 | $1 \times 10^8$ | 22.5 | 1 |
| DP-L4029-AH1A5 S-59/UVA | Day 4 | $3 \times 10^7$ | 27.5 | 3 |
| DP-L4029-AH1A5 S-59/UVA | Day 4, 5, 6 | $1 \times 10^7$ | 23.5 | 2 |
| DP-L4029uvrAB-AH1A5 | Day 4 | $1 \times 10^7$ | >43 | 10 |
| DP-L4029uvrAB-AH1A5 heat killed | Day 4 | $3 \times 10^8$ | 23 | 1 |
| DP-L4029uvrAB-AH1A5 heat killed | Day 4, 5, 6 | $1 \times 10^8$ | 24 | 1 |
| DP-L4029uvrAB-AH1A5 S-59/UVA | Day 4 | $3 \times 10^7$ | 31 | 4 |
| DP-L4029uvrAB-AH1A5 S-59/UVA | Day 4, 5, 6 | $1 \times 10^7$ | >43 | 8 |
| DP-L4406actA-AH1A5 | Day 4 | $1 \times 10^7$ | >43 | 10 |

Example 17

Evaluation of S-59/UVA Treated *Listeria monocytogenes* Localization in Dendritic Cells Using Fluorescence Microscopy The uptake and distribution of *Listeria monocytogenes* within an antigen presenting cell was evaluated by fluorescence microscopy. The dendritic cell line DC 2.4 was cultured on coverslips in a Petri dish at $5 \times 10^5$ cells per dish in complete RPMI media, RPMI-1640 (Gibco) supplemented with 10% FBS (Hyclone), 1× Non-Essential Amino Acids (Cellgro), $5 \times 10^4$ I.U. Penecillin/$5 \times 10^4$ µg Streptomycin (Irvine Scientific), 2 mM L-glutamine (Irvine Scientific) and 1 nM Sodium Pyruvate (Sigma), and incubated overnight at 37° C. (this could be done similarly with other cell lines, e.g. macrophage J774). Stationary phase cultures of *Listeria* strains (DP-L4056, DP-L4027 (LLO-) and DP-L4056uvrAB) were prepared by seeding 3 mL of BHI media with a bacterial colony and growing at 30° C. overnight.

The overnight cultures of *Listeria* were diluted 1:20 in fresh BHI media and stationary phase cultures at 30° C. were grown to an $OD_{600}$ of 0.5-0.6. Approximately 1 mL of the overnight cultures for the DP-L4056 and DP-L4056uvrAB strains were also heat killed at 72° C. for 3-4 hrs. Frozen stocks of psoralen inactivated DP-L4056 and DP-L4056uvrAB *Listeria*, prepared according to the second method of Example 13, were thawed and allowed to recover in stationary phase at 37° C. for 1 hr. Prior to infection, $OD_{600}$ readings of all *Listeria* preparations were obtained, the number of DC 2.4 cells per coverslip were counted and Multiplicity of Infection (MOI, number of bacteria per DC 2.4 cell) for each strain were calculated. Fresh log phase cultures were used to infect cells at an MOI of 5, heat-killed cultures were used at an MOI of 20 and S-59/UVA treated strains at an MOI of 10.

The coverslips were transferred to a 24 well dish and washed 3 times with RPMI lacking Pen/Strep and appropriate dilutions of the *Listeria* strains to give the desired MOI were incubated with the cells in Pen/Strep free media for 30 mins at 37° C. The coverslips were then washed 3 times with Pen/Strep free media and incubated at 37° C. for another 30 mins. At the end of the incubation, the coverslips were washed and incubated in media with 50 µg/ml Gentamycin for 4 hrs at 37° C. Coverslips were then washed in PBS and fixed in 3.5% formaldehyde/PBS for 15 mins at room temperature. Post fixation, coverslips were washed/permeablized with TBS-Tx buffer (25 mM Tris-HCl pH 8.0, 150 mM NaCl, 0.1% Triton X-100) and blocked in 1% BSA/TBS-Tx for 15 mins at room temperature. Coverslips were stained with Rabbit anti-Listeria 0 antigen anti-serum (Difco) for 30 minutes at room temperature and washed in TBS-Tx buffer. Samples were then stained with Fluorescein labeled anti-rabbit secondary antibody (Vector Laboratories) and actin was stained with Rhodamine-Phalloidin (Molecular Probes). Coverslips were washed in TBS-Tx and mounted on slides in VectaShield+DAPI-hardset (Vector Laboratories) in order to stain for cell nuclei. Slides were allowed to dry for at least 8 hrs and cells were visualized on a Nikon TE300-U inverted microscope. Images were taken using a CCD Hamamatsu C4742-95-12NR camera and analyzed using Image-Pro software from Phase 3 Imaging Systems.

Three images were taken for each field; one using a UV-2E/C filter (CHROMA Technology Corp, visualizes DAPI/nuclei), a second with a HYQ TRITC filter (CHROMA Technology Corp, visualizing actin) and a third using a B-1A (HYQ-FITC) filter (CHROMA Technology Corp, visualizing *Listeria*). The three images were then merged to determine if staining for *Listeria* co-localizes with staining for actin. *Listeria* that were unable to escape the phagolysosome appear green while those that were able to escape into the cytosol were able to nucleate actin and therefore appeared yellow due to the co-localization of actin (red) and *Listeria* (green). In order to quantitate the percentage of *Listeria* that was able to escape the lysosome, the total number of *Listeria* in the field were counted and the number of *Listeria* that appeared yellow were determined by counting yellow bacteria or by confirming the presence of the actin from the rhodamine image (see FIG. 21A). The number of *Listeria* that escaped the phagolysosome were divided by the total number of *Listeria* counted and the percentage of phagolysosomal escape was calculated, as reported in Table 22 and represented in FIG. 21B. The results indicate that the heat killed strains and the S-59/UVA treated wild type strain behave like the LLO⁻ strain, i.e. can not escape the phagolysosome, while the uvrAB mutant that is S-59/UVA treated shows substantial ability to escape the phagolysosome.

TABLE 22

Percentage of *Listeria* escaping the phagolysosome for DP-L4056 (+/−S-59/UVA, heat killed), DP-L4027, and DP-L4056uvrAB (+/−S-59/UVA, heat killed).

| Listeria Strain | Treatment | Listeria counted | Cytoplasmic Listeria | % Phagolysosomal escape |
|---|---|---|---|---|
| DP-L4056 | none | 855 | 521 | 61 |
| DP-L4056 | Heat killed | 189 | 0 | 0 |
| DP-L4056 | S-59/UVA | 642 | 1 | 0.16 |
| DP-L4056 uvrAB | none | 795 | 470 | 59 |
| DP-L4056 uvrAB | Heat killed | 162 | 0 | 0 |
| DP-L4056 uvrAB | S-59/UVA | 1047 | 493 | 46.9 |
| DP-L4027 | none | 343 | 5 | 1.4 |

Example 18

Visualization of S-59 UVA Treated *Listeria monocytogenes* uvrAB⁻ Strains Using Gram Stain Wild-type and uvrAB⁻ strains of *Listeria monocytogenes* were grown to an $OD_{600}$ of 0.5, at which point 50 mL of solution was transferred to a clean flask and S-59 was added to a level of 2500 nM for the wild-type strain and 200 nM for the uvrAB⁻ mutant strain. These samples were incubated at 37° C. at 300 rpm for approximately 1 hour ($OD_{600}$ approximately 1.0, approximately $1\times10^9$/mL). A 1 mL aliquot was removed to assess the titer and the remaining was transferred to a 150 mm Petri dish and irradiated at a UVA dose of 6 J/cm2 (FX-1019), resulting in >8 log inactivation for both strains. The treated strains were stored frozen as described in Example 13. These were thawed and diluted 1:10 into BHI medium in a 15 mL tube at a concentration of approximately $1-2\times10^9$ per mL. These were incubated at 37° C. at 300 rpm and aliquots were removed at 0, 2, 4, 6, 8 hours and overnight (approximately 18 hours). The aliquots were spread on glass slides (approximately 50 µL) and allowed to air dry. The smear was heat fixed by passing through a flame three times, then allowed to cool before Gram staining using Fisher Gram Stain Set (catalog #282-407). The slides were viewed on a microscope and photographed and the negative images are shown in FIG. 22. This clearly demonstrates the unique nature of the treated repair deficient strain, which shows chains indicating gene expression but is not able to divide such that the bacteria do not proliferate.

Example 19

Construction of Additional Mutant *Listeria* Strains

Preparation of mutant *Listeria* strains. *Listeria* strains were derived from 10403S (Bishop et al., *J. Immunol.* 139:2005 (1987)). *Listeria* strains with in-frame deletions of the indicated genes were generated by SOE-PCR and allelic exchange with established methods (Camilli, et al, *Mol. Microbiol.* 8:143 (1993)). The mutant strain LLO L461T (DP-L4017) was described in Glomski, et al, *J. Cell. Biol.* 156: 1029 (2002), incorporated by reference herein. The actA⁻ mutant (DP-L4029) is the DP-L3078 strain described in Skoble et al., *J. of Cell Biology,* 150: 527-537 (2000), incorporated by reference herein in its entirety, which has been cured of its prophage. (Prophage curing is described in (Lauer et al., *J. Bacteriol.* 184:4177 (2002); U.S. Patent Publication No. 2003/0203472).) The LLO⁻ mutant (DP-L4027) (Lauer et al., *J. of Bacteriology,* 184:4177-4186 (2002)), and LLO Δ26 (DP-L4042) (Decatur et al, *Science* 290:992 (2000)) were also described previously. Construction of an actA⁻uvrAB⁻ strain is described in the copending U.S. provisional application 60/446,051, filed Feb. 6, 2003, as L4029/uvrAB (see, e.g. Example 7 of that application). DP-L4029uvrAB (actA⁻/uvrAB⁻) was deposited with ATCC Oct. 3, 2003, assigned PTA-5563.

Construction of pKSV7-dl inlB for deletion of inlB from *Listeria* by allelic exchange. Deletion of inlB from *Listeria* DP-L4029 (or from other selected mutant strains or from wild-type *Listeria*) can be effected by allelic exchange, as described by Camilli et al., *Mol. Microbiol.* 8:143-147 (1993). Overlapping PCR can be used to prepare the construct used in the allelic exchange procedure. The source of the internalin B gene is the sequence listed as Genbank accession number AL591975 (Listeria monocytogenes strain EGD, complete genome, segment 3/12; inlB gene region: nts. 97008-98963) and/or the sequence listed as Genbank accession no. NC_003210 (*Listeria monocytogenes* strain EGD, complete genome, inlB gene region; nts. 457008-458963) both of which are incorporated by reference herein in their entirety.

In the primary PCR reactions, approximately 1000 bps of sequence upstream and downstream from the *Listeria* inlB gene 5' and 3' ends, respectively, are amplified using the following template and primers:

Template: DP-L4056 or DP-L4029 genomic DNA

Primer pair 1 (For amplification of region upstream from 5' end of inlB):

Lm-96031F: 5'-GTTAAGTTTCATGTGGACGGCAAAG (SEQ ID NO:22) ($T_m$: 72° C.)

Lm-(3' inlB-R +) 97020R:

5'-<u>AGGTCTTTTTCAGTTAAC</u>TATCCTCTCCTTGATTCTA

GTTAT (SEQ ID NO:23) ($T_m$: 114° C.)

(The underlined sequence complementary to region downstream of InlB carboxy terminus.)

(Amplicon Size (bps): 1007)

Primer pair 2 (For amplification of region downstream from 3' end of inlB):

Lm-(5' inlB-F +) 98911F:

5'-<u>CAAGGAGAGGATAGT</u>TAACTGAAAAAGACCTAAAAAA

GAAGGC (SEQ ID NO:24) ($T_m$: 118° C.)

(The underlined sequence is

```
-continued
    complementary to region upstream of InlB amino terminus.)

Lm-99970R:  5'-TCCCCTGTTCCTATAATTGTTAGCTC (SEQ ID NO:25)  ($T_m$: 74° C.)

(Amplicon size (bps): 1074)
```

In the secondary PCR reaction, the primary PCR amplicons are fused through overlapping PCR, taking advantage of complementarity between reverse primer from pair 1 and the forward primer of pair 2. This results in precise deletion of inlB coding sequence: nts. 97021-98910=1889 bps. The following template and primers were utilized in the secondary PCR reaction:

```
Template: Cleaned primary PCR reactions
Primer pair:

Lm-96043F:  5'-GTGGACGGCAAAGAAACAACCAAAG (SEQ ID NO:26)  ($T_m$: 74° C.)

Lm-99964R:  5'-GTTCCTATAATTGTTAGCTCATTTTTTTC (SEQ ID NO:27)  ($T_m$: 74° C.)

(Amplicon size (bps): 2033)
```

A protocol for completing the construction process is as follows:

The primary PCR reactions (3 temperature cycle) are performed using Vent DNA polymerase (NEB) and 10 µl of a washed 30° C. *Listeria* DP-L40560R DP-L4029 overnight culture. The expected size of *Listeria* amplicons by 1% agarose gel (1007 bps and 1074 bps). The primary PCR reactions are gel purified and the DNA eluted with GeneClean (BIO 101).

A secondary PCR reaction is performed, utilizing approximately equal amounts of each primary reaction as template (ca. 5 µl). The expected size of the *Listeria* amplicon from the secondary PCR reaction is verified by 1% agarose gel (2033 bps). Adenosine residue are added at the 3' ends of *Listeria* dl inlB amplicon with Taq polymerase.

The *Listeria* dl inlB amplicon is then inserted into a pCR2.1-TOPO vector. The pCR2.1-TOPO-dl inlB plasmid DNA is digested with XhoI and KpnI and the 2123 bp fragment is gel purified. The KpnI/XhoI 2123 bp fragment is inserted into a pKSV7 vector that has been prepared by digestion with KpnI and XhoI and treatment with CIAP (pKSV7-dl inlB). The fidelity of dl inlB sequence in pKSV7-dl inlB is then verified. The inlB gene is deleted from desired *Listeria* strains by allelic exchange with pKSV7-dl inlB plasmid.

Construction of antigen-expressing strains. Mutant *Listeria* strains expressing a truncated form of a model antigen ovalbumin (OVA), the immunodominant epitope from mouse colorectal cancer (CT26) known as AH1 (SPSYVYHQF; SEQ ID NO:20), and the altered epitope AH1-A5 (SPSYAYHQF; SEQ ID NO:21; Slansky et al., *Immunity*, 13:529-538 (2000)) were prepared. The pPL2 integrational vector (Lauer et al., *J. Bacteriol.* 184:4177 (2002); U.S. Patent Publication No. 2003/0203472) was used to derive OVA and AH1-A5/OVA recombinant *Listeria* strains containing a single copy integrated into an innocuous site of the *Listeria* genome.

Construction of OVA-expressing *Listeria* (DP-L4056). An antigen expression cassette consisting of hemolysin-deleted LLO fused with truncated OVA and contained in the pPL2 integration vector (pPL2/LLO-OVA) is first prepared. The *Listeria*-OVA vaccine strain is derived by introducing pPL2/LLO-OVA into the phage-cured *L. monocytogenes* strain DP-L4056 at the PSA (Phage from ScottA) attachment site tRNA$^{Arg}$-attBB'.

PCR is used to amplify the hemolysin-deleted LLO using the following template and primers:

```
Source: DP-L4056 genomic DNA

Primers:

Forward (KpnI-LLO nts. 1257-1276):

5'-CTCTGGTACCTCCTTTGATTAGTATATTC (SEQ ID NO:28)

($T_m$: LLO-spec: 52° C. Overall: 80° C.)

Reverse (BamHI-XhoI-LLO nts. 2811-2792):

5'-CAATGGATCCCTCGAGATCATAATTTACTTCATCCC (SEQ ID NO:29)

($T_m$: LLO-spec: 52° C. Overall: 102° C.)
```

PCR is also used to amplify the truncated OVA using the following template and primers:

```
Source: pDP3616 plasmid DNA from DP-E3616 E. coli (Higgins et al., Mol. Molbiol. 31: 1631-1641

(1999)).

Primers:

Forward (XhoI- NcoI OVA cDNA nts. 174-186):

5'-ATTTCTCGAGTCCATGGGGGGTTCTCATCATC (SEQ ID NO:30)

($T_m$: OVA-spec: 60° C. Overall: 88° C.)

Reverse (XhoI-NotI-HindIII):

5'-GGTGCTCGAGTGCGGCCGCAAGCTT (SEQ ID NO:31)

($T_m$: Overall: 82° C.)
```

One protocol for completing the construction process involves first cutting the LLO amplicon with KpnI and BamHI and inserting the KpnI/BamHI vector into the pPL2 vector (pPL2-LLO). The OVA amplicon is then cut with XhoI and NotI and inserted into the pPL2-LLO which has been cut with XhoI/NotI. (Note: The pPL2 vector does not contain any XhoI sites; pDP-3616 contains one XhoI site, that is exploited in the OVA reverse primer design.) The construct pPL2/LLO-OVA is verified by restriction analysis (KpnI-LLO-XhoI-OVA-NotI) and sequencing. The plasmid pPL2/LLO-OVA is introduced into *E. coli* by transformation, followed by introduction and integration into *Listeria* (DP-L4056) by conjugation, exactly as described by Lauer et al. (or into another desired strain of *Listeria*, such as an inlB⁻ mutant or an inlB⁻actA⁻ double mutant).

A description of the insertion of an antigen expression cassette that expresses OVA can also be found in Example 8 of the U.S. provisional application entitled "Free-Living Microbe Based Vaccine Compositions", U.S. Ser. No. 60/511,869, filed Oct. 15, 2003.

Construction of *Listeria* strains expressing AH1/OVA or AH1-A5/OVA. To prepare *Listeria* expressing either the AH1/OVA or the AH1-A5/OVA antigen sequences, inserts bearing the antigen are first prepared from oligonucleotides and then ligated into the vector pPL2-LLO-OVA (prepared as described above).

The following oligonucleotides are used in preparation of the AH1 or AH1-A5 insert:

```
AH1 epitope insert (ClaI-PstI compatible ends):

Top strand oligo (AH1 Top):

5'-CGATTCCCCTAGTTATGTTTACCACCAATTTGCTGCA (SEQ ID NO:32)

Bottom strand oligo (AH1 Bottom):

5'-GCAAATTGGTGGTAAACATAACTAGGGGAAT (SEQ ID NO:33)

AH1-A5 epitope insert (ClaI-AvaII compatible ends):

The sequence of the AH1-A5 epitope is

SPSYAYHQF (SEQ ID NO:21)

(5'-AGT CCA AGT TAT GCA TAT CAT CAA

TTT-3' (SEQ ID NO:34)).

Top: 5'-CGATAGTCCAAGTTATGCATATCATCAATTTGC (SEQ ID NO:35)

Bottom: 5'-GTCGCAAATTGATGATATGCATAACTTGGACT

AT(SEQ ID NO:36)
```

The oligonucletide pair for a given epitope are mixed together at an equimolar ratio, heated at 95° C. for 5 min. The oligonucleotide mixture is then allowed to slowly cool. The annealed oligonucleotide pairs are then ligated at a 200 to 1 molar ratio with pPL2-LLO/OVA plasmid prepared by digestion with the relevant restriction enzymes. The identity of the new construct can be verified by restriction analysis and/or sequencing.

The plasmid can then be introduced into *E. coli* by transformation, followed by introduction and integration into *Listeria* (DP-L4056) by conjugation, exactly as described by Lauer et al. (or into another desired strain of *Listeria*, such as an inlB⁻ mutant or an inlB⁻actA⁻ double mutant).

Example 20

Assessment of In Vivo Cytotoxic Activity in Mice Vaccinated with *Listeria monocytogenes*

A series of studies were done to assess the ability of vaccinated mice to lyse antigen specific target cells in vivo. In the first study, Balb/c mice were vaccinated either intravenously (IV) with *Listeria monocytogenes* strains DP-L4029 (actA⁻), DP-L4029 expressing AH1/A5, and DP-L4029 uvrAB⁻ expressing AH1/A5. The AH1/A5 expressing strains were also treated with S-59 UVA according to the second method of Example 13. The *Listeria* constructs expressing AH1-A5 also express LLO and OVA. Vaccinations were done on day 0, for all groups and additionally on days 1 and 2 for the S-59 treated strains at the dose (0.1 $LD_{50}$) indicated in Table 20. For each strain and control, two groups of 3 mice were vaccinated. A target cell population was prepared by harvesting the spleens of 20 naïve Balb/c mice in RPMI 1640 medium. The cells were dissociated and the red cells lysed. The white blood cells were counted and split into four equal populations. Each group was pulsed with a specific peptide, either target AH1 (SPSYVYHQF (SEQ ID NO:20), from SynPep, Dublin, Calif.), target AH1-A5 (SPSYAYHQF (SEQ ID NO:21), SynPep), or two populations of control (β-gal, TPH-PARIGL (SEQ ID NO:37)), at 0.5 µg/mL for 90 minutes at 37° C. Cells were then washed 3 times in medium, and twice in PBS+0.1% BSA. Cells were resuspended at $1 \times 10^7$ per mL in warm PBS+0.1% BSA (10 mL or less) for labeling with carboxyfluorescein diacetate succinimidyl ester (CFSE, Molecular Probes, Eugene, Oreg.). To the target cell suspensions, 1.25 µL of a 5 mM stock of CFSE was added and the sample mixed by vortexing. To the control cell suspensions, a ten-fold dilution of the CFSE stock was added and the sample mixed by vortexing. The cells were incubated at 37° C. for 10 minutes. Staining was stopped by addition of a large volume (>40 mL) of ice-cold PBS. The cells were washed twice at room temperature with PBS, then resuspended and counted. Each cell suspension was diluted to $50 \times 10^6$ per mL, and 100 µL of each population was mixed and injected via the tail vein of either naïve or vaccinated mice on day 6. For each strain or control, the group of 3 mice was injected with β-gal and AH-1 or β-gal and AH1-A5. After 12-24 hours, the spleens were harvested and a total of $5 \times 10^6$ cells were analyzed by flow cytometry. The high (target) and low (control) fluorescent peaks were enumerated, and the ratio of the two was used to establish the percentage of target cell lysis relative to the HBSS control population. The results are shown in Table 23 and FIG. 23A. (The tables in this example show averages for three mice, while the figures are representative histograms from individual mice for the indicated samples (not necessarily the same mouse).) The vaccination using the S-59 treated stains shows a slightly better response to AH1 for the uvrAB⁻ mutant and a significantly higher response to AH1-A5 for the uvrAB⁻ mutant relative to the S-59 treated actA⁻ strain.

TABLE 23

In vivo cytotoxicity of Balb/c mice vaccinated as indicated on day 0, also days 2 and 3 for S-59 treated strains.

| Immunization | S-59 | Vaccination dose | % of target cells killed | |
|---|---|---|---|---|
| | | | AH1 | AH1-A5 |
| HBSS | − | 100 µL | 0 | 0 |
| actA⁻ | − | $5 \times 10^6$ | 3.8 | 7.2 |
| actA⁻ AH1-A5 | − | $5 \times 10^6$ | 17.9 | 77.2 |
| actA-uvrAB⁻ AH1-A5 | − | $5 \times 10^6$ | 33.6 | 85.1 |
| actA⁻ AH1-A5 | + | $1 \times 10^7$ each day | 7.1 | 3.9 |
| actA⁻uvrAB⁻ AH1-A5 | + | $1 \times 10^7$ each day | 8.7 | 56.1 |

This study was repeated with an additional vaccination at day 14 for all groups and additionally days 15 and 16 for the S-59 treated strains. The labeled target cells were injected on day 20. The results are shown in Table 22 and FIG. 23B. The response to the S-59 treated uvrAB⁻ mutant can be significantly improved with a boost vaccination, this is not the case for the S-59 treated actA⁻ strain.

TABLE 22

In vivo cytotoxicity of Balb/c mice vaccinated as indicated on day 0 and 14, also days 2, 3, 15, and 16 for S-59 treated.

| Immunization | S-59 | Vaccination dose | % of target cells killed | |
|---|---|---|---|---|
| | | | AH1 | AH1-A5 |
| HBSS | − | 100 μL | 0 | 0 |
| actA− | − | 5 × 10⁶ | 1.4 | −5.9 |
| actA− AH1-A5 | − | 5 × 10⁶ | 27.4 | 96.4 |
| actA-uvrAB− AH1-A5 | − | 5 × 10⁶ | 52.9 | 97.0 |
| actA− AH1-A5 | + | 1 × 10⁷ each day | 3.6 | 5.7 |
| actA−uvrAB− AH1-A5 | + | 1 × 10⁷ each day | 19.2 | 84.5 |

A similar study was done using actA−, actA− expressing OVA and actA− uvrAB− expressing OVA, including with and without S-59 treatment for the OVA expressing strains. This study used C57B1/6 mice. Groups of 6 mice were vaccinated day 0 (also 1 and 2 for S-59 treated) and three of each group was injected with labeled target cells on day 6. The remaining mice were vaccinated day 14 (also 15 and 16 for S-59 treated) and injected with labeled target cells on day 20. In this study, the naïve target spleen cells were pulsed with β-gal (low CFSE) or SL8 (high CFSE). The results are shown in Table 25 and FIG. 23C. Again, the response to the S-59 treated uvrAB− mutants is enhanced significantly with a boost vaccination.

TABLE 25

In vivo cytotoxicity of Balb/c mice vaccinated as indicated.

| Immunization | S-59 | Vaccination dose | % of target cells killed | |
|---|---|---|---|---|
| | | | primary | boost |
| HBSS | − | 100 μL | 0 | 0 |
| actA− | − | 1 × 10⁷ | −6.6 | 0.1 |
| actA− OVA | − | 1 × 10⁷ | 98.9 | 97.1 |
| actA-uvrAB− OVA | − | 1 × 10⁷ | 99.5 | 98.1 |
| actA− OVA | + | 1 × 10⁸ each day | 0 | 0 |
| actA−uvrAB− OVA | + | 1 × 10⁸ each day | 46.5 | 84.8 |

Example 21

S-59/UVA Treatment of *Bacillus anthracis* with and without uvrAB Deletion

The allelic exchange methods detailed in Examples 7-9 and Camilli et al., Molecular Micro., 8:143-147 (1993) were used to modify the *Bacillus anthracis* Sterne strain. The virulence of this strain is attenuated (pXO1⁺, pXO2⁻).

The uvrAB gene from *Bacillus anthracis* was identified (Genbank accession number AE017040, *Bacillus anthracis* Ames strain, section 17 of 18 of the complete genome, uvrAB genes coding sequence: nts. 212613-217471) and a plasmid based on pKSV7 with the uvrAB gene deletion was constructed (pKSV7-dl uvrAB) using Splice Overlap Extension (SOE) PCR and the steps described below:

Primary PCR reactions: Approximately 1000 bps of sequence upstream and downstream from the *B. anthracis* uvrAB genes 5' and 3' ends, respectively, were amplified.

Template: *B. anthracis* Sterne genomic DNA

Primer pair 1: Amplification of region 1000 bp upstream from 5' end of uvrB.

(Amplicon Size (bps): 1029)

Ba-225099F: 5'-CTGTGCTTTGCGAATGGAAAGAAGC (SEQ ID NO:38) ($T_m$: 74° C.)

Ba-(3' uvrA-R +) 226109R:

5'-<u>GTTTTCATTCATACACTTAG</u>ACAAGCGTTGGCTTTTG

CACTTC (SEQ ID NO:39) ($T_m$: 120° C.)

(Underlined sequence is complementary to region downstream of uvrA carboxy terminus.) or Ba-226109R:

5'-GACAAGCGTTGGCTTTTGCACTTC (SEQ ID NO:40) ($T_m$: 72° C.)

Primer pair 2: Amplification of region downstream from 3' end of uvrA.

(Amplicon size (bps): 990)

Ba-(3' uvrA-R +) 230779F:

5'-<u>CAAAAGCCAACGCTTGTCT</u>AAGTGTATGAATGAAAAC

CGAGTGG (SEQ ID NO:41) ($T_m$: 126° C.)

(Underlined sequence is complementary to region upstream of uvrB amino terminus.)

or Ba-230779F: 5'-AAGTGTATGAATGAAAACCGAG

TGG (SEQ ID NO:42) ($T_m$: 70° C.)

Ba-231769R: 5'-CATATAAAGGTTCCACAATTGCCTTTTC (SEQ ID NO:43) ($T_m$: 76° C.)

Secondary PCR reaction: Fusion of primary PCR amplicons through SOE PCR, taking advantage of complementarity between reverse primer of pair 1 and the forward primer of pair 2. Results in precise-deletion of uvrAB coding sequence: nts. 226110-230779=4670 bps.

Template: Cleaned primary PCR reactions

Primer pair: (Amplicon size (bps): 1973)

Ba-225118F: 5'-GAAGCAGAAATGAAGCCAATACTCAATC (SEQ ID NO:44) ($T_m$: 78° C.)

Ba-231761R: 5'-GGTTCCACAATTGCCTTTTCAATAATC (SEQ ID NO:45) ($T_m$: 74° C.)

Construction: Primary PCR reactions (3 temperature cycle) were performed using Vent DNA polymerase (NEB) and Sterne strain genomic DNA. Four primary PCR reactions were performed both with and without primers used for splice overlap extension (SOE). (If reactions containing Ba-(3' uvrA-R+) 226109R or Ba-(3' uvrA-R+) 226109R primers did not yield significant amplicon product, then these primers on amplicons from reactions with Ba-225099F/Ba-226109R or Ba-230779F/Ba-231769R primer pairs were used.) The expected size of anthracis primary amplicons by 1% agarose gel (1029 bps and 990 bps) was verified. The reaction was cleaned with S6 columns (BioRad) or GeneClean (BIO 101).

The secondary PCR reaction was performed, utilizing approximately equal amounts of each primary reaction as template (ca. 5 μl) were performed. The expected size of the Listeria amplicon from secondary PCR reaction by 1% agarose gel (1973 bps) was verified.

The anthracis dl uvrAB amplicon was inserted into pCR2.1-Blunt II-TOPO vector. The plasmid pCR2.1-TOPO-dl uvrAB plasmid DNA was digested with KpnI and PstI and gel-purify 2033 bp fragment. The KpnI/PstI 2033 bp fragment was inserted into pKSV7 vector, that had been prepared by digestion with KpnI and PstI and treatment with CIAP (pKSV7-dl uvrAB). The fidelity of dl uvrAB sequence in pKSV7-dl uvrAB was verified.

The uvrAB genes were deleted from B. anthracis Sterne by allelic exchange with pKSV7-dl uvrAB plasmid. The plasmid pKSV7-dl uvrAB was introduced into the B. anthracis Sterne strain by electroporation selecting for chloramphenicol resistance. The electroporation was done using a freezing step that significantly increased the frequency of electroporation. B. anthracis culture was grown O/N in 3 ml BHI 0.5% glycerol shaking at 37° C. 0.5 ml culture was transferred to 50 ml BHI 0.5% glycerol ($OD_{600}$=0.1) in 500 ml E-flask. The sample was incubated at 200 rpm 37° C. (or 0.1-0.2 ml to 25 ml BHI 0.5% glycerol in 250 ml flask). At $OD_{600}$=0.6-0.8 (approx 1 hour 45 min), bacteria were collected in 500 ml disposable sterile filter apparatus. The bacteria were washed 3×25 ml each with cold electroporation buffer (1 mM HEPES 10% glycerol pH 7.4). The cells were resuspended in 1/20 original volume (2.45 ml of e-poration buffer for 50 ml culture) and kept on ice. The efficiency of electroporation can be enhanced by freezing the electrocompetent B. anthracis at −80° C. A 0.2 ml suspension of ice-cold or thawed electrocompetent B. anthracis cells were mixed with 1 μg (1 to 5 ul of miniprep) of "very clean" unmethylated plasmid DNA to 0.2 ml cells suspension in a 0.2 cm gap electroporation cuvette (control=no DNA). The sample was then kept on ice for 15 min. The cells were then pulsed at 25 μFD, 200Ω, 2.5 kV (or, alternatively, 0.4 ml cells were pulsed in 0.4 cm cuvette at 400Ω). Time constant was approximately 4-5 msec. Immediately after pulse, 1 ml BGGM (BHI containing 10% glycerol, 0.4% glucose and 10 mM MgCl2) was added. The cells are transferred to a sterile polyprop. tube and incubated 37° C. 1½ hour, shaking. The cells are pelleted, resuspended in 200 μl BGGM and plated on selective media.

The pKSV7-dl uvrAB was integrated into the B. anthracis chromosome at 41° C. pKSV7-dl uvrAB was allowed to excise and cure at the permissive temperature, resulting in chloramphenicol sensitive colonies. PCR primers were designed to detect the deletion on the chromosome. 20% of the chloramphenicol sensitive colonies harbored the deletion in the B anthracis chromosome. PCR analysis of the uvrAB⁻ strain indicated retention of the pXO1 virulence plasmid.

Two uvrAB⁻ clones (clone 8 and clone 32A) were S-59-treated, along with the parent strain, by growing in BHI at 37° C. at 300 rpm to an $OD_{600}$ of 0.3, at which point 50 mL of solution was transferred to a clean flask and S-59 was added to the concentrations indicated in Table 26. These samples were incubated at 37° C. at 300 rpm with vigorous shaking for approximately 1 hour ($OD_{600}$ approximately 1.0, approximately 1×10⁹/mL). A 1 mL aliquot was removed to assess the titer and the remaining was transferred to a 150 mm Petri dish and irradiated at a UVA dose of 6 J/cm² (FX-1019), resulting in a six-log reduction in titer, as compared to the parental strain, as indicated in Table 26, below, and FIG. 24. This demonstrates a sensitivity to psoralen treatment in B. anthracis that is similar to that observed for Listeria monocytogenes uvrAB⁻ strains.

TABLE 26

Attenuation of Bacillus anthracis Sterne strain vs. uvrAB⁻ mutant with psoralen S-59/UVA treatment.

| S-59 nM | Bacterial log titer | | | Log attenuation | | |
|---|---|---|---|---|---|---|
| | Sterne | uvrAB⁻ (1) | uvrAB⁻ (2) | Sterne | uvrAB⁻ (1) | uvrAB⁻ (2) |
| 0 | 8.26 | 8.13 | 8.31 | — | — | — |
| 25 | — | 7.46 | 7.45 | — | 0.67 | 0.86 |
| 50 | — | 6.31 | 6.28 | — | 1.82 | 2.03 |
| 100 | — | 3.11 | 3.68 | — | 5.02 | 4.63 |
| 200 | 6.84 | <1 | <1 | 1.42 | >7.13 | >7.31 |
| 400 | — | <1 | <1 | — | >7.13 | >7.31 |
| 500 | 5.29 | — | — | 2.97 | — | — |
| 1000 | 3.11 | <1 | <1 | 5.15 | >7.13 | >7.31 |
| 1500 | 1 | — | — | >7.26 | — | — |
| 2500 | 1 | — | — | >7.26 | — | — |
| 5000 | 1 | — | — | >7.26 | — | — |

Example 22

Use of APC-Based Vaccines of the Invention for the In Vivo Treatment of Human Cancers As an example of the treatment or prevention of a human cancer, a vaccine comprising an antigen-presenting cell that has been loaded and activated by infection by a microbe modified so that the proliferation of the microbe is attenuated, wherein the microbial gene expression is substantially unaffected, is administered to an individual. The microbe can be prepared following the protocols of examples 4 and 5, wherein any desired prokaryotic expression cassettes encoding human tumor antigen(s) are incorporated into the microbe, by utilizing, for example the pPL2 integration vector described in Example 8, or any modifications thereof, or by any methods that are common to those in the art. Antigen-presenting cells (APCs) are then loaded and activated with the modified microbes using methods such as those outline herein.

The resulting APC vaccine may be formulated in crude, or preferably purified form. The vaccine composition may be prepared as a liquid suspension. In addition, they may be formulated with additives such as preservatives (e.g. thimerosal, 2-phenoxy ethanol), stabilizers (e.g. lactose, monosodium glutamate), adjuvants (e.g. aluminum hydroxide, aluminum phosphate, cytokines), antibiotics (e.g. neomycin, streptomycin) or other substances. Formulations may be resuspended or diluted in a suitable diluent such as sterile water, saline, isotonic buffered saline (e.g. phosphate buffered to physiological pH), or other suitable diluent.

The vaccine may be administered by a variety of routes, including oral, nasal, intravenous, intradermal, intraperitoneal, intramuscular, intralymphatic and subcutaneous routes, as well as by any route that is relevant for any given malignant or infectious disease. An effective amount of the vaccine will be administered to an individual for treatment. For a therapeutic treatment, an effective amount is a dose that will result in the desired immune response, wherein the immune response either slows the growth of the targeted tumors, reduces the size of the tumors, or preferably eliminates the tumors completely. The administration of the vaccine may be repeated at appropriate intervals, and may be administered simultaneously at multiple distinct sites in the vaccinated individual. For the prophylactic treatment, an effective amount is a dose that will result in a protective immune response such that the likelihood of an individual to develop the cancer is significantly reduced. The vaccination regimen may be comprised of a single dose, or may be repeated at suitable intervals until a protective immune response is established.

The therapeutic treatment of an individual may be started on an individual who has been diagnosed with a cancer as an initial treatment, or may be used in combination with other treatments. For example, individuals who have had tumors surgically removed or who have been treated with radiation therapy or by chemotherapy may be treated with the vaccine in order to reduce or eliminate any residual tumors in the individual, or to reduce the risk of a recurrence of the cancer. The prophylactic treatment of an individual would be started on an individual who has an increased risk of contracting certain cancers, either due to environmental conditions or genetic predisposition.

Example 23

Generation of Recombinant Tumor Ag-Secreting Vaccines Based on Attenuated Strains of *Listeria*

Chicken ovalbumin (OVA) fused with a truncated form of Listeriolysin O (LLO) to facilitate antigen secretion and MHC class I processing was used as a model antigen in studies to evaluate the immunogenicity of selected attenuated *Listeria* strains. The tumor antigen expression cassette was incorporated site-specifically into an innocuous site on the chromosome of a panel of attenuated *Listeria* strains with the proprietary pPL2 integration vector. The recombinant *Listeria* strains expressed and secreted the predicted modified LLO-OVA fusion protein as determined by Western blot analysis (data not shown). The growth of each of these recombinants in liquid broth culture as well as the intracellular growth kinetics was also indistinguishable from its parent. Furthermore, the recombinant OVA-expressing strains were shown to have an IV $LD_{50}$ that was within a factor of two of the unmodified parental strains (Table 27).

*eria*, the inventors have engineered a *Listeria* strain that can be fully inactivated through treatment with psoralen, yet is metabolically active and thus retains its ability to infect cells, escape from the phagolysosome and promote the presentation of encoded antigens via the class I pathway. The engineered *Listeria* strain is exquisitely sensitive to inactivation with psoralens, a group of compounds that form irreversible crosslinks in the genomes of bacteria after illumination with UVA light, so that they are incapable of multiplying. Mutant strains of *Listeria* unable to repair psoralen-mediated DNA damage were created by deleting the ultraviolet light resistance (uvr) AB gene (uvrAB), which is required for nucleotide-excision repair in *Listeria* and other bacteria (Sancar et al., *Ann. Rev. Biochem.*, 57:29-67 (1988)). The psoralen S-59 is one of a number of Cerus compounds used in the DNA crosslinking technology known as Helinx (Lin, L., Psoralen photochemical treatment of platelets, *Science and Medicine*, 1998; Hei, et al., *Transfusion*, 39:239-48 (1999)). At a psoralen concentration that inactivates the *Listeria* uvrAB deletion mutants to the limit of detection, the parental, non-mutant strain having intact DNA repair mechanisms is more than four logs less sensitive to UVA light inactivation (FIG. 25B). S-59/UVA inactivated *Listeria* uvrAB maintained their mitochondrial activity as determined in a MTT assay and retained their capacity to express their genomic repertoire, as determined by $^{35}$S-methionine-labeled pulse-chase experiments (FIG. 26 and FIG. 10). S-59/UVA inactivated *Listeria* uvrAB but not the inactivated parental strain demonstrated continued expression of their genetic repertoire. The expression level of the inactivated parental strain was significantly diminished, indicating that S-59/UVA treatment at the S-59 concentrations required for full inactivation significantly decreases expression of *Listeria* gene products, including likely the expression of an encoded tumor antigen.

TABLE 27

Selected strains of *Listeria monocytogenes*

| Strain | Genotype | Phenotype | $LD_{50}$ of parental strain | $LD_{50}$ of OVA-expressing strain | Fold attenuation/ Parent strain |
|---|---|---|---|---|---|
| DP-L4056 | 10403S phage cured | Wild-type | $5 \times 10^4$ | $1 \times 10^5$ | 2 |
| DP-L4029 | ΔactA | In-frame deletion of actA (actA) gene; strain grows intracellularly, but does not spread from cell-to-cell | $1 \times 10^8$ | $1 \times 10^8$ | 1 |
| L4029-uvrAB | ΔactA; ΔuvrAB | In-frame deletion of actA (actA) gene and uvrAB (uvrAB) genes; strain grows intracellularly, but does not spread from cell-to-cell; enhanced susceptibility to DNA damage such as psoralen-induced DNA cross linking | $1 \times 10^8$ | $1 \times 10^8$ | 1 |

The integration vectors facilitate rapid derivation of multiple recombinant *Listeria* vaccine candidates. A single construct can be mated in parallel into any number of unique genetic backgrounds to rapidly create isogenic strains.

Example 24

Psoralen-Induced DNA Crosslinking to Produce Non-Viable but Metabolically Active *Listeria*

To ensure safety for a *Listeria*-based ex vivo antigen delivery platform, in addition to using genetically attenuated *List-*

Example 25

Non-Viable *Listeria* uvrAB Retain the Ability to Infect DC and Escape from the Phagolysosome In addition to preserving metabolic activity, it is important to demonstrate efficient antigen loading into the MHC class I pathway by S-59/UVA inactivated *Listeria* uvrAB strains upon infection of dendritic cells (DC). The inventors have now demonstrated that infection of DC with a *Listeria* mutant (DP-L4027) that is unable to escape from the phagolysosome by virtue of deletion of the hly gene that encodes LLO eliminates presentation of antigens in context of MHC class I.

To demonstrate escape from the phagolysosome of *Listeria* uvrAB infected DC, the inventors took advantage of the fact the cytoplasmic *Listeria* are surrounded by host-cell actin filaments, so-called "actin clouds", that can be visualized by fluorescence microscopy. Actin polymerization on the *Listeria* surface is mediated by the bacterial ActA protein and other host cell factors. A murine DC cell line, DC2.4, was infected at multiplicity of infection (MOI) of 1 with *Listeria* wt, S-59/UVA inactivated *Listeria* uvrAB and *Listeria* ΔLLO (DP-L4027) for 30 minutes at 37° C. Extracellular bacteria were removed carefully by several washes and DC were incubated for an additional 5 hours at 37° C. in the presence of gentamicin to prevent the growth of extracellular bacteria. DC2.4 infected with wild-type *Listeria* or fully inactivated *Listeria* uvrAB demonstrated typical actin clouds or actin comet tails, typical for cytoplasmic localization of *Listeria* (FIG. 27). However, in DC2.4 cells infected with the *Listeria* LLO null mutant no co-localization of actin and *Listeria* could be observed, indicating that the bacteria were unable to escape from the phagolysosome. This result demonstrated that these DNA repair mutants retain the ability to escape from the phagolysosome and enter the cytosol of the infected cell, where antigen can be secreted, a requisite step for direct presentation via the MHC class I pathway. See also Example 17, above, and FIG. 21.

Example 26

Non-Viable *Listeria* uvrAB Efficiently Load Antigen into the MHC Class I Pathway of Infected Dendritic Cells (DC)

Due to the unique ability of S-59 psoralen inactivated *Listeria* uvrAB to escape the phagolysosome within the infected cell, gene products secreted by cytosolic *Listeria* are processed and presented via the MHC class I pathway. To test the ability of S-59/UVA inactivated *Listeria* uvrAB to load antigen into the MHC class I pathway of DC, DC2.4 cells were infected at a multiplicity of infection (MOI) of 1 with the OVA-expressing *Listeria* strain, L4029 uvrAB OVA, inactivated with different concentrations of S-59. The parental *Listeria* OVA and heat-killed *Listeria* uvrAB OVA served as controls. Presentation of OVA peptide by DC2.4 on class I molecules following phagocytosis of *Listeria* was measured after incubation with B3Z cells. B3Z is a LacZ-inducible $CD8^+$ T-cell hybridoma specific for the $OVA_{257-264}$ (SL8) epitope presented on the murine $K^b$ class I molecule (Sanderson, *Int. Immunol.,* 6:369-76 (1994)). Class I-restricted presentation of SL8 to B3Z cells results in the induction of β-gal synthesis by B3Z. The amount of β-gal produced can be measured by the hydrolysis of the chromogenic substrate CPRG and is an indication of the amount of $SL8/K^b$ complexes presented on the surface of APCs. As shown in FIGS. 9A and 9B, S-59/UVA inactivated *Listeria* uvrAB OVA strain, but not the cognate parental strain, maintained its capacity to load antigen into the MHC class I pathway independent of its ability to multiply. (This is the same data as described in Example 11.) Even at full inactivation using S-59 concentrations of 70 to 100 nM, more than 90% of B3Z activation was maintained. In contrast, the parental *Listeria* OVA strain with intact DNA repair lost its ability to activate the B3Z T-cell hybridoma when higher concentrations of S-59 were used for inactivation. In contrast to the *Listeria* uvrAB OVA strain, B3Z activation and the ability of the parental *Listeria* OVA strain to form colonies on BHI agar plates was closely correlated, suggesting that only viable *Listeria* OVA are capable of infecting DC2.4 cells and loading antigen into the MHC class I pathway. Moreover, heat-killed *Listeria* uvrAB OVA did not result in B3Z activation. This result demonstrates the capacity of *Listeria* to load antigen into the MHC class I pathway can be unlinked from the requirement for multiplication using S-59/UVA inactivated *Listeria*, modified to prevent their capacity to repair psoralen-mediated DNA damage.

To test the ability of *Listeria* uvrAB OVA to load antigen into the MHC class I pathway of primary DC, immature murine BM-DC were infected with fully inactivated S-59/UVA treated *Listeria* uvrAB OVA. Viable *Listeria* uvrAB OVA, the parental strain and L4027 served as controls. As shown in FIG. 28, BM-DC infected with the OVA-expressing but not the parent strains stimulated the B3Z cells in vitro. No significant difference between the live and non-viable S-59/UVA treated *Listeria* uvrAB mutant strain (L4029 uvrAB OVA) was observed, suggesting that MHC class I molecules of primary DC are efficiently loaded with *Listeria*-derived peptides following the escape of the bacteria from the phagolysosome into the cytosol in spite of the inability of *Listeria* uvrAB to multiply. Importantly, *Listeria* actA OVA inactivated by heat-killing did not result in any significant presentation of OVA peptides in the MHC class I pathway suggesting that incubation of DC with heat-killed bacteria does not result in any significant antigen loading of MHC class I molecules.

Example 27

*Listeria* Directly Infect and Activate Human DC

For the development of a potent antigen delivery platform it is widely thought that activation/maturation of DC is required in addition to efficiently delivering antigen into the MHC class I pathway. In situ, immature DC reside in peripheral tissues where they continuously take up and process antigen, but it is the encounter of an activation stimulus, such as that which bacteria provide, that initiates the activation/maturation process, leading to modulation of chemokine receptors and migration of DC to the T cell area of the draining lymph node. We assessed the potency of wild-type *Listeria* (L4056) to induce phenotypic maturation and cytokine production of human monocyte-derived DC. As shown in FIG. 29, encounter of human immature DC with *Listeria* led to up-regulation of the activation markers, CD86 and HLA-DR (FIG. 29A), as well as the maturation marker, CD83 (FIG. 29B). Furthermore, the exposure of human immature DC to *Listeria* increased their immune-stimulatory capacity as shown by their ability to secrete high levels of pro-inflammatory cytokines, such as IL-12p70 and TNF-α (FIG. 29C).

Example 28

S-59/UVA Inactivated *Listeria* uvrAB OVA Induce OVA-Specific Immunity In Vitro We assessed the potency of the S-59/UVA inactivated *Listeria* uvrAB OVA vaccine to induce OVA-specific immunity in vivo. Female C57BL/6 mice were vaccinated intravenously with $1\times10^8$ particles of S-59/UVA inactivated *Listeria* uvrAB OVA. The induction of OVA-specific immunity was assessed 7 days post vaccination. Strikingly, mice that received S-59/UVA inactivated *Listeria* uvrAB OVA but not the parent *Listeria* OVA strain mounted a significant OVA-specific $CD8^+$ T cell response, as shown in FIG. 30. Furthermore, vaccination of mice with heat-killed *Listeria* uvrAB OVA did not result in the induction of OVA-specific immunity.

Example 29

Construction of Two Recombinant Attenuated *Listeria* actA/uvrAB Strains Expressing Full-Length CEA Containing Either the Native (CAP1) or the Enhanced Agonist Cytotoxic T Lymphocyte Epitope (CAP1-6D)

CEA is a 180 kDa large protein found in adenocarcinomas of endodermally derived digestive system epithelium and fetal colon. CEA is attached to the membrane of cells by a GPI-anchor. The protein contains 7 immunoglobulin-like domains and the C-terminus demonstrates homology with the Non-specific Cross-reacting protein, NCA, a member of the carcinoembryonic antigen gene family. We propose to construct the full-length CEA containing either the HLA*A0201-restricted CEA native T cell epitope CAP1 (YLSGANLNL) (SEQ ID NO:51) or the enhancer agonist cytotoxic T lymphocyte peptide CAP1-6D (YLSGADLNL) (SEQ ID NO: 52) (Zaremba et al., *Cancer Res.*, 57:4570-7 (1997)) that has been demonstrated to be more potent at inducing CEA-specific immunity in cancer patients (Table 28) (Fong et al., *Proc. Natl. Acad. Sci. U.S.A.*, 98:8809-14 (2001)).

TABLE 28

| | Plasmid | Antigen | T cell epitope |
|---|---|---|---|
| 1 | pPL2 CEAwt | Full-length CEA | CAP1 |
| 2 | pPL2 CEA-610D | Full-length CEA | CAP1-6D |

The CEA tumor antigen expression plasmids are constructed on the pPL2 backbone, a vector that integrates site-specifically into the *Listeria* genome (Lauer et al., *J. Bacteriol.*; 184:4177-86 (2002)). The two plasmids are constructed so that the secretion signal and PEST elements derived from *Listeria* LLO are fused genetically with full-length CEA cDNA. Starting from the 5' end of the gene construct, the fusion protein will consist of the N-terminal region of LLO to promote bacterial secretion fused to CEA. Precise linkage of the domains is accomplished by overlapping PCR. The fidelity of all plasmid constructs is confirmed by DNA sequencing.

Example 30

Derivation of Two Attenuated Recombinant *Listeria* Strains Containing pPL2 CEAwt and pPL2 CEA-610D Integrated into *Listeria* Strain L4029 uvrAB (ΔactA, ΔuvrAB), and Verify Expression and Secretion of CEA Antigens Integration of the pPL2-CEA constructs adjacent to the tRNA$^{Arg}$ gene in the genome of the *Listeria* strain L4029 uvrAB are accomplished as described previously by Lauer et al., *J. Bacteriol.*, 184:4177-86 (2002). Briefly, plasmids are first introduced into *E. coli* strain SM10 by transformation, and then introduced into the desired strain of *Listeria* by conjugation. *Listeria* trans-conjugants are selected by chloramphenicol (pPL2) and streptomycin (*Listeria* strain) selective media; the efficiency of this process is approximately $1 \times 10^{-4}$. To ensure purity of trans-conjugants, and to ensure integration of the pPL2 backbone into the bacterial chromosome, a limited number of candidate colonies are passaged three times by streaking onto fresh selective media. Precise integration of the CEA construct into the *Listeria* genome are confirmed by colony-PCR.

Antigen expression and secretion of the LLO-CEA fusion protein are determined by Western blotting of whole cell lysates, and TCA precipitated bacterial culture fluids. An LLO-specific rabbit polyclonal antibody and a CEA-specific monoclonal antibody are used to verify expression and secretion of the LLO-CEA fusion protein from recombinant *Listeria*. One can compare the biological properties of the recombinant *Listeria* strains expressing CEA to their respective parent strain. The growth kinetics in brain heart infusion (BHI) broth following inoculation by dilution of a stationary phase culture 1:100 into fresh media are determined. In the past we have expressed proteins of similar or larger size in *Listeria*. However, recombinant protein expression of mammalian gene products in bacteria might pose a challenge dependent on each individual protein. If CEA expression in *Listeria* poses a problem, one can construct *Listeria* strains that express either fragments of CEA or the T cell mini-epitope. The HLA*A0201-restricted CEA native T cell epitope CAP1 (YLSGANLNL) (SEQ ID NO:51) or the enhancer agonist cytotoxic T lymphocyte peptide CAP1-6D (YLSGADLNL) (SEQ ID NO:52) is embedded in-frame within Ovalbumin (OVA) of our existing expression constructs, whereby the secretion signal and PEST elements derived from *Listeria* LLO are fused genetically with OVA. Expression and immunogenicity of T cell mini-epitopes are conserved as previously demonstrated with the gp70 T cell mini-epitopes, AH1 and AH1-A5 and B16 Trp1, Trp2, and gp100 (data not shown).

Example 31

Establishment of Conditions that Fully Inactivate *Listeria* actA/uvrAB CEA Strains by S-59/UVA Treatment, yet Retain Optimal Metabolic Activity, Tumor Antigen Expression, Infection of Antigen Presenting Cells and Phagolysosomal Escape Metabolic activity as a result of gene expression is best preserved with a minimal number of crosslinks. On can readily establish conditions for the minimal amount of S-59/UVA treatment that fully inactivates *Listeria* actA/uvrAB CEA vaccines, leaving antigen expression levels intact. An example of inactivation conditions is the addition of S-59 psoralen to 200 nM in a log-phase culture of $OD_{600}=0.5$, followed by inactivation with 6 J/m$^2$ of UVA light when the culture reaches an optical density of one. Inactivation conditions are optimized by varying concentrations of S-59, UVA dose, the time of S-59 exposure prior to UVA treatment as well as varying the time of treatment during bacterial growth of the *Listeria* actA/uvrAB CEA strain. The parental *Listeria* strain is used as control. Inactivation of *Listeria* (log-kill) is determined by the inability of the bacteria to form colonies on BHI (Brain heart infusion) agar plates. In addition, one can confirm the expression of CEA and virulence factors, such as LLO and p60, of S-59/UVA inactivated *Listeria* using $^{35}$S-pulse-chase experiments to determine the synthesis and secretion of newly expressed proteins post S-59/UVA inactivation. Expression of LLO and p60 using $^{35}$S-metabolic labeling can be routinely determined. S-59/UVA inactivated *Listeria* actA/uvrAB CEA is incubated for 1 hour in the presence of $^{35}$S-Methionine. Antigen expression and secretion of the LLO-CEA fusion protein, endogenous LLO, and p60 is determined of both whole cell lysates, and TCA precipitation of bacterial culture fluids. LLO-, p60- and CEA-specific monoclonal antibodies is used for immuno-precipitation to verify the continued expression and secretion from recombinant *Listeria* post inactivation. The expression level of S-59/UVA inactivated *Listeria* actA/uvrAB CEA is compared to our current *Listeria*-OVA vaccine strain that results in the induction of potent antigen-specific T cell responses. One can select S-59/UVA conditions that lead to reproducible full inactivation with limited affect on expression levels of the assessed gene products.

Example 32

Establishment of a Protocol and Vaccine Strain for Infection of Human Immature Dendritic Cells (Dc) with Inactivated (S-59/UVA) *Listeria* actA/uvrAB CEA Vaccines, that Results in Efficient Presentation of CEA in Context of MHC Class I Optimal conditions for ex vivo infection of DC are determined based on the results of three independent assays: (1) change in phenotype and cytokine profile of human immature DC upon infection, (2) the potency of *Listeria*-infected DC to induce an allogeneic T lymphocyte response, and (3) the potency of *Listeria* actA/uvrAB CEA infected DC to stimulate a CEA-specific HLA*A0201-restricted T cell line in vitro.

1. Determination and Comparison of the Phenotype and Cytokine Secretion Profile of Human Immature DC Infected with Live and Fully Inactivated *Listeria*-CEA Strains. Comparison of the Activation of *Listeria*-Infected Human DC with Commonly Used Activation Signals Such as LPS, TNF-α, and α-CD40.

One can characterize and optimize the efficiency of S-59/UVA inactivated *Listeria* actA/uvrAB CEA strains to infect and activate primary human DC. Human DC are enriched from unmobilized peripheral blood as previously described (Fong et al., *J. Virol.*, 76:11033-41 (2002). Briefly, PBMC are obtained by centrifugation over Ficoll-Hypaque (Pharmacia, Uppsala, Sweden), and then monocytes are depleted by density centrifugation through Percoll (Pharmacia) as previously described Mayordomo et al., *Nat. Med.*, 1: 1297-302 (1995). Monocyte-depleted PBMC are incubated in RPMI 1640 (BioWhittaker, Walkersville, Md.) supplemented with 10% pooled human AB serum without the addition of exogenous cytokines. After a 24-h culture in a humidified incubator at 37° C. with 10% $CO_2$, DC are further enriched from lymphocytes by centrifugation through a 15% (w/v) metrizamide gradient (Sigma, St. Louis, Mo.). The phenotype of the enriched DC population is verified by flow cytometry (HLA-DR expression and lack of CD3, CD14, CD19, and CD56 expression) and dextran uptake. To assess the infectivity of DC with *Listeria*, DC is incubated at different MOI with S-59/UVA inactivated *Listeria* actA/uvrAB CEA strains for one hour. Live *Listeria* are used as comparison. After extensive washes to remove any extracellular *Listeria*, infected DC is further incubated in the presence of 50 µg/mL gentamicin to kill extracellular bacteria. Phenotypic changes upon infection of DC with *Listeria* ΔactAΔuvrAB CEA strains are assessed by determining cell surface expression of CD80, CD83, CD86, and MHC class II using flow cytometry at different time points post infection. Expression of T helper-1 and T helper-2 type cytokines is measured from the supernatant of infected DC cultures using the Cytometric Bead Array Kit (Pharmingen). Infection and activation conditions are compared to commonly used stimuli such as LPS, TNF-α, and α-CD40. Infection conditions are selected that result in potent and consistent stimulation and activation of human DC in vitro as well as secretion of cytokines that are most similar to the parental live *Listeria* strain. If the overall infectivity of DC isolated from peripheral blood without the use of cytokines is low, infection of DC prior to the density gradient centrifugation is assessed. Moreover, additional sources of DC such as monocyte-derived DC is assessed for their infectivity for non-viable and live *Listeria*. Briefly, human monocytes are enriched using negative selection and suspended in medium (RPMI-1640+10% FCS) at $1\times10^6$ cells/mL, supplemented with 1000 U/mL GM-CSF and 1000 U/mL IL-4. After 6-7 days of culture, the phenotype of the in vitro cultured DC population is verified by flow cytometry and dextran uptake. The phenotypic change as well as the cytokine secretion pattern of monocyte-derived DC upon *Listeria* infection is assessed as described previously.

2. Determination and Comparison of the Stimulatory Potency of Human Immature DC Infected with Live or Fully Inactivated *Listeria*-CEA Strains to Activate Allogeneic T Cells In Vitro.

To address the stimulatory capacity of the *Listeria*-infected DC population, one can determine their ability to stimulate primary allo-reactive T cells in mixed leukocyte reactions (MLR). It is widely believed that the relative potency of an APC to elicit immune responses in vivo, which depends on their activation/maturation state, is reflected by their capacity to stimulate an allogeneic T cell response in vitro (Jung et al., Immunity, 17:211 (2002)). Briefly, DC are isolated and infected with fully inactivated *Listeria* actA/uvrAB CEA. The phenotype of the infected cell population is verified by flow cytometry. Various numbers of irradiated (3000 rad) DC are co-cultured with $5\times10^4$ allogeneic responders in 96-well U-bottom plates (Costar, Cambridge, Mass.). PBMC from random donors are used as responders. After 6 days, the cultures are pulsed with 1 µCi of [$^3$H] thymidine for 18 hours. Cells are harvested onto glass fiber sheets and the incorporation of [$^3$H] thymidine is determined by measuring the radioactivity on the scintillation counter. The stimulatory capacity of DC infected with non-viable *Listeria* is compared to DC infected with live *Listeria* as well as DC activated using stimuli such as LPS, TNF-α, and α-CD40.

3. Assessment of the Potency of *Listeria*-Infected Human DC to Activate a CEA-Specific HLA*A0201-Restricted T Cell Line In Vitro. Comparison of Immature Human DC Infected with Either Live or Fully Inactivated *Listeria* to Peptide-Pulsed DC.

Phenotypic changes, cytokine secretions profile as well as the allo-stimulatory capacity of DC represent an indirect measure for the potency of DC to stimulate an antigen-specific T cell response in vivo. The potency of DC to present the recombinant tumor antigen expressed by the fully inactivated *Listeria* actA/uvrAB CEA strain is assessed on the basis of activation of a CEA-specific HLA*A0201-restricted T cell line generated by L. Fong (unpublished data). Briefly, DC is isolated from peripheral blood of HLA*A0201 positive donors as described in Milestone 3-1. Various numbers of irradiated (3000 rad) DC, infected under optimal conditions, are co-cultured with $5\times10^4$ CEA-specific HLA*A0201-restricted T cells in 96-well U-bottom plates (Costar, Cambridge, Mass.). After 24 hours, cell supernatants are collected. T cell activation is measured on the basis of IFN-γ, GM-CSF, or IL-2 secretion. Secreted cytokines are determined using commercially available Cytometric Bead Array kits (Pharmingen). The stimulatory capacity of DC infected with non-viable *Listeria* is compared to DC infected with live *Listeria* as well as DC activated using stimuli such as LPS, TNF-α, and α-CD40.

Example 33

Confirmation of Potency of *Listeria*-Loaded Primary Human DC to Prime CEA-Specific Immunity In Vitro and Select the Lead *Listeria* Strain for Further Development To confirm that S-59/UVA inactivated *Listeria*-infected DC are capable of priming naïve CEA-specific CD8$^+$ T cell response in vitro, human immature DC, infected under the established optimal conditions with *Listeria* actA/uvrAB CEA, are used to stimulate naïve T cells in vitro. The lead *Listeria* actA/uvrAB CEA strain containing either the native or altered T cell epitope is selected based on its potency to induce naïve CEA-specific T cell responses as determined by three independent assays: (1) [$^3$H] thymidine incorporation of the DC-primed T cell cultures; (2) the cytotoxic activity of primed CEA-specific T cell cultures, measured in a $^{51}$Cr release assay; and (3) the frequency of CEA-specific T cells determined by peptide:MHC tetramer staining. Optimal infection is confirmed by phenotypic changes of DC, assessed by determining cell surface expression of CD80, CD83, CD86, and MHC class II using flow cytometry, as well as the cytokine profile secreted by the infected DC. For the induction of primary T cell responses, a constant number of CD45RA$^+$ T lymphocytes ($2\times10^5$/well) is co-incubated with varying numbers of irradiated (3,000 R) *Listeria*-loaded DC for 7 days in 96-well, round-bottom microtiter plates. After 6 days, the cultures are pulsed with 1 µCi of [$^3$H] thymidine for 18 hours. Cells are harvested onto glass fiber sheets and the incorporation of [$^3$H] thymidine is determined by measuring the radioactivity on the scintillation counter (Wallac, Turku, Finland). Furthermore, induction of CEA-specific T cells is assessed in a cytotoxic T cell assay. Briefly, $5\times10^6$ CD45RA$^+$ T lymphocytes are cultured in parallel with irradiated (3,000 R) *Listeria*-loaded DC at a 10:1 ratio in 24-well plates (Costar) at $5\times10^6$ cells/1.5 ml of media. The cytotoxic activity of the T cells is assessed in a standard 4-hour $^{51}$Cr-release assay after 7 days. Briefly, the target cell lines SW403, SW1417, A375, and T2 are incubated in 250 µCi of [$^{51}$Cr] for 2 hours. During this labeling step, T2 cells are also incubated without or with the HLA*0201-restricted target peptides CAP1 and CAP1-6D. The target cell lines are washed three times with RPMI and plated in triplicate with at least 5,000 targets/well in 96-well U-bottom plates (Costar). Effector cells are co-incubated with the $^{51}$Cr-labeled target cells at the described effector/target ratios. After a 4-h culture, supernatants are harvested and counted in a Microbeta counter (Wallac, Turku, Finland). Percent specific lysis is calculated by the formula: 100%×(experimental release−spontaneous release)/(maximum release−spontaneous release). Maximum release is determined by lysis of target cells in PBS containing 0.5% Triton X-100 (Sigma). Lastly, one can determine the frequency of CEA-specific T cells post in vitro priming using MHC/tetramers presenting CAP1 or CAP1-6D, as described previously (Fong et al., *Proc. Natl. Acad. Sci. U.S.A.*, 98:8809-14 (2001)). Cryopreserved CD45RA$^+$ T cells obtained before in vitro priming is analyzed in parallel with the in vitro primed T cell cultures. A total of $1\times10^6$ cells are stained with the corresponding HLA*A0201 phycoerythrin-labeled MHC/tetramer for 30 min at room temperature. Antibodies to CD8 (used for positive gate) and to CD4, CD14, CD19, and CD56 (negative "dump" gate) are added at the recommended concentrations and incubated for 30 min at 4° C. Following the staining, samples are washed twice and analyzed with four-color flow cytometry. We have established the background for tetramer staining previously. 20 volunteer blood donors were assessed with the same methodology and had 0.30%±0.18% and 0.27%±0.14% to CEA$_{605-613}$ and 610D tetramers, respectively (Fong et al., *Proc. Natl. Acad. Sci. USA.*, 98:8809-14 (2001)).

Example 34

Use of Proteinase 3 or PR1 as a Heterologous Antigen

Although some of the procedures outlined in the specific examples above describe the use of CEA antigens as the antigen expressed by the modified *Listeria*, one of ordinary skill in the art will readily recognize that similar procedures may be used to prepare a modified *Listeria* that expresses a different antigen, such as a proteinase-3 or a proteinase-3 derived antigen, to infect dendritic cells in vitro or ex vivo in order to effect loading and activation/maturation. One of ordinary skill in the art will also recognize that the resulting DC vaccines may then be administered to an animal or patient to induce an immune response to proteinase-3 and/or PR1.

For instance, the L4029-uvrAB *Listeria* strain described in the Examples above may be modified with a vector comprising a pPL2 vector backbone or the like encoding the proteinase-3 gene and/or the PR1 epitope to integrate the antigen-expressing sequence into the genome of the *Listeria*. In one example, the PR1 antigen could be expressed as part of a fusion protein such as an LLO-OVA/PR1 fusion protein comprising a truncated LLO sequence fused to OVA in which the PR1 epitope has been embedded. The sequence of such an antigenic protein (LLO-OVA/PR3) that could be expressed by the modified *Listeria* is shown in FIG. 31.

Example 35

Measuring the Ability of Mutant *Listeria* to Escape the Phagolysosome and Promote Class I Antigen Presentation An exemplary protocol for assessing the ability of a particular candidate mutant *Listeria* to escape the phagolysosome of an antigen-presenting cell and promote Class I antigen presentation by the cell is as follows: First, DC2.4 cells are grown on coverslips. The cells are then infected with the desired *Listeria* strain (MOI=100). At 0.5 hpi, the cells rinsed to wash away free *Listeria*. At 1 hpi, gentamicin is added at 50 µg/mL. At 5 hpi, coverslips are washed and fixed for in 3.5% formaldehyde. The coverslips are blocked, stained with rabbit anti-*Listeria* antibody (Difco), and detected with a goat-anti-rabbit FITC secondary (Vector Labs). Actin is detected with Phalloidin-rhodamine (Molecular Probes). The coverslips are mounted with Vectamount+DAPI (Vector Labs) and examined. See also Example 17 and Example 25, above.

Example 36

Generation of Human Monocyte-Derived Dendritic Cells and Infection with *Listeria* Vaccines An outline of an exemplary protocol for generation of human monocyte-derived dendritic cells and infection with *Listeria* vaccines is presented below:

Materials: Human peripheral blood (buffy coat from blood donor preferred); Ficoll-Hypaque (Amersham); dPBS w/o Ca, Mg (MediaTech); RPMI-1640 w/ L-Glutamine (MediaTech); Fetal Bovine Serum, Defined, Heat Inactivated (HyClone); Human GM-CSF (R&D Systems)-stock solution made at 500 U/µL and stored at −20°; Human IL-4 (R&D Systems)-stock solution made at 200 U/µL and stored at −20°; Costar 24-well plates (Fisher).

Monocyte Isolation Media (MIM): To make Solution 1 (Isosmotic Percoll), 50 mL of NaCl solution (500 mL dH$_2$O, 43.84 g NaCl (1.5M)) is added to 450 mL Percoll and mixed. Solution 2 (PBS/Citrate) is prepared by mixing 1000 mL dH$_2$O, 205.6 mg NaH$_2$PO$_4$*2H$_2$O (1.49 mM), 1.30 g Na$_2$HPO$_4$ (9.15 mM)), 8.18 g NaCl (139.97 mM), and 3.82 g C$_6$H$_5$Na$_3$O$_7$*2H$_2$O (13 mM) and bringing the pH to 7.2. 250 mL of isosmotic percoll is then mixed with 250 mL of PBS/citrate. The solution is sterile filtered and stored at 4°

Culture media: RPMI-1640 w. GlutaMax (Gibco)+10% Fetal Calf Serum (Defined, heat inactivated FCS from HyClone is used).

Methods: Ficoll and MIM are warmed to room temperature. 20 mL of Ficoll into each of 2 50 mL conical tubes. Blood is diluted 2 fold with dPBS and mixed well. 25 mL of blood is layered on top of Ficoll in each tube. The tubes are centrifuged at 400×g for 30 minutes at 18-20°.

The mononuclear interface is carefully harvested from the gradient, and placed into a clean 50 mL tube. The remainder of the tube is filled with dPBS. The tube is centrifuged at 100×g for 15 minutes. This pellets the lymphocytes and monocytes, but leaves the platelets suspended. The supernatant is aspirated. The steps of filling the remainder of the tube with dPBS, centrifuging, and aspirating are repeated two more times, for a total of 3 washes.

The pellet is resuspended in 20 mL of dPBS. The suspension is layered onto 20 mL of MIM. The sample is centrifuged at 400×g for 35 minutes at room temperature. The monocytes are harvested from the interface and transferred into a clean tube containing culture media. If culturing DC to use with bacteria, do not use antibiotics.)

The sample is centrifuged at 400×g for 10 minutes and the supernatant aspirated. The pellet is washed 4× in dPBS. After the final wash, cell pellet is resuspended in RPMI-1640+10% FCS. The sample is then counted on hemacytometer using Trypan Blue or using automated counter. The cell suspension is diluted to 1×10$^6$ cells per mL. For each mL of cell suspension, 500 U GM-CSF and 200 U IL-4 are added (1 µL per mL of each if stocks were made as described above). 1 mL per well is plated into Costar 24-well plates. The plates are placed at 37° C., 5% CO$_2$, 100% humidity for 48 hours.

On second day, feeding media for dendritic cells is made up. This consists of 0.5 mL culture media (warm to 37° before use) per well cultured, with 500 U/mL GM-CSF and 200 U/mL IL-4. 0.5 mL from the top of each well is aspirated and replaced with 0.5 mL of fresh feeding media. Plates are placed at 37° C., 5% CO$_2$, 100% humidity for 48 additional hours. Feeding is repeated on day 4. On day 5, cells are ready for use. The cells should always be kept in GM-CSF and IL-4 containing media, or they will revert to macrophages. The dendritic cells are examined phenotypically on the cytometer looking at HLA-DR, CD1a, CD83, and CD86.

*Listeria* Infection of Human DC:

The day 5 dendritic cells (DC) are pelleted and resuspended in fresh media with GM-CSF and IL-4 at 2×10$^6$ cells per mL. 500 µL of suspension is aliquoted to each well of a 24 well plate. Maturation stimuli or bacteria are added in 500 µL. 1 µg of LPS is used for maturation control. (1000 U of IFN-γ or 1 µg of sCD40L can be added to augment this response.)

For *Listeria* infection, between 10-100 *Listeria* per DC is used. Cells are infected for 1 hour, then extracellular bacteria are washed away and cells are resuspended in media containing 50 µg/mL gentamicin. sCD40L will can be added to enhance DC survival and promote greater IL-12p70 release. 1000 U/mL IFN-γ can be added to augment maturation and IL-12p70 secretion. The DC are examined phenotypically on the cytometer looking at HLA-DR, CD1a, CD83, and CD86.

Example 37

Asporagenic *B. anthracis* Vaccine Strains

The spoIIE in-frame deletion. The spoIIE region of *B. anthracis* is identified by homology to the same gene in *B. subtilis*. In order to isolate an in-frame deletion of *B. anthracis* SpoIIE, the spoIIE gene is first amplified by PCR and cloned it into pCR-Blunt II-TOPO (Invitrogen). Next, most of the spoIIE gene is deleted by using the technique of gene splicing by overlap extension (SOE) (Horton et al., Biotechniques 8:528-35 (1990)). This in-frame deleted spoIIE gene is cloned into the shuttle vector pKSV7, which carries a chloramphenicol-resistance gene and cannot replicate at 42° C. (Smith et al., *Biochimie*, 74:705-11 (1992)). pKSV7 containing the deleted spoIIE gene is then electroporated into *B. anthracis*, and cells are grown at 42° C. in the presence of chloramphenicol to select for strains in which the plasmid has integrated by homologous recombination into the spoIIE gene. Further growth at 30° C. without chloramphenicol selection allows excision and loss of the plasmid. Chloramphenicol-sensitive strains should be found at about 1%, and about half of them should contain the deleted spoIIE allele (Camilli et al., (1993)). The presence of the deletion is confirmed by PCR and Southern blot analyses.

The spoIIE/uvrAB double deletion strain. Starting with the spoIIE deletion strain, an in-frame deletion of the uvrA and uvrB genes is made. Once again, the genes of interest are amplified and cloned into pCR-Blunt II-TOPO. Then we shall delete most of the uvrA and uvrB genes by the SOE technique. This in-frame deleted uvrAB region is cloned into pKSV7, and the construct is electroporated into the *B. anthracis* spoIIE deletion strain. Chloramphenicol-resistance is selected at 42° C. in order to select for the integration of the plasmid into the uvrAB region. Growth at 30° C. without drug selection is allowed in order to encourage the growth of segregants that have lost the plasmid. Chloramphenicol-sensitive colonies are picked and tested by PCR for loss of the uvrAB region, and that loss is confirmed by Southern blot analysis.

Example 38

A Temperature Sensitive recA Mutant of *B. Anthracis*

To generate a temperature sensitive recA mutant of *B. anthracis* which grows well at 30° C. and is very sensitive to psoralen at 42° C., a mutation is made in *B. anthracis* which is analogous to the V246M mutation of the temperature sensitive recA mutant of *E. coli*, recA44 (Kawashima et al., 193:288-92 (1984)). To make the *B. anthracis* mutant, the sequence 245 KVVKNK250 (SEQ ID NO:46), which is conserved between *E. coli* and *B. anthracis*, is mutated. The V246M mutation is introduced into the cloned *B. anthracis* recA gene by mismatched oligonucleotide mutagenesis, using the Stratagene Quick Change kit (Stratagene, La Jolla, Calif.). The mutations are confirmed by sequence analysis, and the mutated gene is transferred into pKSV7, in order that they can be introduced into the chromosome of *B. anthracis* spoIIE uvrAB by allelic exchange. Alternatively, the recA gene from the *B. anthracis* strains is deleted and replaced with the recA44(ts) allele of *E. coli*. (It is known that *B. anthracis* recA functions in *E. coli* (Ko et al., J. Bacteriol 184:3917-22 (2002)).)

Example 39

Introduction of Mutations in the Active Sites of *B. anthracis* Antigens

The lethal factor mutation H686A inactivates its protease activity, and the edema factor mutations K346Q and K353Q (together) inactivate its adenyl cyclase activity (Brossier et al., Infect. Immun., 68:1781-6 (2000)). These mutations are introduced into *B. anthracis* strains to be used in vaccines, such as the spoIIE uvrAB and spoIIE uvrAB recAts strains. The lef (lethal factor; SEQ ID NO:80; SEQ ID NO:81) and cya (edema factor, adenyl cyclase; SEQ ID NO:82; SEQ ID NO:83) genes are cloned and mutagenized with the Quick Change kit (Stratagene, La Jolla, Calif.) to create the mutant genes. The mutant genes are then transferred to pKSV7 and finally introduced into the host pXO1 plasmid by allelic exchange.

Example 40

Inducible Expression of Protective Antigen at High Levels

The use of SOS regulatory sequences for expressing protective antigen at high levels. Cheo et al (Cheo et al., J. Bacteriol., 175:5907-15 (1993)) have shown that the consensus sequence GAACN$_4$GTTC (SEQ ID NO:47) defines the LexA repressor site for genes in the SOS response of *B. subtilis*. A similar consensus sequence upstream of the promoters for the *B. anthracis* recA and uvrAB genes, which are part of the SOS regulon, is identified. To make a *B. anthracis* strain that expresses protective antigen at high levels, the protective antigen gene is put under the control of the SOS regulatory sequence and introduced into *B. anthracis* spoIIE uvrAB strain, so that treatment with psoralen will cause high levels of protective antigen to be made. In order to insert this artificial gene into the *B. anthracis* chromosome, an integration vector, such as pPL2, is used (Lauer et al, J. Bacteriol., 184:4177-86 (2002)). The gene of interest, in this case the protective antigen gene under control of a promoter, is inserted in the multicloning site. The plasmid is mated from *E. coli* into *B. anthracis* strains. Since it cannot replicate in gram-positive bacteria, it can only be maintained by integration into the chromosome. The current pPL2 vector contains a phage integrase and phage attachment site from *L. monocytogenes*, and therefore, must be modified by removing the *L. monocytogenes* phage integrase gene and phage attachment site and replacing them with similar elements from a phage of *B. anthracis*, such as gamma phage (Brown et al., J. Infect Dis., 96:34-9 (1955)). Also, the pPL2 vector typically contains chloramphenicol-resistance genes for selection. Since drug resistance genes are undesirable for vaccine work, they are removed. One of the drug resistance genes has been replaced by the gene for D-alanine racemase, which synthesizes D-alanine and allows a D-alanine auxotroph to grow on rich medium without the addition of D-alanine. The other drug resistance gene is replaced by the gene for glutamine synthetase, which synthesizes glutamine and allows growth of a glutamine synthetase mutant bacterium on rich medium without glutamine.

The use of other inducible promoters. In some embodiments, for instance, when the *B. anthracis* strain carries both uvrAB and recA mutations, the SOS response will not occur, since this response depends upon RecA protein. In these cases, it is desirable to use a different sort of inducible promoter. Suitable promoters for this use can be determined by first identifying which proteins are expressed at high levels after S-59/UVA treatment of an uvrAB recA double mutant. The mass spectrometry techniqued described in Lenz et al., *Proc. Natl. Acad. Sci. USA*, 100:12432-12437 (2003), can, for instance, be used for this purpose. Once the proteins expressed at high level under S-59 UVA treatment conditions are determined, the promoters controlling expression of the highly expressed proteins can be identified through techniques known to those of ordinary skill in the art. A promoter identified in this manner can then be fused to the gene expressing the protective antigen. The construct can then be introduced into the chromosome of the mutant *Bacillus anthracis* using one of the integration vectors described herein or another vector known in the art.

Example 41

Exemplary Mutant *B. anthracis* Strains

A variety of different mutant *B. anthracis* strains are prepared using combinations of the methods described in the Examples, above. Exemplary mutant *B. anthracis* strains to be used in vaccine compositions are listed in Table 29.

TABLE 29

*B. anthracis* strains and candidate vaccines

| Strain and/or Genotype | Relevant Characteristics and Phenotype | Use and Vaccine Strain Number |
| --- | --- | --- |
| Ames pXO1+/pXO2+ | Fully virulent wild-type *B. anthracis* (Toxigenic and encapsulated) | Initial host strain for construction of all vaccine candidates Production of virulent spores for challenge experiments in mice and guinea pigs |
| Sterne pXO1+/pXO2− | Toxigenic, non-encapsulated | Production of virulent spores for challenge experiments in mice and guinea pigs |
| spoIIE pXO1+/pXO2+ | Non-sporogenic Toxigenic, encapsulated | Vaccine strain #1 |
| SpoIIE/uvrAB pXO1+/pXO2+ | Non-sporogenic NER-[1] (Increased S-59/UVA sensitivity) Toxigenic, encapsulated | Vaccine strain #2 |

TABLE 29-continued

B. anthracis strains and candidate vaccines

| Strain and/or Genotype | Relevant Characteristics and Phenotype | Use and Vaccine Strain Number |
|---|---|---|
| SpoIIE/uvrAB/recA ts[3]<br>pXO1+/pXO2+ | Non-sporogenic<br>NER-(Increased S-59/UVA sensitivity)<br>Toxigenic, encapsulated | Vaccine strain #3 |
| SpoIIE/uvrAB/recA ts<br>pXO1+/pXO2+ | Non-sporogenic<br>NER-/conditional HR-[4]<br>(Increased S-59/UVA sensitivity)<br>Toxigenic, encapsulated | Vaccine strain #4 |
| spoIIE/uvrAB/pXO1<br>(lef686/cya346/35)/pXO2+ | Non-sporogenic<br>NER-(Increased S-59/UVA sensitivity)<br>Encapsulated<br>Non-toxigenic (LF/EF functional domains mutated) | Vaccine strain #5 |
| spoIIE/uvrAB/recA ts/<br>pXO1(lef686/cya346/35)/<br>pXO2+ | Non-sporogenic<br>NER-/conditional HR-<br>(Increased S-59/UVA sensitivity)<br>Encapsulated<br>Non-toxigenic (LF/EF functional domains mutated) | Vaccine strain #6 |
| spoIIE/uvrAB/<br>pXO1 (lef686/cya346/35)/<br>pXO2+/<br>Pro$_{S-59}$-PA | Non-sporogenic<br>NER-(Increased S-59/UVA sensitivity)<br>Encapsulated<br>Non-toxigenic (LF/EF functional domains mutated)<br>S-59 psoralen inducible PA | Vaccine strain #7 |
| spoIIE/uvrAB/recA ts/<br>pXO1(lef686/cya346/35)/<br>pXO2+/<br>Pro$_{S-59}$-PA | Non-sporogenic<br>NER-/conditional HR-<br>(Increased S-59/UVA sensitivity)<br>Encapsulated<br>Non-toxigenic (LF/EF functional domains mutated)<br>S-59 psoralen inducible PA | Vaccine strain #8 |

[1]NER, nucleotide excision repair
[3]Conditional recA strains under the control of a lacI repressible promoter can also be derived
[4]HR, homologous recombination Example 42

Characterization of Protein Expression Levels, Including Protective Antigen and Capsule, in Psoralen-Inactivated *B. anthracis* Strains To show that inactivated *B. anthracis* strains can still metabolize, the cells are incubated in minimal medium with bicarbonate (Thorne et al., J. Gen. Microbiol., 17:505-16 (1957)). After such incubation the cells are removed by centrifugation and save the supernatant. The supernatant is subjected to SDS-polyacrylamide gel electrophoresis. After staining with Coomassie Blue, protective antigen stands out, and its presence is confirmed by Western blot analysis (Brossier et al., Infect. Immun. 68:5731-4 (2000)) and by mass spectometry. In addition, mass spectrometry is used to identify the other proteins that are excreted under these conditions, using the methods described in Lenz et al., Proc. Natl. Acad. Sci. U.S.A., 100: 12432-12437 (2003). In order to assess whether polyglutamate capsule is made under these conditions, pXO2, which encodes the genes for capsule synthesis, is introduced into the strains by transduction and (Green et al., Infect. Immun., 49:291-7 (1985). Capsule is measured by rocket immunoelectrophoresis (Uchida et al., Mol. Microbiol, 23:1229-40 (1997)).

Example 43

Characterization of the Humoral and Mucosal Responses in Swiss Webster and A/J Mice Immunized with Attenuated *B. anthracis* Strains Mouse Immunization. Mice are injected with the S-59/UVA vaccines by the intramuscular (IM) or the subcutaneous (SC) routes to determine which route of immunization results in the best bacterial-specific humoral and cellular responses. Intranasal (IN) immunization of mice is also tested to assess mucosal responses induced by the candidate vaccines. IN immunization with 5 µl of a designated vaccine preparation into each nare of lightly anesthetized mice is performed as described previously. (Boyaka, et al., J. Immunol., 170: 5636-43 (2003)) Mice are immunized with 0.1 LD$_{50}$ doses of the candidate vaccines. Any of the eight S-59/UVA inactivated vaccine candidates in which a median lethality level is not observed is given at an initial dose of 10$^8$ particles. Mice that are immunized by more than one route are not injected with a combined dose that exceeds the 0.1 LD$_{50}$ dose, or is greater than 10 particles. Mice given multiple immunizations receive consistent vaccine doses with all injections. As immunization on three consecutive days with S-59/UVA inactivated *Listeria* uvrAB resulted in increased humoral and cellular immunity as compared to a single immunization, the same strategy is used with the *B. anthracis* strain vaccines. Mice are also given booster immunizations at 14 days and 28 days following the primary immunization.

Quantification of antibodies to PA, LF, EF, capsule, and whole bacteria. The mucosal and antibody responses in mice immunized with the various vaccine candidates are characterized. Sera is taken from the retroorbital plexus prior to immunization as well as 1 week after each immunization. Saliva and nasal washes for measurement of IgA levels are performed at the time of sacrifice one week after the final immunization. The durability of the humoral and mucosal immunity induced by the candidate vaccines at 45 days after the final immunization is also characterized. Humoral and mucosal responses against PA, capsule, and vegetative bacteria (Sterne strain) are determined by enzyme-linked immunosorbent assays (ELISAs), as published previously (Ballard et al., *Proc. Natl. Acad. Sci. U.S.A*, 93:12531-4 (1996); Rhie et al., *Proc. Natl. Acad. Sci. USA.*, 100:10925-30 (2003)). Briefly, Immulon 96-well Maxisorp plates (Nalge Nunc) are first coated by 5 μg purified PA, LF, EF, BSA conjugated with poly-γ-D-glutamic acid (PGA) capsule prepared as described previously. (Rhie et al., *Proc. Natl. Acad. Sci. U.S.A*, 100: 10925-30 (2003)), or with S-59 psoralen/UVA inactivated bacteria ground under liquid nitrogen using a mortar and pestle in 50 mM carbonate buffer (pH9.6) at 4° C. for 16 h, and blocked with TSTA buffer (50 mM Tris [pH 7.6], 142 mM NaCl, 0.05% sodium azide, 0.05% Tween 20, 2% bovine serum albumin). Serial two-fold dilutions of mouse plasma or mucosal secretions are added to the 96-well plates coated with PA, PGA-BSA, or Sterne respectively. Binding of Abs to the immobilized antigens is determined by incubation with isotype-specific peroxidase goat anti-mouse μ, γ, or αH chain-specific antibodies from Southern Biotechnology Associates (Birmingham, Ala.). Biotinylated rat anti-mouse γ1 (clone G1-7.3), γ2a (clone R19-15), γ2b (clone R12-3), or γ3 (clone R40-82) H chain-specific mAbs (BD PharMingen, San Diego, Calif.) and streptavidin-conjugated peroxidase are used for IgG Ab subclass analysis (Cole, *J. Bacteriol.*, 107:846-52 (1971); Cole et al., *Basic Life Sci.,* 5B:487-95 (1975)). The colorimetric reaction is developed by addition of ABTS substrate (Sigma-Aldrich, St. Louis, Mo.). End-point titers are expressed as the reciprocal $\log_2$ dilution giving OD415>two standard deviations above those obtained with control, non-immunized mice.

Enzyme-linked immunospot (ELISPOT) assay for the detection of Ig-secreting cells. The frequency of PA-specific Ig-secreting lymphocytes is determined by ELISPOT analysis (Boyaka et al., *J. Immunol.,* 170:5636-43 (2003)). Briefly, spleens or cervical lymph nodes of vaccinated and control mice are rapidly dissected out and placed in ice-cooled RPMI 1640 medium and single cell suspensions are prepared. 96-well PVDF-based plates (BD Biosciences, San Jose) are coated overnight with 2.5 μg/ml purified PA (List Biological Laboratories, Campbell, Calif.). The plates are washed, blocked for 2 hrs at 37° C. with 200 μl complete RPMI, and serial dilutions of cell suspensions are added to 96-well plates. Cells are incubated on the plates for 6 hours at 37° C. in 5% $CO_2$. Antigen-specific Antibody Forming Cells (AFC) are detected with isotype-specific biotin-labeled anti-mouse μ, γ, or α H chain-specific antibodies (Southern Biotechnology Associates). After incubation at RT for 2 h, the plates are washed, and goat anti-biotin:1 nm Gold conjugate (GAB1; Ted Pella) is added for 1 hour at RT. After extensive washing, 30 μl of the silver substrate (Silver Enhancing Kit; Ted Pella) is added into each well and the spot development is monitored. Spots in each well are counted using an automated ELISPOT plate reader (CTL, Cleveland). The humoral response is expressed as the number of antibody forming cells per 106 spleen or lymph node cells.

Toxin Neutralization Assays. Neutralizing antibodies induced in mice immunized with the vaccine candidates are evaluated for the ability to protect the J774 macrophage cell line from lethal toxin (PA+LF) (Mock et al., Annu. Rev. Microbiol., 55:647-71 (2001); Boyaka et al. (2003); Rhie et al. (2003)) Briefly, J774 cells (ATCC, Manassus, Va.) are added to 96-well flat-bottom plates (Nunc) at $5 \times 10^4$ cells/well and incubated for 12 hours at 37° C. in 5% CO2. Test serum or mucosal secretions are serially diluted two-fold in TSTA buffer. PA and LF (400 ng/ml PA and 40 ng/ml LF) are added to the antiserum dilutions. After incubation for 1 hour the antiserum/lethal toxin complex mixture is added to the cell suspension and incubated for an additional 5 hours. Cell viability is monitored by the MTT assay (absorbance measured at 540 nm). Assays are performed in triplicate with a negative control (normal serum) and a positive control (MAbs, 14B7 and 1G3) (Mikesell et al., *Infect Immun.,* 39:371-6 (1983); Starnbach et al., *Nature,* 9, (2003)) included in each plate. The mean and standard deviation of each triplicate sample dilution is calculated. The endpoint is expressed as the highest serum dilution exhibiting 50% neutralization of the anthrax toxin as compared to normal control serum.

Example 44

Characterization of the PA-, LF-, and EF-Specific CD4+ T Cell-Mediated Responses in A/J Mice Vaccinated with Modified *B. anthracis*

T cell Proliferation. CD4+ T cell proliferation are determined from PBMC, spleen and lymph node cells of vaccinated and naïve A/J mice. Spleen and cervical lymph nodes are dispersed to obtain single cell suspensions as previously described (Boyaka et al., *J. Immunol.,* 162: 122-8 (1999); Lillard et al., *J. Immunol.,* 166:162-169 (2001); Little et al., *Infect. Immun.,* 65:5171-5 (1997)). CD4+ T cells are isolated by negative selection using the Mouse CD4+ T cell isolation kit from Miltenyi Biotec (Auburn, Calif.). Purified CD4+ T cells from individual mouse spleens, from pooled lymph nodes or PBMCs are cultured at 4×106 cells/ml and stimulated with varying concentrations of PA, LF or EF in the presence of T-cell-depleted, non-dividing syngeneic naïve spleen feeder cells ($8 \times 10^6$ cells/ml) in complete RPMI (RPMI supplemented with 10% FBS, 10 mM Hepes, 2 mM L-glutamine, 1 mM Sodium Pyruvate, non-essential amino acids, 23.8 mM Sodium Bicarbonate, $5 \times 10^{-5}$ M μ-Mercapthoethanol, 100 U/ml penicillin and 100 Ug/ml streptomycin). The replication of splenic feeder cells is arrested by brief photochemical treatment with S-59 psoralen. Cultures are incubated for 4 days at 37° C. and 5% $CO_2$ prior to addition of 0.5 μCi of tritiated thymidine ([3H]TdR) for the final 18 to 20 hours. The cells are harvested onto glass fiber sheets and the amount of incorporated thymidine is determined by measuring the radioactivity on the scintillation counter (Wallac, Turku, Finland).

Analysis of PA-, EF- or LF-induced cytokine responses. CD4+ T cells are isolated by negative selection using the Mouse CD4+ T cell isolation kit from Miltenyi Biotec (Auburn, Calif.). Purified CD4+ T cells from spleens or lymph node of individual mice are cultured in round-bottom 96-well plates at $1 \times 10^5$ cells/well and stimulated with varying concentrations of PA, LF or EF in the presence of T cell-depleted, non-dividing syngeneic naïve spleen feeder cells ($1 \times 10^5$ cells/well) in complete RPMI. The T cell-depleted spleen feeder cells are arrested by a brief photochemical treatment with S-59. T cell cultures are incubated for 2 days at 37° C. and 5% CO2. Expression of T helper-1 and T helper-2 cytokines is determined from supernatants of antigen-stimulated CD4+ T cells using the Th1/Th2 Cytometric Bead Array kit (BD Pharmingen, San Diego, Calif.).

Example 44

Characterization of the Extent of Protection Against Spore and Lethal Toxin Challenge in Swiss Webster and A/J Mice at 45 Days Post Last Immunization Dose with Modified *B. anthracis* Vaccines Protection of mice against lethal toxin challenge. Mice immunized with selected candidate vaccines are challenged by tail vein injection with lethal toxin, as described previously (Price et al., *Infect. Immun.*, 69:4509-15 (2001); Rhie et al. (2003)). Lethal toxin is prepared by mixing recombinant PA and LF recombinant proteins (List Biological Laboratories, Campbell, Calif.) as described (Rhie et al. (2003)). The lethal toxin IV $LD_{50}$ per mouse is approximately 12 µg of PA mixed with 6 µg of LF. The median lethality in mice of freshly prepared lethal toxin is determined by tail vein injection over a 0.1-10 $LD_{50}$ dose range of the published values. The protection studies will likely include lethal toxin challenge over a range of 5-10 times the $LD_{50}$ dose. In this model, unprotected mice succumb within 24 h. Initially, death by anthrax is confirmed in selected mice by plating blood on tryptic soy agar and incubating overnight at 37° C. Plates are observed for colonies with 2-3 mm typical anthracis-like "ground glass" appearance. All mice treated with lethal toxin are monitored daily, and experiments are terminated after 2 weeks and all protected mice are sacrificed.

Spore preparation. Sterne strain spores are prepared as described (Barnard and Friedlander, 1999). Briefly, single colonies are inoculated into 5 ml of FA medium (3.3% tryptone, 2% yeast extract [dialyzed overnight against water], 0.2% L-histidine, 0.8% $Na_2HPO_4$, 0.4% $KH_2PO_4$, 0.74% NaCl) contained in a 100-ml bottle and shaken for 5 h at 37° C. One-tenth-milliliter aliquots are spread on L agar plates, and incubated at 37° C. Bacterial lawns are scraped from the plates, washed extensively with sterile water, heat shocked for 30 min at 60° C., washed with water, purified on 58% Renografin-76 (Bristol-Myers Squibb, Princeton, N.J.) in water, as previously described (Palucka et al., *Nature Medicine,* 5:868-870 (1999)), and washed once more with water. The spores are then sedimented to a pellet at 10,000×g and resuspended in 1% phenol in water. This yield of this process has been published to range from $0.5\times10^9$ to $5.0\times10^9$ spores per plate.

Protection of mice against lethal spore challenge. The $LD_{50}$ value of heat-shocked Sterne strain spores given by intramuscular (IM) injection is determined over a dose range of $10^3$ to $10^8$ spores. To evaluate protection in vaccinated mice against inhalation anthrax, challenge experiments are also performed by intratrachial (IT) spore administration, as described previously (Brook et al., *J. Med. Microbiol.,* 50:702-11 (2001)). Briefly, the tongue of immobilized and anesthetized mice are gently pulled outward and laterally with forceps, and the vaccine is delivered using a syringe fitted with a blunt 1.5 inch 22-gauge needle bent at a gentle angle, approximately 1 inch from the tip. We anticipate that the Sterne strain $LD_{50}$ value administered by IM or IT routes is approximately $10^3$ in A/J mice, and up to 10-fold higher in Swiss Webster mice. The protection studies include up to 100 $LD_{50}$ dose spore challenge. All mice treated with spores are monitored daily, and experiments are terminated after 2 weeks and all protected mice are sacrificed. In all challenge experiments, the mean time to death is determined in non-surviving cohorts.

Example 45

Protective Immunity of the *Listeria* Vaccines Against Challenge with Vaccinia Expressing OVA Model Antigen in Mice The vaccines of the invention show protective immunization against a *Listeria* challenge. To further illustrate the ability to immunize and protect against a pathogen, *Listeria* vaccines with or without OVA antigen and with and without S-59 UVA treatment (second method of Example 13, above) were used to immunize against another microbe, e.g. vaccinia virus that expresses the OVA antigen (VV-OVA). This experiment was performed as a non-limiting example to demonstrate that an antigen specific immunization against other microbes can be achieved with particular compositions of a recombinant *Listeria*-based vaccine.

Recombinant vaccinia virus (WR strain) genetically modified to express OVA (VV-OVA) as a non-limiting example of a model antigen, was obtained from La Jolla Research Institute and prepared in Vero cells using Opticell chambers (BioCrystal, OH). Opticell chambers were seeded with Vero cells in Eagle's Minimal Essential Medium supplemented with L-glutamine, P/S (penicillin/streptomycin), NEAA (non-essential amino acids), $NaHCO_3$, and 10% FBS. When cells reached approximately 75% confluence, the growth medium was removed and replaced with fresh medium containing approximately $1\times10^5$ plaque forming units (PFU)/mL of a pure plaque-purified stock of VV-OVA. When the monolayers revealed >50% cytopathic effect, cells and supernatants were harvested together, subjected to three freeze-thaw cycles, clarified by low-speed centrifugation, and the supernatant stored at −80° C. The titer was determined by plaque assay on Vero-76 cells. Ovalbumin expression by the recombinant was confirmed by a western blot analysis prior to injection into the mice.

C57B1/6 mice (3 per group) were given prime and boost vaccinations by an IV route, according to Table 30 and FIG. 41. 30 days following the first boost immunization, all mice were challenged with an IP injection of $1\times10^7$ PFU of VV-OVA. Five days post VV-OVA challenge, the mice were euthanized and the ovaries harvested by dissection and observed for gross pathology. The ovaries were also combined and assayed for vaccinia plaque forming units. Paired ovaries from individual mice were homogenized in 1 mL of buffer, frozen (liquid nitrogen) and thawed (37° C.) three cycles, with vortexing between each cycle, then stored at −80° C. To assay, samples were thawed, centrifuged at 4° C. to remove debris, and serially diluted for application to Vero cells. Vero-76 cells were plated in 6-well tissue culture plates. When the cell monolayers reached a confluence of about 70-85%, the medium was aspirated from each well and the cells were inoculated with 1 mL of the appropriate dilution of ovary homogenate preparation. One hour later, the medium was aspirated and replaced with 3 mL of 1:1 2× growth medium: 1.5% agarose. Plaques were enumerated after 3-4 days of culture.

TABLE 30

Vaccination of mice with *Listeria monocytogenes* expressing OVA and challenged with vaccinia expressing OVA.

| *Listeria* Vaccine strain | Treatment | Vaccination days | Vaccination dose* |
|---|---|---|---|
| HBSS | — | 0 | 100 μL |
| ΔactA | — | 0, 14 | $1\times10^7$ |
| ΔactA | S-59 UVA | 0, 1, 2, 14, 15, 16 | $3\times10^8$ |
| ΔactA OVA | — | 0, 14 | $1\times10^7$ |
| ΔactA OVA | S-59 UVA | 0, 1, 2, 14, 15, 16 | $3\times10^8$ |
| ΔactAΔuvrAB | — | 0, 14 | $1\times10^7$ |
| ΔactAΔuvrAB | S-59 UVA | 0, 1, 2, 14, 15, 16 | $3\times10^8$ |
| ΔactAΔuvrAB OVA | — | 0, 14 | $1\times10^7$ |
| ΔactAΔuvrAB OVA | S-59 UVA | 0, 1, 2, 14, 15, 16 | $3\times10^8$ |
| ΔactAΔuvrAB OVA | Heat-killed | 0, 1, 2, 14, 15, 16 | $1\times10^9$ |

*All doses administered in 100 μL HBSS.

The results from the experiment demonstrated profound protection against VV-OVA challenge in mice immunized with particular compositions of *Listeria*-OVA vaccines. It is well known to those skilled in the art, that the immune correlate of protection against vaccinia virus challenge is a CD8+ T-cell based response (Snyder, J. T. et. al., J. Virol. 2004 7813:7052-7060). Table 31 and FIG. 42 reveal the titers of VV-OVA in the ovaries of mice from experimental groups, according to Table 30. In particular, mice immunized with S-59/UVA inactivated *Listeria* ΔactAΔuvrAB-OVA, but not S-59/UVA inactivated *Listeria* ΔactA-OVA were protected against challenge with VV-OVA (p=0.0118 two-sided unpaired t-test). These data provide unequivocal conclusive evidence that the DNA repair mutation confers vaccine compositions that can be psoralen killed but retain metabolic activity, and as such, express their genetic repertoire and can thus stimulate a memory-based antigen-specific T-cell immune responses in an immunized warm-blooded animal that is protective against challenge with a pathogen that expresses the said antigen.

TABLE 31

Titers of VV-OVA in the ovaries of vaccinated mice

| *Listeria* Vaccine strain | Treatment | Log PFU/ mL ± SD | Log Reduction |
|---|---|---|---|
| HBSS | — | 6.18 ± 0.21 | N/A |
| ΔactA | — | 5.87 ± 0.36 | 0.31 |
| ΔactA | S-59 UVA | 5.98 ± 0.13 | 0.2 |
| ΔactA OVA | — | <2.31 ± 1.58 | >3.87 |
| ΔactA OVA | S-59 UVA | 4.54 ± 0.62 | 1.63 |
| ΔactAΔuvrAB | — | <4.39 ± 2.59 | >1.79 |
| ΔactAΔuvrAB | S-59 UVA | 5.94 ± 0.19 | 0.24 |
| ΔactAΔuvrAB OVA | — | 3.26 ± 1.29 | 2.91 |
| ΔactAΔuvrAB OVA | S-59 UVA | <1.96 ± 0.51 | >4.21 |
| ΔactAΔuvrAB OVA | Heat-killed | 5.83 ± 1.12 | 0.35 |

Example 46

Construction of *Listeria* Expression Cassettes and Expression Vectors

A. Cloning Vectors

Selected heterologous antigen expression cassette molecular constructs were inserted into pPL2 (Lauer et. al. *J. Bacteriol.* 2002), or pAM401 (Wirth et. al., *J. Bacteriol.* 165:831-836), modified to contain the multiple cloning sequence of pPL2 (Aat II small fragment, 171 bps), inserted between blunted Xba I and Nru I recognition sites, within the tetracycline resistance gene (pAM401-MCS, FIG. 32). In general, the hly promoter and (selected) signal peptide sequence was inserted between the unique Kpn I and Bam HI sites in the pPL2 or pAM401-MCS plasmid vectors. Selected EphA2 genes (sometimes modified to contain N-terminal and C-terminal epitope tags; see description below) were cloned subsequently into these constructs between unique Bam HI and Sac I sites. Molecular constructs based on the pAM401-MCS plasmid vector were introduced by electroporation into selected *Listeria monocytogenes* strains also treated with lysozyme, utilizing methods common to those skilled in the art. The expected plasmid structure in *Listeria*-transfectants was verified by isolating DNA from colonies that formed on chloramphenicol-containing BHI agar plates (10 μg/ml) by restriction enzyme analysis. Recombinant *Listeria* transformed with various pAM401-MCS based heterologous protein expression cassette constructs were utilized to measure heterologous protein expression and secretion, as described below.

The pPL2 based heterologous protein expression cassette constructs were incorporated into the tRNA$^{Arg}$ gene in the genome of selected *Listeria* strains, according to the methods as described previously [Lauer et. al., J. Bacteriol. 184, 4177-4186 (2002)]. Briefly, the pPL2 heterologous protein expression cassette constructs plasmid was first introduced into the *E. coli* host strain SM10 (Simon et. al., Bio/Technology 1:784-791 (1983)] by electroporation or by chemical means. Subsequently, the pPL2-based plasmid was transferred from transformed SM10 to the selected *Listeria* strains by conjugation. Following incubation on drug-selective BHI agar plates containing 7.5 μg of chloramphenicol per ml and 200 μg of streptomycin per ml as described, selected colonies are purified by passaging 3 times on plates with the same composition. To verify integration of the pPL2 vector at the phage attachment site, individual colonies are picked and screened by PCR using the primer pair of forward primer NC16 (5'-gtcaaaacatacgctcttatc-3' (SEQ ID NO:55) and reverse primer PL95 (5'-acataatcagtccaaagtagatgc-3' (SEQ ID NO:56)). Selected colonies having the pPL2-based plasmid incorporated into the tRNA$^{Arg}$ gene in the genome of selected *Listeria* strains yielded a diagnostic DNA amplicon of 499 bps.

B. Promoter

Heterologous protein expression cassettes contained the prfA-dependent hly promoter, which drives the transcription of the gene encoding Listeriolysin O (LLO), and is activated within the microenvironment of the infected cell. Nucleotides 205586-206000 (414 bps) were amplified by PCR from *Listeria monocytogenes*, strain DP-L4056, using the primer pair shown below. The region amplified includes the hly promoter and also the first 28 amino acids of LLO, comprising the secA1 signal peptide (see above) and PEST domain. The expected sequence of this region for *Listeria monocytogenes*, strain EGD can be found in GenBank (Accession number: gi|16802048|ref|NC_003210.1|[16802048]). The primers used in the PCR reaction are as follows:

```
Primer Pair:

Forward (KpnI-LLO nts. 1257-1276):

5'-CTCTGGTACCTCCTTTGATTAGTATATTC (SEQ ID NO:57)

Reverse (Bam HI-LLO nts. X-x):

5'-CTCTGGATCCATCCGCGTGTTTCTTTTCG (SEQ ID NO:58)
(Restriction endonuclease recognition sites are
underlined.)
```

The 422 bp PCR amplicon was cloned into the plasmid vector pCR-XL-TOPO (Invitrogen, Carlsbad, Calif.), according to the manufacturer's specifications. The nucleotide sequences of *Listeria*-specific bases in the pCR-XL-TOPO-hly promoter plasmid clone was determined. *Listeria monocytogenes* strain DP-L4056 contained eight nucleotide base changes flanking the prfA box in the hly promoter, as compared to the EGD strain. The hly promoter alignment for the *Listeria monocytogenes* DP-L4056 and EGD strains is shown in FIG. 33 below.

The 422 bp DNA corresponding to the hly promoter and secA1 LLO signal peptide were liberated from the pCR-XL-TOPO-hly promoter plasmid clone by digestion with Kpn I and Bam HI, and cloned into the pPL2 plasmid vector (Lauer et. al. 2002 J. Bact.), according to conventional methods well-known to those skilled in the art. This plasmid is known as pPL2-hlyP (native).

C. Shine-Dalgarno Sequence

At the 3' end of the promoter is contained a poly-purine Shine-Dalgarno sequence, the element required for engagement of the 30S ribosomal subunit (via 16S rRNA) to the heterologous gene RNA transcript and initiation of translation. The Shine-Dalgarno sequence has typically the following consensus sequence: 5'-NAGGAGGU-$N_{5-10}$-AUG (start codon)-3' (SEQ ID NO:59). There are variations of the poly-purine Shine-Dalgarno sequence Notably, the Listeria hly gene that encodes listerolysin O (LLO) has the following Shine-Dalgarno sequence: AAGGAGAGTGAAACCCATG (SEQ ID NO:60) (Shine-Dalgarno sequence is underlined, and the translation start codon is bolded).

Example 47

Integration of an Expression Cassette into the Listeria Chromosome Via Allelic Exchange As one possible alternative to using an integration vector such as pPL2 to insert a heterologous gene expression cassette into the chromosome of Listeria, allelic exchange may be used.

Briefly, bacteria electroporated with the pKSV7-heterologous protein expression cassette plasmid are selected by plating on BHI agar media containing chloramphenicol (10 μg/ml), and incubated at the permissive temperature of 30° C. Single cross-over integration into the bacterial chromosome is selected by passaging several individual colonies for multiple generations at the non-permissive temperature of 41° C. in media containing chloramphenicol. Finally, plasmid excision and curing (double cross-over) is achieved by passaging several individual colonies for multiple generations at the permissive temperature of 30° C. in BHI media not containing chloramphenicol. Verification of integration of the heterologous protein expression cassette into the bacteria chromosome is verified by PCR, utilizing a primer pair that amplifies a region defined from within the heterologous protein expression cassette to the bacterial chromosome targeting sequence not contained in the pKSV7 plasmid vector construct.

Example 48

Antigen Sequences and Signal Sequences Codon-Optimized for Expression in Listeria monocytogenes A. Codon-Optimized Expression Cassette Encoding a Fusion Protein Comprising LLO Signal Peptide and NY-ESO-1

An expression cassette was designed for expression of the human testis cancer antigen NY-ESO-1 (Genbank Accession No. NM_001327) in Listeria monocytogenes. The sequence of the expression cassette encoding the NY-ESO-1 fused to a secA1 signal peptide (LLO), plus the LLO PEST sequence, is shown in FIG. 34. The sequences coding for the antigen as well as the signal peptide in the expression cassette were codon-optimized for expression in Listeria monocytogenes. The amino acid sequence of the fusion protein encoded by this expression cassette is shown in FIG. 35.

B. Codon-Optimization of Human Mesothelin-Encoding Sequences for Expression in Listeria monocytogenes A codon-optimized polynucleotide sequence encoding human mesothelin, a cancer antigen, is shown in FIG. 36. The sequence shown in FIG. 36 has been codon-optimized for expression in Listeria monocytogenes. The polypeptide sequence encoded by the sequence in FIG. 36 is shown in FIG. 37.

C. Codon-Optimization of Murine Mesothelin-Encoding Sequences for Expression in Listeria monocytogenes A codon-optimized polynucleotide sequence encoding murine mesothelin, a cancer antigen, is shown in FIG. 38. The sequence shown in FIG. 38 has been codon-optimized for expression in Listeria monocytogenes. The polypeptide sequence encoded by the sequence in FIG. 38 is shown in FIG. 39.

Example 49

Codon-Optimization of Signal Peptides for Construction of Recombinant Modified Microbes Some exemplary codon-optimized secA1 signal peptides that can be used in expression cassettes in modified microbes are provided in Table 32, below.

TABLE 32

Signal peptides for construction of recombinant modified microbes

| Signal Peptide Amino Acid Sequence | Signal peptidase Site (') | Native Sequence | Sequence codon-optimized for expression in Lm | Gene | Genus/species |
|---|---|---|---|---|---|
| MKKIMLVFIT LILVSLPIAQ QTEAKDASA FNKENSISSM APPASPPASP KTPIEKKHAD (SEQ ID NO:53) | TEA'KD (SEQ ID NO:69) | ATGAAAAAAATA ATGCTAGTTTTA TTACACTTATATT AGTTAGTCTACCA ATTGCGCAACAA ACTGAAGCAAAG GATGCATCTGCAT TCAATAAAGAAA ATTCAATTTCATC CATGGCACCACC AGCATCTCCGCCT GCAAGTCCTAAG ACGCCAATCGAA AAGAAACACGCG GAT (SEQ ID NO:76) | ATGAAAAAAATT ATGTTAGTTTTA TTACATTAATTTT AGTTAGTTTACCA ATTGCACAACAA ACAGAAGCAAAA GATGCAAGTGCA TTTAATAAAGAA AATAGTATTAGT AGTATGGCACCA CCAGCAAGTCCA CCAGCAAGTCCA AAAACACCAATT GAAAAAAAACAT GCAGAT (SEQ ID NO:77) | hly (LLO) | Listeria monocytogenes |

TABLE 32-continued

Signal peptides for construction of recombinant modified microbes

| Signal Peptide Amino Acid Sequence | Signal peptidase Site (') | Native Sequence | Sequence codon-optimized for expression in Lm | Gene | Genus/species |
|---|---|---|---|---|---|
| MKKRKVLIP LMALSTILVS STGNLEVIQA EV (SEQ ID NO:54) | IQA'EV (SEQ ID NO:70) | ATGAAAAAACGA AAAGTGTTAATA CCATTAATGGCAT TGTCTACGATATT AGTTTCAAGCAC AGGTAATTTAGA GGTGATTCAGGC AGAAGTT (SEQ ID NO:78) | ATGAAAAAACGT AAAGTTTTAATTC CATTAATGGCATT AAGTACAATTTTA GTTAGTAGTACA GGTAATTTAGAA GTTATTCAAGCA GAAGTT (SEQ ID NO:79) | pag (Protective Antigen) | Bacillus anthracis |

Example 50

Vaccines Compositions Based on Dendritic Cells Infected with Psoralen-Killed Metabolically Active Microbial Vaccines Dendritic cells (DC) are the most potent antigen-presenting cell population and are essential for the priming of naïve T cells. Immature DC migrate to injured tissues where they capture both soluble and particulate antigen, before migrating to the secondary lymphatics where they are able to present this antigen to large numbers of naïve T cells. Presentation of acquired antigen by mature DC is critical for induction of antigen-specific immune responses and stimulation of protective T-cell responses. Thus, it is desired in some instances to utilize vaccine compositions to stimulate a desired antigen-specific immune response in an immunized individual, that are based on treatment of autologous cultured DC ex vivo with, for example, peptides related to a desired antigen(s) or recombinant vectors that express a desired antigens), and in concert with appropriate stimulatory signals, resulting in activation and maturation of the DC and presentation of epitopes related to a selected antigen on MHC class I or MHC class II molecules. Cultured DC infected ex vivo with antigen delivery vectors in response can undergo activation, maturation, and MHC-restricted presentation of epitopes, or, alternatively, can be poorly infected with a selected antigen delivery vector, and/or the selected antigen delivery vector interferes with DC function or development. However, in contrast to vaccine compositions based on peptide-pulsed DC, recombinant delivery vectors have the theoretical advantage that for antigens in which the class I and class II T-cell epitopes related to diverse MHC haplotypes are not known, the endogenous antigen processing machinery of the infected DC host programs MHC presentation. Thus, there is a need for recombinant delivery platforms that efficiently infect DC, which in response undergo activation and maturation, and present epitopes derived from the vector-encoded antigen on MHC class I and MHC class II molecules.

As described above, in some embodiments the invention provides vaccine compositions and methods of treatment that are, in part, based on the non-limiting example of cultured immature human dendritic cells infected with a desired photochemically inactivated recombinant *Listeria*, genetically modified such that it is preferably deleted of the UvrAB genes, and expresses and secretes from the bacterium a desired selected heterologous or endogenous antigen. In response to the expression and/or secretion of the antigen by the bacterium, infected DC undergo maturation and activation and present epitopes related to the heterologous antigen on MHC class I and MHC class II molecules. In some embodiments, the vaccine composition is administered to an individual in order to stimulate a desired immune response (e.g., CD4+/CD8+ T-cell responses or antibody responses that are specific for the *Listeria*-encoded heterologous antigen).

By way of example, the induction of heterologous vector-encoded antigen-specific CD8+ T-cell responses in C57BL/6 mice immunized with autologous bone-marrow derived DC infected with S-59 Psoralen/UVA inactivated *Listeria* ΔactA/ΔinlB/ΔuvrAB encoding chicken ovalbumin (OVA) is described below.

Generation of dendritic cells, infection with *Listeria*-based vaccines, and immunization. Dendritic cells were generated using the previously published techniques of Lutz et. al. (J. Immunol. Methods. 1999. 223:77-92). Briefly, whole bone marrow was cultured on bacterial grade Petri dishes at a concentration of 2×05 cells per mL of media containing RPMI 1640 (Gibco, Carlsbad, Calif.), 10% FCS (HyClone, Logan, Utah), 100 units penicillin, 100 ug/mL streptomycin (Gibco), 200 mM L-glutamine (Gibco), 100 mM sodium pyruvate (Gibco), 10 mM MEM non-essential amino acids (Gibco), 0.03 mM β-mercaptoethanol (Sigma-Aldrich, St. Louis), and 20 ng/mL murine GM-CSF (R&D Systems, Minneapolis, Minn.). On day 3 and 6, media wash replenished with fresh GM-CSF. On day 10, non-adherent cells were harvested and verified phenotypically to be myeloid dendritic cells (MHC class II high, CD11c high, CD86 intermediate). For infection, DC were suspended at $2\times10^6$ per mL of media, and $1\times10^8$ of the indicated *Listeria* strain were added (final multiplicity of infection=50 bacterium:1 DC). Tubes were mixed on a rotating mixer at 8 rpm for 1 hour at 37° C. Cells were then washed three times with PBS to remove residual extracellular bacteria, and then $3\times10^6$ of each dendritic cell preparation was transferred intravenously to each animal. 7 days later, mice were sacrificed, spleens harvested, and single celled suspensions created.

For intracellular cytokine staining (ICS) analysis, cells were first stimulated for 5 hours with the relevant peptide in the presence of brefeldin A. Cells were surface stained for CD4 FITC (eBioscience, San Diego) and CD8 PerCP (BD Biosciences, San Jose), then fixed and permeabilized and stained for intracellular IFN-γ and TNF. For tetramer staining, cells were stained directly ex vivo with CD4 FITC, CD8 PerCP and $K^b$-SIINFEKL tetramer (Beckman-Coulter, Miami). Samples were acquired on flow cytometer (FACS-Calibur, BD Biosciences) and analyzed using FloJo (Treestar software, Ashland, Oreg.).

Slides for microscopy were made using a Shandon Cytospin II, and stained using a modified Wright's Stain.

The results indicated that induction of potent OVA-specific CD8+ T cell responses in C57BL/6 mice immunized intravenously with autologous bone marrow-derived DC infected with S-59 psoralen/UVA inactivated *Listeria*-OVA is dependent on deletion of the bacterial UvrAB genes (FIG. 50). FIG. 50(*a*) shows the phenotypic verification of dendritic cells prior to infection, as shown by double staining of CD11c$^{hi}$/MHC class II$^{hi}$. FIG. 50(*b*) shows the photomicrographs of DC at one hour post infection with indicated *Listeria* vaccine and treatment, demonstrating comparable levels of bacteria in DC infected with S-59 Psoralen inactivated *Listeria* ΔactA/ΔinlB/ΔuvrAB, *Listeria* ΔactA/ΔinlB/ΔuvrAB-OVA, or *Listeria* ΔactA/ΔinlB-OVA. Significant levels of intracellular bacteria were not observed in DC infected with heat-killed *Listeria* ΔactA/ΔinlB/ΔuvrAB-OVA. FIG. 50(*c*) shows the ICS analysis of splenocytes from immunized mice which demonstrates that efficient priming of CD8+ OVA (SIINFEKL)-specific K$^b$-restricted T cells occurred only in mice immunized with DC infected with S-59 psoralen/UVA *Listeria*-OVA vaccine containing DNA repair mutation (Listeria ΔactA/ΔinlB/ΔuvrAB-OVA), and not in mice immunized with DC infected with S-59 psoralen/UVA *Listeria*-OVA vaccine with intact DNA repair (Listeria ΔactA/ΔinlB-OVA). FIG. 50(*d*) shows the K$^b$-SIINFEKL tetramer analysis of splenocytes from the immunized mice. Efficient priming of CD8+ OVA (SIINFEKL)-specific K$^b$-restricted T cells was observed only in mice immunized with DC infected with S-59 psoralen/UVA *Listeria*-OVA vaccine containing DNA repair mutation (Listeria ΔactA/ΔinlB/ΔuvrAB-OVA), but not in mice immunized with DC infected with S-59 psoralen/UVA *Listeria*-OVA vaccine with intact DNA repair (Listeria ΔactA/ΔinlB-OVA).

Example 51

Sequences Useful in Production of Recombinant or Mutant *Bacillus anthracis* Strains Recombinant and/or mutant *Bacillus anthracis* strains are described in the Examples above and in the U.S. Provisional Application, "Modified *Bacillus Anthracis*, Vaccine Compositions and Methods of Use Thereof", filed Jun. 30, 2004. Information is provided in the Table 33, below regarding some sequences of use in construction of some of the recombinant *B. anthracis* strains described above. Each of the sequences identified by accession number or by other reference in Table 32 is incorporated by reference herein in its entirety.

TABLE 33

Additional *B. anthracis* sequence information (including Genbank accession numbers)

| Bacteria | Accession # | Gene | Location | Coordinates |
| --- | --- | --- | --- | --- |
| *B. anthracis* Ames | NC_003997 | SpoIIE | Chromosome | 64936-67314 |
| *B. anthracis* Sterne | NC_001496 | Cya (edema factor) | pXO1 virulence plasmid | 154224-156626 |
| *B. anthracis* Ames | NC_007322 | PagA (Protective antigen) | pXO1 virulence plasmid | 143779-146073 |
| *B. anthracis* Ames | NC_007322 | Lef (Lethal factor) | pXO1 virulence plasmid | 149357-151786 |
| *B. anthracis* Ames | NC_003997 | LexA (lex repressor) | Chromosome | 3453806-3454426 |
| *B. anthracis* Ames | NC_003997 | recA | Chromosome | 3590268-3591626 (Intron 3590691-3591017; Ko M., et. al., J Bacteriol. 2002 Ko, M. et. al., 184: 3917-3922) |

In addition, the *B. subtilis* SOS promoter binding region is identified as 5'-CGAACRNRYGTTYC-3' (SEQ ID NO:84; Winterling, K. W. et. al., J. Bacteriol. 1998 180:2201-2211).

All publications, patents, patent applications, and accession numbers (including both polynucleotide and polypeptide sequences) cited herein are hereby incorporated by reference in their entirety for all purposes to the same extent as if each individual publication, patent or patent application were specifically and individually indicated to be so incorporated by reference.

What we claim is:

1. A composition comprising modified bacteria, the genomic DNA of said modified bacteria comprising:
   (i) interstrand crosslinks introduced between the strands of genomic DNA double helix, said interstrand crosslinks inhibiting replication of said modified bacteria, (ii) one or more genetic mutations in uvr gene(s), said mutation(s) inhibiting excision repair of said interstrand crosslinks, and (iii) a nucleic acid sequence encoding a heterologous polypeptide operably linked to a promoter sequence directing expression of the heterologous polypeptide by the modified bacteria; and
   a pharmaceutically acceptable excipient.

2. The composition of claim 1, wherein the composition is in a formulation suitable for oral delivery.

3. The composition of claim 1, wherein the composition is in a formulation suitable for nasal delivery.

4. The composition of claim 2, wherein the formulation is a solid formulation comprising a solid-based dry material.

5. The composition of claim 2, wherein said formulation is in the form of a liquid.

6. The composition of claim 1, wherein the genetic mutations in uvr gene(s) comprise deletions in the uvrA and uvrB genes such that the modified bacteria do not produce functional uvrA and uvrB gene products.

7. The composition of claim 1, wherein the bacteria are selected from *Salmonella, Shigella* sp., *Mycobacterium tuberculosis, E. coli, Neisseria meningitides, Brucella abortus, Brucella melitensis, Borrelia burgdorferi*, and *Francisella tularensis*.

8. A method of inducing an immune response to an antigen in a mammalian subject, the method comprising administering to an individual a composition according to claim 1, wherein said heterologous polypeptide comprises said antigen.

9. The method of claim 8, wherein said composition is orally administered.

10. The method of claim 8, wherein said composition is nasally administered.

11. The composition of claim 1, wherein the modified bacteria are *Listeria monocytogenes* bacteria.

12. The composition of claim 11, wherein the genetic mutations in uvr gene(s) comprise deletions in the uvrA and uvrB genes such that the *Listeria monocytogenes* bacteria do not produce functional uvrA and uvrB gene products.

13. The method of claim 8, wherein said composition is administered intravenously.

14. The method of claim 8, wherein said composition is administered intraperitoneally.

15. The method of claim 8, wherein said composition is administered intramuscularly.

16. The method of claim 8, wherein said composition is administered subcutaneously.

17. The composition of claim 1, wherein the heterologous polypeptide comprises a polypeptide sequence from a virus selected from the group consisting of human immunodeficiency virus, feline immunodeficiency virus, herpes simplex virus, cytomegalovirus, human metapneumovirus, Epstein-Barr virus, varicella zoster virus, hepatitis B virus, hepatitis A virus, hepatitis C virus, delta hepatitis virus, hepatitis E virus, and hepatitis G virus.

18. The composition of claim 1, wherein the heterologous polypeptide comprises a polypeptide sequence from a bacterial species selected from the group consisting of *Mycobacterium, Bacillus, Yersinia, Salmonella, Neisseria, Borrelia, Chlamydia*, and *Bordetella*.

19. The composition of claim 1, wherein the heterologous polypeptide comprises a polypeptide sequence from a parasite species selected from the group consisting of *Plasmodium* and *Toxoplasma*.

* * * * *

SEQUENCE LISTING

<160> NUMBER OF SEQ ID NOS: 84

<210> SEQ ID NO 1

-continued

```
<211> LENGTH: 8
<212> TYPE: PRT
<213> ORGANISM: Murine

<400> SEQUENCE: 1

Ser Ile Ile Asn Phe Glu Lys Leu
 1               5

<210> SEQ ID NO 2
<211> LENGTH: 12
<212> TYPE: PRT
<213> ORGANISM: Listeria monocytogenes

<400> SEQUENCE: 2

Asn Glu Lys Tyr Ala Gln Ala Tyr Pro Asn Val Ser
 1               5                  10

<210> SEQ ID NO 3
<211> LENGTH: 9
<212> TYPE: PRT
<213> ORGANISM: Murine

<400> SEQUENCE: 3

Val Ala Tyr Gly Arg Gln Val Tyr Leu
 1               5

<210> SEQ ID NO 4
<211> LENGTH: 8
<212> TYPE: PRT
<213> ORGANISM: Herpes simplex virus

<400> SEQUENCE: 4

Ser Ser Ile Glu Phe Ala Arg Leu
 1               5

<210> SEQ ID NO 5
<211> LENGTH: 2915
<212> TYPE: DNA
<213> ORGANISM: Listeria monocytogenes

<400> SEQUENCE: 5
atcacgaaaa atcccgctta tattttgaat aagcgggatt ttgattattt tttcttagct      60
gttgcaattc gttcttccgt gcgttcttta tcgcgttcta aaattggttt caagtattta     120
cctgtataag attttttga  gcgagcgatt ttttcaggtg tgccggttgc aataatttga     180
ccgccaccat cgccaccttc tggacctaaa tcaatcaagt aatcagcttg tttgataacg     240
tcaagattat gctcaataac aagtactgta tcgccattct cttctacaag tctttgtaat     300
actttgagta aacgaccaat atcatctgcg tggagtccgg tagttggttc atccagaata     360
tagaaagatt ttccgttact acgtttatga agttccgaag ctagtttgac gcgctgcgct     420
tcaccacctg aaagcgtagt tgcaggttgt ccaagtcgaa tatagccaag accaacatct     480
acaattgttt gaagtttacg cgcaattctt ggttggttgg tgaaatattc tagtccttcc     540
tctacagtca tttctaatac ttcagcaata tttttgcctt tataacgaat atctaacgtc     600
tcaccattgt atcgttttcc atgacaaact tcacagggta catatacatc aggcaagaaa     660
tgcatttcaa ttttgatgat tccgtcgcct ttacacgcct cgcaacggcc acctttacg      720 ttaaaactaa agcgaccttt tttataacca cgaactttgg cttcattagt acttgcgaaa     780
aggtcacgaa tatcatcgaa agctcctgta taagtagctg gattcgatct cggtgttctt     840
ccgattggtg attggtcaat attgataatt ttttctaggt tttcgatgcc ttttattcct     900
```

```
ttgtgttcac ctggttttgc gtggtttcta tttagttttc tcgctaacgc ttttcgcagt    960
acttcattca ctaacgaact tttacctgaa cctgaaactc cagttacaca ggaaaaagta   1020
gctagtggaa ttttttgcatt tacgtttttg agattatttg ctttagcacc aataatttct   1080
aattctagtc cgttaccttt tctacgttta gcagggactg gaataaattt tttacctgaa   1140
agatagtcac cagtgatgga attttttatta ttggcaactt cttctggtgt tccggctgca   1200
acaattcgtc cgccgtgttc tcctgcacct ggaccaatat caataagata tctgcggcc   1260
atcatcgtat cttcgtcatg ctcaacgaca ataagcgtgt ttccaatgtc acgcatactt   1320
tggagtgtgc tgattaaacg atcattatct cgttgatgaa gaccgatgga aggttcatct   1380
aaaatataaa gtacaccagt aagtctggaa ccgatttgtg tagcaagtcg aattcgttgc   1440
gcttcgccac cagaaagcgt cccagctgca cggctcattg ttaggtagtc gagcccaaca   1500
tttttaaga agcctagtct agcacgaact tctttgaaaa ttggcgctgc aatttgtgtt   1560
tcttttcag atagttctaa gccatcgaag aaagcaagtg cttcattaat agaaaactca   1620
ctgatttgcc caatatgatg gtcgtttact ttaacggaaa gtgtttcttc ttttagacga   1680
tagcctttac aagatggaca tggtaaatca gtcatatatt gcgccatttg atcgcgtgtg   1740
aaatcggaat ttgtttcacg atagcgacgt tcgatatttg gaagtatccc ttcaaacgga   1800
atccacgttt cgcgtgtcat accgaaatca ttttttgtatt cgaagtagaa ttctttatct   1860
tttgatccat ttaaaataat atctaattct tctttggata gcttctcaag aggtgtatcc   1920
atatctattc caaattcttt acaggcagaa gctagcattt gcgggtagta ctgtgaacta   1980
attgggcgcc aaggaataat agcaccttca tttagagaca tacttctatc aggaataacc   2040
gtgtcgacat cgacttcaag tttagtccca agtccatcac atgtggggca agcgccaaat   2100
gggctgttga aagagaacat tcttggttct aattccaccaa cggaaaaacc acaataaggg   2160
cacgcatagt gttcactaaa taataattct ttatccccca ttatatcaac aaccgcataa   2220
ccatcagcta aacgaagagc agcttcaatg gaatcataca gacgagtatt gatgccctct   2280
ttaatcacaa tgcgatcaat aatgatttca atagaatgct ttttgttttt ctcaatttca   2340
atttcgtcat tgatatcata aatttctcca tcaacacgaa ttcgaacata tccttctttt   2400
ttgatttcct caatagttttt cttatgtgtc ccttttttac cagaaacgat tggagccatt   2460
atttgaatac gtgtttttttc tgggtattct agaaacacgat ctaccatttg ttcgattgtt   2520
tgagaagtga tttcaatacc gtgatttgga caaaccggat gcccaacacg agcataaagt   2580
aagcgcaaat agtcatggat ttctgtaact gtcccaacag tggaacgtgg attacggctt   2640
gttgtttttt gatcaatcga aatggcaggg cttaatcctt caattaaatc cacatctggt   2700
ttatccattt gccctaaaaa ttggcgtgca tatgcggaca aagactctac ataacgtctt   2760
tgtccttctg cataaatcgt atcaaaagca agcgaagatt tacctgaacc tgaaagccca   2820
gtcataacta ctaatttgtc tctaggaatc tctacatcaa tgttttttaa gttatgggct   2880
cttgcaccct gaattactat tttctcttta tccaa                              2915
```

<210> SEQ ID NO 6
<211> LENGTH: 1991
<212> TYPE: DNA
<213> ORGANISM: Listeria monocytogenes

<400> SEQUENCE: 6

```
tcatccttcc gctttatttt ccagtaaagc atcgcgaagt tcagcagcac gttcgaaatc     60
aagtgcttta gctgcttctt tcatttcatg ttccatacct tcaatgaata catcgcgttc   120
```

-continued

```
tttcttagac attttgctta aatcatgttg cttcactgct tctctttcat ctgcggcaga      180
agtcgctgcg atgataccac gaatttcttt tttgattgtt tttggcgtaa tgccgtgttt      240
ttcattatat tcaatttgga ttttacgacg gcgttctgtt tcgccaatag aattgcgcat      300
cgaatcggtc atttatcag catacatgat tactcgaccg ttttcattac gagcagctcg       360
acccattgtt tgaattaagg aacgctcgga acgaaggaat ccttctttgt ccgcatctaa      420
aatagcgaca agagatactt caggtaaatc gattccttca cgaagtaagt taattccaac      480
gataacatca tacacaccaa gtcgaaggtc acgaatgatt tcgattcgct cgagcgtctt     540
cacttccgag tggagatact gtactttaac accagcttct ttgagatagt tggttaaatc     600
ctcggacatt tttttcgtta aggtggtgat taaaacacgt tcattttttct cgacgcgatc    660 gttaatctca tccattaagt catcaatttg tccttgaatc ggacggattt ctacgattgg    720
gtctagcaag ccagttggtc gaatgatttg ttcaatgaca tctggatttt tttctaattc    780
gtaagggcct ggtgtagcgg atataaacat aatttgattg atatgcttct caaattcttc    840
taaacgaagc ggcctattat ctagagcgct aggcaatcta aagccatgat caactagcat    900
ttgttttctg gcttggtccc cgttaaacat accacgaatt tgcggcatcg taacgtgtga    960
ctcatcaatt accatttgga aatcatctgg gaagtaatcg agtaacgtgt atggtgtaac    1020
tcccgctgga cgaagggata aatgtctaga atagttctca ataccagagc aatagcccat    1080
ttcttccatc atttccaaat cataattcgt tcgctgttca aggcgctgag cttctagcaa    1140
tttattatct gcacgtaaaa ctttaagacg gtcttcgagt tcagctttta tattaacaat    1200
tgcttttttc ataatatcag gtctggtgac aaagtgagat gccgggaaaa tggaaacatg    1260
ttctctttct cctataattt caccagtaag tgcatctact tctctaattc gttcaatttc    1320
atcaccgaaa aattcaatcc gcatacagtg ttcatctctt gaagctggga aaatttcgac    1380
aacatcaccg cgaacacgga agcgtccacg ttgaaaatct atatcatttc gatcatattg    1440
aatatctact aatttgcgca gtagctgatc acggctaatt tccatgccaa cacgaagcga    1500
aacgagcatc tctccatatt caatcggcga acctaagcca tagatacacg atacactcgc    1560
aatgataatt acatcgcgac gttcaaaaag cgcagcagta gcagagtgac gaagcttatc    1620
gatttcatca ttgatacttg catctttttc gatatatgtg tcactttgcg gaacataggc    1680
ttctggttga tagtaatcat agtaactgac aaaatattct acagcgttat ttgggaaaaa    1740
ctctttaaac tcgctataca gctgtcccgc taacgtctta ttgtgagcca tgacaagtgt    1800
cggcttattc acttcttgaa tcacattgga tacggtaaaa gttttccctg taccggttgc    1860
accaagtaaa gtttggtgtt tcaagccttt ttttaatccc gcaactaatt gttctatcgc    1920
tctaggttgg tctccttgtg ggctatactt agaaactaac tcaaatttat ccttcaactc    1980
ggattccccc t                                                          1991
```

<210> SEQ ID NO 7
<211> LENGTH: 26
<212> TYPE: DNA
<213> ORGANISM: Artificial Sequence
<220> FEATURE:
<223> OTHER INFORMATION: PCR Primer

<400> SEQUENCE: 7
gcaagtatac agttaagttt gtaacg                                              26

<210> SEQ ID NO 8
<211> LENGTH: 24
<212> TYPE: DNA

<213> ORGANISM: Artificial Sequence
<220> FEATURE:
<223> OTHER INFORMATION: PCR Primer

<400> SEQUENCE: 8
ctttccgaag tggaagaaag catg    24

<210> SEQ ID NO 9
<211> LENGTH: 6654
<212> TYPE: DNA
<213> ORGANISM: Listeria monocytogenes

<400> SEQUENCE: 9

| | | | | | |
|---|---|---|---|---|---|
| gcaagtatac | agttaagttt | gtaacgattt | gttttgattt | agactcaaaa | cgtaaagttt | 60 |
| cttcatctac | acgtaaagtc | gttttatcaa | agaagatttt | aagtgcttca | tcttctggat | 120 |
| attctttgaa | tagtttaatc | atcgcgtgaa | ctttgatatc | gttcgaatcg | gatggtttaa | 180 |
| attcaatatt | accattagca | atttcgaatt | ctaaaataga | aagtgttgtg | tcatgataaa | 240 |
| tgaaatcacg | ttcgattttc | gttgaagtta | agaacgggaa | tggcatatct | tcacttgtt | 300 |
| taaatgcact | atttaggaaa | gaaccgattt | tttcaccagc | ttgggataaa | tcattaacca | 360 |
| tattgcgcat | ggagtcttca | cgatctttag | aagaattttc | gccgccttct | tcttcatctc | 420 |
| tttcatgatt | ttctggagtc | ggttctgggc | gtcttttacg | acttttttgga | ggtgtataag | 480 |
| gatttccttg | attgttccaa | cctttactgt | aatcatatga | tggttcttct | tttgtttctt | 540 |
| cttcgatttg | ttcttcttct | ctcggagctg | cagatcgacg | aatattttct | tttgctgctg | 600 |
| ttttaccttc | tttttttggaa | atattttcaa | gtagagtaag | ggcttcttca | gtggatataa | 660 |
| taccttgttt | tactaattcg | agaatacgtt | tacgttcatt | ttccattttc | atttcctcct | 720 |
| ataatttagg | ctaaactatt | ttaggcttgc | tttcacatgc | aagtgacata | tctgttttat | 780 |
| ctatgactct | attatgaagg | aaaatataat | ttctgtcata | caaccagagg | atgattattt | 840 |
| gtttggactt | tgggtggttt | ggtcttaaga | atcacgaaaa | atcccgctta | tattttgaat | 900 |
| aagcgggatt | tgattatttt | tttcttagct | gttgcaattc | gttcttccgt | gcgttctta | 960 |
| tcgcgttcta | aaattggttt | caagtatta | cctgtataag | attttttga | gcgagcgatt | 1020 |
| ttttcaggtg | tgccggttgc | aataatttga | ccgccaccat | cgccaccttc | tggacctaaa | 1080 |
| tcaatcaagt | aatcagcttg | tttgataacg | tcaagtattat | gctcaataac | aagtactgta | 1140 |
| tcgccattct | cttctacaag | tctttgtaat | actttgagta | aacgaccaat | atcatctgcg | 1200 |
| tggagtccgg | tagttggttc | atccagaata | tagaaagatt | ttccgttact | acgtttatga | 1260 |
| agttccgaag | ctagtttgac | gcgctgcgct | tcaccacctg | aaagcgtagt | tgcaggttgt | 1320 |
| ccaagtcgaa | tatagccaag | accaacatct | acaattgttt | gaagtttacg | cgcaattctt | 1380 |
| ggttggttgg | tgaaatattc | tagtccttcc | tctacagtca | tttctaatac | ttcagcaata | 1440 |
| tttttgcctt | tataacgaat | atctaacgtc | tcaccattgt | atcgttttcc | atgacaaact | 1500 |
| tcacagggta | catatacatc | aggcaagaaa | tgcatttcaa | ttttgatgat | tccgtcgcct | 1560 |
| ttacacgcct | cgcaacggcc | acctttacg | ttaaaactaa | agcgaccttt | tttataacca | 1620 |
| cgaactttgg | cttcattagt | acttgcgaaa | aggtcacgaa | tatcatcgaa | agctcctgta | 1680 |
| taagtagctg | gattcgatct | cggtgttctt | ccgattggtg | attggtcaat | attgataatt | 1740 |
| ttttctaggt | tttcgatgcc | ttttatttct | ttgtgttcac | ctggttttgc | gtggtttcta | 1800 |
| tttagttttc | tcgctaacgc | ttttcgcagt | acttcattca | ctaacgaact | tttacctgaa | 1860 |
| cctgaaactc | cagttacaca | ggaaaaagta | gctagtggaa | ttttttgcatt | tacgttttg | 1920 |

```
agattatttg ctttagcacc aataatttct aattctagtc cgttaccttt tctacgttta    1980
gcagggactg gaataaattt tttacctgaa agatagtcac cagtgatgga atttttatta    2040
ttggcaactt cttctggtgt tccggctgca acaattcgtc cgccgtgttc tcctgcacct    2100
ggaccaatat caataagata atctgcggcc atcatcgtat cttcgtcatg ctcaacgaca    2160
ataagcgtgt ttccaatgtc acgcatactt ggagtgtgc tgattaaacg atcattatct    2220
cgttgatgaa gaccgatgga aggttcatct aaaatataaa gtacaccagt aagtctggaa    2280
ccgatttgtg tagcaagtcg aattcgttgc gcttcgccac cagaaagcgt cccagctgca    2340
cggctcattt ttaggtagtc gagcccaaca tttttttaaga agcctagtct agcacgaact    2400
tctttgaaaa ttggcgctgc aatttgtgtt tcttttcag atagttctaa gccatcgaag    2460
aaagcaagtg cttcattaat agaaaactca ctgatttgcc caatatgatg gtcgtttact    2520
ttaacggaaa gtgtttcttc ttttagacga tagcctttac aagatggaca tggtaaatca    2580
gtcatatatt gcgccatttg atcgcgtgtg aaatcggaat ttgtttcacg atagcgacgt    2640
tcgatatttg gaagtatccc ttcaaacgga atccacgttt cgcgtgtcat accgaaatca    2700 ttttttgtatt cgaagtagaa ttcttttatct tttgatccat ttaaaataat atctaattct    2760
tctttggata gcttctcaag aggtgtatcc atatctattc caaattcttt acaggcagaa    2820
gctagcattt gcgggtagta ctgtgaacta attgggcgcc aaggaataat agcaccttca    2880
tttagagaca tacttctatc aggaataacc gtgtcgacat cgacttcaag tttagtccca    2940
agtccatcac atgtggggca agcgccaaat gggctgttga agagaacat tcttggttct    3000 aattcaccaa cggaaaaacc acaataaggg cacgcatagt gttcactaaa taataattct    3060
ttatccccca ttatatcaac aaccgcataa ccatcagcta acgaagagc agcttcaatg    3120 gaatcataca gacgagtatt gatgccctct ttaatcacaa tgcgatcaat aatgatttca    3180
atagaatgct ttttgttttt ctcaatttca atttcgtcat tgatatcata aatttctcca    3240
tcaacacgaa ttcgaacata tccttctttt ttgatttcct caatagtttt cttatgtgtc    3300
ccttttttac cagaaacgat tggagccatt atttgaatac gtgttttttc tgggtattct    3360
agaacacgat ctaccatttg ttcgattgtt tgagaagtga tttcaatacc gtgatttgga    3420 caaccggat gcccaacacg agcataaagt aagcgcaaat agtcatggat ttctgtaact    3480
gtcccaacag tggaacgtgg attacggctt gttgttttttt gatcaatcga atggcaggg    3540 cttaatcctt caattaaatc cacatctggt ttatccattt gccctaaaaa ttggcgtgca    3600
tatgcggaca aagactctac ataacgtctt tgtccttctg cataaatcgt atcaaaagca    3660
agcgaagatt tacctgaacc tgaaagccca gtcataacta ctaatttgtc tctaggaatc    3720
tctacatcaa tgtttttttaa gttatgggct cttgcaccct gaattactat tttctcttta    3780
tccaatttcg cttcatcctt ccgcttttat ttccagtaaa gcatcgcgaa gttcagcagc    3840
acgttcgaaa tcaagtgctt tagctgcttc tttcatttca tgttccatac cttcaatgaa    3900
tacatcgcgt tctttcttag acattttgct taaatcatgt tgcttcactg cttctctttc    3960
atctgcggca gaagtcgctg cgatgatacc acgaatttct ttttttgattg ttttttggcgt    4020 aatgccgtgt ttttcattat attcaatttg gattttacga cggcgttctg tttcgccaat    4080
agaattgcgc atcgaatcgg tcattttatc agcatacatg attactcgac cgttttcatt    4140
acgagcagct cgacccattg tttgaattaa ggaacgctcg gaacgaagga atccttcttt    4200
gtccgcatct aaaatagcga caagagatac ttcaggtaaa tcgattcctt cacgaagtaa    4260
gttaattcca acgataacat catacacacc aagtcgaagg tcacgaatga tttcgattcg    4320
```

```
ctcgagcgtc ttcacttccg agtggagata ctgtacttta acaccagctt ctttgagata    4380
gttggttaaa tcctcggaca ttttttttcgt taaggtggtg attaaaacac gttcattttt    4440
ctcgacgcga tcgttaatct catccattaa gtcatcaatt tgtccttgaa tcggacggat    4500
ttctacgatt gggtctagca agccagttgg tcgaatgatt tgttcaatga catctggatt    4560
tttttctaat tcgtaagggc ctggtgtagc ggatataaac ataatttgat tgatatgctt    4620
ctcaaattct tctaaacgaa gcggcctatt atctagagcg ctaggcaatc taaagccatg    4680
atcaactagc atttgttttc tggcttggtc cccgttaaac ataccacgaa tttgcggcat    4740
cgtaacgtgt gactcatcaa ttaccatttg gaaatcatct gggaagtaat cgagtaacgt    4800
gtatggtgta actcccgctg gacgaaggga taaatgtcta gaatagttct caataccaga    4860
gcaatagccc atttcttcca tcatttccaa atcataattc gttcgctgtt caaggcgctg    4920
agcttctagc aatttattat ctgcacgtaa aactttaaga cggtcttcga gttcagcttt    4980
tatattaaca attgcttttt tcataatatc aggtctggtg acaaagtgag atgccgggaa    5040
aatggaaaca tgttctcttt ctcctataat ttcaccagta agtgcatcta cttctctaat    5100
tcgttcaatt tcatcaccga aaaattcaat ccgcatacag tgttcatctc ttgaagctgg    5160
gaaaatttcg acaacatcac cgcgaacacg gaagcgtcca cgttgaaaat ctatatcatt    5220
tcgatcatat tgaatatcta ctaatttgcg cagtagctga tcacggctaa tttccatgcc    5280
aacacgaagc gaaacgagca tctctccata ttcaatcggc gaacctaagc catagataca    5340
cgatacactc gcaatgataa ttacatcgcg acgttcaaaa agcgcagcag tagcagagtg    5400
acgaagctta tcgatttcat cattgatact tgcatctttt tcgatatatg tgtcactttg    5460
cggaacatag gcttctggtt gatagtaatc atagtaactg acaaaatatt ctacagcgtt    5520
atttgggaaa aactctttaa actcgctata cagctgtccc gctaacgtct tattgtgagc    5580
catgacaagt gtcggcttat ttacttcttg aatcacattg gatacggtaa aagttttccc    5640
tgtaccggtt gcaccaagta aagtttggtg tttcaagcct ttttttaatc ccgcaactaa    5700
ttgttctatc gctctaggtt ggtctccttg tgggctatac ttagaaacta actcaaattt    5760
atccttcaac tcggattccc cctattctgt atctgtccga ttctggtatc tgaaaagctt    5820
tgtttgtaaa aggtctagca aagcaaaaag cggatttttc agatccgtta atgtttctat    5880
tttatcataa atattttaat tagcctagca aaaaccgaac atattttcgc atttgttgaa    5940
aaataaaaaa cgcaacctgt tgattacgct tttctttatt ttatcacttt tacgcttttc    6000
tacctatata tttgctttgt taaaaatcac tgccactctt ctttaaacgt cgcagcatat    6060
acgttgcaag cacaaaacca atggtcatcg aaaaagcatc aataataatt agccacatag    6120
aactcgtata acctaacttg gcagaagcag caatcaaaat caccatcaaa agcaagccga    6180
cataacgatt ataagtgatt ctcgcaaaaa gaataacaag gaggcaaggg aaaataagcg    6240
cagatataat ttgatccatc ttacgttcct ccccctttt tatgcgtctc gtaatgcttt    6300
ggtcgttatt tccgttgtaa gctgtggtaa ttctgttttt tcgataccht tttcagcaag    6360
catatctggt aaaatttctt ttaaaaagta cttaacgctc gccatttctc ggtactcata    6420
aatggttgca agtgcctcac tatagatttc cacaaaaata ttttctggat ttccttttg    6480
aatttcgcca aaggattcat ataacaaatc tactttatca gaaattgcga ggattttccc    6540
ttccaacgta ctgtccttac cttctttttag caaatgacga taaatcggct ggtacgtttc    6600
tggaatttcc cgttcaataa agttttttgt catgctttct tccacttcgg aaag          6654
```

<210> SEQ ID NO 10

<211> LENGTH: 4612
<212> TYPE: DNA
<213> ORGANISM: Listeria monocytogenes

<400> SEQUENCE: 10
ccggttgcaa taatttgacc gccaccatcg ccaccttctg gacctaaatc aatcaagtaa 60
tcagcttgtt tgataacgtc aagattatgc tcaataacaa gtactgtatc gccattctct 120
tctacaagtc tttgtaatac tttgagtaaa cgaccaatat catctgcgtg gagtccggta 180
gttggttcat ccagaatata gaaagatttt ccgttactac gtttatgaag ttccgaagct 240
agtttgacgc gctgcgcttc accacctgaa agcgtagttg caggttgtcc aagtcgaata 300
tagccaagac caacatctac aattgtttga agtttacgcg caattcttgg ttggttggtg 360
aaatattcta gtccttcctc tacagtcatt tctaatactt cagcaatatt tttgccttta 420
taacgaatat ctaacgtctc accattgtat cgttttccat gacaaacttc acagggtaca 480
tatacatcag gcaagaaatg catttcaatt ttgatgattc cgtcgccttt acacgcctcg 540
caacggccac cttttacgtt aaaactaaag cgaccttttt tataaccacg aactttggct 600
tcattagtac ttgcgaaaag gtcacgaata tcatcgaaag ctcctgtata agtagctgga 660
ttcgatctcg gtgttcttcc gattggtgat tggtcaatat tgataatttt ttctaggttt 720
tcgatgcctt ttatttcttt gtgttcacct ggttttgcgt ggtttctatt tagttttctc 780
gctaacgctt ttcgcagtac ttcattcact aacgaacttt tacctgaacc tgaaactcca 840
gttacacagg aaaaagtagc tagtggaatt tttgcattta cgtttttgag attatttgct 900
ttagcaccaa taatttctaa ttctagtccg ttaccttttc tacgtttagc agggactgga 960
ataaattttt tacctgaaag atagtcacca gtgatggaat ttttattatt ggcaacttct 1020
tctggtgttc cggctgcaac aattcgtccg ccgtgttctc ctgcacctgg accaatatca 1080
ataagataat ctgcggccat catcgtatct tcgtcatgct caacgacaat aagcgtgttt 1140
ccaatgtcac gcatactttg gagtgtgctg attaaacgat cattatctcg ttgatgaaga 1200
ccgatggaag gttcatctaa aatataaagt acaccagtaa gtctggaacc gatttgtgta 1260
gcaagtcgaa ttcgttgcgc ttcgccacca gaaagcgtcc cagctgcacg gctcattgtt 1320
aggtagtcga gcccaacatt ttttaagaag cctagtctag cacgaacttc tttgaaaatt 1380
ggcgctgcaa tttgtgtttc tttttcagat agttctaagc catcgaagaa agcaagtgct 1440
tcattaatag aaaactcact gatttgccca atatgatggt cgtttacttt aacggaaagt 1500
gtttcttctt ttagacgata gcctttacaa gatggacatg gtaaatcagt catatattgc 1560
gccatttgat cgcgtgtgaa atcggaattt gtttcacgat agcgacgttc gatatttgga 1620
agtatccctt caaacggaat ccacgtttcg cgtgtcatac cgaaatcatt tttgtattcg 1680
aagtagaatt ctttatcttt tgatccattt aaaataatat ctaattcttc tttggatagc 1740
ttctcaagag gtgtatccat atctattcca aattctttac aggcagaagc tagcatttgc 1800
gggtagtact gtgaactaat tgggcgccaa ggaataatag caccttcatt tagagacata 1860
cttctatcag gaataaccgt gtcgacatcg acttcaagtt tagtcccaag tccatcacat 1920
gtggggcaag cgccaaatgg gctgttgaaa gagaacattc ttggttctaa ttcaccaacg 1980
gaaaaaccac aataagggca cgcatagtgt tcactaaata ataattcttt atcccccatt 2040
atatcaacaa ccgcataacc atcagctaaa cgaagagcag cttcaatgga atcatacaga 2100
cgagtattga tgccctcttt aatcacaatg cgatcaataa tgatttcaat agaatgcttt 2160
ttgtttttct caatttcaat ttcgtcattg atatcataaa tttctccatc aacacgaatt 2220

```
cgaacatatc cttctttttt gatttcctca atagttttct tatgtgtccc ttttttacca    2280
gaaacgattg gagccattat ttgaatacgt gttttttctg ggtattctag aacacgatct    2340
accatttgtt cgattgtttg agaagtgatt tcaataccgt gatttggaca aaccggatgc    2400
ccaacacgag cataaagtaa gcgcaaatag tcatggattt ctgtaactgt cccaacagtg    2460
gaacgtggat tacggcttgt tgttttttga tcaatcgaaa tggcagggct taatccttca    2520
attaaatcca catctggttt atccatttgc cctaaaaatt ggcgtgcata tgcggacaaa    2580
gactctacat aacgtctttg tccttctgca taaatcgtat caaaagcaag cgaagattta    2640
cctgaacctg aaagcccagt cataactact aatttgtctc taggaatctc tacatcaatg    2700 tttttttaagt tatgggctct tgcaccctga attactattt tctctttatc caatttcgct    2760
tcatccttcc gcttttatt ccagtaaagc atcgcgaagt tcagcagcac gttcgaaatc     2820
aagtgcttta gctgcttctt tcatttcatg ttccatacct tcaatgaata catcgcgttc    2880
tttcttagac attttgctta aatcatgttg cttcactgct tctctttcat ctgcggcaga    2940
agtcgctgcg atgataccac gaatttcttt tttgattgtt tttggcgtaa tgccgtgttt    3000
ttcattatat tcaatttgga ttttacgacg gcgttctgtt tcgccaatag aattgcgcat    3060
cgaatcggtc attttatcag catacatgat tactcgaccg ttttcattac gagcagctcg    3120
acccattgtt tgaattaagg aacgctcgga acgaaggaat ccttctttgt ccgcatctaa    3180
aatagcgaca agagatactt caggtaaatc gattccttca cgaagtaagt taattccaac    3240
gataacatca tacacaccaa gtcgaaggtc acgaatgatt tcgattcgct cgagcgtctt    3300
cacttccgag tggagatact gtactttaac accagcttct ttgagatagt tggttaaatc    3360
ctcggacatt ttttcgtta aggtggtgat taaaacacgt tcatttttct cgacgcgatc      3420
gttaatctca tccattaagt catcaatttg tccttgaatc ggacggattt ctacgattgg    3480
gtctagcaag ccagttggtc gaatgatttg ttcaatgaca tctggatttt tttctaattc    3540
gtaagggcct ggtgtagcgg atataaacat aatttgattg atatgcttct caaattcttc    3600
taaacgaagc ggcctattat ctagagcgct aggcaatcta aagccatgat caactagcat    3660
ttgttttctg gcttggtccc cgttaaacat accacgaatt tgcggcatcg taacgtgtga    3720
ctcatcaatt accatttgga aatcatctgg gaagtaatcg agtaacgtgt atggtgtaac    3780
tcccgctgga cgaagggata aatgtctaga atagttctca ataccagagc aatagcccat    3840
ttcttccatc atttccaaat cataattcgt tcgctgttca aggcgctgag cttctagcaa    3900
tttattatct gcacgtaaaa ctttaagacg gtcttcgagt tcagctttta tattaacaat    3960 tgctttttc ataatatcag gtctggtgac aaagtgagat gccgggaaaa tggaaacatg     4020
ttctctttct cctataattt caccagtaag tgcatctact tctctaattc gttcaatttc    4080
atcaccgaaa aattcaatcc gcatacagtg ttcatctctt gaagctggga aaatttcgac    4140
aacatcaccg cgaacacgga agcgtccacg ttgaaaatct atatcatttc gatcatattg    4200
aatatctact aatttgcgca gtagctgatc acggctaatt tccatgccaa cacgaagcga    4260
aacgagcatc tctccatatt caatcggcga acctaagcca tagatacacg atacactcgc    4320
aatgataatt acatcgcgac gttcaaaaag cgcagcagta gcagagtgac gaagcttatc    4380
gatttcatca ttgatacttg catcttttc gatatatgtg tcactttgcg gaacataggc     4440
ttctggttga tagtaatcat agtaactgac aaaatattct acagcgttat ttgggaaaaa    4500
ctctttaaac tcgctataca gctgtcccgc taacgtctta ttgtgagcca tgacaagtgt    4560
cggcttattt acttcttgaa tcacattgga tacggtaaaa gttttccctg ta            4612
```

<210> SEQ ID NO 11
<211> LENGTH: 2042
<212> TYPE: DNA
<213> ORGANISM: Listeria monocytogenes

<400> SEQUENCE: 11

| | | | | | |
|---|---|---|---|---|---|
| gcaagtatac | agttaagttt | gtaacgattt | gttttgattt | agactcaaaa | cgtaaagttt | 60 |
| cttcatctac | acgtaaagtc | gttttatcaa | agaagatttt | aagtgcttca | tcttctggat | 120 |
| attctttgaa | tagtttaatc | atcgcgtgaa | ctttgatatc | gttcgaatcg | gatggtttaa | 180 |
| attcaatatt | accattagca | atttcgaatt | ctaaaataga | aagtgttgtg | tcatgataaa | 240 |
| tgaaatcacg | ttcgattttc | gttgaagtta | agaacgggaa | tggcatatct | ttcacttgtt | 300 |
| taaatgcact | atttaggaaa | gaaccgattt | tttcaccagc | ttgggataaa | tcattaacca | 360 |
| tattgcgcat | ggagtcttca | cgatctttag | aagaattttc | gccgccttct | tcttcatctc | 420 |
| tttcatgatt | ttctggagtc | ggttctgggc | gtcttttacg | actttttgga | ggtgtataag | 480 |
| gatttccttg | attgttccaa | cctttactgt | aatcatatga | tggttcttct | tttgtttctt | 540 |
| cttcgatttg | ttcttcttct | ctcggagctg | cagatcgacg | aatattttct | tttgctgctg | 600 |
| ttttaccttc | tttttttggaa | atattttcaa | gtagagtaag | ggcttcttca | gtggatataa | 660 |
| taccttgttt | tactaattcg | agaatacgtt | tacgttcatt | ttccattttc | atttcctcct | 720 |
| ataatttagg | ctaaactatt | ttaggcttgc | tttcacatgc | aagtgacata | tctgttttat | 780 |
| ctatgactct | attatgaagg | aaaatataat | ttctgtcata | caaccagagg | atgattattt | 840 |
| gtttggactt | tgggtggttt | ggtcttaaga | atcacgaaaa | atcccgctta | tattttgaat | 900 |
| aagcgggatt | ttgattattt | tttcttagct | gttgcaattc | gttcttccgt | gcgttctttg | 960 |
| tcgcgttcta | aaattggttt | caagtattta | cctgtataag | attttttttga | gcgagcgatt | 1020 |
| ttttcaggtg | tgccggttgc | accaagtaaa | gtttggtgtt | tcaagccttt | ttttaatccc | 1080 |
| gcaactaatt | gttctatcgc | tctaggttgg | tctccttgtg | ggctatactt | agaaactaac | 1140 |
| tcaaatttat | ccttcaactc | ggattccccc | tattctgtat | ctgtccgatt | ctggtatctg | 1200 |
| aaaagctttg | tttgtaaaag | gtctagcaaa | gcaaaaagcg | gattttttcag | atccgttaat | 1260 |
| gtttctattt | tatcataaat | attttaatta | gcctagcaaa | aaccgaacat | attttcgcat | 1320 |
| ttgttgaaaa | ataaaaaacg | caacctgttg | attacgcttt | tctttatttt | atcactttta | 1380 |
| cgcttttcta | cctatatatt | tgctttgtta | aaaatcactg | ccactcttct | ttaaacgtcg | 1440 |
| cagcatatac | gttgcaagca | caaaccaat | ggtcatcgaa | aaagcatcaa | taataattag | 1500 |
| ccacatagaa | ctcgtataac | ctaacttggc | agaagcagca | atcaaaatca | ccatcaaaag | 1560 |
| caagccgaca | taacgattat | aagtgattct | cgcaaaaaga | ataacaagga | ggcaagggaa | 1620 |
| aataagcgca | gatataattt | gatccatctt | acgttcctcc | cccttttttta | tgcgtctcgt | 1680 |
| aatgctttgg | tcgttattc | cgttgtaagc | tgtggtaatt | ctgttttttc | gatacctttt | 1740 |
| tcagcaagca | tatctggtaa | aatttctttt | aaaaagtact | taacgctcgc | catttctcgg | 1800 |
| tactcataaa | tggttgcaag | tgcctcacta | tagatttcca | caaaaatatt | ttctggattt | 1860 |
| ccttttttgaa | tttcgccaaa | ggattcatat | aacaaatcta | ctttatcaga | aattgcgagg | 1920 |
| attttccctt | ccaacgtact | gtccttacct | tcttttagca | aatgacgata | aatcggctgg | 1980 |
| tacgtttctg | gaatttcccg | ttcaataaag | tttttttgtca | tgctttcttc | cacttcggaa | 2040 |
| ag | | | | | | 2042 |

<210> SEQ ID NO 12

```
<211> LENGTH: 29
<212> TYPE: DNA
<213> ORGANISM: Artificial Sequence
<220> FEATURE:
<223> OTHER INFORMATION: PCR Primer

<400> SEQUENCE: 12
ctctggtacc tcctttgatt agtatattc                                            29

<210> SEQ ID NO 13
<211> LENGTH: 32
<212> TYPE: DNA
<213> ORGANISM: Artificial Sequence
<220> FEATURE:
<223> OTHER INFORMATION: PCR Primer

<400> SEQUENCE: 13
ctcctcgaga tccgcgtgtt tcttttcgat tg                                        32

<210> SEQ ID NO 14
<211> LENGTH: 31
<212> TYPE: DNA
<213> ORGANISM: Artificial Sequence
<220> FEATURE:
<223> OTHER INFORMATION: PCR Primer

<400> SEQUENCE: 14
ctcctcgagt ccatgggggg ttctcatcat c                                         31

<210> SEQ ID NO 15
<211> LENGTH: 24
<212> TYPE: DNA
<213> ORGANISM: Artificial Sequence
<220> FEATURE:
<223> OTHER INFORMATION: PCR Primer

<400> SEQUENCE: 15
ctcctcgagt gcggccgcaa gctt                                                 24

<210> SEQ ID NO 16
<211> LENGTH: 21
<212> TYPE: DNA
<213> ORGANISM: Artificial Sequence
<220> FEATURE:
<223> OTHER INFORMATION: PCR Primer

<400> SEQUENCE: 16
gtcaaaacat acgctcttat c                                                    21

<210> SEQ ID NO 17
<211> LENGTH: 24
<212> TYPE: DNA
<213> ORGANISM: Artificial Sequence
<220> FEATURE:
<223> OTHER INFORMATION: PCR Primer

<400> SEQUENCE: 17
acataatcag tccaaagtag atgc                                                 24

<210> SEQ ID NO 18
<211> LENGTH: 2762
<212> TYPE: DNA
<213> ORGANISM: Bacillus anthracis

<400> SEQUENCE: 18
actacttgct ctggcgttcc ggaagcaacg atttgtccac ctttgtctcc gccttctggt          60
```

```
ccaaggtcaa cgatataatc cgctgtttta attacatcta aattatgttc aatgacaagt    120
accgtctcac cgctctcaac aagacgttgc agcacttcta gaagacgggc gatatcatgc    180
gcatgtaaac cagtcgttgg ctcgtctaaa atgtatagtg tacgtcctgt agaacgacgg    240
tgtaattcag aagctaattt cacacgctgt gcttcaccac cagataaagt cgtggctggt    300
tgccctaatt tcatataacc aagcccaacg tctacaagcg tttgaagttt acgtttaatt    360
tttgggatat tagcgaagaa ctctactccg tcttcaatcg tcatccctaa cacttcagaa    420
atgttttat ctttatattt cacttctaac gtttcacggt tgtaacgttt accgtgacaa     480
acttcacacg gaacgtatac gtctggtaag aagtgcatct caatttaat aattccatca    540
ccacggcacg cttcacaacg tccacctttt acgttaaagc tgaaacgccc ttttgatat    600
ccgcgcactt tcgcttcatt cgtttgcgca aacacatcac gaatatcatc gaacacacct    660
gtataggttg ctggattaga acgtggtgta cgaccgattg gcgattgatc aatatcgata    720
actttatcta aatgctcaag accttaatt tctttatgag tacctggctt cgcttcgct     780
ttatataact tttgcgctaa cgatttatat agtacttcat taatcatcgt acttttacct    840
gatccagata caccgttac cgctacaaac gtaccaagcg ggaatgacat cttcgcgttc     900
tttaagttat tctctttgc accgacaatc tccactttac gtccatcacc tttacgtctt    960
tcaagtggaa ctggaataaa ctcttaccg cttaaatact tacctgttag tgaattctca   1020
tcttgcatca cttcagctgg tgtacccgct gatacaactt gtccaccgtg aatacctgcg   1080
ccaggcccga tatccagtaa ataatcagct gccatcatcg tatcttcatc atgctcaaca   1140
acaattaacg tattacctaa atcacgcatt tcttgcaatg tacgaataag acgatcgtta   1200
tcgcgctgat gcaaaccgat agaaggctca tcaagaatgt aaagcacccc agtaagacgc   1260
gaaccaattt gcgttgctaa acgaatacgt tgcgcctcac caccagataa agttcctgcg   1320
gcacgactta acgttaaata atctaaacca acgtttacta agaacccaac gcgctcttga   1380
atttctctta aaattaaatg ggcaattttt tgttgtttct ctgttagctc cacatttgag   1440
aagaattcct gtacttcttg aacagaatac ttcgttacat cagcaatcgt ttttccgcca   1500
acgaaaacag ctaaacttc aggctttaag cgtccgcctt tacacttcgg acaagcttgt    1560
tctgccatat acttttccat ttgctcacga atgtaatccg aactcgtctc acgataacga   1620
cgttcaatat ttggaataac accttcaaat aaaatctcat tttcctttac ttgaccaaat   1680
tcatttacat agcggaaata aactttctct tcaccgcttc cgtacaacac tttatcaaat   1740
aaatctttcg gtatatcttt tacaggcaca tccatatcca cgccataatg attacataca   1800
gattgtaaaa gctgtgggta atattgtgaa cttgtcggtt cccaaggcgc aatcgcatgc   1860
tcatttaatg ataaatccca gttcggaata acaagttcta atctacctc taactttgag    1920
ccaagcccat cacaagaagg acatgcaccg aacggactat tgaatgagaa catacgcggc   1980
tctaattctc caattgaaaa accacaatgc ggacaagcat gatgttcact aaatagaagc   2040
tcctcttctc ccataacatc gattaacact cgtccccgc caagctttaa tgcactttca    2100
agagaatcag caagacggct tgcgattcct tcttttacaa caatacgtc aattacaact    2160
tcaatagaat gcttcttatt tttatctaac gcaatatctt cagacacatc gagcatttca   2220
ccatcaacac gtacacgaac ataaccttgc ttcttaatat cttcaagtac ttttacatgt   2280
gcacctttac gcccagaaac gataggagct aacacttgta atttcgtacg ttcagggtac   2340
tcaagtacac ggtctaccat ttgctctact gtttgcgatg taattcaat gccatgattc     2400
ggacaaattg gcgtaccaat tcgcgcaaat aataaacgta agtaatcata aatctccgtt   2460
```

```
accgttccaa cagttgaacg cggattacga ctcgtcgttt tttgatcgat tgaaatcgct    2520
ggagataagc cttcaatcgt atctacatcc ggcttatcca tttgccctaa aaactggcgt    2580
gcatacgcag ataacgattc tacgtatctg cgctgcccct ctgcataaat cgtatcaaat    2640
gctaatgagg atttccctga accagacaat cctgttacaa cgacaagttg atttctcgga    2700
atggttacat caatattttt taagttatgt gctctagcac cttttacaac gataaaatcc    2760
tt                                                                  2762

<210> SEQ ID NO 19
<211> LENGTH: 1908
<212> TYPE: DNA
<213> ORGANISM: Bacillus anthracis

<400> SEQUENCE: 19
tgcttttgct gcttctttca tttctgcttc catcttcgca attgtctttt cacgctcttt      60
tttcgtcatc ttcttagctg gcgtcgcttc atatgtttcc ggctcttcag cagctgtcgt     120
tgcacggatt acatcacgca cacctttttg aatcgttttc ggcgtaatac catgctcttc     180
attgtaagct tcttgtatac tacgacgacg cttcgtctct tcaatcgcaa tccccatcga     240
tctcgttata cgatctgcgt acataataac gcgaccgttt tcattacgtg ctgcacggcc     300
aattgtttga attaacgaac gctctgaacg caagaatcct tccttatcgg catctaaaat     360
agctacaagg gatacttctg gaatatctaa tccttctcgc aataagttaa taccaacgag     420
aacatcaaac ttaccaaggc gaagatctcg tataatttca atacgttcta acgttttcac     480
ttcagaatgc agataattca ccttaattcc tacatctttt aagtagtctg ttaaatcctc     540
tgacatcttc ttcgttaaag ttgtaattaa tacacgttca tttttgcaa tgcgatcttg      600 aatctctcct aatagatcgt caatctgccc ttcaattggt cgtatatcaa ttggcggatc     660
taaaagccct gttggacgaa taatttgttc tattacttct ggcgactgct ctaattcata     720
cggtcctggc gttgctgaaa cgtaaataac ttgattcgtt ttctcttcaa actcatcaaa     780
tgtgagcggt ctattatcta agctgatggg cagacggaat ccatgatcca caagcacttg     840
tttacgcgct tggtccccgt tatacatcgc tcttacttgc ggcactgata cgtgggactc     900
atccataacg attaagaaat ctttcgggaa atagtctaat aacgtatacg gcgttgcacc     960
cgctggacga agtgttaaat gacgggaata gttttcaatc cctgaacaaa agcccatctc    1020
gcgcatcatt tctaaatcat aacgtgtacg ctgttctata cgctgcgctt ctaacaactt    1080
accgttatca tttaattcct ttaaacgctc ttctaattct ttttcgatat tttcaatagc    1140
gaccttcatc ttttcttcac gtgtaacgaa gtgagatgct gggaagattg ctacatgatc    1200
acgttctgct aatacttctc ccgttaaagc atttacttcg cgaatacgat caatttcatc    1260
gccaaaaaac tcaattcgaa tgcaatgctc gtcaagtgat gccgggaaga tttcaactac    1320
atctccgcgc acgcggaatg taccacgctt gaaatcaata tcattacgtc catactgcac    1380
atcaacaagt tcacgaagca attgattgcg gtcctttttcc ataccaactc gaagtgaaac    1440
aactaactcg cggtattctt ctggagaacc taaaccatat atacacgaaa cactcgcaac    1500
aataattaca tcatcccgtt caaataatgc ggacgttgct gagtgacgca atttatcgat    1560
ttcatcatta atctgcgcgt cttttttcaat aaacgtatct gtttgtggca catacgcttc    1620
tggctgataa taatcgtaat aactaacaaa atattcaact gcattattcg ggaaaaagtc    1680
tttcaactca ctatataact gtcctgctaa cgttttattg tgagccatga caagcgttgg    1740
cttttgcact tctttaatga catttgaaat cgtaaatgtc ttacccgttc ctgtcgcccc    1800
```

-continued

```
aagcaacact tgctttttct ttccactatt aattccctct acaagcttct ctatagctac    1860
cggctgatca ccttgcgggg aatacgctga gacaatttca aattgacg                 1908
```

<210> SEQ ID NO 20
<211> LENGTH: 9
<212> TYPE: PRT
<213> ORGANISM: Murine

<400> SEQUENCE: 20

Ser Pro Ser Tyr Val Tyr His Gln Phe
1               5

<210> SEQ ID NO 21
<211> LENGTH: 9
<212> TYPE: PRT
<213> ORGANISM: Artificial Sequence
<220> FEATURE:
<223> OTHER INFORMATION: PCR Primer

<400> SEQUENCE: 21

Ser Pro Ser Tyr Ala Tyr His Gln Phe
1               5

<210> SEQ ID NO 22
<211> LENGTH: 25
<212> TYPE: DNA
<213> ORGANISM: Artificial Sequence
<220> FEATURE:
<223> OTHER INFORMATION: PCR Primer

<400> SEQUENCE: 22

```
gttaagtttc atgtggacgg caaag                                           25
```

<210> SEQ ID NO 23
<211> LENGTH: 42
<212> TYPE: DNA
<213> ORGANISM: Artificial Sequence
<220> FEATURE:
<223> OTHER INFORMATION: PCR Primer

<400> SEQUENCE: 23

```
aggtcttttt cagttaacta tcctctcctt gattctagtt at                        42
```

<210> SEQ ID NO 24
<211> LENGTH: 43
<212> TYPE: DNA
<213> ORGANISM: Artificial Sequence
<220> FEATURE:
<223> OTHER INFORMATION: PCR Primer

<400> SEQUENCE: 24

```
caaggagagg atagttaact gaaaaagacc taaaaaagaa ggc                       43
```

<210> SEQ ID NO 25
<211> LENGTH: 26
<212> TYPE: DNA
<213> ORGANISM: Artificial Sequence
<220> FEATURE:
<223> OTHER INFORMATION: PCR Primer

<400> SEQUENCE: 25

```
tcccctgttc ctataattgt tagctc                                          26
```

<210> SEQ ID NO 26
<211> LENGTH: 25
<212> TYPE: DNA

```
<213> ORGANISM: Artificial Sequence
<220> FEATURE:
<223> OTHER INFORMATION: PCR Primer

<400> SEQUENCE: 26
gtggacggca agaaacaac caaag                                          25

<210> SEQ ID NO 27
<211> LENGTH: 29
<212> TYPE: DNA
<213> ORGANISM: Artificial Sequence
<220> FEATURE:
<223> OTHER INFORMATION: PCR Primer

<400> SEQUENCE: 27
gttcctataa ttgttagctc attttttc                                      29

<210> SEQ ID NO 28
<211> LENGTH: 29
<212> TYPE: DNA
<213> ORGANISM: Artificial Sequence
<220> FEATURE:
<223> OTHER INFORMATION: PCR Primer

<400> SEQUENCE: 28
ctctggtacc tcctttgatt agtatattc                                     29

<210> SEQ ID NO 29
<211> LENGTH: 36
<212> TYPE: DNA
<213> ORGANISM: Artificial Sequence
<220> FEATURE:
<223> OTHER INFORMATION: PCR Primer

<400> SEQUENCE: 29
caatggatcc ctcgagatca taatttactt catccc                             36

<210> SEQ ID NO 30
<211> LENGTH: 32
<212> TYPE: DNA
<213> ORGANISM: Artificial Sequence
<220> FEATURE:
<223> OTHER INFORMATION: PCR Primer

<400> SEQUENCE: 30
atttctcgag tccatggggg gttctcatca tc                                 32

<210> SEQ ID NO 31
<211> LENGTH: 25
<212> TYPE: DNA
<213> ORGANISM: Artificial Sequence
<220> FEATURE:
<223> OTHER INFORMATION: PCR Primer

<400> SEQUENCE: 31
ggtgctcgag tgcggccgca agctt                                         25

<210> SEQ ID NO 32
<211> LENGTH: 37
<212> TYPE: DNA
<213> ORGANISM: Artificial Sequence
<220> FEATURE:
<223> OTHER INFORMATION: PCR Primer

<400> SEQUENCE: 32
cgattcccct agttatgttt accaccaatt tgctgca                            37
```

```
<210> SEQ ID NO 33
<211> LENGTH: 31
<212> TYPE: DNA
<213> ORGANISM: Artificial Sequence
<220> FEATURE:
<223> OTHER INFORMATION: PCR Primer

<400> SEQUENCE: 33
gcaaattggt ggtaaacata actaggggaa t                              31

<210> SEQ ID NO 34
<211> LENGTH: 27
<212> TYPE: DNA
<213> ORGANISM: Artificial Sequence
<220> FEATURE:
<223> OTHER INFORMATION: PCR Primer

<400> SEQUENCE: 34
agtccaagtt atgcatatca tcaattt                                   27

<210> SEQ ID NO 35
<211> LENGTH: 33
<212> TYPE: DNA
<213> ORGANISM: Artificial Sequence
<220> FEATURE:
<223> OTHER INFORMATION: PCR Primer

<400> SEQUENCE: 35
cgatagtcca agttatgcat atcatcaatt tgc                            33

<210> SEQ ID NO 36
<211> LENGTH: 34
<212> TYPE: DNA
<213> ORGANISM: Artificial Sequence
<220> FEATURE:
<223> OTHER INFORMATION: PCR Primer

<400> SEQUENCE: 36
gtcgcaaatt gatgatatgc ataacttgga ctat                           34

<210> SEQ ID NO 37
<211> LENGTH: 9
<212> TYPE: PRT
<213> ORGANISM: E. coli

<400> SEQUENCE: 37

Thr Pro His Pro Ala Arg Ile Gly Leu
 1               5

<210> SEQ ID NO 38
<211> LENGTH: 25
<212> TYPE: DNA
<213> ORGANISM: Artificial Sequence
<220> FEATURE:
<223> OTHER INFORMATION: PCR Primer

<400> SEQUENCE: 38
ctgtgctttg cgaatggaaa gaagc                                     25

<210> SEQ ID NO 39
<211> LENGTH: 43
<212> TYPE: DNA
<213> ORGANISM: Artificial Sequence
<220> FEATURE:
<223> OTHER INFORMATION: PCR Primer

<400> SEQUENCE: 39
```
gttttcattc atacacttag acaagcgttg gcttttgcac ttc              43

<210> SEQ ID NO 40
<211> LENGTH: 24
<212> TYPE: DNA
<213> ORGANISM: Artificial Sequence
<220> FEATURE:
<223> OTHER INFORMATION: PCR Primer

<400> SEQUENCE: 40
gacaagcgtt ggcttttgca cttc                                   24

<210> SEQ ID NO 41
<211> LENGTH: 44
<212> TYPE: DNA
<213> ORGANISM: Artificial Sequence
<220> FEATURE:
<223> OTHER INFORMATION: PCR Primer

<400> SEQUENCE: 41
caaaagccaa cgcttgtcta agtgtatgaa tgaaaaccga gtgg             44

<210> SEQ ID NO 42
<211> LENGTH: 25
<212> TYPE: DNA
<213> ORGANISM: Artificial Sequence
<220> FEATURE:
<223> OTHER INFORMATION: PCR Primer

<400> SEQUENCE: 42
aagtgtatga atgaaaaccg agtgg                                  25

<210> SEQ ID NO 43
<211> LENGTH: 28
<212> TYPE: DNA
<213> ORGANISM: Artificial Sequence
<220> FEATURE:
<223> OTHER INFORMATION: PCR Primer

<400> SEQUENCE: 43
catataaagg ttccacaatt gccttttc                               28

<210> SEQ ID NO 44
<211> LENGTH: 28
<212> TYPE: DNA
<213> ORGANISM: Artificial Sequence
<220> FEATURE:
<223> OTHER INFORMATION: PCR Primer

<400> SEQUENCE: 44
gaagcagaaa tgaagccaat actcaatc                               28

<210> SEQ ID NO 45
<211> LENGTH: 27
<212> TYPE: DNA
<213> ORGANISM: Artificial Sequence
<220> FEATURE:
<223> OTHER INFORMATION: PCR Primer

<400> SEQUENCE: 45
ggttccacaa ttgccttttc aataatc                                27

<210> SEQ ID NO 46
<211> LENGTH: 6
<212> TYPE: PRT
<213> ORGANISM: Bacillus anthracis

<400> SEQUENCE: 46

Lys Val Val Lys Asn Lys
  1               5

<210> SEQ ID NO 47
<211> LENGTH: 12
<212> TYPE: DNA
<213> ORGANISM: Bacillus subtilis
<220> FEATURE:
<221> NAME/KEY: misc_feature
<222> LOCATION: 5, 6, 7, 8
<223> OTHER INFORMATION: n = A,T,C or G

<400> SEQUENCE: 47
gaacnnnngt tc                                                         12

<210> SEQ ID NO 48
<211> LENGTH: 331
<212> TYPE: PRT
<213> ORGANISM: Artificial Sequence
<220> FEATURE:
<223> OTHER INFORMATION: PCR Primer

<400> SEQUENCE: 48

Met Lys Lys Ile Met Leu Val Phe Ile Thr Leu Ile Leu Val Ser Leu
  1               5                  10                  15

Pro Ile Ala Gln Gln Thr Glu Ala Lys Asp Ala Ser Ala Phe Asn Lys
             20                  25                  30

Glu Asn Ser Ile Ser Ser Met Ala Pro Ala Ser Pro Pro Ala Ser
         35                  40                  45

Pro Lys Thr Pro Ile Glu Lys Lys His Ala Asp Glu Ile Asp Ser Pro
 50                  55                  60

Ser Tyr Val Tyr His Gln Phe Ala Ala Asp Gln Ala Arg Glu Leu Ile
 65                  70                  75                  80

Asn Ser Trp Val Glu Ser Gln Thr Asn Gly Ile Ile Arg Asn Val Leu
                 85                  90                  95

Gln Pro Ser Ser Val Asp Ser Gln Thr Ala Met Val Leu Val Asn Ala
            100                 105                 110

Ile Val Phe Lys Gly Leu Trp Glu Lys Thr Phe Lys Asp Glu Asp Thr
        115                 120                 125

Gln Ala Met Pro Phe Arg Val Thr Glu Gln Glu Ser Lys Pro Val Gln
130                 135                 140

Met Met Tyr Gln Ile Gly Leu Phe Arg Val Ala Ser Met Ala Ser Glu
145                 150                 155                 160

Lys Met Lys Ile Leu Glu Leu Pro Phe Ala Ser Gly Thr Met Ser Met
                165                 170                 175

Leu Val Leu Leu Pro Asp Glu Val Ser Gly Leu Glu Gln Leu Glu Ser
            180                 185                 190

Ile Ile Asn Phe Glu Lys Leu Thr Glu Trp Thr Val Leu Gln Glu Leu
        195                 200                 205

Asn Val Thr Val Arg Thr Ser Ser Asn Val Met Glu Glu Arg Lys Ile
    210                 215                 220

Lys Val Tyr Leu Pro Arg Met Lys Met Glu Glu Lys Tyr Asn Leu Thr
225                 230                 235                 240

Ser Val Leu Met Ala Met Gly Ile Thr Asp Val Phe Ser Ser Ser Ala
                245                 250                 255

Asn Leu Ser Gly Ile Ser Ser Ala Glu Ser Leu Lys Ile Ser Gln Ala
            260                 265                 270

Val His Ala Ala His Ala Glu Ile Asn Glu Ala Gly Arg Glu Val Val
            275                 280                 285

Gly Ser Ala Glu Ala Gly Val Asp Ala Ala Ser Val Ser Glu Glu Phe
            290                 295                 300

Arg Ala Asp His Pro Phe Leu Phe Cys Ile Lys His Ile Ala Thr Asn
305                 310                 315                 320

Ala Val Leu Phe Phe Gly Arg Cys Val Ser Pro
            325                 330

<210> SEQ ID NO 49
<211> LENGTH: 8
<212> TYPE: PRT
<213> ORGANISM: Gallus gallus

<400> SEQUENCE: 49

Ser Ile Ile Asn Phe Glu Lys Leu
1               5

<210> SEQ ID NO 50
<211> LENGTH: 9
<212> TYPE: PRT
<213> ORGANISM: Homo sapien

<400> SEQUENCE: 50

Val Leu Gln Glu Leu Asn Val Thr Val
1               5

<210> SEQ ID NO 51
<211> LENGTH: 9
<212> TYPE: PRT
<213> ORGANISM: Homo sapien

<400> SEQUENCE: 51

Tyr Leu Ser Gly Ala Asn Leu Asn Leu
1               5

<210> SEQ ID NO 52
<211> LENGTH: 9
<212> TYPE: PRT
<213> ORGANISM: Artificial Sequence
<220> FEATURE:
<223> OTHER INFORMATION: PCR Primer

<400> SEQUENCE: 52

Tyr Leu Ser Gly Ala Asp Leu Asn Leu
1               5

<210> SEQ ID NO 53
<211> LENGTH: 55
<212> TYPE: PRT
<213> ORGANISM: Listeria monocytogenes

<400> SEQUENCE: 53

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Asp Pro Asp Lys Thr Pro
        35                  40                  45

Ile Glu Lys Lys His Ala Asp
    50                  55

```
<210> SEQ ID NO 54
<211> LENGTH: 31
<212> TYPE: PRT
<213> ORGANISM: Bacillus anthracis

<400> SEQUENCE: 54

Met Lys Lys Arg Lys Val Leu Ile Pro Leu Met Ala Leu Ser Thr Ile
 1               5                  10                  15

Leu Val Ser Ser Thr Gly Asn Leu Glu Val Ile Gln Ala Glu Val
            20                  25                  30

<210> SEQ ID NO 55
<211> LENGTH: 21
<212> TYPE: DNA
<213> ORGANISM: Artificial Sequence
<220> FEATURE:
<223> OTHER INFORMATION: PCR Primer

<400> SEQUENCE: 55
gtcaaaacat acgctcttat c                                          21

<210> SEQ ID NO 56
<211> LENGTH: 24
<212> TYPE: DNA
<213> ORGANISM: Artificial Sequence
<220> FEATURE:
<223> OTHER INFORMATION: PCR Primer

<400> SEQUENCE: 56
acataatcag tccaaagtag atgc                                       24

<210> SEQ ID NO 57
<211> LENGTH: 29
<212> TYPE: DNA
<213> ORGANISM: Artificial Sequence
<220> FEATURE:
<223> OTHER INFORMATION: PCR Primer

<400> SEQUENCE: 57
ctctggtacc tcctttgatt agtatattc                                  29

<210> SEQ ID NO 58
<211> LENGTH: 29
<212> TYPE: DNA
<213> ORGANISM: Artificial Sequence
<220> FEATURE:
<223> OTHER INFORMATION: PCR Primer

<400> SEQUENCE: 58
ctctggatcc atccgcgtgt ttcttttcg                                  29

<210> SEQ ID NO 59
<211> LENGTH: 16
<212> TYPE: RNA
<213> ORGANISM: Artificial Sequence
<220> FEATURE:
<223> OTHER INFORMATION: Concensus sequence
<220> FEATURE:
<221> NAME/KEY: misc_feature
<222> LOCATION: 1, 9, 10, 11, 12, 13
<223> OTHER INFORMATION: n = A,T,C or G

<400> SEQUENCE: 59
naggaggunn nnnaug                                                16

<210> SEQ ID NO 60
<211> LENGTH: 19
```

-continued

```
<212> TYPE: DNA
<213> ORGANISM: Listeria monocytogenes

<400> SEQUENCE: 60
aaggagagtg aaacccatg                                                    19

<210> SEQ ID NO 61
<211> LENGTH: 60
<212> TYPE: DNA
<213> ORGANISM: Listeria monocytogenes

<400> SEQUENCE: 61
gtggcaaacg gtatttggca ttattaggtt aaaaaatgta aaggagagt gaaacccatg        60

<210> SEQ ID NO 62
<211> LENGTH: 60
<212> TYPE: DNA
<213> ORGANISM: Listeria monocytogenes

<400> SEQUENCE: 62
gtggcaaacg gtatttggca ttattaggtt aaaaaatgta aaggagagt gaaacccatg        60

<210> SEQ ID NO 63
<211> LENGTH: 966
<212> TYPE: DNA
<213> ORGANISM: Artificial Sequence
<220> FEATURE:
<223> OTHER INFORMATION: Heterologous Expression Cassette

<400> SEQUENCE: 63
ggtacctcct ttgattagta tattcctatc ttaaagttac ttttatgtgg aggcattaac       60
atttgttaat gacgtcaaaa ggatagcaag actagaataa agctataaag caagcatata     120
atattgcgtt tcatctttag aagcgaattt cgccaatatt ataattatca aaagagaggg     180
gtggcaaacg gtatttggca ttattaggtt aaaaaatgta aaggagagt gaaacccatg      240 aaaaaaatta tgttagtttt tattacatta attttagtta gtttaccaat tgcacaacaa     300
acagaagcaa aagatgcaag tgcatttaat aaagaaaata gtattagtag tatggcacca    360
ccagcaagtc caccagcaag tccaaaaaca ccaattgaaa aaaacatgc agatggatcc     420 caagcagaag gtcgcggaac aggaggaagt acaggagatg cagacggacc aggaggacca    480
ggaataccag acggaccagg aggaaatgca ggaggcccag gcgaagcagg cgcaacagga    540
ggaagaggac caagggagc aggagcagca cgagcatcag gaccaggagg cggagcacca    600
agaggaccac atggcggagc ggcaagcgga ttaaatggat gttgtagatg tggagcacgc    660
ggaccagaat caagcttttt agaatttat ttagccatgc catttgcaac cccaatggaa    720
gcagaattag cacgaagatc attagcacaa gatgccccac cattaccagt accaggagtt     780
ttattaaaag agtttacagt atcaggcaat attttaacaa tacgtttaac agcagcagac    840
catcgtcaat tacaactatc tatcagttca tgtttacaac aattatccttt attaatgtgg    900 attacacaat gttttttacc agttttttta gcacaaccac catcaggaca aagaagataa    960
gagctc                                                                966

<210> SEQ ID NO 64
<211> LENGTH: 240
<212> TYPE: PRT
<213> ORGANISM: Artificial Sequence
<220> FEATURE:
<223> OTHER INFORMATION: Fusion Protein

<400> SEQUENCE: 64
```

```
Met Lys Lys Ile Met Leu Val Phe Ile Thr Leu Ile Leu Val Ser Leu
  1               5                  10                  15

Pro Ile Ala Gln Gln Thr Glu Ala Lys Asp Ala Ser Ala Phe Asn Lys
             20                  25                  30

Glu Asn Ser Ile Ser Ser Met Ala Pro Pro Ala Ser Pro Ala Ser
         35                  40                  45

Pro Lys Thr Pro Ile Glu Lys Lys His Ala Asp Gly Ser Gln Ala Glu
 50                  55                  60

Gly Arg Gly Thr Gly Gly Ser Thr Gly Asp Ala Asp Gly Pro Gly Gly
 65              70                  75                  80

Pro Gly Ile Pro Asp Gly Pro Gly Gly Asn Ala Gly Gly Pro Gly Glu
             85                  90                  95

Ala Gly Ala Thr Gly Gly Arg Gly Pro Arg Gly Ala Gly Ala Ala Arg
            100                 105                 110

Ala Ser Gly Pro Gly Gly Ala Pro Arg Gly Pro His Gly Gly Ala
            115                 120                 125

Ala Ser Gly Leu Asn Gly Cys Cys Arg Cys Gly Ala Arg Gly Pro Glu
            130                 135                 140

Ser Arg Leu Leu Glu Phe Tyr Leu Ala Met Pro Phe Ala Thr Pro Met
145                 150                 155                 160

Glu Ala Glu Leu Ala Arg Arg Ser Leu Ala Gln Asp Ala Pro Leu
                165                 170                 175

Pro Val Pro Gly Val Leu Leu Lys Glu Phe Thr Val Ser Gly Asn Ile
                180                 185                 190

Leu Thr Ile Arg Leu Thr Ala Ala Asp His Arg Gln Leu Gln Leu Ser
                195                 200                 205

Ile Ser Ser Cys Leu Gln Gln Leu Ser Leu Leu Met Trp Ile Thr Gln
            210                 215                 220

Cys Phe Leu Pro Val Phe Leu Ala Gln Pro Pro Ser Gly Gln Arg Arg
225                 230                 235                 240

<210> SEQ ID NO 65
<211> LENGTH: 1869
<212> TYPE: DNA
<213> ORGANISM: Artificial Sequence
<220> FEATURE:
<223> OTHER INFORMATION: Codon-optimized sequence

<400> SEQUENCE: 65
atggcattgc caactgcacg tccattacta ggtagttgcg gtacaccagc actaggttct      60
ttattatttt tgttattttc tctaggttgg gttcaaccaa gtcgtacatt agcaggtgaa     120
acaggtcaag aagcagcacc acttgacggt gtattaacga atccaccaaa tatatcaagt     180
ttaagtccac gtcaattatt aggttttcca tgtgcagaag tttcaggttt aagtacagaa     240
cgtgtccgtg agtagcagt tgcattagca caaaaaaacg ttaaattatc tacagaacag     300
ttacgttgtt tagcccatag attaagcgaa ccaccagaag acttagatgc acttcctta     360 gaccttcttt tattcttaaa tccagatgca ttttcaggac acaaagcatg tacacgtttt     420
tttagtcgaa ttacaaaagc caatgttgat ttattacctc gtgggctcc tgaaagacaa     480 cgttattac ctgctgcatt agcatgctgg ggtgttcgcg tagcttatt aagtgaagcc     540 gatgttcgtg ctttagggggg tttagcatgt gatttacctg gtcgtttcgt tgcagaatca     600
gcagaagtgt tattaccgag attagtttca tgcccaggac ttttagatca agatcaacaa     660
gaggcagcta gagcagctct tcaaggagga ggccccacca tggcccacc aagtacatgg     720
```

-continued

```
agtgtttcta caatggatgc gttaagaggt ttattaccgg ttttaggaca accaattatt      780
cgtagtattc cacaaggcat tgtagcagca tggcgtcaac gtagttctcg tgatccgtct      840
tggcgacaac cagaacgtac aattctacgt ccaagatttc gtagagaagt agaaaaaacg      900
gcgtgtccta gtggcaaaaa agcacgtgaa attgatgaaa gtttaatttt ttataaaaaa      960
tgggaattag aagcatgtgt cgatgcagca ttactagcta cacaaatgga tcgtgttaat     1020
gctattccat tcacatatga acaattagat gttttaaagc ataaattaga cgaattatat     1080
ccacaaggtt atccagaatc agttattcaa catttaggtt acttattttt aaaaatgagt     1140
ccagaagaca tacgcaaatg gaatgttaca agtttagaaa cattaaaagc gcttttagaa     1200
gttaacaaag gtcatgaaat gagtccacaa gttgctacgt taattgatag attcgttaaa     1260
ggccgtggtc aattagataa agatacttta gatacattaa cagcatttta tcctggctac     1320
ttatgcagtt tatcaccaga agaattaagt tccgttccac cgagtagtat ctgggcagtt     1380
cgtccgcaag atttagatac atgcgaccca cgtcaattag atgttttata tccaaaagca     1440
agattagctt tccaaaatat gaacggtagt gaatatttcg taaaaattca atcctttta      1500
ggtggtgcac caactgaaga tctaaaagca ttaagccaac aaaatgtaag tatggattta     1560
gctacgttta tgaaattacg tacagatgca gttctaccat taacagttgc agaagttcaa     1620
aaattattag gtccacacgt agaaggatta aaagcagaag aacgtcaccg tccagttcgc     1680
gattggattt tacgtcaacg tcaagatgat ttagatacat taggtttagg tttacaaggc     1740
ggtattccga atggatattt agtgttagat ttatctgttc aagaagcatt aagtggtaca     1800
ccgtgtttat taggtccagg tccagtttta acagtgttag cattattatt agccagtaca     1860
ttagcttaa                                                             1869
```

<210> SEQ ID NO 66
<211> LENGTH: 622
<212> TYPE: PRT
<213> ORGANISM: Homo sapien

<400> SEQUENCE: 66

```
Met Ala Leu Pro Thr Ala Arg Pro Leu Leu Gly Ser Cys Gly Thr Pro
 1               5                  10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Thr Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175
```

```
Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
                260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
                340                 345                 350

Lys His Lys Leu Asp Glu Leu Tyr Pro Gln Gly Tyr Pro Glu Ser Val
            355                 360                 365

Ile Gln His Leu Gly Tyr Leu Phe Leu Lys Met Ser Pro Glu Asp Ile
370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
                405                 410                 415

Arg Phe Val Lys Gly Arg Gly Gln Leu Asp Lys Asp Thr Leu Asp Thr
                420                 425                 430

Leu Thr Ala Phe Tyr Pro Gly Tyr Leu Cys Ser Leu Ser Pro Glu Glu
            435                 440                 445

Leu Ser Ser Val Pro Pro Ser Ser Ile Trp Ala Val Arg Pro Gln Asp
    450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495

Gln Ser Phe Leu Gly Gly Ala Pro Thr Glu Asp Leu Lys Ala Leu Ser
            500                 505                 510

Gln Gln Asn Val Ser Met Asp Leu Ala Thr Phe Met Lys Leu Arg Thr
        515                 520                 525

Asp Ala Val Leu Pro Leu Thr Val Ala Glu Val Gln Lys Leu Leu Gly
    530                 535                 540

Pro His Val Glu Gly Leu Lys Ala Glu Glu Arg His Arg Pro Val Arg
545                 550                 555                 560

Asp Trp Ile Leu Arg Gln Arg Gln Asp Asp Leu Asp Thr Leu Gly Leu
                565                 570                 575

Gly Leu Gln Gly Gly Ile Pro Asn Gly Tyr Leu Val Leu Asp Leu Ser
            580                 585                 590

Val Gln Glu Ala Leu Ser Gly Thr Pro Cys Leu Leu Gly Pro Gly Pro
```

| 595 | 600 | 605 |

Val Leu Thr Val Leu Ala Leu Leu Leu Ala Ser Thr Leu Ala
       610              615              620

<210> SEQ ID NO 67
<211> LENGTH: 1878
<212> TYPE: DNA
<213> ORGANISM: Artificial Sequence
<220> FEATURE:
<223> OTHER INFORMATION: Codon-optimized sequence

<400> SEQUENCE: 67

| | | | |
|---|---|---|---|
| atggcattac caacggctcg cccattatta ggttcttgtg gttcaccaat ttgtagtcgc | 60 |
| agttttttat tattattact atctttaggt tggattccgc gtttacaaac acaaaccact | 120 |
| aaaacaagtc aagaagctac attattgcat gcagtcaatg gcgcagcaga ttttgcaagt | 180 |
| ttaccaacag gcttatttct tggtcttaca tgtgaagaag ttagtgattt aagtatggaa | 240 |
| caagcaaaag gtttagcgat ggcggttcgc caaaaaaata ttacattacg tggtcatcaa | 300 |
| ttacgttgtt tagcacgtcg tttaccacga catttaacag atgaagaatt aaatgctcta | 360 |
| ccattagact tattattatt tttaaatcca gcaatgtttc aggtcaaca agcatgtgcc | 420 |
| cattttttca gtttaatttc gaaagcaaat gtagatgttt taccgagacg tagcttagaa | 480 |
| cgtcaacgtc ttttaatgga agcattaaaa tgtcaaggtg tttatggttt ccaagttagt | 540 |
| gaagcagatg ttcgtgcact tggtggttta gcttgtgatt taccagggaa atttgtagca | 600 |
| cgttctagtg aagtattatt accatggtta gcaggttgtc aaggtccatt agatcaaagt | 660 |
| caagaaaaag cagttcgtga agtcttacgt agtggtcgta ctcaatatgg cccacctagc | 720 |
| aaatggagtg ttagtacgtt agatgcatta caaagtttag tagctgtttt agatgaaagt | 780 |
| attgttcaga gtattccaaa agatgtgaaa gcagagtggt acaacatat tcccgtgac | 840 |
| ccatctcgtt taggtagtaa attaacagtt attcatccac gttttcgccg cgacgcagaa | 900 |
| caaaaagcat gtccaccagg taagaaacca tataagtag atgaagattt aattttttat | 960 |
| cagaattggg aattagaagc ctgtgttgat ggtacaatgt tagcacgtca atggatttta | 1020 |
| gttaatgaaa ttccatttac atatgaacaa ttaagtatct ttaaacataa attagataaa | 1080 |
| acatatccac aaggttatcc agaatcgtta attcaacaat taggtcattt ttttcgttat | 1140 |
| gttagtccag aagacattca tcaatggaat gttacaagtc cagatacagt taaaacttta | 1200 |
| ttaaaagtta gtaaaggtca aaaaatgaat gctcaagcaa ttgcattagt cgcatgttat | 1260 |
| ttacgtggag gtggtcaatt agatgaagat atggttaaag cattagggga tattccatta | 1320 |
| tcatatttat gtgatttctc cccacaagac ttacattcag ttccaagtag tgttatgtgg | 1380 |
| ttagttggtc cacaaggttt agataaatgt agtcaacgtc atttaggttt actttatcaa | 1440 |
| aaagcatgta gtgcgtttca aaatgttagt ggtttagaat attttgaaaa atcaaaaaca | 1500 |
| tttttaggag gtgcatctgt aaaagattta cgcgcattaa gtcaacataa tgtaagtatg | 1560 |
| gatatcgcaa catttaaacg tttacaagtc gatagtctag ttggtcttag tgtagcagaa | 1620 |
| gttcaaaaat tattagggcc gaatattgta gatttaaaaa cagaagaaga taaaagtcca | 1680 |
| gttcgtgact ggttatttcg acaacatcag aaagacttag atcgtcttgg attaggttta | 1740 |
| caaggtggta ttccaaatgg ttatttagtt ttagatttta atgtacgtga agcatttagt | 1800 |
| tcaagagcga gtttattagg tccaggtttt gtgttaattt ggattccagc attactacca | 1860 |
| gcacttcgtt tatcataa | 1878 |

-continued

```
<210> SEQ ID NO 68
<211> LENGTH: 625
<212> TYPE: PRT
<213> ORGANISM: Murine

<400> SEQUENCE: 68
```

Met Ala Leu Pro Thr Ala Arg Pro Leu Leu Gly Ser Cys Gly Ser Pro
1               5                   10                  15

Ile Cys Ser Arg Ser Phe Leu Leu Leu Leu Ser Leu Gly Trp Ile
                20                  25                  30

Pro Arg Leu Gln Thr Gln Thr Thr Lys Thr Ser Gln Glu Ala Thr Leu
            35                  40                  45

Leu His Ala Val Asn Gly Ala Ala Asp Phe Ala Ser Leu Pro Thr Gly
        50                  55                  60

Leu Phe Leu Gly Leu Thr Cys Glu Glu Val Ser Asp Leu Ser Met Glu
65                  70                  75                  80

Gln Ala Lys Gly Leu Ala Met Ala Val Arg Gln Lys Asn Ile Thr Leu
                85                  90                  95

Arg Gly His Gln Leu Arg Cys Leu Ala Arg Arg Leu Pro Arg His Leu
            100                 105                 110

Thr Asp Glu Glu Leu Asn Ala Leu Pro Leu Asp Leu Leu Leu Phe Leu
        115                 120                 125

Asn Pro Ala Met Phe Pro Gly Gln Gln Ala Cys Ala His Phe Phe Ser
130                 135                 140

Leu Ile Ser Lys Ala Asn Val Asp Val Leu Pro Arg Arg Ser Leu Glu
145                 150                 155                 160

Arg Gln Arg Leu Leu Met Glu Ala Leu Lys Cys Gln Gly Val Tyr Gly
                165                 170                 175

Phe Gln Val Ser Glu Ala Asp Val Arg Ala Leu Gly Gly Leu Ala Cys
            180                 185                 190

Asp Leu Pro Gly Lys Phe Val Ala Arg Ser Ser Glu Val Leu Leu Pro
        195                 200                 205

Trp Leu Ala Gly Cys Gln Gly Pro Leu Asp Gln Ser Gln Glu Lys Ala
210                 215                 220

Val Arg Glu Val Leu Arg Ser Gly Arg Thr Gln Tyr Gly Pro Pro Ser
225                 230                 235                 240

Lys Trp Ser Val Ser Thr Leu Asp Ala Leu Gln Ser Leu Val Ala Val
                245                 250                 255

Leu Asp Glu Ser Ile Val Gln Ser Ile Pro Lys Asp Val Lys Ala Glu
            260                 265                 270

Trp Leu Gln His Ile Ser Arg Asp Pro Ser Arg Leu Gly Ser Lys Leu
        275                 280                 285

Thr Val Ile His Pro Arg Phe Arg Arg Asp Ala Glu Gln Lys Ala Cys
290                 295                 300

Pro Pro Gly Lys Glu Pro Tyr Lys Val Asp Glu Asp Leu Ile Phe Tyr
305                 310                 315                 320

Gln Asn Trp Glu Leu Glu Ala Cys Val Asp Gly Thr Met Leu Ala Arg
                325                 330                 335

Gln Met Asp Leu Val Asn Glu Ile Pro Phe Thr Tyr Glu Gln Leu Ser
            340                 345                 350

Ile Phe Lys His Lys Leu Asp Lys Thr Tyr Pro Gln Gly Tyr Pro Glu
        355                 360                 365

Ser Leu Ile Gln Gln Leu Gly His Phe Phe Arg Tyr Val Ser Pro Glu
370                 375                 380

Asp Ile His Gln Trp Asn Val Thr Ser Pro Asp Thr Val Lys Thr Leu

```
                385                 390                 395                 400
Leu Lys Val Ser Lys Gly Gln Lys Met Asn Ala Gln Ala Ile Ala Leu
                    405                 410                 415

Val Ala Cys Tyr Leu Arg Gly Gly Gln Leu Asp Glu Asp Met Val
                420                 425                 430

Lys Ala Leu Gly Asp Ile Pro Leu Ser Tyr Leu Cys Asp Phe Ser Pro
                    435                 440                 445

Gln Asp Leu His Ser Val Pro Ser Ser Val Met Trp Leu Val Gly Pro
                    450                 455                 460

Gln Gly Leu Asp Lys Cys Ser Gln Arg His Leu Gly Leu Leu Tyr Gln
465                 470                 475                 480

Lys Ala Cys Ser Ala Phe Gln Asn Val Ser Gly Leu Glu Tyr Phe Glu
                    485                 490                 495

Lys Ile Lys Thr Phe Leu Gly Gly Ala Ser Val Lys Asp Leu Arg Ala
                    500                 505                 510

Leu Ser Gln His Asn Val Ser Met Asp Ile Ala Thr Phe Lys Arg Leu
                    515                 520                 525

Gln Val Asp Ser Leu Val Gly Leu Ser Val Ala Glu Val Gln Lys Leu
                    530                 535                 540

Leu Gly Pro Asn Ile Val Asp Leu Lys Thr Glu Asp Lys Ser Pro
545                 550                 555                 560

Val Arg Asp Trp Leu Phe Arg Gln His Gln Lys Asp Leu Asp Arg Leu
                    565                 570                 575

Gly Leu Gly Leu Gln Gly Gly Ile Pro Asn Gly Tyr Leu Val Leu Asp
                580                 585                 590

Phe Asn Val Arg Glu Ala Phe Ser Ser Arg Ala Ser Leu Leu Gly Pro
                    595                 600                 605

Gly Phe Val Leu Ile Trp Ile Pro Ala Leu Leu Pro Ala Leu Arg Leu
                    610                 615                 620

Ser
625

<210> SEQ ID NO 69
<211> LENGTH: 5
<212> TYPE: PRT
<213> ORGANISM: Listeria monocytogenes
<220> FEATURE:
<221> NAME/KEY: VARIANT
<222> LOCATION: (3)...(4)
<223> OTHER INFORMATION: Cleavage between position 3 and 4 = signal
      peptidase site

<400> SEQUENCE: 69

Thr Glu Ala Lys Asp
1               5

<210> SEQ ID NO 70
<211> LENGTH: 5
<212> TYPE: PRT
<213> ORGANISM: Bacillus anthracis
<220> FEATURE:
<221> NAME/KEY: VARIANT
<222> LOCATION: (3)...(4)
<223> OTHER INFORMATION: Cleavage between position 3 and 4 = signal
      peptidase site

<400> SEQUENCE: 70

Ile Gln Ala Glu Val
1               5
```

```
<210> SEQ ID NO 71
<211> LENGTH: 17
<212> TYPE: RNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: 1, 9, 10, 11, 12, 13, 14
<223> OTHER INFORMATION: n = A,T,C or G

<400> SEQUENCE: 71
naggaggunn nnnnaug                                                   17

<210> SEQ ID NO 72
<211> LENGTH: 18
<212> TYPE: RNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: 1, 9, 10, 11, 12, 13, 14, 15
<223> OTHER INFORMATION: n = A,T,C or G

<400> SEQUENCE: 72
naggaggunn nnnnnaug                                                  18

<210> SEQ ID NO 73
<211> LENGTH: 19
<212> TYPE: RNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: 1, 9, 10, 11, 12, 13, 14, 15, 16
<223> OTHER INFORMATION: n = A,T,C or G

<400> SEQUENCE: 73
naggaggunn nnnnnnaug                                                 19

<210> SEQ ID NO 74
<211> LENGTH: 20
<212> TYPE: RNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: 1, 9, 10, 11, 12, 13, 14, 15, 16, 17
<223> OTHER INFORMATION: n = A,T,C or G

<400> SEQUENCE: 74
naggaggunn nnnnnnnaug                                                20

<210> SEQ ID NO 75
<211> LENGTH: 21
<212> TYPE: RNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: 1, 9, 10, 11, 12, 13, 14, 15, 16, 17, 18
<223> OTHER INFORMATION: n = A,T,C or G

<400> SEQUENCE: 75
naggaggunn nnnnnnnnau g                                              21
```

-continued

```
<210> SEQ ID NO 76
<211> LENGTH: 177
<212> TYPE: DNA
<213> ORGANISM: Listeria monocytogenes

<400> SEQUENCE: 76
atgaaaaaaa taatgctagt ttttattaca cttatattag ttagtctacc aattgcgcaa      60
caaactgaag caaggatgc atctgcattc aataaagaaa attcaatttc atccatggca     120
ccaccagcat ctccgcctgc aagtcctaag acgccaatcg aaagaaaca cgcggat        177

<210> SEQ ID NO 77
<211> LENGTH: 177
<212> TYPE: DNA
<213> ORGANISM: Artificial Sequence
<220> FEATURE:
<223> OTHER INFORMATION: Codon-optimized Sequence

<400> SEQUENCE: 77
atgaaaaaaa ttatgttagt ttttattaca ttaattttag ttagtttacc aattgcacaa      60
caaacagaag caaagatgc aagtgcattt aataaagaaa atagtattag tagtatggca     120
ccaccagcaa gtccaccagc aagtccaaaa acaccaattg aaaaaaaaca tgcagat       177

<210> SEQ ID NO 78
<211> LENGTH: 93
<212> TYPE: DNA
<213> ORGANISM: Bacillus anthracis

<400> SEQUENCE: 78
atgaaaaaac gaaaagtgtt aataccatta atggcattgt ctacgatatt agtttcaagc      60
acaggtaatt tagaggtgat tcaggcagaa gtt                                   93

<210> SEQ ID NO 79
<211> LENGTH: 93
<212> TYPE: DNA
<213> ORGANISM: Artificial Sequence
<220> FEATURE:
<223> OTHER INFORMATION: Codon-optimized Sequence

<400> SEQUENCE: 79
atgaaaaaac gtaaagtttt aattccatta atggcattaa gtacaatttt agttagtagt      60
acaggtaatt tagaagttat tcaagcagaa gtt                                   93

<210> SEQ ID NO 80
<211> LENGTH: 809
<212> TYPE: PRT
<213> ORGANISM: Bacillus anthracis

<400> SEQUENCE: 80

Met Asn Ile Lys Lys Glu Phe Ile Lys Val Ile Ser Met Ser Cys Leu
  1               5                  10                  15

Val Thr Ala Ile Thr Leu Ser Gly Pro Val Phe Ile Pro Leu Val Gln
                 20                  25                  30

Gly Ala Gly Gly His Gly Asp Val Gly Met His Val Lys Glu Lys Glu
             35                  40                  45

Lys Asn Lys Asp Glu Asn Lys Arg Lys Asp Glu Glu Arg Asn Lys Thr
         50                  55                  60

Gln Glu Glu His Leu Lys Glu Ile Met Lys His Ile Val Lys Ile Glu
 65                  70                  75                  80

Val Lys Gly Glu Glu Ala Val Lys Lys Glu Ala Ala Glu Lys Leu Leu
                 85                  90                  95
```

-continued

```
Glu Lys Val Pro Ser Asp Val Leu Glu Met Tyr Lys Ala Ile Gly Gly
            100                 105                 110

Lys Ile Tyr Ile Val Asp Gly Asp Ile Thr Lys His Ile Ser Leu Glu
            115                 120                 125

Ala Leu Ser Glu Asp Lys Lys Ile Lys Asp Ile Tyr Gly Lys Asp
            130                 135                 140

Ala Leu Leu His Glu His Tyr Val Tyr Ala Lys Glu Gly Tyr Glu Pro
145                 150                 155                 160

Val Leu Val Ile Gln Ser Ser Glu Asp Tyr Val Glu Asn Thr Glu Lys
            165                 170                 175

Ala Leu Asn Val Tyr Tyr Glu Ile Gly Lys Ile Leu Ser Arg Asp Ile
            180                 185                 190

Leu Ser Lys Ile Asn Gln Pro Tyr Gln Lys Phe Leu Asp Val Leu Asn
            195                 200                 205

Thr Ile Lys Asn Ala Ser Asp Ser Asp Gly Gln Asp Leu Leu Phe Thr
            210                 215                 220

Asn Gln Leu Lys Glu His Pro Thr Asp Phe Ser Val Glu Phe Leu Glu
225                 230                 235                 240

Gln Asn Ser Asn Glu Val Gln Glu Val Phe Ala Lys Ala Phe Ala Tyr
            245                 250                 255

Tyr Ile Glu Pro Gln His Arg Asp Val Leu Gln Leu Tyr Ala Pro Glu
            260                 265                 270

Ala Phe Asn Tyr Met Asp Lys Phe Asn Glu Gln Glu Ile Asn Leu Ser
            275                 280                 285

Leu Glu Glu Leu Lys Asp Gln Arg Met Leu Ala Arg Tyr Glu Lys Trp
            290                 295                 300

Glu Lys Ile Lys Gln His Tyr Gln His Trp Ser Asp Ser Leu Ser Glu
305                 310                 315                 320

Glu Gly Arg Gly Leu Leu Lys Lys Leu Gln Ile Pro Ile Glu Pro Lys
            325                 330                 335

Lys Asp Asp Ile Ile His Ser Leu Ser Gln Glu Glu Lys Glu Leu Leu
            340                 345                 350

Lys Arg Ile Gln Ile Asp Ser Ser Asp Phe Leu Ser Thr Glu Glu Lys
            355                 360                 365

Glu Phe Leu Lys Lys Leu Gln Ile Asp Ile Arg Asp Ser Leu Ser Glu
            370                 375                 380

Glu Glu Lys Glu Leu Leu Asn Arg Ile Gln Val Asp Ser Ser Asn Pro
385                 390                 395                 400

Leu Ser Glu Lys Glu Lys Glu Phe Leu Lys Lys Leu Lys Leu Asp Ile
            405                 410                 415

Gln Pro Tyr Asp Ile Asn Gln Arg Leu Gln Asp Thr Gly Gly Leu Ile
            420                 425                 430

Asp Ser Pro Ser Ile Asn Leu Asp Val Arg Lys Gln Tyr Lys Arg Asp
            435                 440                 445

Ile Gln Asn Ile Asp Ala Leu Leu His Gln Ser Ile Gly Ser Thr Leu
            450                 455                 460

Tyr Asn Lys Ile Tyr Leu Tyr Glu Asn Met Asn Ile Asn Asn Leu Thr
465                 470                 475                 480

Ala Thr Leu Gly Ala Asp Leu Val Asp Ser Thr Asp Asn Thr Lys Ile
            485                 490                 495

Asn Arg Gly Ile Phe Asn Glu Phe Lys Lys Asn Phe Lys Tyr Ser Ile
            500                 505                 510

Ser Ser Asn Tyr Met Ile Val Asp Ile Asn Glu Arg Pro Ala Leu Asp
```

Asn Glu Arg Leu Lys Trp Arg Ile Gln Leu Ser Pro Asp Thr Arg Ala
            530                 535                 540
Gly Tyr Leu Glu Asn Gly Lys Leu Ile Leu Gln Arg Asn Ile Gly Leu
545                 550                 555                 560
Glu Ile Lys Asp Val Gln Ile Ile Lys Gln Ser Glu Lys Glu Tyr Ile
                565                 570                 575
Arg Ile Asp Ala Lys Val Val Pro Lys Ser Lys Ile Asp Thr Lys Ile
            580                 585                 590
Gln Glu Ala Gln Leu Asn Ile Asn Gln Glu Trp Asn Lys Ala Leu Gly
            595                 600                 605
Leu Pro Lys Tyr Thr Lys Leu Ile Thr Phe Asn Val His Asn Arg Tyr
610                 615                 620
Ala Ser Asn Ile Val Glu Ser Ala Tyr Leu Ile Leu Asn Glu Trp Lys
625                 630                 635                 640
Asn Asn Ile Gln Ser Asp Leu Ile Lys Lys Val Thr Asn Tyr Leu Val
                645                 650                 655
Asp Gly Asn Gly Arg Phe Val Phe Thr Asp Ile Thr Leu Pro Asn Ile
                660                 665                 670
Ala Glu Gln Tyr Thr His Gln Asp Glu Ile Tyr Glu Gln Val His Ser
                675                 680                 685
Lys Gly Leu Tyr Val Pro Glu Ser Arg Ser Ile Leu Leu His Gly Pro
            690                 695                 700
Ser Lys Gly Val Glu Leu Arg Asn Asp Ser Glu Gly Phe Ile His Glu
705                 710                 715                 720
Phe Gly His Ala Val Asp Asp Tyr Ala Gly Tyr Leu Leu Asp Lys Asn
                725                 730                 735
Gln Ser Asp Leu Val Thr Asn Ser Lys Lys Phe Ile Asp Ile Phe Lys
                740                 745                 750
Glu Glu Gly Ser Asn Leu Thr Ser Tyr Gly Arg Thr Asn Glu Ala Glu
            755                 760                 765
Phe Phe Ala Glu Ala Phe Arg Leu Met His Ser Thr Asp His Ala Glu
770                 775                 780
Arg Leu Lys Val Gln Lys Asn Ala Pro Lys Thr Phe Gln Phe Ile Asn
785                 790                 795                 800
Asp Gln Ile Lys Phe Ile Ile Asn Ser
            805

```
<210> SEQ ID NO 81
<211> LENGTH: 2430
<212> TYPE: DNA
<213> ORGANISM: Bacillus anthracis

<400> SEQUENCE: 81
atgaatataa aaaagaatt tataaaagta attagtatgt catgtttagt aacagcaatt      60
actttgagtg gtcccgtctt tatccccctt gtacagggg cgggcggtca tggtgatgta     120
ggtatgcacg taaagagaa agagaaaaat aaagatgaga ataagagaaa agatgaagaa     180
cgaaataaaa cacaggaaga gcatttaaag gaaatcatga acacattgt aaaaatagaa     240 gtaaaagggg aggaagctgt taaaaaagag gcagcagaaa agctacttga gaaagtacca     300
tctgatgttt tagagatgta taagcaatt ggaggaaaga tatatattgt ggatggtgat     360
attacaaaac atatatcttt agaagcatta tctgaagata gaaaaaaat aaaagacatt     420 tatgggaaag atgctttatt acatgaacat tatgtatatg caaagaagg atatgaaccc     480
```

| | | |
|---|---|---|
| gtacttgtaa tccaatcttc ggaagattat gtagaaaata ctgaaaaggc actgaacgtt | 540 | |
| tattatgaaa taggtaagat attatcaagg gatattttaa gtaaaattaa tcaaccatat | 600 | |
| cagaaatttt tagatgtatt aaataccatt aaaaatgcat ctgattcaga tggacaagat | 660 | |
| cttttattta ctaatcagct taaggaacat cccacagact tttctgtaga attcttggaa | 720 | |
| caaaatagca atgaggtaca agaagtattt gcgaaagctt ttgcatatta tatcgagcca | 780 | |
| cagcatcgtg atgttttaca gctttatgca ccggaagctt ttaattacat ggataaattt | 840 | |
| aacgaacaag aaataaatct atccttggaa gaacttaaag atcaacggat gctggcaaga | 900 | |
| tatgaaaaat gggaaaagat aaaacagcac atcaacact ggagcgattc tttatctgaa | 960 | |
| gaaggaagag gactttaaa aaagctgcag attcctattg agccaaagaa agatgacata | 1020 | |
| attcattctt tatctcaaga agaaaaagag cttctaaaaa gaatacaaat tgatagtagt | 1080 | |
| gatttttat ctactgagga aaaagagttt ttaaaaaagc tacaaattga tattcgtgat | 1140 | |
| tctttatctg aagaagaaaa agagctttta aatagaatac aggtggatag tagtaatcct | 1200 | |
| ttatctgaaa aagaaaaaga gttttaaaa aagctgaaac ttgatattca accatatgat | 1260 | |
| attaatcaaa ggttgcaaga tacaggaggg ttaattgata gtccgtcaat taatcttgat | 1320 | |
| gtaagaaagc agtataaaag ggatattcaa aatattgatg ctttattaca tcaatccatt | 1380 | |
| ggaagtacct tgtacaataa aatttatttg tatgaaaata tgaatatcaa taaccttaca | 1440 | |
| gcaaccctag gtgcggattt agttgattcc actgataata ctaaaattaa tagaggtatt | 1500 | |
| ttcaatgaat tcaaaaaaaa tttcaaatat agtatttcta gtaactatat gattgttgat | 1560 | |
| ataaatgaaa ggcctgcatt agataatgag cgtttgaaat ggagaatcca attatcacca | 1620 | |
| gatactcgag caggatattt agaaaatgga aagcttatat tacaaagaaa catcggtctg | 1680 | |
| gaaataaagg atgtacaaat aattaagcaa tccgaaaaag aatatataag gattgatgcg | 1740 | |
| aaagtagtgc caaagagtaa aatagataca aaaattcaag aagcacagtt aaatataaat | 1800 | |
| caggaatgga ataaagcatt agggttacca aaatatacaa agcttattac attcaacgtg | 1860 | |
| cataatagat atgcatccaa tattgtagaa agtgcttatt taatattgaa tgaatggaaa | 1920 | |
| aataatattc aaagtgatct tataaaaaag gtaacaaatt acttagttga tggtaatgga | 1980 | |
| agatttgttt ttaccgatat tactctccct aatatagctg aacaatatac acatcaagat | 2040 | |
| gagatatatg agcaagttca ttcaaaaggg ttatatgttc cagaatcccg ttctatatta | 2100 | |
| ctccatggac cttcaaaagg tgtagaatta aggaatgata gtgagggttt tatacacgaa | 2160 | |
| tttggacatg ctgtggatga ttatgctgga tatctattag ataagaacca atctgattta | 2220 | |
| gttacaaatt ctaaaaaatt cattgatatt tttaaggaag aagggagtaa tttaacttcg | 2280 | |
| tatgggagaa caaatgaagc ggaattttt gcagaagcct ttaggttaat gcattctacg | 2340 | |
| gaccatgctg aacgtttaaa agttcaaaaa aatgctccga aaactttcca atttattaac | 2400 | |
| gatcagatta agttcattat taactcataa | 2430 | |

<210> SEQ ID NO 82
<211> LENGTH: 800
<212> TYPE: PRT
<213> ORGANISM: Bacillus anthracis

<400> SEQUENCE: 82

Met Thr Arg Asn Lys Phe Ile Pro Asn Lys Phe Ser Ile Ile Ser Phe
 1               5                  10                  15

Ser Val Leu Leu Phe Ala Ile Ser Ser Gln Ala Ile Glu Val Asn
            20                  25                  30

```
Ala Met Asn Glu His Tyr Thr Glu Ser Asp Ile Lys Arg Asn His Lys
     35                  40                  45

Thr Glu Lys Asn Lys Thr Glu Lys Glu Lys Phe Lys Asp Ser Ile Asn
 50                  55                  60

Asn Leu Val Lys Thr Glu Phe Thr Asn Glu Thr Leu Asp Lys Ile Gln
 65                  70                  75                  80

Gln Thr Gln Asp Leu Leu Lys Lys Ile Pro Lys Asp Val Leu Glu Ile
                 85                  90                  95

Tyr Ser Glu Leu Gly Gly Glu Ile Tyr Phe Thr Asp Ile Asp Leu Val
                100                 105                 110

Glu His Lys Glu Leu Gln Asp Leu Ser Glu Glu Lys Asn Ser Met
                115                 120                 125

Asn Ser Arg Gly Glu Lys Val Pro Phe Ala Ser Arg Phe Val Phe Glu
130                 135                 140

Lys Lys Arg Glu Thr Pro Lys Leu Ile Ile Asn Ile Lys Asp Tyr Ala
145                 150                 155                 160

Ile Asn Ser Glu Gln Ser Lys Glu Val Tyr Tyr Glu Ile Gly Lys Gly
                165                 170                 175

Ile Ser Leu Asp Ile Ile Ser Lys Asp Lys Ser Leu Asp Pro Glu Phe
                180                 185                 190

Leu Asn Leu Ile Lys Ser Leu Ser Asp Asp Ser Asp Ser Ser Asp Leu
                195                 200                 205

Leu Phe Ser Gln Lys Phe Lys Glu Lys Leu Glu Leu Asn Asn Lys Ser
210                 215                 220

Ile Asp Ile Asn Phe Ile Lys Glu Asn Leu Thr Glu Phe Gln His Ala
225                 230                 235                 240

Phe Ser Leu Ala Phe Ser Tyr Tyr Phe Ala Pro Asp His Arg Thr Val
                245                 250                 255

Leu Glu Leu Tyr Ala Pro Asp Met Phe Glu Tyr Met Asn Lys Leu Glu
                260                 265                 270

Lys Gly Gly Phe Glu Lys Ile Ser Glu Ser Leu Lys Lys Glu Gly Val
                275                 280                 285

Glu Lys Asp Arg Ile Asp Val Leu Lys Gly Glu Lys Ala Leu Lys Ala
290                 295                 300

Ser Gly Leu Val Pro Glu His Ala Asp Ala Phe Lys Lys Ile Ala Arg
305                 310                 315                 320

Glu Leu Asn Thr Tyr Ile Leu Phe Arg Pro Val Asn Lys Leu Ala Thr
                325                 330                 335

Asn Leu Ile Lys Ser Gly Val Ala Thr Lys Gly Leu Asn Val His Gly
                340                 345                 350

Lys Ser Ser Asp Trp Gly Pro Val Ala Gly Tyr Ile Pro Phe Asp Gln
                355                 360                 365

Asp Leu Ser Lys Lys His Gly Gln Gln Leu Ala Val Glu Lys Gly Asn
                370                 375                 380

Leu Glu Asn Lys Lys Ser Ile Thr Glu His Glu Gly Glu Ile Gly Lys
385                 390                 395                 400

Ile Pro Leu Lys Leu Asp His Leu Arg Ile Glu Glu Leu Lys Glu Asn
                405                 410                 415

Gly Ile Ile Leu Lys Gly Lys Lys Glu Ile Asp Asn Gly Lys Lys Tyr
                420                 425                 430

Tyr Leu Leu Glu Ser Asn Asn Gln Val Tyr Glu Phe Arg Ile Ser Asp
                435                 440                 445

Glu Asn Asn Glu Val Gln Tyr Lys Thr Lys Glu Gly Lys Ile Thr Val
450                 455                 460
```

-continued

| | | | | | | | | | | | | | | |
|---|---|---|---|---|---|---|---|---|---|---|---|---|---|---|
|Leu|Gly|Glu|Lys|Phe|Asn|Trp|Arg|Asn|Ile|Glu|Val|Met|Ala|Lys|Asn|
|465| | | | |470| | | | |475| | | | |480|

Val Glu Gly Val Leu Lys Pro Leu Thr Ala Asp Tyr Asp Leu Phe Ala
            485                 490                 495

Leu Ala Pro Ser Leu Thr Glu Ile Lys Lys Gln Ile Pro Gln Lys Glu
            500                 505                 510

Trp Asp Lys Val Val Asn Thr Pro Asn Ser Leu Glu Lys Gln Lys Gly
            515                 520                 525

Val Thr Asn Leu Leu Ile Lys Tyr Gly Ile Glu Arg Lys Pro Asp Ser
530                 535                 540

Thr Lys Gly Thr Leu Ser Asn Trp Gln Lys Gln Met Leu Asp Arg Leu
545                 550                 555                 560

Asn Glu Ala Val Lys Tyr Thr Gly Tyr Thr Gly Asp Val Val Asn
                565                 570                 575

His Gly Thr Glu Gln Asp Asn Glu Glu Phe Pro Glu Lys Asp Asn Glu
            580                 585                 590

Ile Phe Ile Ile Asn Pro Glu Gly Glu Phe Ile Leu Thr Lys Asn Trp
            595                 600                 605

Glu Met Thr Gly Arg Phe Ile Glu Lys Asn Ile Thr Gly Lys Asp Tyr
610                 615                 620

Leu Tyr Tyr Phe Asn Arg Ser Tyr Asn Lys Ile Ala Pro Gly Asn Lys
625                 630                 635                 640

Ala Tyr Ile Glu Trp Thr Asp Pro Ile Thr Lys Ala Lys Ile Asn Thr
                645                 650                 655

Ile Pro Thr Ser Ala Glu Phe Ile Lys Asn Leu Ser Ser Ile Arg Arg
            660                 665                 670

Ser Ser Asn Val Gly Val Tyr Lys Asp Ser Gly Asp Lys Asp Glu Phe
            675                 680                 685

Ala Lys Lys Glu Ser Val Lys Lys Ile Ala Gly Tyr Leu Ser Asp Tyr
            690                 695                 700

Tyr Asn Ser Ala Asn His Ile Phe Ser Gln Glu Lys Lys Arg Lys Ile
705                 710                 715                 720

Ser Ile Phe Arg Gly Ile Gln Ala Tyr Asn Glu Ile Glu Asn Val Leu
                725                 730                 735

Lys Ser Lys Gln Ile Ala Pro Glu Tyr Lys Asn Tyr Phe Gln Tyr Leu
            740                 745                 750

Lys Glu Arg Ile Thr Asn Gln Val Gln Leu Leu Thr His Gln Lys
            755                 760                 765

Ser Asn Ile Glu Phe Lys Leu Leu Tyr Lys Gln Leu Asn Phe Thr Glu
770                 775                 780

Asn Glu Thr Asp Asn Phe Glu Val Phe Gln Lys Ile Ile Asp Glu Lys
785                 790                 795                 800

<210> SEQ ID NO 83
<211> LENGTH: 2403
<212> TYPE: DNA
<213> ORGANISM: Bacillus anthracis

<400> SEQUENCE: 83
atgactagaa ataaatttat acctaataag tttagtatta tatccttttc agtattacta      60
tttgctatat cctcctcaca ggctatagaa gtaaatgcta tgaatgaaca ttacactgag     120
agtgatatta aagaaaacca taaaactgaa aaaataaaa ctgaaaaaga aaatttaaa      180 gacagtatta ataacttagt taaaacagaa tttaccaatg aaactttaga taaatacag     240

```
cagacacaag acttattaaa aaagatacct aaggatgtac ttgaaattta tagtgaatta       300
ggaggagaaa tctattttac agatatagat ttagtagaac ataaggagtt acaagattta       360
agtgaagaag agaaaaatag tatgaatagt agaggtgaaa aagttccgtt tgcatcccgt       420
tttgtatttg aaaagaaaag ggaaacacct aaattaatta taaatatcaa agattatgca       480
attaatagtg aacaaagtaa agaagtatat tatgaaattg gaaaggggat ttctcttgat       540
attataagta aggataaatc tctagatcca gagttttaa atttaattaa gagtttaagc        600
gatgatagtg atagtagcga ccttttattt agtcaaaaat ttaaagagaa gctagaattg       660
aataataaaa gtatagatat aaattttata aagaaaatt taactgaatt tcagcatgcg        720
ttttctttag cgttttctta ttattttgca cctgaccata gaacggtatt agagttatat       780
gcccccgaca tgtttgagta tatgaataag ttagaaaaag ggggatttga gaaaataagt       840
gaaagtttga agaaagaagg tgtggaaaaa gataggattg atgtgctgaa aggagaaaaa       900
gcacttaaag cttcaggttt agtaccagaa catgcagatg cttttaaaaa aattgctaga       960
gaattaaata catatattct ttttaggcct gttaataagt tagctacaaa ccttattaaa      1020
agtggtgtgg ctacaaaggg attgaatgtt catggaaaga gttcggattg gggccctgta      1080
gctggataca taccatttga tcaagattta tctaagaagc atggtcaaca attagctgtc      1140
gagaaaggaa atttagaaaa taaaaaatca attacagagc atgaaggtga ataggtaaa       1200 ataccattaa agttagacca tttaagaata gaagagttaa aggaaaatgg gataattttg      1260
aagggtaaaa aagaaattga taatggtaaa aaatatattt tgttagaatc gaataatcag      1320
gtatatgaat ttagaattag cgatgaaaac aacgaagtac aatacaagac aaaagaaggt      1380
aaaattactg ttttaggga aaaattcaat tggagaaata tagaagtgat ggctaaaaat       1440
gtagaagggg tcttgaagcc gttaacagct gactatgatt tatttgcact tgccccaagt      1500
ttaacagaaa taaaaaaaca aataccacaa aaagaatggg ataaagtagt taacacccca      1560
aattcattag aaaagcaaaa aggtgttact aatttattga ttaaatatgg aattgagagg      1620
aaaccggatt caactaaggg aactttatca aattggcaaa acaaatgct tgatcgtttg       1680 aatgaagcag tcaaatatac aggatataca ggggggatg tggttaacca tggcacagag      1740
caagataatg aagagtttcc tgaaaaagat aacgaaattt ttataattaa tccagaaggt      1800
gaatttatat taactaaaaa ttgggagatg acaggtagat ttatagaaaa aaacattacg      1860
ggaaaagatt atttatatta ttttaaccgt tcttataata aaatagctcc tggtaataaa      1920
gcttatattg agtggactga tccgattaca aaagccaaaa taaataccat ccctacgtca      1980
gcagagttta taaaaaactt atccagtatc agaagatctt caaatgtagg agtttataaa      2040
gatagtggcg acaaagacga atttgcaaaa aagaaagcg tgaaaaaat tgcaggatat       2100 ttgtcagact attacaattc agcaaatcat attttttctc aggaaaaaaa gcgtaaaata      2160
tcaatatttc gtggaatcca agcctataat gaaattgaaa atgttctaaa atctaaacaa      2220
atagcaccag aatacaaaaa ttattttcaa tatttaaagg aaaggattac caatcaagtt      2280
caattgcttc taacacatca aaaatctaat attgaattta aattattgta taaacaatta      2340
aactttacag aaaatgaaac ggataatttt gaggtcttcc aaaaaattat tgatgaaaaa      2400
taa                                                                    2403

<210> SEQ ID NO 84
<211> LENGTH: 14
<212> TYPE: DNA
<213> ORGANISM: Bacillus Subtilis
<220> FEATURE:
```

```
<221> NAME/KEY: misc_feature
<222> LOCATION: 6,8
<223> OTHER INFORMATION: R = Purine
<220> FEATURE:
<221> NAME/KEY: misc_feature
<222> LOCATION: 9,13
<223> OTHER INFORMATION: Y = Pyrmidine
<220> FEATURE:
<221> NAME/KEY: misc_feature
<222> LOCATION: 7
<223> OTHER INFORMATION: n = A,T,C or G

<400> SEQUENCE: 84
cgaacrnryg ttyc                                                          14
```